US009248109B2

(12) United States Patent
Yu et al.

(10) Patent No.: US 9,248,109 B2
(45) Date of Patent: Feb. 2, 2016

(54) HIGH PENETRATION PRODRUG COMPOSITIONS OF PEPTIDES AND PEPTIDE-RELATED COMPOUNDS

(76) Inventors: Chongxi Yu, Plainfield, IL (US); Lina Xu, Shanghai (CN); Yuhua Chen, Shanghai (CN); Binbing Yan, Shanghai (CN); Shiqian Tu, Shanghai (CN)

( * ) Notice: Subject to any disclaimer, the term of this patent is extended or adjusted under 35 U.S.C. 154(b) by 0 days.

(21) Appl. No.: 13/291,904

(22) Filed: Nov. 8, 2011

(65) Prior Publication Data

US 2012/0156279 A1 Jun. 21, 2012

Related U.S. Application Data

(63) Continuation of application No. PCT/US2010/072561, filed on May 10, 2010, which is a continuation-in-part of application No. 12/463,374, filed on May 8, 2009.

(30) Foreign Application Priority Data

May 8, 2009 (CN) .............................. 200910135997

(51) Int. Cl.
| A61K 31/145 | (2006.01) |
| A61K 31/222 | (2006.01) |
| A61K 31/40 | (2006.01) |
| A61K 31/4184 | (2006.01) |
| A61K 47/48 | (2006.01) |
| C07D 403/12 | (2006.01) |
| C07D 403/14 | (2006.01) |
| C07K 5/062 | (2006.01) |
| C07K 5/065 | (2006.01) |
| C07K 5/103 | (2006.01) |
| C07K 5/107 | (2006.01) |
| C07K 5/11 | (2006.01) |
| C07K 7/06 | (2006.01) |
| C07K 7/56 | (2006.01) |
| A61K 9/00 | (2006.01) |
| A61K 47/42 | (2006.01) |

(52) U.S. Cl.
CPC ............. *A61K 31/145* (2013.01); *A61K 31/222* (2013.01); *A61K 31/40* (2013.01); *A61K 31/4184* (2013.01); *A61K 47/48023* (2013.01); *C07D 403/12* (2013.01); *C07D 403/14* (2013.01); *C07K 5/06026* (2013.01); *C07K 5/06078* (2013.01); *C07K 5/1013* (2013.01); *C07K 5/1016* (2013.01); *C07K 5/1019* (2013.01); *C07K 7/06* (2013.01); *C07K 7/56* (2013.01); *A61K 9/0014* (2013.01); *A61K 47/42* (2013.01)

(58) Field of Classification Search
CPC .................................................... A61K 31/145
See application file for complete search history.

(56) References Cited

U.S. PATENT DOCUMENTS

| 4,746,509 | A | 5/1988 | Haggiage et al. | |
| 5,556,942 | A | 9/1996 | Kauvar et al. | |
| 6,011,049 | A | 1/2000 | Whitcomb | |
| 6,693,135 | B2 | 2/2004 | Yeager et al. | |
| 7,052,715 | B2 | 5/2006 | Fishman | |
| 7,256,210 | B2 | 8/2007 | Man et al. | |
| 2003/0204063 | A1* | 10/2003 | Gravel et al. | ................. 530/399 |
| 2004/0121947 | A1 | 6/2004 | Ghosh et al. | |
| 2004/0162239 | A1 | 8/2004 | Allan et al. | |
| 2004/0186058 | A1 | 9/2004 | Zimmer | |
| 2004/0229920 | A1 | 11/2004 | Garvey et al. | |
| 2005/0020810 | A1 | 1/2005 | Ternansky et al. | |
| 2005/0261202 | A1 | 11/2005 | Brown et al. | |
| 2006/0058219 | A1 | 3/2006 | Miller | |
| 2007/0149457 | A1* | 6/2007 | Rubin et al. | ..................... 514/12 |
| 2009/0074734 | A1* | 3/2009 | Rottiers | ...................... 424/93.21 |

FOREIGN PATENT DOCUMENTS

| EP | 0784984 A2 | 7/1997 |
| EP | 1605064 A1 | 12/2005 |
| WO | 93/07902 | 4/1993 |
| WO | 9703939 A1 | 2/1997 |

(Continued)

OTHER PUBLICATIONS

Dzierzbicka et al., 2006, Synthesis of analogues of anthraquinones linked to tuftsin or retro-tuftsin residues as potential topoisomerase inhibitors, Journal of Peptide Science, 12: 670-678.*

(Continued)

*Primary Examiner* — Amber D Steele

(74) *Attorney, Agent, or Firm* — Perkins Coie LLP; Yingli Wang

(57) ABSTRACT

The invention provides compositions of novel high penetration compositions (HPC) or high penetration prodrugs (HPP) of peptides and peptide-related compounds, which are capable of crossing biological barriers with higher penetration efficiency comparing to their parent drugs. The HPPs are capable of being converted to parent drugs or drug metabolites after crossing the biological barrier and thus can render treatments for the conditions that the parent drugs or metabolites can. Additionally, the HPPs/HPCs are capable of reaching areas that parent drugs may not be able to access or to render a sufficient concentration at the target areas and therefore render novel treatments. The HPPs/HPCs can be administered to a subject through various administration routes, e.g., locally delivered to an action site of a condition with a high concentration or systematically administered to a biological subject and enter the general circulation with a faster rate.

26 Claims, 180 Drawing Sheets

(56) References Cited

FOREIGN PATENT DOCUMENTS

| | | | |
|---|---|---|---|
| WO | 97/41824 A2 | 11/1997 | |
| WO | 00/66104 A2 | 11/2000 | |
| WO | 02/067917 A1 | 9/2002 | |
| WO | 03/022270 A1 | 3/2003 | |
| WO | 2004047771 A1 | 6/2004 | |
| WO | 2006074249 A1 | 7/2006 | |
| WO | WO 2007/070562 * | 6/2007 | ............ A61K 38/12 |
| WO | 2008/007171 A1 | 1/2008 | |
| WO | 2008/010025 A1 | 1/2008 | |
| WO | 2008/012602 A1 | 1/2008 | |
| WO | 2008/012603 A1 | 1/2008 | |
| WO | 2008/021605 A1 | 1/2008 | |
| WO | 2008/017903 A1 | 2/2008 | |
| WO | 2008/020270 A1 | 2/2008 | |
| WO | 2008/026776 | 3/2008 | |
| WO | 2008/029199 A1 | 3/2008 | |
| WO | 2008/029200 A1 | 3/2008 | |
| WO | 2008/044095 A1 | 4/2008 | |
| WO | 2008056207 A1 | 5/2008 | |
| WO | WO 2008/056207 * | 5/2008 | ............ C07C 323/26 |
| WO | 2008/072032 A1 | 6/2008 | |
| WO | 2008/087493 A1 | 7/2008 | |
| WO | 2008/093173 A1 | 8/2008 | |
| WO | 2008/149181 A1 | 12/2008 | |
| WO | 2010/065936 A1 | 6/2010 | |

OTHER PUBLICATIONS

Agrawal et al., 2000, Tuftsin-bearing liposomes in treatment of macrophage-based infections, Advanced Drug Delivery Reviews, 41: 135-146.*
Berge, S.M., et al., "Pharmaceutical Salts," J. Pharm. Sci. 66(1):1-19 (1977).
Chinese Intellectual Property Office, International Search Report and Written Opinion for PCT/CN2010/072561, dated Aug. 26, 2010.
Doherty, A.M., "Endothelin: A New Challenge," J. Med. Chem. 35(9):1493-1508 (1992).
Emson, P.C. and B.E.B. Sandberg, "Cholecystokinin and Substance P in the Central Nervous System," Annu. Rep. Med. Chem. 18:31-39 (1983).
Erlanson-Albertsson, C., et al., "Enterostatin—A Peptide Regulating Fat Intake," Obes. Res. 5(4):360-372 (1997).
Garrison, J. C., et al., "Renin and Angiotensin," Pharmacological Basis of Therapeutics, A.G. Gillman, et al., Eds., New York, Pergamon Press, 1990, p. 749-763.
Jaffe, J.H., et al., "Ch. 21: Opioid Analgesics and Antagonists," Goodman and Gilman's Pharmacological Basis of Therapeutics, 8th Ed., New York, Pergamon Press, 1990, p. 485-521.
Jorpes, J.E., "The Isolation and Chemistry of Secretin and Cholecystokinin," Gastroenterology 55(2):157-164 (1968).
Kamm, O., et al., "The Active Principles of the Posterior Lobe of the Pituitary Gland. I. The Demonstration of the Presence of Two Active Principles. II. The Separation of the Two Principles and Their Concentration in the Form of Potent Solid Preparations," J. Am. Chem. Soc. 50:573-601 (1928).
Kisliuk, R.L., "Ch. 27: Amino Acids, Peptides and Proteins," Principles of Medicinal Chemistry, 4th Ed., W.O. Foye, et al. Eds., Williams & Wilkins 4th Ed. 1995, p. 601-621.
Kunz, H., et al., "The 2-(2-Pyridyl)Ethoxycarbonyl-(Pyoc) Residue—An Acid—and Base-Stable, Hydrophilic Protecting Group for the Amino Function in Peptide Synthesis," Angew. Chem. Int. Ed. Engl. 22(10):783-784 (1983).
Milosovich, S., et al., "Testosteronyl-4-Dimethylaminobutyrate-HCl: A Prodrug with Improved Skin Penetration Rate," J. Pharm. Sci. 82(2):227-228 (1993).
Najjar, V.A., "Immunologically Active Peptides," Mol Cell. Biochem. 41:1-136 (1981).
Okada, S., et al., "Enterostatin (Val-Pro-Asp-Pro-Arg), the Activation Peptide of Procolipase, Selectively Reduces Fat Intake," Physiol. Behav. 49(6):1185-1189 (1991).
Pierce, J. G., et al., "Further Distribution Studies on the Oxytocic Hormone of the Posterior Lobe of the Pituitary Gland and the Preparation of an Active Crystalline Flavianate," J. Biol. Chem. 199:929-940 (1952).
Ray, M. V.L., et al., "Production of Recombinant Salmon Calcitonin by in Vitro Amidation of an *Escherichia Coli* Produced Precursor Peptide," Biotechnology 11(1):64-70 (1993).
Sanger, F., "Chemistry of Insulin," Br. Med. Bull. 16(3):183-188 (1960).
Schally, A.V., et al., "Hypothalamic Regulatory Hormones," Annu. Rev. Biochem. 47:89-128 (1978).
Sorhede, M., et al., "Enterostatin: A Gut-Brain Peptide Regulating Fat Intake in Rat," J. Physiol. Paris. 87(4):273-275 (1993).
Weisskopf, M.G., et al., "The Opioid Peptide Dynorphin Mediates Heterosynaptic Depression of Hippocampal Mossy Fibre Synapses and Modulates Long-Term Potentiation," Nature 362(6419):423-427 (1993).
Fleisher, D., et al., "Improved Oral Drug Delivery: Solubility Limitations Overcome by the Use of Prodrugs," Adv. Drug Deliv. Rev. 19:115-130 (1996).
Jona, J. A., et al., "Design of Novel Prodrugs for the Enhancement of the Transdermal Penetration of Indomethacin," Int. J. Pharm. 123:127-136 (1995).
Korean Intellectual Property Office, International Preliminary Report on Patentability for PCT/IB2006/054170, dated May 12, 2009.
Sloan, K. B., et al., "Designing for Topical Delivery: Prodrugs Can Make the Difference," Med. Res. Rev. 23(6):763-793 (2003).
Andrews, J.M., "Determination of Minimum Inhibitory Concentrations," Journal of Antimicrobial Chemotherapy 48, suppl. S1: 5-16 (2001).
Battaglino, R., et al., "Fluoxetine Treatment Increases Trabecular Bone Formation in Mice (Fluoxetine Affects Bone Mass)," J. Cell Biochem. 100(6)1387-1394 (2007).
Bundgaard, H., et al., "Means to Enhance Penetration (1) Prodrugs as a Means to Improve the Delivery of Peptide Drugs," Adv. Drug Del. Rev. 8:1-38 (1992).
Carrico, D., et al., "In Vitro and in Vivo Antimalarial of Peptidomimetic Protein Farnesyltransferase Inhibitors with Improved Membrane Permeability," Bioorg. Med. Chem. 12(24):6517-6526 (2004).
Database Caplus [Online] Chemical Abstracts Service, Columbus, OH, US; "Effect of Penicillinase on Certain Salts and Esters of Penicillin," retrieved from STN database accession No. 61:33936 (2001).
Drachman, D.B., et al., "Cycloxygenase 2 Inhibition Protects Motor Neurons and Prolongs Survival in a Transgenic Mouse Model of ALS," Annals of Neurology 52:771-778 (2002).
Fix, J. A., et al., "Short-Chain Alkyl Esters of L-Dopa as Prodrugs for Rectal Absorption," Pharma. Res. 6(6):501-505 (1989).
Ginaldi, L., et al., "Osteoporosis, Inflammation and Ageing," Immunity & Ageing 2:14 (2005).
Gonzalez-Muniz, R., et al., "Ketomethylene and (Cyanomethylene)amino Pseudopeptide Analogues of the C-Terminal hexapeptide of Neurotensin," J. Med. Chem. 38:1015-1021 (1995).
Horan, P. J., et al., "Antinociceptive Profile of Biphalin, a Dimeric Enkephalin Analog," J. Pharmacology & Experimental Therapeutics 265(3)1446-1454 (1993).
Hovgaard, L., et al., "Drug Delivery Studies in Caco-2 Monolayers. Synthesis, Hydrolysis, and Transport of O-Cyclopropane Carboxylic Acid Ester Prodrugs of Varius B-Blocking Agents," Pharm. Res. 12(3):387-392 (1995).
Hovgaard, L., et al., "Permeation Studies on O-Cyclopropanoyl Ester Prodrugs of B-Blockers in Caco-2 Cell Monolayers," Proceed. Intern: Symp. Control. Rel. Bioact. Mater. 20:238-239 (1993).
Kim, Y.K., et al., "Relationship of Stereochemical and Skeletal Diversity of Small Molecules to Cellular Measurement Space," J. Am. Chem. Soc. 126:14740-14745 (2004).
Lung, F.D. T., et al., "Development of non-phosphorylated Cyclic Thioether Peptide Binding to the Grb2-SH2 Domain," Lett. Pept. Sci. 6:45-49 (1999).

(56) References Cited

OTHER PUBLICATIONS

Moss, J., et al., "Prodrugs of Peptides. 8. In Vitro Study of Intestinal Metabolism and Penetration of Thyrotropin-Releasing Hormone (TRH) and Its Prodrugs," Int. J. Pharm. 66:183-191 (1990).

Oliyai, R., "Prodrugs of Peptides and Peptidomimetics for Improved Formulation and Delivery," Adv. Drug Del. Rev. 19:275-286 (1996).

Oliyai, R., et al., "Prodrugs of Peptides and Proteins for Improved Formulation and Delivery," Annu. Rev. Pharmacol. Toxicol. 32:521-544 (1993).

Pan, D.S., et al., "Inhibitory Effect of Progesterone on Inflammatory Factors after Experimental Traumatic Brain Injury," Biomed. Environ. Sci. 20(5):432-438 (2007).

Raisz, L., "Pathogenesis of Osteoporosis: Concepts, Conflicts, and Prospects," J. Clin. Invest. 115(12):3318-3325 (2005).

Roof, R.L., et al., "Gender Differences in Acute CNS Trauma and Stroke: Neuroprotective Effects of Estrogen and Progesterone," J. Neurotrauma 17(5):367-388 (2000).

Scheurer, U., et al., "Morphine-Like Action of Enkephalin Analog FK 33-824 on Motility of the Isolated Rat Colon," J. Pharmacol. Exp. Ther. 219(2):534-539 (1981).

Scott, I. L., "Keystone Symposia: Inflammation and Cancer, Breckenridge, CO, USA, Feb. 27-Mar. 3, 2005," Technical Reports 10(13)1-17.

Tozkoparan, B., et al.,"6-Benzylidenethiazolo[3,2-b]-1,24-Triazole-5(6H)-Ones Sybstituted with Ibprofen: Synthesis, Characterization and Evaluation of Anti-Inflammatory Activity," Eur. J. Med. Chem. 35(7-8):743-750 (2000).

Walensky, L. D., et al., "Activation of Apoptosis in Vivo by a Hydrocarbon-Stapled BH3 Helix," Science 305:1466-1470 (2004).

Wright, D.W., et al., "ProTECT: A Randomized Clinical Trial of Progesterone for Acute Traumatic Brain Injury," Ann. Emerg. Med. 49(4):391-402 (2007).

Xiao, G., et al., "Improved Outcomes from the Administration of Progesterone for Patients with Acute Severe ttraumatic bbrain iinjury: A Randomized Controlled Trial," Crit. Care 12:R61 (2008).

Yang, S., et al., "Specificity of RGS10A as a Key Component in the RANKL Signaling Mechanism for Osteoclast Differentiation," J. Cell Sci. 120:3362-3371 (2007).

Yu, L., et al., A Simple and Efficient Method for the Syntheses of Thioether Cyclic Peptides, Tetrahedron Letters 39:6633-6636 (1998).

* cited by examiner

Structure 2

Structure 3

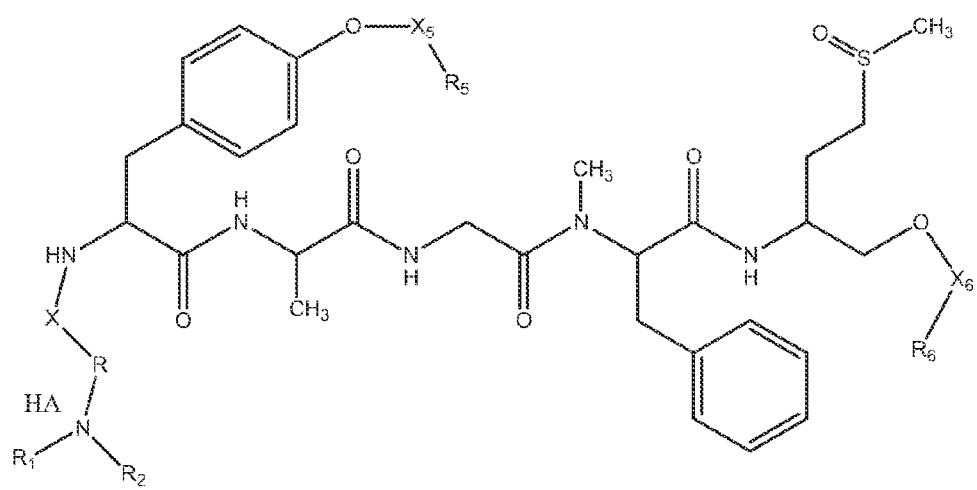
Structure 10
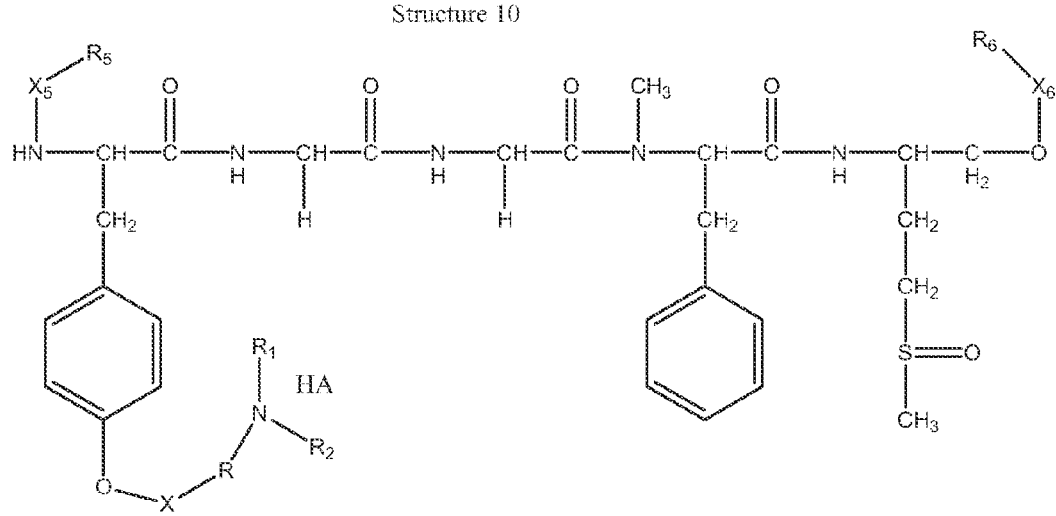
Structure 11
FIG. 1-5

Structure 12

Structure 13

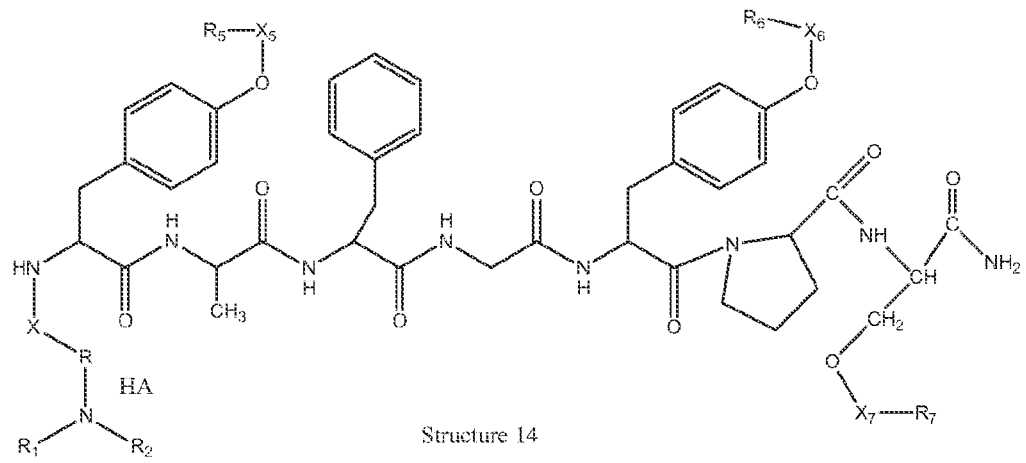
Structure 14
FIG. 1-6 (continued)
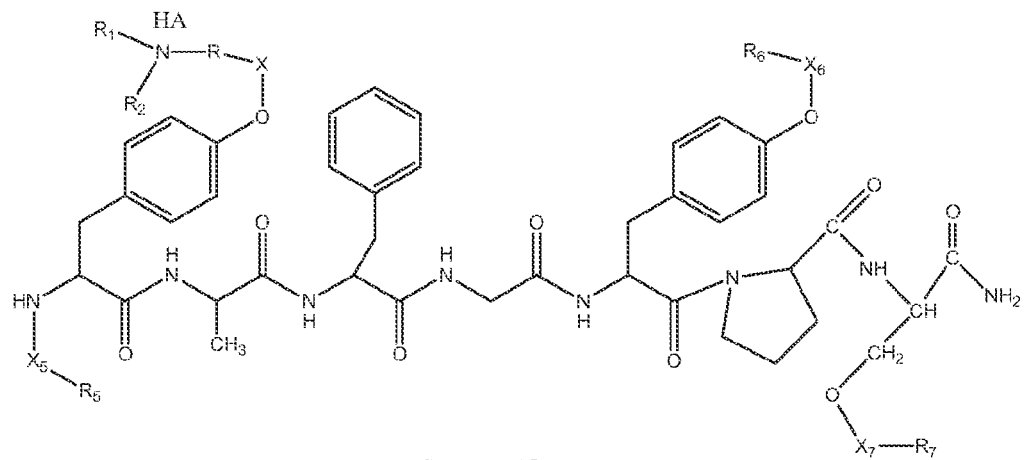
Structure 15
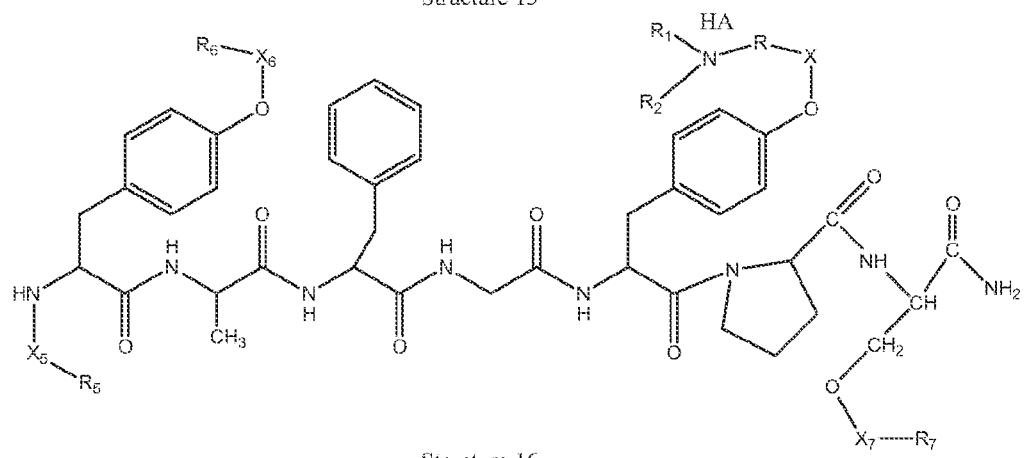
Structure 16
FIG. 1-7

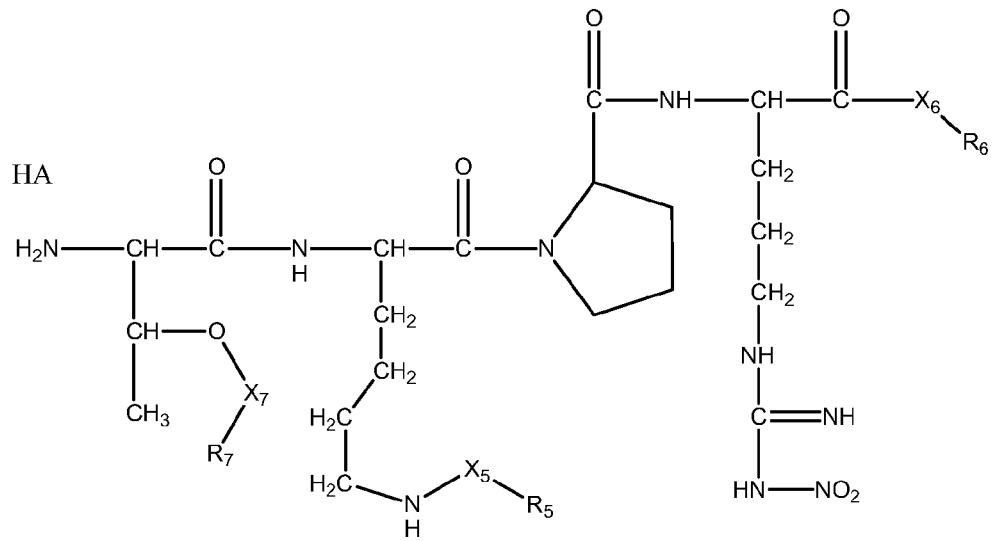
Structure 17
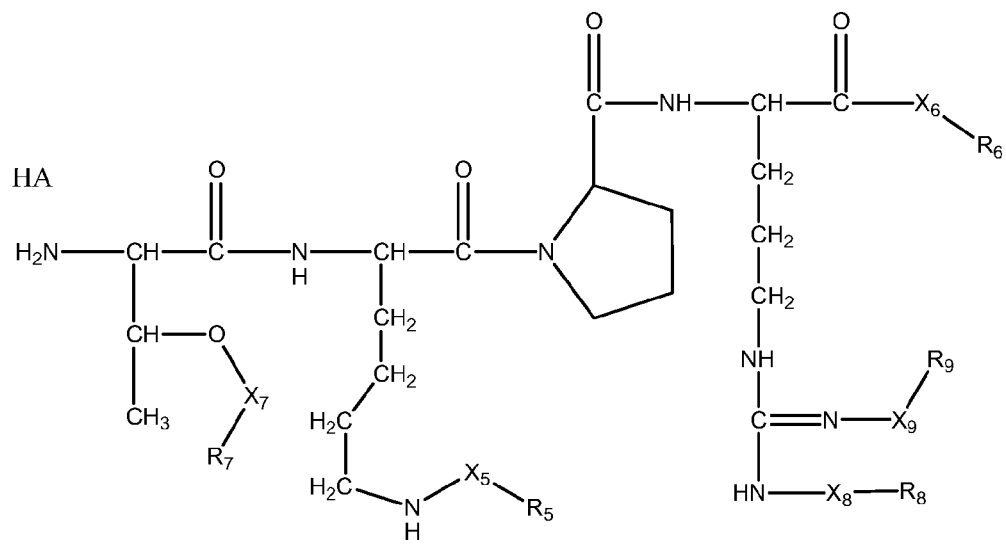
Structure 18
Figure 1-8

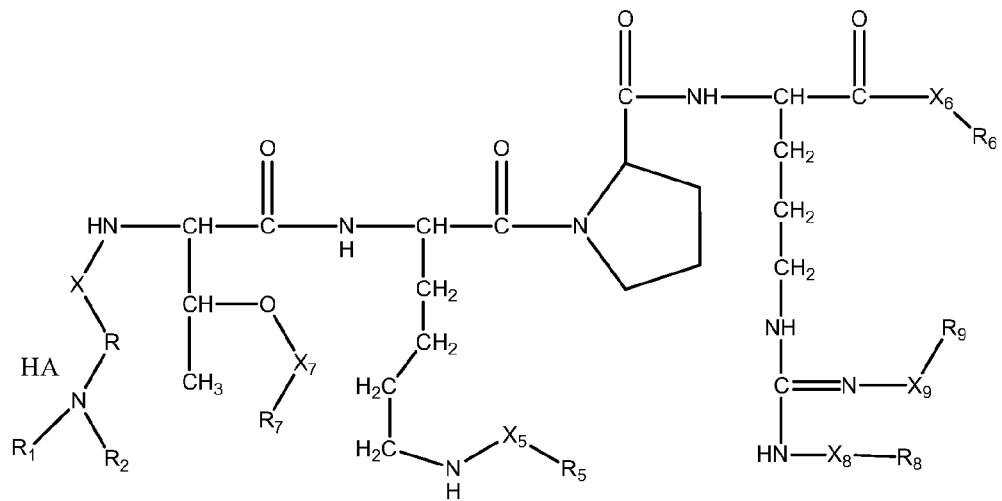
Structure 19
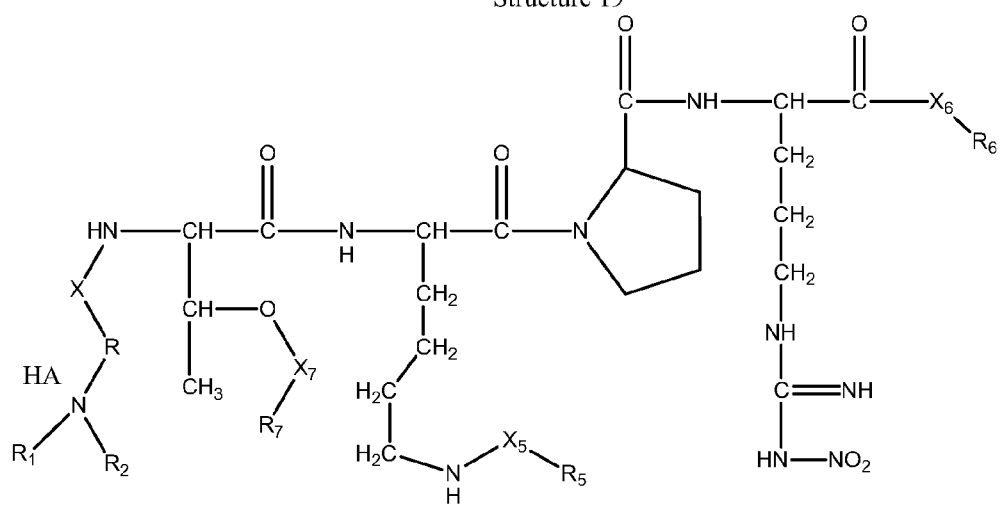
Structure 20
Figure 1-9

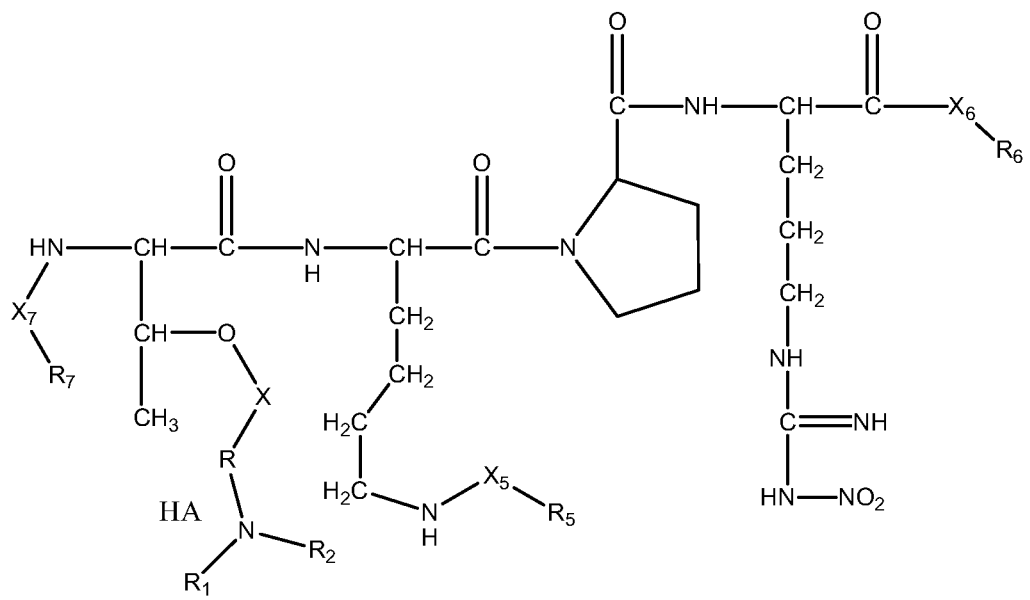
Structure 21
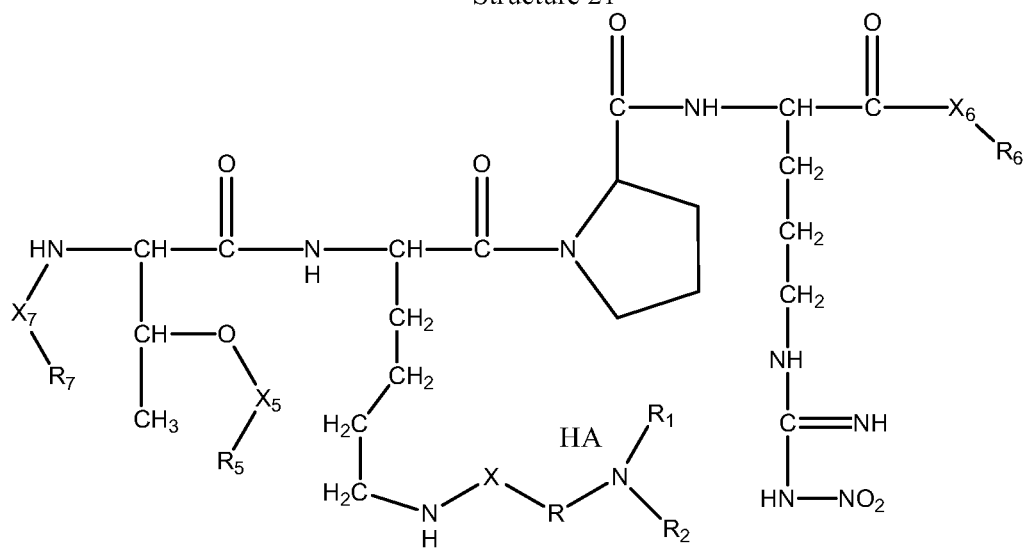
Structure 22
Figure 1-10

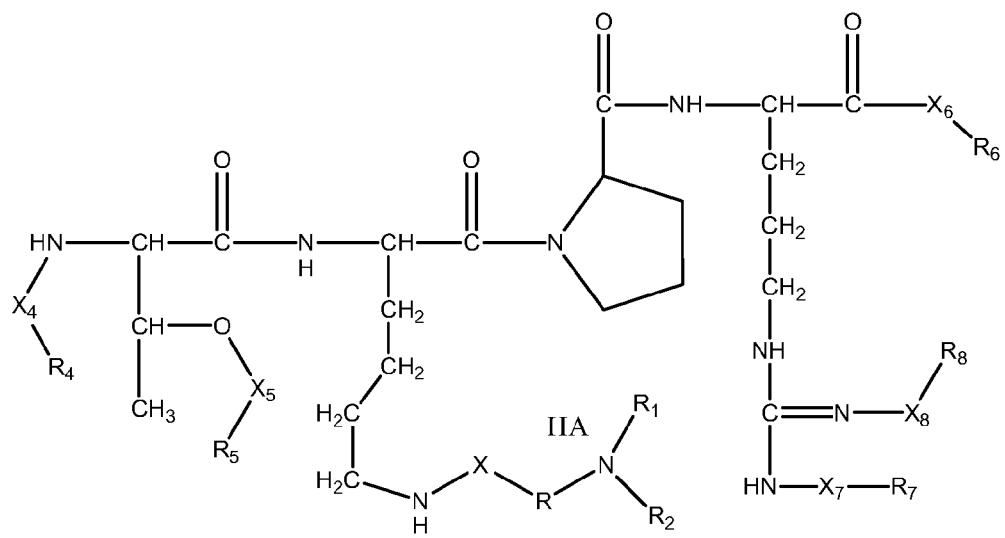
Structure 23
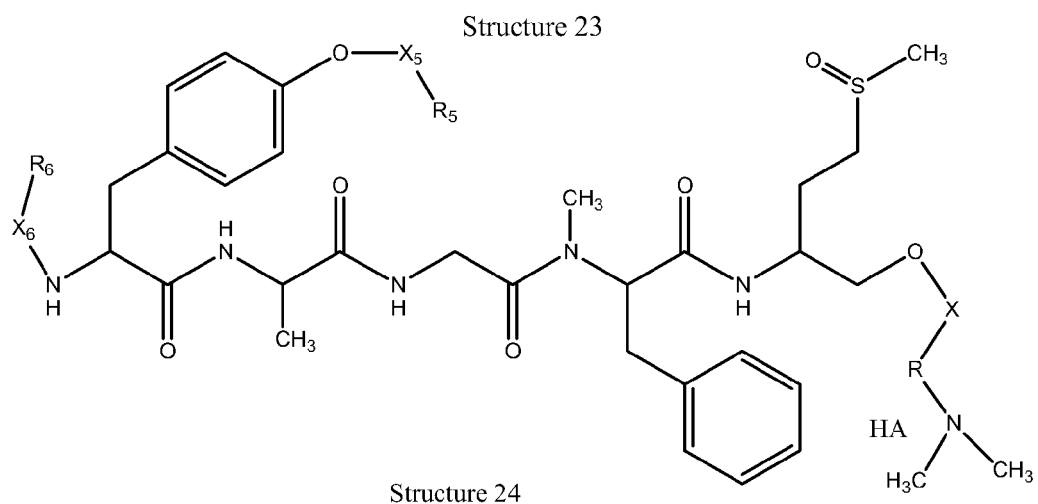
Structure 24
Figure 1-11

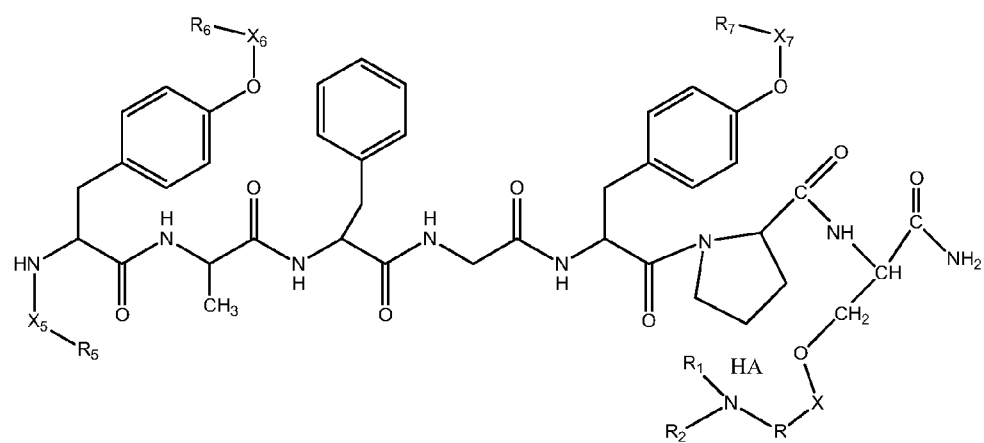
Structure 25
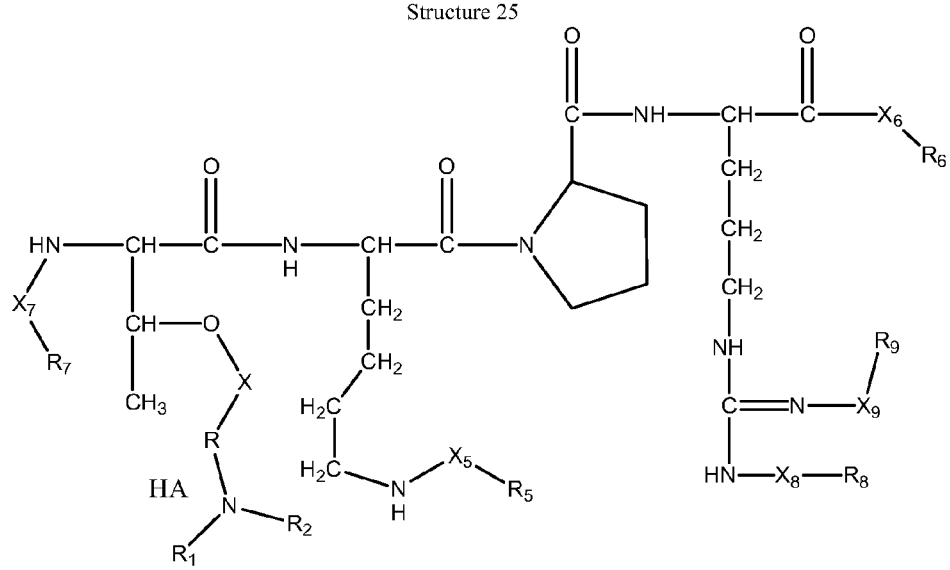
Structure 26
Figure 1-12

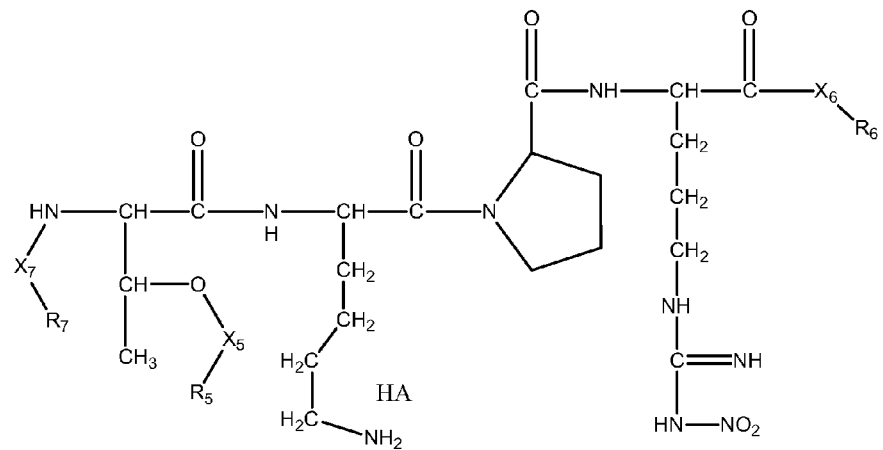
Structure 27
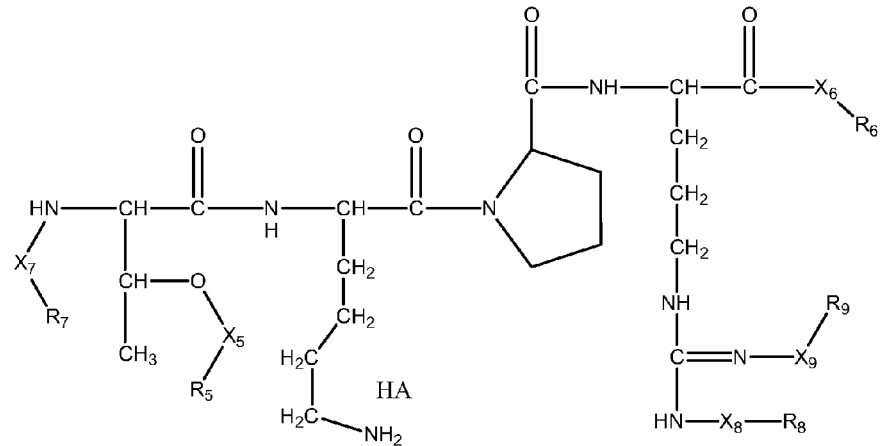
Structure 28
Figure 1-13

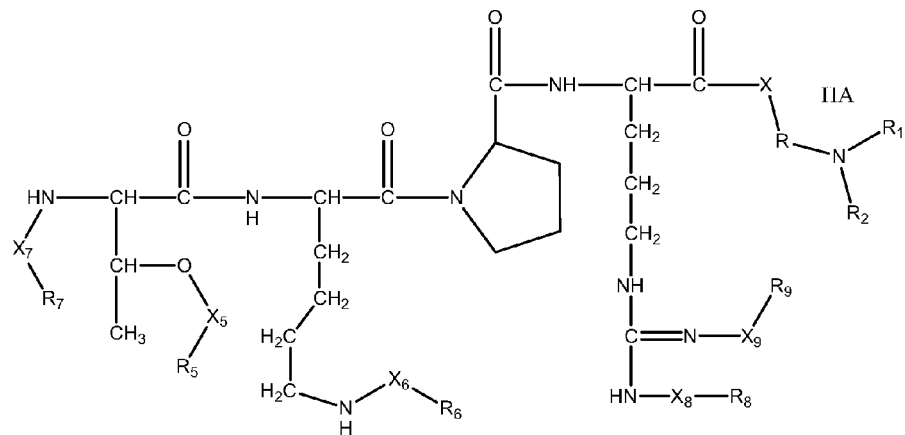
Structure 29
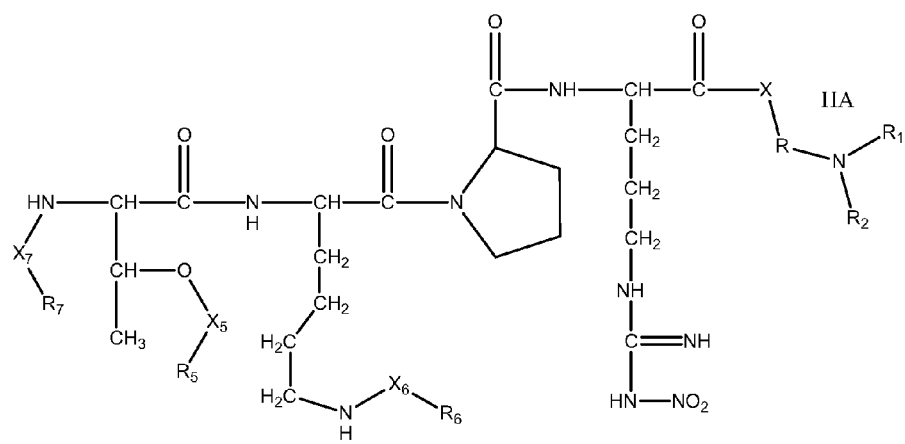
Structure 30
Figure 1-14

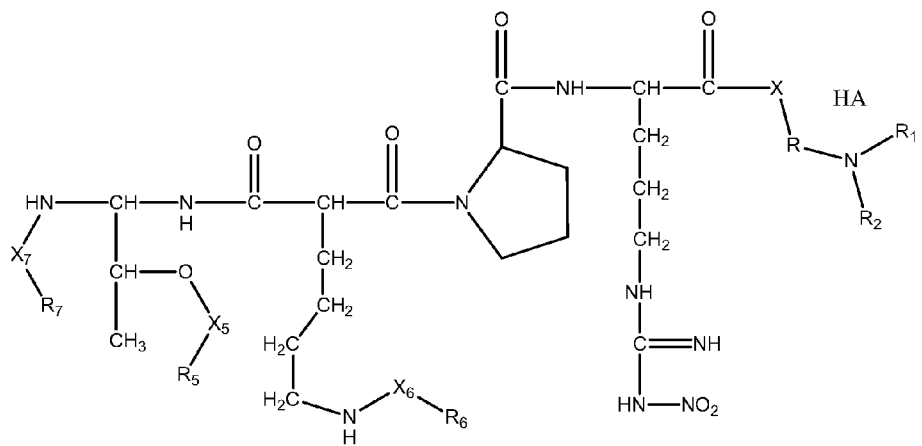
Structure 31
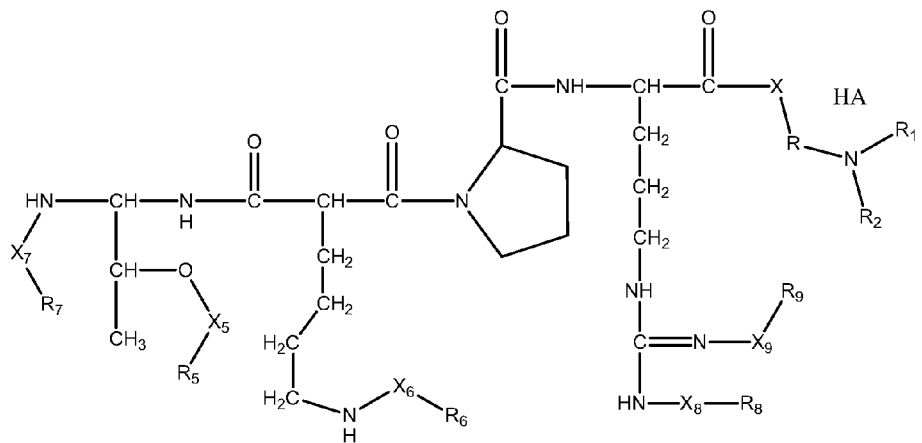
Structure 32
Figure 1-15

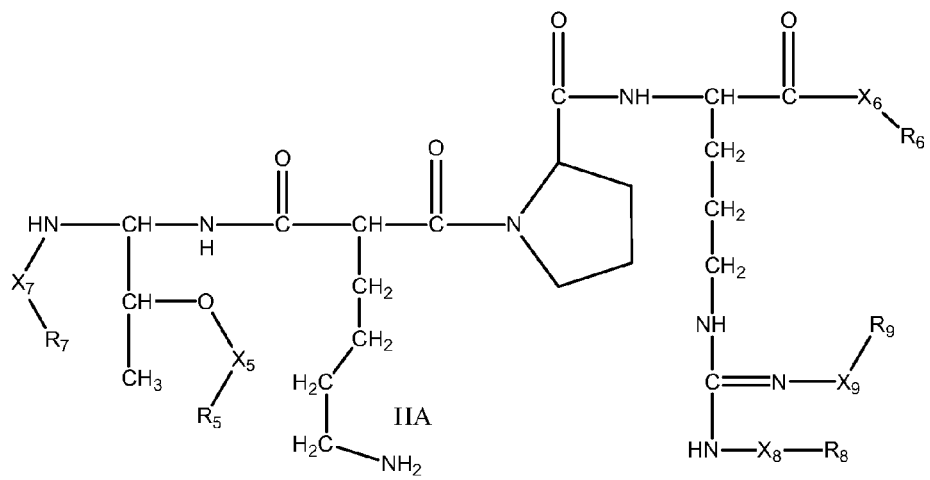
Structure 33
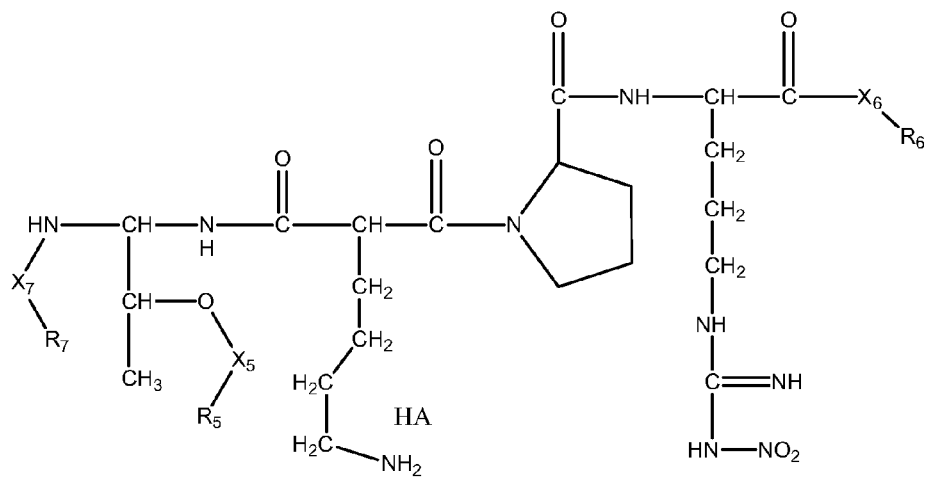
Structure 34
Figure 1-16

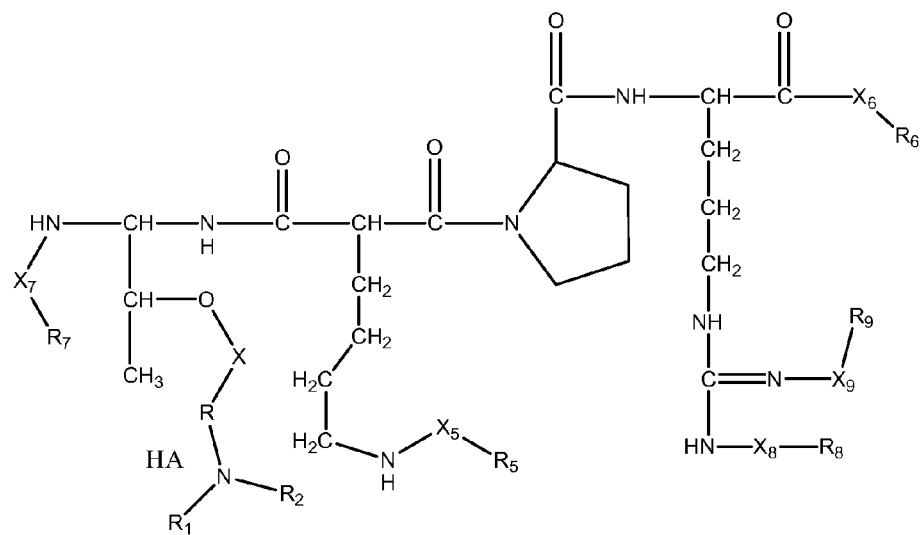
Structure 35
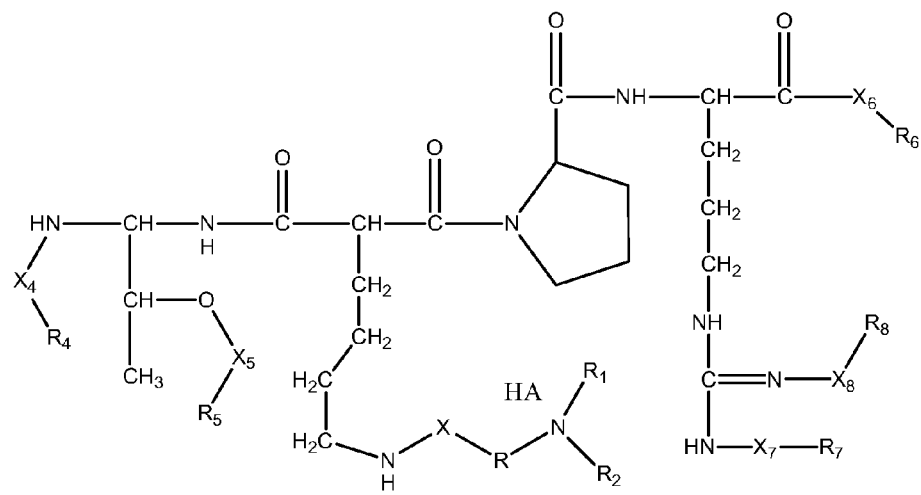
Structure 36
Figure 1-17

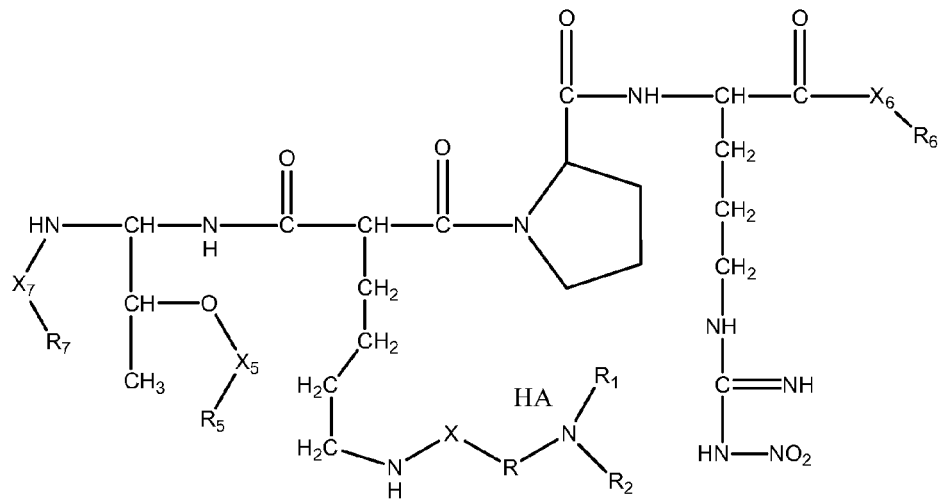
Structure 37
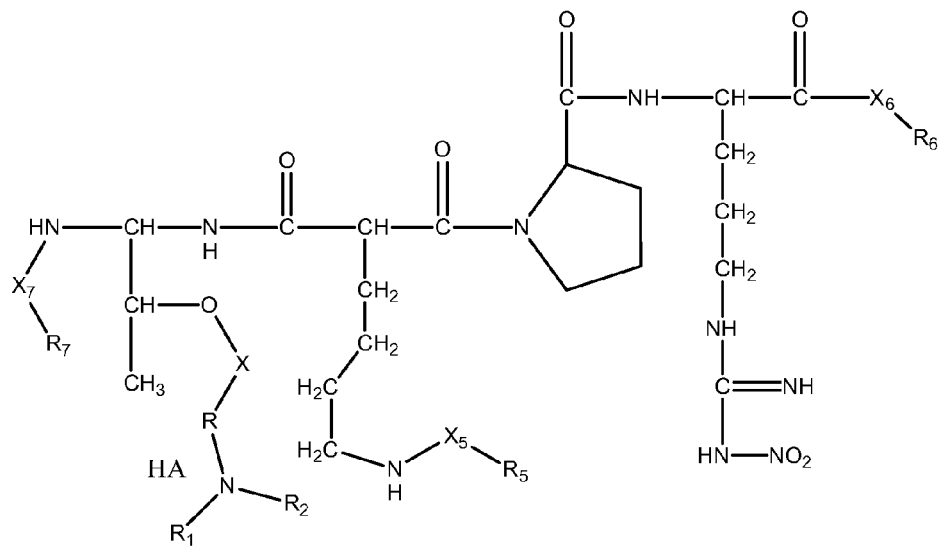
Structure 38
Figure 1-18

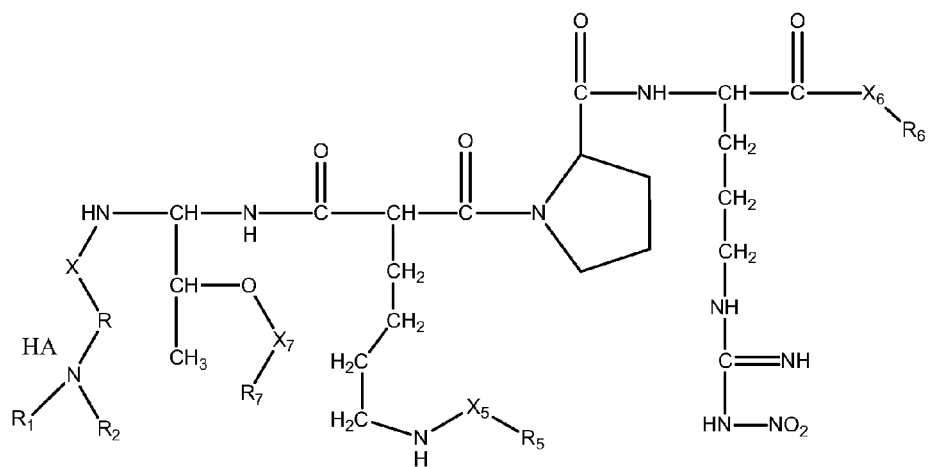
Structure 39
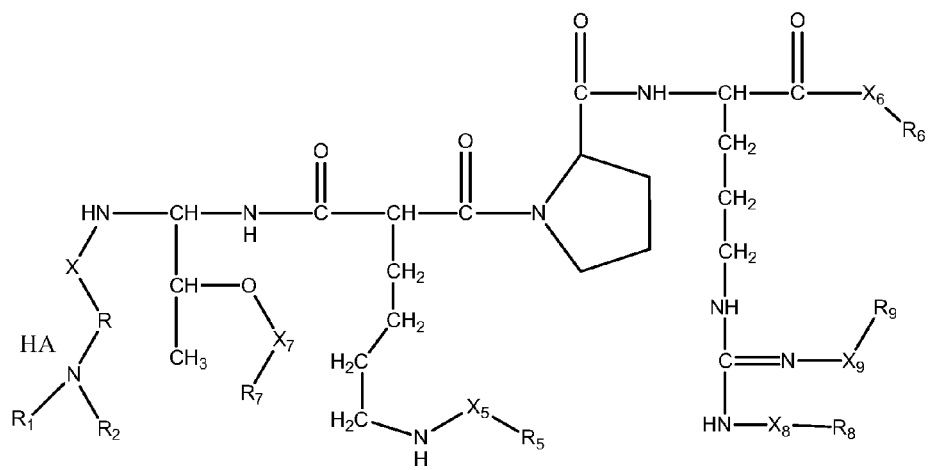
Structure 40
Figure 1-19

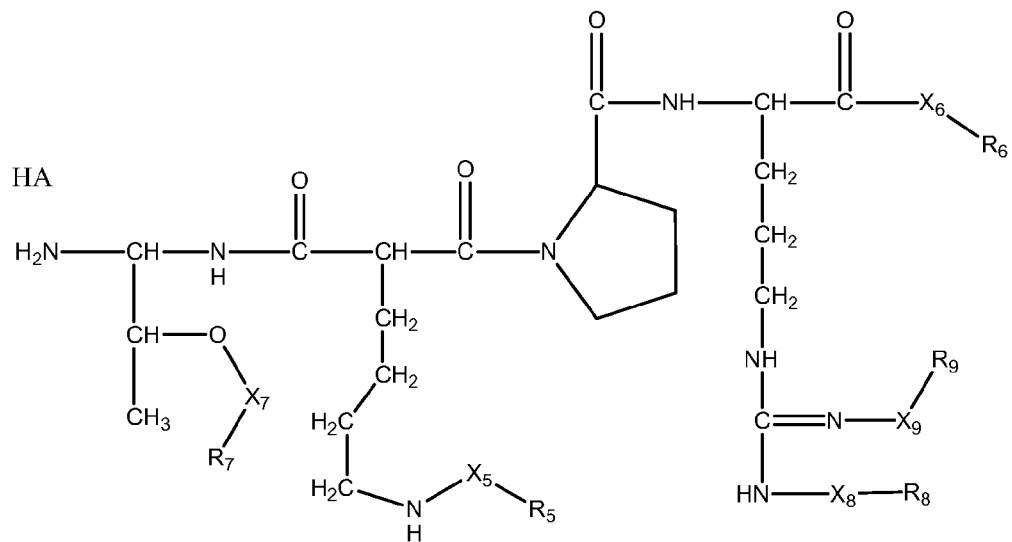
Structure 41
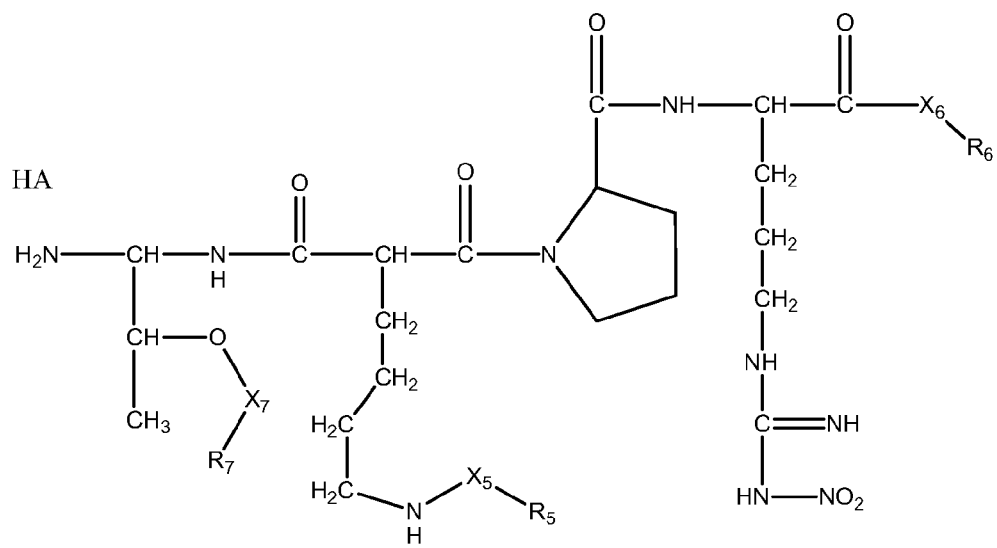
Structure 42
Figure 1-20

Structure 43

Structure 44

Structure 47

Structure 48

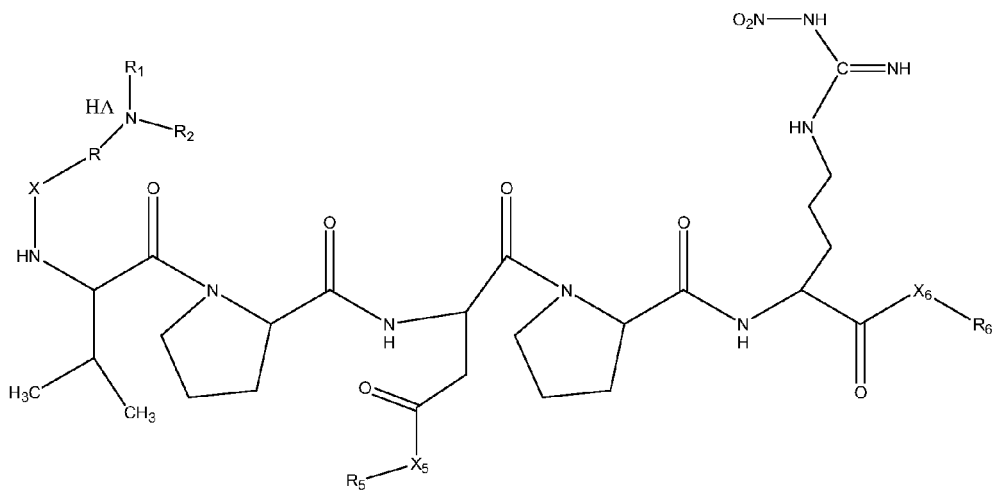
Structure 49
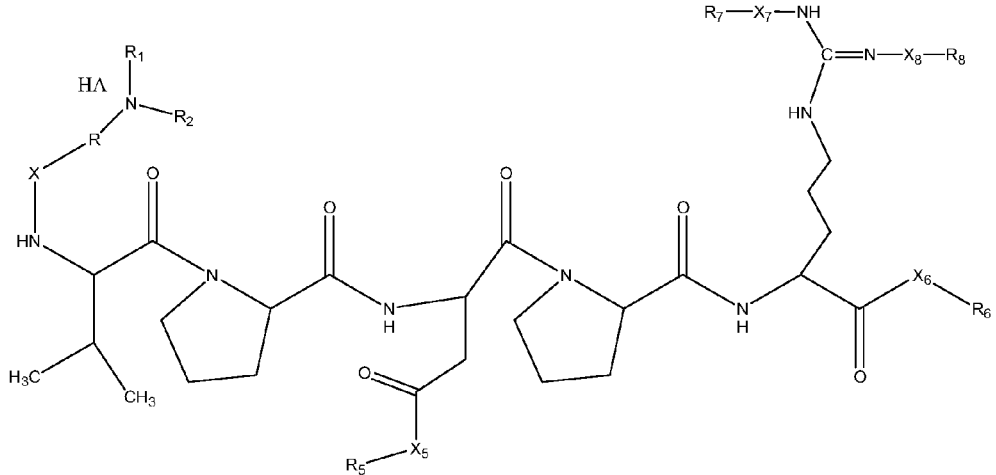
Structure 50
Figure 1-24

Structure 51

Structure 52

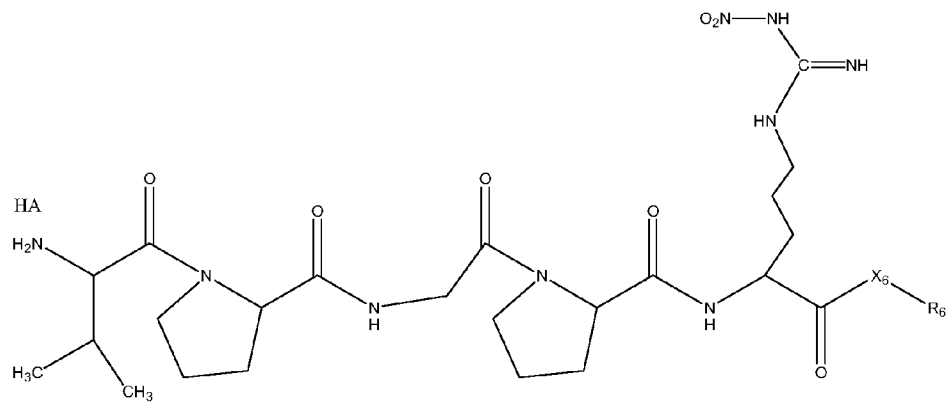
Structure 53
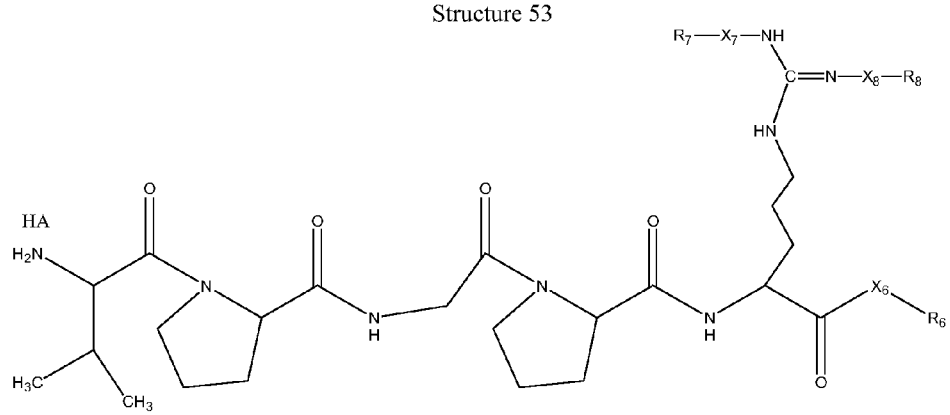
Structure 54
Figure 1-26

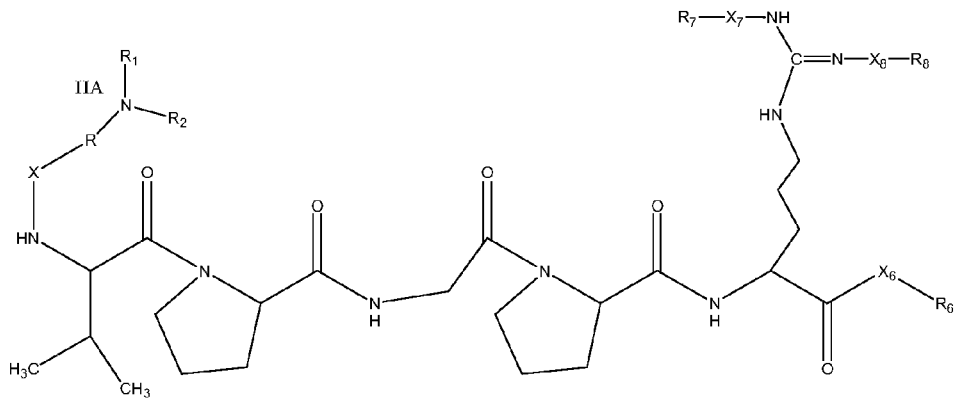
Structure 55
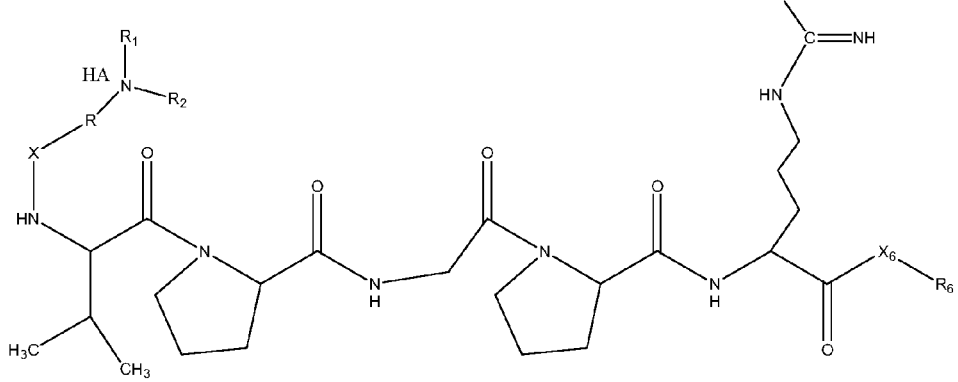
Structure 56
Figure 1-27

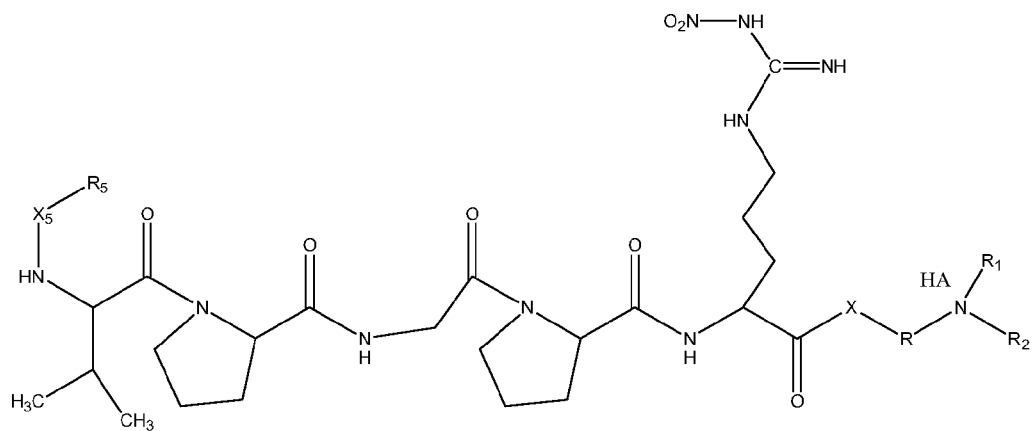
Structure 57
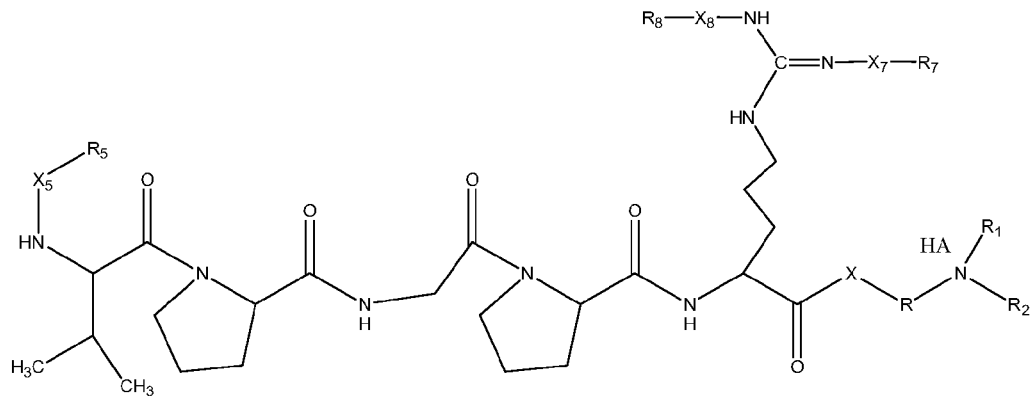
Structure 58
Figure 1-28

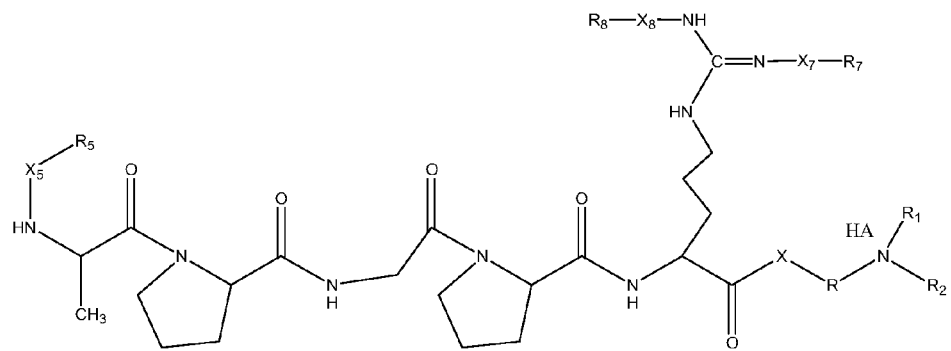
Structure 59
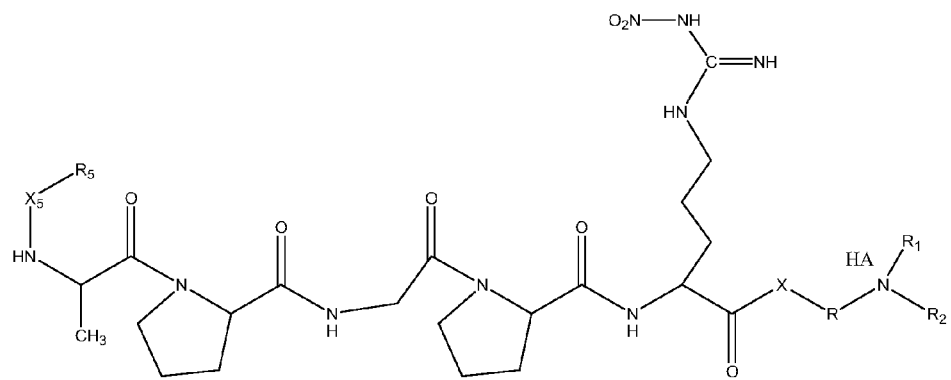
Structure 60
Figure 1-29

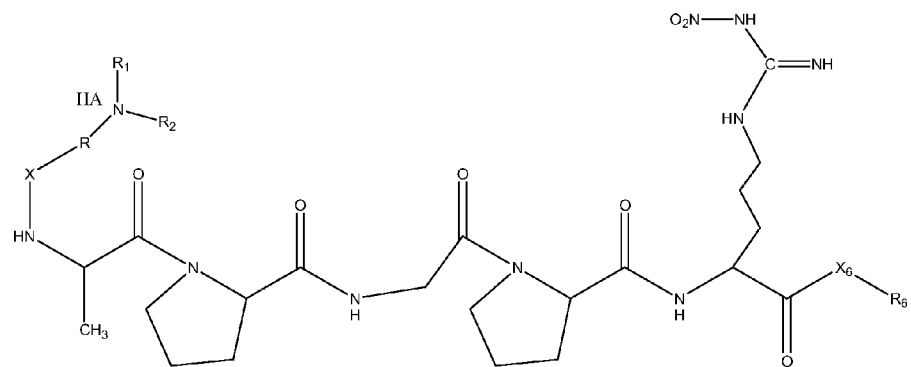
Structure 61
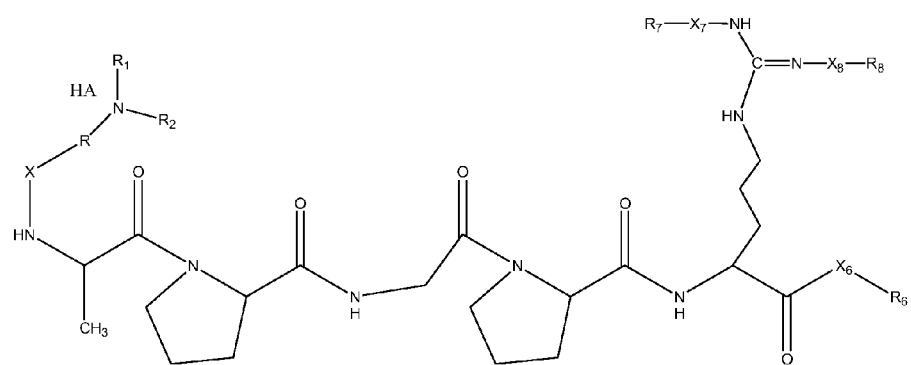
Structure 62
Figure 1-30

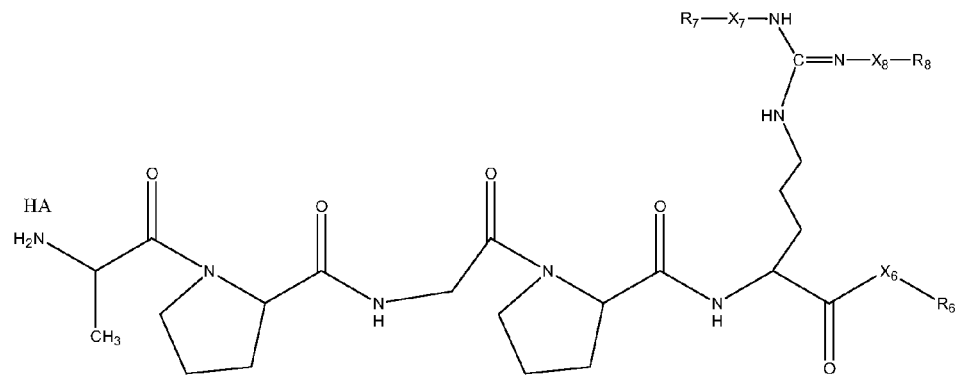
Structure 63
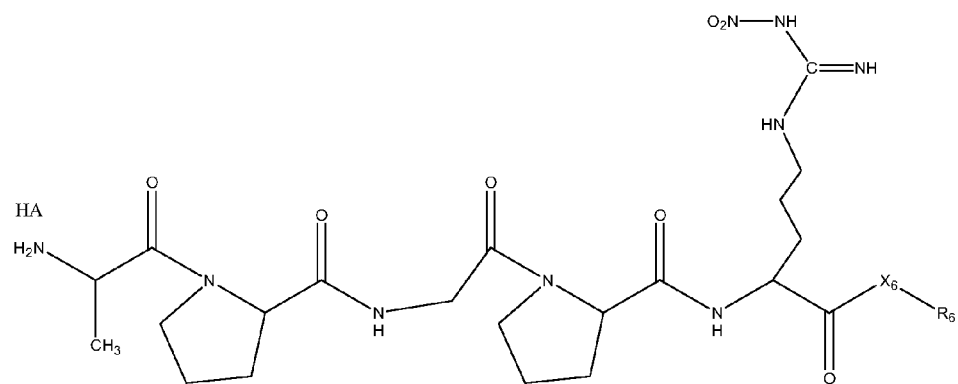
Structure 64
Figure 1-31

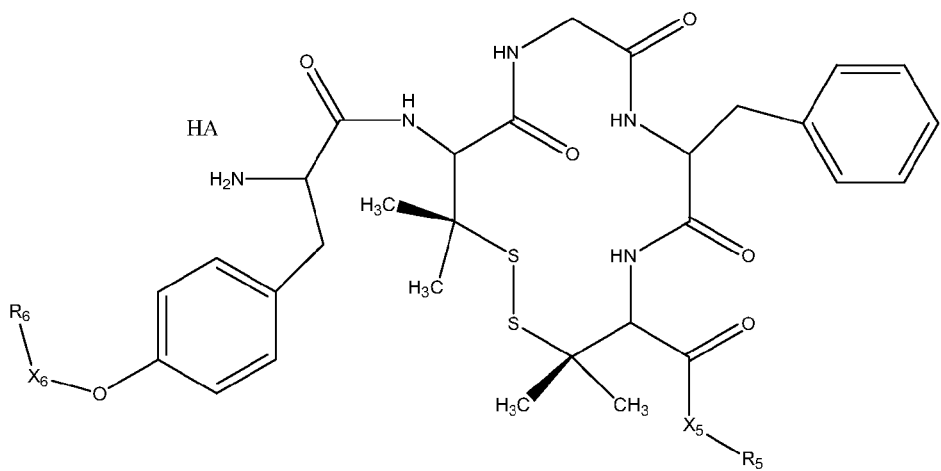
Structure 65
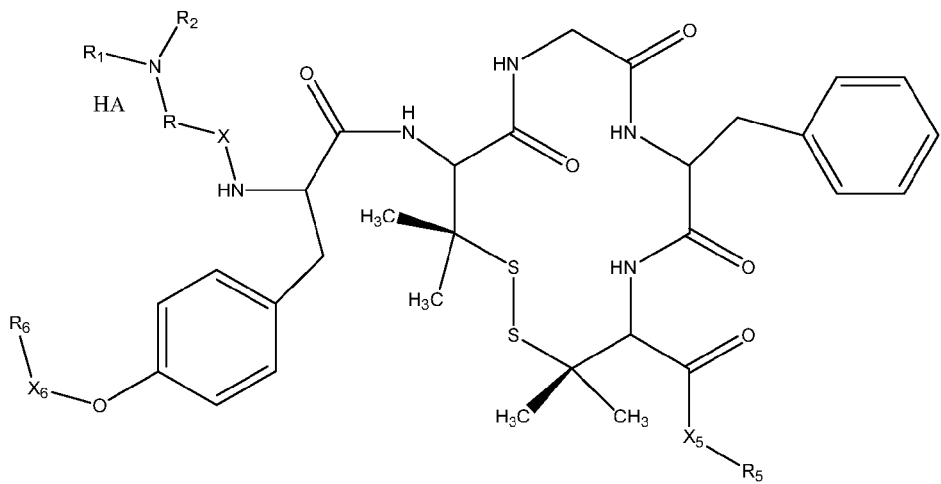
Structure 66
Figure 1-32

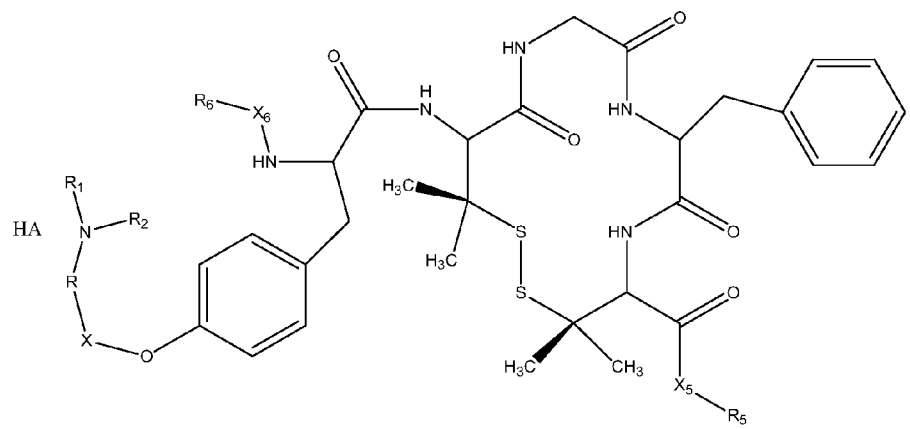
Structure 67
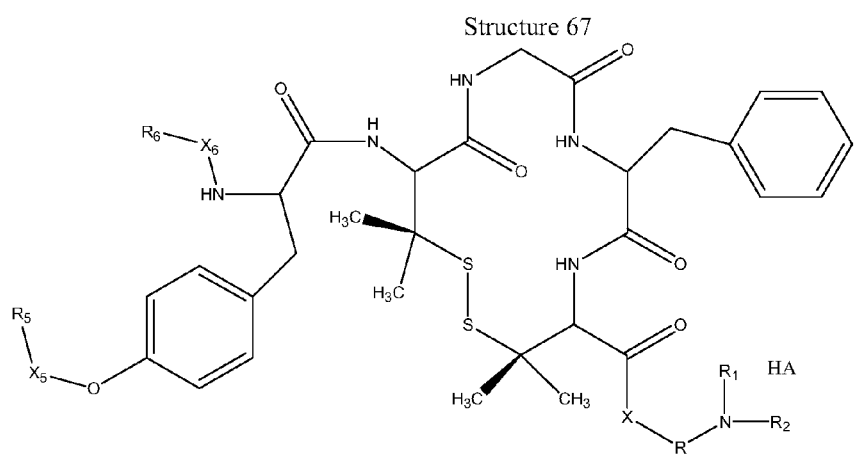
Structure 68
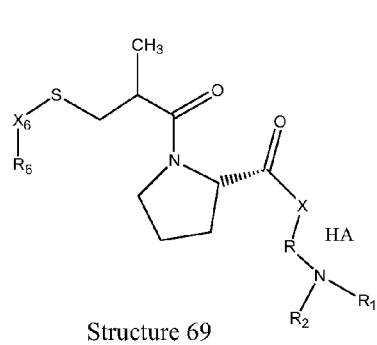
Structure 69
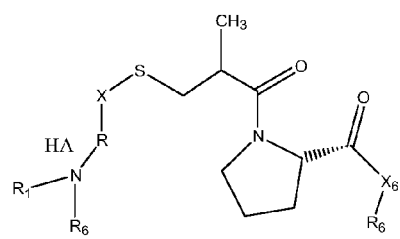
Structure 70
Figure 1-33

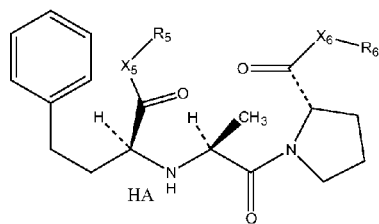
Structure 71
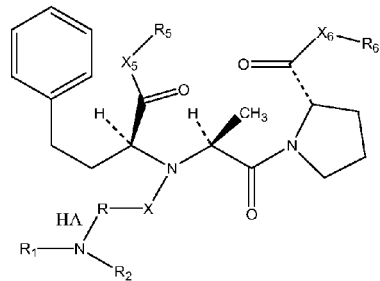
Structure 72
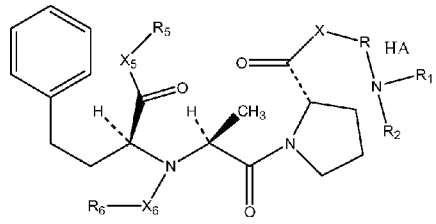
Structure 73
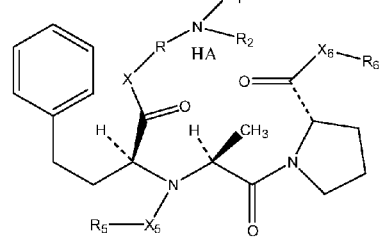
Structure 74
Figure 1-34

Structure 75

Structure 76

Structure 77

Structure 78

Structure 79

Structure 80

Structure 85

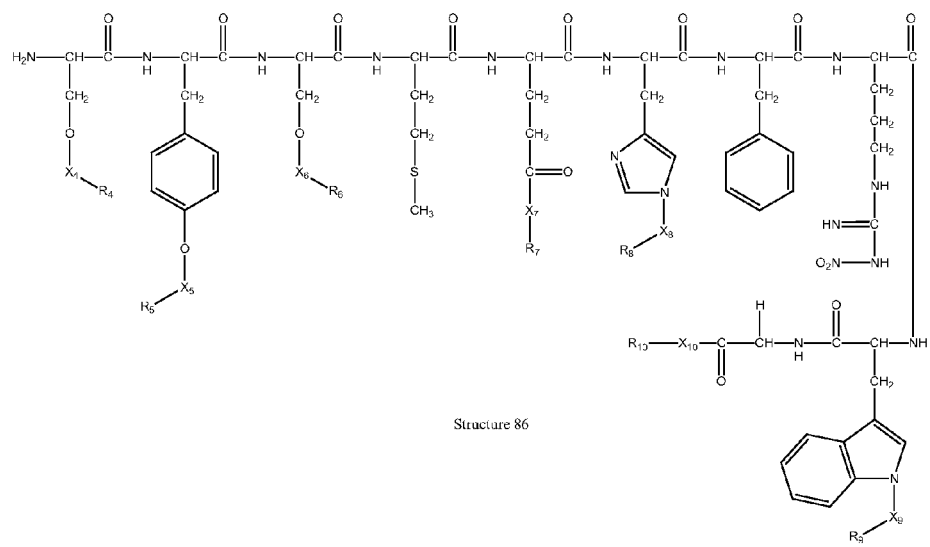
Structure 86
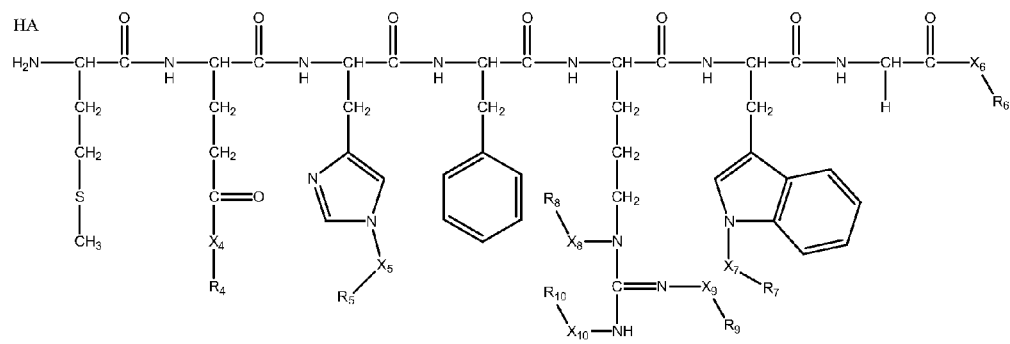
Structure 87
Figure 1-43

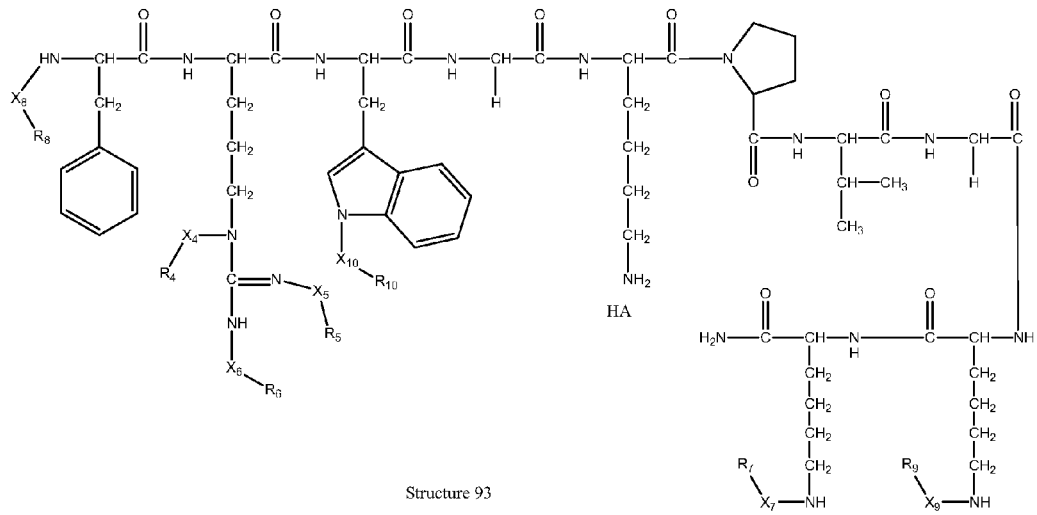
Structure 93
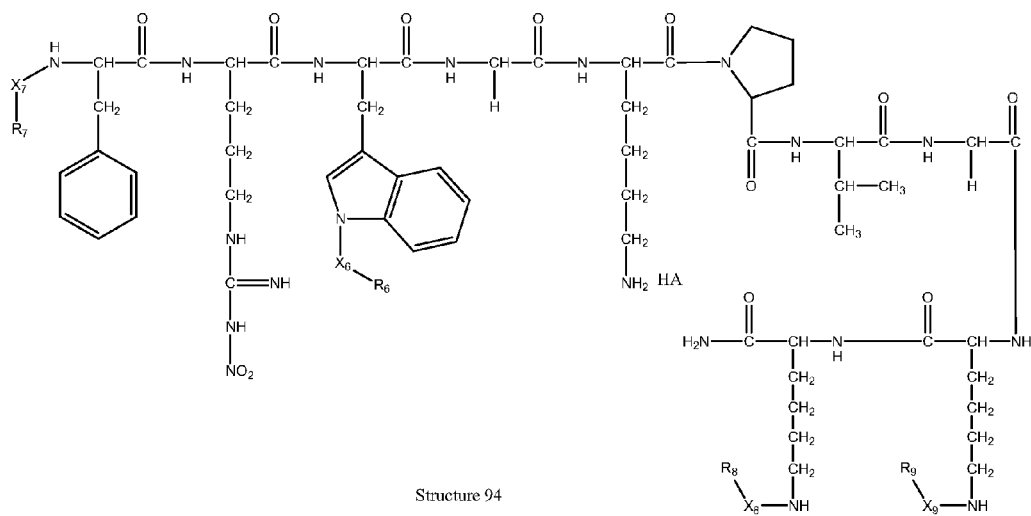
Structure 94
Figure 1-47

Structure 95

Structure 96

Structure 97

Structure 98

Structure 99

Structure 100

Structure 102

Structure 104

Structure 105

Structure 106

Structure 107

Structure 108

Structure 137

Structure 138

Structure 139

Structure 141

Structure 142

Structure 143

Structure 145

Structure 147

Structure 148

Structure 149

Structure 150

Structure 151

Structure 154

Structure 155

Structure 162

Structure 163

Structure 164

Structure 172

Structure 174

Structure 176

Structure 178

Structure 179

Structure 180

Structure 181

Structure 196

Structure 197

Structure 198

Structure 199

Structure 201

Structure 202

Structure 206

Structure 207

Structure 208

Structure 220

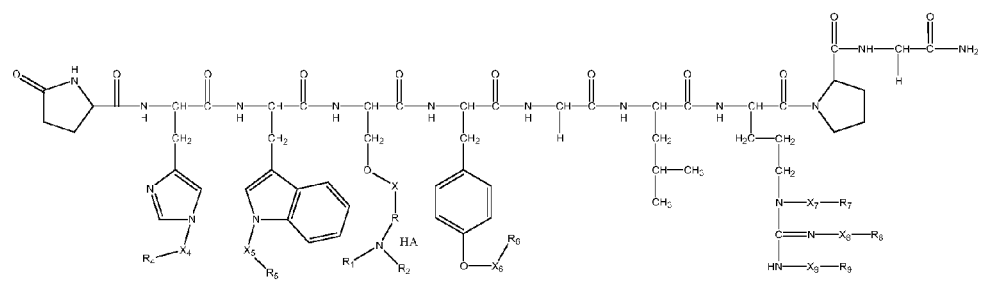
Structure 226
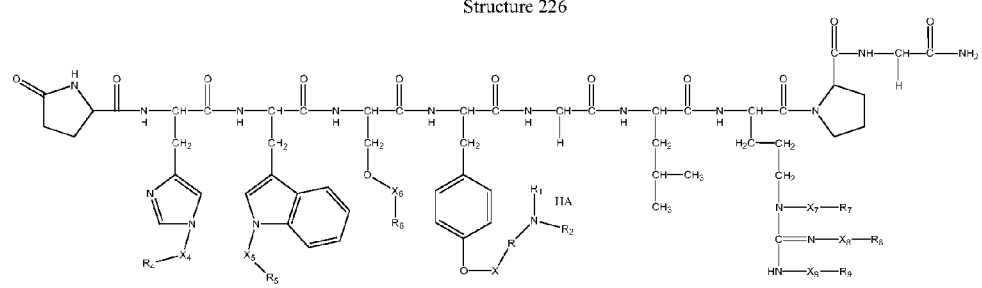
Structure 227
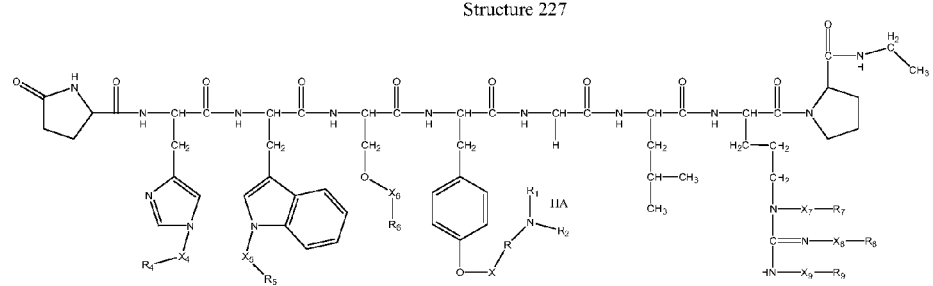
Structure 228
Figure 1-130

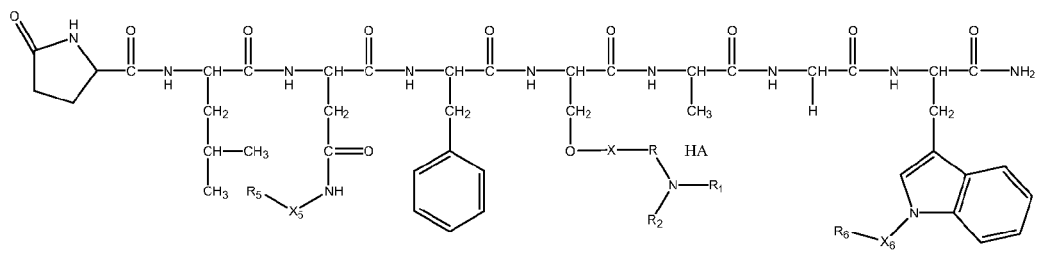
Structure 234
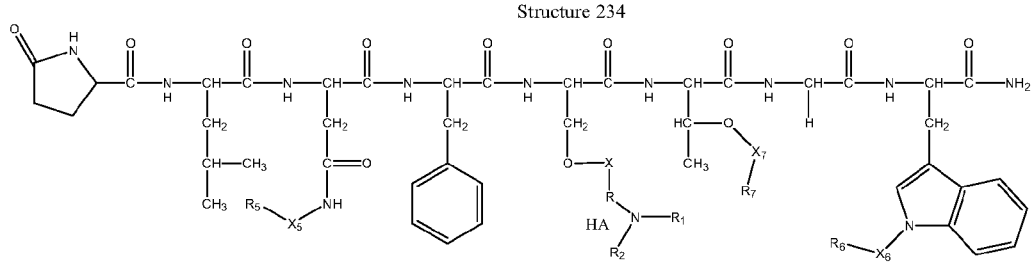
Structure 235
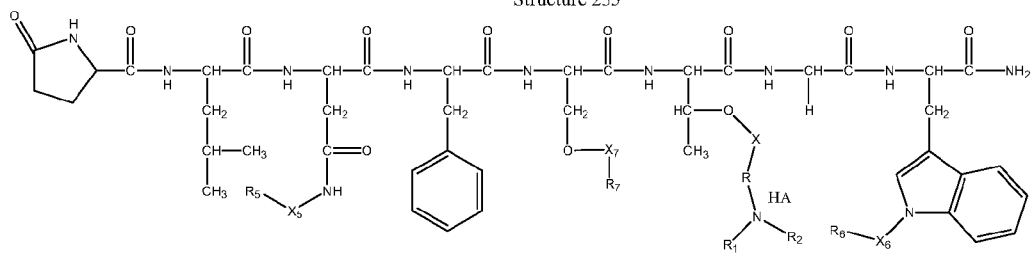
Structure 236
Figure 1-133

Structure 241

Structure 242

Structure 246

Structure 247

Structure 248

Structure 249

Strucutre 250

Strucutre 251

Structure 252

Structure 253

Structure 254

Structure 270

Structure 271

Structure 272

Structure 273

Structure 274

Structure 279

Structure 281

Structure 291

Structure 292

Structure 297

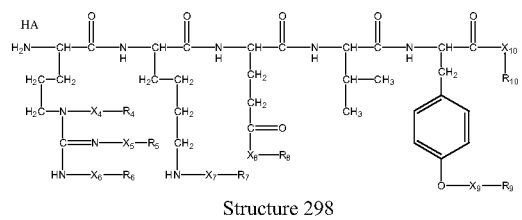
Structure 298
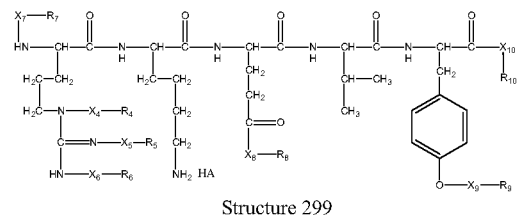
Structure 299
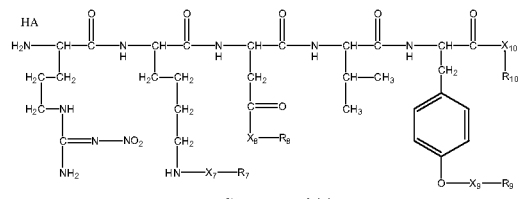
Structure 300
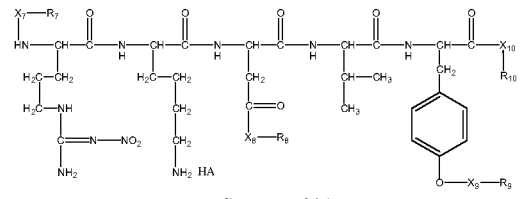
Structure 301
Figure 1-163

Strucutre 302

Strucutre 303

Structure 316

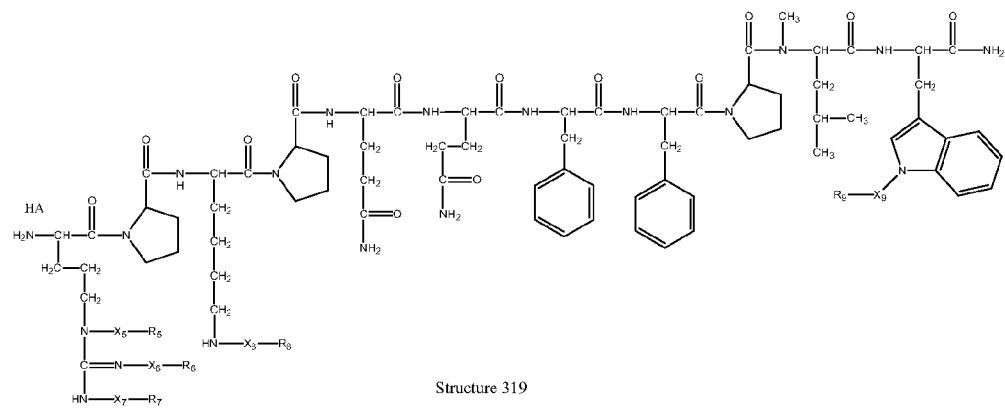
Structure 319
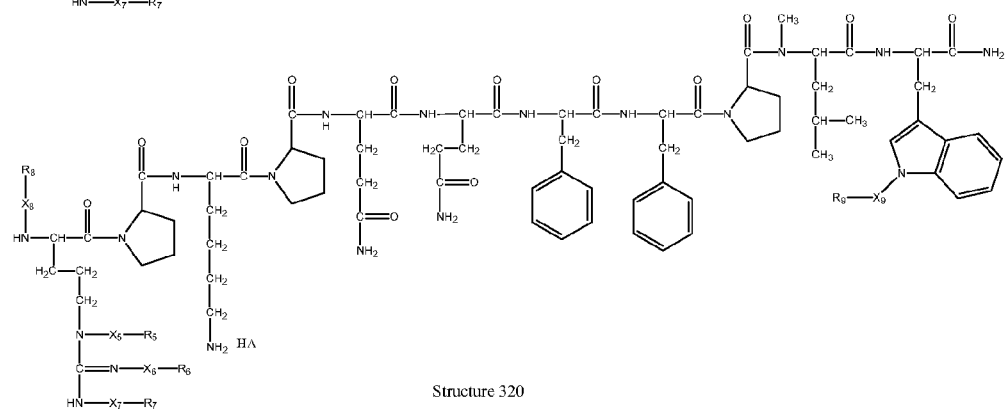
Structure 320
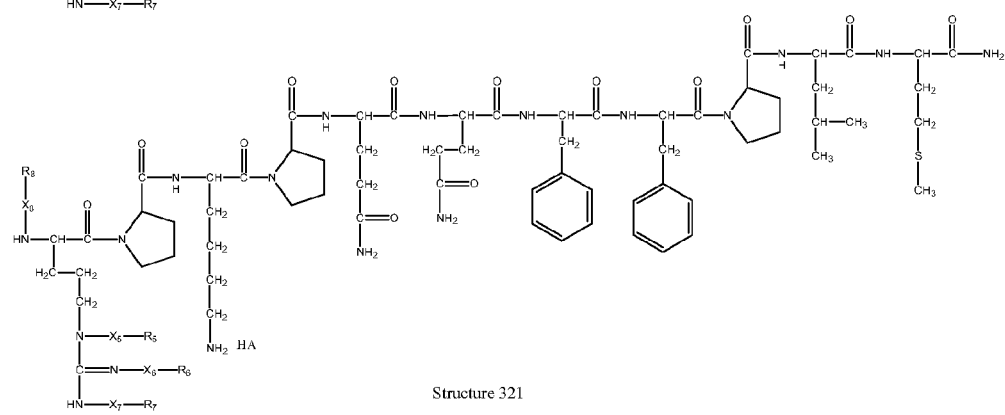
Structure 321
Figure 1-171

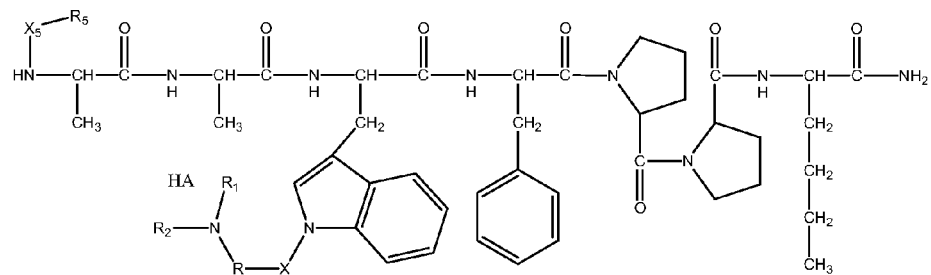
Structure 329
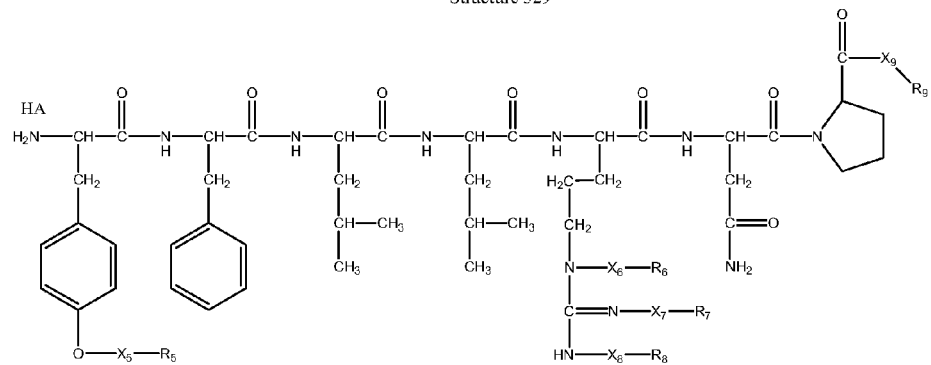
Structure 330
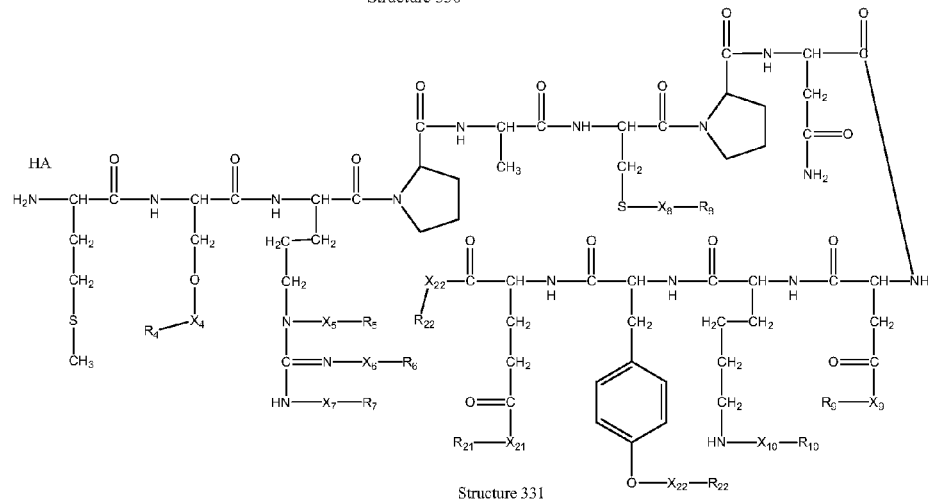
Structure 331
Figure 1-174

Structure 339

Structure 340

Structure 341

Structure 342

Structure 343

Structure 344

Structure 345

HIGH PENETRATION PRODRUG COMPOSITIONS OF PEPTIDES AND PEPTIDE-RELATED COMPOUNDS

CROSS-REFERENCE TO RELATED APPLICATIONS

The present application is a continuation of International Application No. PCT/CN2010/072561, filed on May 10, 2010 and designating the U.S., which is a continuation in part of and claims priority to U.S. patent application Ser. No. 12/463,374, filed on May 8, 2009, both of which are incorporated herein by reference. International Application No. PCT/CN2010/072561 and the present application both also claim priority to Chinese Patent Application No. 200910135997.0, filed on May 8, 2009, which is incorporated herein by reference.

The instant application contains a Sequence Listing which has been submitted in ASCII format via EFS-Web and is hereby incorporated by reference in its entirety. Said ASCII copy, created on Nov. 26, 2012, is named SequenceListing.txt and is 59,000 kilobytes in size.

FIELD OF THE INVENTION

This invention relates to the field of pharmaceutical compositions capable of penetrating one or more biological barriers and methods of using the pharmaceutical compositions for preventing, diagnosing and/or treating condition or disease in human and animals that are treatable by peptides or peptide-related compounds. The invention also relates to methods of using the pharmaceutical compositions for screening new drug candidates and methods of using the pharmaceutical compositions for diagnosing a condition in a biological subject. A method for synthesis of HPPs/HPCs of peptides from N-terminal to C-terminal has been developed.

BACKGROUND OF THE INVENTION

Peptides are polymers formed by linking amino acids with amide bonds. Peptides play various roles in a biological system. For example, peptide hormone is the largest group of hormones which modulate various biological processes in biological subjects. One nanogram of hyrotropin-releasing hormone injected into a mouse increases the uptake of iodide from the blood into the thyroid gland (R.L. Kisliuk, Principles of Medicinal Chemistry, 4$^{th}$ Ed., W.O. Foye, et al. Eds., Williams & Wilkins, 4$^{th}$ Ed. 1995, p. 606). Tuftsin (Thr-Lys-Pro-Arg (SEQ ID NO: 6)) stimulates phagocytosis and promotes antibody-dependent cellular cytotoxicity (V.A. Najjar, Mol. Cell. Biochem. 41, 1, 1981). Met-enkephaline (Tyr-Gly-Gly-Phe-Met (SEQ ID NO: 1)) isolated from brain and small intestine, acts as morphine does, in that it binds to the same receptor and has analgesic activity (J.R.Jaffe and W.R. Martin, in Pharmacological Basis of Therapeutics, A.G. Gilman, et al., Eds., New York, Pergamon Press, 1990, p. 481). Other examples of peptide hormones include, without limitation, oxytocin (Pierce et al., J. Biol. Chem. 199, 929, 1952), vasopressin (Kamm et al., J. Am. Chem. Soc. 50, 573, 1928), angiotensin (J.C. Garrison and M.J. Peach, in Pharmacological Basis of Therapeutics, A.G. Gilman, et al., Eds., New York, Pergamon Press, 1990, p. 749), gastrin (P.C. Emson and B.E.B. Sandberg, Annu, Rep. Med. Chem., 18, 31, 1983), somatostatin (A.V. Schally, et al., Annu. Rev. Biochem., 47, 89, 1978), dynorphin (M.G. Weisskopf, et al., Nature, 362, 423, 1993), endothelin (A.M. Doherty, J. Med. Chem., 35, 1493, 1992), secretin (E. Jorper, Gastroenterology, 55, 157, 1968), calcitonin (M.V.L. Ray, et al., Biotechnology, 11, 64, 1993), insulin (F. Sanger, Br. Med. Bull., 16, 183, 1960), and competence stimulating peptide (CSP).

Another group of peptides are anti-microbial peptides which have been found to participate in innate immunity in a wide variety of organisms (Reddy et al. 2004). These peptides and others have attracted much interest due to their potential usefulness in treating infections, especially because they are often effective against bacterial strains that have become resistant to conventional antibiotics. One well-known class of anti-microbial peptides is the tachyplesins. Another class of anti-microbial peptides is histatin peptides and the derivatives. Another class of antimicrobial peptide is hepcidin, which is also referred as LEAP-1, for liver-expressed antimicrobial peptide.

Another group of peptides are calcium binding peptides that bind specifically to calcified surfaces. One example of a calcium binding peptide comprises three amino acid repeat sequence $(X-Y-Z)_n$, wherein X is aspartic acid, glutamic acid, asparagine, alanine or glutamine, Y and Z are alanine, serine, threonine, phosphoserine, or phosphothreonine, and n is a number from 1 to 40.

Unfortunately, peptides and peptide related compounds are rapidly proteolysized by proteolytic enzymes. When peptides and peptide related compounds are taken orally, they will be proteolysized in a few minutes. Other systematic administrations of peptides and peptide related compounds are painful, and in many cases require frequent and costly office visits to treat chronic conditions.

Therefore, a need exists in the art for novel compositions that are capable of being delivered efficiently and effectively to the action site of a condition (e.g., a disease) to prevent, reduce or treat conditions as well as minimize adverse side effects.

SUMMARY OF THE INVENTION

One aspect of the invention is directed to a high penetration prodrug (HPP) or high penetration composition (HPC) comprising a functional unit covalently linked to a transportational unit through a linker. The terms "HPP" and "HPC" are used alone or together herein and are interchangeable unless specifically noted.

In certain embodiments, a functional unit of a HPP or HPC comprises a moiety of an agent, wherein the efficient and effective delivery of the agent to a biological subject and/or transportation of the agent across one or more biological barriers are/is desired.

In certain embodiments, a functional unit may be hydrophilic, lipophilic, or amphiphilic (i.e., both hydrophilic and lipophilic). For example, the lipophilic nature of a function unit may be inherent or achieved by converting the hydrophilic moieties of a functional unit to lipophilic moieties.

In certain embodiments, a functional unit of a HPP or HPC comprises a moiety of a peptide or peptide-related compound. A peptide-related compound is a compound comprising a peptide structure, a peptide metabolite, or an agent that can be metabolized into a peptide or peptide metabolite after a HPP or HPC penetrates one or more biological barriers. A peptide-related compound further includes a compound that is an analog or mimic of a peptide or a peptide metabolite, or an agent that can be metabolized into an analogue or mimic of a peptide or a peptide metabolite, after a HPP or HPC penetrates one or more biological barriers. Examples of peptides include, but are not limited to, peptide hormones (e.g. hyrotropin-releasing hormone, tuftsin (Thr-Lys-Pro-Arg (SEQ ID NO: 6)), met-enkephaline (Tyr-Gly-Gly-Phe-Met (SEQ ID NO: 1)), oxytocin, angiotensin, gastrin, somatostatin, dynorphin, endothelin, secretin, calcitonin, and insulin), enterostatins (e.g. Val-Pro-Asp-Pro-Arg (VPDPR) (SEQ ID NO: 10), Val-Pro-Gly-Pro-Arg (VPGPR) (SEQ ID NO: 11), and Ala-Pro-Gly-Pro-Arg (APGPR) (SEQ ID NO: 12)), Melanocortin II (cyclo(1,6)-Ac-Nle-Asp-His-Phe-Arg-Trp-Lys-OH (SEQ ID NO: 173)), opioid peptides (e.g. Met-enkephalin (H-Tyr-Gly-Gly-Phe-Met-OH (SEQ ID NO: 174)), Leu-enkephalin (H-Tyr-Gly-Gly-Phe-Leu-OH (SEQ ID NO: 175)), H-Tyr-D-Ala-Gly-N-Me-Phe-Met(O)-OL (SEQ ID NO: 176), and H-Tyr-D-Ala-Gly-Phe-Leu-OH (SEQ ID NO: 177)), neuropeptides, alkaloids, anti-inflammation peptides, anti-microbial peptides (e.g. competence stimulating peptides, tachyplesins, histatin peptides and the derivatives), calcium binding peptides, regulation peptides, peptide vaccines, and peptide mimics (e.g. α-helix mimics and β-sheet mimics).

In certain embodiments, a transportational unit of a HPP or HPC comprises a protonatable amine group that is capable of facilitating or enhancing the transportation or crossing of the HPP or HPC through one or more biological barriers. In certain embodiments, the protonatable amine group is substantially protonated at the pH of the biological barriers through which a HPP or HPC penetrates. In certain embodiments, the amine group can be reversibly protonated or deprotonated.

In certain embodiments, a linker covalently links the functional unit to the transportational unit of a HPP or HPC and comprises a bond that is capable of being cleaved after the HPP or HPC penetrates across one or more biological barriers. The cleavable bond comprises, for example, a covalent bond, an ether, a thioether, an amide, an ester, a thioester, a carbonate, a carbamate, a phosphate or an oxime bond.

Another aspect of the invention relates to a pharmaceutical composition comprising at least one HPP or HPC of a peptide or peptide-related compound and a pharmaceutically acceptable carrier.

Another aspect of the invention relates to a method for penetrating a biological barrier using a HPP or HPC of a peptide or peptide-related compound.

Another aspect of the invention relates to a method for diagnosing the onset, development, or remission of a condition in a biological subject by using a HPP or HPC of a peptide or peptide-related compound. In certain embodiments, the HPP (or HPC) or the functional unit thereof is detectable. In certain embodiments, the HPP/HPC or the functional unit of the HPP/HPC is inherently detectable, labeled with, or conjugated to, a detectable marker.

Another aspect of the invention relates to a method for screening functional units, linkers, or transportational units for desired characteristics.

Another aspect of the invention relates to a method for preventing, ameliorating, or treating a condition in a biological subject by administering to the subject a composition in accordance with the invention. In certain embodiments, the method relates to treating a condition in a subject treatable by peptides or peptide-related compounds by administering to the subject a therapeutically effective amount of a peptide HPP/HPC, or a pharmaceutical composition thereof. In certain embodiments, the conditions treatable by the method include, without limitation, pain, injuries, imflammation related conditions, microorganism related conditions, neuropeptide related conditions, hormone related conditions, tumor, abnormal blood pressure, obesity, brain injuries, allergy, male and female sexual dysfunction, metastasis, and other conditions relating to: tuftsin. antepartum, postpartum, anti-AD activities, antidiuretic activities, calcium homeostasis, melanocyte, hormone release, platelet aggregation, activities of CNS, and phagocytosis.

In certain embodiments, a pharmaceutical composition of a HPP/HPC is administered to a biological subject via various routes including, but not limited to, oral, enteral, buccal, nasal, topical, rectal, vaginal, aerosol, transmucosal, epidermal, transdermal, dermal, ophthalmic, pulmonary, subcutaneous, and/or parenteral routes. In certain preferred embodiments, a pharmaceutical composition of HPP is administered orally, transdermally, topically, subcutaneously and/or parenterally.

In accordance with the advantages of the invention, without intending to be limited by any particular mechanism, a therapeutically effective amount of a HPP or HPC can be administered locally to a site of condition with a less dosage at a higher concentration. The advantages of the invention also include, for example, avoidance of systematic administration, reduction of adverse effects (e.g., pain of injection, gastrointestinal/renal effects, and other side effect), and possible novel treatments due to high local concentration of a HPP, HPC or active agent. The advantages further include, for example, systematic administration of a HPP or HPC to a biological subject to achieve faster and more efficient bioavailability, penetration of biological barriers (e.g., the blood brain barrier) which have been difficult to cross, and new indications as a result of passing through biological barriers.

DETAILED DESCRIPTION OF THE INVENTION

Figure 1:
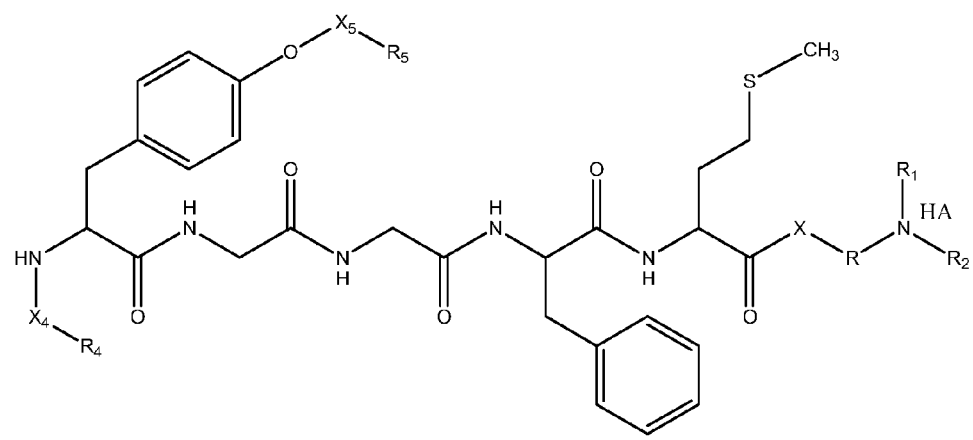
FIG. 1: Structures of Structure 2 (SEQ ID NO: 1), Structure 3 (SEQ ID NO: 1), Structure 4 (SEQ ID NO: 1), Structure 5 (SEQ ID NO: 1), Structure 6 (SEQ ID NO: 2), Structure 7 (SEQ ID NO: 2), Structure 8 (SEQ ID NO: 2), Structure 9 (SEQ ID NO: 2), Structure 10 (SEQ ID NO: 3), Structure 11 (SEQ ID NO: 4), Structure 12 (SEQ ID NO: 3), Structure 13 (SEQ ID NO: 5), Structure 14 (SEQ ID NO: 5), Structure 15 (SEQ ID NO: 5), Structure 16 (SEQ ID NO: 51, Structure 17 (SEQ ID NO: 6), Structure 18 (SEQ ID NO: 6), Structure 19 (SEQ ID NO: 6), Structure 20 (SEQ ID NO: 6), Structure 21 (SEQ ID NO: 6), Structure 22 (SEQ ID NO: 6), Structure 23 (SEQ ID NO: 6), Structure 24 (SEQ ID NO: 3), Structure 25 (SEQ ID NO: 7), Structure 26 (SEQ ID NO: 6), Structure 27 (SEQ ID NO: 6), Structure 28 (SEQ ID NO: 6), Structure 29 (SEQ ID NO: 6), Structure 30 (SEQ ID NO: 6), Structure 31 (SEQ ID NO: 8), Structure 32 (SEQ ID NO: 8), Structure 33 (SEQ ID NO: 8), Structure 34 (SEQ ID NO: 8), Structure 35 (SEQ ID NO: 8), Structure 36 (SEQ ID NO: 8), Structure 37 (SEQ ID NO: 8), Structure 38 (SEQ ID NO: 8), Structure 39 (SEQ ID NO: 8), Structure 40 (SEQ ID NO: 8), Structure 41 (SEQ ID NO: 8), Structure 42 (SEQ ID NO: 8), Structure 43 (SEQ ID NO: 9), Structure 44 (SEQ ID NO: 9), Structure 45 (SEQ ID NO: 10), Structure 46 (SEQ ID NO: 10), Structure 47 (SEQ ID NO: 10), Structure 48 (SEQ ID NO: 10), Structure 49 (SEQ ID NO: 10), Structure 50 (SEQ ID NO: 10), Structure 51 (SEQ ID NO: 10), Structure 52 (SEQ ID NO: 10), Structure 53 (SEQ ID NO: 11), Structure 54 (SEQ ID NO: 11), Structure 55 (SEQ ID NO: 11), Structure 56 (SEQ ID NO: 11), Structure 57 (SEQ ID NO: 11), Structure 58 (SEQ ID NO: 11), Structure 59 (SEQ ID NO: 12), Structure 60 (SEQ ID NO: 12), Structure 61 (SEQ ID NO: 12), Structure 62 (SEQ ID NO: 12), Structure 63 (SEQ ID NO: 12), Structure 64 (SEQ ID NO: 12), Structure 65 (SEQ ID NO: 13), Structure 66 (SEQ ID NO: 13), Structure 67 (SEQ ID NO: 13), Structure 68 (SEQ ID NO: 13), Structure 69 (SEQ ID NO: 14), Structure 70 (SEQ ID NO: 14), Structure 71 (SEQ ID NO: 15), Structure 72 (SEQ ID NO: 15), Structure 73 (SEQ ID NO: 15), Structure 74 (SEQ ID NO: 15), Structure 75 (SEQ ID NO: 16), Structure 76 (SEQ ID NO: 16), Structure 77 (SEQ ID NO: 17), Structure 78 (SEQ ID NO: 17), Structure 79 (SEQ ID NO: 17), Structure 80 (SEQ ID NO: 17), Structure 81 (SEQ ID NO: 18), Structure 82 (SEQ ID NO: 18), Structure 83 (SEQ ID NO: 19), Structure 84 (SEQ ID NO: 19), Structure 85 (SEQ ID NO: 20), Structure 86 (SEQ ID NO: 20), Structure 87 (SEQ ID NO: 21), Structure 88 (SEQ ID NO: 21), Structure 89 (SEQ ID NO: 22), Structure 90 (SEQ ID NO: 22), Structure 91 (SEQ ID NO: 22), Structure 92 (SEQ ID NO: 22), Structure 93 (SEQ ID NO: 22), Structure 94 (SEQ ID NO: 22), Structure 95 (SEQ ID NO: 22), Structure 96 (SEQ ID NO: 22), Structure 97 (SEQ ID NO: 23), Structure 98 (SEQ ID NO: 23), Structure 99 (SEQ ID NO: 23), Structure 100 (SEQ ID NO: 23), Structure 101 (SEQ ID NO: 24), Structure 102 (SEQ ID NO: 24), Structure 103 (SEQ ID NO: 24), Structure 104 (SEQ ID NO: 24), Structure 105 (SEQ ID NO: 25), Structure 106 (SEQ ID NO: 25), Structure 107 (SEQ ID NO: 26), Structure 108 (SEQ ID NO: 26), Structure 109 (SEQ ID NO: 26), Structure 110 (SEQ ID NO: 27), Structure 111 (SEQ ID NO: 27), Structure 112 (SEQ ID NO: 28), Structure 113 (SEQ ID NO: 28), Structure 114 (SEQ ID NO: 29), Structure 115 (SEQ ID NO: 29), Structure 116 (SEQ ID NO: 30), Structure 117 (SEQ ID NO: 30), Structure 118 (SEQ ID NO: 31), Structure 119 (SEQ ID NO: 31), Structure 120 (SEQ ID NO: 32), Structure 121 (SEQ ID NO: 32), Structure 122 (SEQ ID NO: 33), Structure 123 (SEQ ID NO: 33), Structure 124 (SEQ ID NO: 34), Structure 125 (SEQ ID NO: 34), Structure 126 (SEQ ID NO: 35), Structure 127 (SEQ ID NO: 35), Structure 128 (SEQ ID NO: 36), Structure 129 (SEQ ID NO: 36), Structure 130 (SEQ ID NO: 37), Structure 131 (SEQ ID NO: 37), Structure 132 (SEQ ID NO: 38), Structure 133 (SEQ ID NO: 39), Structure 134 (SEQ ID NO: 39), Structure 135 (SEQ ID NO: 40), Structure 136 (SEQ ID NO: 41), Structure 137 (SEQ ID NO: 41 ), Structure 138 (SEQ ID NO: 41), Structure 139 (SEQ ID NO: 42), Structure 140 (SEQ ID NO: 42), Structure 141 (SEQ ID NO: 43), Structure 142 (SEQ ID NO: 43), Structure 143 (SEQ ID NO: 43), Structure 144 (SEQ ID NO: 43), Structure 145 (SEQ ID NO: 44), Structure 146 (SEQ ID NO: 44), Structure 147 (SEQ ID NO: 44), Structure 148 (SEQ ID NO: 44), Structure 149 (SEQ ID NO: 45), Structure 150 (SEQ ID NO: 45), Structure 151 (SEQ ID NO: 45), Structure 152 (SEQ ID NO: 45), Structure 153 (SEQ ID NO: 45), Structure 154 (SEQ ID NO: 46), Structure 155 (SEQ ID NO: 46), Structure 156 (SEQ ID NO: 47), Structure 157 (SEQ ID NO: 47), Structure 158 (SEQ ID NO: 47), Structure 159 (SEQ ID NO: 48), Structure 160 (SEQ ID NO: 48), Structure 161 (SEQ ID NO: 49), Structure 162 (SEQ ID NO: 49), Structure 163 (SEQ ID NO: 50), Structure 164 (SEQ ID NO: 50), Structure 165 (SEQ ID NO: 51), Structure 166 (SEQ ID NO: 52), Structure 167 (SEQ ID NO: 53), Structure 168 (SEQ ID NO: 54), Structure 169 (SEQ ID NO: 55), Structure 170 (SEQ ID NO: 56), Structure 171 (SEQ ID NO: 56), Structure 172 (SEQ ID NO: 57), Structure 173 (SEQ ID NO: 58), Structure 174 (SEQ ID NO: 58), Structure 175 (SEQ ID NO: 59), Structure 176 (SEQ ID NO: 60), Structure 177 (SEQ ID NO: 60), Structure 178 (SEQ ID NO: 61), Structure 179 (SEQ ID NO: 62), Structure 180 (SEQ ID NO: 63), Structure 181 (SEQ ID NO: 64), Structure 182 (SEQ ID NO: 65), Structure 183 (SEQ ID NO: 66), Structure 184 (SEQ ID NO: 67), Structure 185 (SEQ ID NO: 68), Structure 186 (SEQ ID 69), Structure 187 (SEQ ID NO: 70), Structure 188 (SEQ ID NO: 71), Structure 189 (SEQ ID NO: 72), Structure 190 (SEQ ID NO: 73), Structure 191 (SEQ ID NO: 74), Structure 192 (SEQ ID NO: 75), Structure 193 (SEQ ID NO: 76), Structure 194 (SEQ ID NO: 77), Structure 195 (SEQ ID NO: 78), Structure 196 (SEQ ID NO: 79), Structure 197 (SEQ ID NO: 79), Structure 198 (SEQ ID NO: 80), Structure 199 (SEQ ID NO: 80), Structure 200 (SEQ ID NO: 81), Structure 201 (SEQ ID NO: 81), Structure 202 (SEQ ID NO: 82), Structure 203 (SEQ ID NO: 82), Structure 204 (SEQ ID NO: 83), Structure 205 (SEQ ID NO: 84) , Structure 206 (SEQ ID NO: 85), Structure 207 (SEQ ID NO: 86), Structure 208 (SEQ ID NO: 87), Structure 209 (SEQ ID NO: 88), Structure 210 (SEQ ID NO: 88), Structure 211 (SEQ ID NO: 89), Structure 212 (SEQ ID NO: 89), Structure 213 (SEQ ID NO: 90), Structure 214 (SEQ ID NO: 90), Structure 215 (SEQ ID NO: 91), Structure 216 (SEQ ID NO: 92), Structure 217 (SEQ ID NO: 93), Structure 218 (SEQ ID NO: 94), Structure 219 (SEQ ID NO: 95), Structure 220 (SEQ ID NO: 95), Structure 221 (SEQ ID NO: 96), Structure 222 (SEQ ID NO: 97), Structure 223 (SEQ ID NO: 97), Structure 224 (SEQ ID NO: 97), Structure 225 (SEQ ID NO: 97), Structure 226 (SEQ ID NO: 98), Structure 227 (SEQ ID NO: 98), Structure 228 (SEQ ID NO: 99), Structure 229 (SEQ ID NO: 99), Structure 230 (SEQ ID NO: 100), Structure 231 (SEQ ID NO: 101), Structure 232 (SEQ ID NO: 101), Structure 233 (SEQ ID NO: 101), Structure 234 (SEQ ID NO: 102), Structure 235 (SEQ ID NO: 103), Structure 236 (SEQ ID NO: 103), Structure 237 (SEQ ID NO: 104), Structure 238 (SEQ ID NO: 105), Structure 239 (SEQ ID NO: 105), Structure 240 (SEQ ID NO: 106), Structure 241 (SEQ ID NO: 107), Structure 242 (SEQ ID NO: 108), Structure 243 (SEQ ID NO: 109), Structure 244 (SEQ ID NO: 110), Structure 245 (SEQ ID NO: 205), Structure 246 (SEQ ID NO: 205), Structure 247 (SEQ ID NO: 111), Structure 248 (SEQ ID NO: 112), Structure 249 (SEQ ID NO: 113), Structure 250 (SEQ ID NO: 114), Structure 251 (SEQ ID NO: 115), Structure 252 (SEQ ID NO: 116), Structure 253 (SEQ ID NO: 117), Structure 254 (SEQ ID NO: 117), Structure 255 (SEQ ID NO: 118), Structure 256 (SEQ ID NO: 119), Structure 257 (SEQ ID NO: 120), Structure 258 (SEQ ID NO: 121), Structure 259 (SEQ ID NO: 122), Structure 260 (SEQ ID NO: 123), Structure 261 (SEQ ID NO: 124 Structure 262 (SEQ ID NO: 125), Structure 263 (SEQ ID NO: 126), Structure 264 (SEQ ID NO: 127), Structure 265 (SEQ ID NO: 128), Structure 266 (SEQ ID NO: 129), Structure 267 (SEQ ID NO: 130), Structure 268 (SEQ ID NO: 131), Structure 269 (SEQ ID NO: 132), Structure 270 (SEQ ID NO: 133), Structure 271 (SEQ ID NO: 133), Structure 272 (SEQ ID NO: 134), Structure 273 (SEQ ID NO: 134), Structure 274 (SEQ ID NO: 134), Structure 275 (SEQ ID NO: 134), Structure 276 (SEQ ID NO: 135), Structure 277 (SEQ ID NO: 136), Structure 278 (SEQ ID NO: 137), Structure 279 (SEQ ID NO: 138), Structure 280 (SEQ ID NO: 138), Structure 281 (SEQ ID NO: 138), Structure 282 (SEQ ID NO: 138), Structure 283 (SEQ ID NO: 139 Structure 284 (SEQ ID NO: 139), Structure 285 (SEQ ID NO: 139), Structure 286 (SEQ ID NO: 140), Structure 287 (SEQ ID NO: 140), Structure 288 (SEQ ID NO: 141), Structure 289 (SEQ ID NO: 142), Structure 290 (SEQ ID NO: 142), Structure 291 (SEQ ID NO: 142), Structure 292 (SEQ ID NO: 143), Structure 293 (SEQ ID NO: 143), Structure 294 (SEQ ID NO: 144), Structure 295 (SEQ ID NO: 144), Structure 296 (SEQ ID NO: 206), Structure 297 (SEQ ID NO: 206), Structure 298 (SEQ ID NO: 145), Structure 299 (SEQ ID NO: 145), Structure 300 (SEQ ID NO: 145), Structure 301 (SEQ ID NO: 145), Structure 302 (SEQ ID NO: 146), Structure 303 (SEQ ID NO: 146), Structure 304 (SEQ ID NO: 147), Structure 305 (SEQ ID NO: 148 Structure 306 (SEQ ID NO: 148), Structure 307 (SEQ ID NO: 149), Structure 308 (SEQ ID NO: 150), Structure 309 (SEQ ID NO: 150), Structure 310 (SEQ ID NO: 151), Structure 311 (SEQ ID NO: 152), Structure 312 (SEQ ID NO: 153), Structure 313 (SEQ ID NO: 154), Structure 314 (SEQ ID NO: 155), Structure 315 (SEQ ID NO: 156), Structure 316 (SEQ ID NO: 156), Structure 317 (SEQ ID NO: 157), Structure 318 (SEQ ID NO: 157), Structure 319 (SEQ ID NO: 158), Structure 320 (SEQ ID NO: 158), Structure 321 (SEQ ID NO: 159), Structure 322 (SEQ ID NO: 159), Structure 323 (SEQ ID NO: 160), Structure 324 (SEQ ID NO: 160), Structure 325 (SEQ ID NO: 161), Structure 326 (SEQ ID NO: 162), Structure 327 (SEQ ID NO: 162), Structure 328 (SEQ ID NO: 162), Structure 329 (SEQ ID NO: 163), Structure 330 (SEQ ID NO: 164), Structure 331 (SEQ ID NO: 165), Structure 332 (SEQ ID NO: 165), Structure 333 (SEQ ID NO: 166), Structure 334 (SEQ ID NO: 166), Structure 335 (SEQ ID NO: 166), Structure 336 (SEQ ID NO: 167), Structure 337 (SEQ ID NO: 167), Structure 338 (SEQ ID NO: 168), Structure 339 (SEQ ID NO: 168), Structure 340 (SEQ ID NO: 169), Structure 341 (SEQ ID NO: 170), Structure 342 (SEQ ID NO: 170), Structure 343 (SEQ ID NO: 171), Structure 344 (SEQ ID NO: 172), and Structure 345 (SEQ ID NO: 172).
Figure 1:
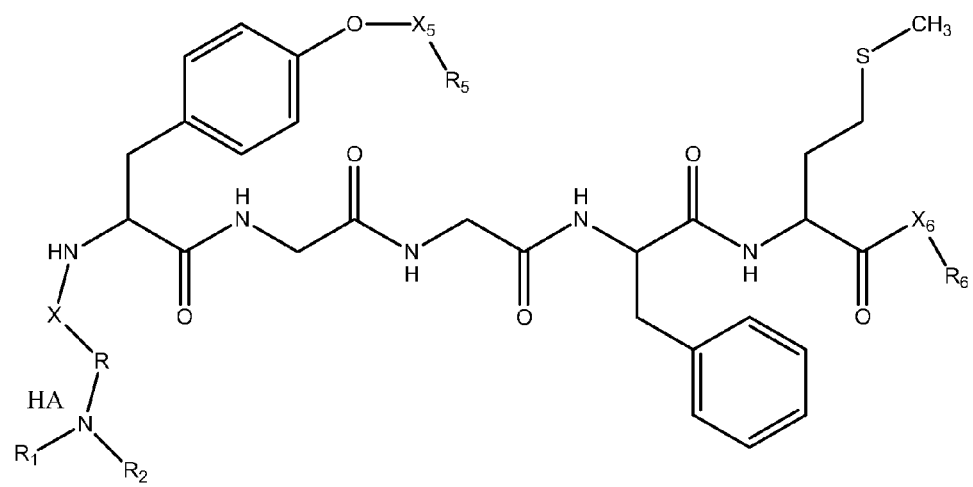

I. Structures of a High Penetration Prodrug (HPP) or High Penetration Composition (HPC) of a Peptide or Peptide-Related Compound One aspect of the invention is directed to a high penetration prodrug (HPP) or a high penetration composition (HPC). The term "high penetration prodrug" or "HPP" or "high penetration composition" or "HPC" as used herein refers to a composition comprising a functional unit covalently linked to a transportational unit through a linker.

A functional unit of a HPP/HPC which comprises a moiety of a parent drug has the properties of: 1) the delivery of the parent drug or the HPP/HPC into a biological subject and/or the transportation of the parent drug across a biological barrier are/is desired, 2) the HPP/HPC is capable of penetrating or crossing a biological barrier, and 3) the HPP/HPC is capable of being cleaved so as to turn the moiety of a parent drug into the parent drug or a metabolite of the parent drug.

In certain embodiments, a functional unit may be hydrophilic, lipophilic, or amphiphilic (hydrophilic and lipophilic). The lipophilic moiety of the functional unit may be inherent or achieved by converting one or more hydrophilic moieties of the functional unit to lipophilic moieties. For example, a lipophilic moiety of a functional unit is produced by converting one or more hydrophilic groups of the functional unit to lipophilic groups via organic synthesis. Examples of hydrophilic groups include, without limitation, carboxylic, hydroxyl, thiol, amine, phosphate/phosphonate and carbonyl groups. Lipophilic moieties produced via the modification of these hydrophilic groups include, without limitation, ethers, thioethers, esters, thioesters, carbonates, carbamates, amides, phosphates and oximes. In certain embodiments, a functional unit is lipophilicized by acetylation. In certain embodiments, a functional unit is lipophilicized by esterification.

In certain embodiments, a parent drug of a HPP or HPC is selected from the group consisting of a peptide and a peptide-related compound. The moiety of a peptide or peptide-related compound can be further converted to a lipophilic moiety as described supra. As used herein, the term "peptide HPP/HPC" refers to a HPP or HPC of a peptide or peptide-related compound. As used herein, the term "peptide HPPs/HPCs" refers to HPPs or HPCs of peptides or peptide-related compounds.

Peptides are well known in the art and are used in connection with various conditions. As used herein, a peptide refers to a sequence of amino acids, wherein the sequence length is about 2 to about 50 amino acids. For example, a peptide may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acids. A peptide may comprise both D-amino acids and/or L-amino acids.

An amino acid is a compound comprising both amine and carboxyl functional groups. The carbon atom next to the carbonyl group of a carboxyl functional group is called the alpha-carbon. Amino acids with a side chain bonded to an alpha-carbon are referred to as alpha amino acids. In amino acids that have an amino group and a carbon chain attached to the alph-carbon, the carbons are labeled in order as alpha, beta, gamma, and so on from the carbonyl carbon. An amino acid which has the amino group attached to the beta or gamma-carbon is referred to as beta or gamma amino acid respectively, and so on.

An alpha amino acid is an amino acid which has amino and carboxylate groups bonded to the same carbon (the alpha carbon). The alpha carbon is one atom away from the carboxylate group. An alpha amino acid has a structure of Structure 1:

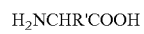

H$_2$NCHR'COOHStructure 1 including stereoisomers and pharmaceutically acceptable salts thereof, wherein:
R' is selected from the group consisting of substituted and unsubstituted imidazolyl, substituted and unsubstituted quanidino, substituted and unsubstituted carboxyl, substituted and unsubstituted carboxamide, substituted and unsubstituted alkyl, substituted and unsubstituted cycloalkyl, substituted and unsubstituted heterocloalkyl, substituted and unsubstituted alkoxyl, substituted and unsubstituted alkylthio, substituted and unsubstituted alkylamino, substituted and unsubstituted alkylcarbonyl, substituted and unsubstituted perfluoroalkyl, substituted and unsubstituted alkyl halide, substituted and unsubstituted aryl, and substituted and unsubstituted heteroaryl groups.

In certain embodiments, an amino acid has Structure 1, including stereoisomers and pharmaceutically acceptable salts thereof, wherein:
R' is selected from the group consisting of H—, CH$_3$, HN=C(NH$_2$)—NH—(CH$_2$)$_3$—, H$_2$N—CO—CH$_2$—, HOOC—CH$_2$—, HS—CH$_2$—, H$_2$N—CO—(CH$_2$)$_2$—, HS—(CH$_2$)$_2$—, HOOC—(CH$_2$)$_2$—, CH$_3$—CH$_2$—CH(CH$_3$)—, (CH$_3$)$_2$CH—CH$_2$—, H$_2$N—(CH$_2$)$_4$—, CH$_3$—S—(CH$_2$)$_2$—, Phenyl-CH$_2$—, HO—CH$_2$—, CH$_3$—CH(OH)—, 4-OH-Phenyl-CH$_2$—, CH$_3$—CH(CH$_3$)—,

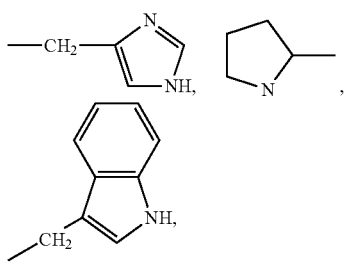

and
derivatives thereof.

Examples of alpha amino acid include, without limitation, alanine (Ala), arginine (Arg), asparagine (Asn), aspartic acid (Asp), cysteine (Cys), glutamic acid (Glu), glutamine (Gln), glycine (Gly), histidine (His), homocysteine (Hcy), homoserine (Hse), isoleucine (Ile), leucine (Leu), lysine (Lys), methionine (Met), norleucine (Nle), norvaline (Nva), ornithine (Orn), penicillamine (Pen), phenylalanine (Phe), proline (Pro), serine (Ser), tyrosine (Thr), threonine (Trp), tryptophan (Tyr), valine (Val), pyroglutamic acid (pGLU), dinitrobenzylated lysine (dnp-LYS), phosphorylated threonine (pTHR), phosphorylated serine (pSER), phosphorylated tyrosine (pTYR), citrulline (CIT), N-methylated alanine (nme-ALA), N-methylated isoleucine (nme-ILE), N-methylated leucine (nme-LEU), N-methylated phenylalanine (nme-PHE), N-methylated valine (nme-VAL), N-methylated serine (nme-SER), N-methylated threonine (nme-THR), N-methylated tyrosine (nme-TYR), alpha amino-butyric acid (alpha-ABA), iso-aspartic acid (iso-ASP), acetylated lysine (Ac-LYS), 2-methyl alanine (2-Me-ALA) and oxamic Acid (OXA).

A beta amino acid is an amino acid which has an amino group bonded to the beta carbon which is the second carbons away from the carboxylate group. Examples of beta amino acid include, without limitation, beta-alanine (β-Ala), beta-arginine (β-Arg), beta-asparagine (β-Asn), beta-aspartic acid (β-Asp), beta-cysteine (β-Cys), beta-glutamic acid (β-Glu), beta-glutamine (β-Gln), beta-histidine (β-His), beta-isoleucine (β-Ile), beta-leucine (β-Leu), beta-lysine (β-Lys), beta-methionine (β-Met), beta-phenylalanine (β-Phe), beta-proline (β-Pro), beta-serine (β-Ser), beta-tyrosine (β-Thr), beta-threonine (β-Trp), beta-tryptophan (β-Tyr) and beta-valine (β-Val).

A gamma amino acid is an amino acid which has an amino group bonded to the gamma carbon which is the third carbons away from the carboxylate group. Examples of gamma amino acid include, without limitation, gamma-glutamic acid (γ-GLU).

A peptide-related compound is a compound comprising a peptide structure, a peptide metabolite, or an agent that can be metabolized into a peptide or peptide metabolite after a peptide HPP/HPC penetrates one or more biological barriers. A peptide-related compound further includes a compound that is an analog or mimic of a peptide or a peptide metabolite, or an agent that can be metabolized into an analog or mimic of a peptide or a peptide metabolite, after a peptide HPP/HPC penetrates one or more biological barriers.

Examples of peptides and peptide-related compounds include, but are not limited to, peptide hormones, neuropeptides, alkaloids, anti-microbial peptides, anti-inflammation peptides, peptide toxins, regulation peptides, calcium binding peptides, peptide vaccines and peptide mimics.

Peptide hormones are a class of peptides that have endocrine functions in living animals. Peptide hormones are also identified in plants with important roles in cell-to-cell communication and plant defense. Peptide hormones are produced by various organs and tissues, e.g. heart (atrial-natriuretic peptide (ANP), atrial natriuretic factor (ANF)), pancreas (e.g. insulin, enterostatin, somatostatin), the gastrointestinal tract (cholecystokinin, gastrin (e.g. gastrin-34, gastrin-17 and gastrin-14), opioid peptides (e.g. Met-enkephalin, Leu-enkephalin, H-Tyr-D-Ala-Gly-N-Me-Phe-Met(O)-OL (SEQ ID NO: 176), and H-Tyr-D-Ala-Gly-Phe-Leu-OH (SEQ ID NO: 177)), cholecystokinin, secretin, motilin, vasoactive intestinal peptide, and enteroglucagon), adipose tissue stores (e.g. leptin), pituitary (e.g. luteinizing hormone, follicle-stimulating hormone, prolactin, adrenocorticotrophic hormone (ACTH), growth hormone, antidiuretic hormone, oxytocin, Melanocortin (e.g. Melanocortin II)), thyroid (e.g. calcitonin), spleen (e.g. tuftsin), brain (e.g. oxytocin, dynorphin), liver (e.g. angiotensin, angiotensin I and angiotensin II), endothelium (e.g. endothelin). Other examples of peptide hormone include, without limitation, thyrotropin-releasing hormone (TRH) and bradykinin.

Neuropeptides are peptides that are found in neural tissues that are involved in regulatory and signaling processes. Examples of neuropeptides include, without limitation, neurotransimtters (e.g. N-Acetylaspartylglutamic acid, gastrin, cholecycstokinin, neuropeptide Y, vasopressin, oxytocin, secretin, Substance P, somatostatin, vasoactive intestinal peptide (VIP), opioids (e.g. enkephalin, dynorphin, endorphin), galanin, neurotensin, TRH, atrial-natriuretic peptide.

Alkaloids are peptides usually from plants, fungi and some animals such as shellfish. Alkaloids involved into defend of one organism from consuming by other organisms. Examples of alkaloids include, without limitation, ergotamine, pandamine, dynorphin A-(1-8)-octapeptide, N beta-(D-Leu-D-Arg-D-Arg-D-Leu-D-Phe)-naltrexamine (SEQ ID NO: 207).

Anti-microbial peptides are peptides that inhibit the growth of microorganisms, such as bacterial cells, fungi and protozoa. Examples of anti-microbial peptides include, without limitation, bacitracin, gramicidin, valinomicin, competence stimulating peptides, tachyplesins, histatin peptides and the derivatives thereof, Examples of anti-inflammation peptides are peptides having sequences of Seq ID: 47, Seq ID: 48, and Seq ID: 49. (Table A)

Peptide toxins are peptides that are poisonous. Examples of peptide toxins are palutoxins, agatoxins and curtatoxins.

Regulation peptides are peptides that regulate one or more processes in an biological subject. Examples of regulation peptides include, without limitation, anserine and carnosine.

Other examples of peptides and peptide-related compounds include calcium binding peptides, peptide vaccines [e.g. p45(IEIGLEGKGFEPTLEALFGK (SEQ ID NO: 187)) and p210 (KTTKQSFDLS VKAQY KKNKH (SEQ ID NO: 188))] and peptide mimics (e.g. α-helix mimics and β-sheet mimics).

In certain embodiments, a functional unit of a peptide HPP/HPC comprises a moiety having a structure of Structure F-1:

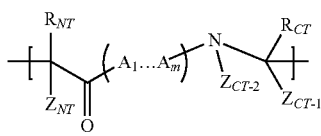

Structure F-1 including stereoisomers and pharmaceutically acceptable salts thereof, wherein:

each $A_1$-$A_m$ is independently selected from the group consisting of 2-naphthylalanine, substituted and unsubstituted alkyl, substituted and unsubstituted cycloalkyl, substituted and unsubstituted heterocycloalkyl, substituted and unsubstituted alkoxyl, substituted and unsubstituted alkenyl, substituted and unsubstituted alkynyl, substituted and unsubstituted aryl, substituted and unsubstituted heteroaryl residues and Structure A:

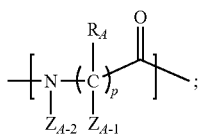

Structure A p of each $A_1$-$A_m$ is an independently selected integer;

$Z_{A-1}$ on each carbon of each $A_1$-$A_m$, $Z_{A-2}$ for each $A_1$-$A_m$, $Z_{NT}$, $Z_{CT-1}$, and $Z_{CT-2}$ are independently selected from the group consisting of H, $CH_3$, $C_2H_5$, $C_3H_7$, $CF_3$, $C_2F_5$, $C_3F_7$, substituted and unsubstituted alkyl, substituted and unsubstituted perfluoroalkyl, and substituted and unsubstituted alkyl halide;

$R_A$ on each carbon of each $A_1$-$A_m$, $R_{NT}$ and $R_{CT}$ are selected from the group consisting of H, substituted and unsubstituted imidazolyl, substituted and unsubstituted quanidino, substituted and unsubstituted carboxyl, substituted and unsubstituted carboxamide, substituted and unsubstituted alkyl, substituted and unsubstituted cycloalkyl, substituted and unsubstituted heterocycloalkyl, substituted and unsubstituted alkoxyl, substituted and unsubstituted alkylthio, substituted and unsubstituted alkylamino, substituted and unsubstituted alkylcarbonyl, substituted and unsubstituted perfluoroalkyl, substituted and unsubstituted alkyl halide, substituted and unsubstituted aryl, and substituted and unsubstituted heteroaryl groups;

when a p of a $A_1$-$A_m$ is an integer no less than 2, $R_A$ on each carbon can be the same or different, $Z_{A-1}$ on each carbon can be the same or different;

an amino and a carboxyl functional group on a peptide chain may further form lactam bridges; and a thiol group may further form disulfide bridges.

In certain embodiments, a functional unit of a peptide HPP/HPC comprises a moiety having a structure selected from the group consisting of Structure F-1 as defined supra, including stereoisomers and pharmaceutically acceptable salts thereof, wherein a $R_A$ of a $A_1$-$A_m$ may be further lipophilicized by acetylation or esterification.

In certain embodiments, a functional unit of a peptide HPP/HPC comprises a moiety having a structure of Structure F-1 as defined supra, including stereoisomers and pharmaceutically acceptable salts thereof, wherein m is selected from the group consisting of 0, 1, 2, 3, 4, 5, 6, 7, 8, 9, 10, 11, 12. . . . and 100.

In certain embodiments, the functional unit of a peptide HPP/HPC comprises a moiety having a structure of Structure F-1 as defined supra, including stereoisomers and pharmaceutically acceptable salts thereof, wherein p is 1, 2, or 3.

In certain embodiments, the functional unit of a peptide HPP/HPC comprises a moiety having a structure of Structure F-1 as defined supra, including stereoisomers and pharmaceutically acceptable salts thereof, wherein:

p is 1, 2 or 3;

$Z_{A-1}$ on each carbon of each $A_1$-$A_m$, $Z_{A-2}$ for each $A_1$-$A_m$, $Z_{NT}$, $Z_{CT-1}$, and $Z_{CT-2}$ are independently selected from the group consisting of H, $CH_3$, $C_2H_5$, $C_3H_7$, $CF_3$, $C_2F_5$, $C_3F_7$, substituted and unsubstituted alkyl, substituted and unsubstituted cycloalkyl, substituted and unsubstituted heterocycloalkyl, substituted and unsubstituted perfluoroalkyl, and substituted and unsubstituted alkyl halide;

$R_A$ on each carbon of each $A_1$-$A_m$, $R_{NT}$ and $R_{CT}$ are selected from the group consisting of H, substituted and unsubstituted imidazolyl, substituted and unsubstituted quanidino, substituted and unsubstituted carboxyl, substituted and unsubstituted carboxamide, substituted and unsubstituted alkyl, substituted and unsubstituted cycloalkoxyl, substituted and unsubstituted heterocycloalkyl, substituted and unsubstituted alkoxyl, substituted and unsubstituted alkylthio, substituted and unsubstituted alkylamino, substituted and unsubstituted alkylcarbonyl, substituted and unsubstituted perfluoroalkyl, substituted and unsubstituted alkyl halide, substituted and unsubstituted aryl, and substituted and unsubstituted heteroaryl groups;

when a p of a $A_1$-$A_m$ is an integer no less than 2, $R_A$ on each carbon can be the same or different, $Z_{A-1}$ on each carbon can be the same or different;

an amino and an carboxyl functional group on a peptide chain may further form lactam bridges; and a thiol group may further form disulfide bridges.

As used herein, the term "pharmaceutically acceptable salt" means those salts of compounds of the invention that are safe for application in a subject. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,11-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

As used herein, unless specified otherwise, the term "alkyl" means a branched or unbranched, saturated or unsaturated, monovalent or multivalent hydrocarbon group, including saturated alkyl groups, alkenyl groups and alkynyl groups. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene. In certain embodiments, the hydrocarbon group contains 1 to 30 carbons. In certain embodiments, the hydrocarbon group contains 1 to 20 carbons. In certain embodiments, the hydrocarbon group contains 1 to 12 carbons.

As used herein, unless specified otherwise, the term "cycloalkyl" means an alkyl which contains at least one ring and no aromatic rings. Examples of cycloalkyl include, but are not limited to, cyclopropyl, cyclobutyl, cyclopentyl, cyclohexyl, cycloheptyl, cyclooctyl, cyclononyl, cyclodecyl, cycloundecyl and cyclododecyl. In certain embodiments, the hydrocarbon chain contains 1 to 30 carbons. In certain embodiments, the hydrocarbon group contains 1 to 20 carbons. In certain embodiments, the hydrocarbon group contains 1 to 12 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl or heterocycloalkyl, which contains one or more oxygen atoms. Examples of alkoxyl include, but are not limited to, —CH$_2$—OH, —OCH$_3$, —O-alkyl, -alkyl-OH, -alkyl-O-alkyl-, wherein the two alkyls can be the same or different.

As used herein, unless specified otherwise, the term "alkyl halide" means an alkyl, cycloalkyl or heterocycloalkyl, which contains one or more halogen atoms, wherein the halogen atoms can be the same or different. The term "halogen" means fluorine, chlorine, bromine or iodine. Examples of alkyl halide include, but are not limited to, -alkyl-F, -alkyl-Cl, -alkyl-Br, -alkyl-I, -alkyl(F)—, -alkyl(Cl)—, -alkyl(Br)— and -alkyl(I)—.

As used herein, unless specified otherwise, the term "alkylthio" means an alkyl, cycloalkyl or heterocycloalkyl, which contains one or more sulfur atoms. Examples of alkylthio include, but are not limited to, —CH$_2$—SH, —SCH$_3$, —S-alkyl, -alkyl-SH, -alkyl-5-alkyl-, wherein the two alkyls can be the same or different.

As used herein, unless specified otherwise, the term "alkylamino" means an alkyl, cycloalkyl or heterocycloalkyl, which contains one or more nitrogen atoms. Examples of alkylamino include, but are not limited to, —CH$_2$—NH, —NCH$_3$, —N(alkyl)-alkyl, —N-alkyl, -alkyl-NH$_2$, -alkyl-N-alkyl and -alkyl-N(alkyl)-alkyl wherein the alkyls can be the same or different.

As used herein, unless specified otherwise, the term "alkylcarbonyl" means an alkyl, cycloalkyl or heterocycloalkyl, which contains one or more carbonyl groups. Examples of alkylcarbonyl group include, but are not limited to, aldehyde group (—R—C(O)—H), ketone group (—R—C(O)—R'), carboxylic acid group (R—COOH), ester group (—R—COO—R'), carboxamide, (—R—COO—N(R')R''), enone group (—R—C(O)—C(R)=C(R'')R'''), acyl halide group (—R—C(O)—X) and acid anhydride group (—R—C(O)—O—C(O)—R'), wherein R, R', R'' and R''' are the same or different alkyl, cycloalkyl, or heterocycloalkyl.

As used herein, unless specified otherwise, the term "perfluoroalkyl" means an alkyl, cycloalkyl or heterocycloalkyl, which contains one or more fluoro group, including, without limitation, perfluoromethyl, perfluoroethyl, perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur ("heteroaryl").

Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl, quanidino and benzothiazolyl.

In certain embodiments, a transportational unit of a HPP/HPC comprises a protonatable amine group that is capable of facilitating the transportation or crossing of the HPP/HPC through one or more biological barriers (e.g., >about 10 times, >about 50 times, >about 100 times, >about 300 times, >about 500 times, >about 1,000 times faster than the parent drug). In certain embodiments, the protonatable amine group is substantially protonated at a physiological pH. In certain embodiments, the amine group can be reversibly protonated. In certain embodiments, the transportational unit may or may not be cleaved from the functional unit after the penetration of HPP/HPC through one or more biological barriers. In certain embodiments, the transportational unit may be from the functional unit, especially for peptides or peptide-related compounds that have at least a free amino group. In certain embodiments, when there are more than one protonatable group in a peptide or peptide-related compound, the peptide or peptide-related compound is modified so that only one or two protonatable amine groups are left, and all other protonatable groups are protected.

In certain embodiments, the protonatable amine group is selected from the group consisting of pharmaceutically acceptable substituted and unsubstituted primary amine groups, pharmaceutically acceptable substituted and unsubstituted secondary amine groups, and pharmaceutically acceptable substituted and unsubstituted tertiary amine groups.

In certain embodiments, the protonatable amine group is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr:

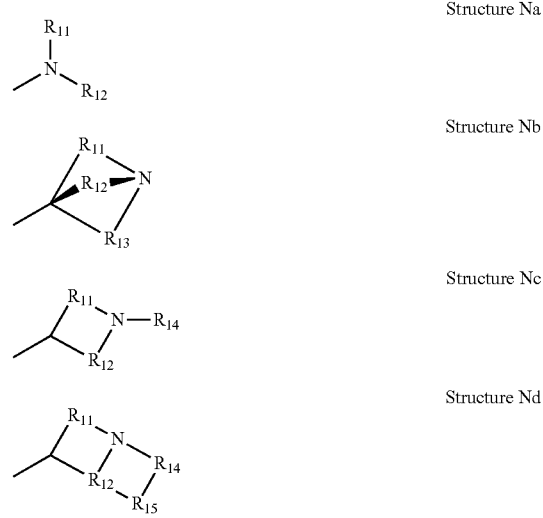

Structure Ne
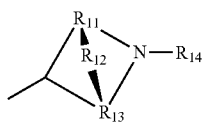

Structure Nf
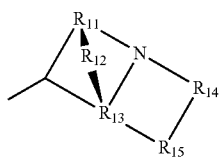

Structure Ng
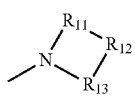

Structure Nh
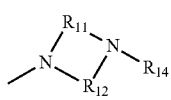

Structure Ni
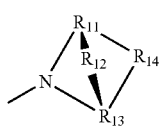

Structure Nj
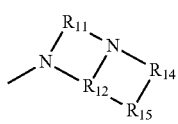

Structure Nk
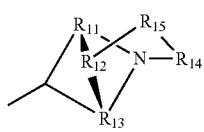

Structure Nl
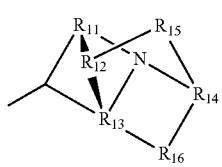

Structure Nm
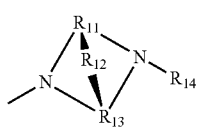

Structure Nn
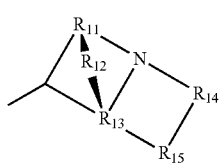

Structure No
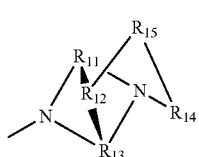

Structure Np
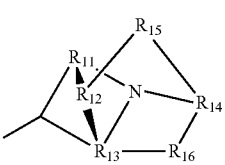

Structure Nq
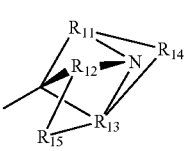

Structure Nr
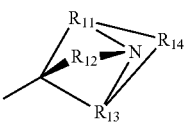

including stereoisomers and pharmaceutically acceptable salts thereof.

As used herein, unless specified otherwise, each $R_{11}$-$R_{16}$ is independently selected from the group consisting of nothing, H, $CH_2COOR_{11}$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NR_{11}$, or any other pharmaceutically acceptable groups.

In certain embodiments, a linker covalently linking a functional unit and a transportational unit of a HPP/HPC comprises a bond that is capable of being cleaved after the HPP/HPC penetrates across one or more BBs. The cleavable bond comprises, for example, a covalent bond, an ether, thioether, amide, ester, thioester, carbonate, carbamate, phosphate or oxime bond.

In certain embodiments, a peptide HPP/HPC has the following Structure L-1:

Structure L-1
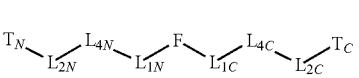

including stereoisomers and pharmaceutically acceptable salts thereof, wherein:

F is a functional unit of a peptide HPP/HPC. Examples of F include Structure F-1 as defined supra;

$T_C$ and $T_N$ are independently selected from the group consisting of nothing, H, substituted and unsubstituted alkyl, substituted and unsubstituted cycloalkyl, substituted and unsubstituted heterocycloalkyl, substituted and unsubstituted alkyloxyl, substituted and unsubstituted alkenyl, substituted and unsubstituted alkynyl, substituted and unsubstituted aryl, substituted and unsubstituted heteroaryl groups, Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra;

$L_{1C}$ and $L_{1N}$ are independently selected from the group consisting of nothing, O, S, N($L_3$), —N($L_3$)—CH$_2$—O, —N($L_3$)—CH$_2$—N($L_5$)-, —O—CH$_2$—O—, —O—CH($L_3$)—O, and —S—CH($L_3$)—O—;

$L_{2C}$ and $L_{2N}$ are independently selected from the group consisting of nothing, O, S, N($L_3$), —N($L_3$)—CH$_2$—O, —N($L_3$)—CH$_2$—N($L_5$)-, —O—CH$_2$—O—, —O—CH($L_3$)—O, —S—CH($L_3$)—O—, —O-$L_3$-, —N-$L_3$-, —S-$L_3$-, —N($L_3$)-$L_5$- and $L_3$;

$L_{4C}$ and $L_{4N}$ are independently selected from the group consisting of nothing, C=O, C=S,

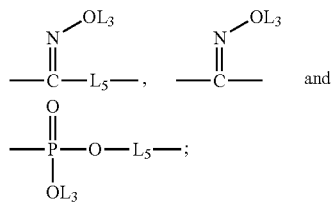

for each $L_{1C}$, $L_{1N}$, $L_{2C}$, $L_{2N}$, $L_{4C}$ and $L_{4N}$, $L_3$ and $L_6$ are independently selected from the group consisting of nothing, H, CH$_2$COO$L_6$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, N$L_3$, or any other pharmaceutically acceptable groups;

$L_6$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)O$L_6$, CH=CH, C≡C, CH$L_6$, C$L_6L_7$, aryl, heteroaryl, or cyclic groups; and $L_7$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)O$L_6$, CH=CH, C≡C, CH$L_6$, C$L_6L_7$, aryl, heteroaryl, or cyclic groups.

In certain embodiments, a HPP or HPC of a peptide or peptide-related compound comprises the structure of Structure L-1, including stereoisomers and pharmaceutically acceptable salts thereof, wherein:

F, $L_{1C}$, $L_{1N}$, $L_{2C}$, $L_{2N}$, $T_C$ and $T_N$ are defined as supra; and $L_{4C}$ and/or $L_{4N}$ are/is C=O.

In certain embodiments, a HPP or HPC of a peptide or peptide-related compound comprises the structure of Structure L-1, including stereoisomers and pharmaceutically acceptable salts thereof, wherein:

F, $L_{1C}$, $L_{1N}$, $L_{2C}$, $L_{2N}$, $L_{4C}$ and $L_{4N}$ are defined as supra;

$T_C$ is a transportational unit of a peptide HPP/HPC. For example, $T_C$ is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra; and $T_N$ is selected from the group consisting of nothing, H, substituted and unsubstituted alkyl, substituted and unsubstituted cycloalkyl, and substituted and unsubstituted heterocycloalkyl, substituted and unsubstituted alkyloxyl, substituted and unsubstituted alkenyl, substituted and unsubstituted alkynyl, substituted and unsubstituted aryl, and substituted and unsubstituted heteroaryl groups.

In certain embodiments, a HPP or HPC of a peptide or peptide-related compound comprises the structure of Structure L-1, including stereoisomers and pharmaceutically acceptable salts thereof, wherein:

F, $L_{1C}$, $L_{1N}$, $L_{2C}$, $L_{2N}$, $L_{4C}$ and $L_{4N}$ are defined as supra;

$T_N$ is a transportational unit of a peptide HPP/HPC. For example, $T_N$ is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra; and $T_C$ is selected from the group consisting of nothing, H, substituted and unsubstituted alkyl, substituted and unsubstituted cycloalkyl, and substituted and unsubstituted heterocycloalkyl, substituted and unsubstituted alkyloxyl, substituted and unsubstituted alkenyl, substituted and unsubstituted alkynyl, substituted and unsubstituted aryl, and substituted and unsubstituted heteroaryl groups.

In certain embodiments, a peptide HPP/HPC has the following Structure L-2:

Structure L-2

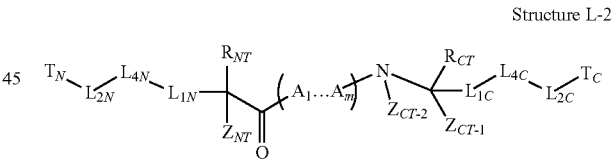

including stereoisomers and pharmaceutically acceptable salts thereof, wherein: each $A_1$-$A_m$ is independently selected from the group consisting of 2-naphthylalanine, substituted and unsubstituted alkyl, substituted and unsubstituted cycloalkyl, and substituted and unsubstituted heterocycloalkyl, substituted and unsubstituted alkoxyl, substituted and unsubstituted alkenyl, substituted and unsubstituted alkynyl, substituted and unsubstituted aryl, substituted and unsubstituted heteroaryl residues, Structure A and Structure B:

Structure A

-continued

Structure B

[Structure B diagram showing chemical structure with L1B, L4B, L2B, TB, RB, ZA-2, ZA-1, N, C, O groups]

p of each $A_1$-$A_m$ is an independently selected integer;

$T_B$ of each $A_1$-$A_m$, $T_C$ and $T_N$ are independently selected from the group consisting of nothing, H, substituted and unsubstituted alkyl, substituted and unsubstituted cycloalkyl, and substituted and unsubstituted heterocycloalkyl, substituted and unsubstituted alkyloxyl, substituted and unsubstituted alkenyl, substituted and unsubstituted alkynyl, substituted and unsubstituted aryl, substituted and unsubstituted heteroaryl groups, Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra;

$L_{1B}$ of each $A_1$-$A_m$, $L_{1C}$ and $L_{1N}$ are independently selected from the group consisting of nothing, O, S, —N($L_3$)-, —N($L_3$)—CH$_2$—O, —N($L_3$)—CH$_2$—N($L_5$)-, —O—CH$_2$—O—, —O—CH($L_3$)-O, and —S—CH($L_3$)—O—;

$L_{2B}$ of each $A_1$-$A_m$, $L_{2C}$ and $L_{2N}$ are independently selected from the group consisting of nothing, O, S, —N($L_3$)-, —N($L_3$)—CH$_2$—O, —N($L_3$)—CH$_2$—N($L_5$)-, —O—CH$_2$—O—, —O—CH($L_3$)-O, —S—CH($L_3$)—O—, —O-$L_3$-, —N-$L_3$-, —S-$L_3$-, —N($L_3$)-$L_5$- and $L_3$;

$L_{4B}$ of each $A_1$-$A_m$, $L_{4C}$ and $L_{4N}$ are independently selected from the group consisting of C=O, C=S,

[chemical structures showing N-OL3, C-L5, C, P-O-L5 groups]

and $L_3$ and $L_5$ are defined the same as supra;

$Z_{A-1}$ on each carbon of each $A_1$-$A_m$, $Z_{A-2}$ for each $A_1$-$A_m$, $Z_{NT}$, $Z_{CT-1}$ and $Z_{CT-2}$ are independently selected from the group consisting of H, CH$_3$, C$_2$H$_5$, C$_3$H$_7$, CF$_3$, C$_2$F$_5$, C$_3$F$_7$, substituted and unsubstituted alkyl, substituted and unsubstituted perfluoroalkyl, and substituted and unsubstituted alkyl halide;

$R_A$ on each carbon of each $A_1$-$A_m$, $R_B$ on each carbon of each $A_1$-$A_m$, $R_{NT}$ and $R_{CT}$ are independently selected from the group consisting of substituted and unsubstituted imidazolyl, substituted and unsubstituted quanidino, substituted and unsubstituted carboxyl, substituted and unsubstituted carboxamide, substituted and unsubstituted alkyl, substituted and unsubstituted cycloalkyl, and substituted and unsubstituted heterocycloalkyl, substituted and unsubstituted alkoxyl, substituted and unsubstituted alkylthio, substituted and unsubstituted alkylamino, substituted and unsubstituted alkylcarbonyl, substituted and unsubstituted perfluoroalkyl, substituted and unsubstituted alkyl halide, substituted and unsubstituted aryl, and substituted and unsubstituted heteroaryl groups;

when a p of a $A_1$-$A_m$ is an integer no less than 2, $R_A$ or $R_B$ on each carbon can be the same or different, $Z_{A-1}$ on each carbon can be the same or different;

an amino and an carboxyl functional group on a peptide chain may further form lactam bridges; and a thiol group may further form disulfide bridges.

Examples of Peptide HPPs/HPCs.

In certain embodiments, a peptide HPP/HPC includes a compound having a structure selected from the group consisting of Structure 2 (SEQ ID NO: 1), Structure 3 (SEQ ID NO: 1), Structure 4 (SEQ ID NO: 1), Structure 5 (SEQ ID NO: 1), Structure 6 (SEQ ID NO: 2), Structure 7 (SEQ ID NO: 2), Structure 8 (SEQ ID NO: 2), Structure 9 (SEQ ID NO: 2), Structure 10 (SEQ ID NO: 3), Structure 11 (SEQ ID NO: 4), Structure 12 (SEQ ID NO: 3), Structure 13 (SEQ ID NO: 5), Structure 14 (SEQ ID NO: 5), Structure 15 (SEQ ID NO: 5), Structure 16 (SEQ ID NO: 5), Structure 17 (SEQ ID NO: 6), Structure 18 (SEQ ID NO: 6), Structure 19 (SEQ ID NO: 6), Structure 20 (SEQ ID NO: 6), Structure 21 (SEQ ID NO: 6), Structure 22 (SEQ ID NO: 61), Structure 23 (SEQ ID NO: 6), Structure 24 (SEQ ID NO: 3), Structure 25 (SEQ ID NO: 7), Structure 26 (SEQ ID NO: 6), Structure 27 (SEQ ID NO: 6), Structure 28 (SEQ ID NO: 6), Structure 29 (SEQ ID NO: 6), Structure 30 (SEQ ID NO: 6), Structure 31 (SEQ ID NO: 8), Structure 32 (SEQ ID NO: 8), Structure 33 (SEQ ID NO: 8), Structure 34 (SEQ ID NO: 8), Structure 35 (SEQ ID NO: 8), Structure 36 (SEQ ID NO: 8), Structure 37 (SEQ ID NO: 8), Structure 38 (SEQ ID NO: 8), Structure 39 (SEQ ID NO: 8), Structure 40 (SEQ ID NO: 8), Structure 41 (SEQ ID NO: 8), Structure 42 (SEQ ID NO: 8), Structure 43 (SEQ ID NO: 9), Structure 44 (SEQ ID NO: 9), Structure 45 (SEQ ID NO: 10), Structure 46 (SEQ ID NO: 10), Structure 47 (SEQ ID NO: 10), Structure 48 (SEQ ID NO: 10), Structure 49 (SEQ ID NO: 10), Structure 50 (SEQ ID NO: 10), Structure 51 (SEQ ID NO: 10), Structure 52 (SEQ ID NO: 10), Structure 53 (SEQ ID NO: 11), Structure 54 (SEQ ID NO: 11), Structure 55 (SEQ ID NO: 11), Structure 56 (SEQ ID NO: 11), Structure 57 (SEQ ID NO: 11), Structure 58 (SEQ ID NO: 11), Structure 59 (SEQ ID NO: 12), Structure 60 (SEQ ID NO: 12), Structure 61 (SEQ ID NO: 12), Structure 62 (SEQ ID NO: 12), Structure 63 (SEQ ID NO: 12), Structure 64 (SEQ ID NO: 12), Structure 65 (SEQ ID NO: 13), Structure 66 (SEQ ID NO: 13), Structure 67 (SEQ ID NO: 13), Structure 68 (SEQ ID NO: 13), Structure 69 (SEQ ID NO: 14), Structure 70 (SEQ ID NO: 14), Structure 71 (SEQ ID NO: 15), Structure 72 (SEQ ID NO: 15), Structure 73 (SEQ ID NO: 15), Structure 74 (SEQ ID NO: 15), Structure 75 (SEQ ID NO: 16), Structure 76 (SEQ ID NO: 16), Structure 77 (SEQ ID NO: 17), Structure 78 (SEQ ID NO: 17), Structure 79 (SEQ ID NO: 17), Structure 80 (SEQ ID NO: 17), Structure 81 (SEQ ID NO: 18), Structure 82 (SEQ ID NO: 18), Structure 83 (SEQ ID NO: 19), Structure 84 (SEQ ID NO: 19), Structure 85 (SEQ ID NO: 20), Structure 86 (SEQ ID NO: 20), Structure 87 (SEQ ID NO: 21), Structure 88 (SEQ ID NO: 21), Structure 89 (SEQ ID NO: 22), Structure 90 (SEQ ID NO: 22), Structure 91 (SEQ ID NO: 22), Structure 92 (SEQ ID NO: 22), Structure 93 (SEQ ID NO: 22), Structure 94 (SEQ ID NO: 22), Structure 95 (SEQ ID NO: 22), Structure 96 (SEQ ID NO: 22), Structure 97 (SEQ ID NO: 23), Structure 98 (SEQ ID NO: 23), Structure 99 (SEQ ID NO: 23), Structure 100 (SEQ ID NO: 23), Structure 101 (SEQ ID NO: 24), Structure 102 (SEQ ID NO: 24), Structure 103 (SEQ ID NO: 24) , Structure 104 (SEQ ID NO: 24), Structure 105 (SEQ ID NO: 25), Structure 106 (SEQ ID NO: 25), Structure 107 (SEQ ID NO: 26), Structure 108 (SEQ ID NO: 26), Structure 109 (SEQ ID NO: 26), Structure 110 (SEQ ID NO: 27), Structure 111 (SEQ ID NO: 27), Structure 112

(SEQ ID NO: 28), Structure 113 (SEQ ID NO: 28), Structure 114 (SEQ ID NO: 29), Structure 115 (SEQ ID NO: 29), Structure 116 (SEQ ID NO: 30), Structure 117 (SEQ ID NO: 30), Structure 118 (SEQ ID NO: 31), Structure 119 (SEQ ID NO: 31), Structure 120 (SEQ ID NO: 32), Structure 121 (SEQ ID NO: 32), Structure 122 (SEQ ID NO: 33), Structure 123 (SEQ ID NO: 33), Structure 124 (SEQ ID NO: 34), Structure 125 (SEQ ID NO: 34), Structure 126 (SEQ ID NO: 35), Structure 127 (SEQ ID NO: 35), Structure 128 (SEQ ID NO: 36), Structure 129 (SEQ ID NO: 36), Structure 130 (SEQ ID NO: 37), Structure 131 (SEQ ID NO: 37), Structure 132 (SEQ ID NO: 38), Structure 133 (SEQ ID NO: 39), Structure 134 (SEQ ID NO: 39), Structure 135 (SEQ ID NO: 40), Structure 136 (SEQ ID NO: 41), Structure 137 (SEQ ID NO: 41), Structure 138 (SEQ ID NO: 41), Structure 139 (SEQ ID NO: 42), Structure 140 (SEQ ID NO: 42), Structure 141 (SEQ ID NO: 43), Structure 142 (SEQ ID NO: 43), Structure 143 (SEQ ID NO: 43), Structure 144 (SEQ ID NO: 43), Structure 145 (SEQ ID NO: 44), Structure 146 (SEQ ID NO: 44), Structure 147 (SEQ ID NO: 44), Structure 148 (SEQ ID NO: 44), Structure 149 (SEQ ID NO: 45), Structure 150 (SEQ ID NO: 45), Structure 151 (SEQ ID NO: 45), Structure 152 (SEQ ID NO: 45), Structure 153 (SEQ ID NO: 45), Structure 154 (SEQ ID NO: 46), Structure 155 (SEQ ID NO: 46), Structure 156 (SEQ ID NO: 47), Structure 157 (SEQ ID NO: 47), Structure 158 (SEQ ID NO: 47), Structure 159 (SEQ ID NO: 48), Structure 160 (SEQ ID NO: 48), Structure 161 (SEQ ID NO: 49), Structure 162 (SEQ ID NO: 49), Structure 163 (SEQ ID NO: 50), Structure 164 (SEQ ID NO: 50), Structure 165 (SEQ ID NO: 51), Structure 166 (SEQ ID NO: 52), Structure 167 (SEQ ID NO: 53), Structure 168 (SEQ ID NO: 54), Structure 169 (SEQ ID NO: 55), Structure 170 (SEQ ID NO: 56), Structure 171 (SEQ ID NO: 56), Structure 172 (SEQ ID NO: 57), Structure 173 (SEQ ID NO: 58), Structure 174 (SEQ ID NO: 58), Structure 175 (SEQ ID NO: 59), Structure 176 (SEQ ID NO: 60), Structure 177 (SEQ ID NO: 60), Structure 178 (SEQ ID NO: 61), Structure 179 (SEQ ID NO: 62), Structure 180 (SEQ ID NO: 63), Structure 181 (SEQ ID NO: 64), Structure 182 (SEQ ID NO: 65), Structure 183 (SEQ ID NO: 66), Structure 184 (SEQ ID NO: 67), Structure 185 (SEQ ID NO: 68), Structure 186 (SEQ ID NO: 69), Structure 187 (SEQ ID NO: 70), Structure 188 (SEQ ID NO: 71), Structure 189 (SEQ ID NO: 72), Structure 190 (SEQ ID NO: 73), Structure 191 (SEQ ID NO: 74), Structure 192 (SEQ ID NO: 75), Structure 193 (SEQ ID NO: 76), Structure 194 (SEQ ID NO: 77 Structure 195 (SEQ ID NO: 78), Structure 196 (SEQ ID NO: 79), Structure 197 (SEQ ID NO: 79), Structure 198 (SEQ ID NO: 80), Structure 199 (SEQ ID NO: 80), Structure 200 (SEQ ID NO: 81), Structure 201 (SEQ ID NO: 81), Structure 202 (SEQ ID NO: 82), Structure 203 (SEQ ID NO: 82), Structure 204 (SEQ ID NO: 83), Structure 205 (SEQ ID NO: 84), Structure 206 (SEQ ID NO: 85), Structure 207 (SEQ ID NO: 86), Structure 208 (SEQ ID NO: 87), Structure 209 (SEQ ID NO: 88), Structure 210 (SEQ ID NO: 88), Structure 211 (SEQ ID NO: 89), Structure 212 (SEQ ID NO: 89), Structure 213 (SEQ ID NO: 90), Structure 214 (SEQ ID NO: 90), Structure 215 (SEQ ID NO: 91), Structure 216 (SEQ ID NO: 92), Structure 217 (SEQ ID NO: 93), Structure 218 (SEQ ID NO: 94), Structure 219 (SEQ ID NO: 95), Structure 220 (SEQ ID NO: 95), Structure 221 (SEQ ID NO: 96), Structure 222 (SEQ ID NO: 96), Structure 223 (SEQ ID NO: 97), Structure 224 (SEQ ID NO: 97), Structure 225 (SEQ ID NO: 97), Structure 226 (SEQ ID NO: 98), Structure 227 (SEQ ID NO: 98), Structure 228 (SEQ ID NO: 99), Structure 229 (SEQ ID NO: 99), Structure 230 (SEQ ID NO: 100), Structure 231 (SEQ ID NO: 101), Structure 232 (SEQ ID NO: 101), Structure 233 (SEQ ID NO: 101), Structure 234 (SEQ ID NO: 102), Structure 235 (SEQ ID NO: 103), Structure 236 (SEQ ID NO: 103), Structure 237 (SEQ ID NO: 104), Structure 238 (SEQ ID NO: 105), Structure 239 (SEQ ID NO: 105), Structure 240 (SEQ ID NO: 106), Structure 241 (SEQ ID NO: 107), Structure 242 (SEQ ID NO: 108), Structure 243 (SEQ ID NO: 109), Structure 244 (SEQ ID NO: 110), Structure 245 (SEQ ID NO: 205), Structure 246 (SEQ ID NO: 205), Structure 247 (SEQ ID NO: 111), Structure 248 (SEQ ID NO: 112), Structure 249 (SEQ ID NO: 113), Structure 250 (SEQ ID NO: 114), Structure 251 (SEQ ID NO: 115), Structure 252 (SEQ ID NO: 116), Structure 253 (SEQ ID NO: 117), Structure 254 (SEQ ID NO: 117), Structure 255 (SEQ ID NO: 118), Structure 256 (SEQ ID NO: 119), Structure 257 (SEQ ID NO: 120), Structure 258 (SEQ ID NO: 121), Structure 259 (SEQ ID NO: 122), Structure 260 (SEQ ID NO: 123), Structure 261 (SEQ ID NO: 124), Structure 262 (SEQ ID NO: 125), Structure 263 (SEQ ID NO: 126), Structure 264 (SEQ ID NO: 127), Structure 265 (SEQ ID NO: 128), Structure 266 (SEQ ID NO: 129), Structure 267 (SEQ ID NO: 130), Structure 268 (SEQ ID NO: 131), Structure 269 (SEQ ID NO: 132), Structure 270 (SEQ ID NO: 133), Structure 271 (SEQ ID NO: 133), Structure 272 (SEQ ID NO: 134), Structure 273 (SEQ ID NO: 134), Structure 274 (SEQ ID NO: 134), Structure 275 (SEQ ID NO: 134), Structure 276 (SEQ ID NO: 135), Structure 277 (SEQ ID NO: 136), Structure 278 (SEQ ID NO: 137), Structure 279 (SEQ ID NO: 138), Structure 280 (SEQ ID NO: 138), Structure 281 (SEQ ID NO: 138), Structure 282 (SEQ ID NO: 138), Structure 283 (SEQ ID NO: 139), Structure 284 (SEQ ID NO: 139), Structure 285 (SEQ ID NO: 139), Structure 286 (SEQ ID NO: 140), Structure 287 (SEQ ID NO: 140), Structure 288 (SEQ ID NO: 141), Structure 289 (SEQ ID NO: 142), Structure 290 (SEQ ID NO: 142), Structure 291 (SEQ ID NO: 142), Structure 292 (SEQ ID NO: 143), Structure 293 (SEQ ID NO: 143), Structure 294 (SEQ ID NO: 144), Structure 295 (SEQ ID NO: 144), Structure 296 (SEQ ID NO: 206), Structure 297 (SEQ ID NO: 206), Structure 298 (SEQ ID NO: 145), Structure 299 (SEQ ID NO: 145), Structure 300 (SEQ ID NO: 145), Structure 301 (SEQ ID NO: 145), Structure 302 (SEQ ID NO: 146), Structure 303 (SEQ ID NO: 146), Structure 304 (SEQ ID NO: 147), Structure 305 (SEQ ID NO: 148), Structure 306 (SEQ ID NO: 148), Structure 307 (SEQ ID NO: 149), Structure 308 (SEQ ID NO: 150), Structure 309 (SEQ ID NO: 150), Structure 310 (SEQ ID NO: 151), Structure 311 (SEQ ID NO: 152), Structure 312 (SEQ ID NO: 153), Structure 313 (SEQ ID NO: 154), Structure 314 (SEQ ID NO: 155), Structure 315 (SEQ ID NO: 156), Structure 316 (SEQ ID NO: 156), Structure 317 (SEQ ID NO: 157), Structure 318 (SEQ ID NO: 157), Structure 319 (SEQ ID NO: 158), Structure 320 (SEQ ID NO: 158), Structure 321 (SEQ ID NO: 159), Structure 322 (SEQ ID NO: 159), Structure 323 (SEQ ID NO: 160), Structure 324 (SEQ ID NO: 160), Structure 325 (SEQ ID NO: 161), Structure 326 (SEQ ID NO: 162), Structure 327 (SEQ ID NO: 162), Structure 328 (SEQ ID NO: 162), Structure 329 (SEQ ID NO: 163), Structure 330 (SEQ ID NO: 164), Structure 331 (SEQ ID NO: 165), Structure 332 (SEQ ID NO: 165), Structure 333 (SEQ ID NO: 166), Structure 334 (SEQ ID NO: 166), Structure 335 (SEQ ID NO: 166), Structure 336 (SEQ ID NO: 167), Structure 337 (SEQ ID NO: 167), Structure 338 (SEQ ID NO: 168), Structure 339 (SEQ ID NO: 168), Structure 340 (SEQ ID NO: 169), Structure 341 (SEQ ID NO: 170), Structure 342 (SEQ ID NO: 170), Structure 343 (SEQ ID NO: 171), Structure 344 (SEQ ID NO: 172), and Structure 345 (SEQ ID NO: 172) as shown in FIG. 1, including stereoisomers and pharmaceutically acceptable salts thereof, wherein:

R is selected from the group consisting of H, substituted and unsubstituted alkyl, substituted and unsubstituted cycloalkyl, and substituted and unsubstituted heterocycloalkyl, substituted and unsubstituted alkoxyl, substituted and unsubstituted alkylthio, substituted and unsubstituted alkylamino, substituted and unsubstituted aryl, and substituted and unsubstituted heteroaryl residues;

X, $X_4$, $X_5$, $X_6$, $X_7$, $X_8$, $X_9$, $X_{10}$, $X_{21}$, $X_{22}$, $X_{23}$, $X_{24}$, $X_{25}$, $X_{26}$, and $X_{27}$ are independently selected from the group consisting of C=O, C=S, COO, CSO, $CH_2OCO$, $COOCH_2OCO$, $COCH_2OCO$, $CH_2$—O—$CH(CH_2OR_4)_2$, $CH_2$—O—CH$(CH_2OCOR_4)_2$, $SO_2$, PO(OR), $NO_2$, NO, O, S, $NR_5$, and nothing;

$R_1$, $R_2$, $R_4$, $R_5$, $R_6$, $R_7$, $R_8$, $R_9$, $R_{10}$, $R_{21}$, $R_{22}$, $R_{23}$, $R_{24}$, $R_{25}$, $R_{26}$, and $R_{27}$ are independently selected from the group consisting of H, O, $NO_2$, substituted and unsubstituted alkyl, substituted and unsubstituted cycloalkyl, and substituted and unsubstituted heterocycloalkyl, substituted and unsubstituted alkoxyl, substituted and unsubstituted alkylthio, substituted and unsubstituted alkylamino, substituted and unsubstituted alkenyl, substituted and unsubstituted alkynyl, substituted and unsubstituted aryl, and substituted and unsubstituted heteroaryl residues;

as used herein, unless specified otherwise, the term "HA" is nothing or a pharmaceutically acceptable acid, e.g. hydrochloride, hydrobromide, hydroiodide, nitric acid, sulfuric acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid or pamoic acid; and Ar is selected from the group consisting of phenyl, 2'-naphthyl, 4-iodophenyl, substituted and unsubstituted aryl, and substituted and unsubstituted heteroaryl residues.

The corresponding parent peptides of peptide HPPs/HPCs having structure of Structures 2-343 are listed below in Tables A (I) and (II):

TABLE A

Parent peptide of peptide HPPs/HPCs having structure of Structures 2-345

(I)

| Peptide HPP/HPC | Parent drug | SEQ ID NO. | Peptide group | Function |
|---|---|---|---|---|
| Structure 2 | Tyr-Gly-Gly-Phe-Met | 1 | Opioid peptide Met-enkephalin | Analgesic activity |
| Structure 3 | Tyr-Gly-Gly-Phe-Met | 1 | Opioid peptide Met-enkephalin | Analgesic activity |
| Structure 4 | Tyr-Gly-Gly-Phe-Met | 1 | Opioid peptide Met-enkephalin | Analgesic activity |
| Structure 5 | Tyr-Gly-Gly-Phe-Met | 1 | Opioid peptide Met-enkephalin | Analgesic activity |
| Structure 6 | Tyr-Xaa-Gly-Phe-Leu | 2 | Opioid peptide Leu-enkephalin | Analgesic activity |
| Structure 7 | Tyr-Xaa-Gly-Phe-Leu | 2 | Opioid peptide Leu-enkephalin | Analgesic activity |
| Structure 8 | Tyr-Xaa-Gly-Phe-Leu | 2 | Opioid peptide Leu-enkephalin | Analgesic activity |
| Structure 9 | Tyr-Xaa-Gly-Phe-Leu | 2 | Opioid peptide Leu-enkephalin | Analgesic activity |
| Structure 10 | Tyr-Ala-Gly-Xaa1-Xaa2 | 3 | Opioid peptide mimetic | Analgesic activity |
| Structure 11 | Tyr-Gly-Gly-Xaa1-Xaa2 | 4 | Opioid peptide mimetic | Analgesic activity |
| Structure 12 | Tyr-Ala-Gly-Xaa1-Xaa2 | 3 | Opioid peptide mimetic | Analgesic activity |
| Structure 13 | Tyr-D-Ala-Phe-Gly-Tyr-Pro-Ser | 5 | Opioid peptide dermorphin | Analgesic activity |
| Structure 14 | Tyr-D-Ala-Phe-Gly-Tyr-Pro-Ser | 5 | Opioid peptide dermorphin | Analgesic activity |
| Structure 15 | Tyr-D-Ala-Phe-Gly-Tyr-Pro-Ser | 5 | Opioid peptide dermorphin | Analgesic activity |
| Structure 16 | Tyr-D-Ala-Phe-Gly-Tyr-Pro-Ser | 5 | Opioid peptide dermorphin | Analgesic activity |

TABLE A-continued

Parent peptide of peptide HPPs/HPCs having structure of Structures 2-345

| | | | | |
|---|---|---|---|---|
| Structure 17 | Thr-Lys-Pro-Arg | 6 | Tuftsin | Stimulate phagocytosis |
| Structure 18 | Thr-Lys-Pro-Arg | 6 | Tuftsin | Stimulate phagocytosis |
| Structure 19 | Thr-Lys-Pro-Arg | 6 | Tuftsin | Stimulate phagocytosis |
| Structure 20 | Thr-Lys-Pro-Arg | 6 | Tuftsin | Stimulate phagocytosis |
| Structure 21 | Thr-Lys-Pro-Arg | 6 | Tuftsin | Stimulate phagocytosis |
| Structure 22 | Thr-Lys-Pro-Arg | 6 | Tuftsin | Stimulate phagocytosis |
| Structure 23 | Thr-Lys-Pro-Arg | 6 | Tuftsin | Stimulate phagocytosis |
| Structure 24 | Tyr-Ala-Gly-Xaa1-Xaa2 | 3 | Opioid peptide mimetic | Analgesic activity |
| Structure 25 | Tyr-Ala-Phe-Gly-Tyr-Pro-Ser | 7 | Opioid peptide dermorphin | Analgesic activity |
| Structure 26 | Thr-Lys-Pro-Arg | 6 | Tuftsin | Stimulate phagocytosis |
| Structure 27 | Thr-Lys-Pro-Arg | 6 | Tuftsin | Stimulate phagocytosis |
| Structure 28 | Thr-Lys-Pro-Arg | 6 | Tuftsin | Stimulate phagocytosis |
| Structure 29 | Thr-Lys-Pro-Arg | 6 | Tuftsin | Stimulate phagocytosis |
| Structure 30 | Thr-Lys-Pro-Arg | 6 | Tuftsin | Stimulate phagocytosis |
| Structure 31 | Xaa3-Lys-Pro-Arg | 8 | retro inverso-tuftsin | Agonist of tuftsin |
| Structure 32 | Xaa3-Lys-Pro-Arg | 8 | retro inverso-tuftsin | Agonist of tuftsin |
| Structure 33 | Xaa3-Lys-Pro-Arg | 8 | retro inverso-tuftsin | Agonist of tuftsin |
| Structure 34 | Xaa3-Lys-Pro-Arg | 8 | retro inverso-tuftsin | Agonist of tuftsin |
| Structure 35 | Xaa3-Lys-Pro-Arg | 8 | retro inverso-tuftsin | Agonist of tuftsin |
| Structure 36 | Xaa3-Lys-Pro-Arg | 8 | retro inverso-tuftsin | Agonist of tuftsin |
| Structure 37 | Xaa3-Lys-Pro-Arg | 8 | retro inverso-tuftsin | Agonist of tuftsin |
| Structure 38 | Xaa3-Lys-Pro-Arg | 8 | retro inverso-tuftsin | Agonist of tuftsin |
| Structure 39 | Xaa3-Lys-Pro-Arg | 8 | retro inverso-tuftsin | Agonist of tuftsin |
| Structure 40 | Xaa3-Lys-Pro-Arg | 8 | retro inverso-tuftsin | Agonist of tuftsin |
| Structure 41 | Xaa3-Lys-Pro-Arg | 8 | retro inverso-tuftsin | Agonist of tuftsin |
| Structure 42 | Xaa3-Lys-Pro-Arg | 8 | retro inverso-tuftsin | Agonist of tuftsin |

TABLE A-continued

Parent peptide of peptide HPPs/HPCs having structure of Structures 2-345

| | | | |
|---|---|---|---|
| Structure 43 | Nle-cyclo[Asp-His-D-Phe-Arg-Trp-Lys] | 9 Melanocortin II | melanocortin agonists male and female sexual dysfunction |
| Structure 44 | Nle-cyclo[Asp-His-D-Phe-Arg-Trp-Lys] | 9 Melanocortin II | melanocortin agonists male and female sexual dysfunction |
| Structure 45 | Val-Pro-Asp-Pro-Arg | 10 Enterostatins | Anti-obese |
| Structure 46 | Val-Pro-Asp-Pro-Arg | 10 Enterostatins | Anti-obese |
| Structure 47 | Val-Pro-Asp-Pro-Arg | 10 Enterostatins | Anti-obese |
| Structure 48 | Val-Pro-Asp-Pro-Arg | 10 Enterostatins | Anti-obese |
| Structure 49 | Val-Pro-Asp-Pro-Arg | 10 Enterostatins | Anti-obese |
| Structure 50 | Val-Pro-Asp-Pro-Arg | 10 Enterostatins | Anti-obese |
| Structure 51 | Val-Pro-Asp-Pro-Arg | 10 Enterostatins | Anti-obese |
| Structure 52 | Val-Pro-Asp-Pro-Arg | 10 Enterostatins | Anti-obese |
| Structure 53 | Val-Pro-Gly-Pro-Arg | 11 Enterostatins | Anti-obese |
| Structure 54 | Val-Pro-Gly-Pro-Arg | 11 Enterostatins | Anti-obese |
| Structure 55 | Val-Pro-Gly-Pro-Arg | 11 Enterostatins | Anti-obese |
| Structure 56 | Val-Pro-Gly-Pro-Arg | 11 Enterostatins | Anti-obese |
| Structure 57 | Val-Pro-Gly-Pro-Arg | 11 Enterostatins | Anti-obese |
| Structure 58 | Val-Pro-Gly-Pro-Arg | 11 Enterostatins | Anti-obese |
| Structure 59 | Ala-Pro-Gly-Pro-Arg | 12 Enterostatins | Anti-obese |
| Structure 60 | Ala-Pro-Gly-Pro-Arg | 12 Enterostatins | Anti-obese |
| Structure 61 | Ala-Pro-Gly-Pro-Arg | 12 Enterostatins | Anti-obese |
| Structure 62 | Ala-Pro-Gly-Pro-Arg | 12 Enterostatins | Anti-obese |
| Structure 63 | Ala-Pro-Gly-Pro-Arg | 12 Enterostatins | Anti-obese |
| Structure 64 | Ala-Pro-Gly-Pro-Arg | 12 Enterostatins | Anti-obese |
| Structure 65 | Tyr-Xaa4-Gly-Phe-Xaa4 | 13 Opioid peptide mimetic | Analgesic activity |
| Structure 66 | Tyr-Xaa4-Gly-Phe-Xaa4 | 13 Opioid peptide mimetic | Analgesic activity |
| Structure 67 | Tyr-Xaa4-Gly-Phe-Xaa4 | 13 Opioid peptide mimetic | Analgesic activity |
| Structure 68 | Tyr-Xaa4-Gly-Phe-Xaa4 | 13 Opioid peptide mimetic | Analgesic activity |
| Structure 69 | Xaa5-Pro | 14 Angiotensin II antagonists | Anti-hypertension |
| Structure 70 | Xaa5-Pro | 14 Angiotensin II antagonists | Anti-hypertension |
| Structure 71 | Xaa24-Pro | 15 Angiotensin II antagonists | Anti-hypertension |
| Structure 72 | Xaa24-Pro | 15 Angiotensin II antagonists | Anti-hypertension |

TABLE A-continued

Parent peptide of peptide HPPs/HPCs having structure of Structures 2-345

| | | | | |
|---|---|---|---|---|
| Structure 73 | Xaa24-Pro | 15 | Angiotensin II antagonists | Anti-hypertension |
| Structure 74 | Xaa24-Pro | 15 | Angiotensin II antagonists | Anti-hypertension |
| Structure 75 | Cys-Tyr-Ile-Gln-Asn-Cys-Pro-Leu-Gly | 16 | Oxytocin | Antepartum Postpartum |
| Structure 76 | Cys-Tyr-Ile-Gln-Asn-Cys-Pro-Leu-Gly | 16 | Oxytocin | Antepartum Postpartum |
| Structure 77 | Cys-Tyr-Phe-Gln-Asn-Cys-Pro-Arg-Gly | 17 | Vasopressin | Antidiuretic |
| Structure 78 | Cys-Tyr-Phe-Gln-Asn-Cys-Pro-Arg-Gly | 17 | Vasopressin | Antidiuretic |
| Structure 79 | Cys-Tyr-Phe-Gln-Asn-Cys-Pro-Arg-Gly | 17 | Vasopressin | Antidiuretic |
| Structure 80 | Cys-Tyr-Phe-Gln-Asn-Cys-Pro-Arg-Gly | 17 | Vasopressin | Antidiuretic |
| Structure 81 | Ser-Tyr-Ser-Met-Glu-His-Phe-Arg-Trp-Gly-Lys-Pro-Val-Gly-Lys-Lys-Arg | 18 | adrenocorticotropic hormone | Regulation of activity of CNS |
| Structure 82 | Ser-Tyr-Ser-Met-Glu-His-Phe-Arg-Trp-Gly-Lys-Pro-Val-Gly-Lys-Lys-Arg | 18 | adrenocorticotropic hormone | Regulation of activity of CNS |
| Structure 83 | Ser-Tyr-Ser-Met-Glu-His-Phe-Arg-Trp-Gly-Lys-Pro-Val | 19 | adrenocorticotropic hormone | Regulation of activity of CNS |
| Structure 84 | Ser-Tyr-Ser-Met-Glu-His-Phe-Arg-Trp-Gly-Lys-Pro-Val | 19 | adrenocorticotropic hormone | Regulation of activity of CNS |
| Structure 85 | Ser-Tyr-Ser-Met-Glu-His-Phe-Arg-Trp-Gly | 20 | adrenocorticotropic hormone | Regulation of activity of CNS |
| Structure 86 | Ser-Tyr-Ser-Met-Glu-His-Phe-Arg-Trp-Gly | 20 | adrenocorticotropic hormone | Regulation of activity of CNS |
| Structure 87 | Met-Glu-His-Phe-Arg-Trp-Gly | 21 | adrenocorticotropic hormone | Regulation of activity of CNS |
| Structure 88 | Met-Glu-His-Phe-Arg-Trp-Gly | 21 | adrenocorticotropic hormone | Regulation of activity of CNS |
| Structure 89 | Phe-Arg-Trp-Gly-Lys-Pro-Val-Gly-Lys-Lys | 22 | adrenocorticotropic hormone | Regulation of activity of CNS |
| Structure 90 | Phe-Arg-Trp-Gly-Lys-Pro-Val-Gly-Lys-Lys | 22 | adrenocorticotropic hormone | Regulation of activity of CNS |
| Structure 91 | Phe-Arg-Trp-Gly-Lys-Pro-Val-Gly-Lys-Lys | 22 | adrenocorticotropic hormone | Regulation of activity of CNS |
| Structure 92 | Phe-Arg-Trp-Gly-Lys-Pro-Val-Gly-Lys-Lys | 22 | adrenocorticotropic hormone | Regulation of activity of CNS |
| Structure 93 | Phe-Arg-Trp-Gly-Lys-Pro-Val-Gly-Lys-Lys | 22 | adrenocorticotropic hormone | Regulation of activity of CNS |
| Structure 94 | Phe-Arg-Trp-Gly-Lys-Pro-Val-Gly-Lys-Lys | 22 | adrenocorticotropic hormone | Regulation of activity of CNS |
| Structure 95 | Phe-Arg-Trp-Gly-Lys-Pro-Val-Gly-Lys-Lys | 22 | adrenocorticotropic hormone | Regulation of activity of CNS |
| Structure 96 | Phe-Arg-Trp-Gly-Lys-Pro-Val-Gly-Lys-Lys | 22 | adrenocorticotropic hormone | Regulation of activity of CNS |

TABLE A-continued

Parent peptide of peptide HPPs/HPCs having structure of Structures 2-345

| | | | |
|---|---|---|---|
| Structure 97 | Lys-Pro-Val-Gly-Lys-Lys-Arg-Arg-Pro-Val-Lys-Val-Tyr-Pro | 23 adrenocorticotropic hormone | Regulation of activity of CNS |
| Structure 98 | Lys-Pro-Val-Gly-Lys-Lys-Arg-Arg-Pro-Val-Lys-Val-Tyr-Pro | 23 adrenocorticotropic hormone | Regulation of activity of CNS |
| Structure 99 | Lys-Pro-Val-Gly-Lys-Lys-Arg-Arg-Pro-Val-Lys-Val-Tyr-Pro | 23 adrenocorticotropic hormone | Regulation of activity of CNS |
| Structure 100 | Lys-Pro-Val-Gly-Lys-Lys-Arg-Arg-Pro-Val-Lys-Val-Tyr-Pro | 23 adrenocorticotropic hormone | Regulation of activity of CNS |
| Structure 101 | Arg-Pro-Val-Lys-Val-Tyr-Pro-Asp-Gly-Ala-Glu-Asp-Glu-Ser-Ala-Glu-Ala-Phe-Pro-Leu-Glu-Phe | 24 adrenocorticotropic hormone | Regulation of activity of CNS |
| Structure 102 | Arg-Pro-Val-Lys-Val-Tyr-Pro-Asp-Gly-Ala-Glu-Asp-Glu-Ser-Ala-Glu-Ala-Phe-Pro-Leu-Glu-Phe | 24 adrenocorticotropic hormone | Regulation of activity of CNS |
| Structure 103 | Arg-Pro-Val-Lys-Val-Tyr-Pro-Asp-Gly-Ala-Glu-Asp-Glu-Ser-Ala-Glu-Ala-Phe-Pro-Leu-Glu-Phe | 24 adrenocorticotropic hormone | Regulation of activity of CNS |
| Structure 104 | Arg-Pro-Val-Lys-Val-Tyr-Pro-Asp-Gly-Ala-Glu-Asp-Glu-Ser-Ala-Glu-Ala-Phe-Pro-Leu-Glu-Phe | 24 adrenocorticotropic hormone | Regulation of activity of CNS |
| Structure 105 | Val-Phe-Pro-Leu-Glu-Phe | 25 adrenocorticotropic hormone | Regulation of activity of CNS |
| Structure 106 | Val-Phe-Pro-Leu-Glu-Phe | 25 adrenocorticotropic hormone | Regulation of activity of CNS |
| Structure 107 | Lys-Leu-Val-Phe-Phe | 26 Amyloid peptide | Anti-AD |
| Structure 108 | Lys-Leu-Val-Phe-Phe | 26 Amyloid peptide | Anti-AD |
| Structure 109 | Lys-Leu-Val-Phe-Phe | 26 Amyloid peptide | Anti-AD |
| Structure 110 | Asp-Arg-Val-Tyr-Ile-His-Pro-Phe-His-Leu | 27 Angiotentensin | Control blood pressure |
| Structure 111 | Asp-Arg-Val-Tyr-Ile-His-Pro-Phe-His-Leu | 27 Angiotentensin | Control blood pressure |
| Structure 112 | Asp-Arg-Val-Tyr-Ile-His-Pro-Phe | 28 Angiotentensin | Control blood pressure |
| Structure 113 | Asp-Arg-Val-Tyr-Ile-His-Pro-Phe | 28 Angiotentensin | Control blood pressure |
| Structure 114 | Asp-Arg-Val-Tyr-Ile-His-Pro-Ala | 29 Angiotentensin | Control blood pressure |
| Structure 115 | Asp-Arg-Val-Tyr-Ile-His-Pro-Ala | 29 Angiotentensin | Control blood pressure |
| Structure 116 | Asp-Arg-Val-Tyr-Ile-Xaa7-Pro-Phe | 30 Angiotentensin II agonist | Control blood pressure |
| Structure 117 | Asp-Arg-Val-Tyr-Ile-Xaa7-Pro-Phe | 30 Angiotentensin II agonist | Control blood pressure |

TABLE A-continued

Parent peptide of peptide HPPs/HPCs having structure of Structures 2-345

| Structure 118 | Ser-Arg-Val-Tyr-Ile-His-Pro-Phe | 31 | Angiotentensin II agonist | Control blood pressure |
| Structure 119 | Ser-Arg-Val-Tyr-Ile-His-Pro-Phe | 31 | Angiotentensin II agonist | Control blood pressure |
| Structure 120 | Asp-Arg-Val-Tyr-Ile-His-Pro-Ile | 32 | Angiotentensin II agonist | Control blood pressure |
| Structure 121 | Asp-Arg-Val-Tyr-Ile-His-Pro Ile | 32 | Angiotentensin II agonist | Control blood pressure |
| Structure 122 | MeGly-Arg-Val-Tyr-Ile-His-Pro-Phe | 33 | Angiotentensin II agonist | Control blood pressure |
| Structure 123 | MeGly-Arg-Val-Tyr-Ile-His-Pro-Phe | 33 | Angiotentensin II agonist | Control blood pressure |
| Structure 124 | MeGly-Arg-Val-Tyr-Ile-His-Pro-Ile | 34 | Angiotentensin II antagonist | Control blood pressure |
| Structure 125 | MeGly-Arg-Val-Tyr-Ile-His-Pro-Ile | 34 | Angiotentensin II antagonist | Control blood pressure |
| Structure 126 | MeGly-Arg-Val-Tyr-Val-His-Pro-Ala | 35 | Angiotentensin II agonist | Control blood pressure |
| Structure 127 | MeGly-Arg-Val-Tyr-Val-His-Pro-Ala | 35 | Angiotentensin II agonist | Control blood pressure |
| Structure 128 | Asp-Arg-Val-Tyr-Ile-His-Pro-Thr | 36 | Angiotentensin II agonist | Control blood pressure |
| Structure 129 | Asp-Arg-Val-Tyr-Ile-His-Pro-Thr | 36 | Angiotentensin II agonist | Control blood pressure |
| Structure 130 | Asp-Arg-Val-Tyr-Ile-His-Pro | 37 | Angiotentensin II agonist | Control blood pressure |
| Structure 131 | Asp-Arg-Val-Tyr-Ile-His-Pro | 37 | Angiotentensin II agonist | Control blood pressure |
| Structure 132 | Val-Tyr-Ile-His-Pro-Phe | 38 | Angiotentensin II agonist | Control blood pressure |
| Structure 133 | Arg-Val-Tyr-Ile-His-Pro-Phe | 39 | Angiotentensin II agonist | Control blood pressure |
| Structure 134 | Arg-Val-Tyr-Ile-His-Pro-Phe | 39 | Angiotentensin II agonist | Control blood pressure |
| Structure 135 | Glu-Gly-Val-Tyr-Val-His-Pro-Val | 40 | Angiotentensin II antagonist | Control blood pressure |
| Structure 136 | Xaa9-Tyr-Lys(Arg)-His-Pro-Ile | 41 | Angiotentensin II AT2 receptor | Control blood pressure |
| Structure 137 | Xaa9-Tyr-Lys(Arg)-His-Pro-Ile | 41 | Angiotentensin II agonist | Control blood pressure |
| Structure 138 | Xaa9-Tyr-Lys(Arg)-His-Pro-Ile | 41 | Angiotentensin II agonist | Control blood pressure |
| Structure 139 | Arg-Leu-Cys-Arg-Ile-Val-Val-Ile-Arg-Val-Cys-Arg | 42 | Antimicrobial peptide | Antimicrobial |
| Structure 140 | Arg-Leu-Cys-Arg-Ile-Val-Val-Ile-Arg-Val-Cys-Arg | 42 | Antimicrobial peptide | Antimicrobial |
| Structure 141 | Ala-Leu-Trp-Lys-Thr-Met-Leu-Lys-Lys-Leu-Gly-Thr-Met-Ala-Leu-His-Ala-Gly | 43 | Antimicrobial peptide | Antimicrobial |

TABLE A-continued

Parent peptide of peptide HPPs/HPCs having structure of Structures 2-345

| | | | |
|---|---|---|---|
| Structure 142 | Ala-Leu-Trp-Lys-Thr-Met-Leu-Lys-Lys-Leu-Gly-Thr-Met-Ala-Leu-His-Ala-Gly | 43 Antimicrobial peptide | Antimicrobial |
| Structure 143 | Ala-Leu-Trp-Lys-Thr-Met-Leu-Lys-Lys-Leu-Gly-Thr-Met-Ala-Leu-His-Ala-Gly | 43 Antimicrobial peptide | Antimicrobial |
| Structure 144 | Ala-Leu-Trp-Lys-Thr-Met-Leu-Lys-Lys-Leu-Gly-Thr-Met-Ala-Leu-His-Ala-Gly | 43 Antimicrobial peptide | Antimicrobial |
| Structure 145 | Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln | 44 Antimicrobial peptide | Antimicrobial |
| Structure 146 | Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln | 44 Antimicrobial peptide | Antimicrobial |
| Structure 147 | Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln | 44 Antimicrobial peptide | Antimicrobial |
| Structure 148 | Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-Gln | 44 Antimicrobial peptide | Antimicrobial |
| Structure 149 | Gly-Met-Ala-Ser-Lys-Ala-Gly-Ala-Ile-Ala-Gly-Lys-Ile-Ala-Lys-Val-Ala-Leu-Lys-Ala-Leu | 45 Antimicrobial peptide | Antimicrobial |
| Structure 150 | Gly-Met-Ala-Ser-Lys-Ala-Gly-Ala-Ile-Ala-Gly-Lys-Ile-Ala-Lys-Val-Ala-Leu-Lys-Ala-Leu | 45 Antimicrobial peptide | Antimicrobial |
| Structure 151 | Gly-Met-Ala-Ser-Lys-Ala-Gly-Ala-Ile-Ala-Gly-Lys-Ile-Ala-Lys-Val-Ala-Leu-Lys-Ala-Leu | 45 Antimicrobial peptide | Antimicrobial |
| Structure 152 | Gly-Met-Ala-Ser-Lys-Ala-Gly-Ala-Ile-Ala-Gly-Lys-Ile-Ala-Lys-Val-Ala-Leu-Lys-Ala-Leu | 45 Antimicrobial peptide | Antimicrobial |
| Structure 153 | Gly-Met-Ala-Ser-Lys-Ala-Gly-Ala-Ile-Ala-Gly-Lys-Ile-Ala-Lys-Val-Ala-Leu-Lys-Ala-Leu | 45 Antimicrobial peptide | Antimicrobial |
| Structure 154 | Met-Arg-Gly-Phe-Val | 46 Antibiotic resistance peptide | Antibiotic resistance |
| Structure 155 | Met-Arg-Gly-Phe-Val | 46 Antibiotic resistance peptide | Antibiotic resistance |
| Structure 156 | Met-Gln-Met-Lys-Lys-Val-Leu-Asp-Ser | 47 Anti-inflammatory peptide | Anti-inflammation |

TABLE A-continued

Parent peptide of peptide HPPs/HPCs having structure of Structures 2-345

| | | | |
|---|---|---|---|
| Structure 157 | Met-Gln-Met-Lys-Lys-Val-Leu-Asp-Ser | 47 Anti-inflammatory peptide | Anti-inflammation |
| Structure 158 | Met-Gln-Met-Lys-Lys-Val-Leu-Asp-Ser | 47 Anti-inflammatory peptide | Anti-inflammation |
| Structure 159 | His-Asp-Met-Asn-Lys-Val-Leu-Asp-Leu | 48 Anti-inflammatory peptide | Anti-inflammation |
| Structure 160 | His-Asp-Met-Asn-Lys-Val-Leu-Asp-Leu | 48 Anti-inflammatory peptide | Anti-inflammation |
| Structure 161 | Met-Gln-Met-Asn-Lys-Val-Leu-Asp-Ser | 49 Anti-inflammatory peptide | Anti-inflammation |
| Structure 162 | Met-Gln-Met-Asn-Lys-Val-Leu-Asp-Ser | 49 Anti-inflammatory peptide | Anti-inflammation |
| Structure 165 | Arg-Pro-Pro-Gly-Phe-Ser-Pro-Phe-Arg | 51 bradykinin | Induction of hypotension |
| Structure 166 | D-Arg-Arg-Pro-Xaa26-Gly-Phe-Ser-Phe-Leu-Arg | 52 Bradykinin antagonist | Control blood pressure |
| Structure 167 | Arg-Pro-Pro-Gly-Phe-Ser-Pro-Phe | 53 Bradykinin agonist | Control blood pressure |
| Structure 168 | Arg-Pro-Pro-Gly-Phe-Ser-Pro-Leu | 54 Bradykinin antagonist | Control blood pressure |
| Structure 169 | Arg-Pro-Pro-Gly-Phe-Ser-D-Phe-Phe-Arg | 55 Bradykinin antagonist | Control blood pressure |
| Structure 170 | Asp-Tyr-Met-Gly-Trp-Met-Asp-Phe | 56 Gastrin | Control of food intake |
| Structure 171 | Asp-Tyr-Met-Gly-Trp-Met-Asp-Phe | 56 Gastrin | Control of food intake |
| Structure 172 | Gly-Trp-Thr-Leu-Asn-Ser-Ala-Gly-Tyr-Leu-Leu-Gly-Pro-Pro-Pro-Gly-Phe-Ser-Pro-Phe-Arg | 57 Galanin antagonist | Control of food intake |
| Structure 173 | Gly-Trp-Thr-Leu-Asn-Ser-Ala-Gly-Tyr-Leu-Leu-Gly-Pro-Arg-Pro-Lys-Pro-Gln-Gln-Trp-Phe-Trp-Leu-Leu | 58 Galanin antagonist | Control of food intake |
| Structure 174 | Gly-Trp-Thr-Leu-Asn-Ser-Ala-Gly-Tyr-Leu-Leu-Gly-Pro-Arg-Pro-Lys-Pro-Gln-Gln-Trp-Phe-Trp-Leu-Leu | 58 Galanin antagonist | Control of food intake |
| Structure 175 | Gly-Trp-Thr-Leu-Asn-Ser-Ala-Gly-Tyr-Leu-Leu-Gly-Pro-Gln-Gln-Phe-Phe-Gly-Leu-Met | 59 Galanin antagonist | Control of food intake |
| Structure 176 | Cys-Gly-Asn-Leu-Ser-Thr-Cys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro | 60 calcitonin | Calcium homeostasis |

TABLE A-continued

Parent peptide of peptide HPPs/HPCs having structure of Structures 2-345

| | | | | |
|---|---|---|---|---|
| Structure 177 | Cys-Gly-Asn-Leu-Ser-Thr-Cys-Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro | 60 | calcitonin | Calcium homeostasis |
| Structure 178 | Ala-Ala-Gly-Ile-Leu-Thr-Val | 61 | melanoma-associated antigen peptide | Anti-tumor |
| Structure 179 | Asn-Ala-Ala-Arg-Gln-Gly-Phe-Leu-Asn-Thr-Leu-Val-Val-Leu-His-Arg-Ala-Gly-Ala-Arg | 62 | melanoma-associated antigen peptide | Anti-tumor |
| Structure 180 | Tyr-Met-Asp-Gly-Thr-Met-Ser-Gln-Val | 63 | melanoma-associated antigen peptide | Anti-tumor |
| Structure 181 | Ile-Ile-Ser-Ala-Val-Val-Gly-Ile-Leu | 64 | melanoma-associated antigen peptide | Anti-tumor |
| Structure 182 | His-His-Leu-Gly-Gly-Ala-Lys-Gln-Ala-Gly-Asp-Val | 65 | Fibrinogen peptide | Inhibit platelet aggregation |
| Structure 183 | His-His-Leu-Gly-Gly-Ala-Lys-Gln-Ala-Gly-Asp-Val | 66 | Fibrinogen peptide | Inhibit platelet aggregation |
| Structure 184 | Glu-His-Ile-Pro-Ala | 67 | Fibrinogen peptide | Inhibit platelet aggregation |
| Structure 185 | Arg-Gly-Asp-Val | 68 | Fibrinogen peptide | Inhibit platelet aggregation |
| Structure 186 | Cyclo[Arg-Gly-Asp-D-Phe-Val] | 69 | Fibrinogen peptide | Inhibit platelet aggregation |
| Structure 187 | Arg-Gly-Asp-Ser | 70 | Fibrinogen peptide | Inhibit platelet aggregation |
| Structure 188 | Thr-Asp-Val-Asn-Gly-Asp-Gly-Arg-His-Asp-Leu | 71 | Fibrinogen peptide | Inhibit platelet aggregation |
| Structure 189 | Gly-Pro-Arg-Pro | 72 | Fibrinogen peptide | Inhibit platelet aggregation |
| Structure 190 | D-Arg-Gly-Asp-Trp | 73 | Fibrinogen peptide | Inhibit platelet aggregation |
| Structure 191 | Trp-Thr-Val-Pro-Thr-Ala | 74 | Fibrinogen peptide | Inhibit platelet aggregation |
| Structure 192 | Cys-Arg-Lys-Gln-Ala-Ala-Ser-Ile-Lys-Val-Ala-Val-Ser | 75 | Laminin peptide | Inhibit metastasis |
| Structure 193 | Leu-Gly-Thr-Ile-Pro-Gly | 76 | Laminin peptide | Inhibit metastasis |
| Structure 194 | Tyr-Ile-Gly-Ser-Arg | 77 | Laminin peptide | Inhibit metastasis |
| Structure 195 | Ser-Ala-Gly-Thr | 78 | Vitronectin peptide | Inhibit metastasi |
| Structure 196 | Cys-Arg-Lys-Gln-Ala-Ala-Ser-Ile-Lys-Val-Ala-Val-Ser | 79 | Laminin peptide | Inhibit metastasis |
| Structure 197 | Cys-Arg-Lys-Gln-Ala-Ala-Ser-Ile-Lys-Val-Ala-Val-Ser | 79 | Laminin peptide | Inhibit metastasis |

TABLE A-continued

Parent peptide of peptide HPPs/HPCs having structure of Structures 2-345

| | | | |
|---|---|---|---|
| Structure 198 | Val-His-Phe-Phe-Lys-Asn-Ile-Val-Thr-Ala-Arg-Thr-Pro | 80 EAE inducing peptides | Control allergic encephalomyelitis |
| Structure 199 | Val-His-Phe-Phe-Lys-Asn-Ile-Val-Thr-Ala-Arg-Thr-Pro | 80 EAE inducing peptides | Control allergic encephalomyelitis |
| Structure 200 | Cys-Ser-Cys-Ser-Ser-Leu-Met-Asn-Lys-Glu-Cys-Val-Tyr-Phe-Cys-His-Leu-Asp-Ile-Ile-Trp | 81 Endothelin peptide | Control blood pressure |
| Structure 201 | Cys-Ser-Cys-Ser-Ser-Leu-Met-Asn-Lys-Glu-Cys-Val-Tyr-Phe-Cys-His-Leu-Asp-Ile-Ile-Trp | 81 Endothelin peptide | Control blood pressure |
| Structure 202 | Ala-Ser-Ala-Ser-Ser-Leu-Met-Asp-Lys-Glu-Ala-Val-Tyr-Phe-Ala-His-Leu-Asp-Ile-Ile-Trp | 82 Endothelin peptide | Control blood pressure |
| Structure 203 | Ala-Ser-Ala-Ser-Ser-Leu-Met-Asp-Lys-Glu-Ala-Val-Tyr-Phe-Ala-His-Leu-Asp-Ile-Ile-Trp | 82 Endothelin peptide | Control blood pressure |
| Structure 204 | Leu-Met-Asp-lys-Glu-Ala-Val-Tyr-Phe-Ala-His-Leu-Asp-Ile-Ile-Trp | 83 Endothelin peptide | Control blood pressure |
| Structure 205 | Asp-Glu-Glu-Ala-Val-Tyr-Phe-Ala-His-Leu-Asp-Ile-Ile-Trp | 84 Endothelin peptide | Control blood pressure |
| Structure 206 | Cys-Val-Tyr-Phe-Cys-His-Leu-Asp-Ile-Ile-Trp | 85 Endothelin peptide antagonist | Control blood pressure |
| Structure 207 | Cyclo(D-Trp-D-Asp-Pro-D-Val-Leu) | 86 Endothelin peptide antagonist | Control blood pressure |
| Structure 208 | Xaa13-Leu-Asp-Ile-Ile-Trp | 87 Endothelin peptide antagonist | Control blood pressure |
| Structure 209 | Cys-Ser-Cys-Ser-Ser-Trp-Leu-Asp-Lys-Glu-Cys-Val-Tyr-Phe-Cys-His-Leu-Asp-Ile-Ile-Trp | 88 Endothelin peptide | Control blood pressure |
| Structure 210 | Cys-Ser-Cys-Ser-Ser-Trp-Leu-Asp-Lys-Glu-Cys-Val-Tyr-Phe-Cys-His-Leu-Asp-Ile-Ile-Trp | 88 Endothelin peptide | Control blood pressure |
| Structure 211 | Cys-Thr-Cys-Phe-Thr-Tyr-Lys-Asp-Cys-Val-Tyr-Tyr-Cys-His-Leu-Asp-Ile-Ile-Trp | 89 Endothelin peptide | Control blood pressure |
| Structure 212 | Cys-Thr-Cys-Phe-Thr-Tyr-Lys-Asp-Cys-Val-Tyr-Tyr-Cys-His-Leu-Asp-Ile-Ile-Trp | 89 Endothelin peptide | Control blood pressure |
| Structure 213 | Val-Gln-Gly-Glu-Glu-Ser-Asn-Asp-Lys | 90 Growth factors | Control growth |
| Structure 214 | Val-Gln-Gly-Glu-Glu-Ser-Asn-Asp-Lys | 90 Growth factors | Control growth |
| Structure 215 | Asp-Val-Val-Asp-Ala-Asp-Glu-Tyr-Leu-Ile-Pro-Gln | 91 Growth factors | Control growth |

TABLE A-continued

Parent peptide of peptide HPPs/HPCs having structure of Structures 2-345

| | | | |
|---|---|---|---|
| Structure 216 | Asp-Ala-Asp-Glu-Tyr-Leu | 92 Growth factors | Control growth |
| Structure 217 | Xaa14-Met-His-Ile-Glu-Ser-Leu-Asp-Ser-Tyr-Thr-Xaa14 | 93 Growth factors | Control growth |
| Structure 218 | Tyr-Arg-Ser-Arg-Lys-Tyr-Ser-Ser-Trp-Tyr | 94 Growth factors | Control growth |
| Structure 219 | Ala-Leu-Leu-Glu-Thr-Tyr-Cys-Ala-Thr-Pro-Ala-Lys-Ser-Glu | 95 Growth factors | Control growth |
| Structure 220 | Ala-Leu-Leu-Glu-Thr-Tyr-Cys-Ala-Thr-Pro-Ala-Lys-Ser-Glu | 95 Growth factors | Control growth |
| Structure 221 | His-D-Trp-Ala-Trp-D-Phe-Lys | 96 Growth hormone releasing peotide | Control growth hormone |
| Structure 222 | His-D-Trp-Ala-Trp-D-Phe-Lys | 96 Growth hormone releasing peotide | Control growth hormone |
| Structure 223 | His-D-Trp-D-Lys-Trp-D-Phe-Lys | 97 Growth hormone releasing peotide | Control growth hormone |
| Structure 224 | His-D-Trp-D-Lys-Trp-D-Phe-Lys | 97 Growth hormone releasing peotide | Control growth hormone |
| Structure 225 | His-D-Trp-D-Lys-Trp-D-Phe-Lys | 97 Growth hormone releasing peotide | Control growth hormone |
| Structure 226 | Xaa15-His-Trp-Ser-Tyr-Gly-Leu-Arg-Pro-Gly | 98 Luteinizing hormone releasing hormone | Control luteinizing hormone |
| Structure 227 | Xaa15-His-Trp-Ser-Tyr-Gly-Leu-Arg-Pro-Gly | 98 Luteinizing hormone releasing hormone | Control luteinizing hormone |
| Structure 228 | Xaa15-His-Trp-Ser-Tyr-Gly-Leu-Arg-Pro | 99 Luteinizing hormone releasing hormone agonist | Control luteinizing hormone |
| Structure 229 | Xaa15-His-Trp-Ser-Tyr-Gly-Leu-Arg-Pro | 99 Luteinizing hormone releasing hormone agonist | Control luteinizing hormone |
| Structure 230 | Xaa15-His-Trp-Ser-His-Asp-Trp-Lys-Pro-Gly | 100 Luteinizing hormone releasing hormone agonist | Control luteinizing hormone |
| Structure 231 | Ala-Gly-Cys-Lys-Asn-Phe-Phe-Trp-Lys-Thr-Phe-Thr-Ser-Cys | 101 somatostatin | Control growth hormone |

TABLE A-continued

Parent peptide of peptide HPPs/HPCs having structure of Structures 2-345

| | | | |
|---|---|---|---|
| Structure 232 | Ala-Gly-Cys-Lys-Asn-Phe-Phe-Trp-Lys-Thr-Phe-Thr-Ser-Cys | 101 somatostatin | Control growth hormone |
| Structure 233 | Ala-Gly-Cys-Lys-Asn-Phe-Phe-Trp-Lys-Thr-Phe-Thr-Ser-Cys | 101 somatostatin | Control growth hormone |
| Structure 234 | Xaa15-Leu-Asn-Phe-Ser-Ala-Gly-Trp | 102 neuropeptide | Regulator of energy metabolism |
| Structure 235 | Xaa15-Leu-Asn-Phe-Ser-Thr-Gly-Trp | 103 neuropeptide | Regulator of energy metabolism |
| Structure 236 | Xaa15-Leu-Asn-Phe-Ser-Thr-Gly-Trp | 103 neuropeptide | Regulator of energy metabolism |
| Structure 237 | Glu-Ala-Leu-Glu-Leu-Ala-Arg-Gly-Ala-Ile-Phe-Gln-Ala | 104 neuropeptide | Brain injury |
| Structure 238 | Ser-Tyr-Ser-Met-Glu-His-Phe-Arg-Trp-Gly-Lys-Pro-Val | 105 Melanocyte stimulating hormones | Control melanocyte |
| Structure 239 | Ser-Tyr-Ser-Met-Glu-His-Phe-Arg-Trp-Gly-Lys-Pro-Val | 105 Melanocyte stimulating hormones | Control melanocyte Food intake |
| Structure 240 | Cys-Nle-Arg-His-Xaa17-Arg-Trp-Gly-Cys | 106 Melanocyte stimulating hormones | Control melanocyte Food intake |
| Structure 241 | Cys-Glu-His-D-Xaa17-Arg-Trp-Gly-Cys-Pro-Pro-Lys-Asp | 107 Melanocyte stimulating hormones | Control melanocyte Food intake |
| Structure 242 | Nle-Asp-His-Phe-Arg-Trp-Lys | 108 Melanocyte stimulating hormones | Control melanocyte Food intake dysfunction |
| Structure 243 | Nle-Asp-His-Xaa17-Arg-Trp-Lys | 109 Melanocyte stimulating hormones | Control melanocyte Food intake |
| Structure 244 | Nle-Gln-His-D-Phe-Arg-D-Trp-Gly | 110 Melanocyte stimulating hormones | Control melanocyte Food intake Anti-inflammation |
| Structure 245 | Nle-Lys-His-D-Phe-Arg-D-Trp-Gly | 205 Melanocyte stimulating hormones | Control melanocyte Food intake Anti-inflamation |
| Structure 246 | Nle-Lys-His-D-Phe-Arg-D-Trp-Gly | 205 Melanocyte stimulating hormones | Control melanocyte Food intake Anti-inflamation |
| Structure 247 | Nle-Asp-His-Xaa17-Arg-Trp-Lys | 111 Melanocyte stimulating hormones | Control melanocyte Food intake male and female sexual dysfunction |
| Structure 248 | Nle-Asp-His-D-Phe-Arg-Trp-Lys | 112 Melanocyte stimulating hormones | Control melanocyte Food intake male and female sexual dysfunction |

TABLE A-continued

Parent peptide of peptide HPPs/HPCs having structure of Structures 2-345

| | | | |
|---|---|---|---|
| Structure 249 | Trp-Ala-Gly-Gly-Asp-Ala-Ser-Gly-Glu | 113 Sleep inducing peptide | Sleep inducing |
| Structure 344 | Arg-Lys-Asp-Val-Tyr | 172 immunostimulant | enhances the production of thymic T cells and may help restore immunocompetence in immunosuppressed subjects |
| Structure 345 | Arg-Lys-Asp-Val-Tyr | 172 immunostimulant | enhances the production of thymic T cells and may help restore immunocompetence in immunosuppressed subjects |

(II)

| Peptide HPP/HPC | Parent Drug | SEQ ID NO. |
|---|---|---|
| Structure163 | Tyr-Thr-Ser-Leu-Ile-His-Ala-Leu-Ile-Gln-Gln-Ser-Gln-Asn-Gln-Gln-Gln-Lys-Asn-Glu-Gln-Glu-Leu-Leu-Glu-Leu-Asp-Lys-Trp-Ala-Ser-Leu-Trp-Asn-Trp-Phe | 50 |
| Structure164 | Tyr-Thr-Ser-Leu-Ile-His-Ala-Leu-Ile-Gln-Gln-Ser-Gln-Asn-Gln-Gln-Gln-Lys-Asn-Glu-Gln-Glu-Leu-Leu-Glu-Leu-Asp-Lys-Trp-Ala-Ser-Leu-Trp-Asn-Trp-Phe | 50 |
| Structure250 | Phe-Met-Arg-Phe | 114 |
| Structure251 | Xaa15-Asp-Pro-Phe-Leu-Arg-Phe | 115 |
| Structure252 | Cys-Nle-Arg-His-Xaa17-Arg-Trp-Gly-Cys | 116 |
| Structure253 | Glu-Ala-Leu-Glu-Leu-Ala-Arg-Gly-Ala-Ile-Phe-Gln-Ala | 117 |
| Structure254 | Glu-Ala-Leu-Glu-Leu-Ala-Arg-Gly-Ala-Ile-Phe-Gln-Ala | 117 |
| Structure255 | Phe-Leu-Phe-Gln-Pro-Gln-Arg-Phe | 118 |
| Structure256 | Tyr-Ile-Asn-Leu-Ile-Tyr-Arg-Leu-Arg-Tyr | 119 |
| Structure257 | His-Tyr-Ile-Asn-Leu-Ile-Thr-Arg-Gln-Arg-Tyr | 120 |
| Structure258 | Tyr-Ile-Asn-Leu-Ile-Thr-Arg-Gln-Arg-Tyr | 121 |
| Structure259 | Ile-Asn-Pro-Ile-Tyr-Arg-Leu-Arg-Tyr | 122 |
| Structure260 | Arg-Phe-Met-Trp-Met-Lys | 123 |
| Structure261 | Tyr-D-Ala-Phe-Asp-Val-Val-Gly | 124 |
| Structure262 | Tyr-D-Ala-Phe-Glu-Val-Val-Gly | 125 |
| Structure263 | Tyr-Xaa4-Gly-Phe-Xaa4 | 126 |
| Structure264 | Tyr-Xaa4-Gly-Xaa19-Xaa4 | 127 |
| Structure265 | Tyr-Pro-Trp-Thr-Gln-Arg-Phe | 128 |
| Structure266 | Phe-Leu-Phe-Gln-Pro-Gln-Arg-Phe | 129 |
| Structure267 | Tyr-Pro-Phe-Phe | 130 |
| Structure268 | Tyr-Pro-Trp-Phe | 131 |
| Structure269 | Xaa25-Tyr-Phe-Gln-Asn-Cys-Pro-D-Arg-Gly | 132 |
| Structure270 | Cys-Tyr-Phe-Gln-Asn-Cys-Pro-Lys-Gly | 133 |

TABLE A-continued

Parent peptide of peptide HPPs/HPCs having structure of Structures 2-345

| | | |
|---|---|---|
| Structure271 | Cys-Tyr-Phe-Gln-Asn-Cys-Pro-Lys-Gly | 133 |
| Structure272 | Tyr-Glu-Glu-Ile-Glu | 134 |
| Structure273 | Tyr-Glu-Glu-Ile-Glu | 134 |
| Structure274 | Tyr-Glu-Glu-Ile-Glu | 134 |
| Structure275 | Tyr-Glu-Glu-Ile-Glu | 134 |
| Structure276 | Thr-Ser-Thr-Glu-Pro-Gln-Tyr-Gln-Pro-Gly-Glu-Asn-Leu | 135 |
| Structure277 | Tyr-Glu | 136 |
| Structure278 | Leu-Arg-Arg-Ala-Ser-Leu-Gly | 137 |
| Structure279 | Arg-Phe-Ala-Arg-Lys-Gly-Ala-Leu-Arg-Gln-Lys-Asn-Val-His-Glu-Val-Lys-Asn | 138 |
| Structure280 | Arg-Phe-Ala-Arg-Lys-Gly-Ala-Leu-Arg-Gln-Lys-Asn-Val-His-Glu-Val-Lys-Asn | 138 |
| Structure281 | Arg-Phe-Ala-Arg-Lys-Gly-Ala-Leu-Arg-Gln-Lys-Asn-Val-His-Glu-Val-Lys-Asn | 138 |
| Structure282 | Arg-Phe-Ala-Arg-Lys-Gly-Ala-Leu-Arg-Gln-Lys-Asn-Val-His-Glu-Val-Lys-Asn | 138 |
| Structure283 | Arg-Phe-Ala-Arg-Lys-Gly-Ala-Leu-Arg-Gln-Lys-Asn-Val | 139 |
| Structure284 | Arg-Phe-Ala-Arg-Lys-Gly-Ala-Leu-Arg-Gln-Lys-Asn-Val | 139 |
| Structure285 | Arg-Phe-Ala-Arg-Lys-Gly-Ala-Leu-Arg-Gln-Lys-Asn-Val | 139 |
| Structure286 | Arg-Phe-Ala-Arg-Lys-Gly-Ser-Leu-Arg-Gln-Lys-Asn-Val | 140 |
| Structure287 | Arg-Phe-Ala-Arg-Lys-Gly-Ser-Leu-Arg-Gln-Lys-Asn-Val | 140 |
| Structure288 | Arg-Phe-Ala-Arg-Lys-Gly-Ala-Leu-Arg-Gln-Lys-Asn-Val | 141 |
| Structure289 | Gln-Lys-Arg-Pro-Ser-Gln-Arg-Ser-Lys-Tyr-Leu | 142 |
| Structure290 | Gln-Lys-Arg-Pro-Ser-Gln-Arg-Ser-Lys-Tyr-Leu | 142 |
| Structure291 | Gln-Lys-Arg-Pro-Ser-Gln-Arg-Ser-Lys-Tyr-Leu | 142 |
| Structure292 | Gly-Lys-Gly-Arg-Gly-Leu-Ser-Leu-Ser-Arg-Phe-Ser-Trp-Gly-Ala | 143 |
| Structure293 | Gly-Lys-Gly-Arg-Gly-Leu-Ser-Leu-Ser-Arg-Phe-Ser-Trp-Gly-Ala | 143 |
| Structure294 | Gly-Lys-Gly-Ala-Gly-Leu-Ser-Leu-Ser-Arg-Phe-Ser-Trp-Gly-Ala | 144 |
| Structure295 | Gly-Lys-Gly-Ala-Gly-Leu-Ser-Leu-Ser-Arg-Phe-Ser-Trp-Gly-Ala | 144 |
| Structure296 | Gly-Lys-Gly-Arg-Gly-Leu-Ser-Leu-Ser-Ala-Phe-Ser-Trp-Gly-Ala | 206 |
| Structure297 | Gly-Lys-Gly-Arg-Gly-Leu-Ser-Leu-Ser-Ala-Phe-Ser-Trp-Gly-Ala | 206 |
| Structure298 | Arg-Lys-Glu-Val-Tyr | 145 |
| Structure299 | Arg-Lys-Glu-Val-Tyr | 145 |
| Structure300 | Arg-Lys-Glu-Val-Tyr | 145 |
| Structure301 | Arg-Lys-Glu-Val-Tyr | 145 |
| Structure302 | D-Phe-Cys-Tyr-D-Trp-Lys-Val-Cys-Trp | 146 |
| Structure303 | D-Phe-Cys-Tyr-D-Trp-Lys-Val-Cys-Trp | 146 |
| Structure304 | Asp-Ser-Phe-Val-Xaa21-Leu-Met | 147 |

TABLE A-continued

Parent peptide of peptide HPPs/HPCs having structure of Structures 2-345

| | | |
|---|---|---|
| Structure305 | Asp-Lys-Phe-Val-Gly-N-Me-Leu-Nle | 148 |
| Structure306 | Asp-Lys-Phe-Val-Gly-N-Me-Leu-Nle | 148 |
| Structure307 | Asp-Ser-Phe-Val-Gly-Leu-Nle | 149 |
| Structure308 | Asp-Tyr-D-Trp-Val-D-Trp-D-Trp-Lys | 150 |
| Structure309 | Asp-Tyr-D-Trp-Val-D-Trp-D-Trp-Lys | 150 |
| Structure310 | Asp-Met-His-Asp-Phe-Phe-Val-Gly-Leu-Met | 151 |
| Structure311 | Leu-Asp-Gln-Trp-Phe-Gly | 152 |
| Structure312 | Asp-Met-His-Asp-Phe-Phe-N-Me-Phe-Gly-Leu-Met | 153 |
| Structure313 | Asp-Met-His-Asp-Phe-Phe-Pro-Gly-Leu-Met | 154 |
| Structure314 | Arg-Pro-Lys-Pro-Gln-Gln-Phe-Phe-Gly-Leu-Met | 155 |
| Structure315 | D-Arg-D-Pro-Lys-Pro-Gln-Gln-D-Trp-Phe-D-Trp-Leu-Leu | 156 |
| Structure316 | D-Arg-D-Pro-Lys-Pro-Gln-Gln-D-Trp-Phe-D-Trp-Leu-Leu | 156 |
| Structure317 | Arg-Pro-Lys-Pro-Gln-Gln-Phe-Phe-D-Pro-Pro-Trp | 157 |
| Structure318 | Arg-Pro-Lys-Pro-Gln-Gln-Phe-Phe-D-Pro-Pro-Trp | 157 |
| Structure319 | Arg-Pro-Lys-Pro-Gln-Gln-Phe-Phe-D-Pro-MeLeu-Trp | 158 |
| Structure320 | Arg-Pro-Lys-Pro-Gln-Gln-Phe-Phe-D-Pro-MeLeu-Trp | 158 |
| Structure321 | Arg-Pro-Lys-Pro-Gln-Gln-Phe-Phe-Pro-Leu-Met | 159 |
| Structure322 | Arg-Pro-Lys-Pro-Gln-Gln-Phe-Phe-Pro-Leu-Met | 159 |
| Structure323 | Arg-Pro-Lys-Pro-Gln-Gln-Phe-Phe-Ser-Leu-Xaa22 | 160 |
| Structure324 | Arg-Pro-Lys-Pro-Gln-Gln-Phe-Phe-Ser-Leu-Xaa22 | 160 |
| Structure325 | Tyr-D-Phe-Phe-D-His-Leu-Met | 161 |
| Structure326 | Arg-Ala-D-Trp-Phe-D-Pro-Pro-Nle | 162 |
| Structure327 | Arg-Ala-D-Trp-Phe-D-Pro-Pro-Nle | 162 |
| Structure328 | Arg-Ala-D-Trp-Phe-D-Pro-Pro-Nle | 162 |
| Structure329 | Ala-Ala-D-Trp-Phe-D-Pro-Pro-Nle | 163 |
| Structure330 | Tyr-Phe-Leu-Leu-Arg-Asn-Pro | 164 |
| Structure331 | Met-Ser-Arg-Pro-Ala-Cys-Pro-Asn-Asp-Lys-Tyr-Glu | 165 |
| Structure332 | Met-Ser-Arg-Pro-Ala-Cys-Pro-Asn-Asp-Lys-Tyr-Glu | 165 |
| Structure333 | Val-Val-Xaa23-Ala-Xaa23 | 166 |
| Structure334 | Val-Val-Xaa23-Ala-Xaa23 | 166 |
| Structure335 | Val-Val-Xaa23-Ala-Xaa23 | 166 |
| Structure336 | His-Cys-Lys-Phe-Trp-Trp | 167 |
| Structure337 | His-Cys-Lys-Phe-Trp-Trp | 167 |
| Structure338 | Thr-Tyr-Ile-Cys-Glu-Val-Glu-Asp-Gln-Lys-Glu-Glu | 168 |
| Structure339 | Thr-Tyr-Ile-Cys-Glu-Val-Glu-Asp-Gln-Lys-Glu-Glu | 168 |
| Structure340 | Tyr-Ala-Gly-Ala-Val-Val-Asn-Asp-Leu | 169 |
| Structure341 | Ile-Leu-Pro-Trp-Lys-Trp-Pro-Trp-Trp-Pro-Trp-Arg-Arg | 170 |

TABLE A-continued

Parent peptide of peptide HPPs/HPCs having structure of Structures 2-345

| | | |
|---|---|---|
| Structure342 | Ile-Leu-Pro-Trp-Lys-Trp-Pro-Trp-Trp-Pro-Trp-Arg-Arg | 170 |
| Structure343 | Thr-Asp-Val-Asn | 171 |

The structures of the unusual amino acids (Xaa1, Xaa2, Xaa3, Xaa4, Xaa5, Xaa7, Xaa9, Xaa13, Xaa14, Xaa15, Xaa17, Xaa19, Xaa21, Xaa22, Xaa23, Xaa24, Xaa25, and Xaa26) appeared in SEQ ID NO. 1-172 are listed in Table B:

TABLE B

Unusual amino acids appeared in SEQ ID NO. 1-172

| Abbreviation | Structure |
|---|---|
| Xaa | (structure with $NH_2$, $R_4$, COOH) wherein $R_4$ is defined the same as supra. |
| Xaa1 (MePhe) | (structure) |
| Xaa2 (Met(O2)-L) | (structure) |
| Xaa3 (Retro-inverso-Thr) | (structure) |
| Xaa4 (D-Pen) | (structure) |
| Xaa5 | (structure) |
| Xaa7 (4-amino Phe) | (structure) |
| Xaa9 | (structure) |
| Xaa13 (Ac-Dip) | (structure) |
| Xaa14 (Cys(Acm)) | (structure) |
| Xaa15 (pGlf) | (structure) |
| Xaa17 (D-Nal(2)) | (structure) |

TABLE B-continued

Unusual amino acids appeared in SEQ ID NO. 1-172

| Abbreviation | Structure |
|---|---|
| Xaa19 | H₂N—CH(—CH₂-C₆H₄-Cl)—C(O)—OH |
| Xaa21 | NH₂—CH₂—CH₂—C(O)—OH |
| Xaa22 | H₂N—CH(—CH₂—CH₂—S(O)₂—CH₃)—C(O)—OH |
| Xaa23 | H₂N—CH(—CH(OH)—CH(CH₃)₂)—CH₂—C(O)—OH |
| Xaa24 | HO—C(O)—CH(—CH₂—C₆H₅)—NH—CH(CH₃)—C(O)—OH |
| Xaa25 | HS—CH₂—CH₂—C(O)—OH |
| Xaa26 | 4-hydroxy-pyrrolidine-2-carboxylic acid |

In certain embodiments, a peptide HPP/HPC includes a compound having a structure selected from the group consisting of Structures 2-345 as defined supra, including stereoisomers and pharmaceutically acceptable salts thereof, wherein:

HA, Ar, X, $X_4$, $X_5$, $X_6$, $X_7$, $X_8$, $X_9$, $X_{10}$, $X_{21}$, $X_{22}$, $X_{23}$, $X_{24}$, $X_{25}$, $X_{26}$, and $X_{27}$ are defined the same as supra;

R is selected from the group consisting of H, substituted and unsubstituted 1-20 carbon alkyl, substituted and unsubstituted cycloalkyl, and substituted and unsubstituted heterocycloalkyl, substituted and unsubstituted 1-20 carbon alkoxyl, substituted and unsubstituted 1-20 carbon alkylthio, substituted and unsubstituted 1-20 carbon alkylamino, substituted and unsubstituted aryl, and substituted and unsubstituted heteroaryl residues;

$R_1$, $R_2$, $R_4$, $R_5$, $R_6$, $R_7$, $R_8$, $R_9$, $R_{10}$, $R_{21}$, $R_{22}$, $R_{23}$, $R_{24}$, $R_{25}$, $R_{26}$, and $R_{27}$ are independently selected from the group consisting of H, O, substituted and unsubstituted 1-20 carbon alkyl, substituted and unsubstituted cycloalkyl, and substituted and unsubstituted heterocycloalkyl, substituted and unsubstituted 1-20 carbon alkoxyl, substituted and unsubstituted 1-20 carbon alkylthio, substituted and unsubstituted 1-20 carbon alkylamino, substituted and unsubstituted 1-20 carbon alkenyl, substituted and unsubstituted 1-20 carbon alkynyl, substituted and unsubstituted aryl, and substituted and unsubstituted heteroaryl residues;

In certain embodiments, a peptide HPP/HPC comprises a structure selected form the group consisting of Structure 1a, Structure 1b, Structure 1c, Structure 1d, Structure 1e, Structure 1f, Structure 1g, and Structure 1h:

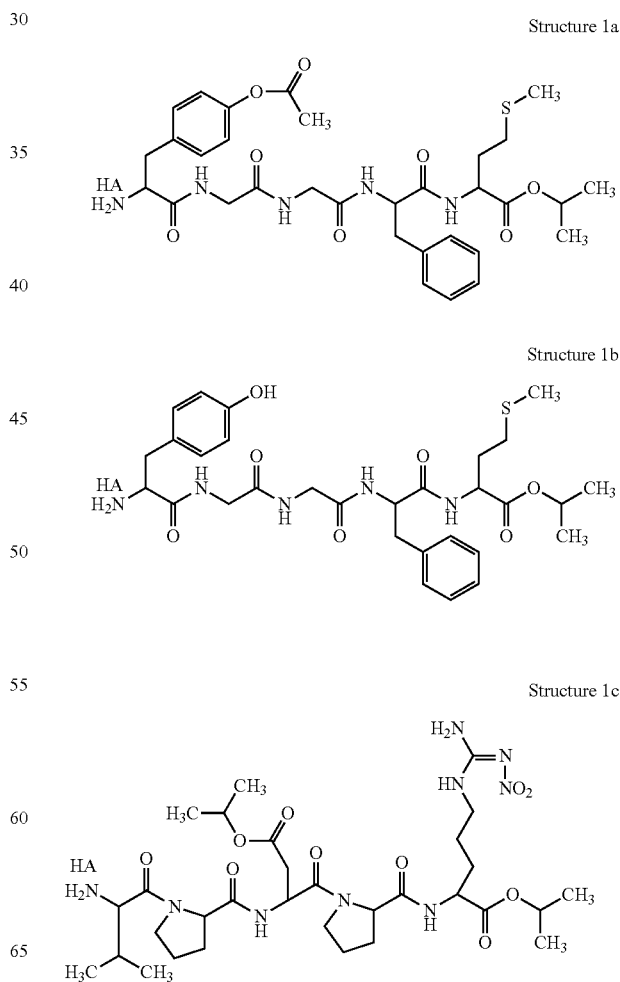

Structure 1a

Structure 1b

Structure 1c

-continued

Structure 1d
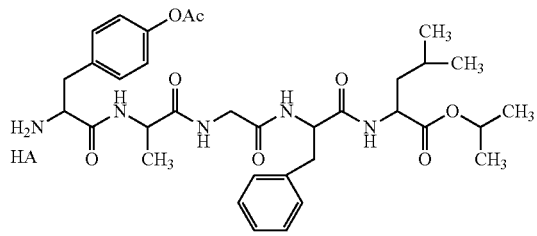

Structure 1e
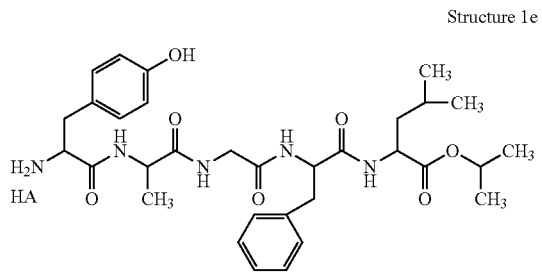

Structure 1f
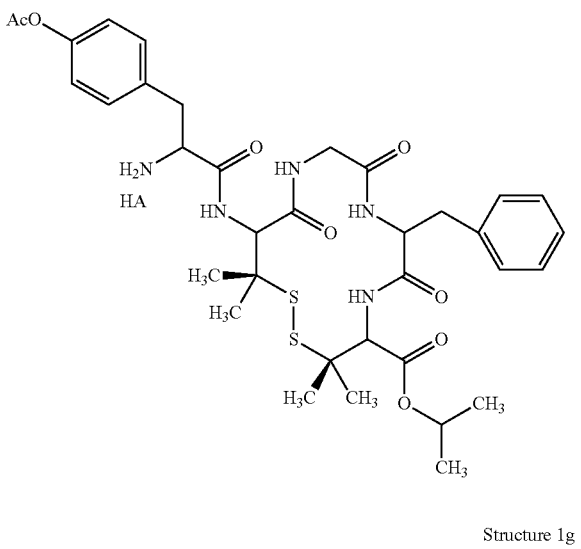

Structure 1g
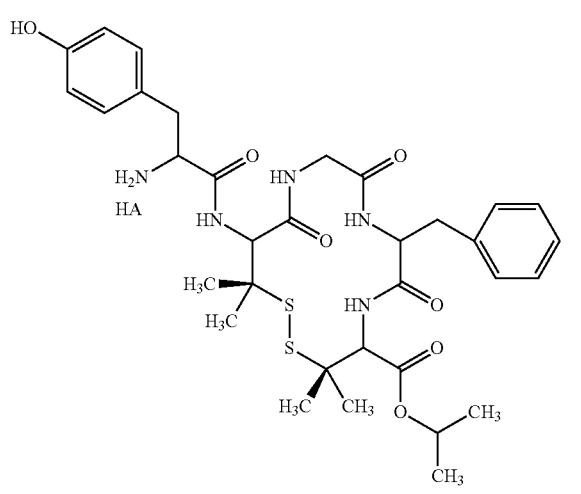

-continued

Structure 1h
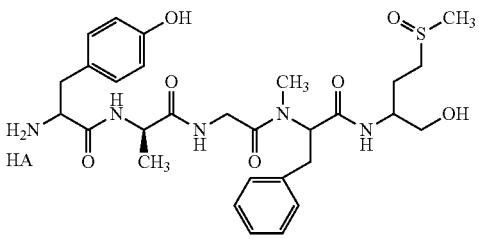

including stereoisomers and pharmaceutically acceptable salts thereof, wherein:

$X_4, X_5, X_6, X_7, X_8, X_9, R_4, R_5, R_6, R_7, R_8, R_9$, and HA are defined the same as supra.

Solid-phase Synthesis of Peptide HPP/HPC

Shorter peptides (<10 amino acids) can be synthesized by solution phase synthesis, but it is very difficult for the synthesis of long peptides by solution phase. HPPs/HPCs of peptides in the present disclosure are modified peptides and cannot be synthesized by standard solid-phase peptide synthesis method (from C-terminal to N-terminal).

In certain embodiments, a peptide HPP/HPC is synthesized from N-terminal to C-terminal, wherein the synthesis method comprises the following steps:

A method of preparing a peptide HPC using solid-phase synthesis comprising:

a) providing a chemically modified resin (e.g. trityl chloride resin and carbonate ester resin);

b) protecting the carboxylic group of all the natural or modified amino acid residues as desired according to the peptide HPC with a protecting group (e.g. 2-(4-nitrophenylsulfonyl)ethyl group and 9-fluorenylmethyl group) to provide a COOH-protected amino acid residue;

c) coupling the COOH-protected amino acid residue at the N-terminal of the peptide HPC to the chemically modified resin to provide an immobilized COOH-protected peptide HPC precursor having one amino acid residue;

d) deprotecting the protected carboxylic group of the immobilized COOH-protected peptide HPC precursor using deprotecting reagents (e.g. 1% DBU/20% piperidine/79% DMF, or other reagents that can deprotect the protected carboxylic group); to provide an immobilized COOH-unprotected peptide HPC precursor having one amino acid residue;

e) repeating steps c) and d) using the COOH-protected amino acid residue of the peptide HPC until an immobilized C-unprotected peptide HPC precursor having all amino acid residues except for the C-terminal amino acid residue is provided;

f) linking a C-terminal amino acid residue with linking a C-terminal amino acid residue with $R_T$ via covalent bond to provide a modified C-terminal amino acid wherein $R_T$ is selected from the group consisting of substituted and unsubstituted alkyl, substituted and unsubstituted cycloalkyl, substituted and unsubstituted heterocloalkyl, substituted and unsubstituted alkyloxyl, substituted and unsubstituted alkenyl, substituted and unsubstituted alkynyl, substituted and unsubstituted aryl, substituted and unsubstituted heteroaryl, and transportational unit selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra;

g) coupling the modified C-terminal amino acid to the immobilized C-unprotected peptide HPC precursor obtained from step e) to provide an immobilized peptide HPC; and h) releasing the immobilized peptide HPC from the resin to provide the peptide HPC.

In certain embodiments, a chemically modified resin can be coupled directly with the protected amino acid, or a chemically modified resin can be further modified first and then couple with the COOH-protected amino acid;

In certain embodiments, a peptide HPP/HPC comprising a transportational unit on the C-terminal amino acid is prepared by coupling to the peptide chain the C-terminal amino acid wherein the carboxylic group is linked to a transportational unit as described supra. For example, the transportational unit is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra.

In certain embodiments, a peptide HP/HPC comprising a transportational unit on the C-terminal amino acid is prepared by coupling to the peptide chain the C-terminal amino acid wherein the carboxylic group is protected, deprotecting the carboxylic group, and finally coupling to a transportational unit. For example, the transportational unit is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra.

In certain embodiments, releasing the peptide HPP/HPC is accomplished with high yield. For example, in certain embodiments, the resin is a trityl chloride resin wherein the releasing step can be accomplished by reacting with TFA/DCM (e.g. 5%). In certain embodiments, the resin is a carbonate ester resin, and the releasing step can be accomplished by reacting with Pd—C (e.g. 10% in methanol) and $H_2$.

In certain embodiments, the coupling reaction is carried out in the presence of coupling reagents. Examples of coupling reagents include, without limitation, HBTU/DIPEA/HOBt, TBTU/DIPEA/HOBt, BOP/DIPEA/HOBt, HATU/DIPEA/HOBt, and DIC/HOB, and combinations thereof.

As used herein, unless defined otherwise:

"DBU" means 1,8-diazabicyclo[5,4,0]undec-7-ene;
"DMF" means dimethylformamide;
"DIPEA" means N,N-diisopropylethylamine;
"HBTU" means O-Benzotriazole-N,N,N',N'-tetramethyluronium-hexafluoro phosphate;
"HOBt" means 1-hydroxylbenzotriazole;
"TBTU" means O-Benzotriazole-N,N,N',N'-tetramethyluronium-tetrafluoroborate;
"BOP" means benzotriazole-1-yl-N-oxy-tris(pyrrolidino) phosphonium hexafluorophosphate;
"HATU" means N-[(dimethylamino)-1H-1,2,3-triazolo[4,5-b]pyridino-1-ylmethylene]-N-methylmethanaminium hexafluorophosphate N-oxide;
"DIC" means diisopropylcarbodiimide; and
"TFA" means trifluoroacetic acid.

II. Pharmaceutical compositions comprising HPPs/HPCs

Another aspect of the invention relates to a pharmaceutical composition comprising at least one peptide HPP/HPC and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a HPP/HPC from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., a HPP/HPC, of the formulation and suitable for use in contact with the tissue or organ of a biological system without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. water, acetone and alcohol.

The concentration of HPP/HPC in these formulations can vary widely, and will be selected primarily based on fluid volumes, viscosities, body weight and the like in accordance with the particular mode of administration selected and the biological system's needs. For example, the concentration can be 0.0001% to 100%, 0.001% to 50%, 0.01% to 30%, 0.1% to 10% wt.

The compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges.

Thus, a typical pharmaceutical composition for intravenous administration would be about $10^{-10}$ g to about 100 g, about $10^{-10}$ g to about $10^{-3}$ g, about $10^{-9}$ g to about $10^{-6}$ g, about $10^{-6}$ g to about 100 g, about 0.001 g to about 100 g, about 0.01 g to about 10 g, or about 0.01 g to about 1 g per subject per day. Dosages from about 0.01 mg, up to about 50 g, per subject per day may be used. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

III. Applications of HPPs/HPCs i) Methods for Penetrating a Biological Barrier.

Another aspect of the invention relates to a method of using a composition of the invention in penetrating one or more biological barriers in a biological subject. The method comprises a step of administering to a biological subject a HPP/HPC or a peptide or peptide-related compound, or a pharmaceutical composition thereof. In certain embodiments, a HPP/HPC exhibits more than about 10 times or higher, 50 times or higher, >about 100 times or higher, >about 200 time higher, >about 300 times or higher, >about 500 times or higher, >about 1,000 times or higher penetration rate through one or more biological barriers than its parent drug.

The term "biological barrier" as used herein refers to a biological layer that separates an environment into different spatial areas or compartments, which separation is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a cell layer, a biological structure, an inner surface of subjects, organisms, organs or body cavities, an external surface of subjects, organisms, organs or body cavities, or any combination or plurality thereof.

Examples of a biological membrane include a lipid bilayer structure, eukaryotic cell membrane, prokaryotic cell membrane, and intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies).

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of a cell layer include a lining of eukaryotic cells (e.g., epithelium, lamina propria and smooth muscle or muscularis mucosa (in gastrointestinal tract)), a lining of prokaryotic cells (e.g., surface layer or S-layer which refers to a two dimensional structure monomolecular layer composed of identical proteins or glycoproteins, specifically, an S-layer refers to a part of a cell envelope commonly found in bacteria and archaea), a biofilm (a structured community of microorganisms encapsulated within a self-developed polymeric matrix and adherent to a living or inert surface), and a plant cell layer (e.g., empidermis). The cells may be normal cells or pathological cells (e.g. disease cells, cancer cells).

Examples of biological structures include structures sealed by tight or occluding junctions which provide a barrier to the entry of toxins, bacteria and viruses, e.g. the blood milk barrier and the blood brain barrier (BBB). In particular, BBB is composed of an impermeable class of endothelium, which presents both a physical barrier through tight junctions adjoining neighboring endothelial cells and a transport barrier comprised of efflux transporters. The biological structure may also include a mixture of cells, proteins and sugars (e.g. blood clots).

Examples of the inner surface of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of the external surface of subjects, organisms, organs or body cavities include capillaries (e.g. capillaries in the heart tissue), mucous membranes that are continuous with skin (e.g. such as at the nostrils, the lips, the ears, the genital area, and the anus), outer surface of an organ (e.g. liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani), skin, cuticle (e.g. dead layers of epidermal cells or keratinocytes or superficial layer of overlapping cells covering the hair shaft of an animal, a multi-layered structure outside the epidermis of many invertebrates, plant cuticles or polymers cutin and/or cutan), external layer of the wall of a pollen grain or the external wall layer of a spore), and a combination or plurality thereof.

In addition, a biological barrier further includes a sugar layer, a protein layer or any other biological layer, or a combination or plurality thereof. For example, skin is a biological barrier that has a plurality of biological layers. A skin comprises an epidermis layer (outer surface), a demis layer and a subcutaneous layer. The epidermis layer contains several layers including a basal cell layer, a spinous cell layer, a granular cell layer, and a stratum corneum. The cells in the epidermis are called keratinocytes. The stratum corneum ("horny layer") is the outmost layer of the epidermis, wherein cells here are flat and scale-like ("squamous") in shape. These cells contain a lot of keratin and are arranged in overlapping layers that impart a tough and oilproof and waterproof character to the skin's surface.

ii) Methods for Diagnosing a Condition in a Biological System.

Another aspect of the invention relates to a method of using a composition of the invention in diagnosing a condition in a biological system. The method comprises the following steps:

1) administrating a composition comprising a peptide HPP/HPC to the biological subject;

2) detecting the presence, location or amount of the HPP/HPC, the functional unit of the HP P/HPC or a metabolite thereof in the biological subject; and 3) determining a condition in the biological system.

In certain embodiments, the HPP/HPC (or the agent cleaved from the HPP/HPC) aggregates in the site of action where a condition occurs. In certain embodiments, the presence, location or amount of the functional unit of the HPP/HPC is also detected. In certain embodiments, the onset, development, progress, or remission of a condition (e.g., cancer) associated is also determined.

In certain embodiments, the HPP/HPC is labeled with or conjugated to a detectable agent. Alternatively, the HPP/HPC is prepared to include radioisotopes for detection. Numerous detectable agents are available which can be generally grouped into the following categories:

(a) Radioisotopes, such as $^{35}S$, $^{14}C$, $^{13}C$, $^{15}N$, $^{125}I$, $^{3}H$, and $^{131}I$. The diagnostic agent can be labeled with the radioisotope using the techniques known in the art and radioactivity can be measured using scintillation counting; in addition, the diagnostic agent can be spin labeled for electron paramagnetic resonance for carbon and nitrogen labeling.

(b) Fluorescent agents such as BODIPY, BODIPY analogs, rare earth chelates (europium chelates), fluorescein and its derivatives, FITC, 5,6 carboxyfluorescein, rhodamine and its derivatives, dansyl, Lissamine, phycoerythrin, green fluorescent protein, yellow fluorescent protein, red fluorescent protein and Texas Red. Fluorescence can be quantified using a fluorometer.

(c) Various enzyme-substrate agents, such luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

In certain embodiments, the detectable agent is not necessarily conjugated to the diagnostic agent but is capable of recognizing the presence of the diagnostic agent and the diagnostic agent can be detected.

In certain embodiments, a peptide HPP/HPC can be provided in a kit, i.e., a packaged combination of reagents in predetermined amounts with instructions for performing the diagnostic assay. Where the HPP/HPC is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

iii) Methods for Screening a Substance for a Desired Character

Another aspect of the invention relates to a method of screening a HPP/HPC for a desired character.

In certain embodiments, the method comprises:
1) covalently linking a test functional unit to a transportational unit through a linker to form a test composition (or covalently linking a functional unit to a test transportational unit through a linker, or covalently linking a functional unit to a transportational unit through a test linker)
2) administrating the test composition to a biological system; and
3) determining whether the test composition has the desired nature or character.

In one embodiment, a desired character may include, for example, 1) the ability of a test functional unit to form a high penetration composition or convert back to a parent drug, 2) the penetration ability and/or rate of a test composition, 3) the efficiency and/or efficacy of a test composition, 4) the transportational ability of a test transportational unit, and 5) the cleavability of a test linker.

iv) Methods for Treating a Condition in a Biological Subject

Another aspect of the invention relates to a method of using a composition of the invention in treating a condition in a biological system. The method comprises administrating the pharmaceutical composition to the biological system.

The term "treating" as used herein means curing, alleviating, inhibiting, or preventing. The term "treat" as used herein means cure, alleviate, inhibit, or prevent. The term "treatment" as used herein means cure, alleviation, inhibition or prevention.

The term "biological system," "biological subject" or "subject" as used herein means an organ, a group of organs that work together to perform a certain task, an organism, or a group of organisms. The term "organism" as used herein means an assembly of molecules that function as a more or less stable whole and has the properties of life, such as animal, plant, fungus, or micro-organism.

The term "animal" as used herein means an eukaryotic organism characterized by voluntary movement. Examples of animal include, without limitation, vertebrata (e.g. human, mammals, birds, reptiles, amphibians, fishes, marsipobranchiata and leptocardia), tunicata (e.g. thaliacea, appendicularia, sorberacea and ascidioidea), articulata (e.g. insecta, myriapoda, malacapoda, arachnida, pycnogonida, merostomata, crustacea and annelida), gehyrea (anarthropoda), and helminthes (e.g. rotifera).

The term "plant" as used herein means organisms belonging to the kingdom Plantae. Examples of plant include, without limitation, seed plants, bryophytes, ferns and fern allies. Examples of seed plants include, without limitation, cycads, ginkgo, conifers, gnetophytes, angiosperms. Examples of bryophytes include, without limitation, liverworts, hornworts and mosses. Examples of ferns include, without limitation, ophioglossales (e.g. adders-tongues, moonworts, and grape-ferns), marattiaceae and leptosporangiate ferns. Examples of fern allies include, without limitation, lycopsida (e.g. clubmosses, spikemosses and quillworts), psilotaceae (e.g. lycopodiophyta and whisk ferns) and equisetaceae (e.g. horsetails).

The term "fungus" as used herein means a eukaryotic organism that is a member of the kingdom Fungi. Examples of fungus include, without limitation, chytrids, blastocladiomycota, neocallimastigomycota, zygomycota, glomeromycota, ascomycota and basidiomycota.

The term "micro-organism" as used herein means an organism that is microscopic (e.g. with length scale of micrometer). Examples of micro-organism include, without limitation, bacteria, fungi, archaea, protists and microscopic plants (e.g. green algae) and microscopic animals (e.g. plankton, planarian and amoeba).

Some examples of the conditions the method can treat include conditions that can be treated by the parent drug of the HPP/HPC.

v). Methods of Using Peptide HPPs/HPCs and Pharmaceutical Compositions Thereof in Treatments.

Another aspect of the invention relates to a method of using peptide HPPs/HPCs, or pharmaceutical compositions thereof in treating a condition in a biological system or subject by administrating a peptide HPP/HPC, or a pharmaceutical composition thereof to the biological system or subject.

Peptides and peptides-related compounds can be used to regulate a wide range of biological processes in a biological system. Conditions that are related to such biological processes are treatable by the corresponding peptides or peptide-related compounds, and therefore treatable by peptide HPPs/HPCs, and a pharmaceutical composition thereof.

Such conditions include, but are not limited to, aging, angina, antithrombin deficiency, arrhythmia, atherosclerosis, artrial fibrillation, atrial flutter, blood clots, cardiacischemia, cardiac surgery, cardiomyopathy, cardiovascular abnormalities, carotid artery disease, chest pain, circulation disorders, claudication, collagen vascular diseases, congenital heart diseases, congestive heart failure, coronary artery disease, diabetes, diabetes and hypertension, dyslipidemia, dysrhythmia, elevated triglycerides, heart defect, heart disease, heart failure, heart valve disease, hemangioma, high chlolesterol, hypertriglyceridemia, intermittent claudication, hypertension, Kawasaki disease, heart attack, myocardial ischemia, orthostatic hypotension, peripheral arterial disease, peripheral arterial occlusive disease, peripheral vascular disease, Raynaud's disease, smoking cessation, tachycardia (fast heart rate), thrombosis, varicose veins, vascular diseases, venous leg ulcers, gingivitis, gum diseases, halitosis, oral cancer, periodontal disease, temporomandibular disorders, temporomandibular joint syndrome, sunburn, acne, skin aging, alopecia, anesthesia, athlete's foot, atopic dermatitis, bed sores (decubitus ulcers), bunions, burns, burn infections, cold sores (herpes labialis infections), congenital skin diseases, contact dermatitis, cutaneous lupus erythematosus, diabetic foot ulcers, eczema, excessive sweating, fabry disease, fungal infections, genital herpes, genital warts, hair loss, hair removal, hand dermatitis, head lice, hemangioma, hereditary angioedema, herpes simplex infections, herpes Zoster infections, herpetic neuralgia, hives, ichthyosis, ischemic foot ulcers, keratoses, lupus, male pattern baldness, malignant melanoma, medical prosthetics, melanoma, molluscum contagiosum, mycosis fungoides, onychomycosis, pemphigus vulgaris, postherpetic neuralgia, pressure ulcers, psoriasis and psoriatic disorders, psoriatic arthritis, razor bumps, rosacea, sarcoidosis, scalp disorders, scar tissue, scleroderma, seborrhea, seborrheic dermatitis, shingles, skin cancer, skin infections, skin lipomas, skin wounds, solar lentigines, sporotrichosis, staphylococcai skin infections, stasis dermatitis, stretch marks, systemic fungai infections, sun poisoning, ringworm, tinea capitis, tinea versicolor, urticaria, vitiligo, warts, wounds, acromegaly, adrenal cancer, congenital adrenal hyperplasia, diabetes mellitus (type I and type II), diabetes mellitus (type I), diabetes mellitus (type II), diabetic gastroparesis, diabetic kidney disease, diabetic macular edema, diabetic neuropathy, diabetic retinopathy, diabetic vitreous hemorrhage, dyslipidemia, female hormonal deficiencies/abnormalities, Fredrickson type III. hyperlipoproteinemia, growth hormone deficiencies/abnormalities, gynecomastia, hair removal, hyperlipidemia, hormone deficiencies, hot flash, hyperparathyroidism, idiopathic short stature, indication: diabetes type II, male hormonal deficiencies/abnormalities, McCune-Albright syndrome, menopause disorders, metabolic syndrome, obesity, ovarian cancer, pancreatic cancer, pancreatic disorders, pancreatitis, parathyroid cancer, parathyroid disease, parathyroid disorders, perimenopause, pituitary disorders, polycystic ovarian syndrome, post menopause disorders, post menopause osteopenia, precocious puberty, primary insulin hypersecretion, severe short stature, sexual dysfunction, thyroid disease, thyroid disorders, Turner syndrome, Wilms' tumor, Wilson's disease, abdominal cancer, achalasia, alpha 1 antitrypsin deficiency, anal fissures, appendicitis, Barrett's esophagus, biliary tract cancer, bowel dysfunction, celiac disease, chronic diarrhea, *clostridium difficile*-associated diarrhea, colon cancer, colon polyps, colorectal cancer, constipation, Crohn's disease, diabetic gastroparesis, digestive system neoplasms, duodenal ulcers, Fabry disease, fecal incontinence, functional dyspepsia, gall bladder disorders, gastric cancer, gastric ulcers, gastroenteritis, gastroesophageal reflux disease, gastrointestinal disease and disorders, gastroparesis, heartburn, *helicobacter pylori*, hemorrhoids, hepatic encephalopathy, hepatitis, ileus, infectious colitis, inflammatory bowel disease, intra-abdominal infections, irritable bowel syndrome, liver disease, liver disorders, non-erosive reflux disease, non-ulcer dyspepsia, organ rejection following organ transplantation, post-operative nausea and vomiting, vomiting, rectal cancer, rectal disorders, recurrent diarrhea, stomach cancer, stomach discomfort, ulcerative colitis, abnormal blood vessels, acute myelogenous leukemia, anemia, anemia (non-Hodgking lymphoma), non-small-cell lung cancer, anemic cancer, aneurysm, antiphospholipid syndrome, antithrombin deficiency, aplastic anemia, blood clots, candidemia/candidiasis, chronic renal anemia, Gaucher disease, hematologic cancer, hematological disorders, paroxysmal hemoglobinuria, hemorrhages, hypercalcemia, hypogammaglobulinemia, hyponatremia, idiopathic thrombocytopenic purpura, islet cell cancer, leukemia, B-cell lymphoma, lymphomas, multiple myelomas, myelodysplastic syndromes, myocardial ischemia, occlusions, platelet deficiencies, platelet disorders, red cell disorders, renal anemia, sezary syndrome, sickle cell disease, T-cell lymphoma, thalassemia, thrombocytopenia, von Willebrand's disease, white cell disorders, acquired immune deficiency syndrome (AIDS), AIDS related infections, acute rhinitis, allergies, asthma, anal dysplasia, bacterial infections, canker sores, celiac disease, cervical dysplasia, chickenpox, chronic fatigue syndrome, common cold, common variable immunodeficiency, bacterial conjunctivitis, chronic obstructive pulmonary disease, cutaneous candidiasis, cutaneous T-cell lymphoma, cytomegalovirus infections, dermatomyositis, fever, graft-versus-host disease, hepatitis, hepatitis B, hepatitis C, HIV infections, HIV/AIDS, human papilloma virus infections, hypogammaglobulinemia, idiopathic inflammatory myopathies, influenza, intra-abdominal infections, Kaposi's sarcoma, lupus, lyme tick disease, *mycobacterium avium* complex infection, meningitis, onychomycosis, oral candidiasis, pneumonia, polymyositis (inflammatory muscle disease), postherpetic neuralgia, primary immunodeficiency disorders, respiratory syncytial virus infection, rheumatic fever, allergic rhinitis, rotavirus infection, sarcoidosis, sepsis and septicemia, sexually transmitted diseases, shingles, Sjogren's syndrome, smallpox, soft tissue infections, staphylococcal infections, staphylococcal skin infections, strep throat, systemic candidiasis, systemic lupus erythematosus, throat and tonsil infections, urticaria, vancomycin resistant enterococci, west nile virus infections, acromegaly, ankylosing spondylitis, bone loss, athletic injuries, bone diseases, bone metastases, breast pain, bunions, bursitis, carpal tunnel syndrome, cartilage injuries, chest pain, chronic back pain, chronic leg pain, chronic pain, chronic shoulder pain, claudication, congenital lactic acidosis, connective tissue diseases, dermatomyositis, dupurtren's disease, fibromyalgia, Frozen shoulder, adhesive capsulitis, gout (hyperuricemia), idiopathic inflammatory myopathies, intermittent claudication, joint injuries, knee injuries, multiple sclerosis, muscle pain, muscular dystrophy, musculoskeletal diseases, myasthenia gravis (chronic weakness), myasthenia gravis generalized, orthopedics, osteoarthritis, osteomyelitis, osteoporosis, osteosarcoma, Paget's disease, partial medial meniscectomy, parathyroid disease, post-menopausal osteopenia, post-menopausal osteoporosis, reflex sympathetic dystrophy syndrome, rheumatoid arthritis, sciatica, spinal cord disorders, spinal cord malignancy, spine athroplasty, sprains, tendon injuries, tennis elbow, tic disorders, anal dysplasia, benign prostatic hyperplasia, bladder cancer, bladder disorders, blood cancers, catheter complications, chronic pelvic pain, diabetic kidney disease, enuresis, erectile dysfunction, fabry disease, nocturia, genitourinary prolapse, glomerulonephritis, glomerulosclerosis, idiopathic membranous nephropathy, impotence, interstitial cystitis, kidney cancer, kidney disease, kidney failure, kidney stones, liver cancer, low testosterone, mastectomy, medical prosthetics, nephropathy, Peyronie's disease, premature ejaculation, prostate cancer, prostate disorders, prostatic intraepithelial neoplasia, proteinuria, Reiter's syndrome, renal artery disease, renal cell carcinoma, renal failure, testicular cancer, tyrosinemia, urethral strictures, urinary incontinence, urinary tract infections, urothelial tract cancer, male erectile dysfunction and female sex dysfunction, systemic blood pressure, abortion, hypotensive control, inhibition of platelet aggregation, pulmonary diseases, gastrointestinal disease, inflammation, shock, reproduction, fertility, obesity.

Conditions related to platelet aggregation include, for example, thromboembolis after surgery, carotid endarterectomy, the recurrence of stenosis after coronary angioplasty, thromboembolis complications in chronic arterial fibrillation, aortocornonary-artery-bypass graft occlusion, heart attack, stroke, multi-infract dementia, dementia, hemodialysis shunt thrombosis and arterial embolic complications in patients' prosthetic heart valves.

Some examples of the conditions that are treatable by a method comprising using a peptide HPP/HPC, or a pharmaceutical composition thereof include, without limitation, peptide-hormone related conditions, inflammation and related conditions, platelet aggregation related conditions, neuropeptide related conditions, microorganism related conditions and other conditions regulated by peptides or peptide-related compounds.

In certain embodiments, a method of treating a peptide treatable condition comprises administering to a biological system a peptide HPP/HPC of a peptide or a peptide-related compound such as angiotentensin, angiotensin II antagonists, angiotentensin II AT2 receptor, antimicrobial peptides, antioxytocin, hormones, antidiuretic hormones, adrenocorticotropic hormones, antimicrobial peptide, anti-inflammatory peptide, bradykinin, bradykinin antagonist, endothelin peptides, endothelin peptide antagonist, gastrin, calcitonin, melanoma-associated antigen peptide, laminin peptide, fibrinogen peptide, EAE inducing peptides, growth factors, growth hormone releasing peotides, somatostatin, hormone releasing hormones, luteinizing hormone releasing hormone, neuropeptide, melanocyte stimulating hormones, sleep inducing peptide, amyloid peptide, tuftsin, retro inverso-tuftsin, enterostatins, Melanocortin II, and opioid peptides and mimics.

In certain embodiments, a method of treating a peptide-hormone related condition comprises administering to a biological system a HPP/HPC of a peptide-hormone or a peptide-hormone related compound, or a pharmaceutical composition thereof. In a biological system, hormones regulate a wide range of processes such as energy levels, reproduction, growth and development, homeostasis, and reactions to surroundings, stress and injury. Examples of peptide-hormone related conditions include, without limitation:
a) menopause;
b) bone diseases, e.g. osteoporosis, Paget's disease and bone metastases;
c) growth hormone deficiency;
d) hyperthyroidism or hypothyroidism;
e) metabolism disorder, e.g. obesity, abnormal blood glucose level, abnormal blood lipid level, diabetes mellitus (type I or/and type II) and diabetes-induced complications, including diabetic retinopathy, necrobiotic ulcers, and diabetic proteinuria;
f) abnormal blood pressure, e.g. hypertension and hypotension;
g) skin condition, e.g. psoriasis and psoriatic disorders, acne, cystic acne, pus-filled or reddish bumps, comedones, papules, pustules, nodules, epidermoid cysts, keratosis pilaris, abnormal vascular skin lesions, birthmarks, moles (nevi), skin tags, scleroderma, vitiligo and related diseases, or aging spots (liver spots);
h) autoimmune disease, e.g. discoid lupus erythematosus, systemic lupus erythematosus (SLE), autoimmune hepatitis, clerodarma, Sjogren's syndrome, rheumatoid arthritis, polymyositis, scleroderma, Hashimoto's thyroiditis, juvenile diabetes mellitus, Addison disease, vitiligo, pernicious anemia, glomerulonephritis, pulmonary fibrosis, multiple sclerosis (MS) and Crohn's disease;
i) eye disease, e.g. glaucoma, ocular hypertension, loss of vision after ophthalmic surgery, vision of a warm-blooded animal impaired by cystoid macular edema and cataract;
j) preeclamptic toxemia in high-risk women;
k) male and female sexual dysfunction;
j) allergy and asthma;
k) insomnia;
l) depression and related conditions;
m) cardiovascular diseases, e.g. heart attack, unstable angina, peripheral occlusive arterial disease and stroke;
n) tumor, e.g. benign tumor, breast cancer, colon-rectum cancer, oral cancer, lung or other respiratory system cancers, skin cancers, uterus cancer, pancreatic cancer, prostate cancer, genital cancer, urinary organs cancers, leukemia or other blood and lymph tissues cancer; and
o) metastasis.

In certain embodiments, a method of treating a microorganism related condition comprises administering to a biological system a HPP/HPC of an anti-microbial peptide or a anti-microbial peptide-related compound, or a pharmaceutical composition thereof. Examples of microorganisms related conditions include, without limitation, inflammation and related conditions:
a) pain;
b) injuries;
c) conditions related to microorganisms;
d) inflammation related conditions, e.g. prostate gland inflammation (prostatitis), prostatocystitis, prostate enlarge fibrosis, hemorrhoids, Kawasaki syndrome, gastroenteritis, type-1 membranoproliferative glomerulonephritis, Bartter's syndrome, chronic uveitis, ankylosing spondylitis, hemophilic arthropathy, inflamed hemorrhoids, post irradiation (factitial) proctitis, chronic ulcerative colitis, inflammatory bowel disease, cryptitis, periodontitis, arthritis, and an inflammatory condition in an organ selected from the group consisting of liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani.

In certain embodiments, a method of treating a neuropeptide-related condition comprises administering to a biological system a HPP/HPC of a neuropeptide or a neuropeptide-related compound, or a pharmaceutical composition thereof. Examples of neuropeptide related conditions include, without limitation, pain, and neurodegenerative disease, e.g. Alzheimer's diseases and Parkinson's disease.

Other conditions that are treatable by a HPP/HPC or a pharmaceutical composition thereof include, without limitation, conditions relate to: conditions related to platelet aggregation, e.g. thromboembolis after surgery, carotid endarterectomy, the recurrence of stenosis after coronary angioplasty, thromboembolis complications in chronic arterial fibrillation, aortocornonary-artery-bypass graft occlusion, heart attack, stroke, multi-infract dementia, dementia, hemodialysis shunt thrombosis and arterial embolic complications in patients' prosthetic heart valves; antepartum, postpartum, anti-AD activities, antidiuretic activities, brain injury, calcium homeostasis, melanocye, activities of CNS and phagocytosis, In certain embodiments, a method of treating a condition in a subject amelioratable or treatable with peptides or peptide-related compounds comprises administering a therapeutic effective amount of a peptide HPP/HPC, or a pharmaceutical composition thereof to the subject.

A HPP/HPC or a pharmaceutical composition thereof can be administered to a biological system by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration.

A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

A HPP/HPC or a pharmaceutical composition thereof can be given to a subject in the form of formulations or preparations suitable for each administration route. The formulations useful in the methods of the invention include one or more HPPs/HPCs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of a HPP/HPC which can be combined with a carrier material to produce a pharmaceutically effective dose will generally be that amount of a HPP/HPC which produces a therapeutic effect. Generally, out of one hundred percent, this amount will range from about 1 percent to about ninety-nine percent of the HPP/HPC, preferably from about 20 percent to about 70 percent.

Methods of preparing these formulations or compositions include the step of bringing into association a HPP/HPC with one or more pharmaceutically acceptable carriers and, optionally, one or more accessory ingredients. In general, the formulations are prepared by uniformly and intimately bringing into association a HPP/HPC with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a HPP/HPC as an active ingredient. A compound may also be administered as a bolus, electuary, or paste.

In solid dosage forms for oral administration (e.g., capsules, tablets, pills, dragees, powders, granules and the like), the HPP/HPC is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a HPP/HPC therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the HPP(s)/HPC(s) only, or preferentially, in a certain portion of the gastrointestinal tract, optionally, in a delayed manner. Examples of embedding compositions which can be used include polymeric substances and waxes. The HPP/HPC can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the HPP/HPC, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the HPP/HPC, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more HPPs/HPCs with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal or dermal administration of a HPP composition include powders, sprays, ointments, pastes, creams, lotions, gels, solutions, patches and inhalants. The active component may be mixed under sterile conditions with a pharmaceutically acceptable carrier, such as water, ethanol, and ethanol solution, and with any preservatives, buffers, or propellants which may be required. The ointments, pastes, creams and gels may contain, in addition to the HPP composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the HPP composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

A HPP/HPC or a pharmaceutical composition thereof can be alternatively administered by aerosol. This can be accomplished by preparing an aqueous aerosol, liposomal preparation or solid particles containing the HPPs/HPCs. A nonaqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver HPP compositions to a tumor site. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

In certain embodiments, a transdermal therapeutic application system comprises a peptide HPP/HPC as an active substance for treating conditions treatable by a parent compound thereof, wherein the system is a spray or rub-on solution further comprising a solvent that can dissolve the peptide HPP/HPC. Examples of solvent include, without limitation, organic solvents and inorganic solvents such as water, ethanol, isopropanol, acetone, DMSO, DMF, and combinations thereof.

In certain embodiments, a transdermal therapeutic application system comprises a peptide HPP/HPC as an active substance for treating conditions treatable by a parent compound thereof, wherein the system further comprises a subject comprising an active substance-containing matrix layer and an impermeable backing layer. In certain embodiments, such subject is a patch or a bandage. In certain embodiments, such subject is an active substance reservoir comprising a permeable bottom facing the skin, wherein by controlling the rate of release, the system enables the active ingredient or a metabolite of the active ingredient to reach constantly optimal therapeutic blood levels to increase effectiveness and reduce the side effects of the active ingredient or a metabolite of the active ingredient.

Ophthalmic formulations, eye ointments, powders, solutions and the like, are also contemplated as being within the scope of this invention.

Formulations suitable for parenteral administration comprise a HPP/HPC in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of a HPP/HPC or in biodegradable polymers such as polylactide-polyglycolide. Depending on the ratio of the HPP/HPC to polymer, and the nature of the particular polymer employed, the rate of drug release can be controlled. Examples of other biodegradable polymers include poly (orthoesters) and poly (anhydrides). Depot injectable formulations are also prepared by entrapping the HPP/HPC in liposomes or microemulsions which are compatible with body tissue.

In certain embodiments, a peptide HPP/HPC, or a pharmaceutical composition thereof is delivered to a disease or tumor site in a therapeutically effective dose. As is known in the art of pharmacology, the precise amount of the pharmaceutically effective dose of a HPP/HPC that will yield the most effective results in terms of efficacy of treatment in a given patient will depend upon, for example, the activity, the particular nature, pharmacokinetics, pharmacodynamics, and bioavailability of a particular HPP/HPC, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of a disease caused by pathogenic target microbial organisms, to name a few. However, the above guidelines can be used as the basis for fine-tuning the treatment, e.g., determining the optimum dose of administration, which will require no more than routine experimentation consisting of monitoring the subject and adjusting the dosage. Remington: The Science and Practice of Pharmacy (Gennaro ed. 20.sup.th edition, Williams & Wilkins PA, USA) (2000).

IV. Advantages

Peptides and related compounds are hydrophilic and have limited ability to penetrate the skin membrane barrier. When peptides are taken orally, peptides and related compounds can be rapidly proteolysized by proteolytic enzymes in the GI tract in a few minutes. In the case of injection, administration of peptides is painful and in many cases requires frequent and costly office visits to treat chronic conditions.

In certain embodiments, since a peptide HPP/HPC is capable of crossing one or more biological barriers with higher efficiency than its parent compound, the HPP/HPC can be administered locally (e.g., topically or transdermally) to reach a location where a condition occurs without the necessity of a systematic administration (e.g., oral or parenteral administration). A local administration and penetration of a HPP/HPC allows the HPP/HPC to reach the same level of local concentration of an agent or drug with much less amount or dosage of the HPP/HPC in comparison to a systematic administration of the parent agent or drug; alternatively, a higher level of local concentration which may not be afforded in the systematic administration, or if possible, requires significantly higher dosage of the agent in the systematic administration. The high local concentration of the HPP/HPC or its parent agent if being cleaved enables the treatment of a condition more effectively or much faster than a systematically delivered parent agent and the treatment of new conditions that may not be possible or observed before. The local administration of the HPP/HPC may allow a biological subject to reduce potential sufferings from a systemic administration, e.g., adverse reactions associated with the systematic exposure to the agent, gastrointestinal/renal effects. Additionally, the local administration may allow the HPP/HPC to cross a plurality of biological barriers and reach systematically through, for example, general circulation and thus avoid the needs for systematic administration (e.g., injection) and obviate the pain associated with the parenteral injection.

In certain embodiments, a HPP/HPC or a pharmaceutical composition according to the invention can be administered systematically (e.g., transdermally, orally or parenterally). The HPP/HPC or the active agent (e.g., drug or metabolite) of the HPP/HPC may enter the general circulation with a faster rate than the parent agent and gain faster access to the action site a condition. Additionally, the HPP/HPC can cross a biological barrier (e.g., blood brain barrier) which has not been penetrated if a parent agent is administered alone and thus offer novel treatment of conditions that may not be possible or observed before.

For example, peptide HPPs/HPCs may demonstrate high penetration rate through a biological barrier (e.g., >about 10 times, >about 50 times, >about 100 times, >about 200 times, >about 300 times, >about 1000 times higher than if the peptides or peptide-related compounds are administered alone). No or few adverse side effect is observed from the subjects that took peptide HPPs/HPCs, while side effects (such as nausea, hair loss, and increased susceptibility to infection) are observed from the subjects that took the parent peptides at the similar dosage.

V. Examples

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1

Preparation of a HPP/HPC from a Parent Drug

Preparation of a HPP/HPC from a Parent Drug which Contains at Least One Carboxylic Group In certain embodiments, a parent compound having the following Structure

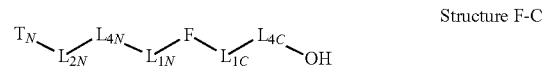

Structure F-C is converted to a HPP/HPC having Structure L-1:

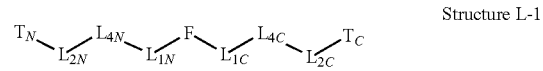

Structure L-1 including stereoisomers and pharmaceutically acceptable salts thereof, wherein:

F, $L_{1C}$, $L_{1N}$, $L_{2C}$, $L_{2N}$, $L_{4C}$ and $L_{4N}$ are defined as supra;

$T_C$ is a transportational unit of a peptide HPP/HPC. For example, $T_C$ is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra; and $T_N$ is selected from the group consisting of nothing, H, substituted and unsubstituted alkyl, substituted and unsubstituted cycloalkyl, substituted and unsubstituted heterocycloalkyl, substituted and unsubstituted alkyloxyl, substituted and unsubstituted alkenyl, substituted and unsubstituted alkynyl, substituted and unsubstituted aryl, and substituted and unsubstituted heteroaryl groups.

In certain embodiments of the invention, a HPP/HPC having Structure L-1 is prepared according to organic synthesis by reacting the parent compounds or derivatives of the parent compounds having Structure D (e.g. acid halides, mixed anhydrides of the parent compounds, etc.):

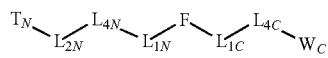

Structure D with compounds of Structure E (Scheme 1):

Structure E wherein $W_C$ is selected from the group consisting of OH, halogen, alkoxycarbonyl and substituted aryloxycarbonyloxy; and F, $L_{1C}$, $L_{1N}$, $L_{2C}$, $L_{2N}$, $L_{4C}$, $L_{4N}$, $T_C$ and $T_N$ are defined as supra.

Scheme 1. Preparation of a HPP/HPC from a parent compound (I).

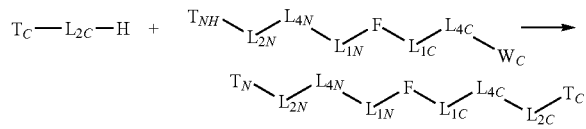

In certain embodiments, a HPP/HPC having Structure L-1 is prepared following Scheme 1 as described supra, wherein $L_{4C}$ is C=O.

In certain embodiments, a parent compound having the following Structure F.

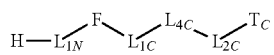

Structure F-N reacts with a compound having the following structure W:

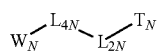

Structure W to obtain a HPP/HPC of Structure L:

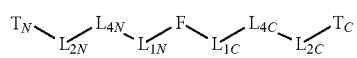

Structure L-1 including stereoisomers and pharmaceutically acceptable salts thereof, wherein:

F, $L_{1C}$, $L_{1N}$, $L_{2C}$, $L_{2N}$, $L_{4C}$ and $L_{4N}$ are defined as supra;

$T_N$ is a transportational unit of a peptide HPP/HPC. For example, $T_N$ is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra; and $T_C$ is selected from the group consisting of nothing, H, substituted and unsubstituted alkyl, substituted and unsubstituted cycloalkyl, substituted and unsubstituted heterocycloalkyl, substituted and unsubstituted alkyloxyl, substituted and unsubstituted alkenyl, substituted and unsubstituted alkynyl, substituted and unsubstituted aryl, and substituted and unsubstituted heteroaryl groups.

$W_N$ is selected from the group consisting of OH, halogen, alkoxycarbonyl and substituted aryloxycarbonyloxy. (Scheme 2)

Scheme 2. Preparation of a HPP/HPC from a parent compound (II).

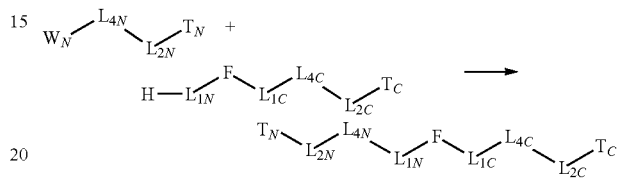

In certain embodiments, a HPP/HPC having a structure of Structure L-2 is prepared by organic synthesis wherein the unwanted reactive sites such as —COOH, —NH$_2$, —OH, or —SH are protected before linking a transportational unit with a functional unit according to one of the synthetic route as described supra. In certain embodiments, the obtained protected HPP/HPC may be further partially or completely deprotected to render a partially protected HPP/HPC or an unprotected HPP/HPC respectively.

Preparation of Ac-Val-Pro-Asp(OEt)-Pro-Arg(diAc)-OCH$_2$CH$_2$N(CH$_2$CH$_3$)$_2$.HCl(SEQ ID NO: 189)

Preparation of H-Arg(diAc)-OCH$_2$CH$_2$N(CH$_2$CH$_3$)$_2$: 30.8 g of Z-Arg-OH was dissolved in 500 ml of acetone. 200 ml of 20% NaOH was added into the reaction mixture. 40 g of acetic anhydride was added into the reaction mixture drop by drop. The mixture was stirred for 2 h at room temperature (RT). The solvent was evaporated off. The residue was extracted with 500 ml of ethyl acetate. The ethyl acetate solution was washed with water (3×100 ml). Ethyl acetate layer was dried over sodium sulfate. The ethyl acetate solution was evaporated to dryness. The residue (Z-Arg(diAc)-OH, 30 g) was dissolved in 300 ml of acetonitrile. The mixture was cooled to 0° C. with ice-water bath. 12 g of N,N-Diethylaminoethanol, 2 g of 4-dimethylaminopyridine, and 22 g of 1,3-dicyclohexylcarbodiimide were added into the reaction mixture. The reaction mixture was stirred for 1 hour at 0° C. and overnight at RT. The solid was removed by filtration and the solution was evaporated to dryness. The residue was extracted with ethyl acetate (2×250 ml). The ethyl acetate solution was washed with 5% sodium bicarbonate (1×500 ml) and water (3×100 ml). The ethyl acetate solution was dried over sodium sulfate. The solution was evaporated to dryness. The residue [Z-Arg(diAc)-OCH$_2$CH$_2$N(CH$_2$CH$_3$)$_2$, 28 g] was dissolved in 300 ml of methanol. 2 g of 10% Pd/C was added into the solution. The mixture was stirred for 10 h under hydrogen at RT. Pd/C was removed by filtration. The solution was evaporated to dryness to obtain 22 g of H-Arg(diAc)-OCH$_2$CH$_2$N(CH$_2$CH$_3$)$_2$.

Preparation of Boc-Asp(OEt)-Pro-OSu: 15 g of L-proline was dissolved in 300 ml of 10% sodium bicarbonate. 150 ml of acetone and 36 g of Boc-Asp(OEt)-OSu were added into the reaction mixture. The mixture was stirred for 5 h at RT. The mixture was washed with ether (1×300 ml). 500 ml of ethyl acetate was added into the aqueous layer. The pH of the mixture was adjusted to 2.4-2.5 with ice-cooled 3N HCl. The ethyl acetate layer was collected and washed with water (3×300 ml). The organic solution was dried over sodium sulfate. The solution was evaporated to dryness. 25 g of the residue (Boc-Asp(OEt)-Pro-OH) and 11 g of N-hydroxysuccinimide were dissolved in 300 ml of dichloromethylene. The mixture was cooled to 0° C. 16 g of 1,3-dicyclohexylcarbodiimide was added into the reaction mixture. The mixture was stirred for 1 hour at 0° C. The solid was removed by filtration. The dichloromethylene solution was washed with 5% sodium bicarbonate (1×200 ml) and water (3×200 ml). The organic solution was dried over sodium sulfate. The solution was evaporated to dryness to obtain 28 g Boc-Asp(OEt)-Pro-OSu.

Preparation of H-Asp(OEt)-Pro-Arg(diAc)-OCH$_2$CH$_2$N(CH$_2$CH$_3$)$_2$.2TFA: 22 g of H-Arg(diAc)-OCH$_2$CH$_2$N(CH$_2$CH$_3$)$_2$ was dissolved in 300 ml of 5% NaHCO$_3$. 24 g of Boc-Asp(OEt)-Pro-OSu in 150 ml of acetone was added into the reaction mixture. The mixture was stirred for 5 h at RT. 500 ml of ethyl acetate was added into the mixture. The ethyl acetate solution was washed with water (3×100 ml). The organic solution was dried over sodium sulfate. The solution was evaporated to dryness. The residue was dissolved in 250 ml of dichloromethylene. 200 ml of trifluoroacetic acid was added into the mixture and the mixture was stirred for 30 min. The mixture was evaporated to dryness to yield 32 g of H-Asp(OEt)-Pro-Arg(diAc)*OCH$_2$CH$_2$N(CH$_2$CH$_3$)$_2$.2TFA.

Preparation of Ac-Val-Pro-OSu: 15 g of L-proline was dissolved in 300 ml of 10% sodium bicarbonate. 150 ml of acetone and 26 g of Ac-Val-OSu were added into the reaction mixture. The mixture was stirred for 5 h at RT. The mixture was washed with ether (1×300 ml). 500 ml of ethyl acetate was added into the aqueous layer. The pH of the mixture was adjusted to 2.4-2.5 with ice-cooled 3N HCl. The ethyl acetate layer was collected and washed with water (3×300 ml). The organic solution was dried over sodium sulfate. The solution was evaporated to dryness. 20 g of the residue (Ac-Val-Pro-OH) and 11 g of N-hydroxysuccinimide were dissolved in 300 ml of dichloromethylene. The mixture was cooled to 0° C. 16 g of 1,3-dicyclohexylcarbodiimide was added into the reaction mixture. The mixture was stirred for 1 hour at 0° C. The solid was removed by filtration. The dichloromethylene solution was washed with 5% sodium bicarbonate (1×200 ml) and water (3×200 ml). The organic solution was dried over sodium sulfate. The solution was evaporated to dryness to yield 20 g Ac-Val-Pro-OSu.

Preparation of Ac-Val-Pro-Asp(OEt)-Pro-Arg(diAc)-OCH$_2$CH$_2$N(CH$_2$CH$_3$)2.HCl (SEQ ID NO: 189): 31 g of H-Asp(OEt)-Pro-Arg(diAc)-OCH$_2$CH$_2$N(CH$_2$CH$_3$)$_2$.2TFA was dissolved in 300 ml of 10% sodium bicarbonate. 150 ml of acetone and 15 g of Ac-Val-Pro-OSu were added into the reaction mixture. The mixture was stirred for 5 h at RT. 500 ml of ethyl acetate was added into the mixture. The organic layer is washed with water (3×100 ml). The ethyl acetate layer was dried over sodium sulfate. Sodium sulfate was removed by filtration. 15 g of HCl gas in dioxane (200 ml) was added into the solution. The solid was collected and washed with ether (3×50 ml). After drying, 20 g of the desired product (hygroscopic product) was obtained. Elementary analysis: C$_{39}$H$_{66}$ClN$_9$O$_{11}$; MW: 872.45. Calculated % C: 53.69; H: 7.62; Cl: 4.06; N: 14.45; O: 20.17; Found % C: 53.61; H: 7.67; Cl: 4.10; N: 14.40, O: 20.22. MS: m/e: 836.4; m/e+1: 836.4.

Preparation of Ac-Tyr(Ac)-Gly-Gly-Phe-Met-OCH$_2$CH$_2$N(CH$_2$CH$_3$)$_2$.HCl (SEQ ID NO: 178)

Preparation of H-Met-OCH$_2$CH$_2$N(CH$_2$CH$_3$)$_2$.TFA: 25 g of Boc-Met-OH was dissolved in 300 ml of dichloromethylene. The mixture was cooled into 0° C. with ice-water bath. 12 g of N,N-Diethylaminoethanol, 2 g of 4-dimethylaminopyridine, and 22 g of 1,3-dicyclohexylcarbodiimide were added into the reaction mixture. The reaction mixture was stirred for 1 hour at 0° C. and overnight at RT. The solid was removed by filtration and the dichloromethylene solution was washed with 5% sodium bicarbonate (1×500 ml) and water (3×100 ml). The ethyl acetate solution was dried over sodium sulfate. The solution was evaporated to dryness. The residue [Boc-Met-OCH$_2$CH$_2$N(CH$_2$CH$_3$)$_2$, 30 g] was dissolved in 250 ml of dichloromethylene. 250 ml of trifluoroacetic acid was added into the mixture and the mixture was stirred for 30 min. The solution was evaporated to dryness to yield 26 g of H-Met-OCH$_2$CH$_2$N(CH$_2$CH$_3$)$_2$.TFA.

Preparation of Boc-Gly-Phe-OSu: 20 g of L-phenylalanine was dissolved in 300 ml of 10% sodium bicarbonate. 150 ml of acetone and 28 g of Boc-Gly-OSu were added into the reaction mixture. The mixture was stirred for 5 h at RT. The mixture was washed with ether (1×300 ml). 500 ml of ethyl acetate was added into the aqueous layer. The pH of the mixture was adjusted to 2.4-2.5 with ice-cooled 3N HCl. The ethyl acetate layer was collected and washed with water (3×300 ml). The organic solution was dried over sodium sulfate. The solution was evaporated to dryness. 22 g of the residue (Boc-Gly-Phe-OH) and 10 g of N-hydroxysuccinimide were dissolved in 300 ml of dichloromethylene. The mixture was cooled to 0° C. 15 g of 1,3-dicyclohexylcarbodiimide was added into the reaction mixture. The mixture was stirred for 1 hour at 0° C. The solid was removed by filtration. The dichloromethylene solution was washed with 5% sodium bicarbonate (1×200 ml) and water (3×200 ml). The organic solution was dried over sodium sulfate. The solution was evaporated to dryness to yield 25 g Boc-Gly-Phe-OSu.

Preparation of H-Gly-Phe-Met-OCH$_2$CH$_2$N(CH$_2$CH$_3$)$_2$.TFA: 25 g of H-Met-OCH$_2$CH$_2$N(CH$_2$CH$_3$)$_2$.TFA was dissolved in 300 ml of 5% NaHCO$_3$. 22 g of Boc-Gly-Phe-OSu in 150 ml of acetone was added into the reaction mixture. The mixture was stirred for 5 h at RT. 500 ml of ethyl acetate was added into the mixture. The ethyl acetate solution was washed with water (3×100 ml). The organic solution was dried over sodium sulfate. The solution was evaporated to dryness. The residue was dissolved in 250 ml of dichloromethylene. 200 ml of trifluoroacetic acid was added into the mixture and the mixture was stirred for 30 min. The mixture was evaporated to dryness to yield 25 g of H-Gly-Phe-Met-OCH$_2$CH$_2$N(CH$_2$CH$_3$)$_2$.TFA.

Preparation of Ac-Tyr(Ac)-Gly-OSu: 11 g of L-glycine was dissolved in 300 ml of 10% sodium bicarbonate. 150 ml of acetone and 36 g of Ac-Tyr(Ac)-OSu were added into the reaction mixture. The mixture was stirred for 5 h at RT. The mixture was washed with ether (1×300 ml). 500 ml of ethyl acetate was added into the aqueous layer. The pH of the mixture was adjusted to 2.4-2.5 with ice-cooled 3 N HCl. The ethyl acetate layer was collected and washed with water (3×300 ml). The organic solution was dried over sodium sulfate. The solution was evaporated to dryness. 28 g of the residue (Ac-Tyr(Ac)-Gly-OH) and 13 g of N-hydroxysuccinimide were dissolved in 300 ml of dichloromethylene. The mixture was cooled to 0° C. 18 g of 1,3-dicyclohexylcarbodiimide was added into the reaction mixture. The mixture was stirred for 1 hour at 0° C. The solid was removed by filtration. The dichloromethylene solution was washed with 5% sodium bicarbonate (1×200 ml) and water (3×200 ml). The organic solution was dried over sodium sulfate. The solution was evaporated to dryness to yield 20 g Ac-Tyr(Ac)-Gly-OSu.

Preparation of Ac-Tyr(Ac)-Gly-Gly-Phe-Met-OCH$_2$CH$_2$N(CH$_2$CH$_3$)$_2$.HCl (SEQ ID NO: 178): 24 g of H-Gly-Phe-Met-OCH$_2$CH$_2$N(CH$_2$CH$_3$)$_2$.TFA was dissolved in 300 ml of 10% sodium bicarbonate. 150 ml of acetone and 15 g of Ac-Tyr(Ac)-Gly-OSu were added into the reaction mixture. The mixture was stirred for 5 h at RT. 500 ml of ethyl acetate was added into the mixture. The organic layer was washed with water (3×100 ml). The ethyl acetate layer was dried over sodium sulfate. Sodium sulfate was removed by filtration. 15 g of HCl gas in dioxane (200 ml) was added into the solution. The solid was collected and washed with ether (3 ×50 ml). After drying, 18 g of the desired product (hygroscopic product) was obtained. Elementary analysis: C$_{37}$H$_{53}$ClN$_6$O$_9$S; MW: 793.37. Calculated % C: 56.01; H, 6.73; Cl: 4.47; N: 10.59; O: 18.15; S: 4.04. Found % C: 55.96; H: 6.76; Cl: 4.52; N: 10.54, O: 18.19; S: 4.03. MS: m/e: 757.4; m/e+1: 758.4.

Preparation of Ac-Val-Pro-Gly-Pro-Arg(diAc)-OCH$_2$CH$_2$N(CH$_2$CH$_3$)$_2$. HCl(SEQ ID NO: 183)

Preparation of Boc-Gly-Pro-OSu: 15 g of L-proline was dissolved in 300 ml of 10% sodium bicarbonate. 150 ml of acetone and 27.2 g of Boc-Gly-OSu were added into the reaction mixture. The mixture was stirred for 5 h at RT. The mixture was washed with ether (1×300 ml). 500 ml of ethyl acetate was added into the aqueous layer. The pH of the mixture was adjusted to 2.4-2.5 with ice-cooled 3 N HCl. The ethyl acetate layer was collected and washed with water (3×300 ml). The organic solution was dried over sodium sulfate. The solution was evaporated to dryness. 21 g of the residue (Boc-Gly-Pro-OH) and 11 g of N-hydroxysuccinimide were dissolved in 300 ml of dichloromethylene. The mixture was cooled to 0° C. 17 g of 1,3-dicyclohexylcarbodiimide was added into the reaction mixture. The mixture was stirred for 1 hour at 0° C. The solid was removed by filtration. The dichloromethylene solution was washed with 5% sodium bicarbonate (1×200 ml) and water (3×200 ml). The organic solution was dried over sodium sulfate. The solution was evaporated to dryness to yield 23 g Boc-Gly-Pro-OSu.
Preparation of H-Gly-Pro-Arg(diAc)-OCH$_2$CH$_2$N(CH$_2$CH$_3$)$_2$.2TFA: 22 g of H-Arg(diAc)-OCH$_2$CH$_2$N(CH$_2$CH$_3$)$_2$ was dissolved in 300 ml of 5% NaHCO$_3$. 20 g of Boc-Gly-Pro-OSu in 150 ml of acetone was added into the reaction mixture. The mixture was stirred for 5 h at RT. 500 ml of ethyl acetate was added into the mixture. The ethyl acetate solution was washed with water (3×100 ml). The organic solution was dried over sodium sulfate. The solution was evaporated to dryness. The residue was dissolved in 250 ml of dichloromethylene. 200 ml of trifluoroacetic acid was added into the mixture and the mixture was stirred for 30 min. The mixture was evaporated to dryness to yield 28 g of H-Gly-Pro-Arg(diAc)-OCH$_2$CH$_2$N(CH$_2$CH$_3$)$_2$.2TFA.
Preparation of Ac-Val-Pro-Gly-Pro-Arg(diAc)-OCH$_2$CH$_2$N(CH$_2$CH$_3$)$_2$.HCl(SEQ ID NO: 183): 26 g of H-Gly-Pro-Arg(diAc)-OCH$_2$CH$_2$N(CH$_2$CH$_3$)$_2$.2TFA was dissolved in 300 ml of 10% sodium bicarbonate. 150 ml of acetone and 15 g of Ac-Val-Pro-OSu were added into the reaction mixture. The mixture was stirred for 5 h at RT. 500 ml of ethyl acetate was added into the mixture. The organic layer was washed with water (3×100 ml). The ethyl acetate layer was dried over sodium sulfate. Sodium sulfate was removed by filtration. 15 g of HCl gas in dioxane (200 ml) was added into the solution. The solid was collected, washed with ether (3×50 ml) and dried to obtain yielded 18 g of the desired product (hygroscopic product). Elementary analysis: C$_{35}$H$_{60}$ClN$_9$O$_9$; MW: 786.36. Calculated % C: 53.46; H: 7.69; Cl: 4.51; N: 16.03; O: 18.31; Found % C: 53.43; H: 7.73; Cl: 4.55; N: 16.01, O: 18.29. MS: m/e: 750.4; m/e+1: 751.4.

Preparation of Cyclo(1,6)-Ac-Nle-Asp-His-Phe-Arg (diAc)-Trp-Lys-OCH$_2$CH$_2$N(CH$_2$CH$_3$)$_2$.HCl.(SEQ ID NO: 180)

Preparation of Ac-Nle-Asp(OFm)-OH: 43 g of H-Asp (OFm)-OH.TFA and 27 g of Ac-Nle-OSu were suspended in 300 ml of acetone. 300 ml of 5% NaHCO$_3$ was added into the reaction mixture. The mixture was stirred for overnight at RT. The mixture was washed with ether (1×300 ml). 500 ml of ethyl acetate was added into the aqueous layer. The pH of the mixture was adjusted to 2.4-2.5 with ice-cooled 3 N HCl. The ethyl acetate layer was collected and washed with water (3×300 ml). The organic solution was dried over sodium sulfate. The solution was evaporated to dryness to yield 42 g of Ac-Nle-Asp(OFm)-OH.
Preparation of Fmoc-Trp-Lys(4-Pyoc)-OH: H-Lys(4-Pyoc)-OH was prepared according to reference (H. Kunz and S. Birnbach, Tetrahedron Lett., 25, 3567, 1984; H. Kunz and R. Barthels, Angew. Chem., Int. Ed. Engl., 22, 783, 1983). 33 g of H-Lys(4-Pyoc)-OH was suspended in 300 ml of 5% NaHCO$_3$. 300 ml of acetone and 52 g of Fmoc-Trp-OSu were added into the reaction mixture. The mixture was stirred for overnight at RT. The mixture was washed with ether (1×500 ml). 500 ml of ethyl acetate was added into the mixture and the pH of the mixture was adjusted to 2.2-2.3 with 3 N HCl. The ethyl acetate layer was collected and washed with water. The organic solution was dried over sodium sulfate. The organic solution was evaporated to dryness to yield 55 g of Fmoc-Trp-Lys(4-Pyoc)-OH.
Preparation of Cyclo(1,6)-Ac-Nle-Asp-His-Phe-Arg (diAc)-Trp-Lys-OH:(SEQ ID NO: 190): 100 g of Wang resin was suspended in 700 ml of DMF Solution containing 50 g of Fmoc-Trp-Lys(4-Pyoc)-OH, 13 g of 1-Hydroxybenzotriazole, 2 g of 4-dimethylaminopyridine, and 12 g of N,N'-diisopropylcarbodiimide. The mixture was stirred overnight at RT. The resin was collected by filtration and washed with DMF (3×400 ml), methanol (3×400 ml), and dichloromethylene (3×400 ml). 700 ml of 20% piperidine was added into the resin. The mixture was stirred for 30 min. The resin was collected by filtration and washed with DMF (3×400 ml), methanol (3×400 ml), and dichloromethylene (3×400 ml). 700 ml of DMF, 48 g of Fmoc-Arg(diAc)-OH, 13 g of 1-Hydroxybenzotriazole, 35 ml of triethylamine, and 38 g of O-(Benzotriazol-1-yl)-N,N,N',N'-tetramethyluronium were added into the resin. The mixture was stirred for 2 hours at RT. The resin was collected by filtration and washed with DMF (3×400 ml), methanol (3×400 ml), and dichloromethylene (3×400 ml). 700 ml of 20% piperidine was added into the resin. The mixture was stirred for 30 min. The resin was collected by filtration and washed with DMF (3×400 ml), methanol (3×400 ml), and dichloromethylene (3×400 ml). 700 ml of DMF, 39 g of Fmoc-Phe-OH, 13 g of 1-Hydroxybenzotriazole, 35 ml of triethylamine, and 38 g of O-(Benzotriazol-1-yl)-N,N,N',N'-tetramethyluronium were added into the resin. The mixture was stirred for 2 hours at RT. The resin was collected by filtration and washed with DMF (3×400 ml), methanol (3×400 ml), and dichloromethylene (3×400 ml). 700 ml of 20% piperidine was added into the resin. The mixture was stirred for 30 min. The resin was collected by filtration and washed with DMF (3×400 ml), methanol (3×400 ml), and dichloromethylene (3×400 ml). 700 ml of DMF, 60 g of Fmoc-His(Fmoc)-OH, 13 g of 1-Hydroxybenzotriazole, 35 ml of triethylamine, and 38 g of O-(Benzotriazol-1-yl)-N,N,N',N'-tetramethyluronium were added into the resin. The mixture was stirred 2 hours at RT. The resin was collected by filtration and washed with DMF (3×400 ml), methanol (3×400 ml), and dichloromethylene (3×400 ml). 700 ml of 20% piperidine was added into the resin. The mixture was stirred for 30 min. The resin was collected by filtration and washed with DMF (3×400 ml), methanol (3×400 ml), and dichloromethylene (3×400 ml). 700 ml of DMF, 60 g of Ac-Nle-Asp(OFm)-OH, 13 g of 1-Hydroxybenzotriazole, 35 ml of triethylamine, and 38 g of O-(Benzotriazol-1-yl)-N,N,N',N'-tetramethyluronium were added into the resin. The mixture was stirred 2 hours at RT. The resin was collected by filtration and washed with DMF (3×400 ml), methanol (3×400 ml), and dichloromethylene (3×400 ml). The peptide resin was suspended in 700 ml of DMF. 50 g of MeI was added into the reaction mixture. The mixture was stirred for 1 h at RT and 1 h at 50° C. The resin was collected by filtration and washed with DMF (3×400 ml), methanol (3×400 ml), and dichloromethylene (3×400 ml). 700 ml of 30% piperidine was added into the resin. The mixture was stirred for 60 min. The resin was collected by filtration and washed with DMF (3×400 ml), methanol (3×400 ml), and dichloromethylene (3×400 ml). 700 ml of DMF, 13 g of 1-Hydroxybenzotriazole, 35 ml of triethylamine, and 38 g of O-(Benzotriazol-1-yl)-N,N,N',N'-tetramethyluronium were added into the resin. The mixture was stirred 10 hours at RT. The resin was collected by filtration and washed with DMF (3×400 ml), methanol (3×400 ml), and dichloromethylene (3×400 ml). 500 ml of trifluoroacetic acid was added into the resin and the mixture was stirred for 1 hour at RT. The resin was removed by filtration and the solution was evaporated to dryness. The residue was washed with ether (3×100 ml).

Preparation of Cyclo(1,6)-Ac-Nle-Asp-His-Phe-Arg(diAc)-Trp-Lys-OCH$_2$CH$_2$N(CH$_2$CH$_3$)$_2$.HCl (SEQ ID NO: 180): 10 g of Cyclo(1,6)-Ac-Nle-Asp-His-Phe-Arg(diAc)-Trp-Lys-OH (SEQ ID NO: 190) was dissolved in 300 ml of DMF. The mixture was cooled into 0° C. with ice-water bath. 12 g of N,N-Diethylaminoethanol, 2 g of 4-dimethylaminopyridine, and 22 g of 1,3-dicyclohexylcarbodiimide were added into the reaction mixture. The reaction mixture was stirred for 1 hour at 0° C. and overnight at RT. The solid was removed by filtration and the dichloromethylene solution was washed with 5% sodium bicarbonate (1×500 ml) and water (3×100 ml). The ethyl acetate solution was dried over sodium sulfate. 2 g of HCl in dioxane (20 ml) was added into the solution. The solid was collected and washed with ether (3×30 ml). Yield was 8 g of the final product.

Solid-Phase Synthesis of Peptide HPP/HPC

A peptide HPP/HPC of a peptide is prepared using trityl chloride resin and 2-(4-nitrophenylsulfonyl)ethyl group as the carboxylic group protecting group (Scheme 3), wherein:

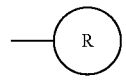

is resin;

X$^1$ is selected from the group consisting of H, Cl, methyl, and methoxyl;

R$^1$, R$^2$, ... R$^n$ are side chains of amino acids of the peptide HPP/HPC numbered 1, 2, ... n respectively from the N-terminal to C-terminal;

coupling reagents are selected from the group consisting of HBTU/DIPEA/HOBt, TBTU/DIPEA/HOBt, BOP/DIPEA/HOBt, HATU/DIPEA/HOBt, DIC/HOB, and combinations thereof; and R$_T$ is selected from the group consisting of substituted and unsubstituted alkyl, substituted and unsubstituted cycloalkyl, substituted and unsubstituted heterocloalkyl, substituted and unsubstituted alkyloxyl, substituted and unsubstituted alkenyl, substituted and unsubstituted alkynyl, substituted and unsubstituted aryl, substituted and unsubstituted heteroaryl groups, and a transportational unit selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra.

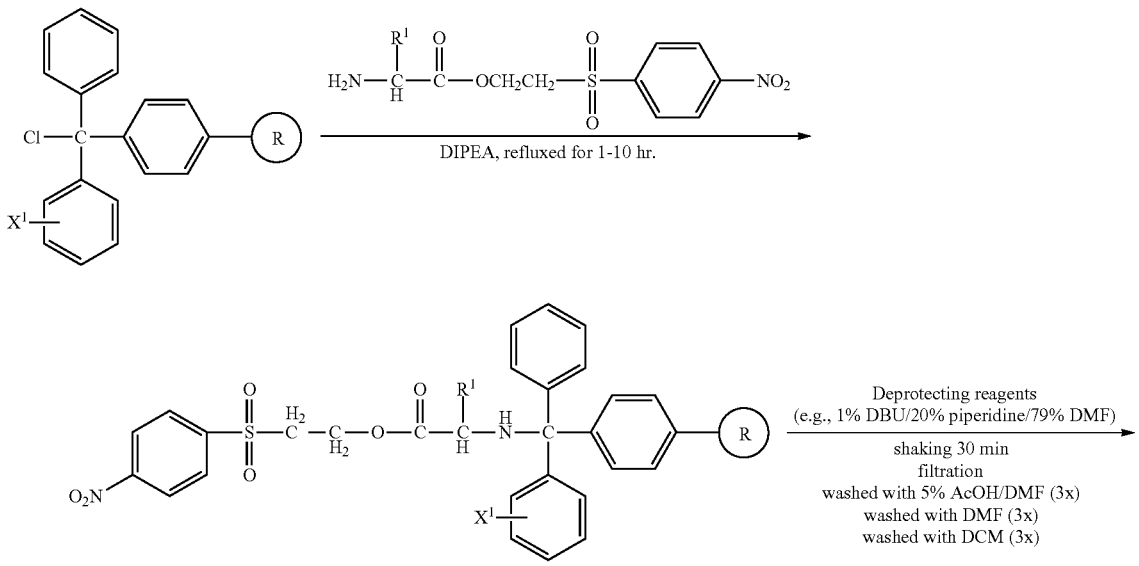

Scheme 3: Synthesis of peptide HPP/HPC using trityl chloride resin and 2-(4-nitrophenylsulfonyl)ethyl group as the carboxylic group protecting group.

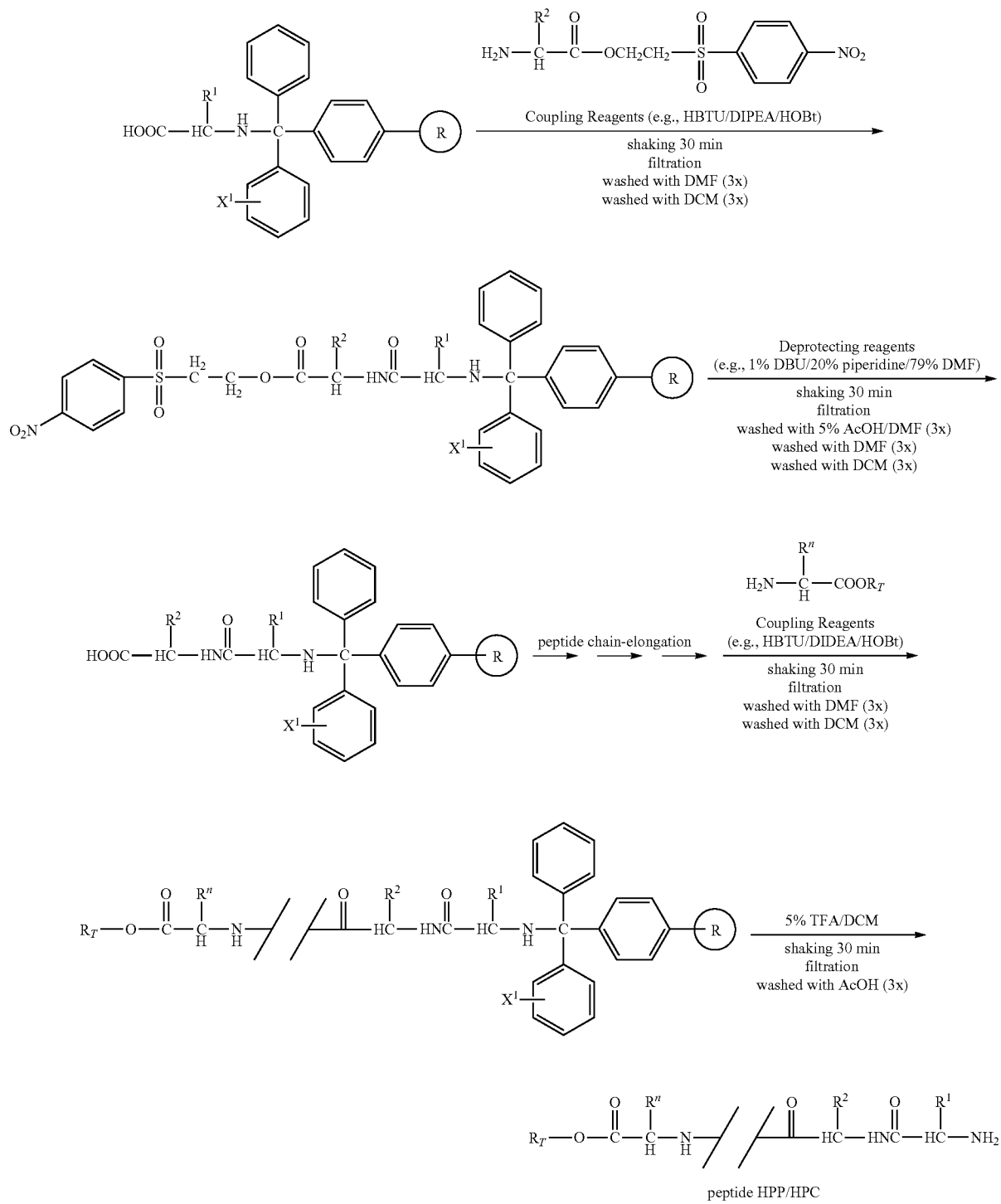
As used herein, unless defined otherwise "DCM" means dichloromethane.
In certain embodiments, a peptide HPP/HPC is prepared using trityl chloride resin and 9-fluorenylmethyl group as the carboxylic group protecting group (Scheme 4), wherein,
$X^1, R^1, R^2, \ldots R^n, R_T$, and coupling reagents are defined the same as supra.

Scheme 4: Synthesis of a peptide HPP/HPC using trityl chloride resin and 9-fluorenylmethyl group as the carboxylic group protecting group.
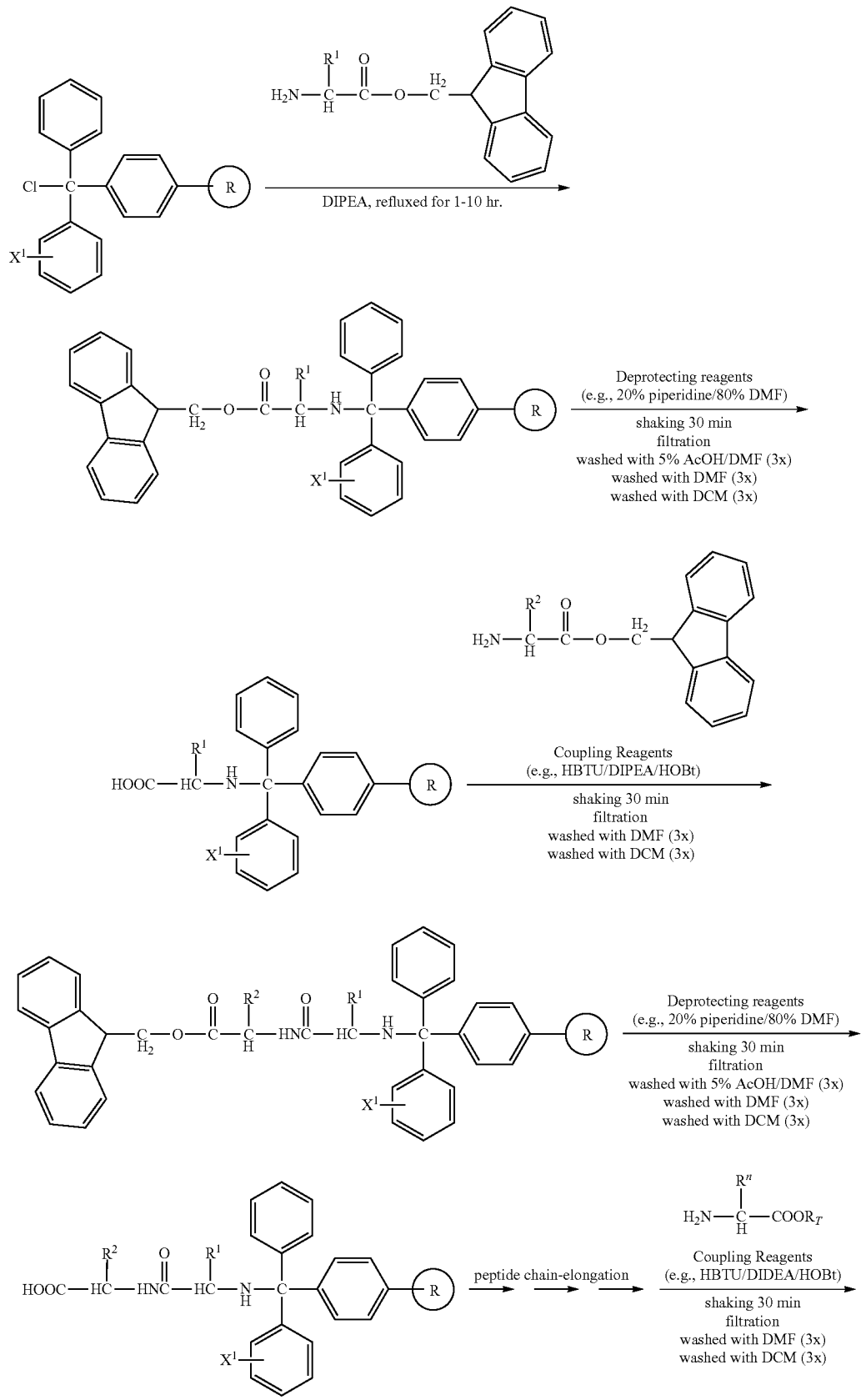

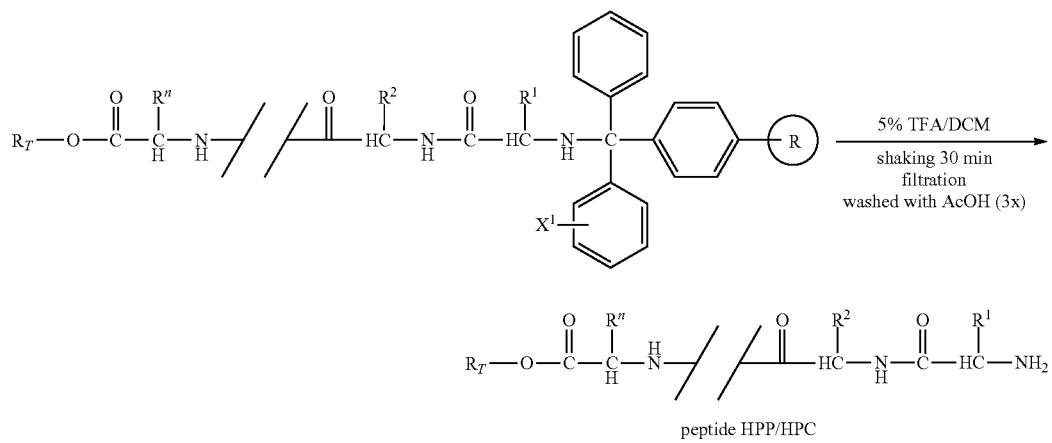

peptide HPP/HPC

In certain embodiments, a peptide HPP/HPC is prepared using carbonate ester resin and 9-fluorenylmethyl group as the carboxylic group protecting group (Scheme 5), wherein,

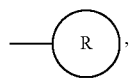

$R^1, R^2, \ldots R^n, R_T$, and coupling reagents are defined the same as supra.

Scheme 5: Synthesis of a peptide HPP/HPC using carbonate ester resin and 9-fluorenylmethyl group as the carboxylic group protecting group.

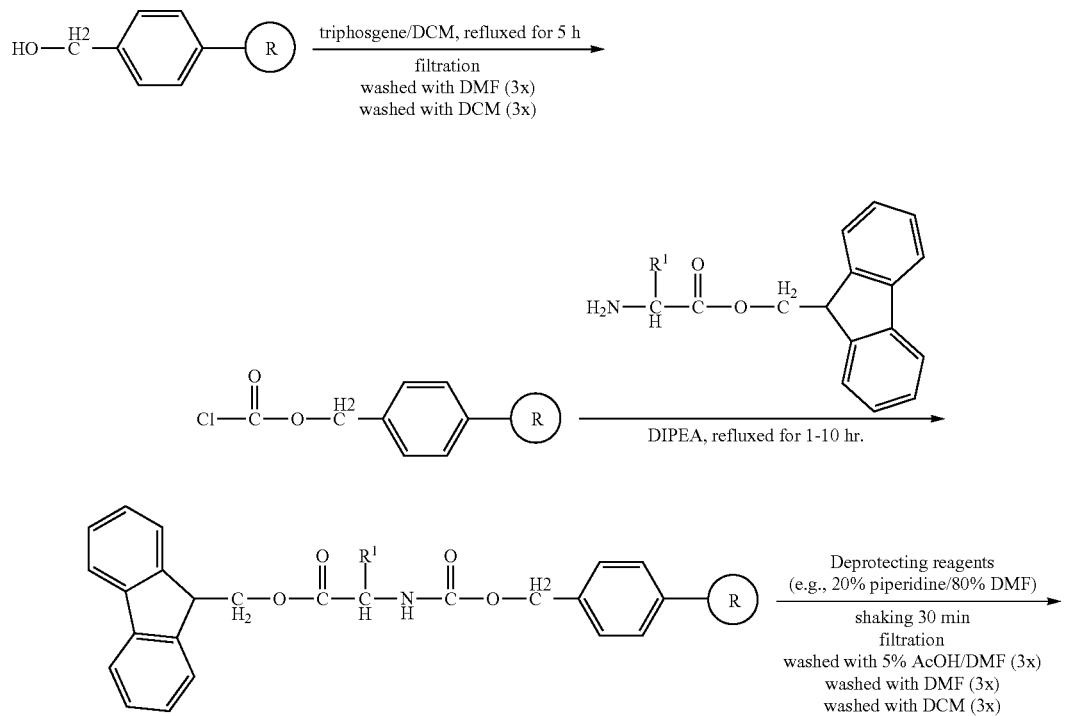

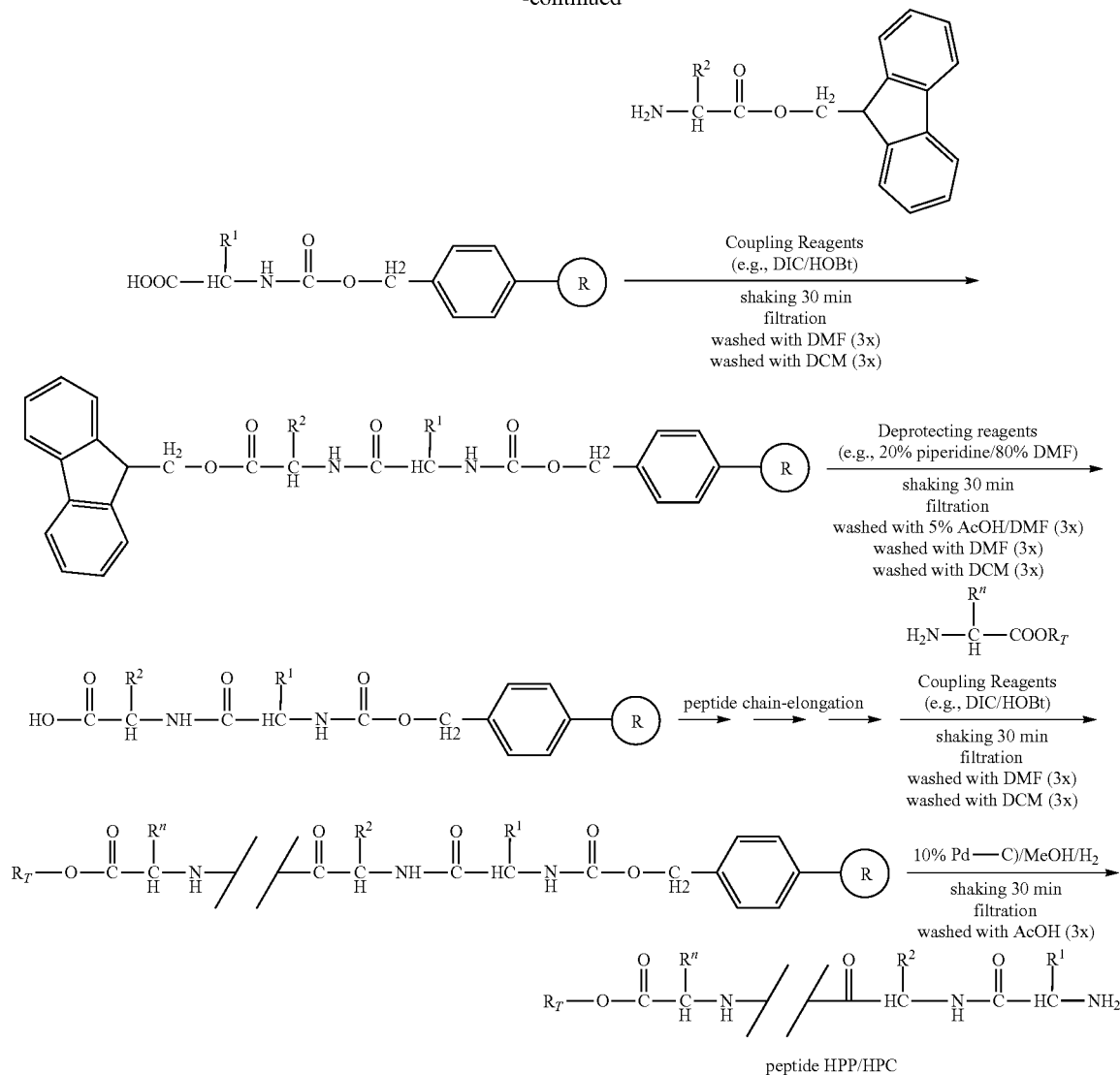

In certain embodiments, a peptide HPP/HPC is prepared using carbonate ester resin and 2-(4-nitrophenylsulfonyl)ethyl group as the carboxylic group protecting group (Scheme 6), wherein,

—⬤R , $R^1, R^2, \ldots R^n, R_T$, and coupling reagents are defined the same as supra.

Scheme 6 Synthesis of a peptide HPP/HPC using carbonate ester resin and 2-(4-nitrophenylsulfonyl)ethyl group as the carboxylic group protecting group.

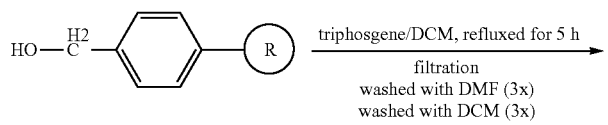

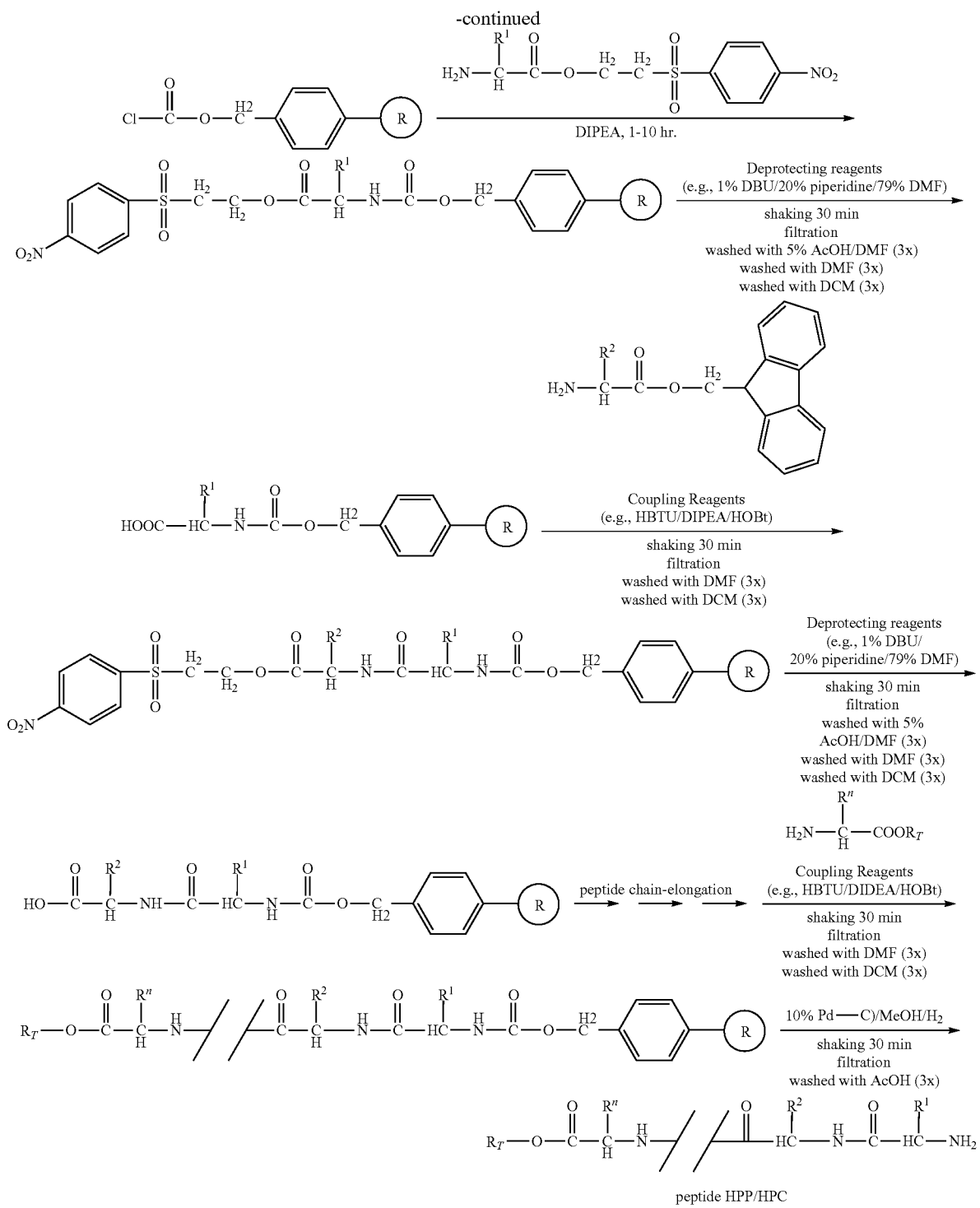

Example 2

Peptide Hpps/Hpcs Showed Higher In Vitro Penetration Rates Across Human Skin Comparing to their Parent Drugs The penetration rates of HPPs/HPCs and their parent drugs through human skin were measured in vitro by modified Franz cells. The Franz cells had two chambers, the top sample chamber and the bottom receiving chamber. The human skin tissue (360-400 p.m thick) that separated the top and the receiving chambers was isolated from the anterior or posterior thigh areas.

Figures 1, 2:
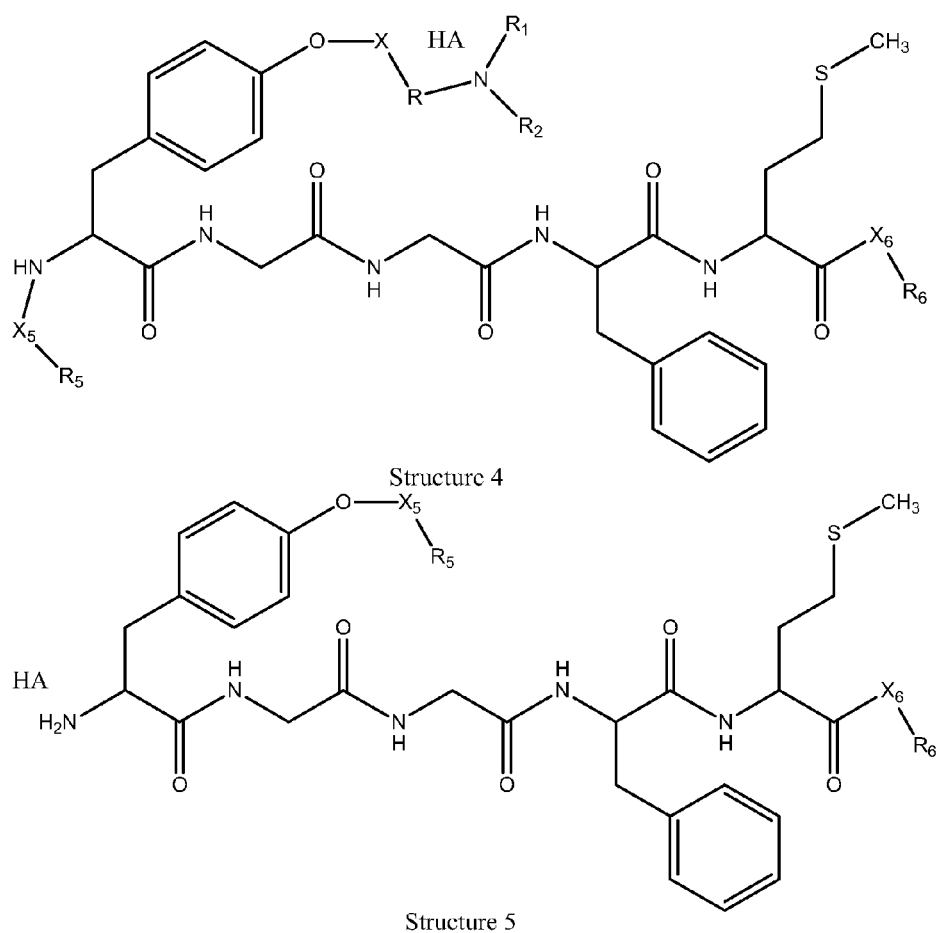
FIG. 2: Cumulative amounts of Ac-Tyr(Ac)-Gly-Gly-Phe-Met-OCH$_2$CH$_2$N(CH$_2$CH$_3$)$_2$.HCl (SEQ ID NO: 178), HCl.(CH$_3$)$_2$NCH$_2$CH$_2$CH$_2$CO-Tyr(Ac)-Gly-Gly-Phe-Met-OCH$_2$CH$_2$CH$_2$CH$_3$ (SEQ ID NO: 179), cyclo(1,6)-Ac-Nle-Asp-His-Phe-Arg(diAc)-Trp-Lys-OCH$_2$CH$_2$N(CH$_2$CH$_3$)$_2$.HCl (SEQ ID NO: 180), cyclo(1,6)-H-Nle-Asp-His-D-Phe(4-I)-Arg(Ac)-Trp-Lys-NH$_2$.HCl (SEQ ID NO: 181), cyclo(1,6)-H-Nle-Asp-His-D-Ala(2-naphthyl)-Arg(NO$_2$)-Trp-Lys-NH$_2$.HCl (SEQ ID NO: 182), Ac-Val-Pro-Gly-Pro-Arg(diAc)-OCH$_2$CH$_2$N(CH$_2$CH$_3$)$_2$.HCl (SEQ ID NO: 183), Ac-Tyr-Gly-Gly-Phe-Met-OH (SEQ ID NO: 184), cyclo(1,6)-Ac-Nle-Asp-His-Phe-Arg-Trp-Lys-OH (SEQ ID NO: 173), cyclo(1,6)-Ac-Nle-Asp-His-D-Phe(4-I)-Arg-Trp-Lys-NH$_2$ (SEQ ID NO: 185) and H-Val-Pro-Gly-Pro-Arg-OH (SEQ ID NO: 186), crossing isolated human skin tissue in Franz cells (n=5). In each case, the vehicle was pH 7.4 phosphate buffer (0.2 M).
Figures 1, 2, 3:
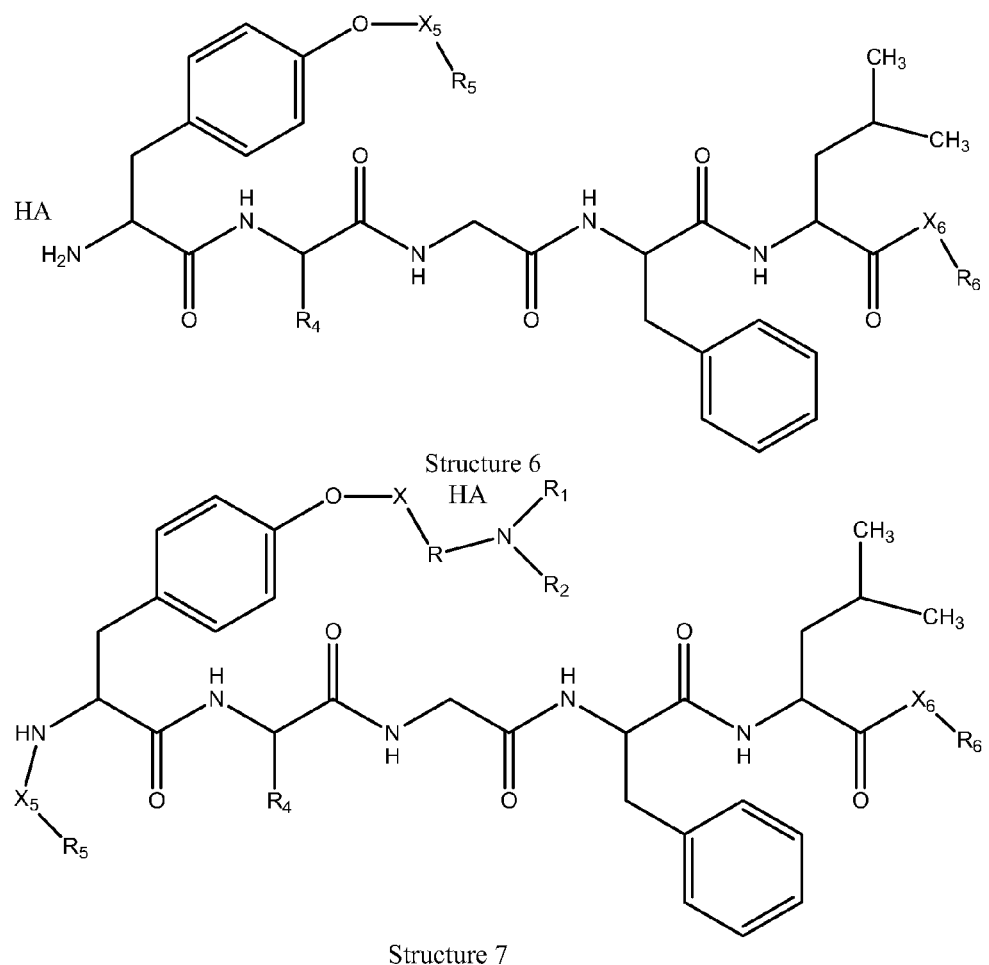
Figures 1, 2, 3, 4:
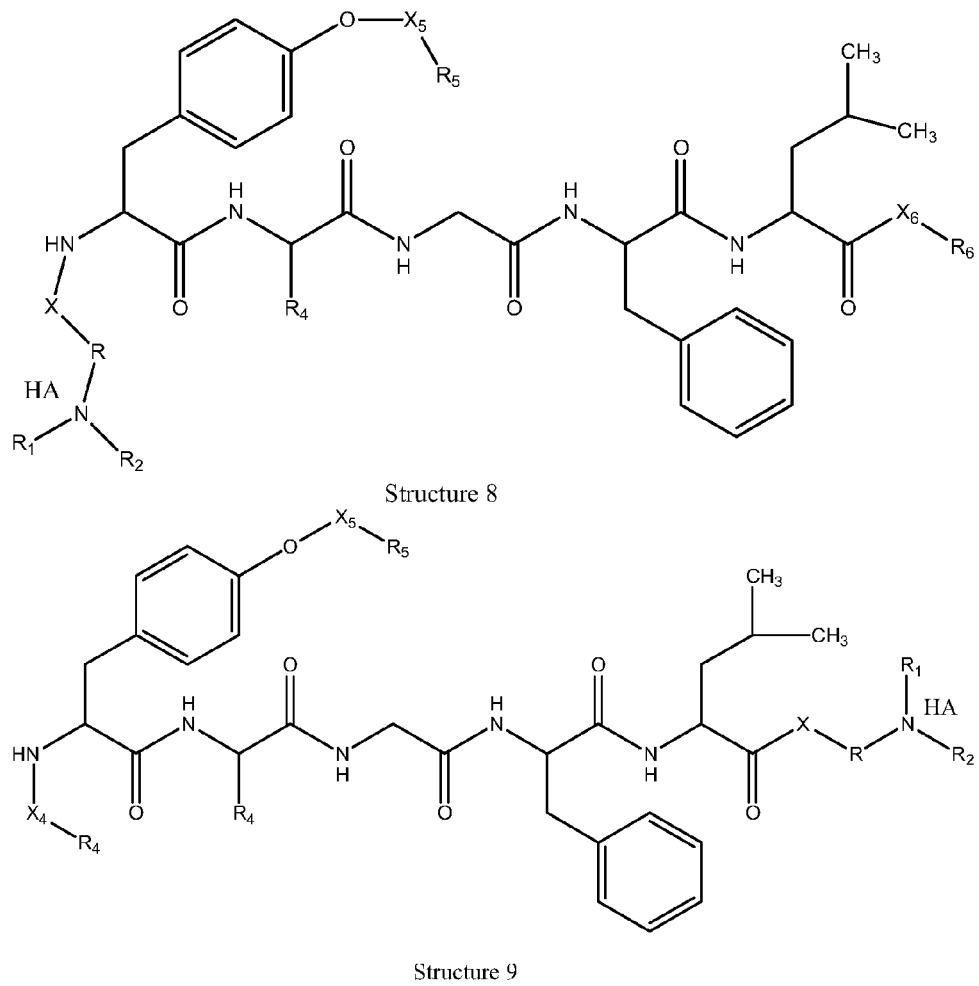
Figures 1, 2, 3, 4, 5:
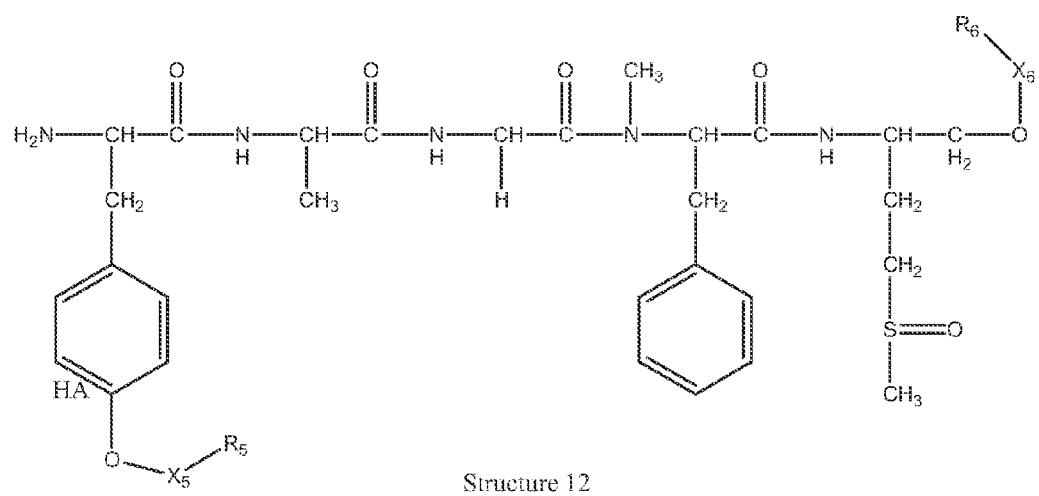
Figures 1, 2, 3, 4, 5, 6:
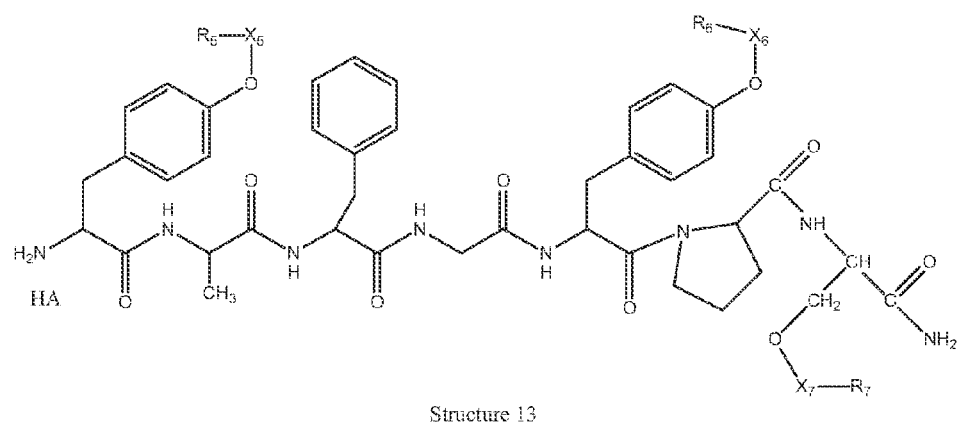
Figures 1, 2, 3, 4, 5, 6, 7, 8, 9, 10, 11, 12, 13, 14, 15, 16, 17, 18, 19, 20, 21:
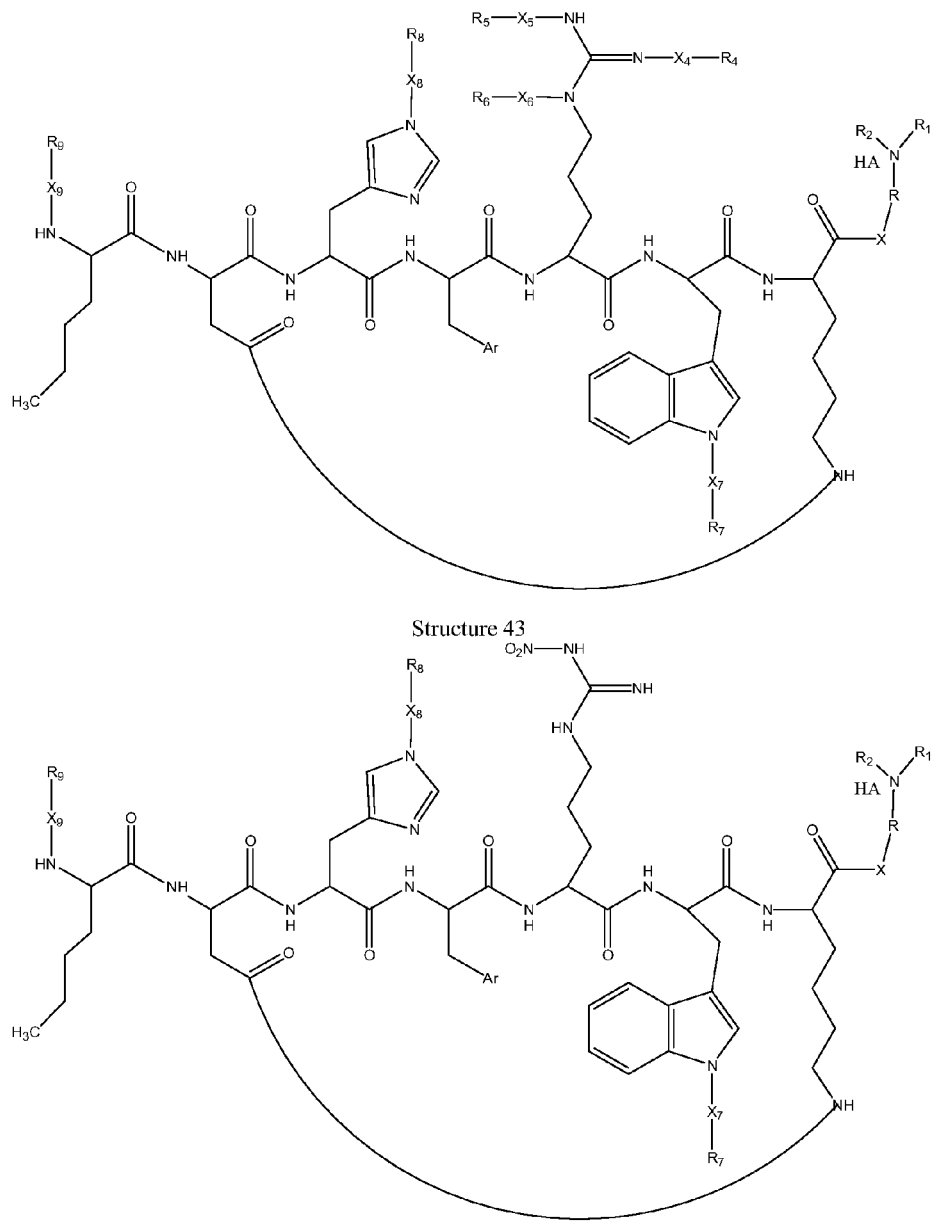
Figures 1, 2, 3, 4, 5, 6, 7, 8, 9, 10, 11, 12, 13, 14, 15, 16, 17, 18, 19, 20, 21, 22:
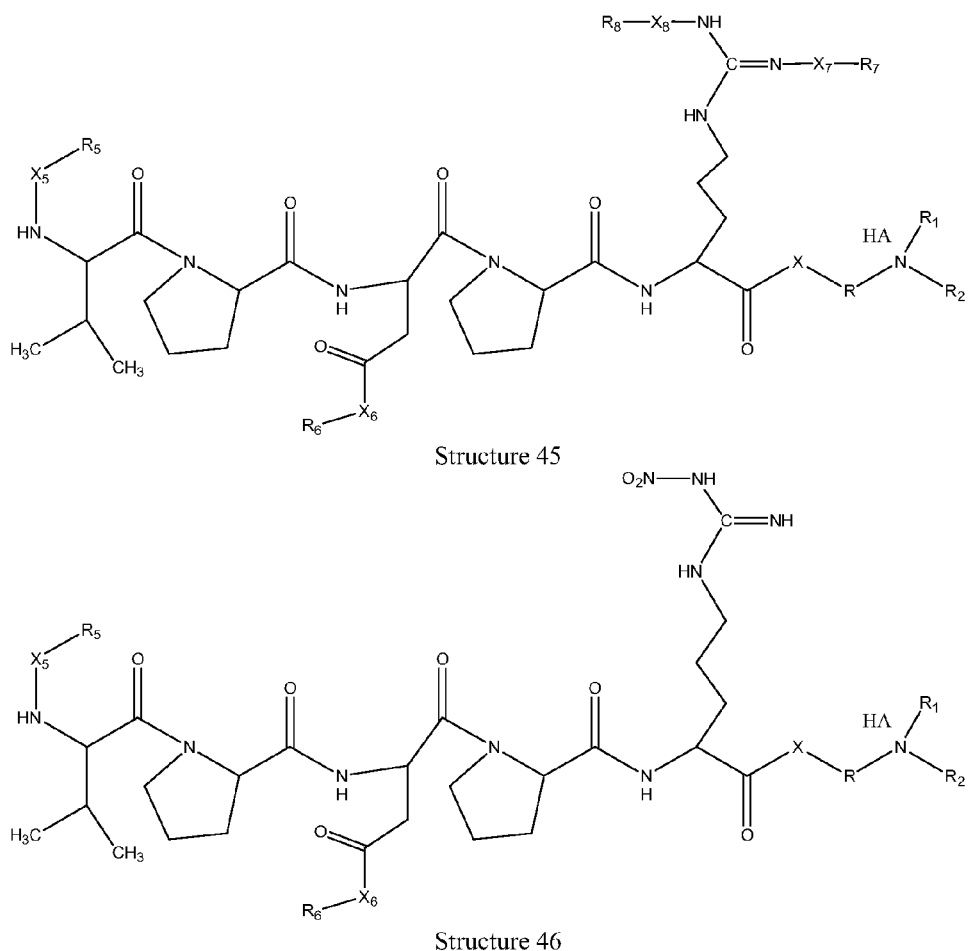
Figures 1, 2, 3, 4, 5, 6, 7, 8, 9, 10, 11, 12, 13, 14, 15, 16, 17, 18, 19, 20, 21, 22, 23:
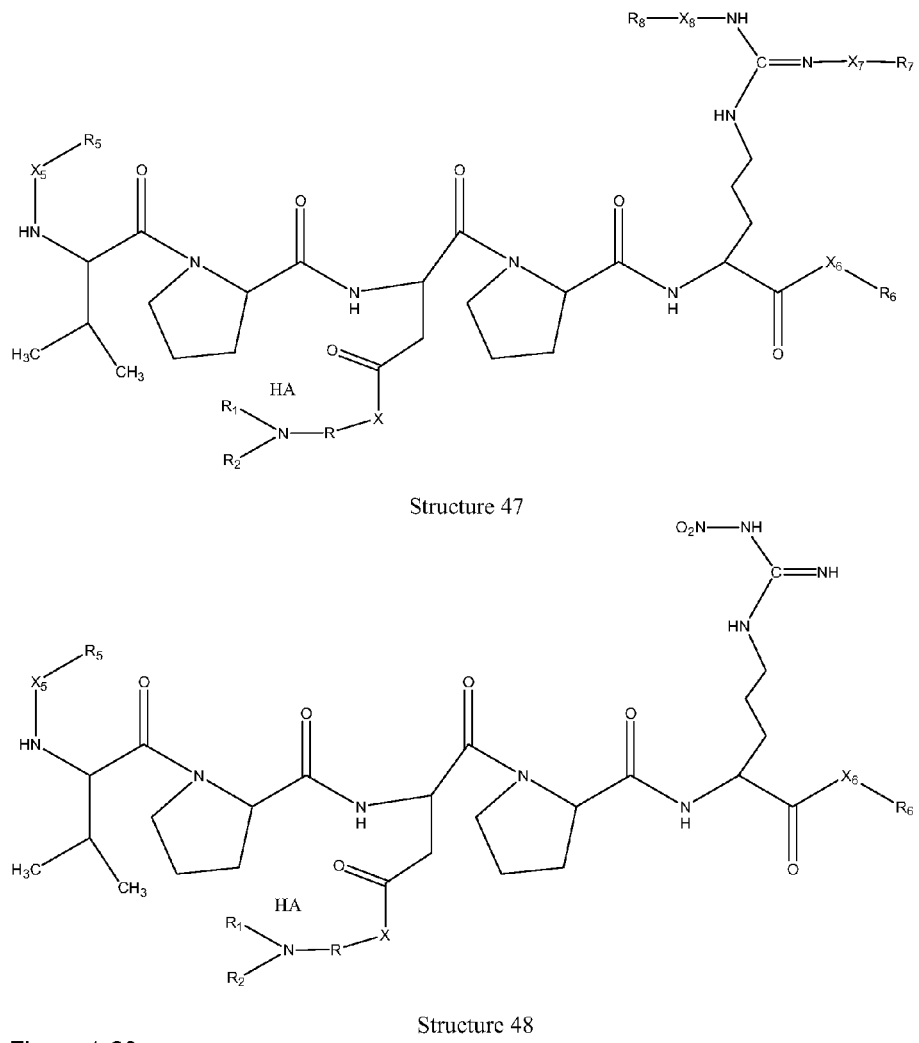
Figures 1, 2, 3, 4, 5, 6, 7, 8, 9, 10, 11, 12, 13, 14, 15, 16, 17, 18, 19, 20, 21, 22, 23, 24, 25:
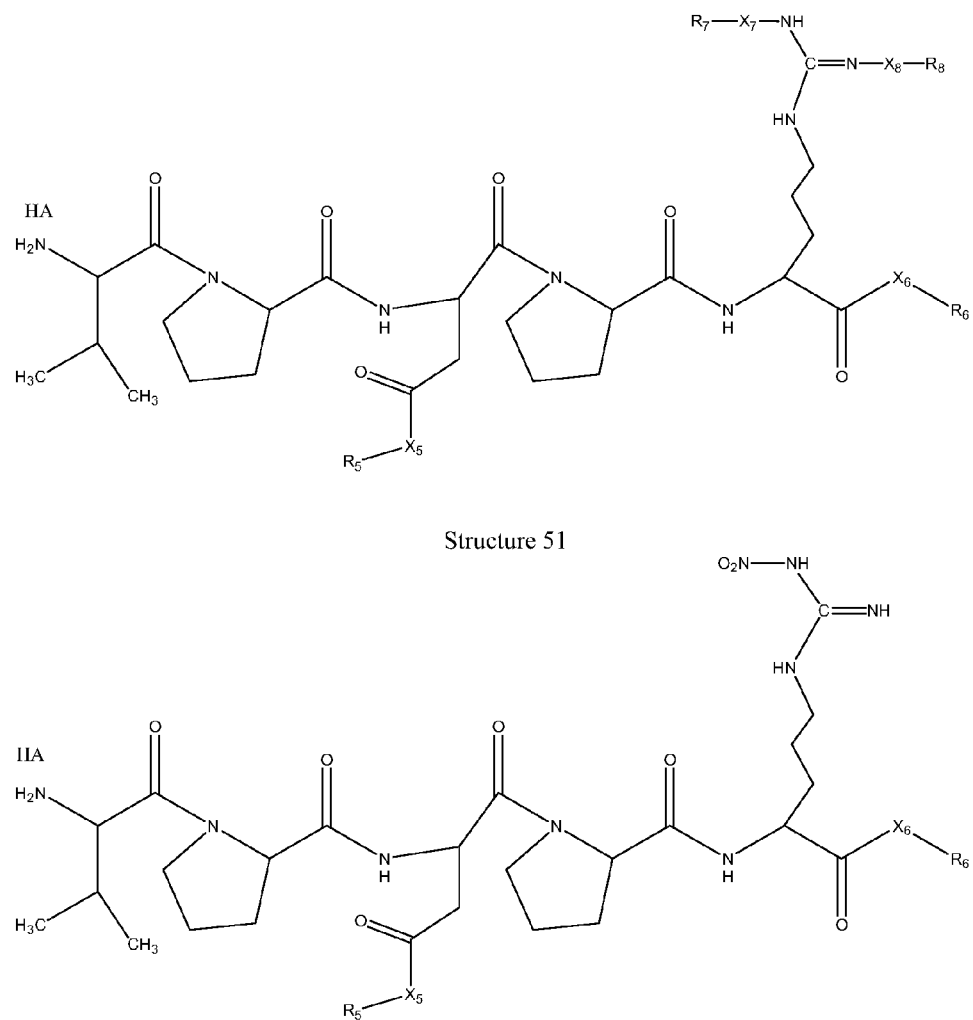
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
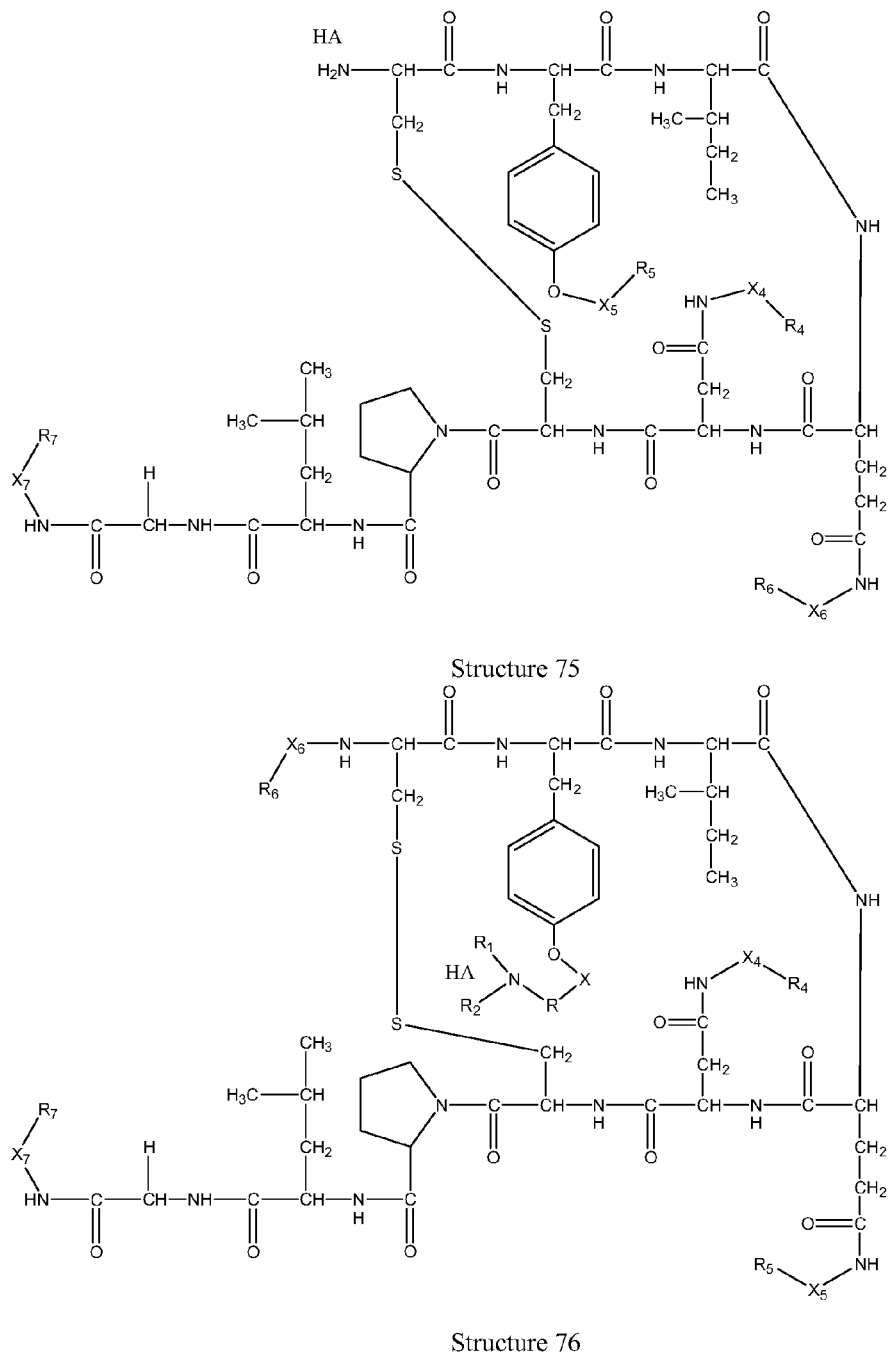
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
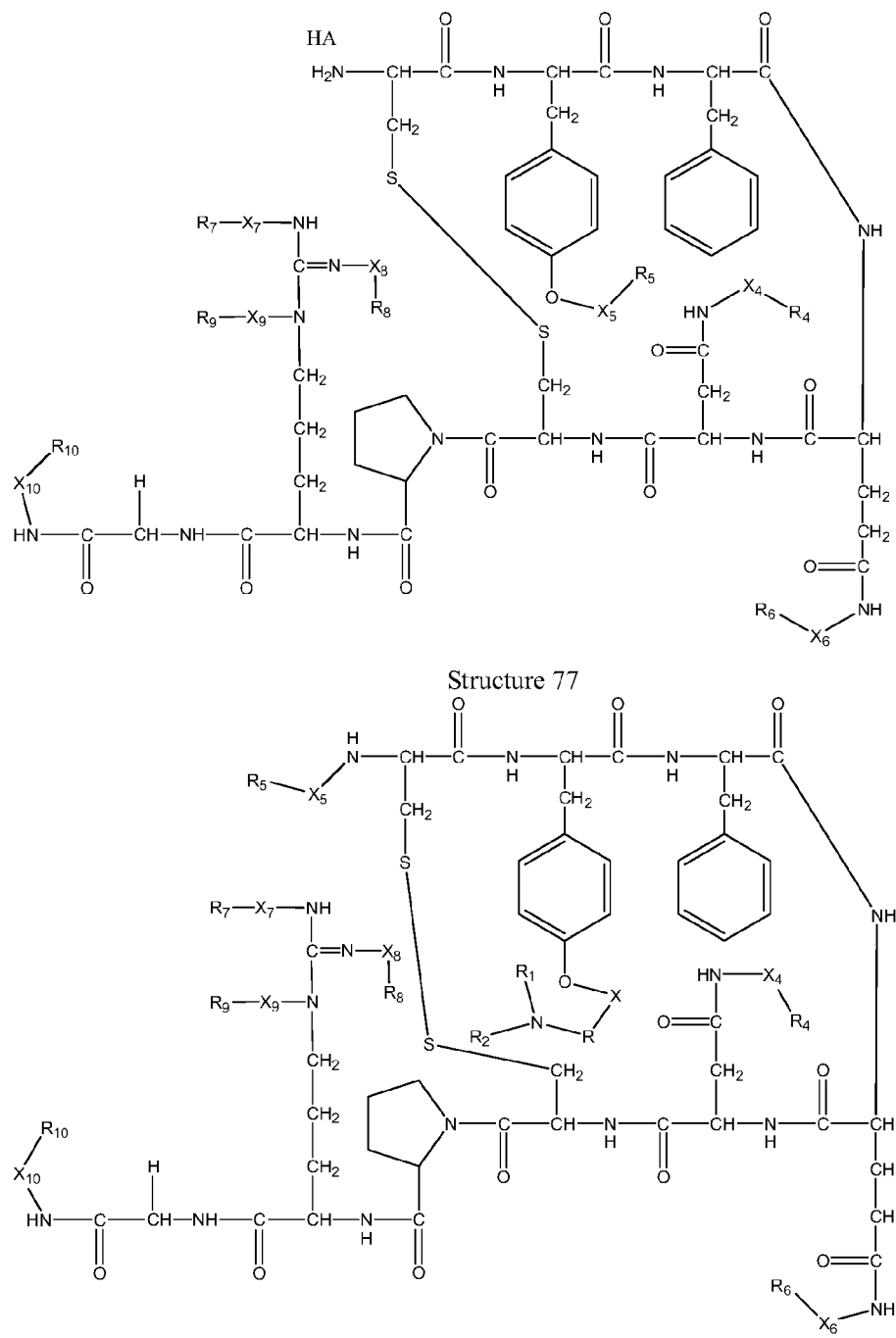
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
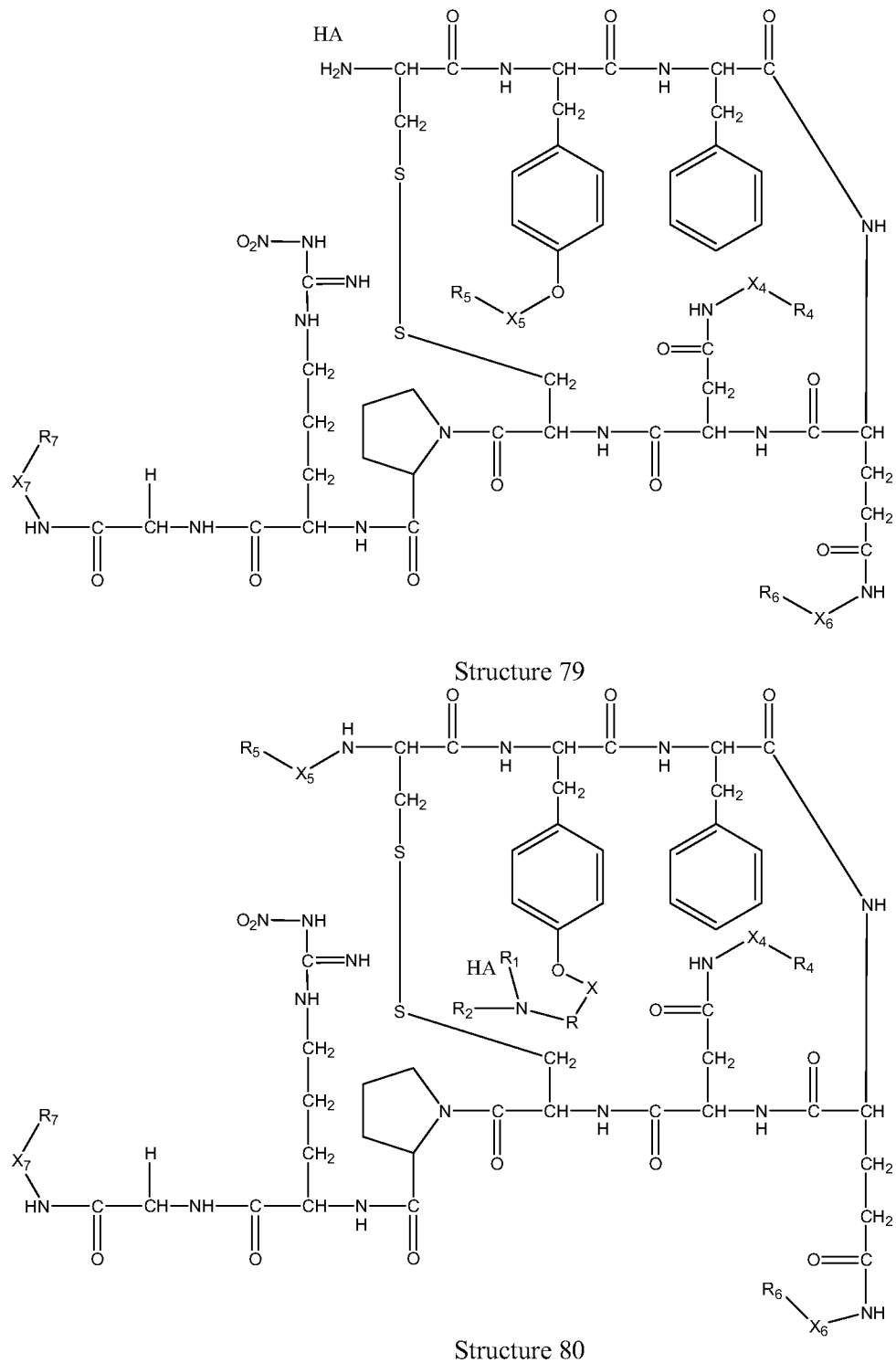
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
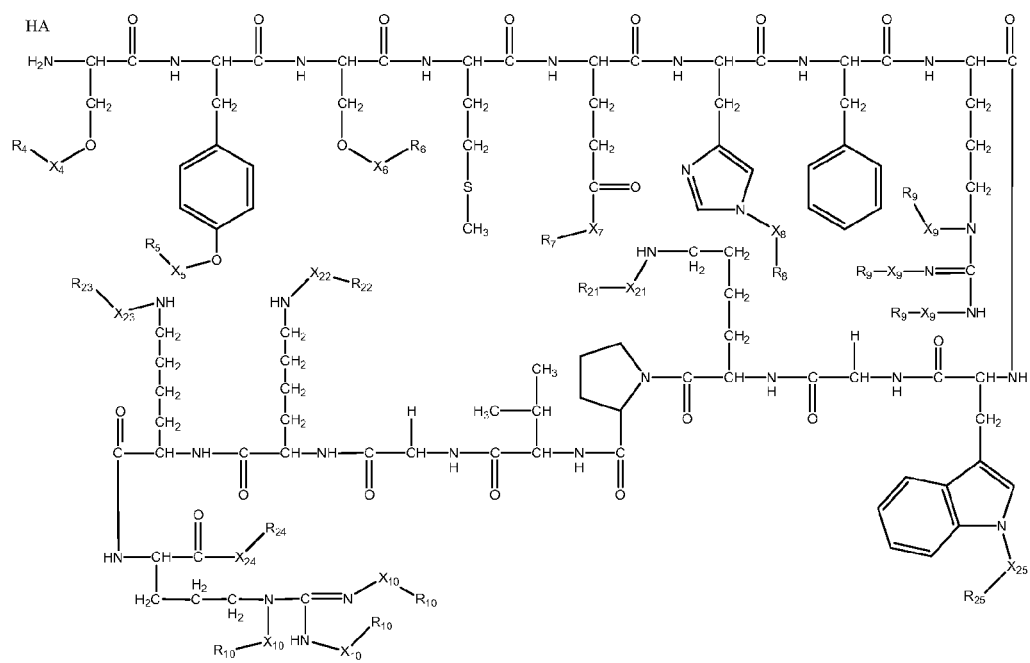
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
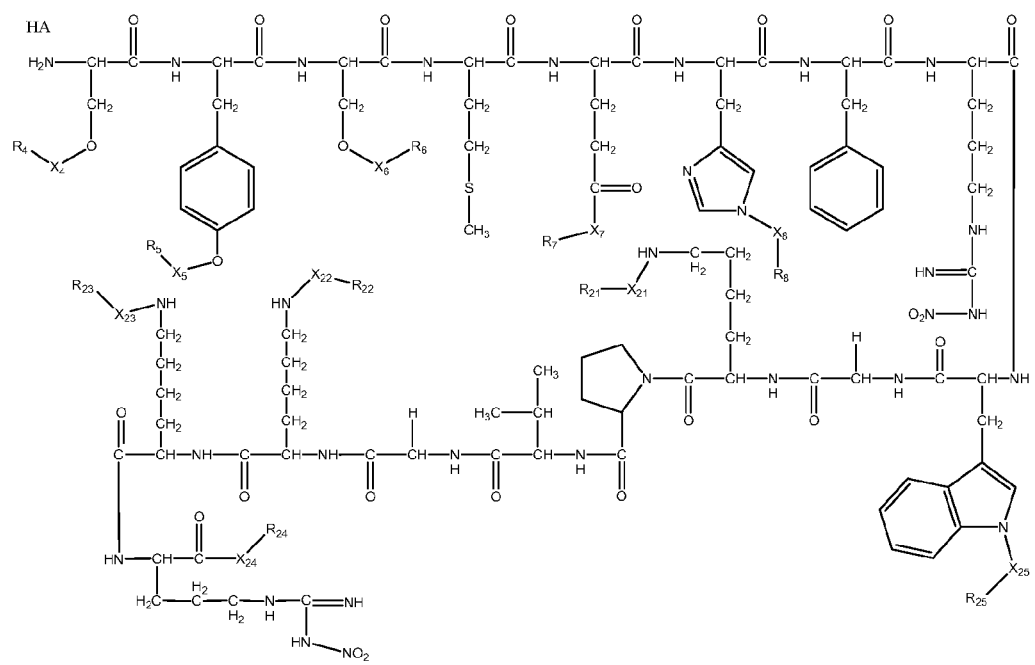
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
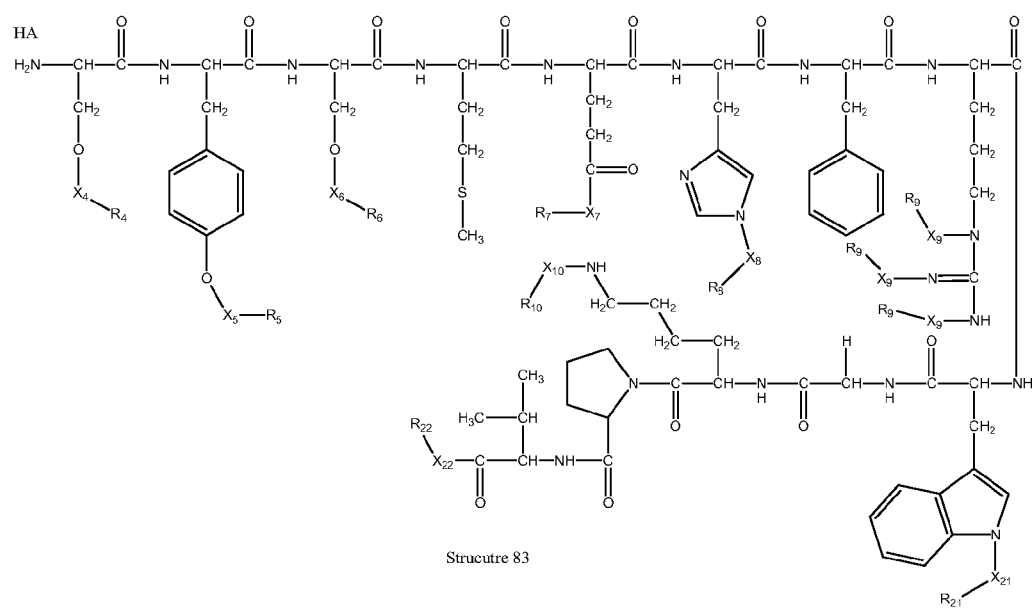
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
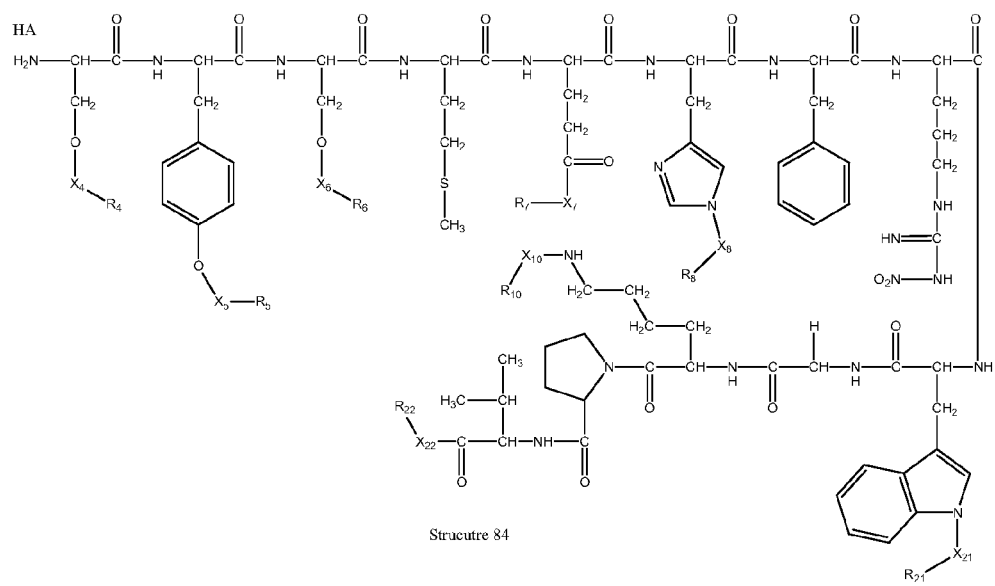
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
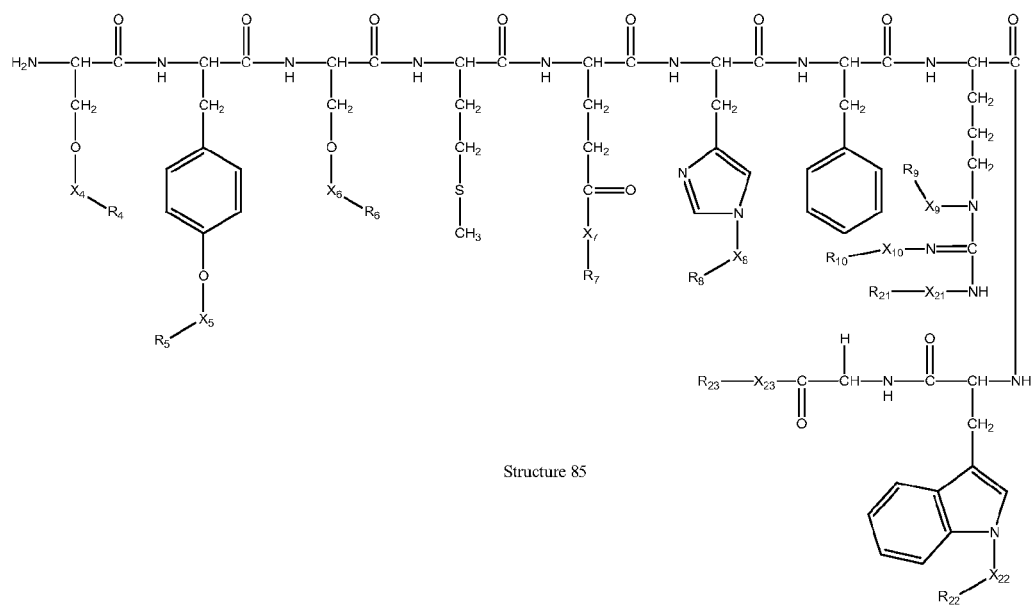
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
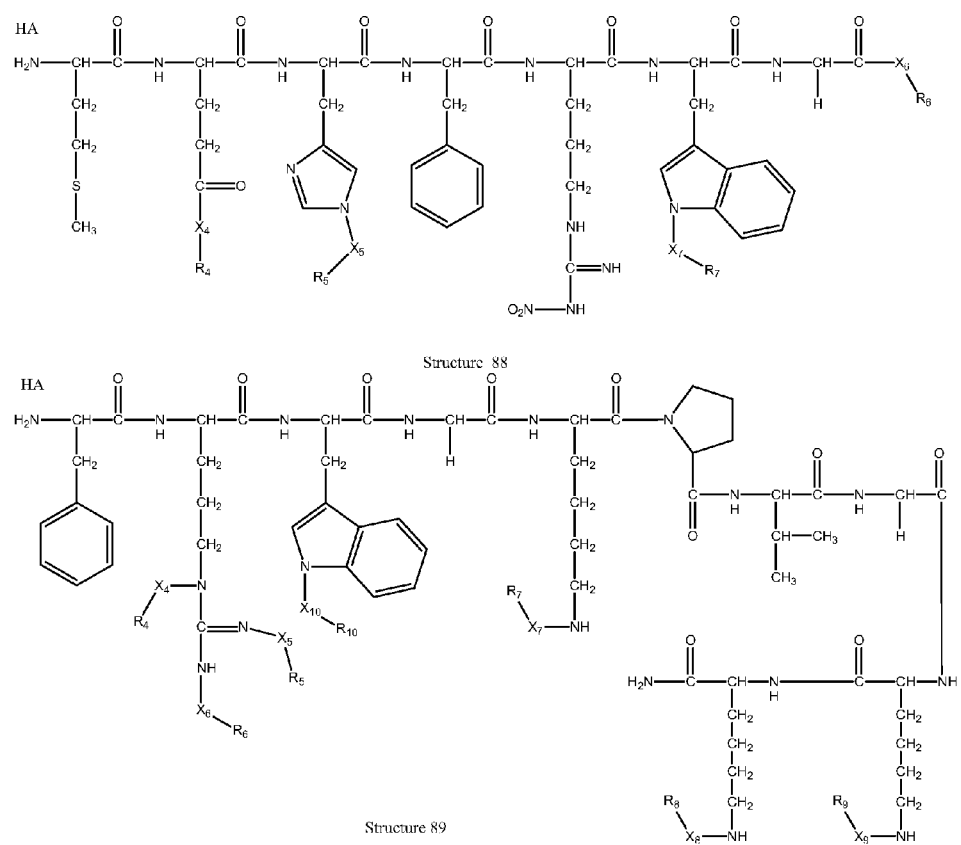
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
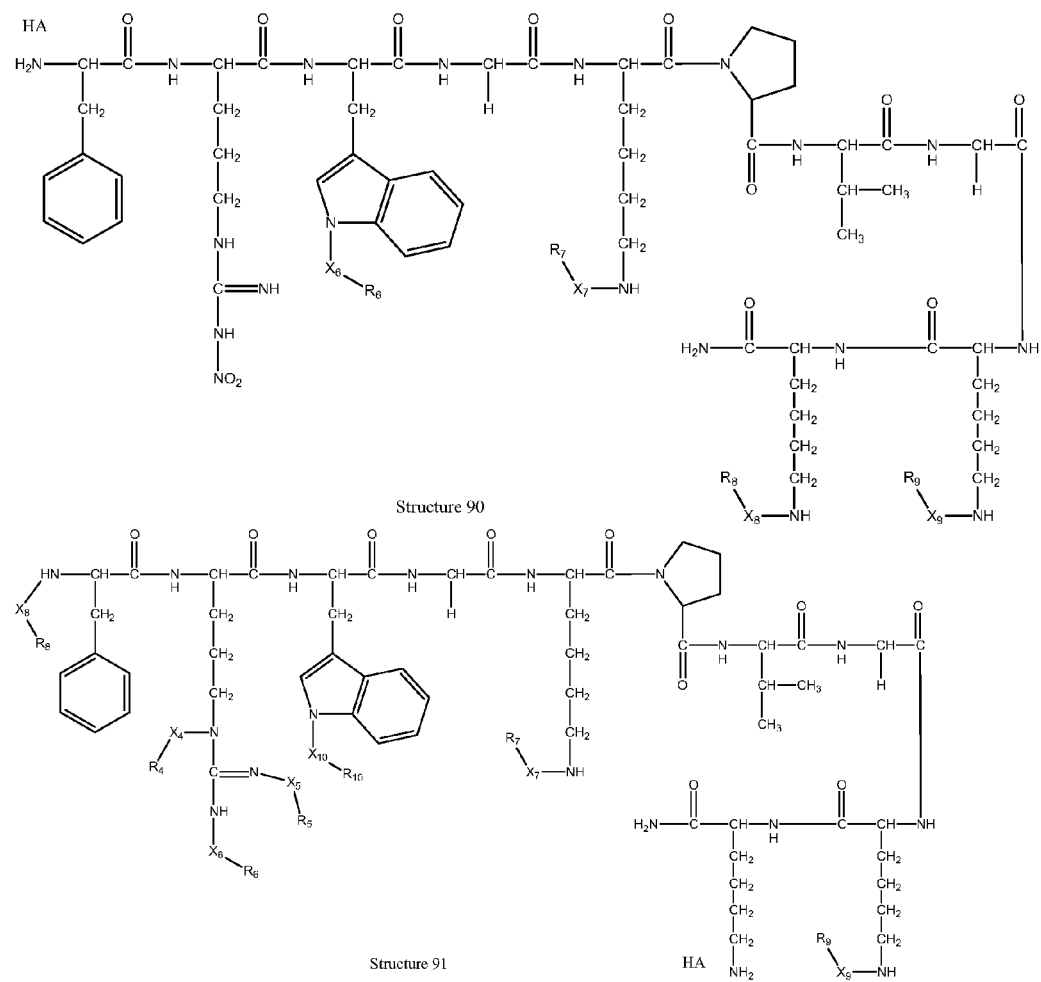
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
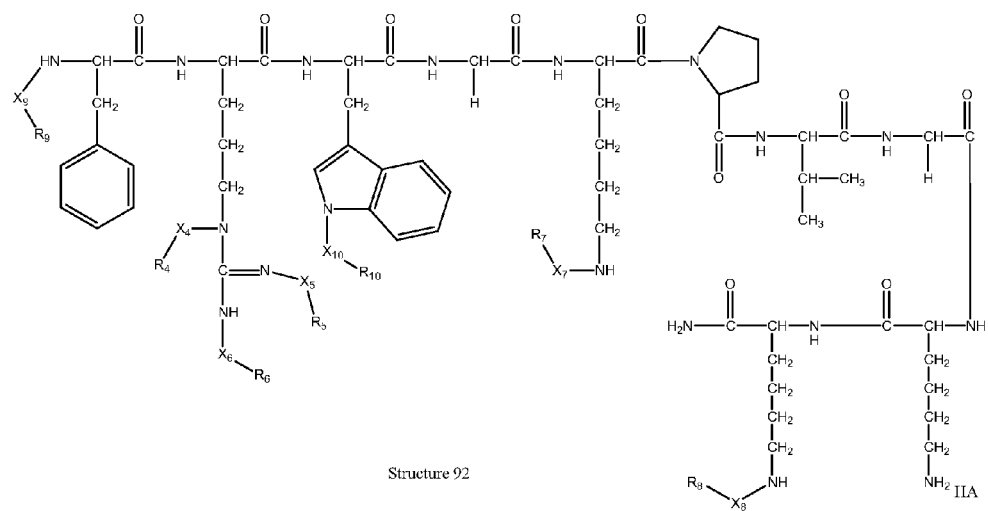
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
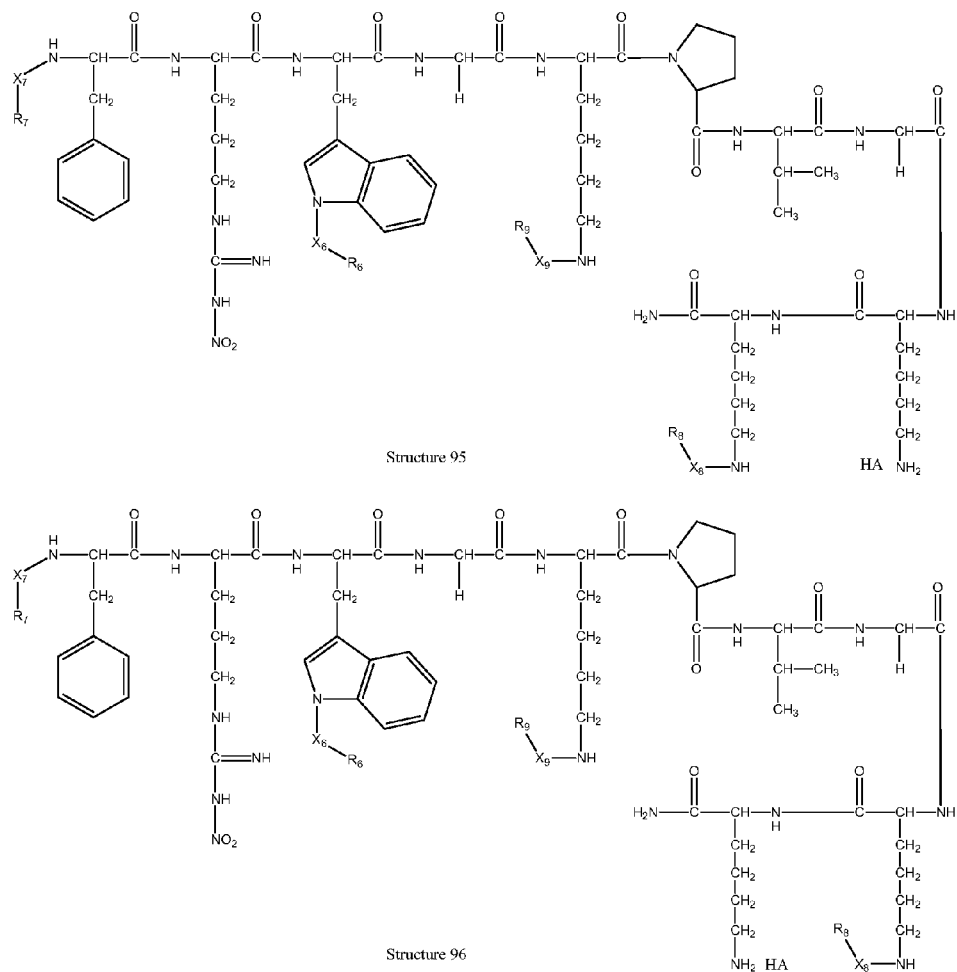
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
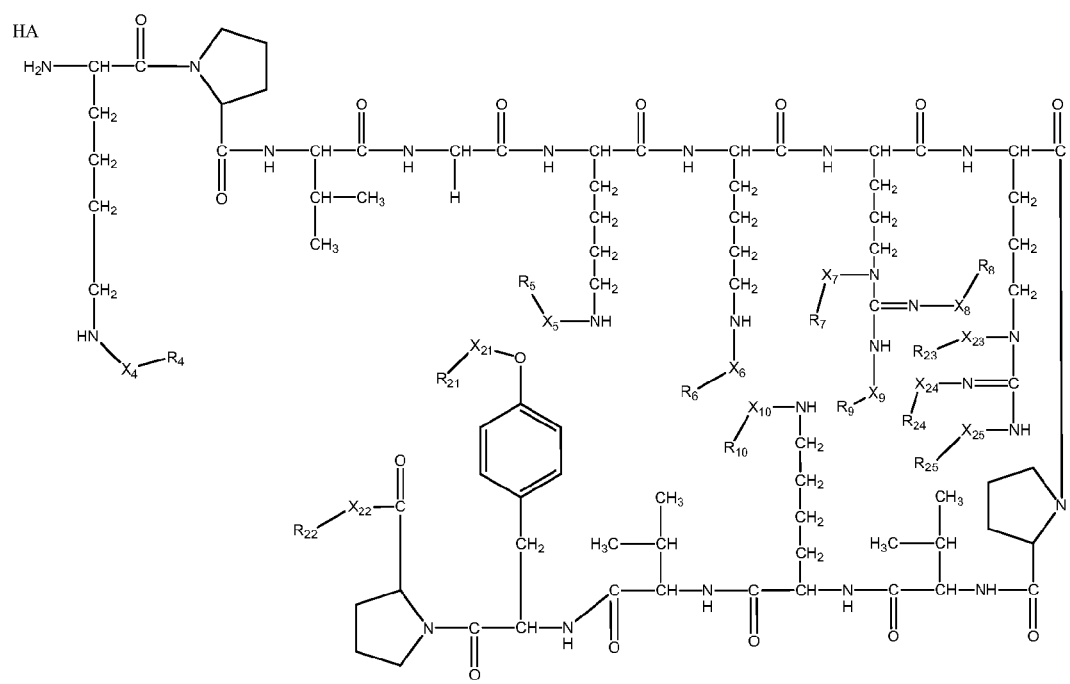
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
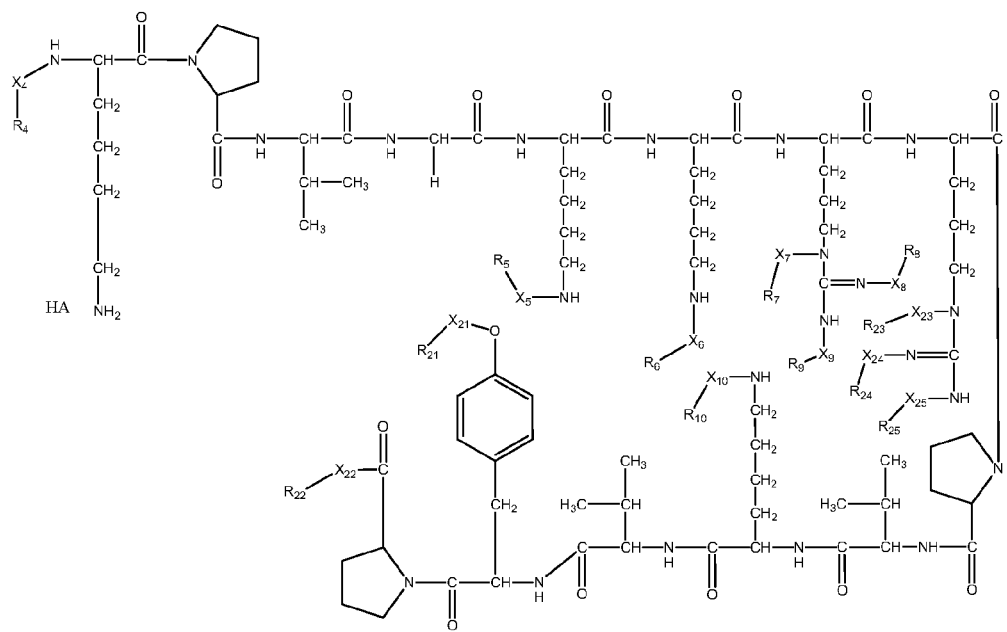
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
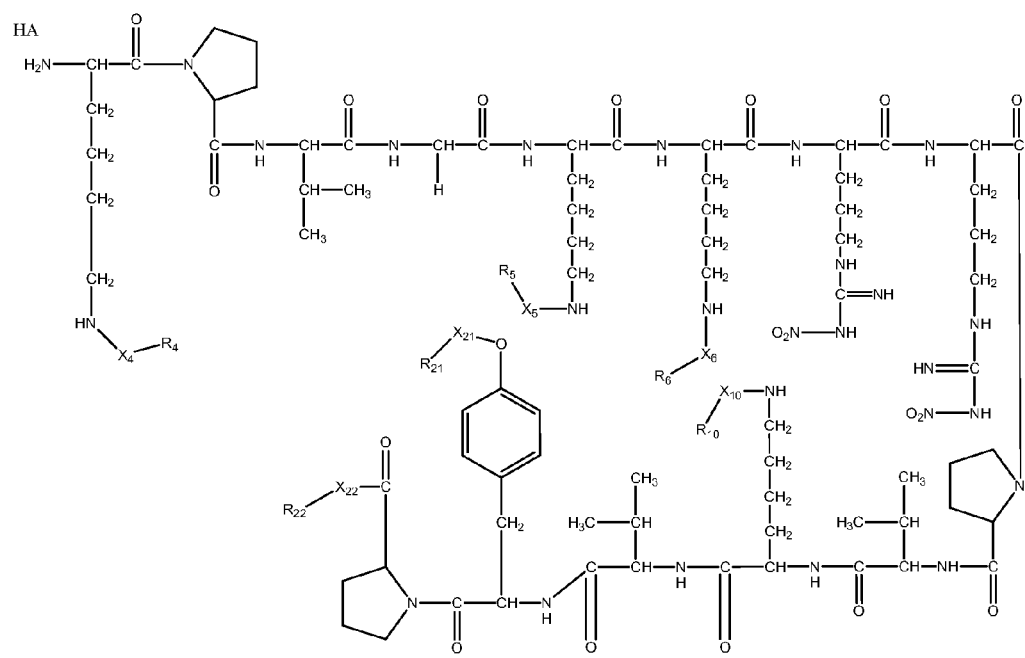
Figures 1, 52:
Figures 1, 53:
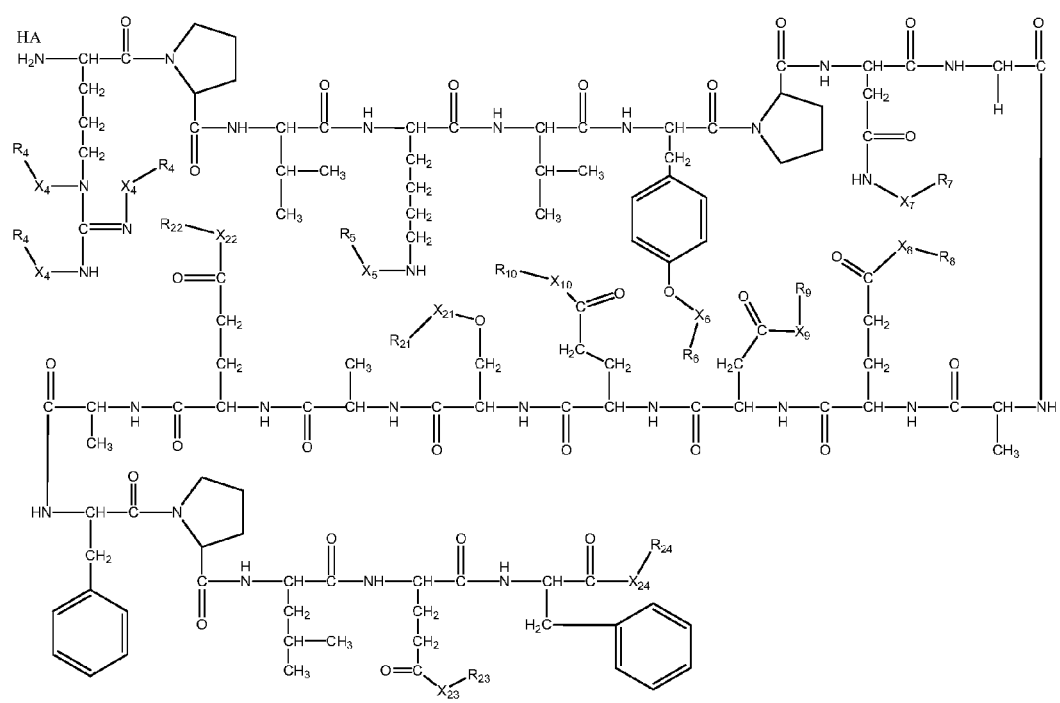
Figures 1, 54:
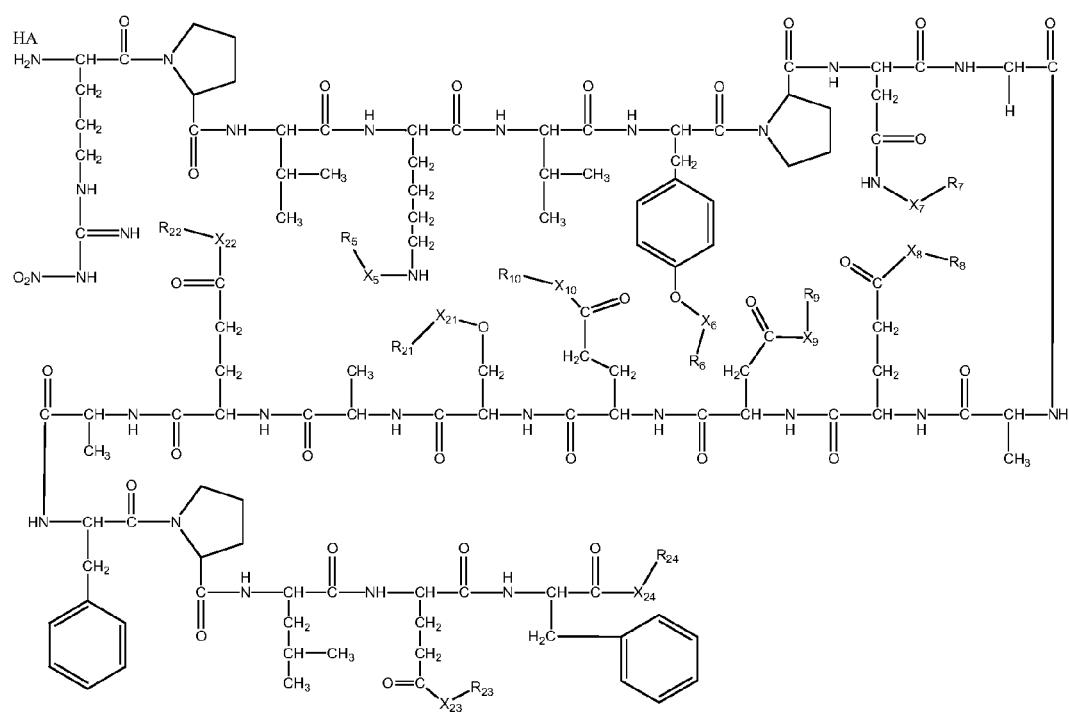
Figures 1, 55:
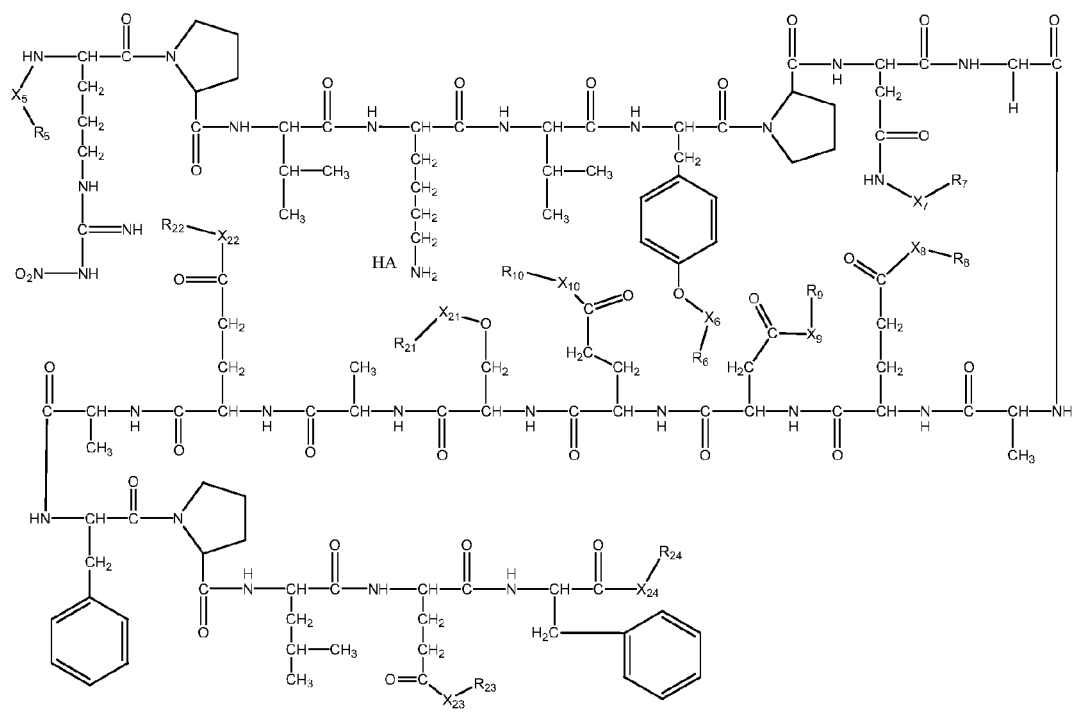
Figure 1:
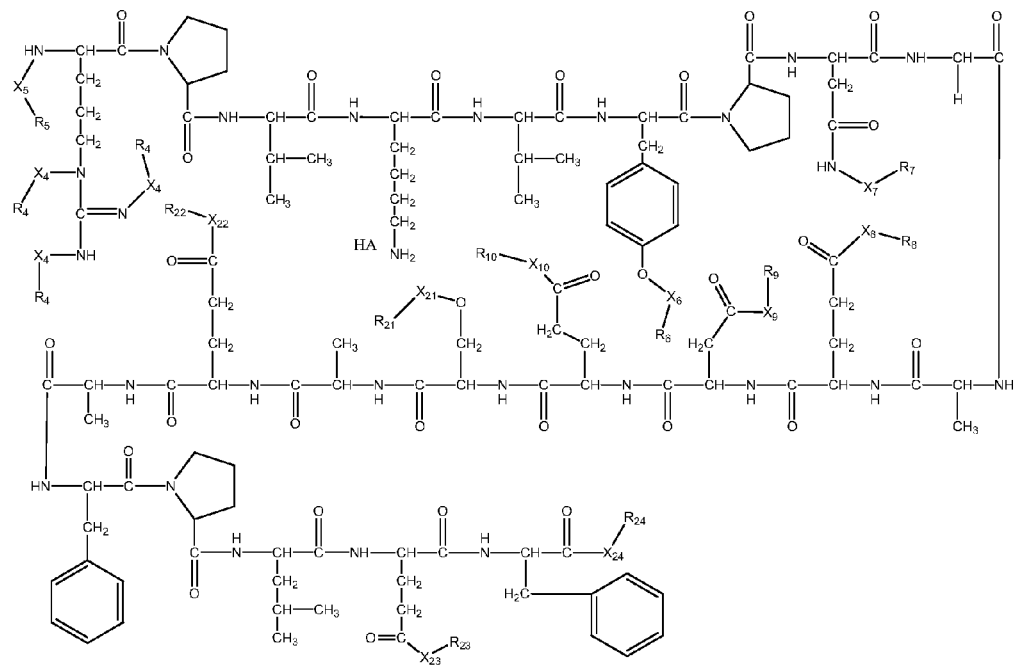
Figure 56:
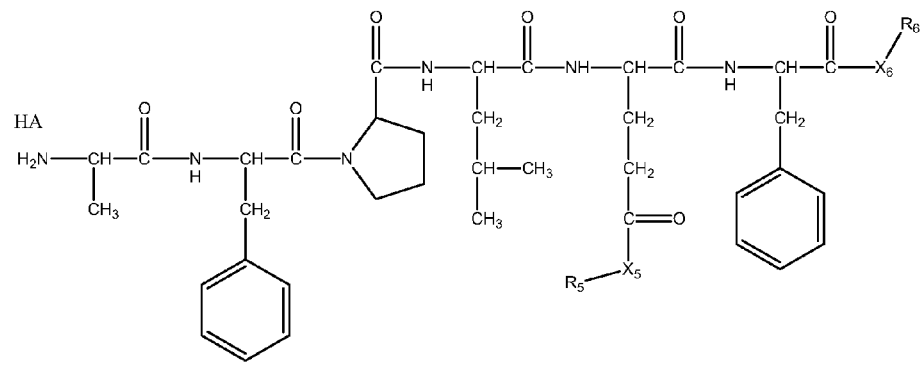
Figures 1, 57:
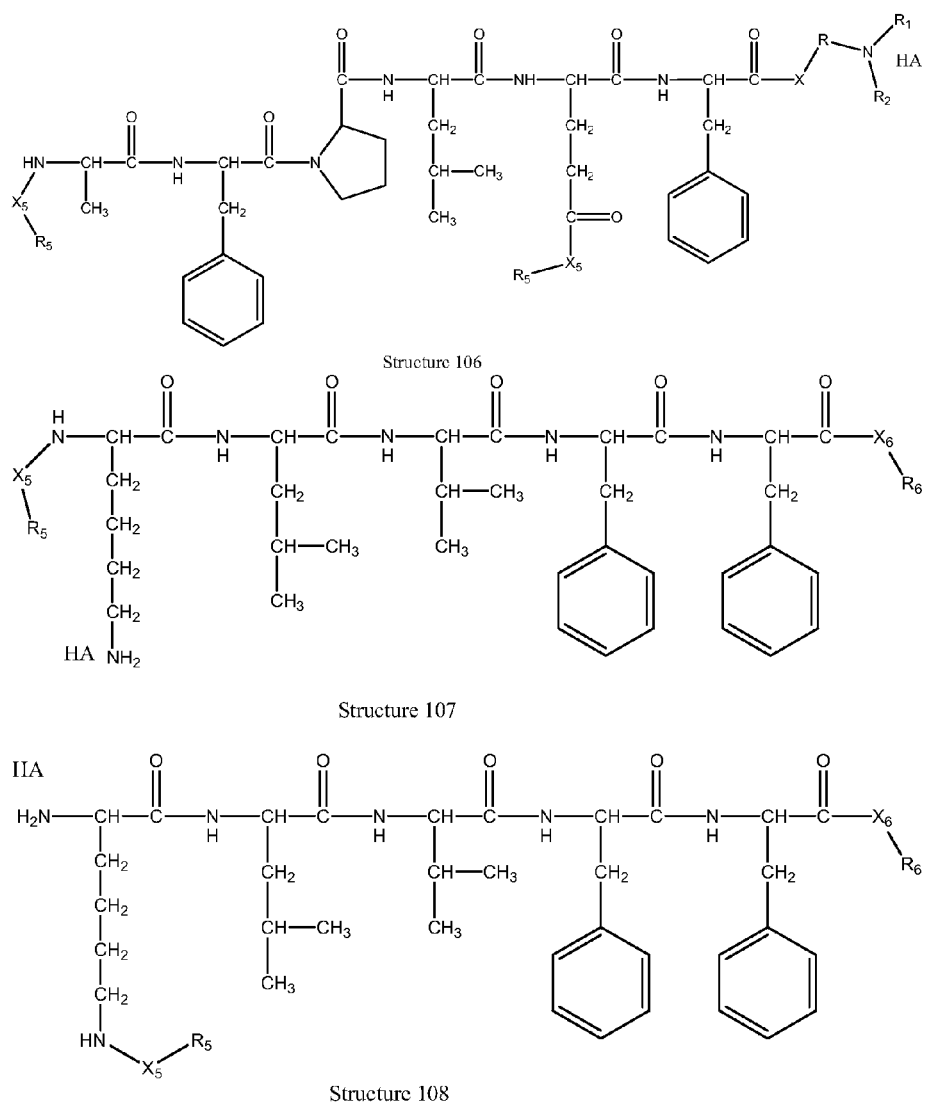
Figures 1, 58:
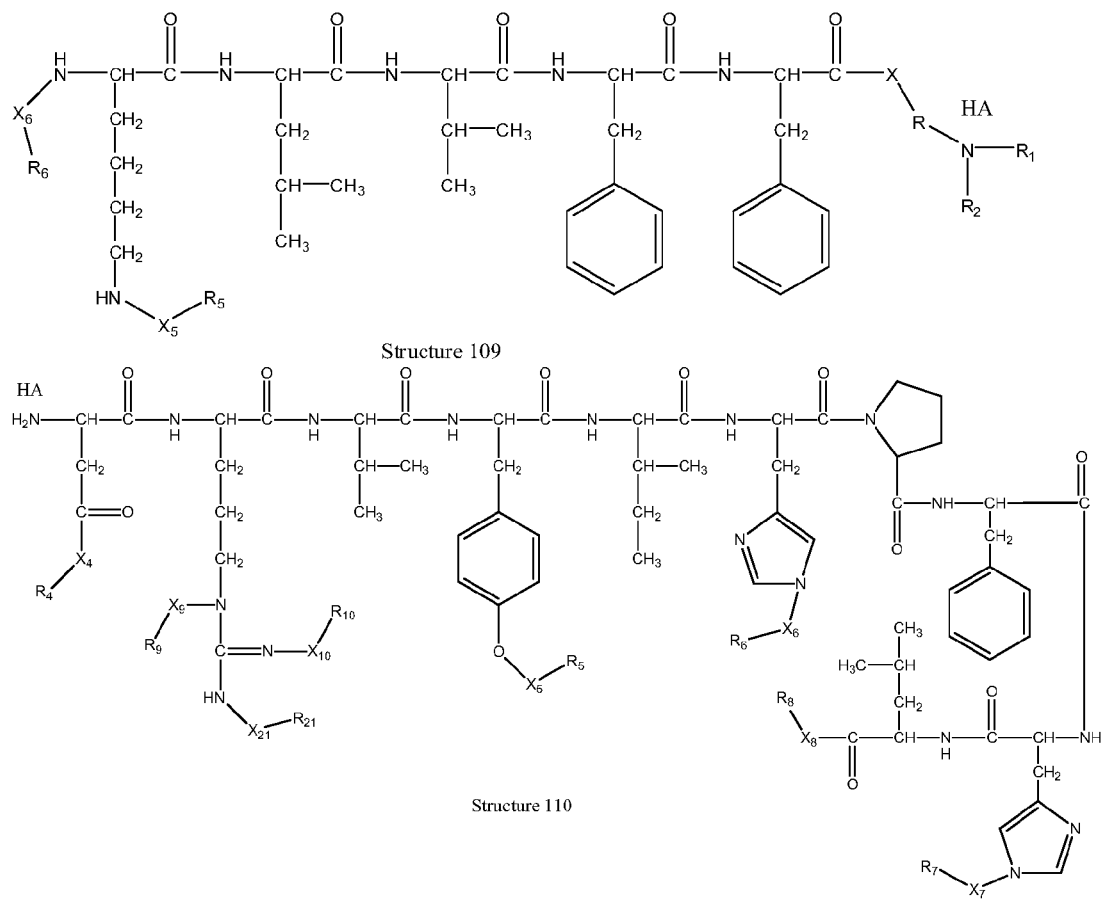
Figures 1, 59:
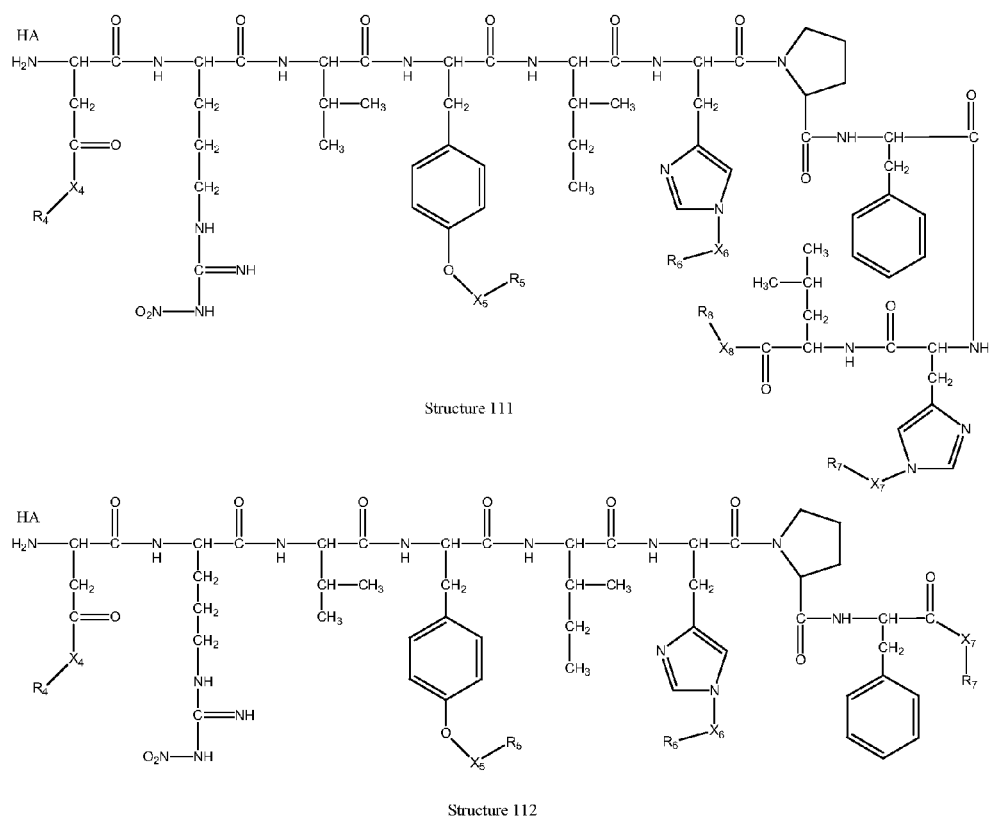
Figures 1, 60:
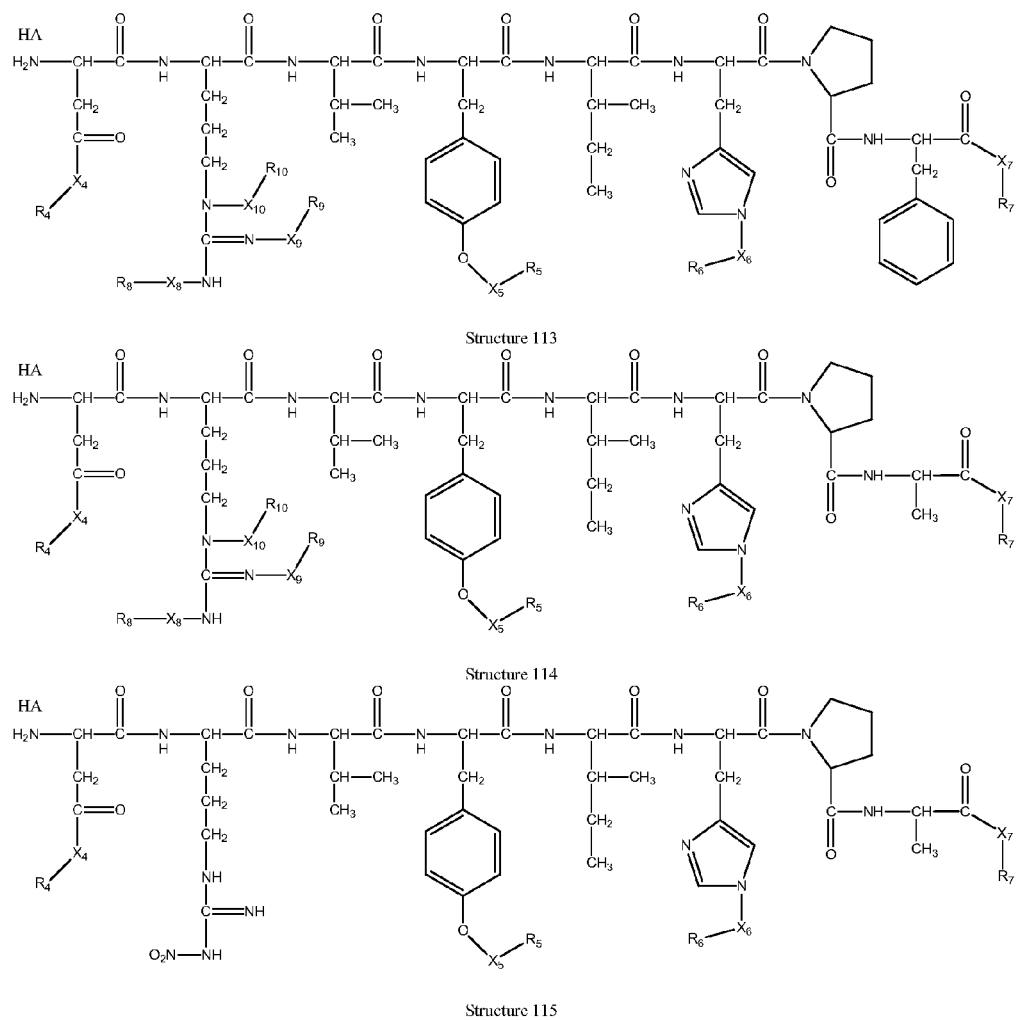
Figures 1, 61:
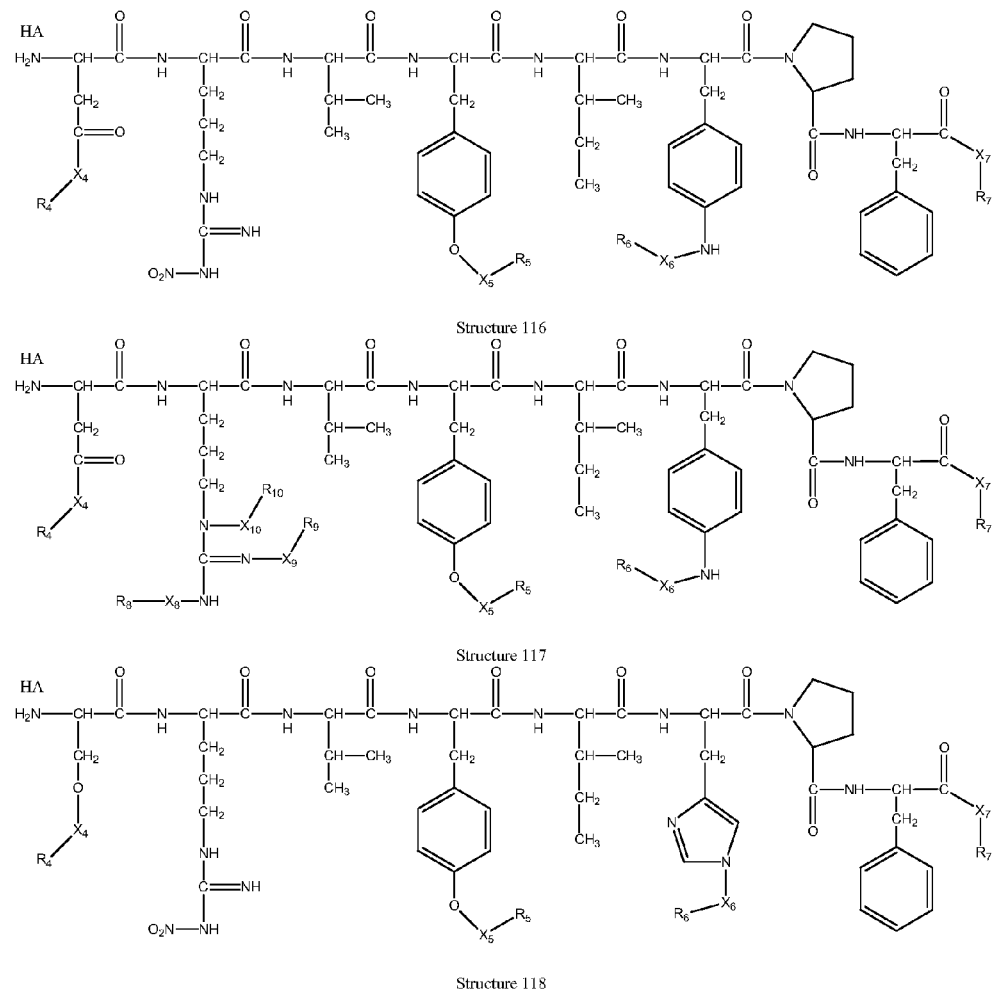
Figures 1, 62:
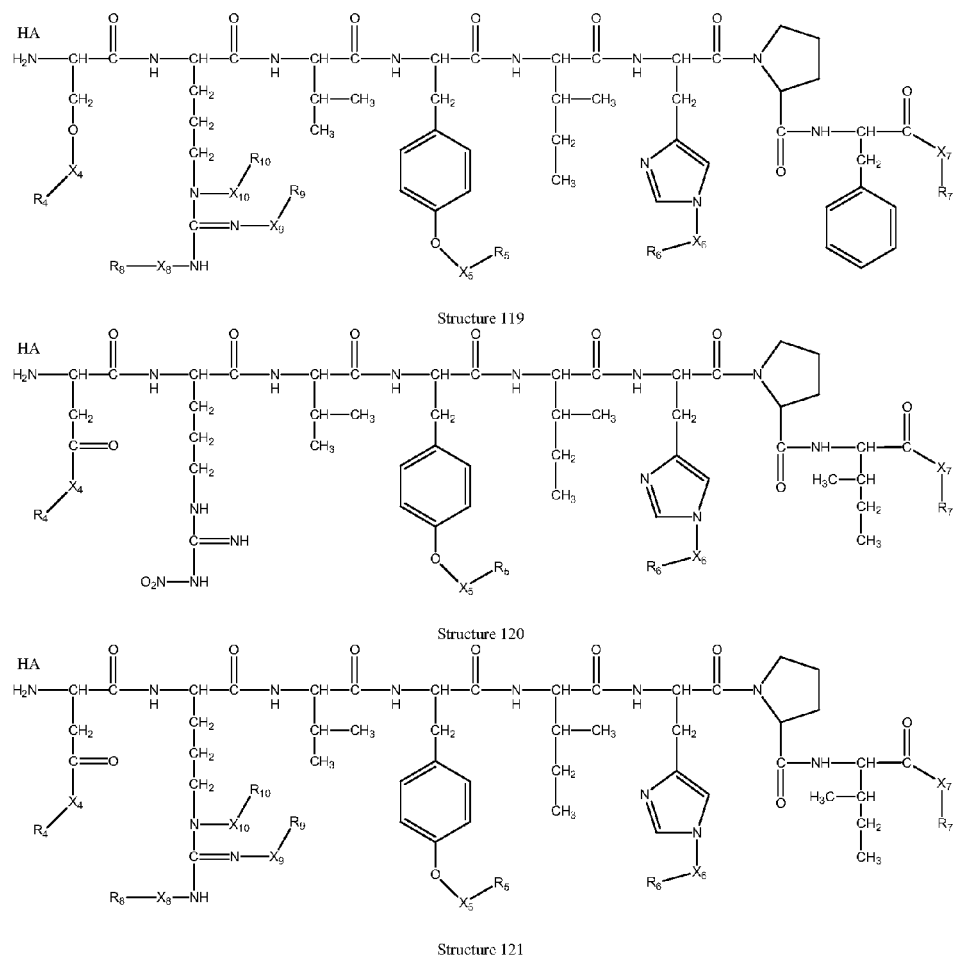
Figures 1, 63:
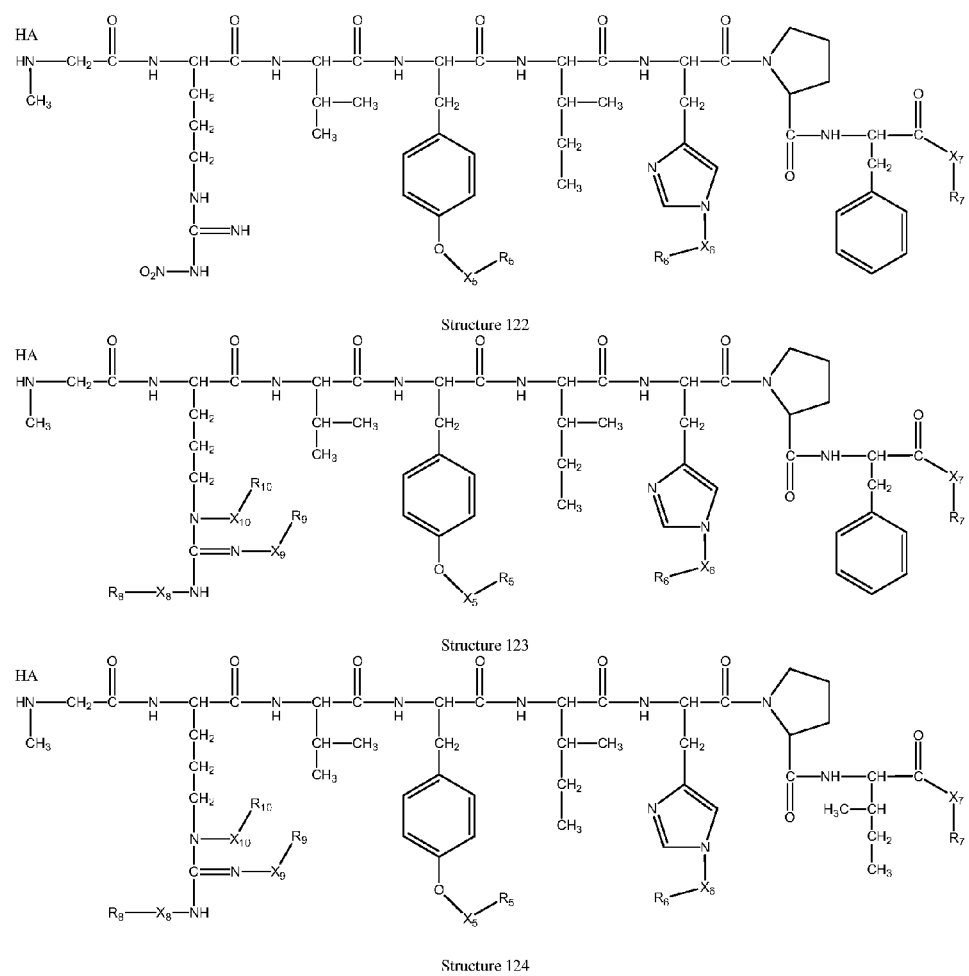
Figures 1, 64:
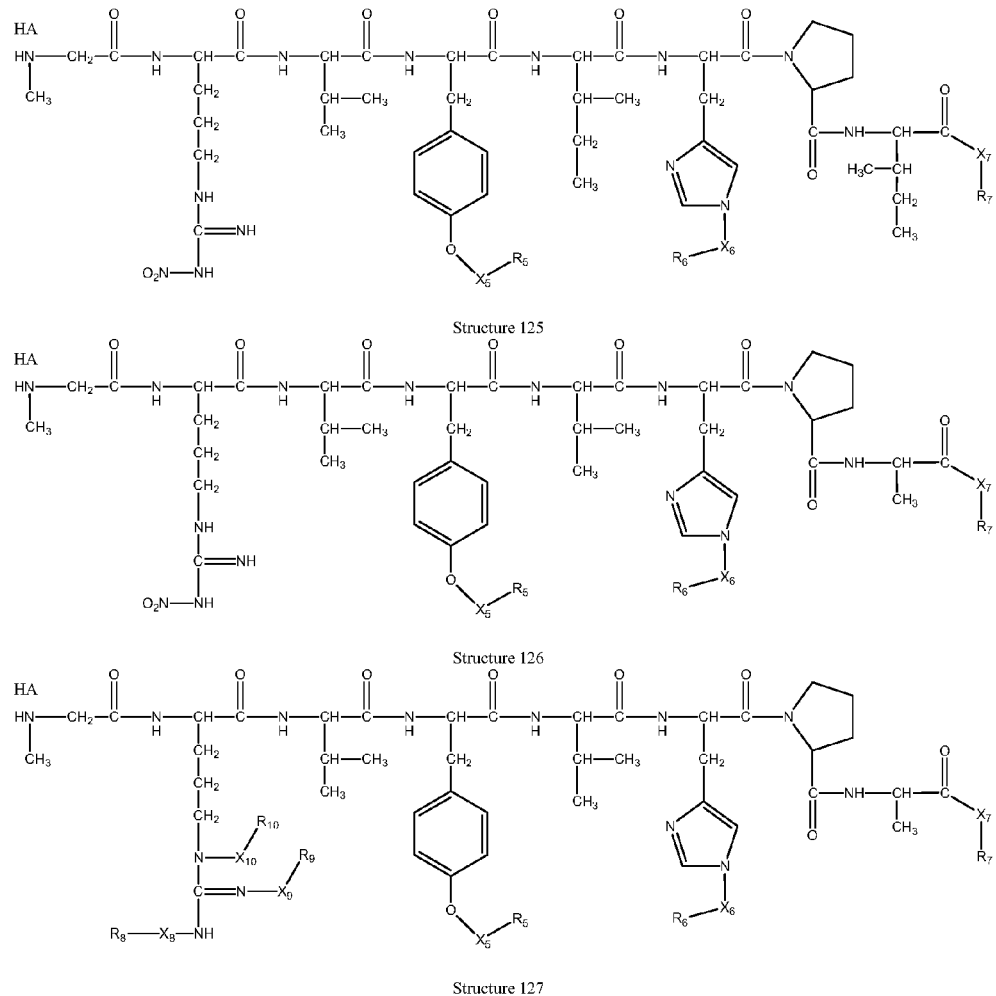
Figures 1, 65:
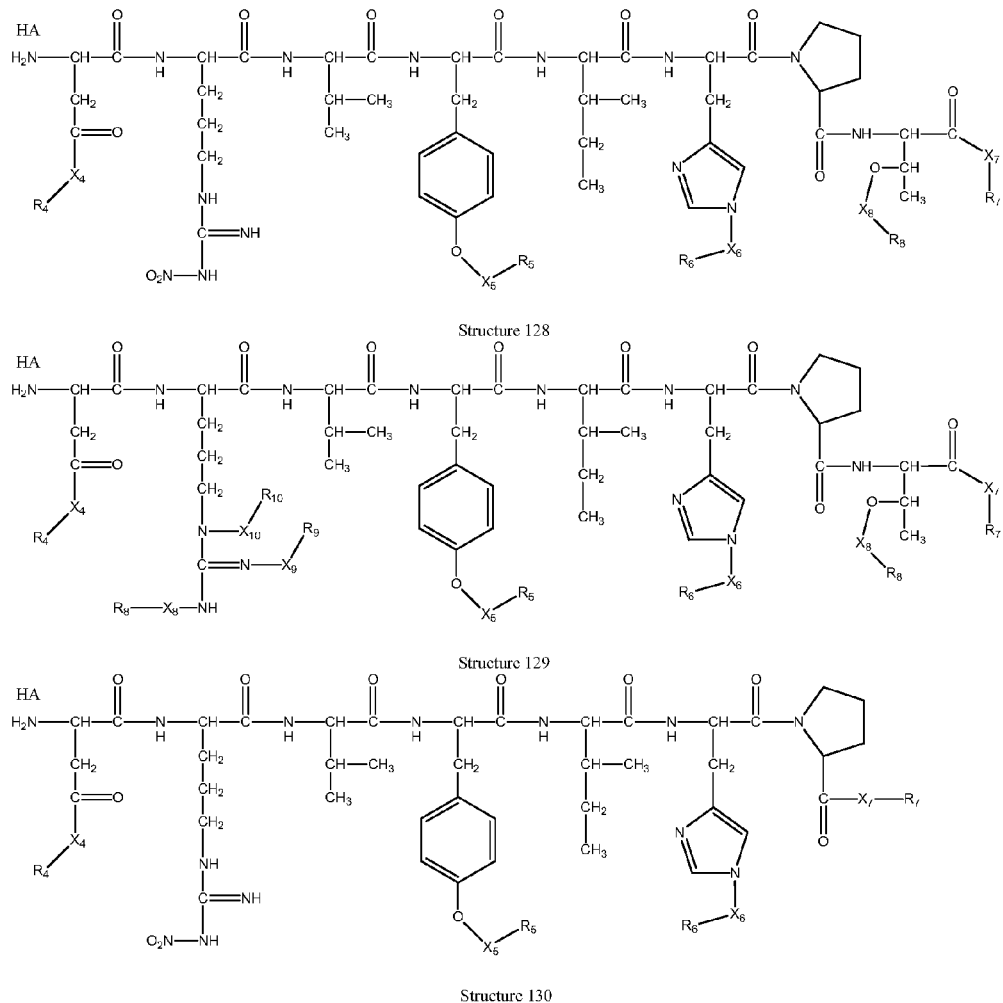
Figures 1, 66:
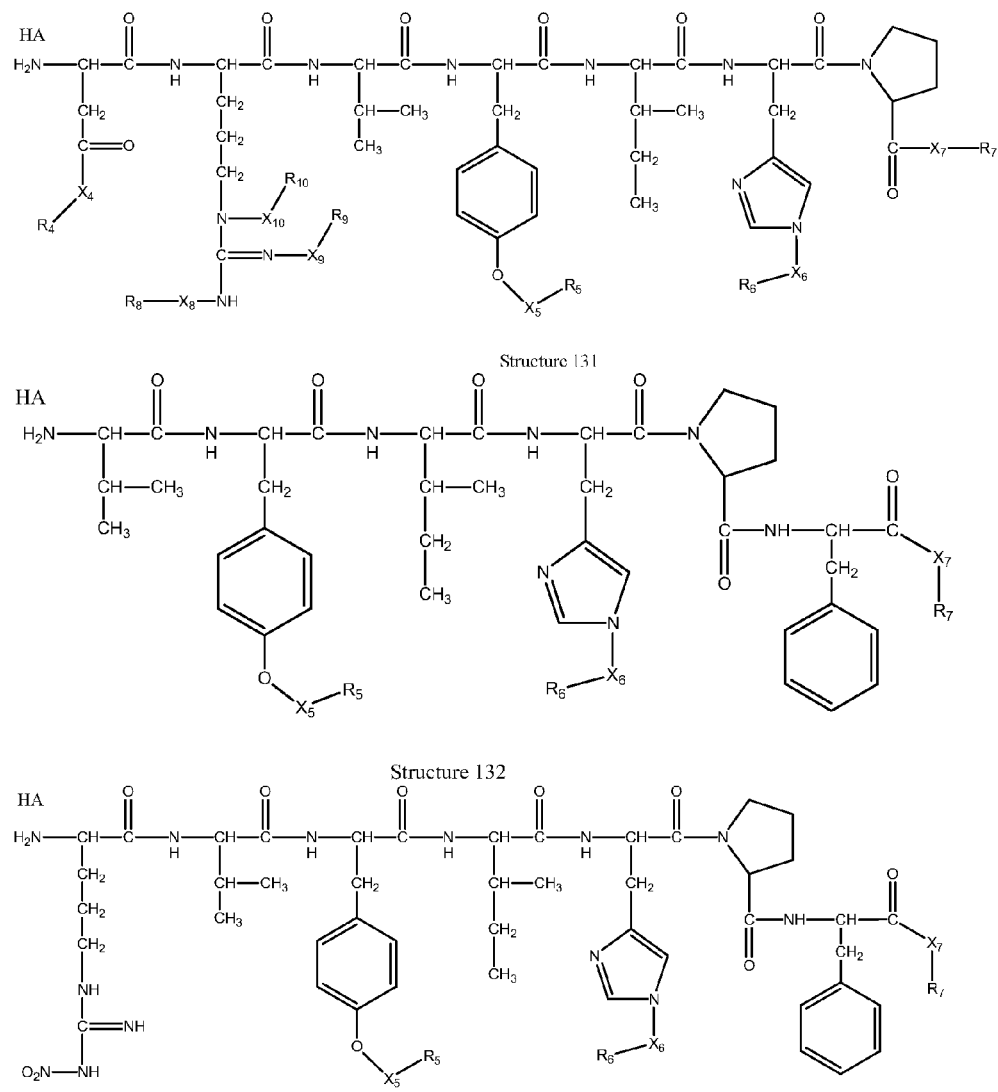
Figures 1, 67:
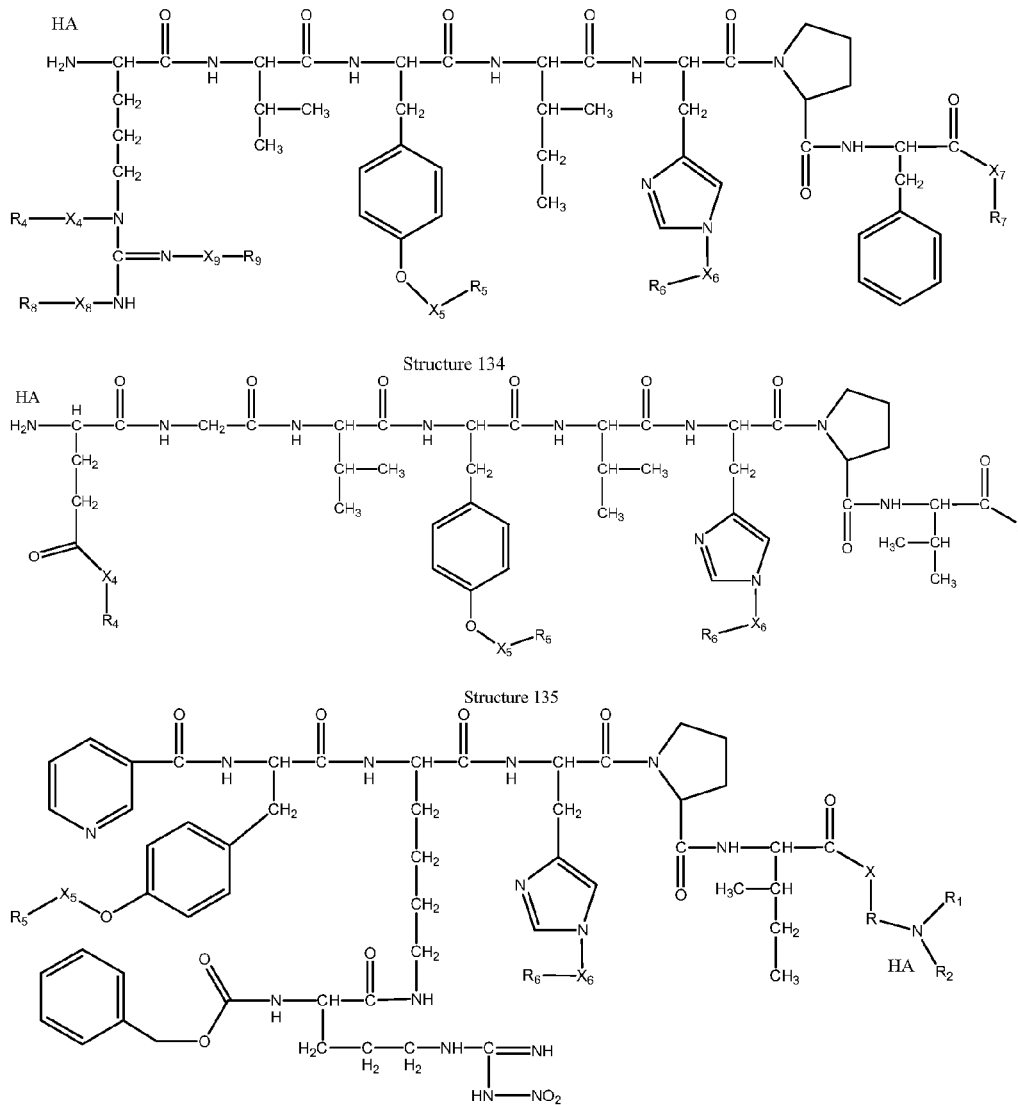
Figures 1, 68:
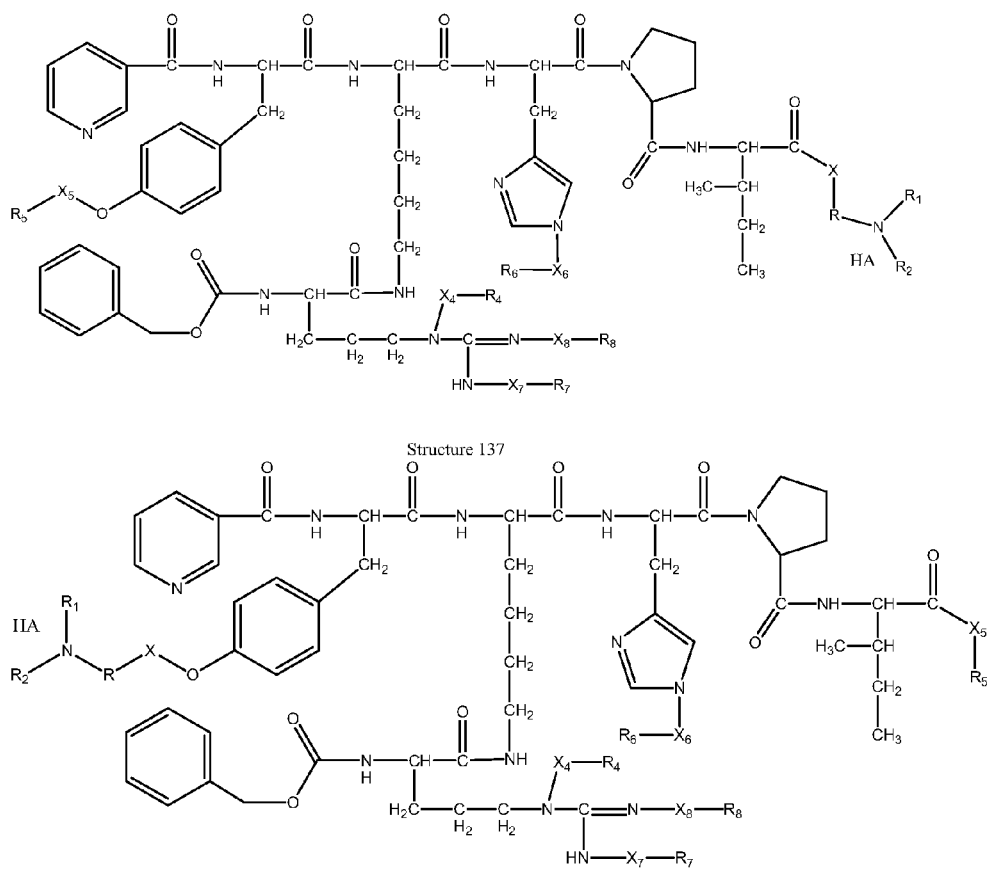
Figures 1, 69:
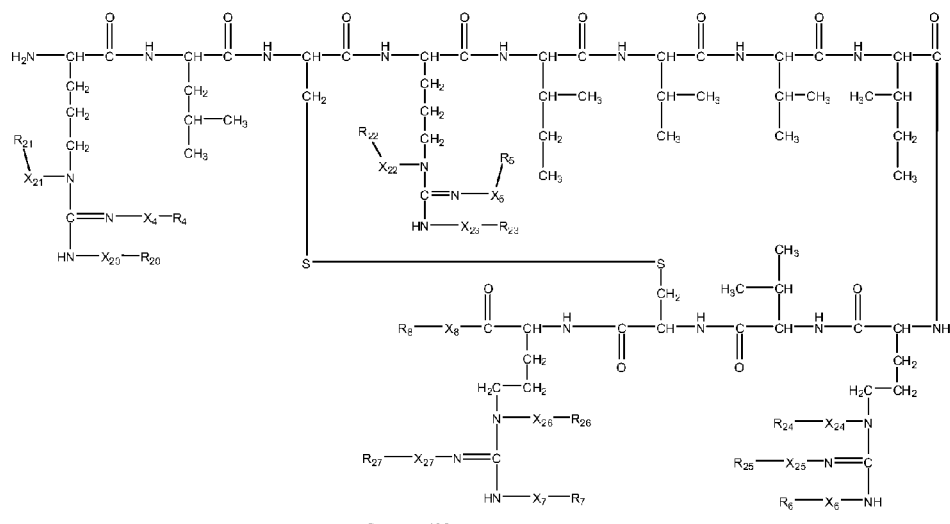
Figures 1, 70:
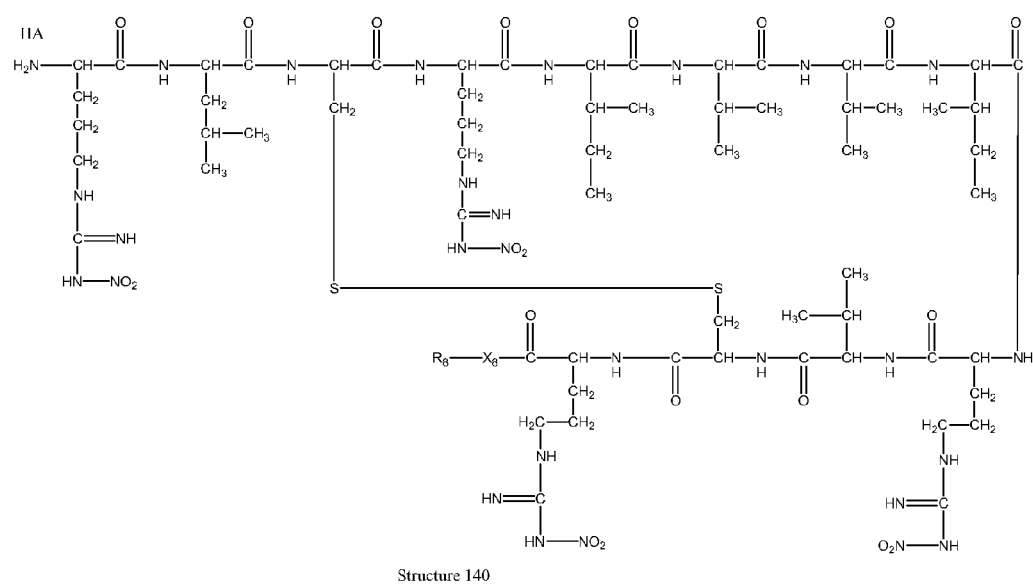
Figures 1, 71:
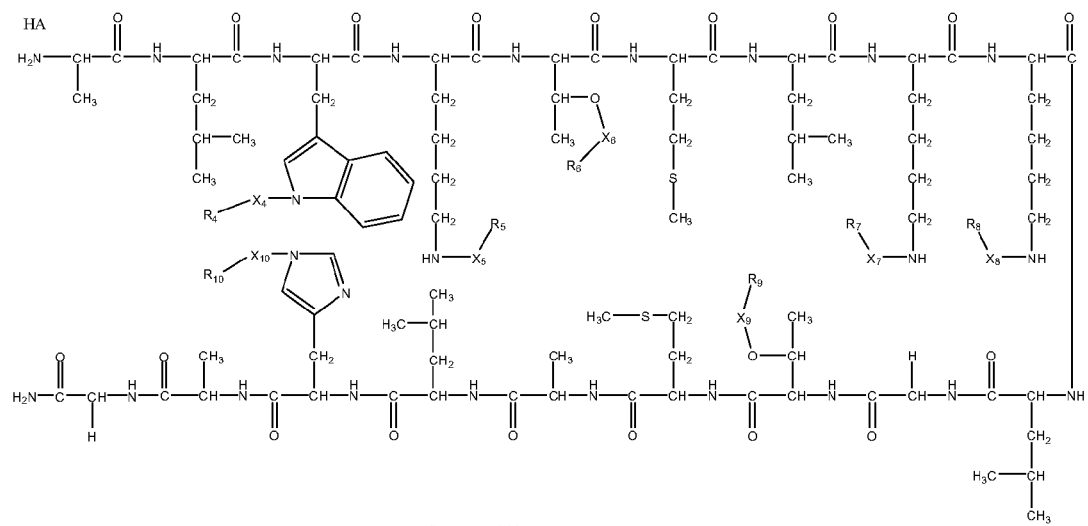
Figures 1, 72:
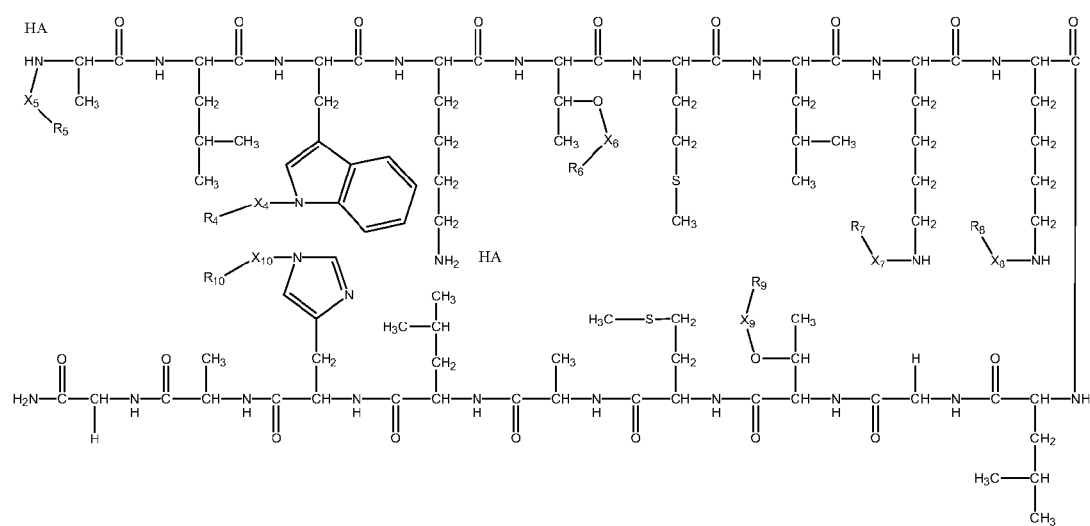
Figures 1, 73:
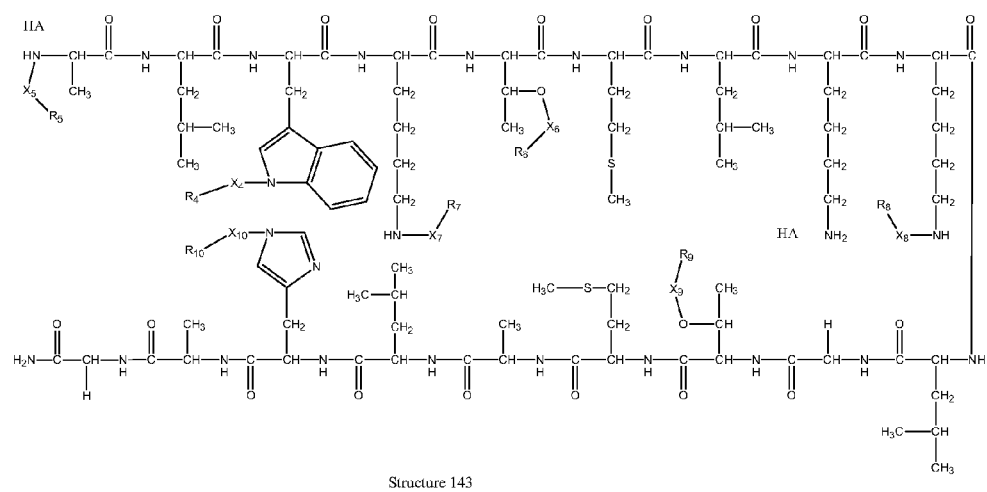
Figures 1, 74:
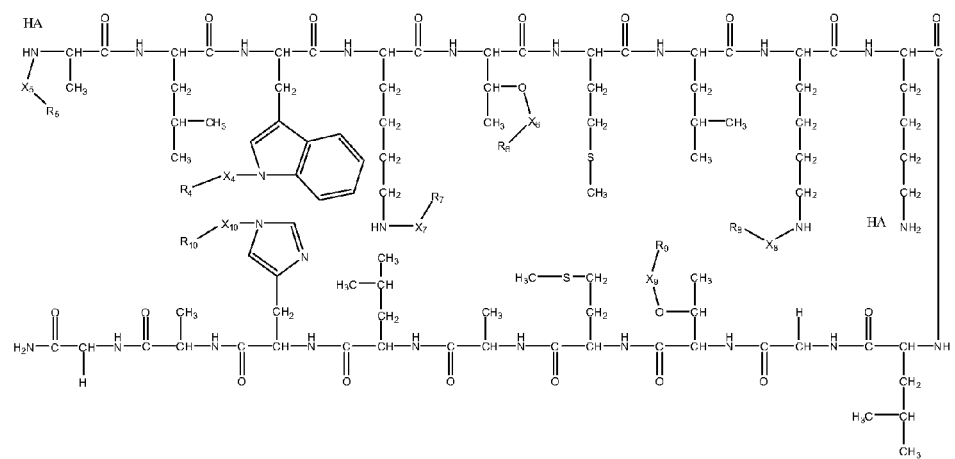
Figures 1, 75:
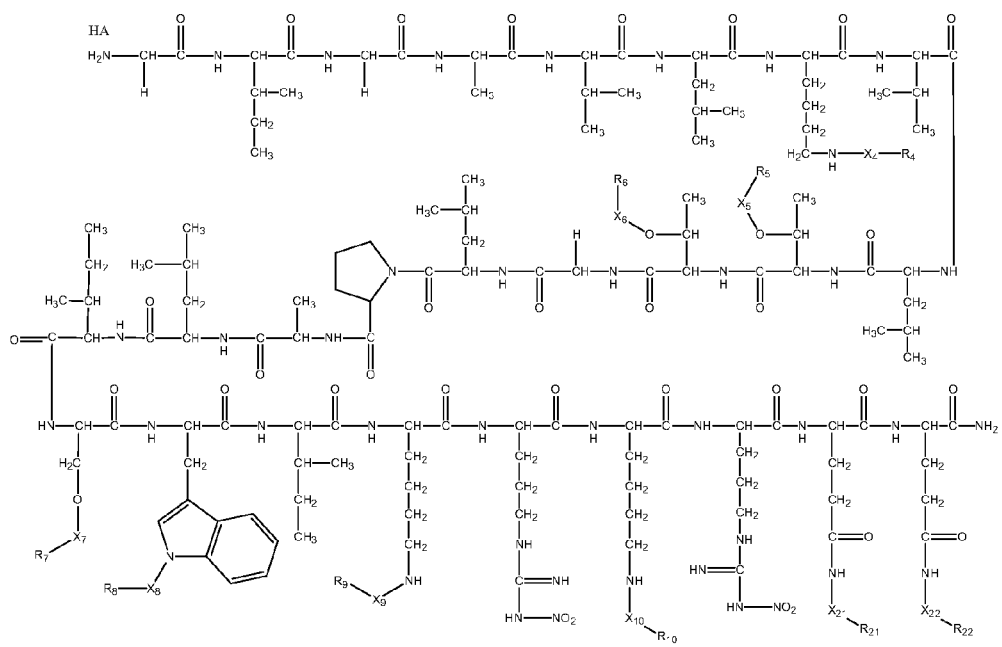
Figures 1, 76:
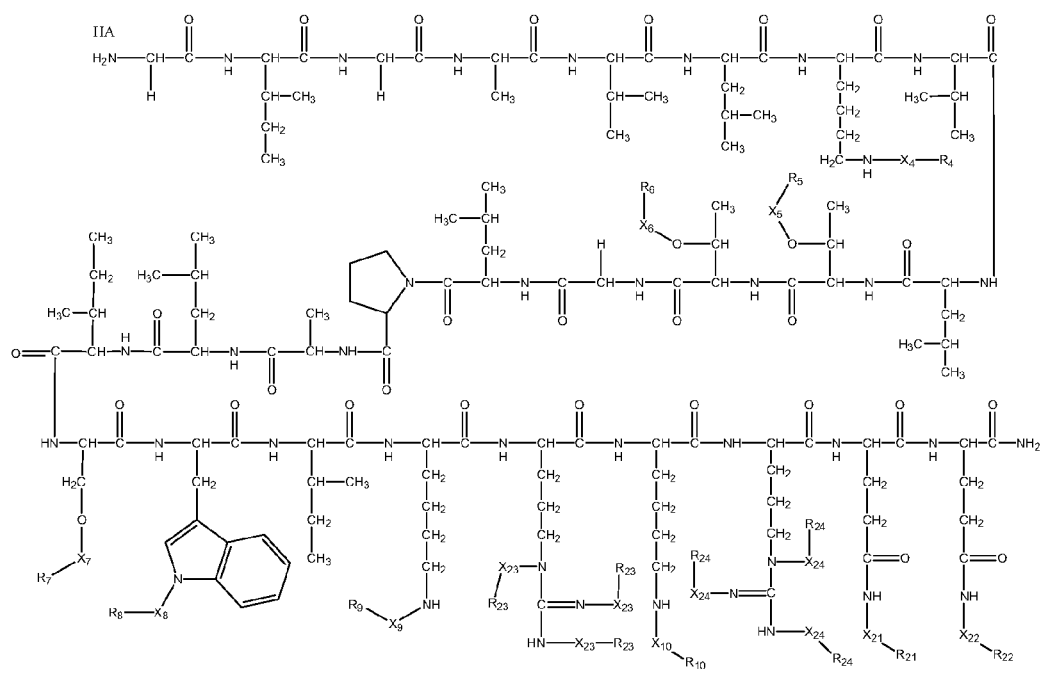
Figures 1, 77:
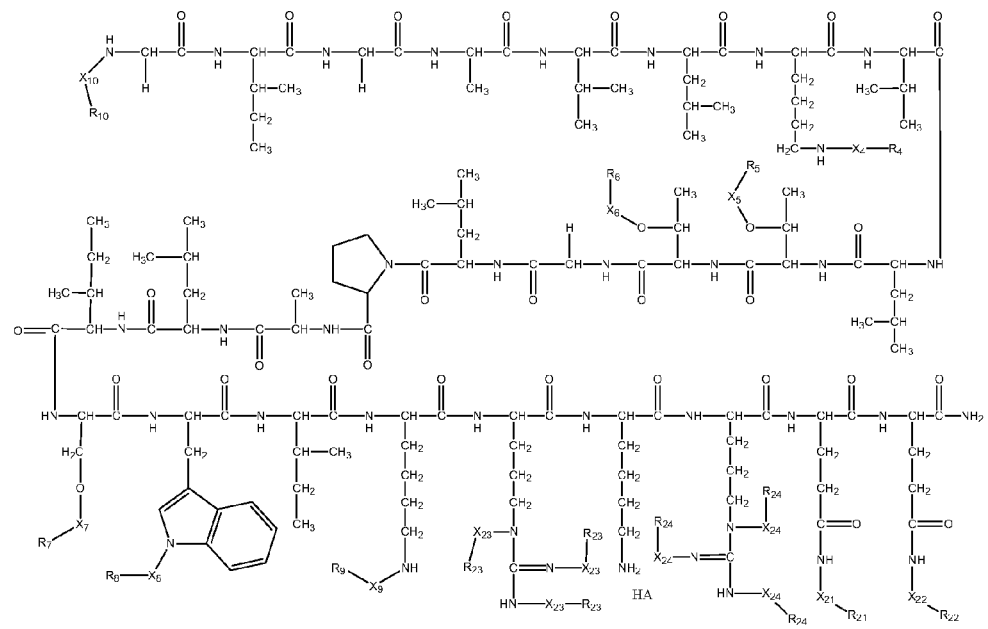
Figures 1, 78:
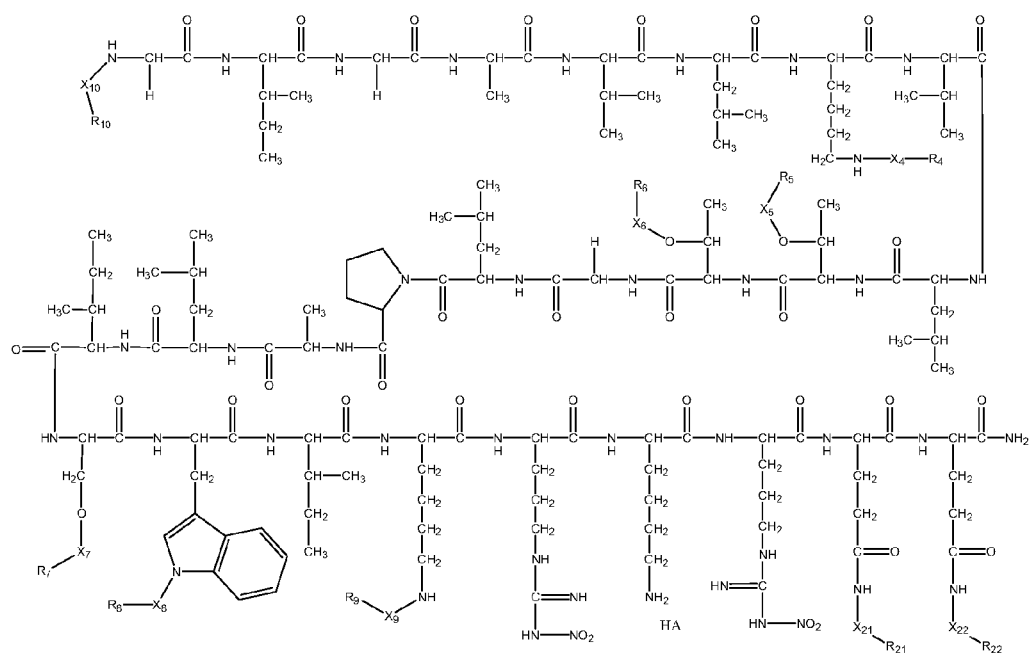
Figures 1, 79:
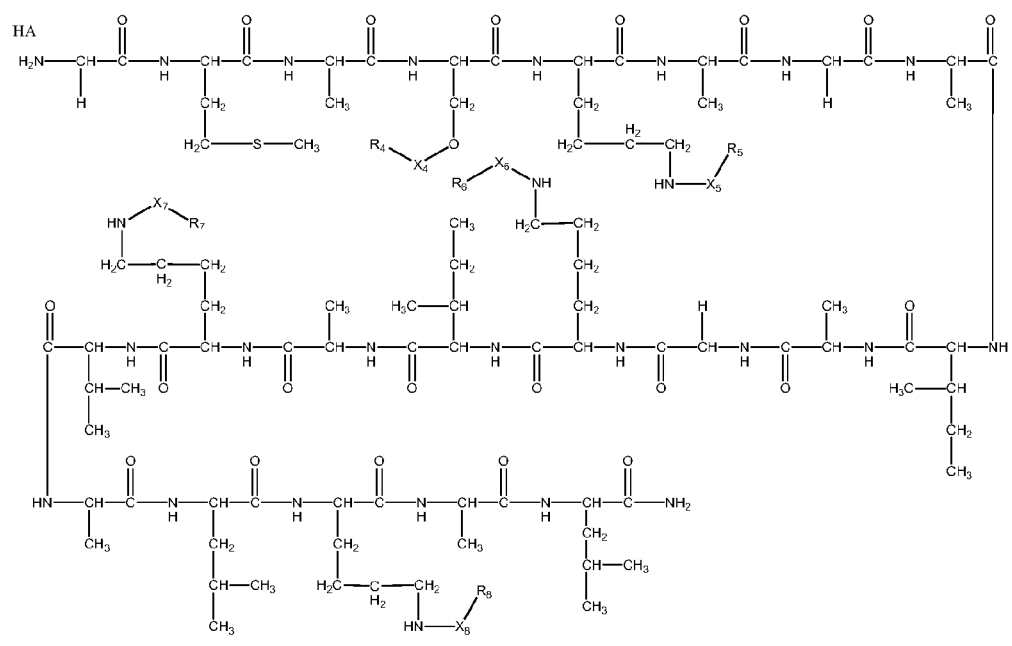
Figures 1, 80:
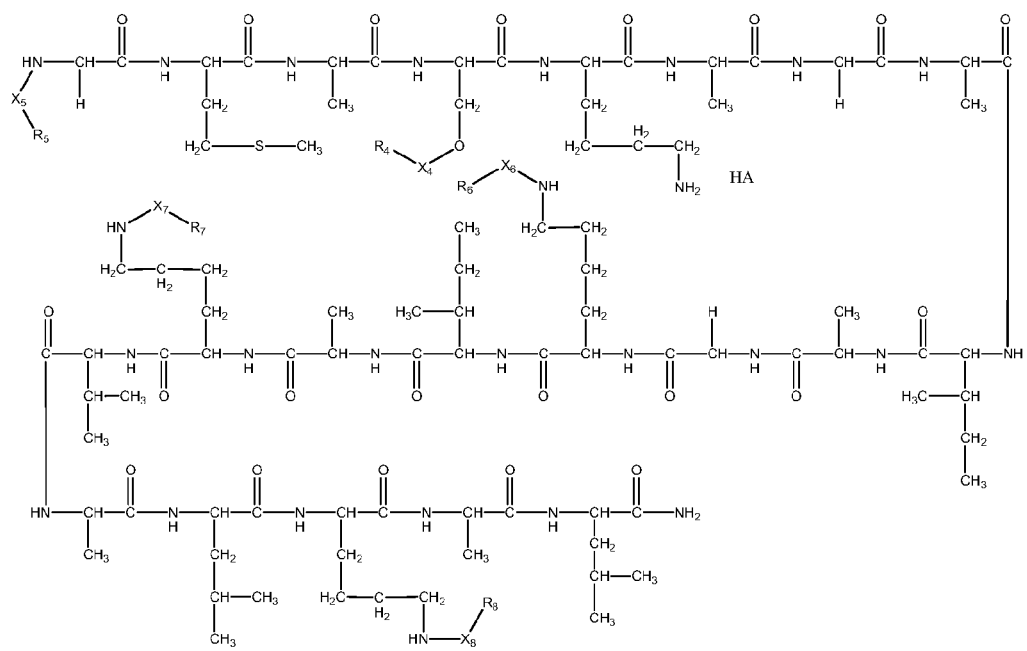
Figures 1, 81:
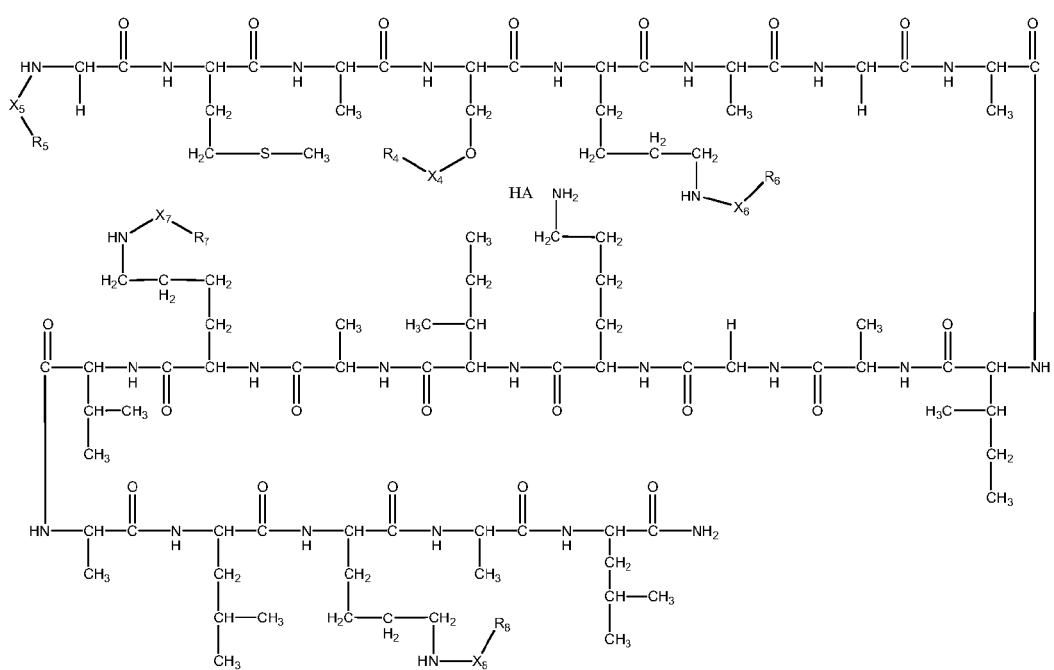
Figures 1, 82:
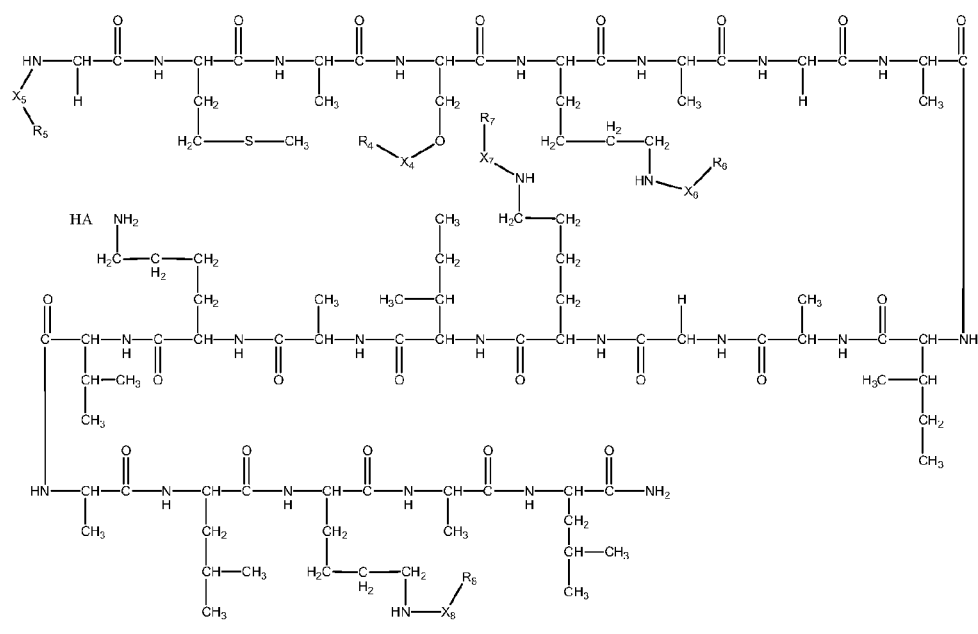
Figures 1, 83:
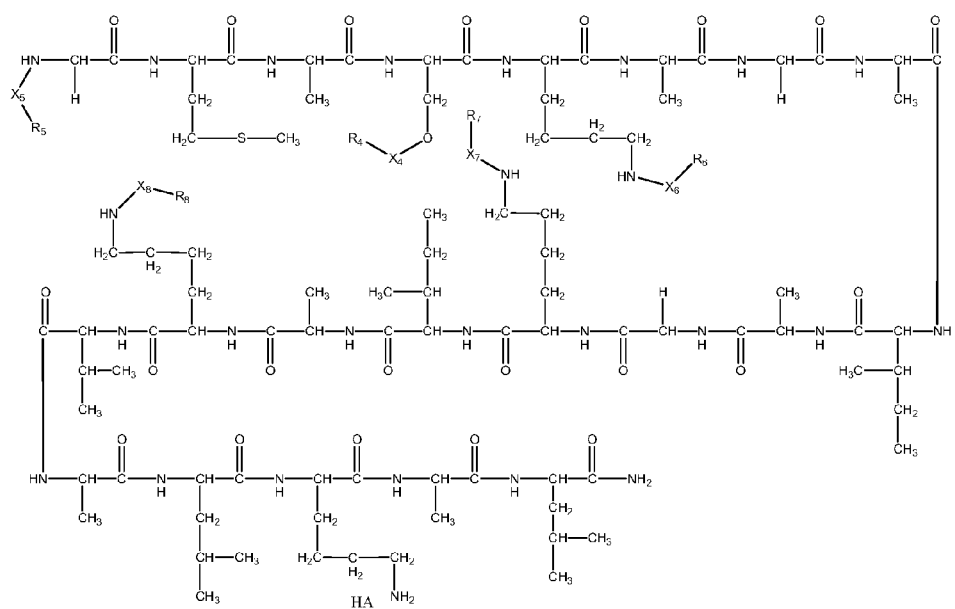
Figures 1, 84:
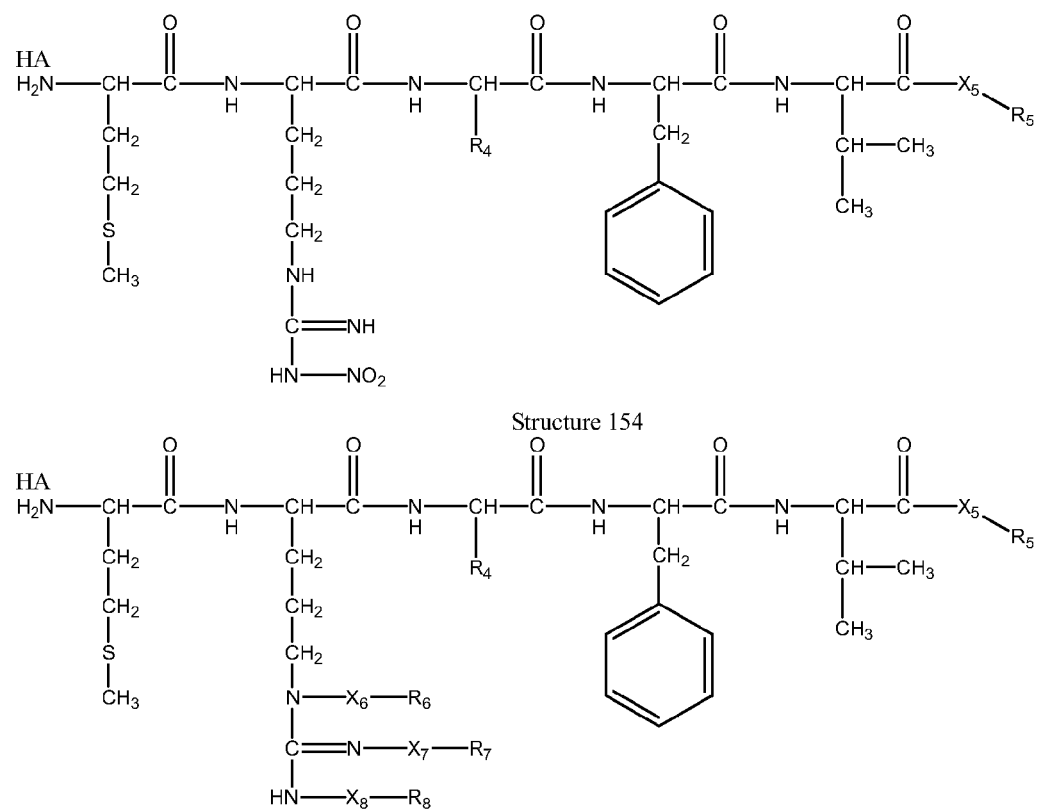
Figures 1, 85:
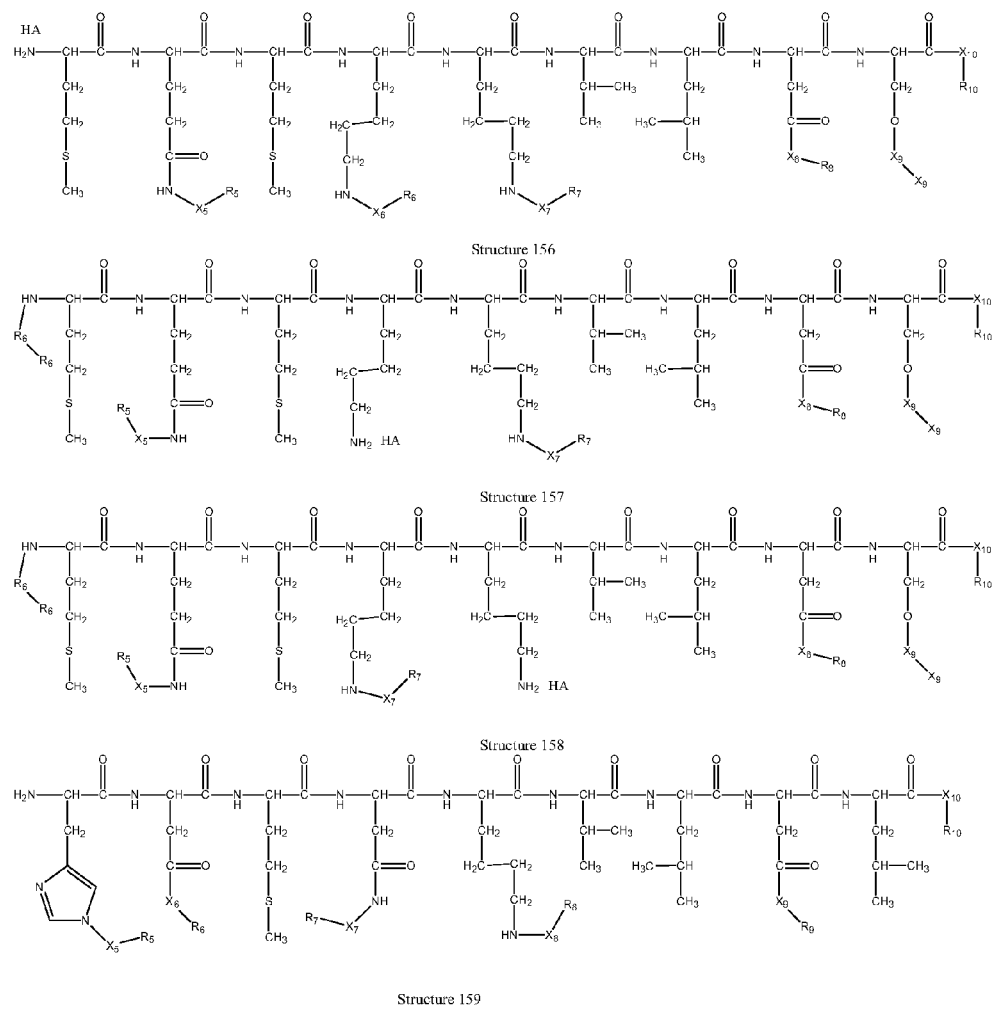
Figures 1, 86:
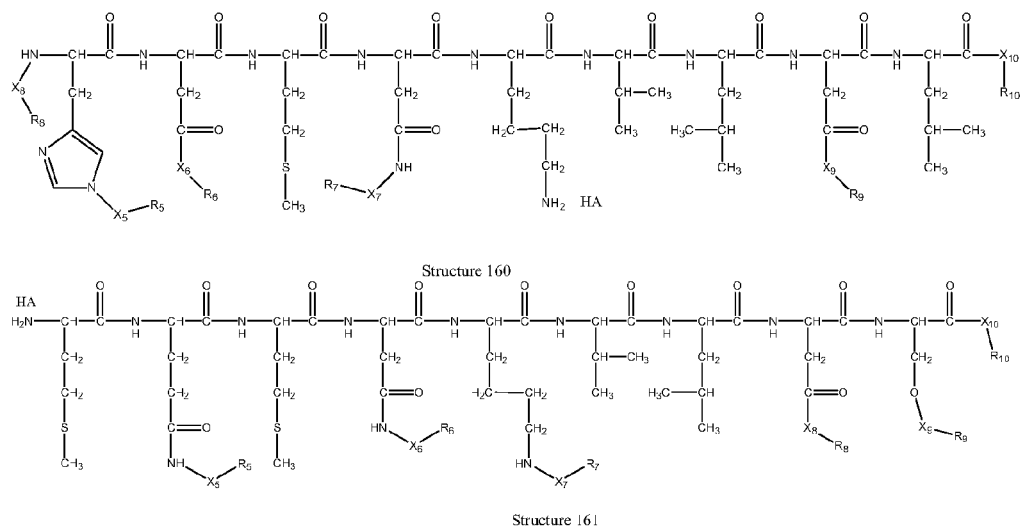
Figures 1, 87:
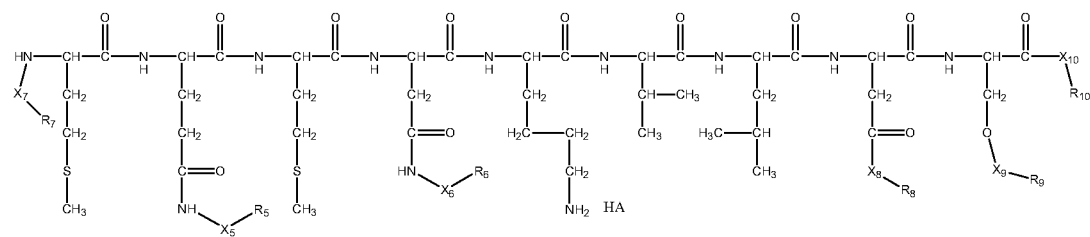
Figures 1, 88:
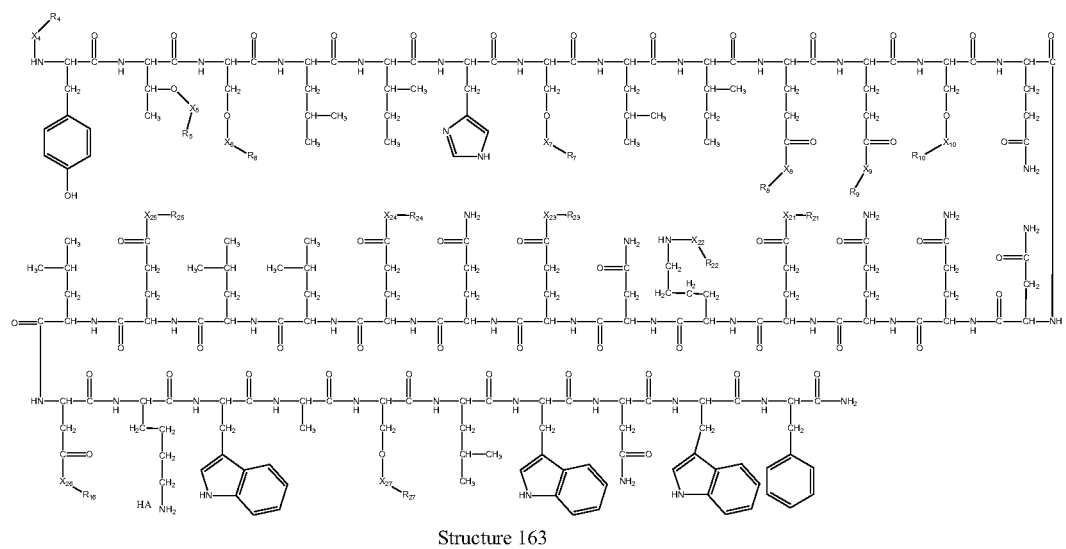
Figures 1, 89:
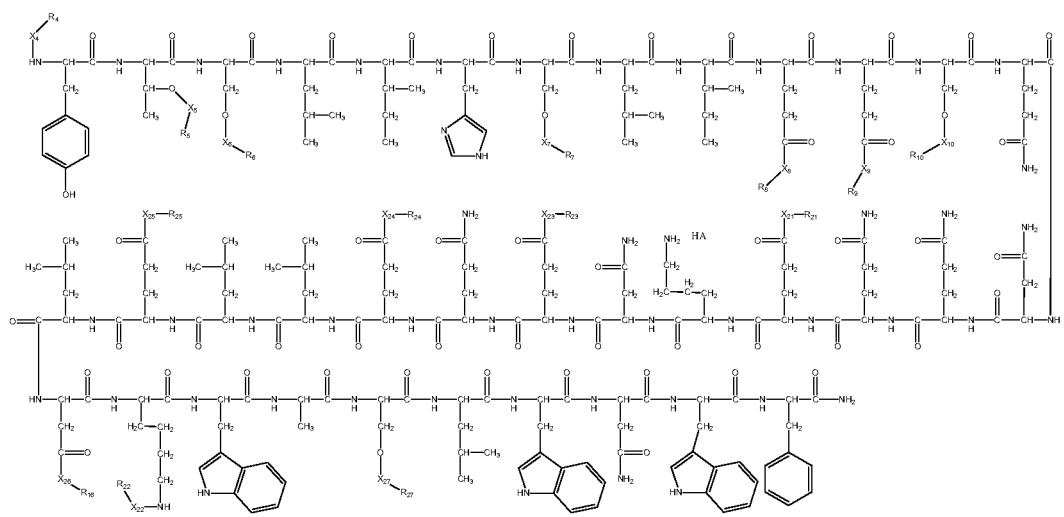
Figures 1, 90:
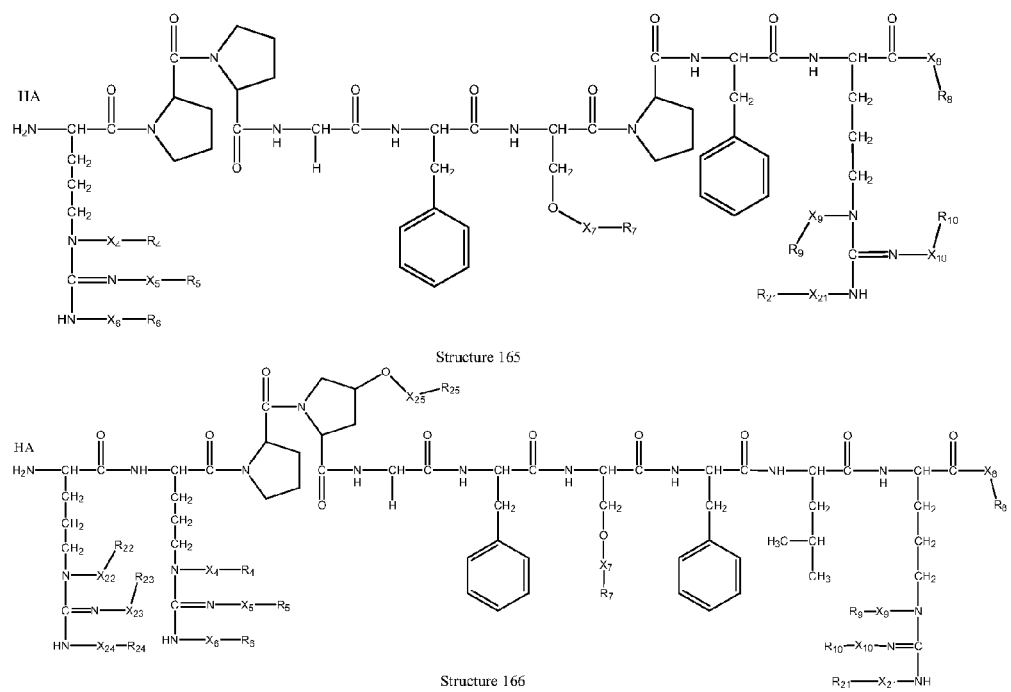
Figures 1, 91:
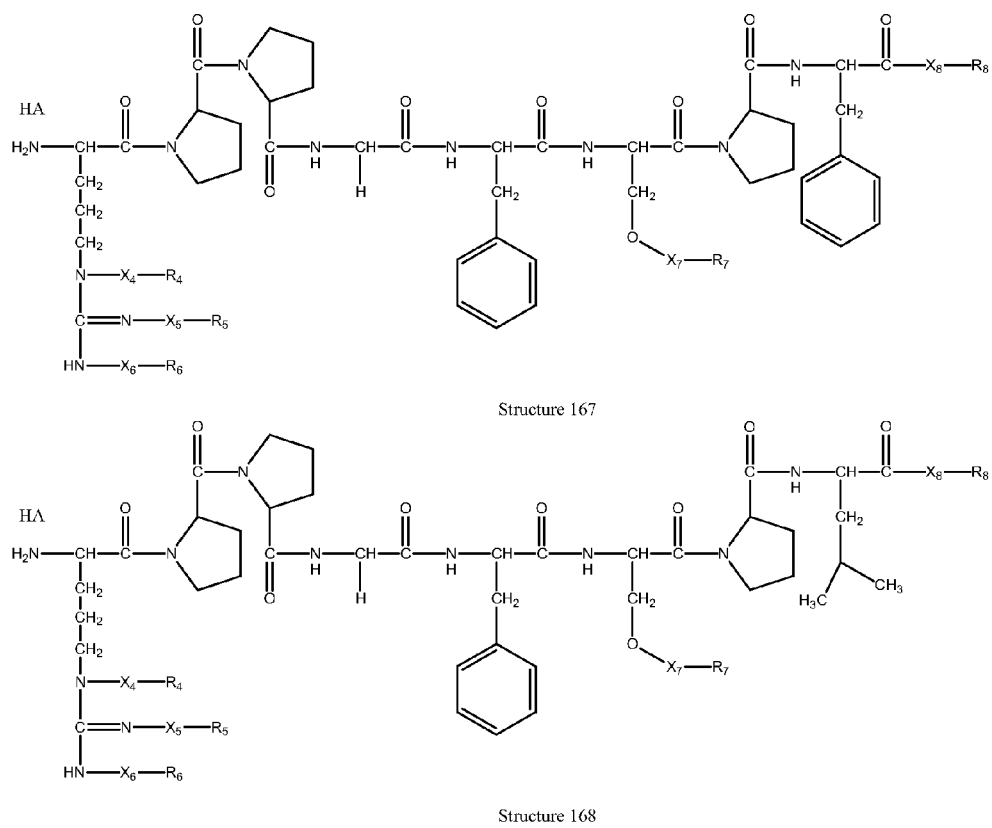
Figures 1, 92:
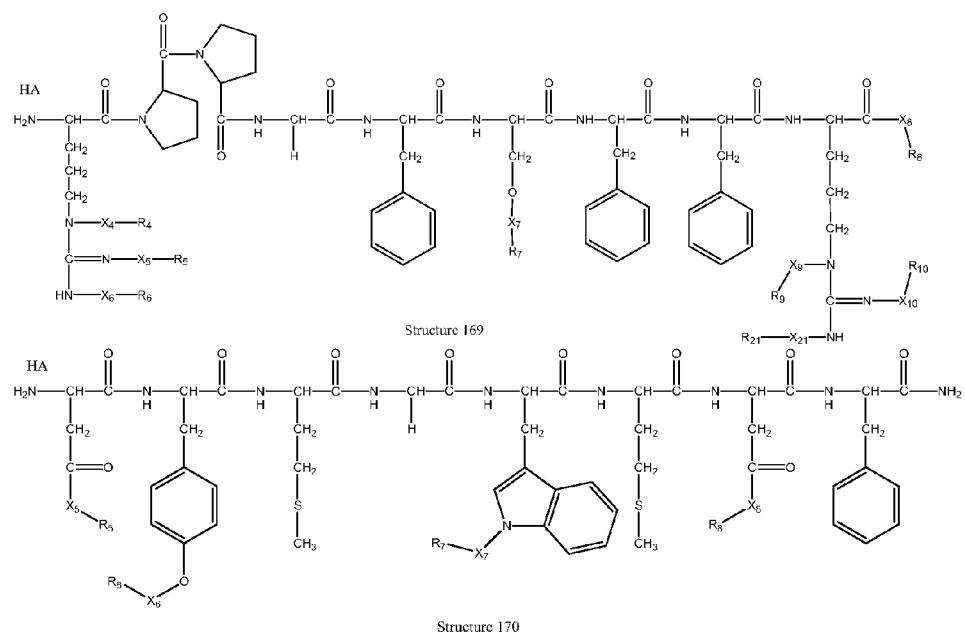
Figures 1, 93:
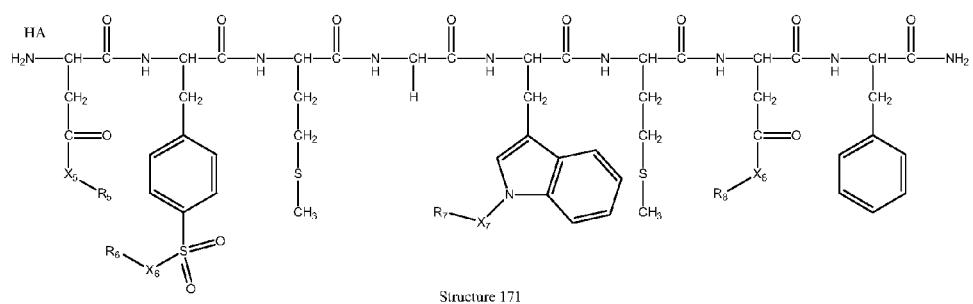
Figures 1, 94:
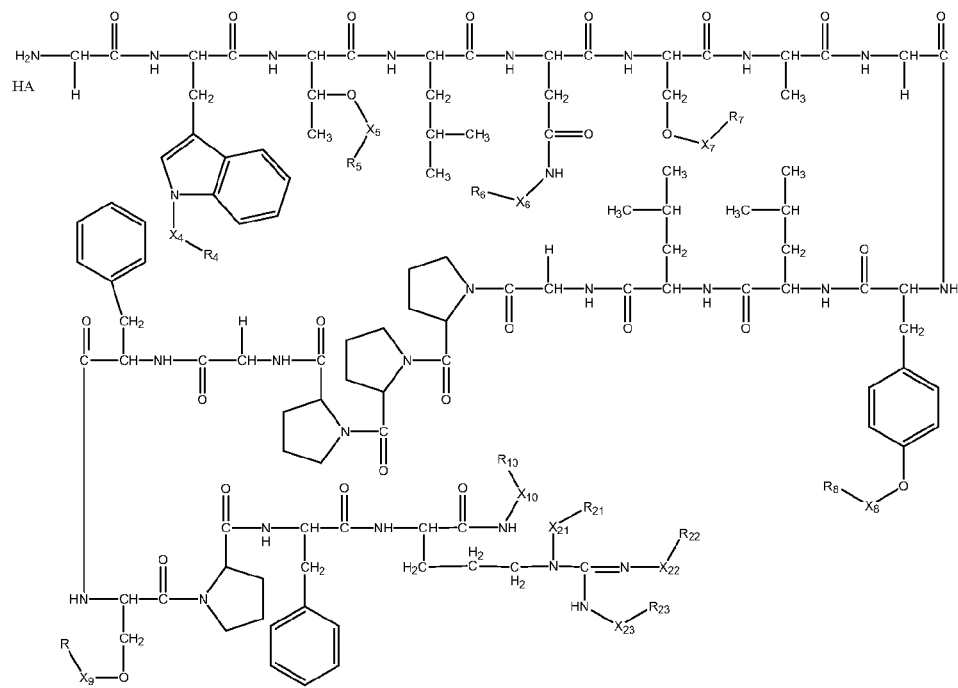
Figures 1, 95:
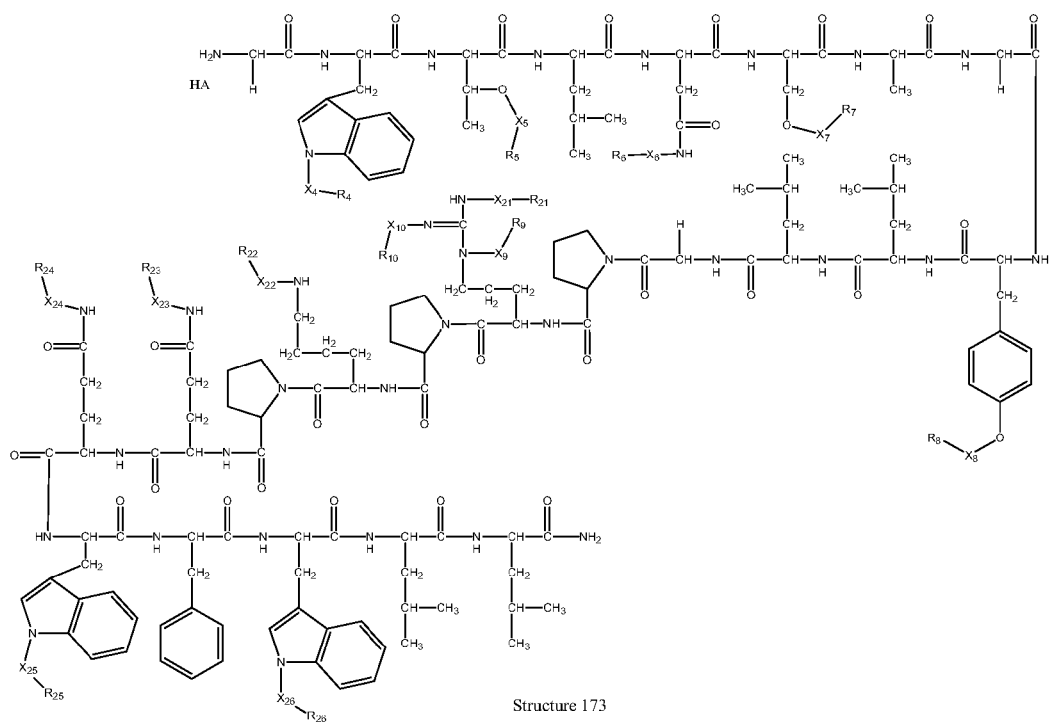
Figures 1, 96:
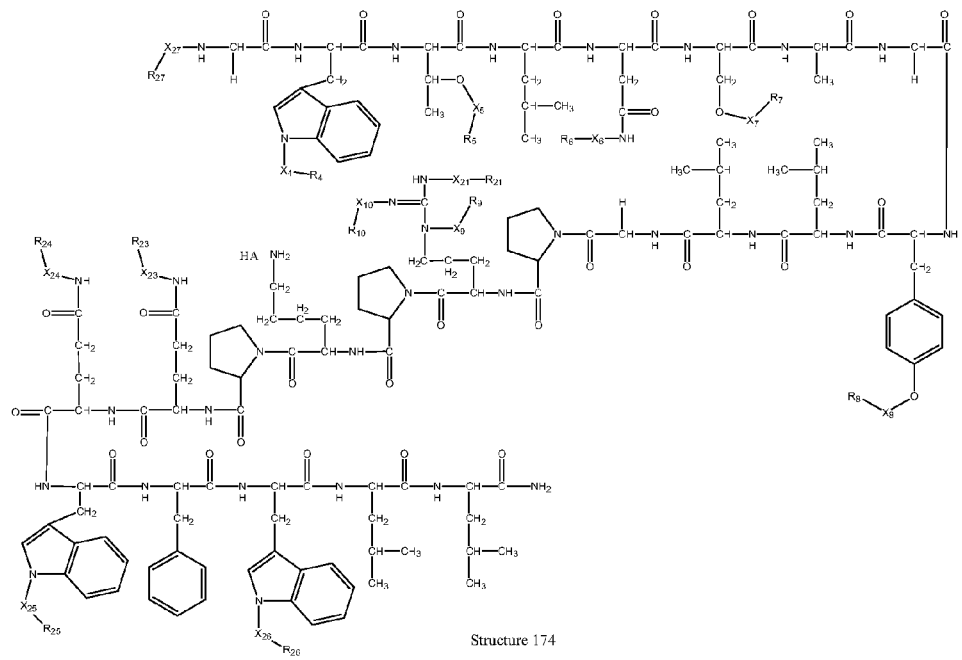
Figures 1, 97:
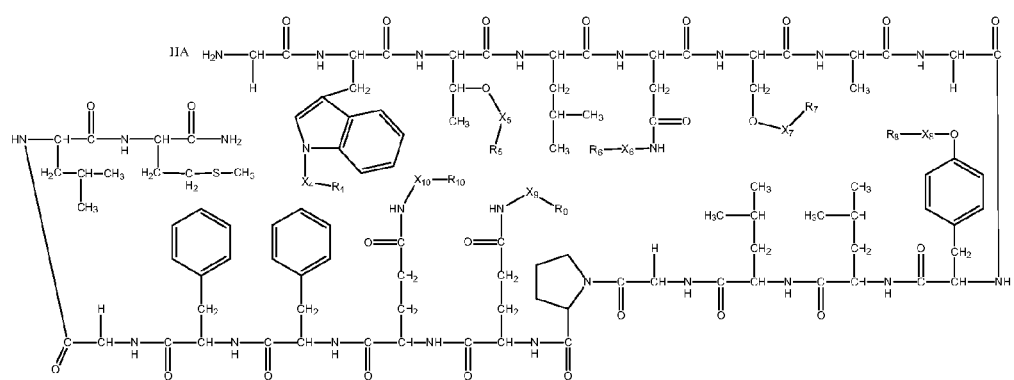
Figures 1, 98:
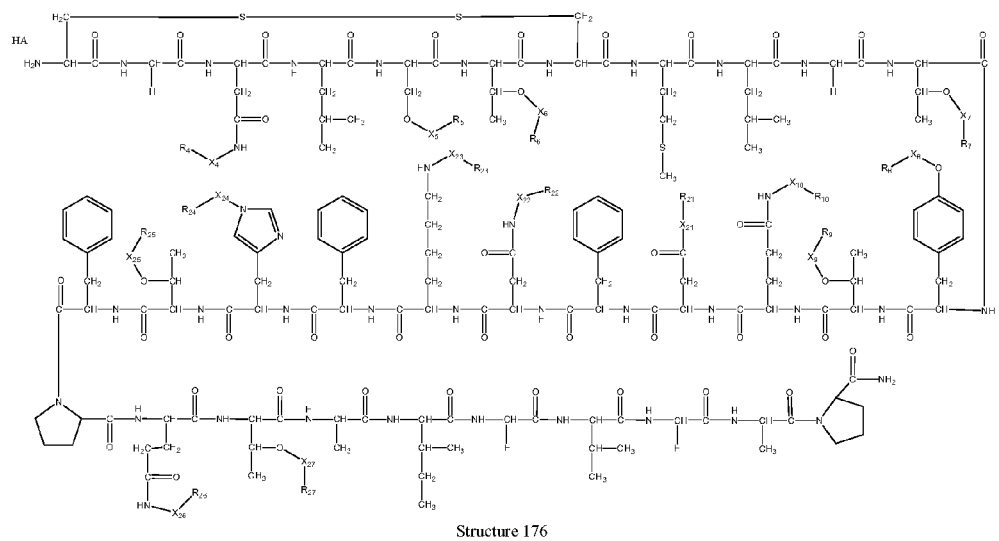
Figures 1, 99:
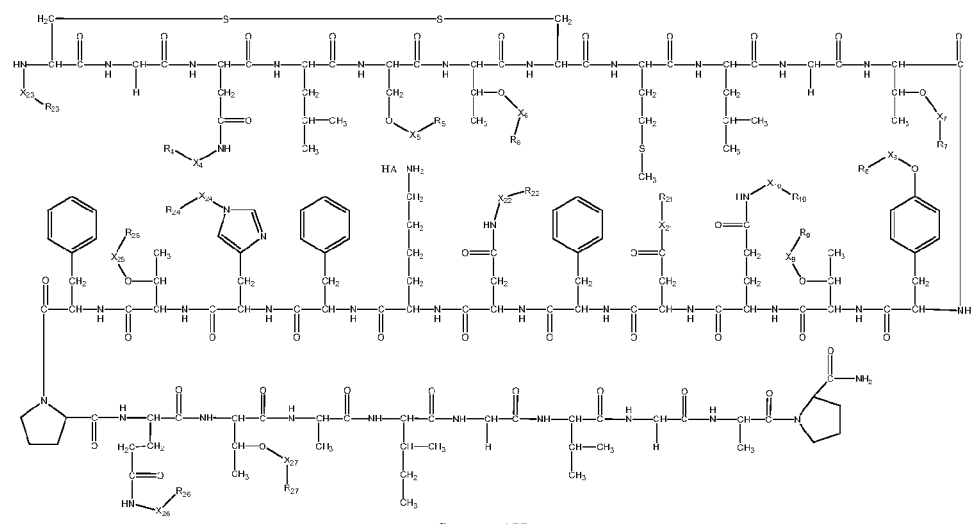
Figures 1, 100:
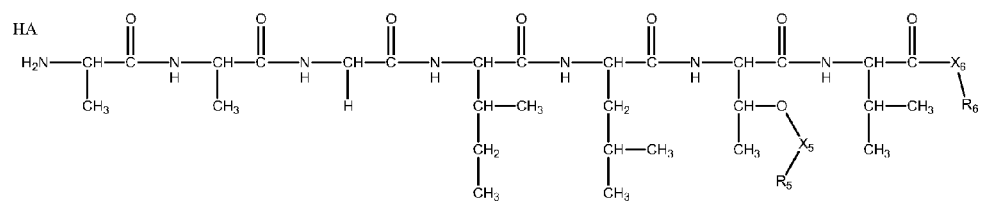
Figures 1, 101:
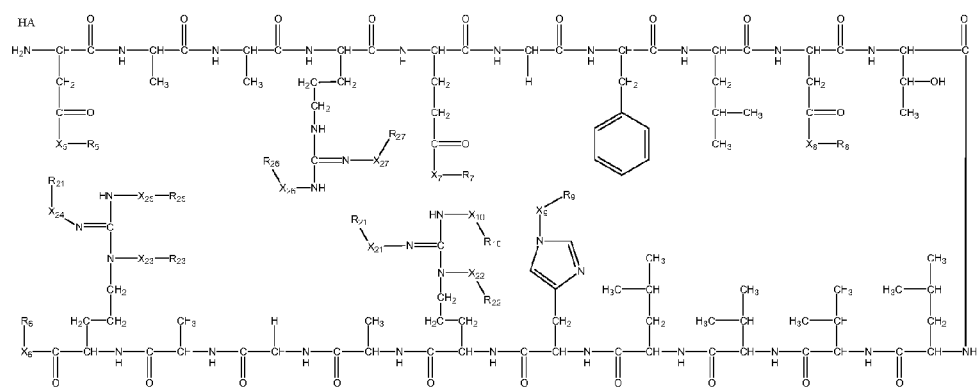
Figures 1, 102:
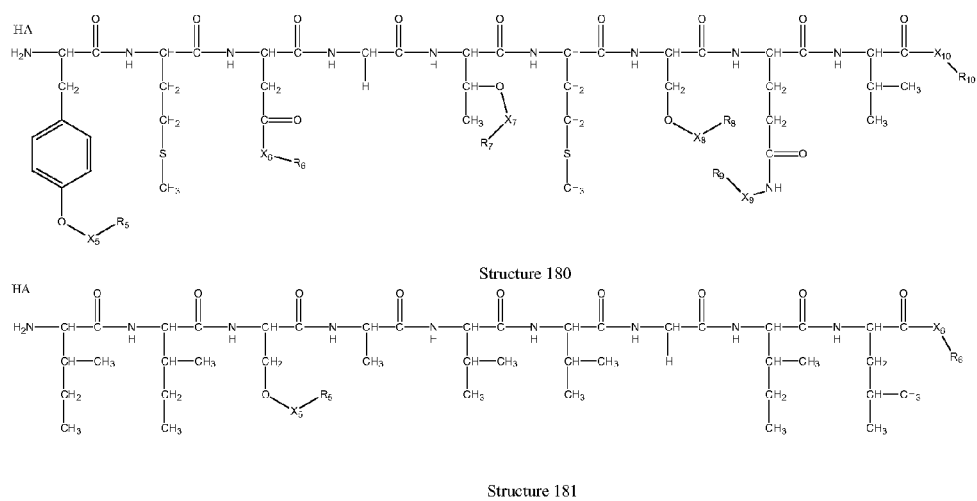
Figures 1, 103:
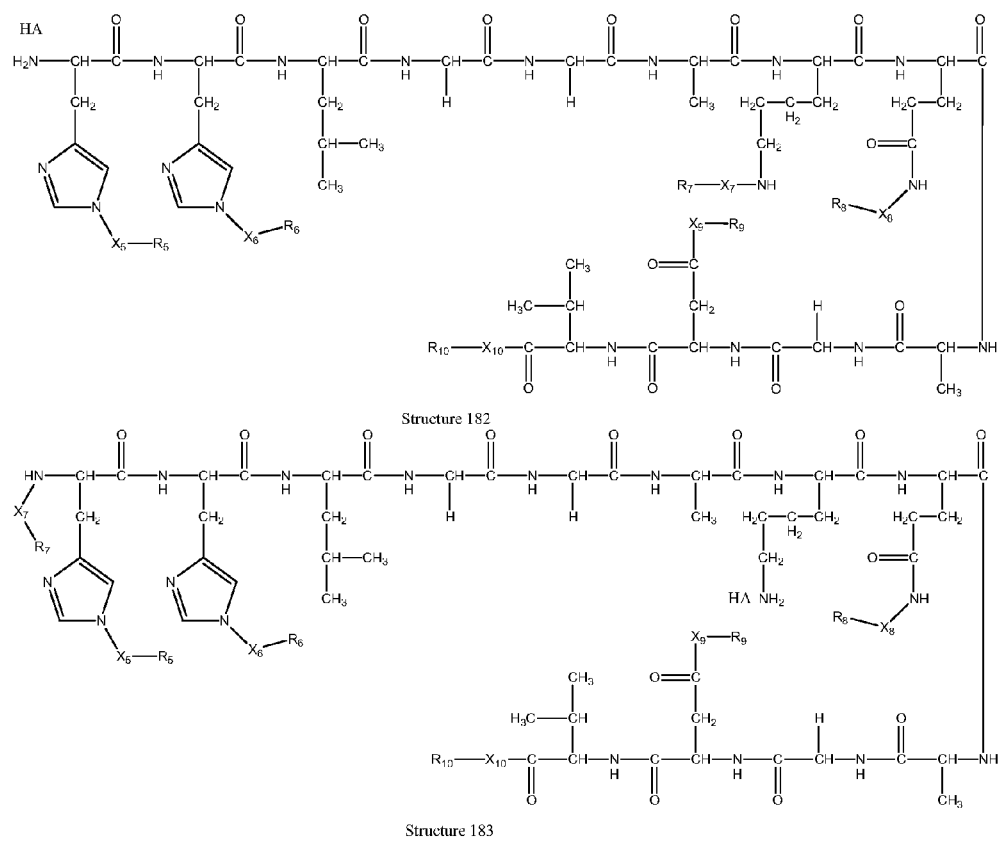
Figures 1, 104:
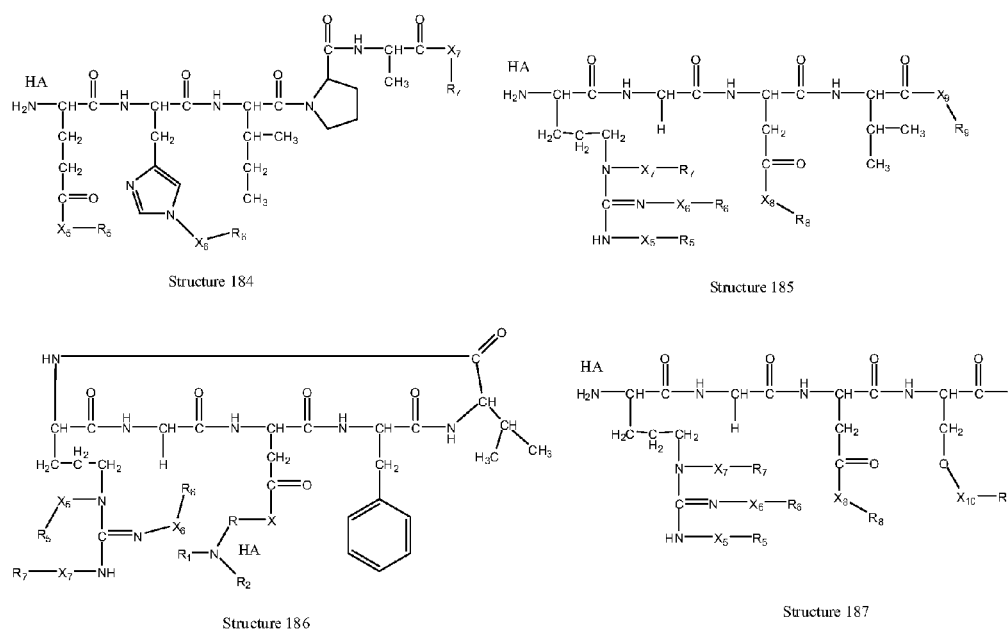
Figures 1, 105:
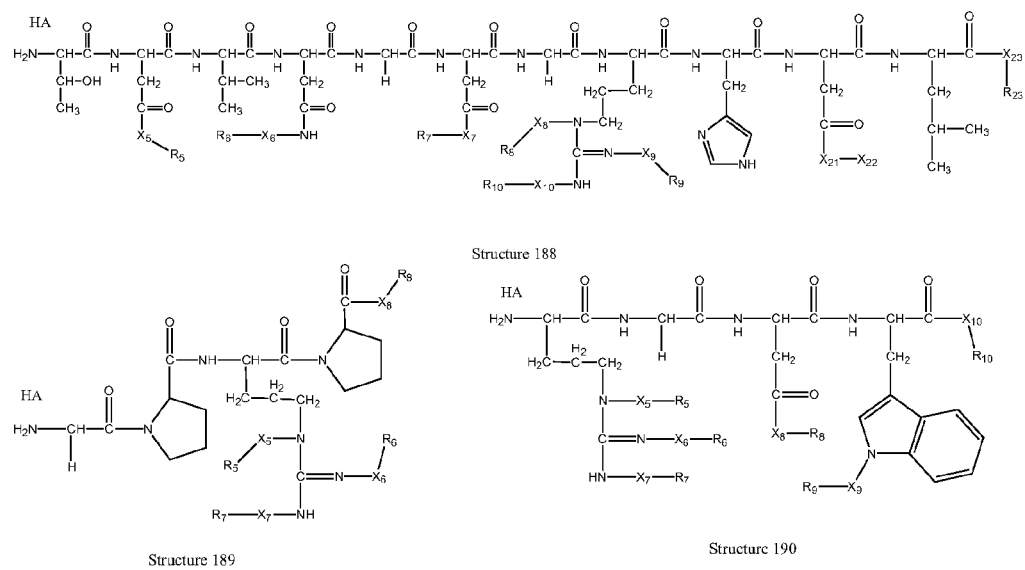
Figures 1, 106:
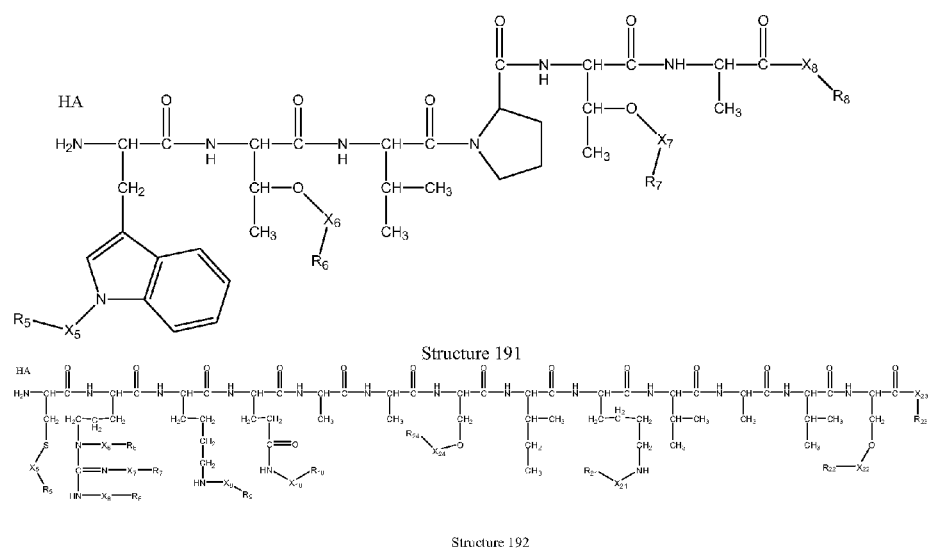
Figures 1, 107:
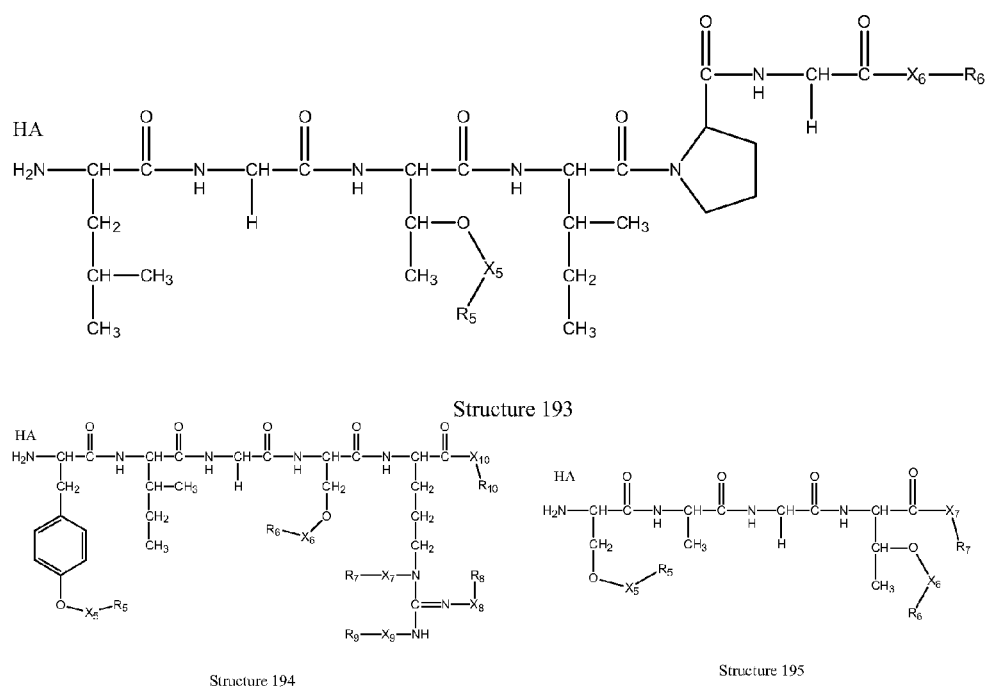
Figures 1, 108:
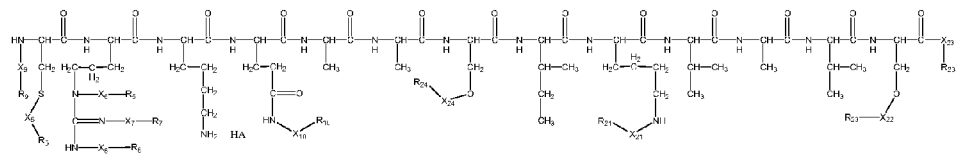
Figures 1, 109:
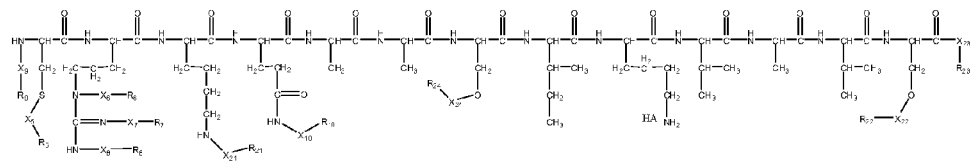
Figures 1, 110:
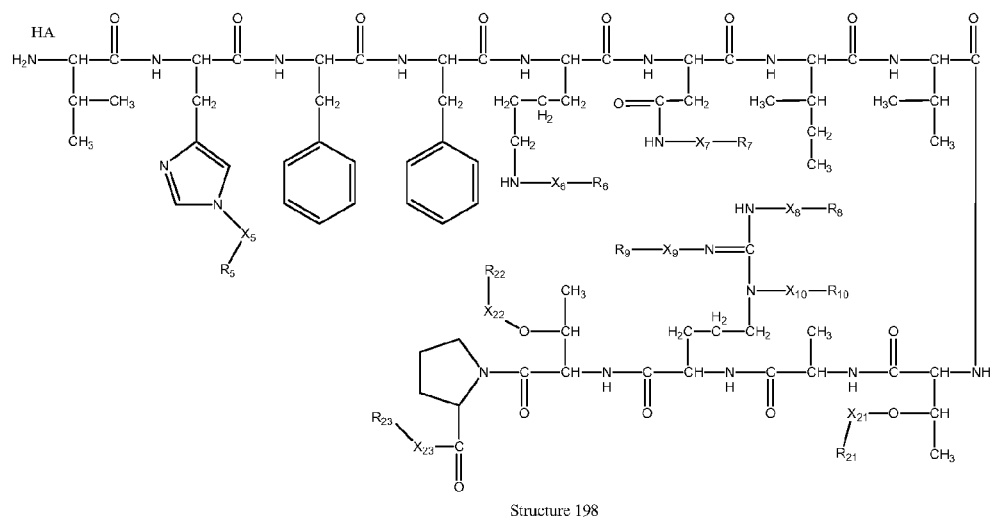
Figures 1, 111:
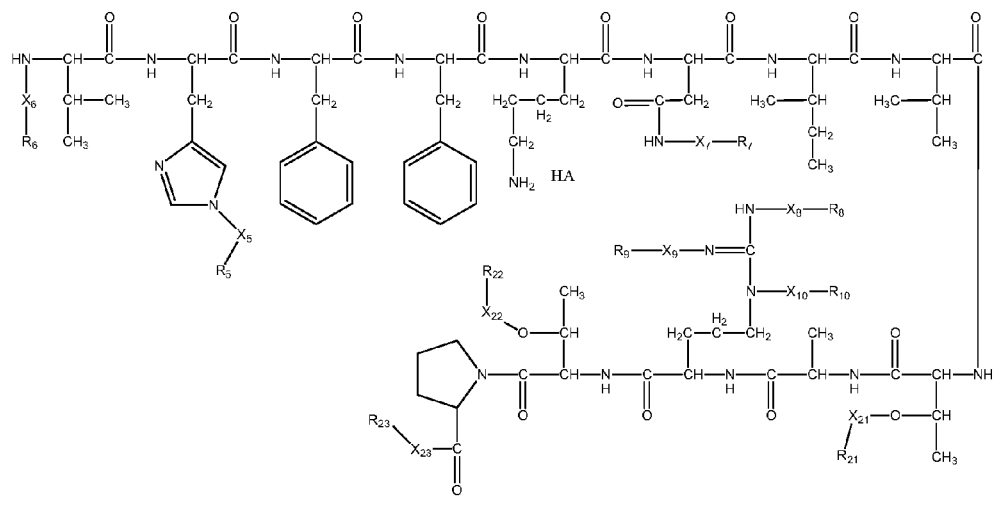
Figures 1, 112:
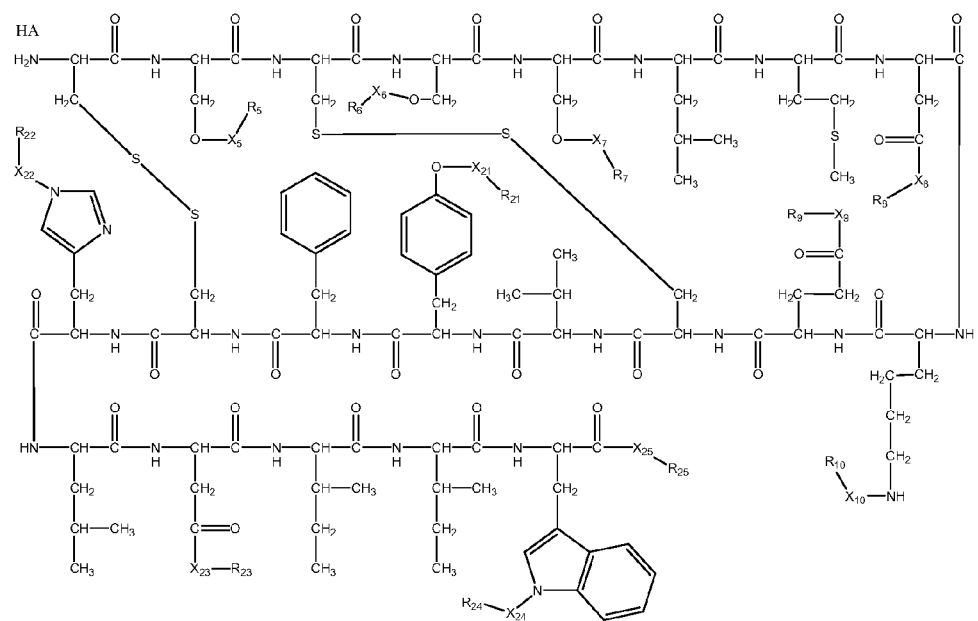
Figures 1, 113:
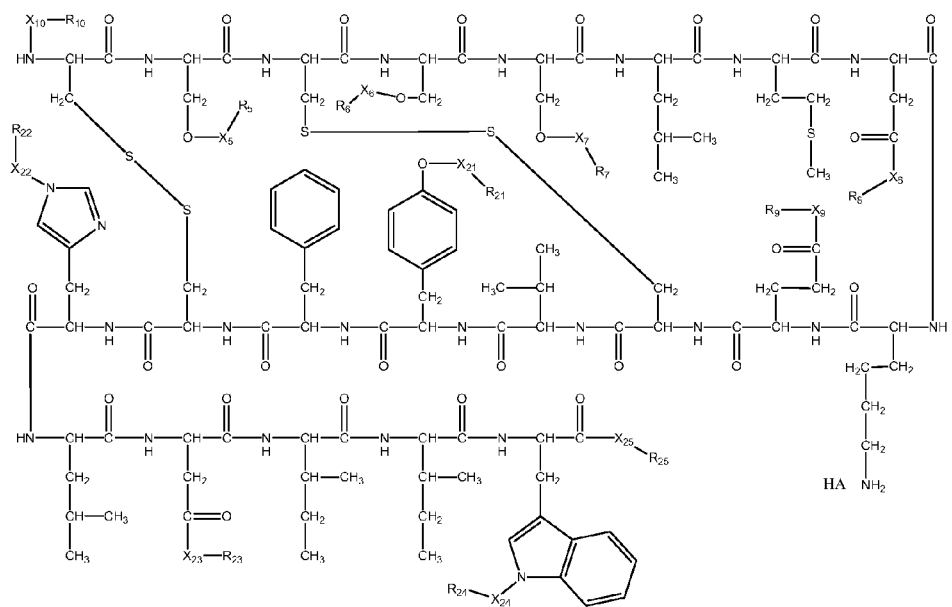
Figures 1, 114:
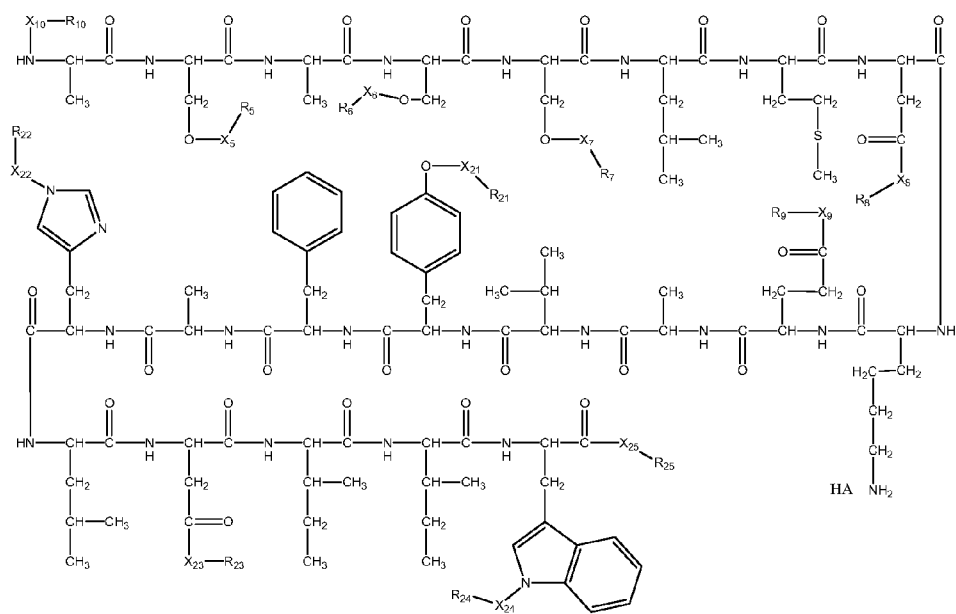
Figures 1, 115:
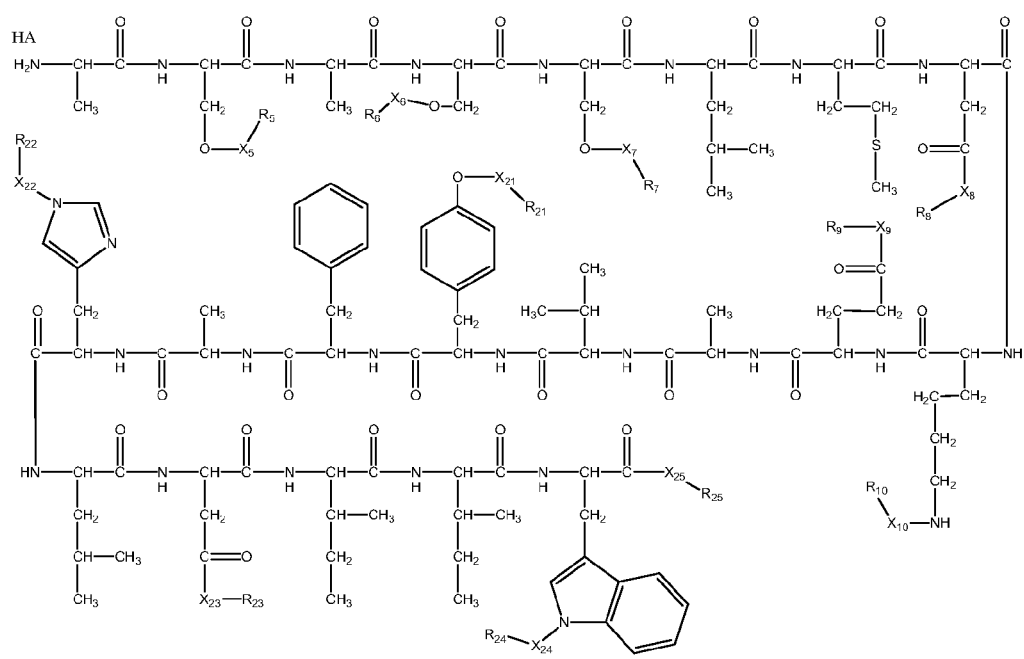
Figures 1, 116:
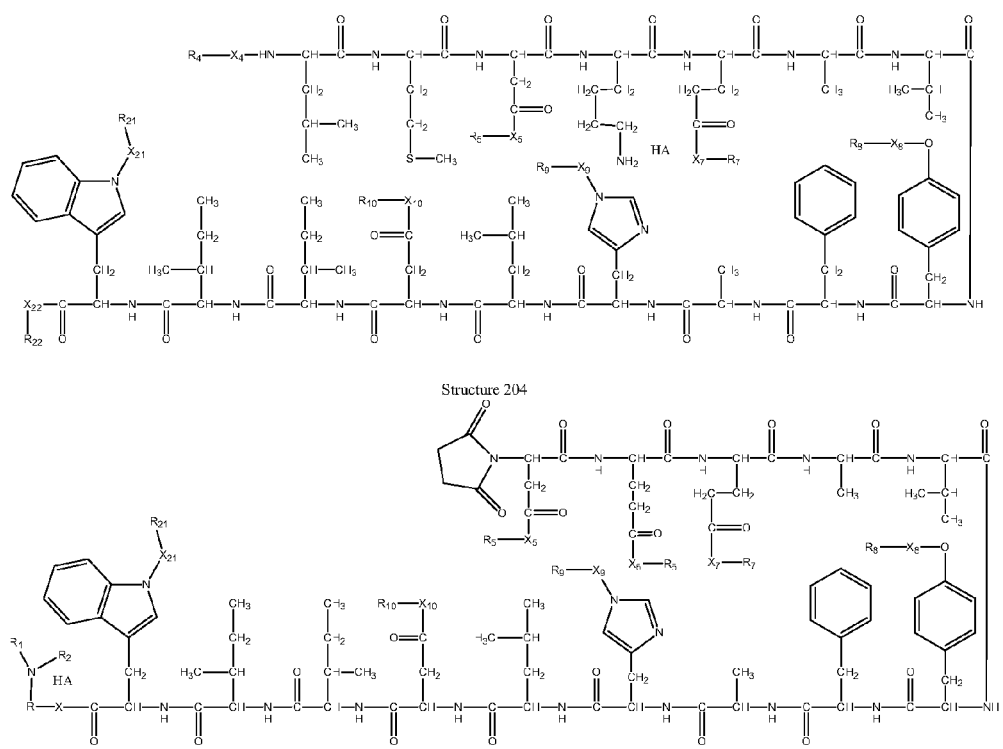
Figures 1, 117:
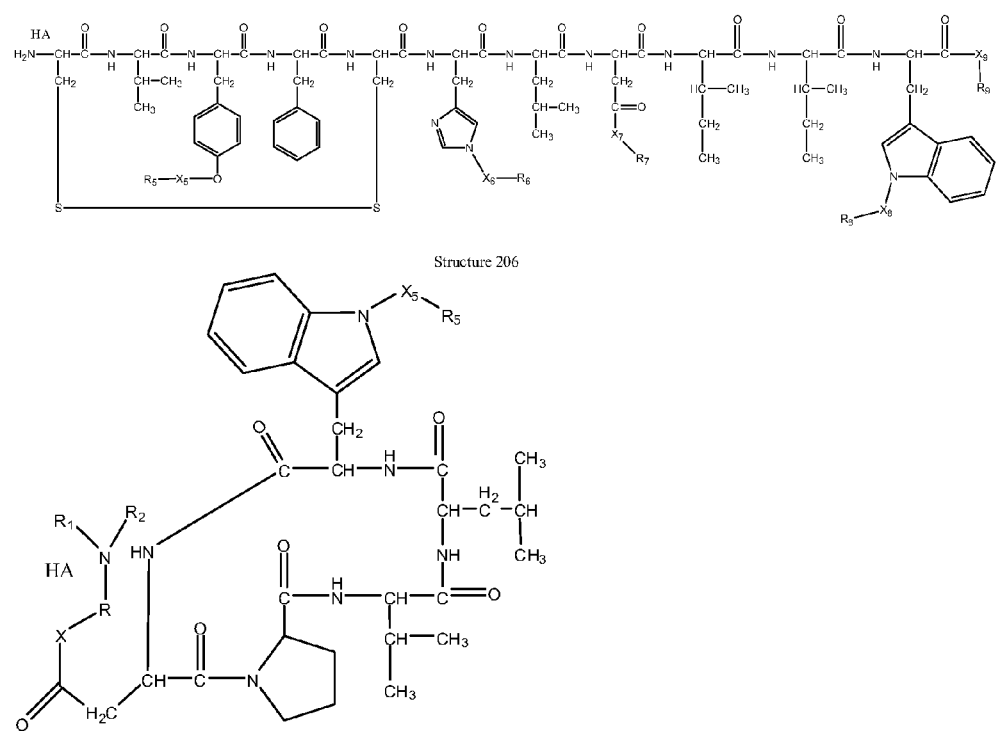
Figures 1, 118:
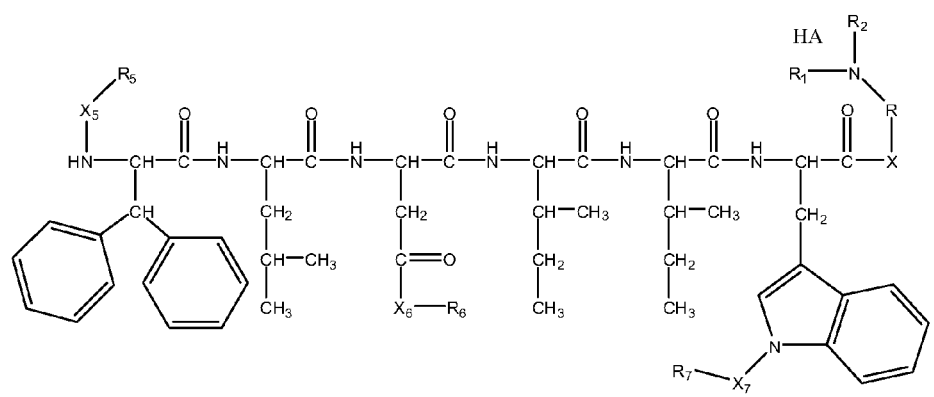
Figures 1, 119:
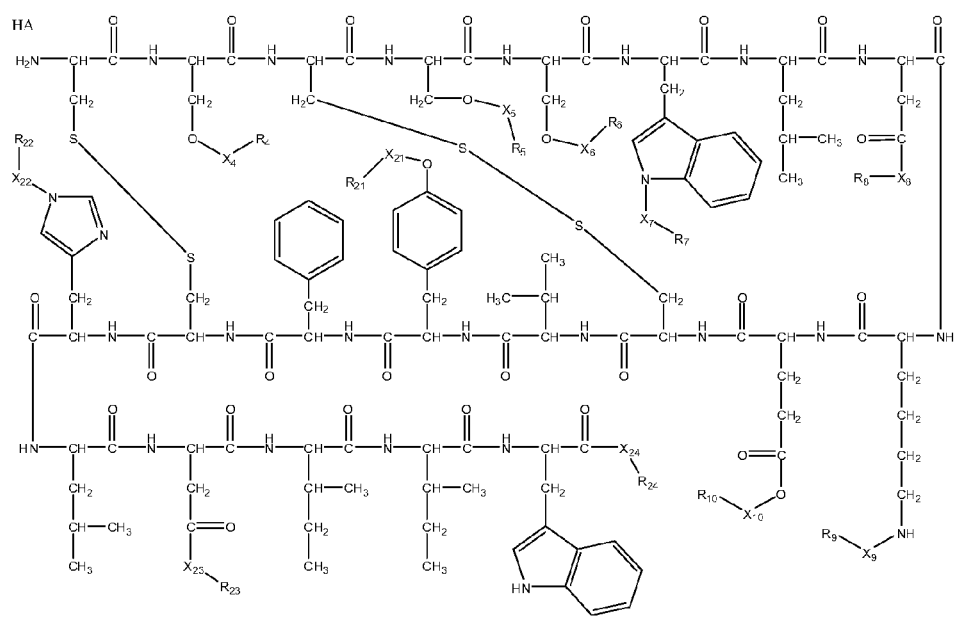
Figures 1, 120:
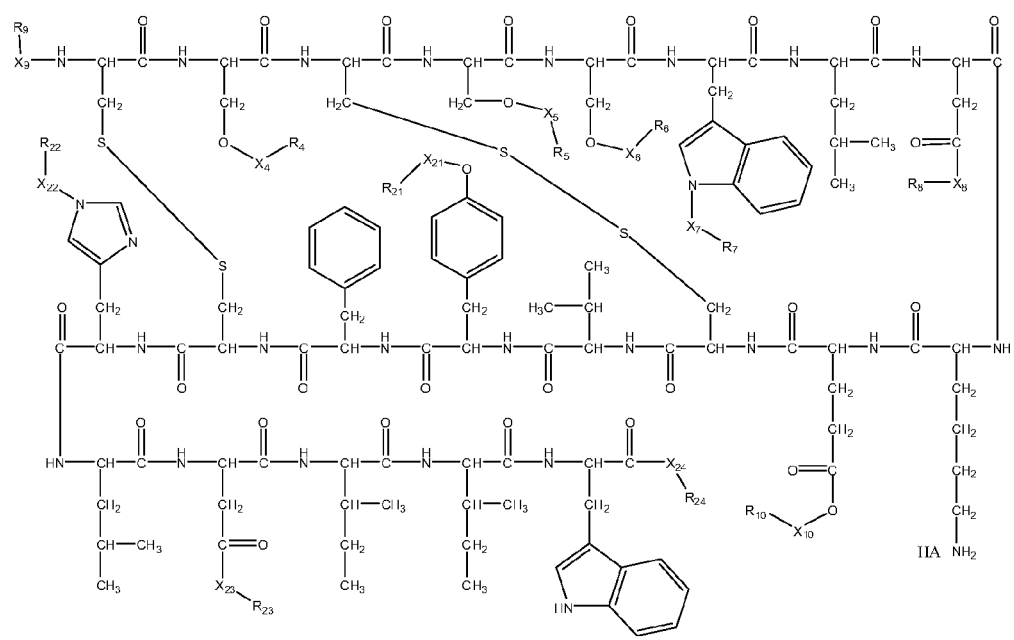
Figures 1, 121:
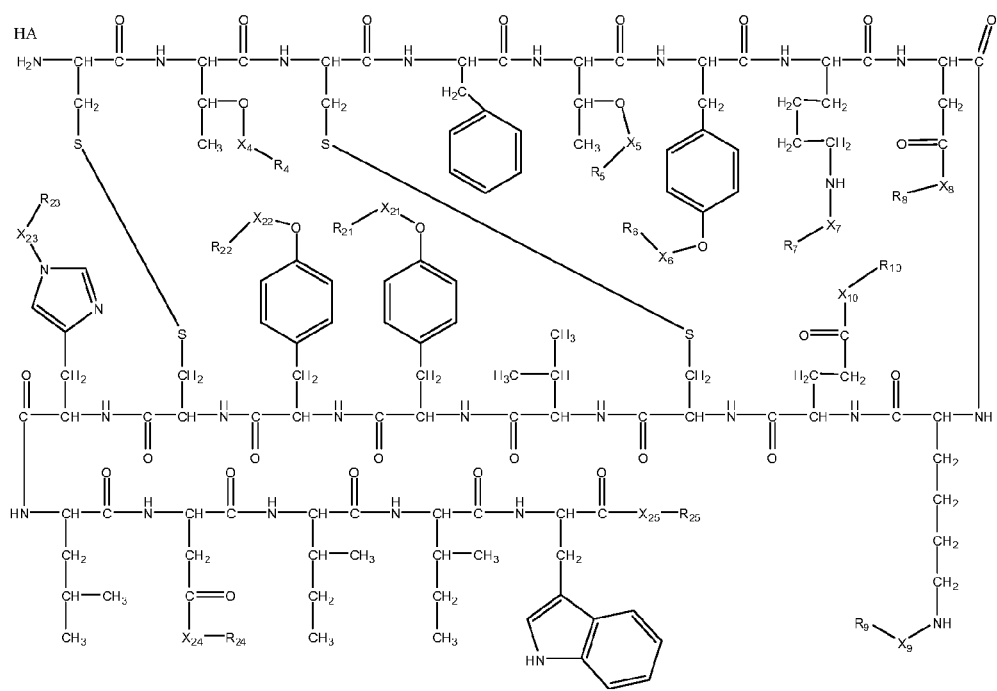
Figures 1, 122:
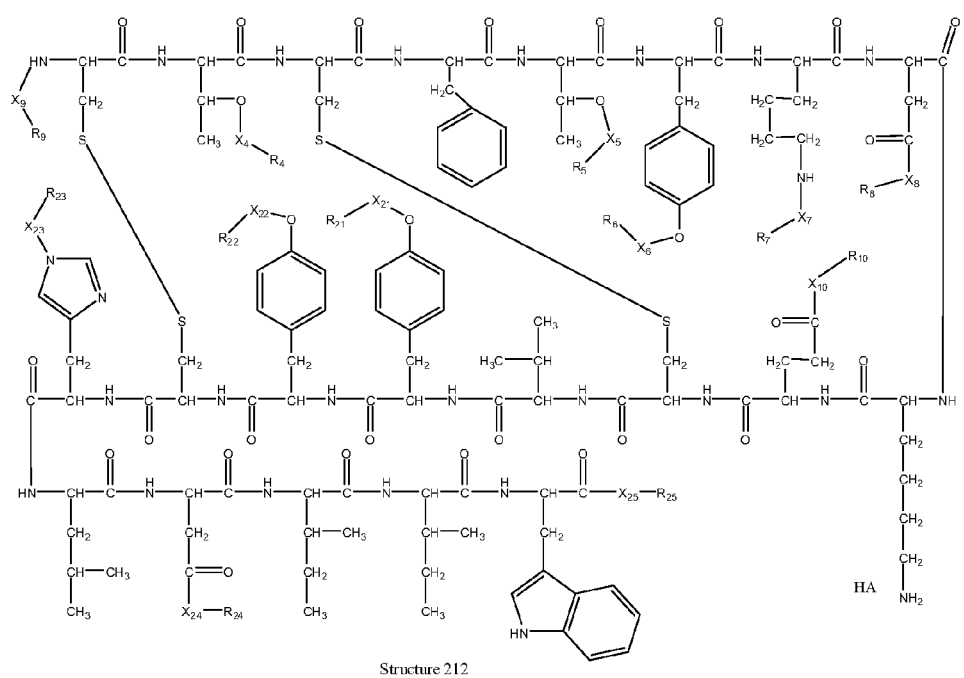
Figures 1, 123:
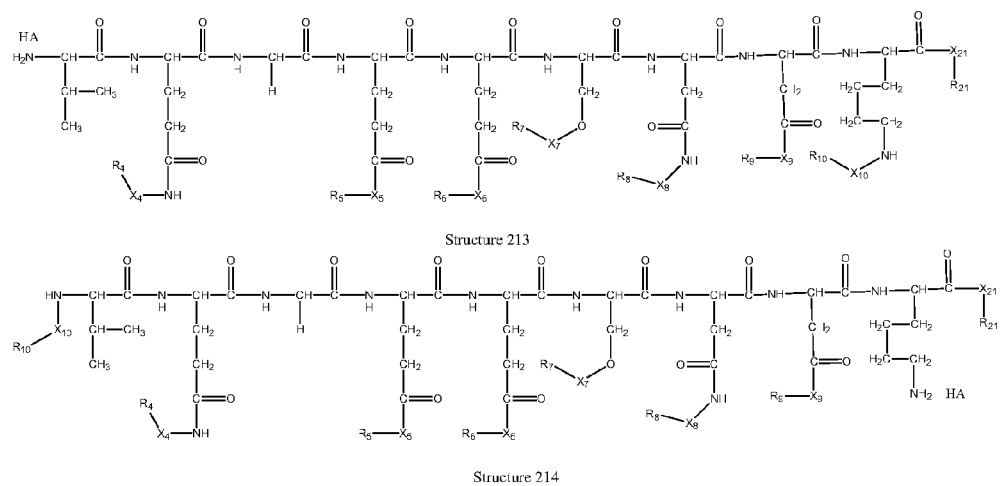
Figures 1, 124:
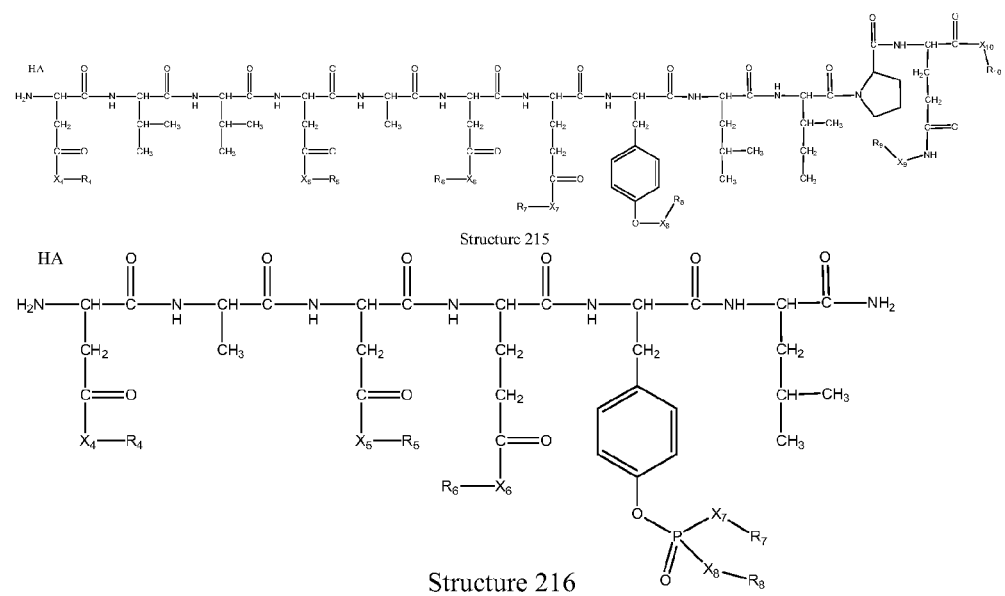
Figures 1, 125:
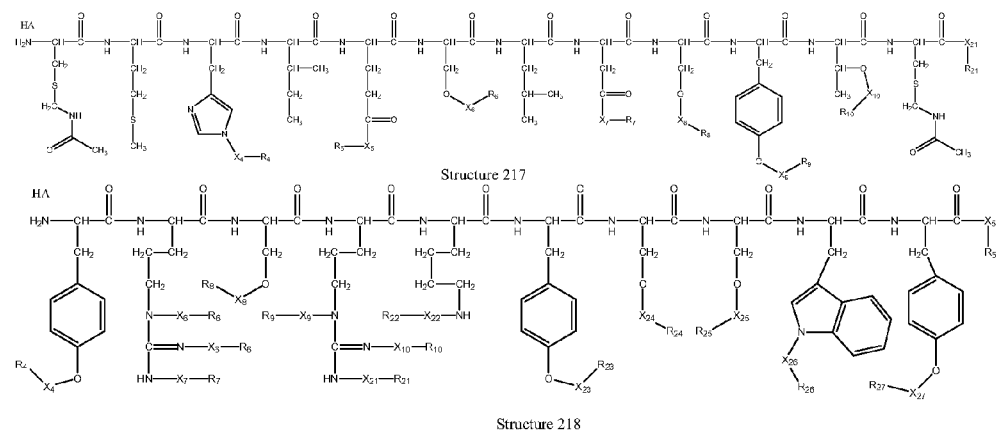
Figures 1, 126:
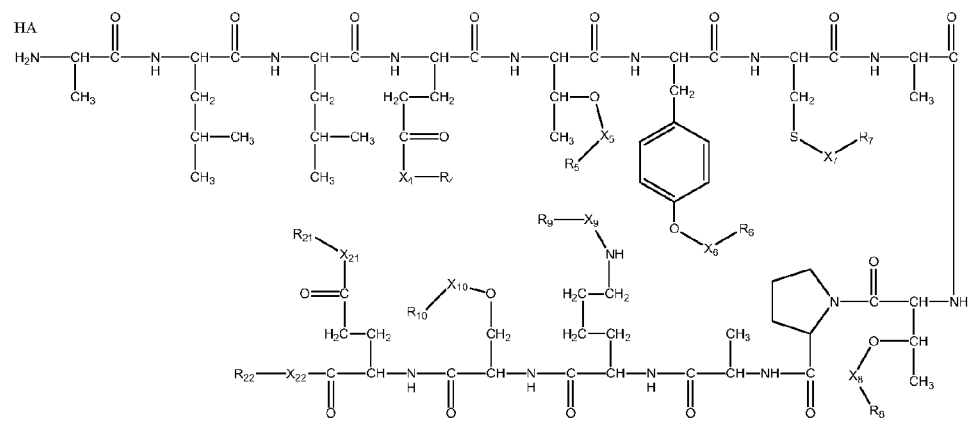
Figures 1, 127:
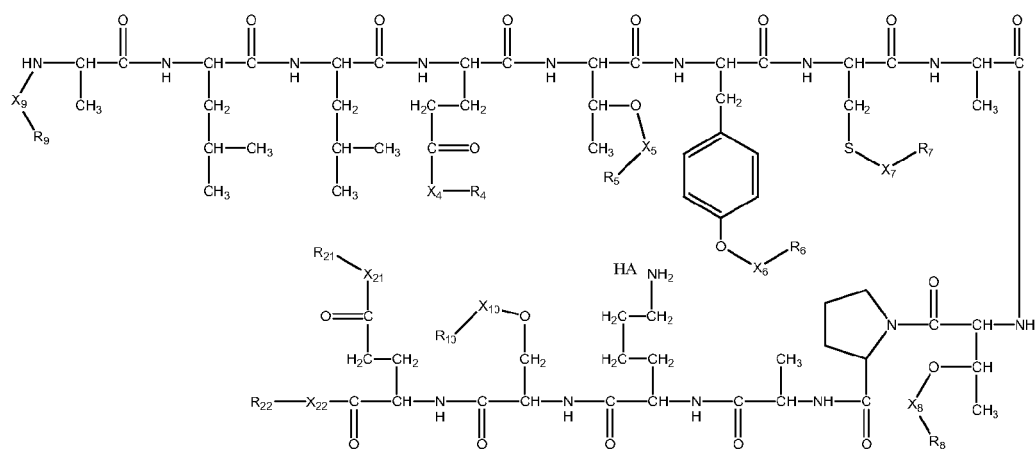
Figures 1, 128:
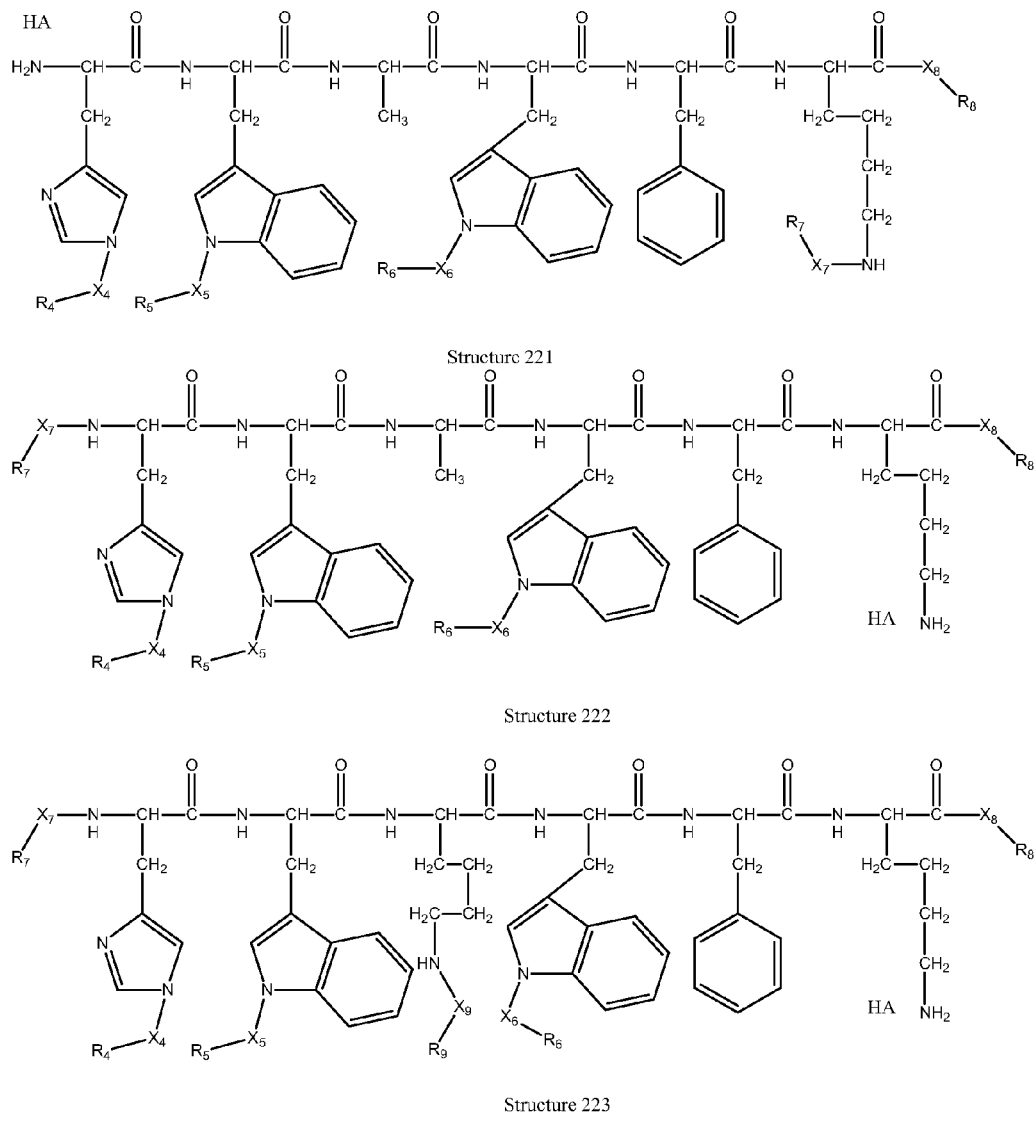
Figures 1, 129:
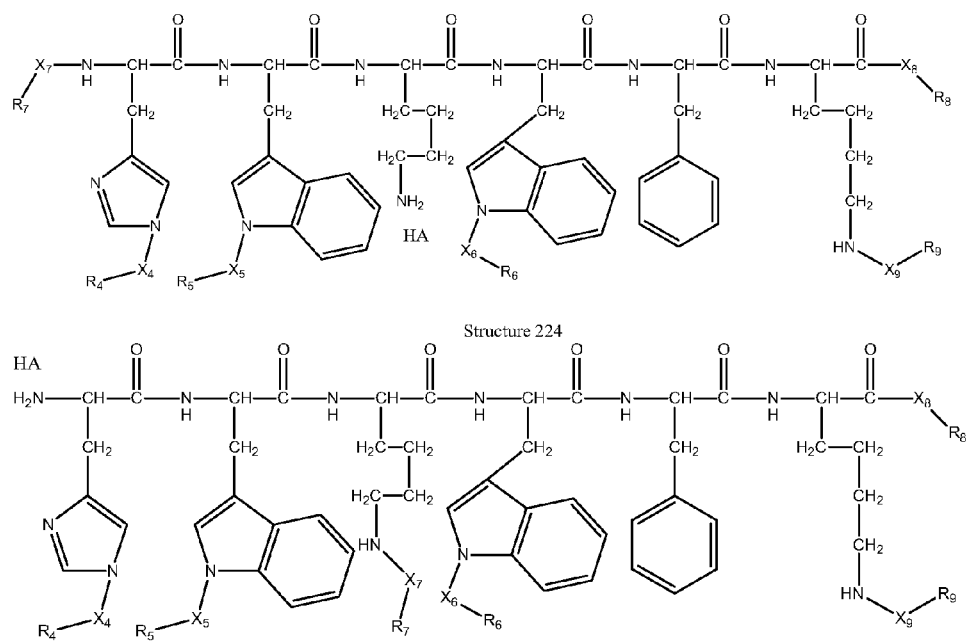
Figures 1, 131:
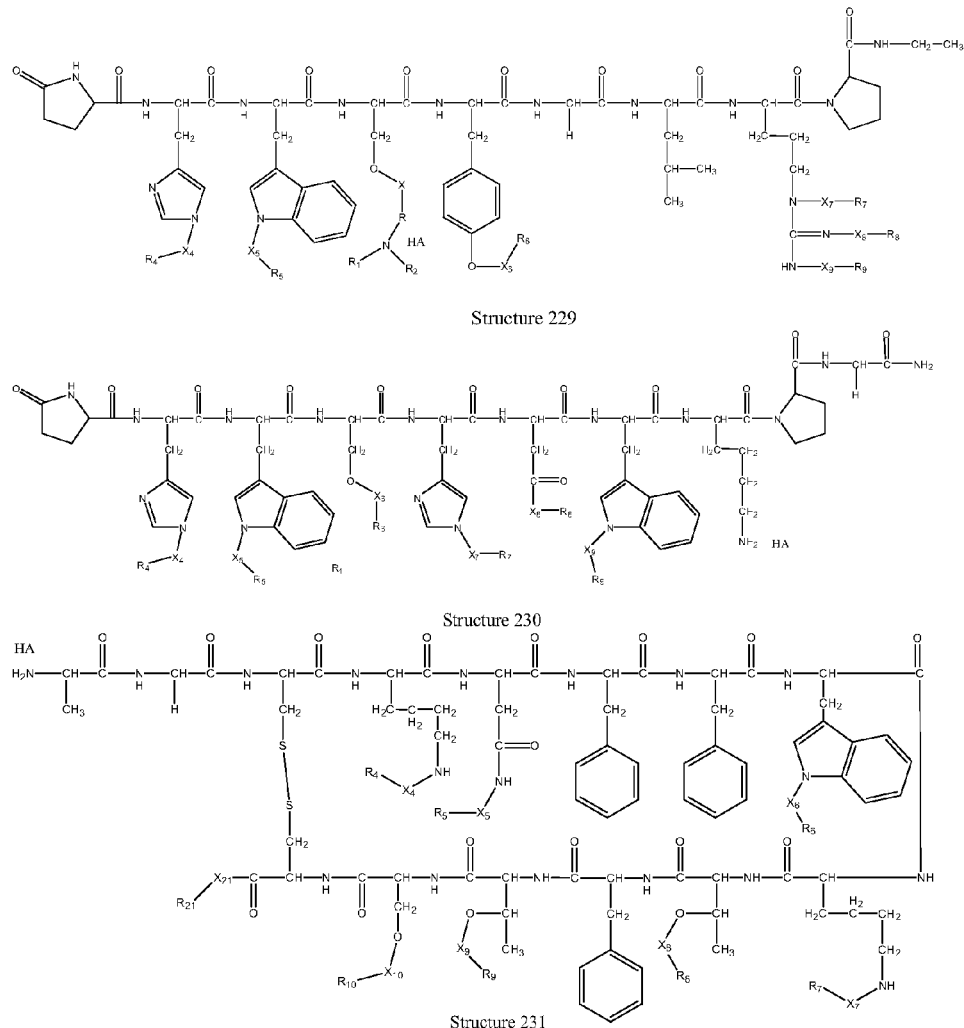
Figures 1, 132:
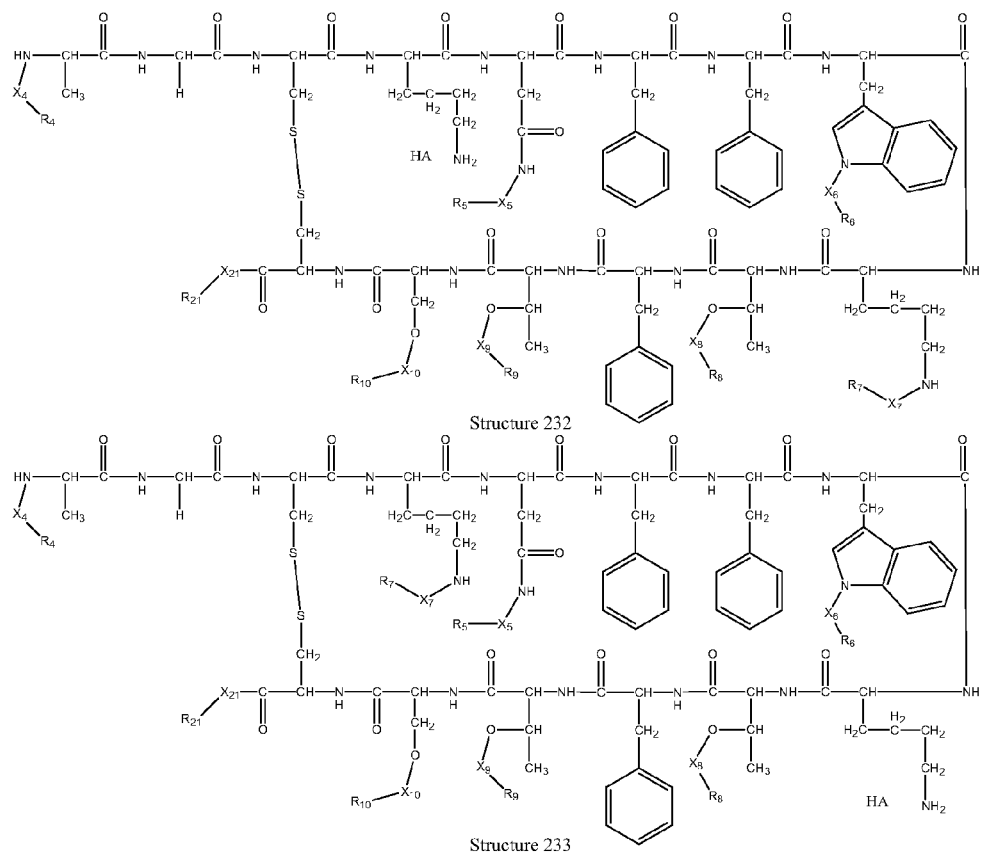
Figures 1, 134:
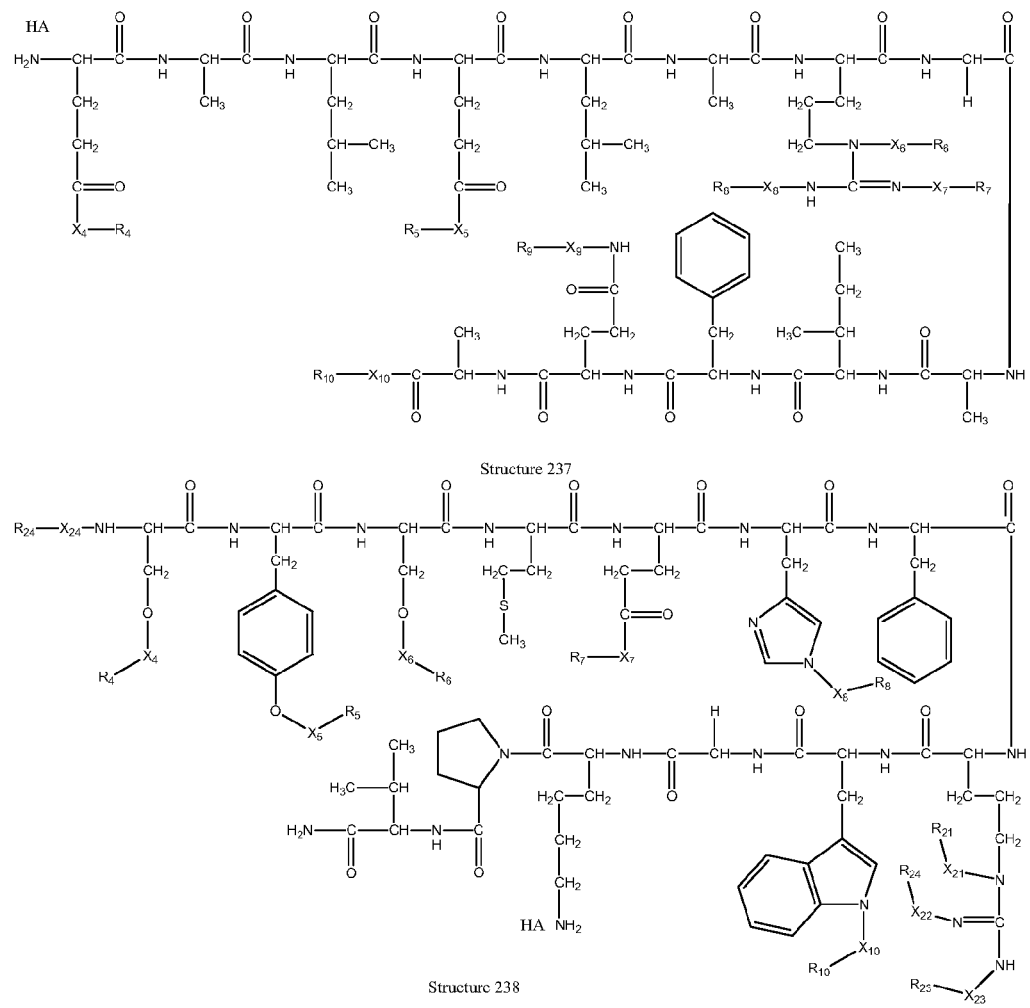
Figure 1:
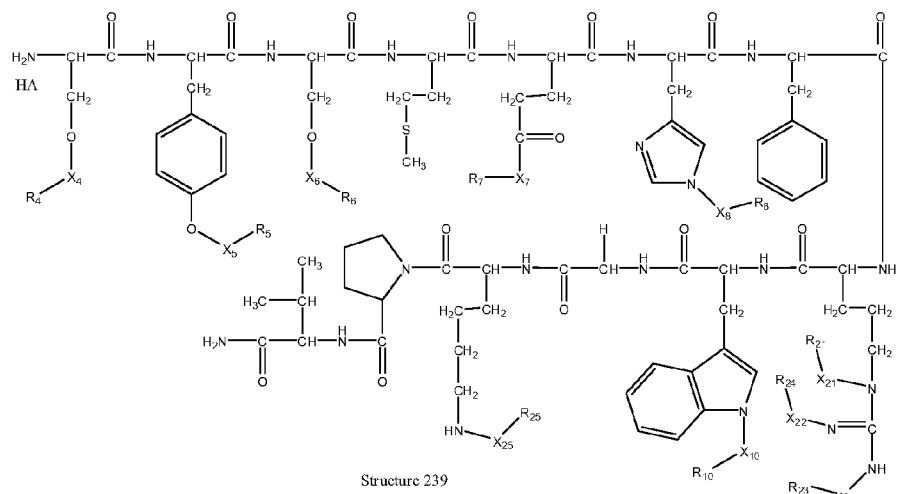
Figure 135:
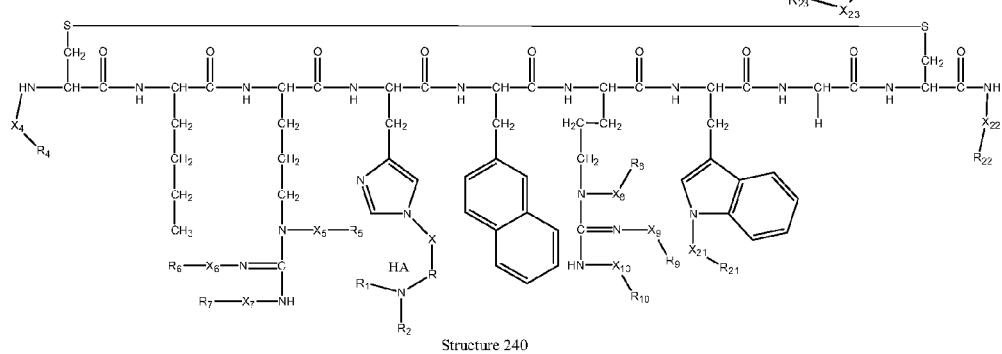
Figures 1, 136:
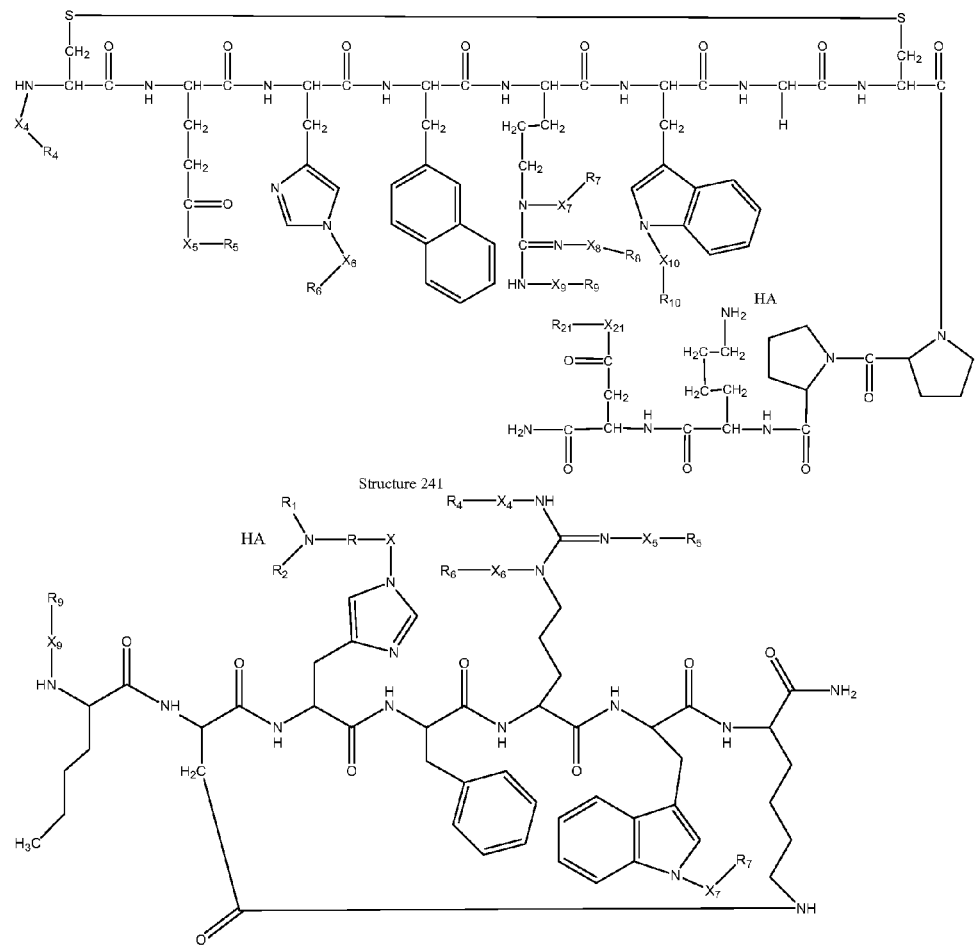
Figures 1, 137:
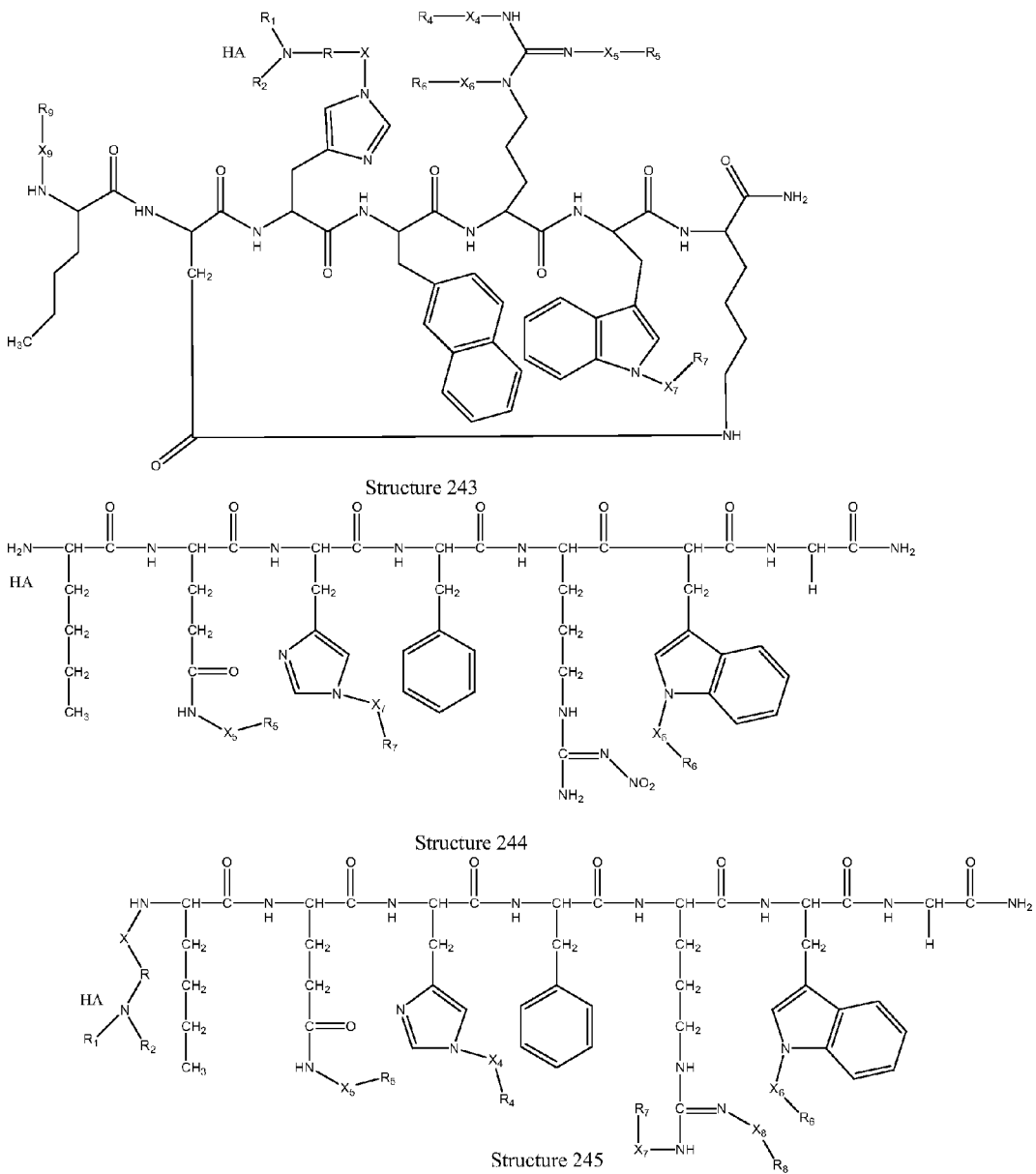
Figures 1, 138:
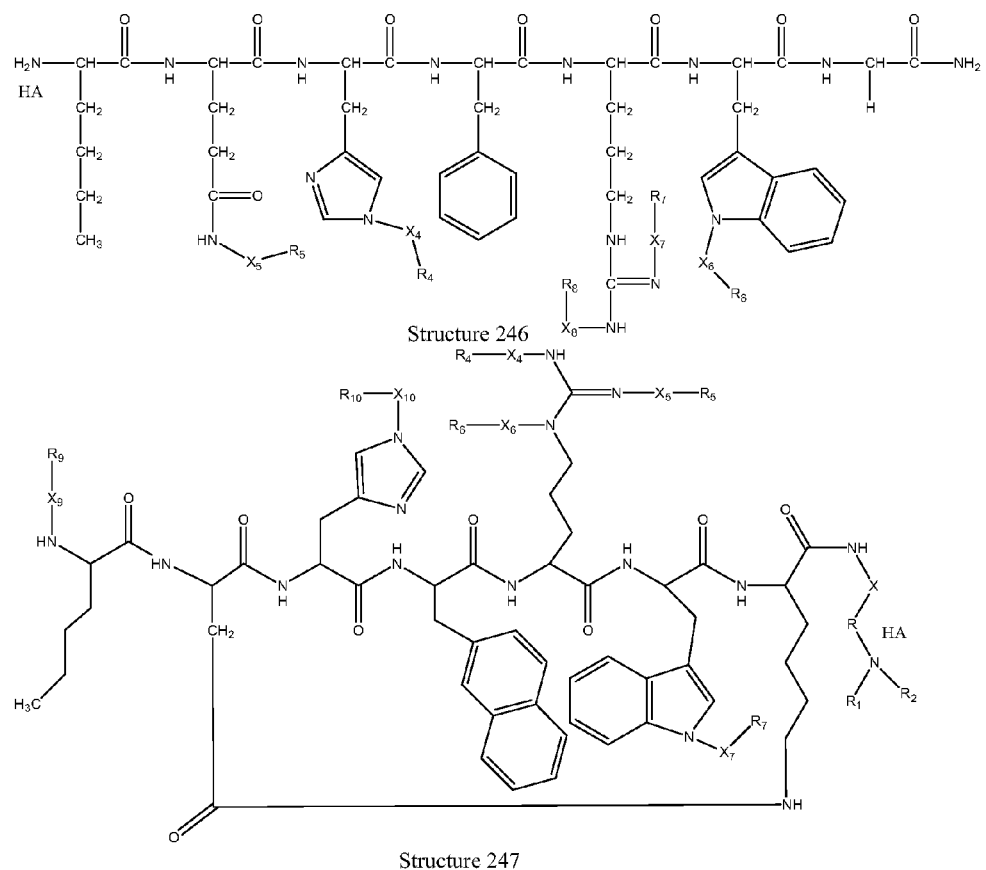
Figures 1, 139:
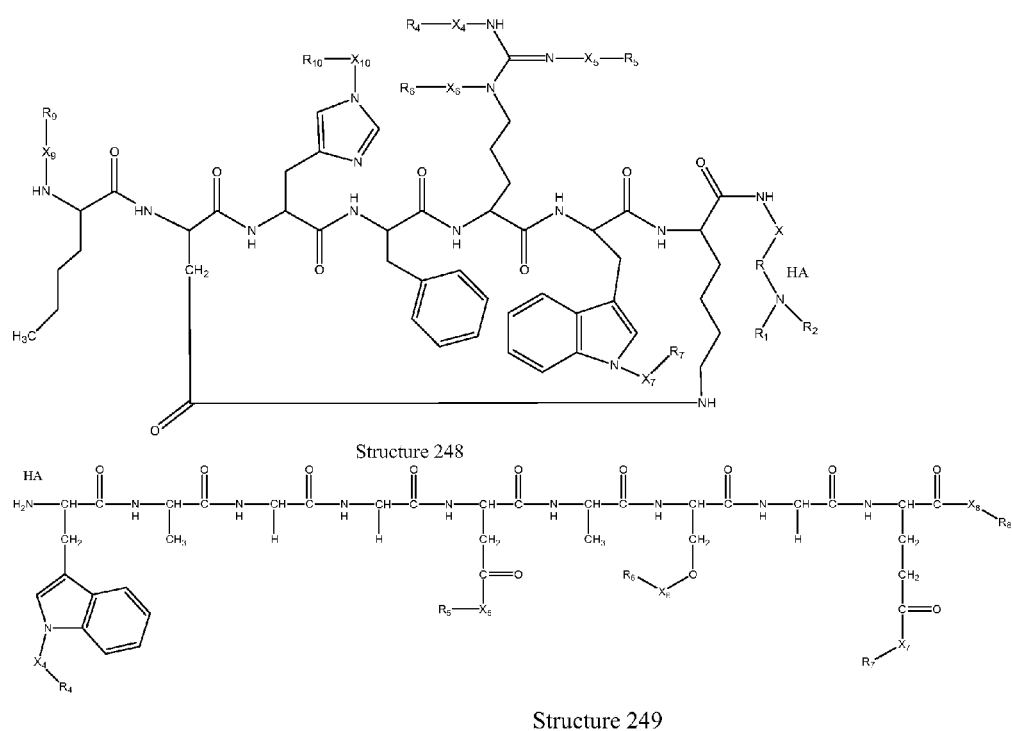
Figure 1:
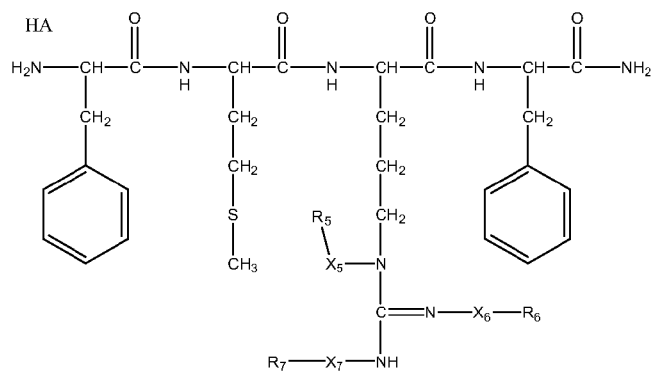
Figure 140:
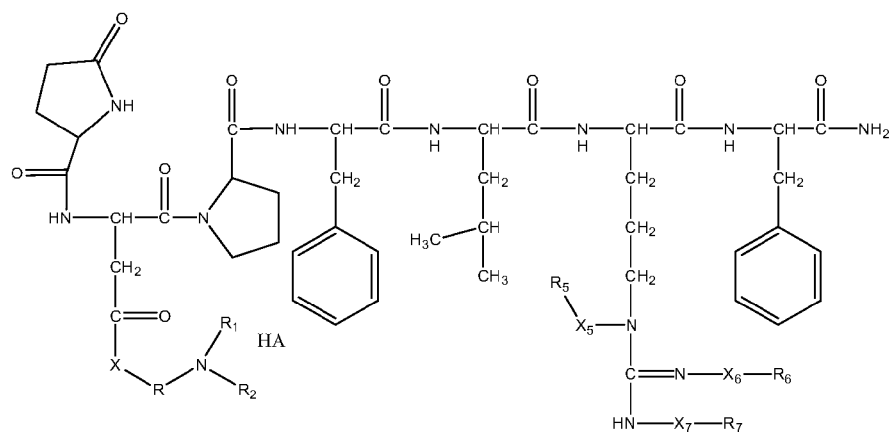
Figures 1, 141:
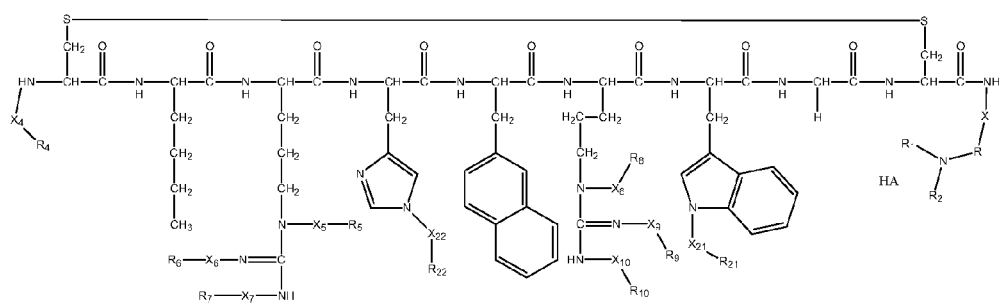
Figures 1, 142:
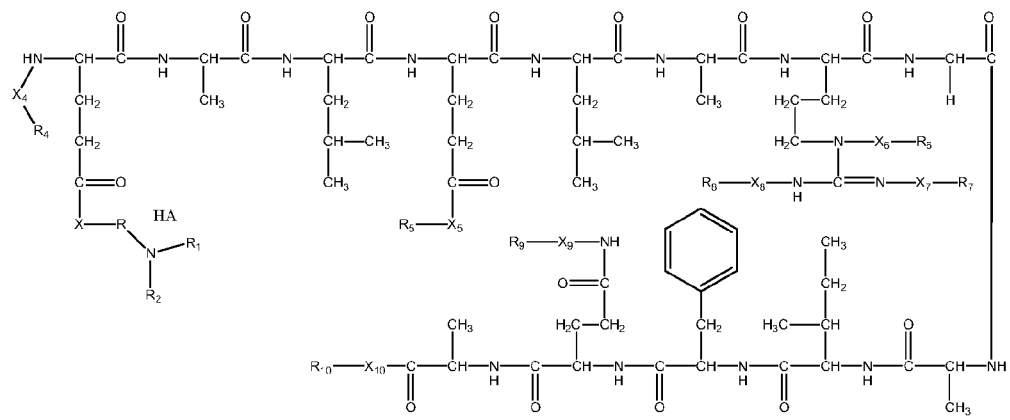
Figures 1, 143:
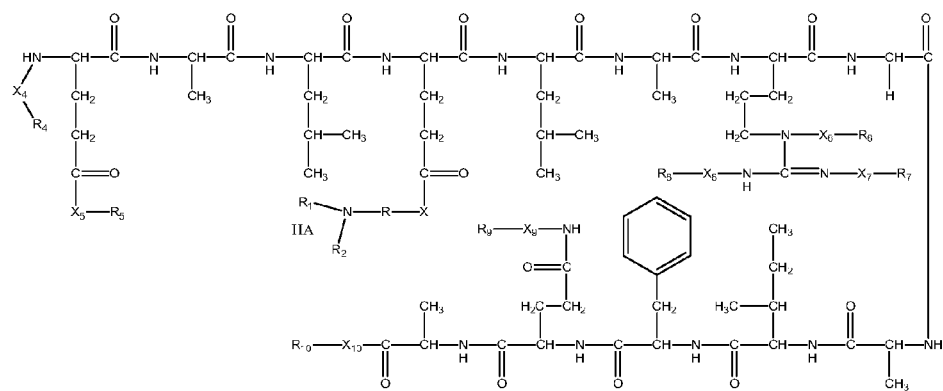
Figures 1, 144:
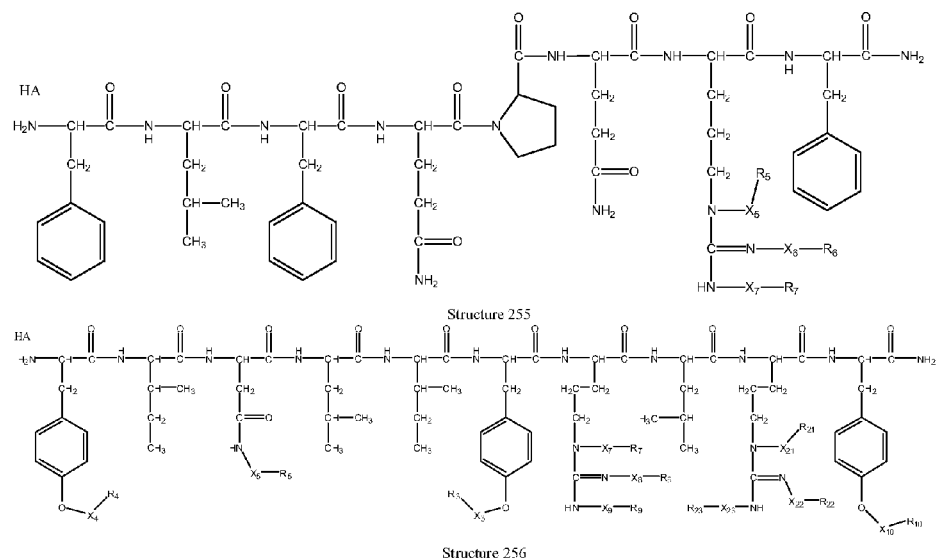
Figures 1, 145:
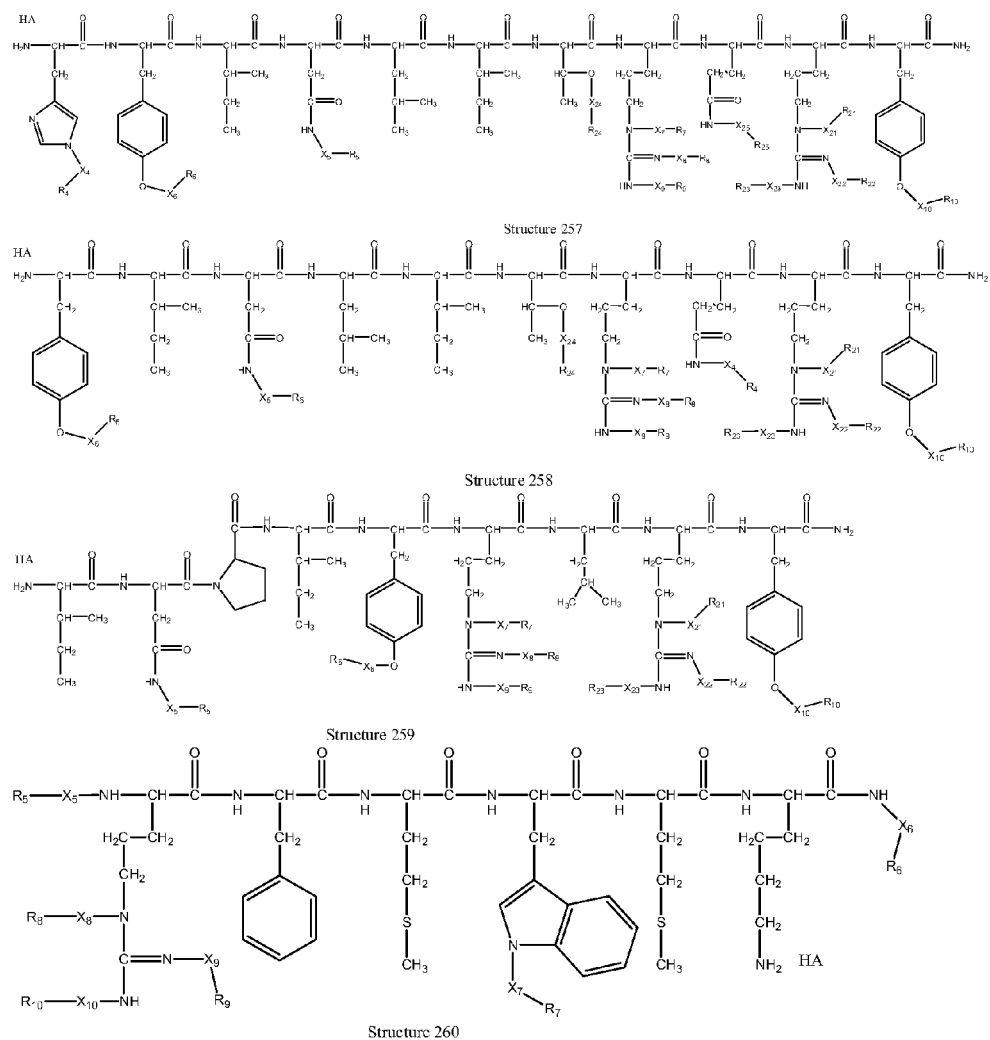
Figures 1, 146:
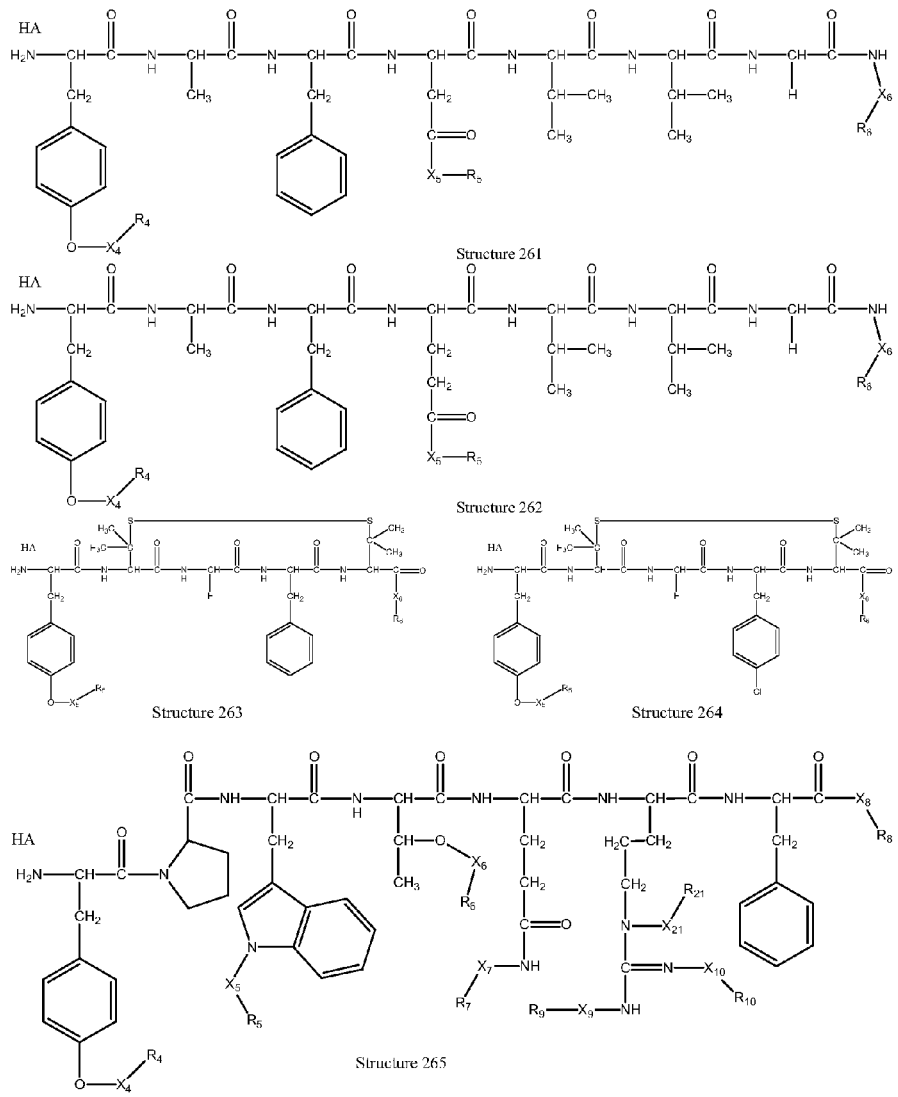
Figures 1, 147:
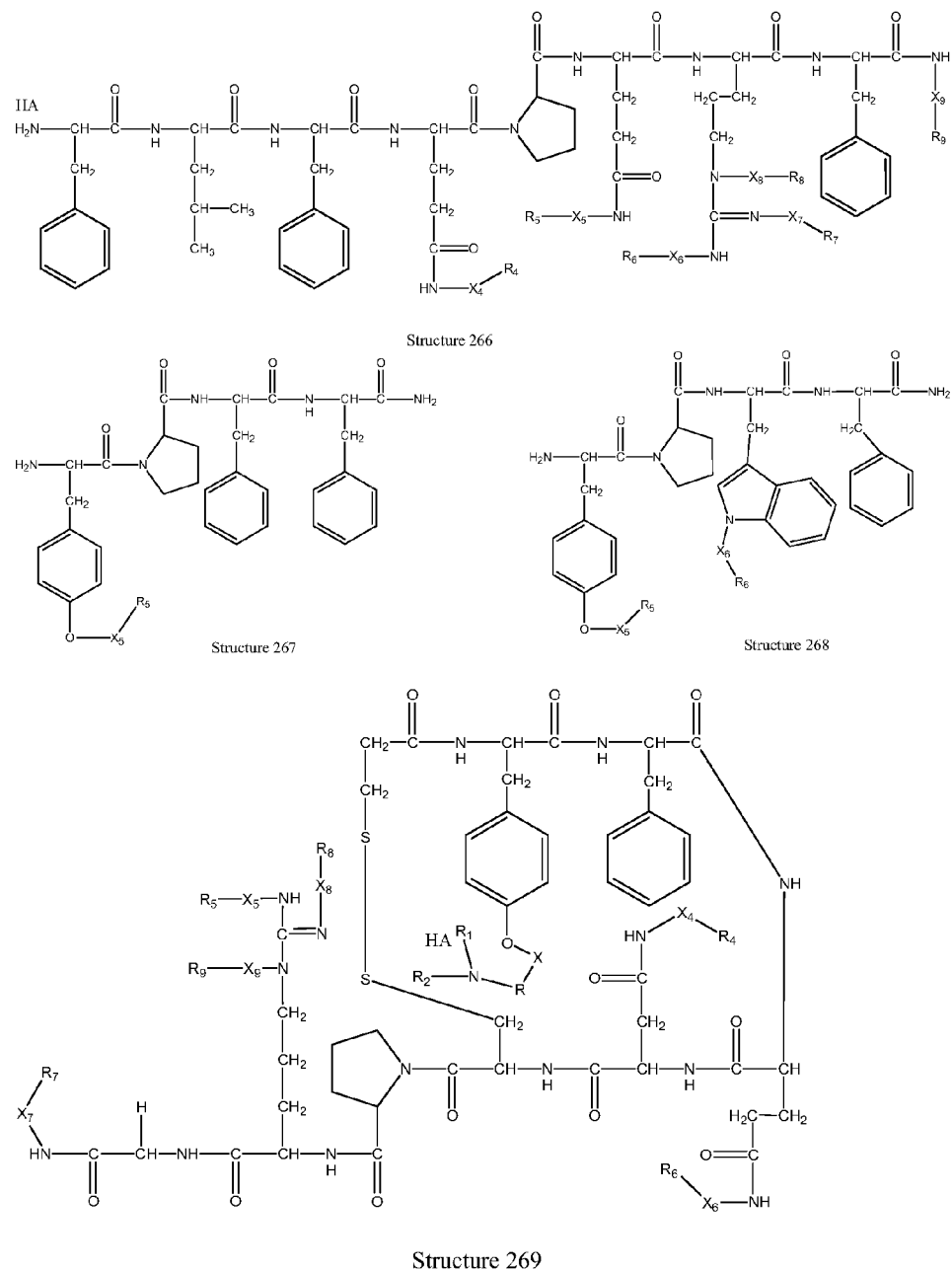
Figure 1:
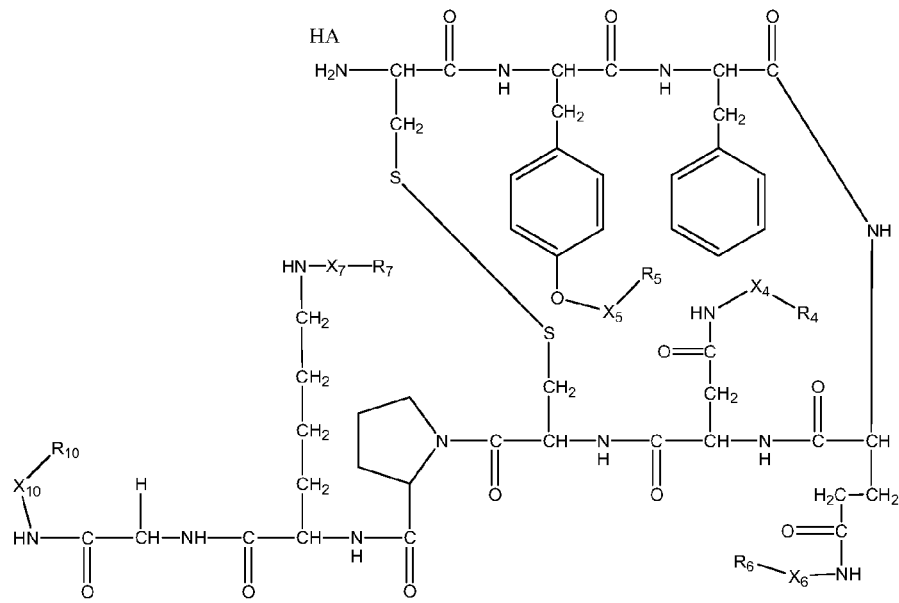
Figure 148:
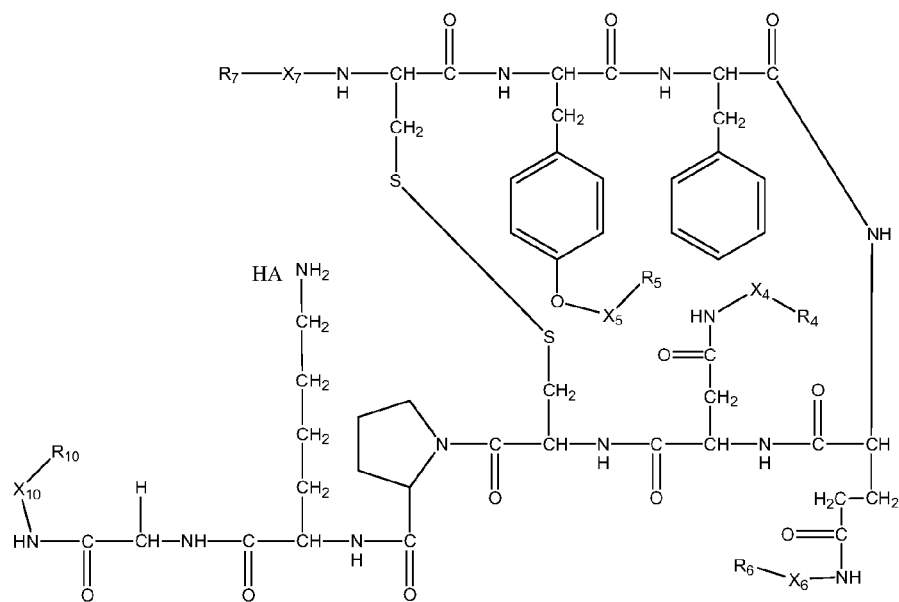
Figures 1, 149:
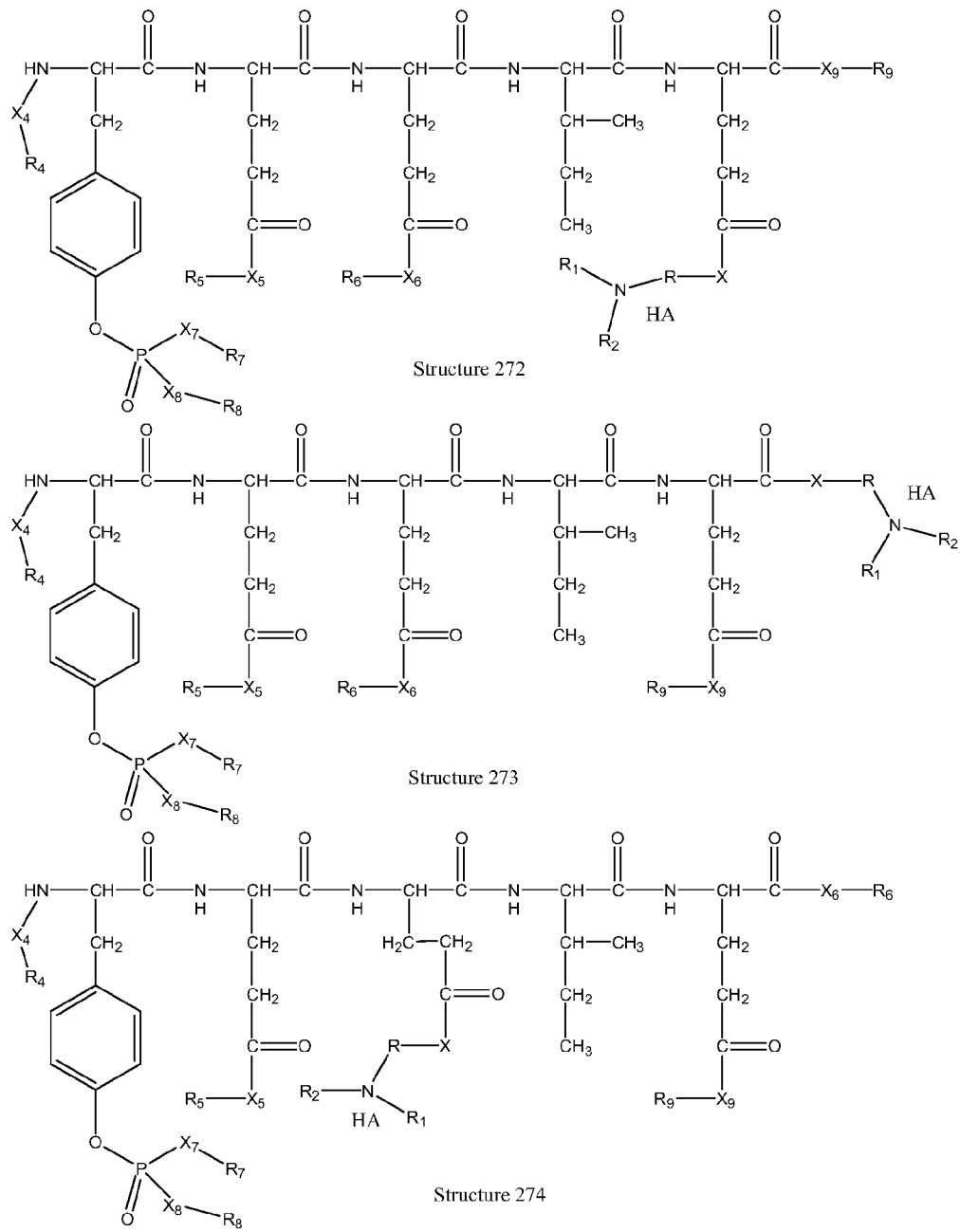
Figures 1, 150:
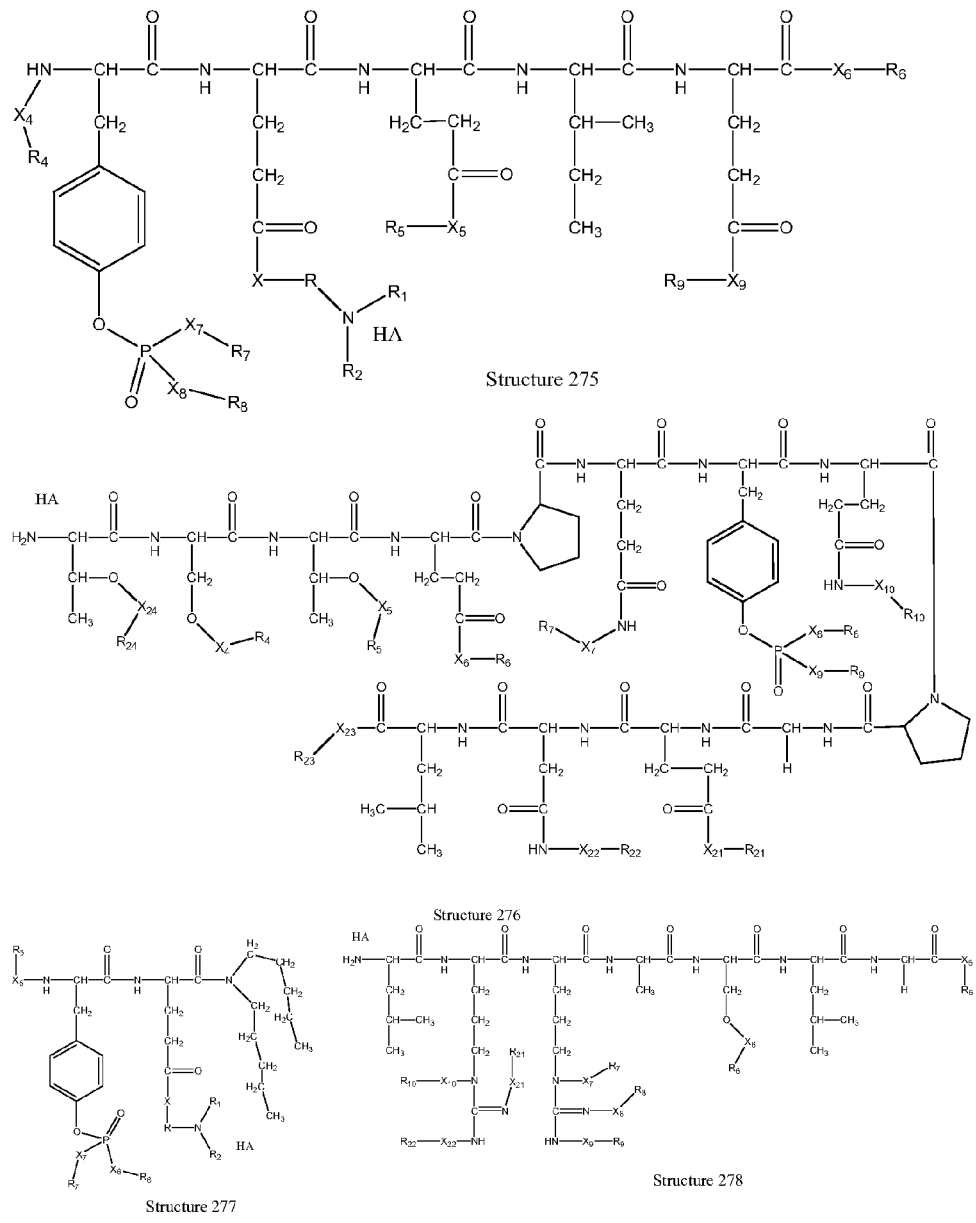
Figures 1, 151:
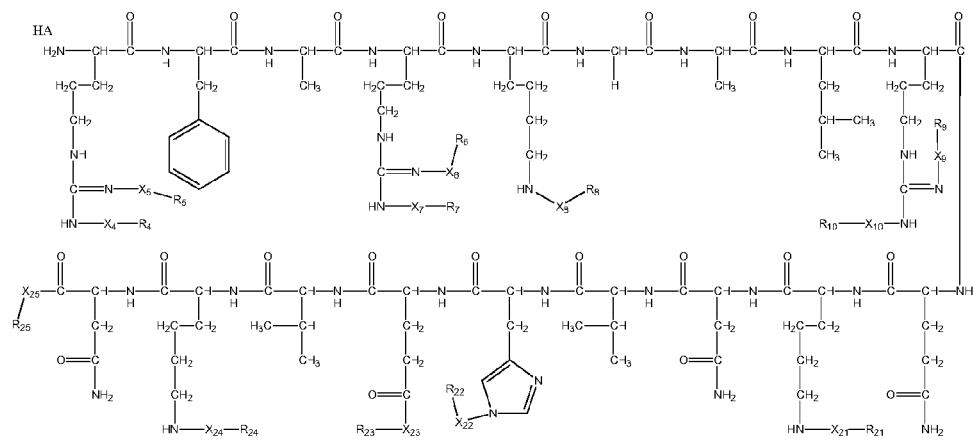
Figures 1, 152:
Figures 1, 153:
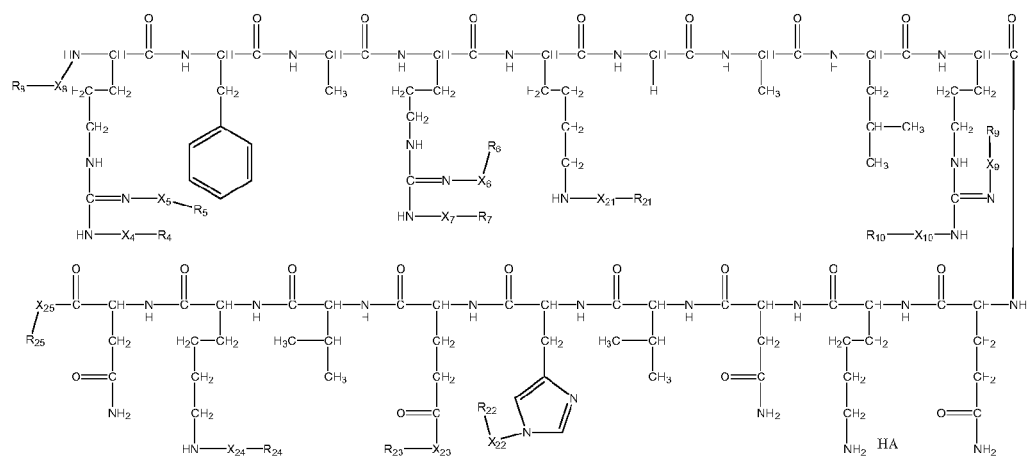
Figures 1, 154:
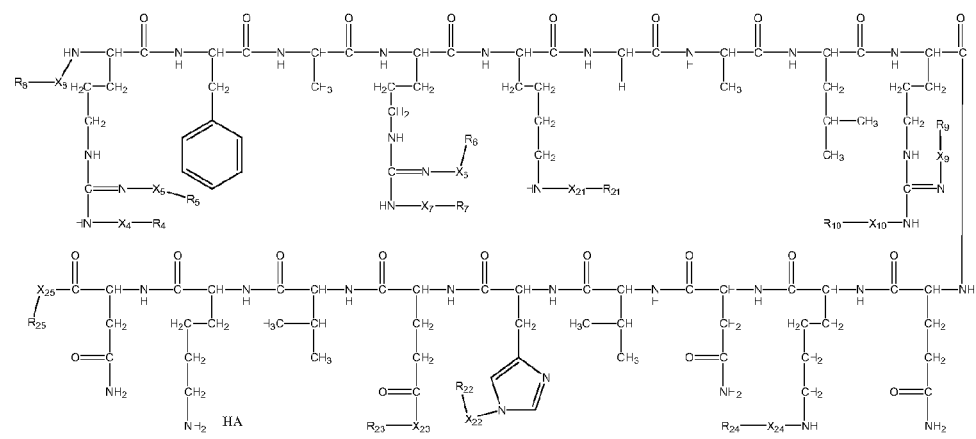
Figures 1, 155:
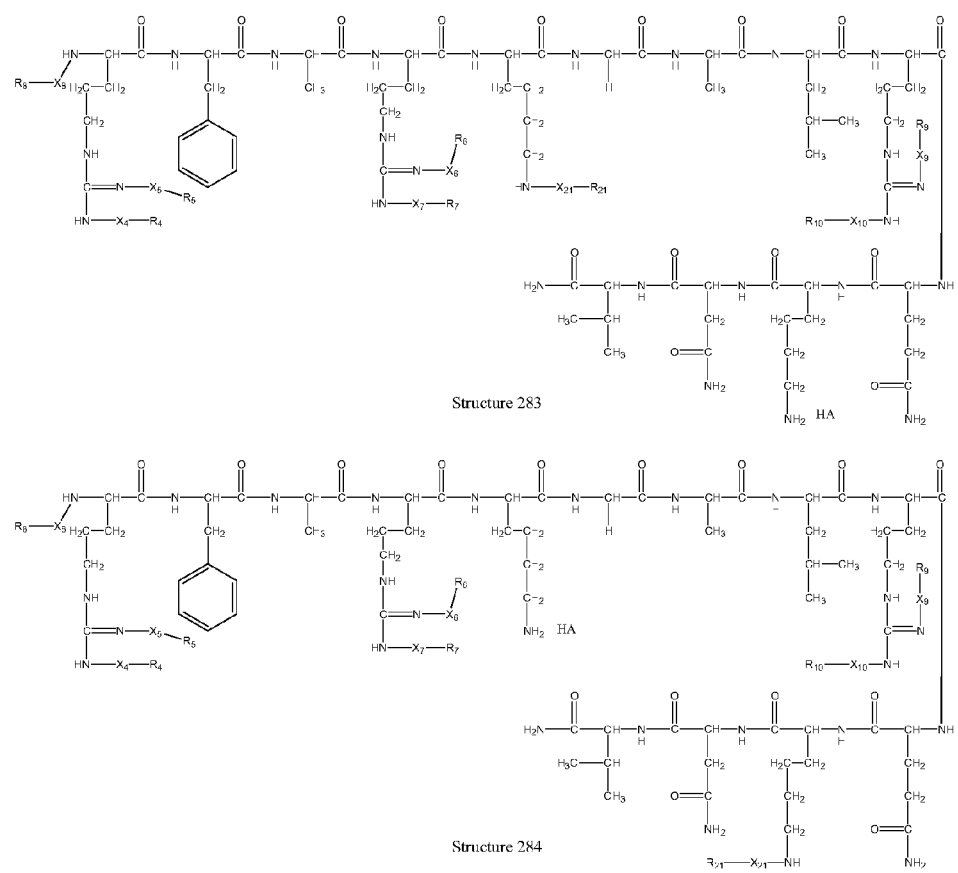
Figures 1, 156:
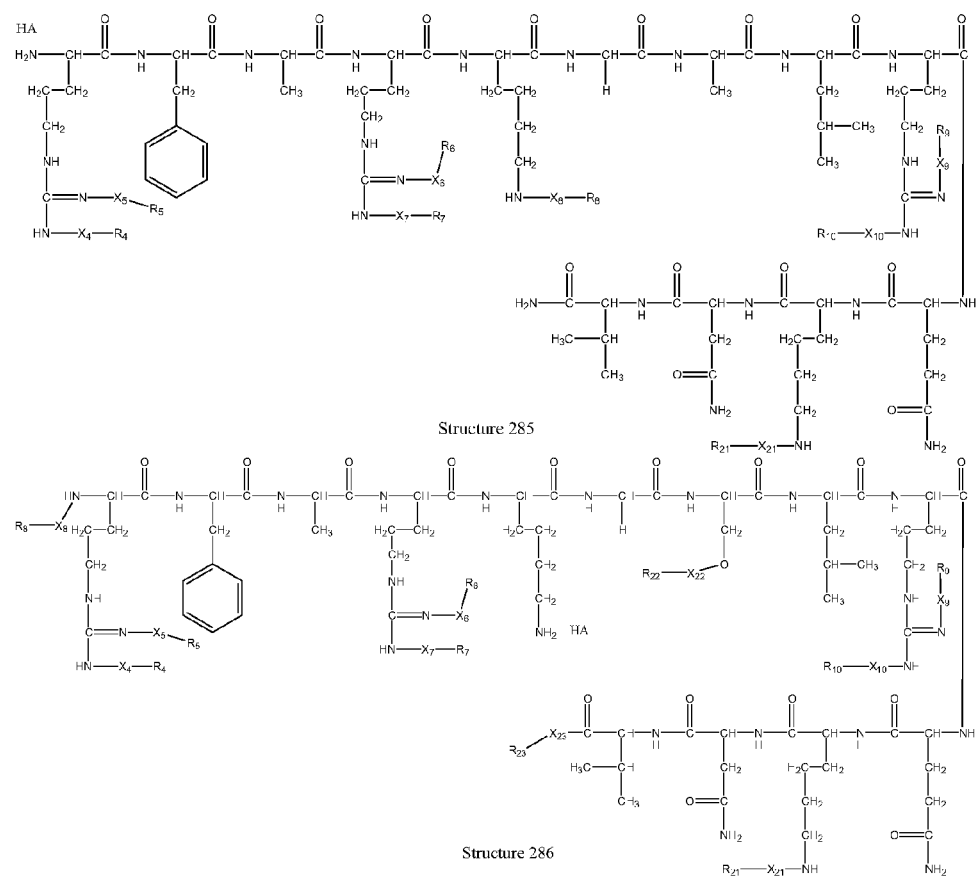
Figures 1, 157:
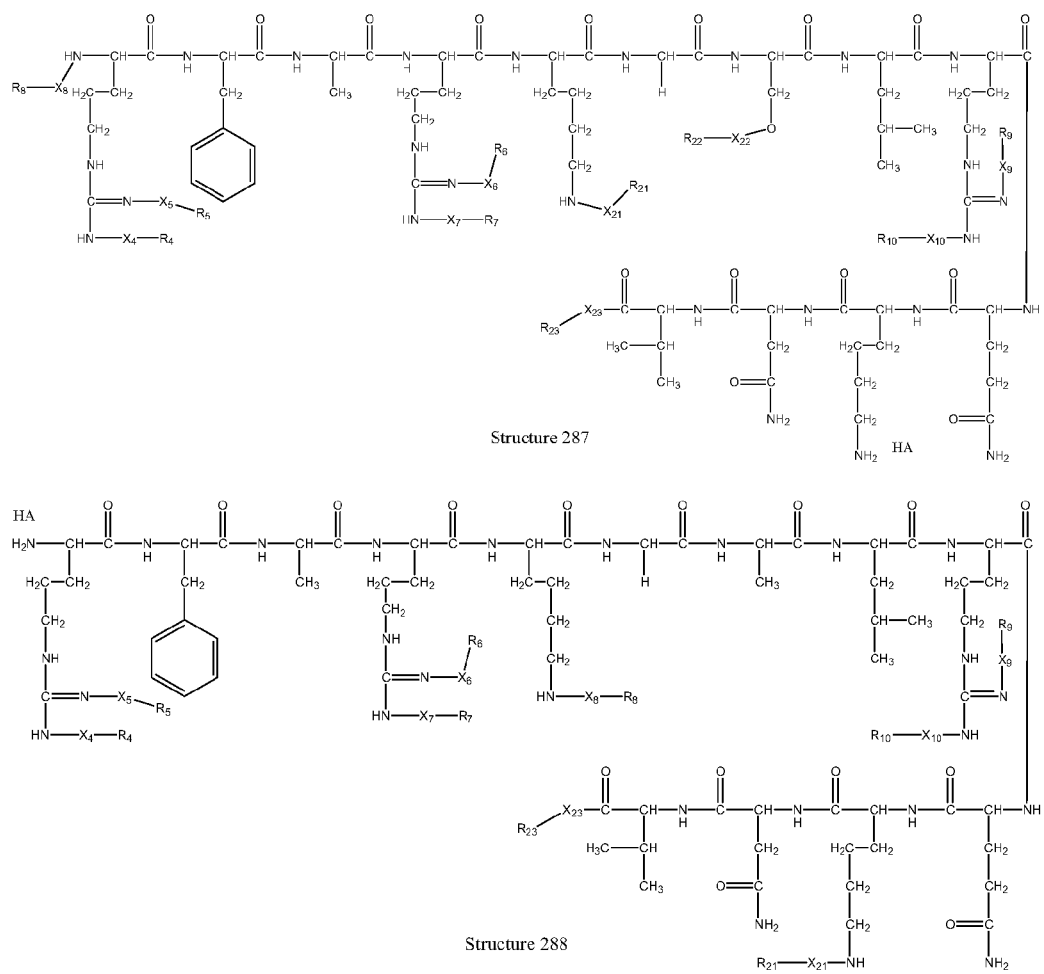
Figures 1, 158:
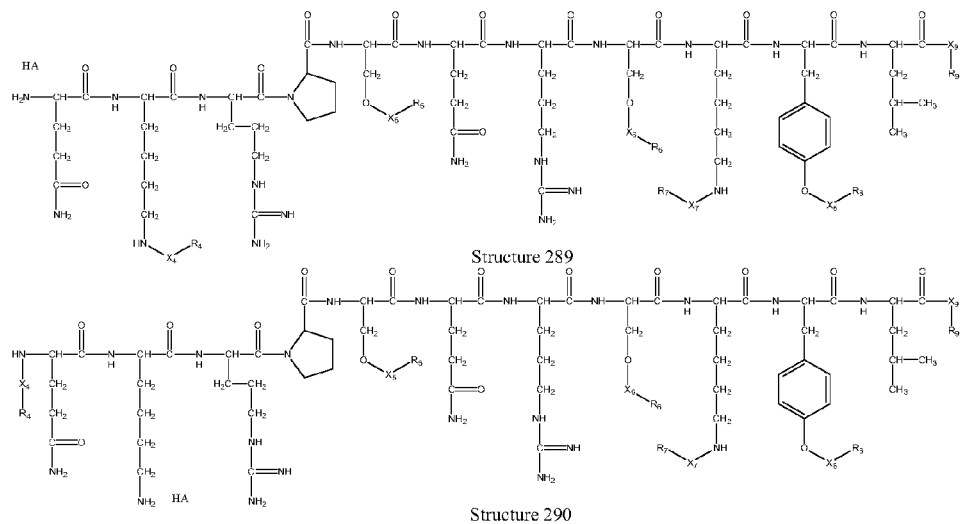
Figure 1:
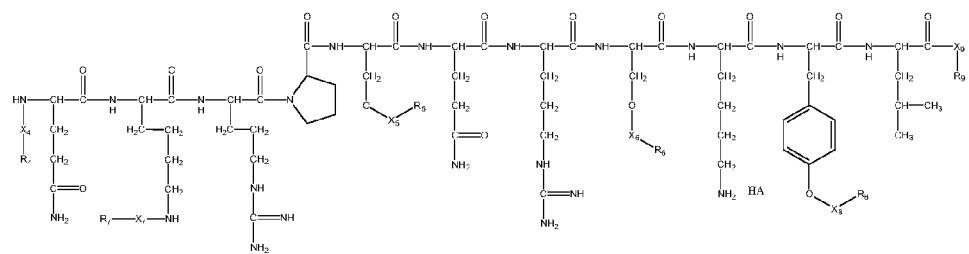
Figure 159:
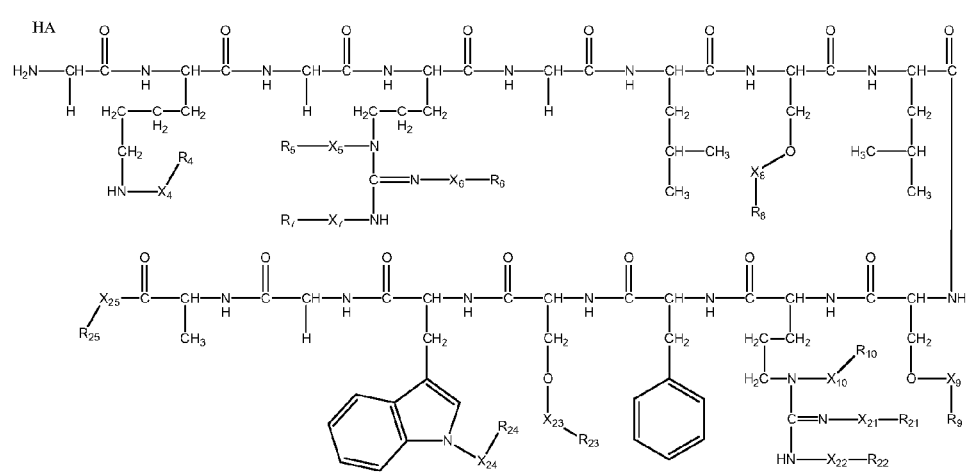
Figures 1, 160:
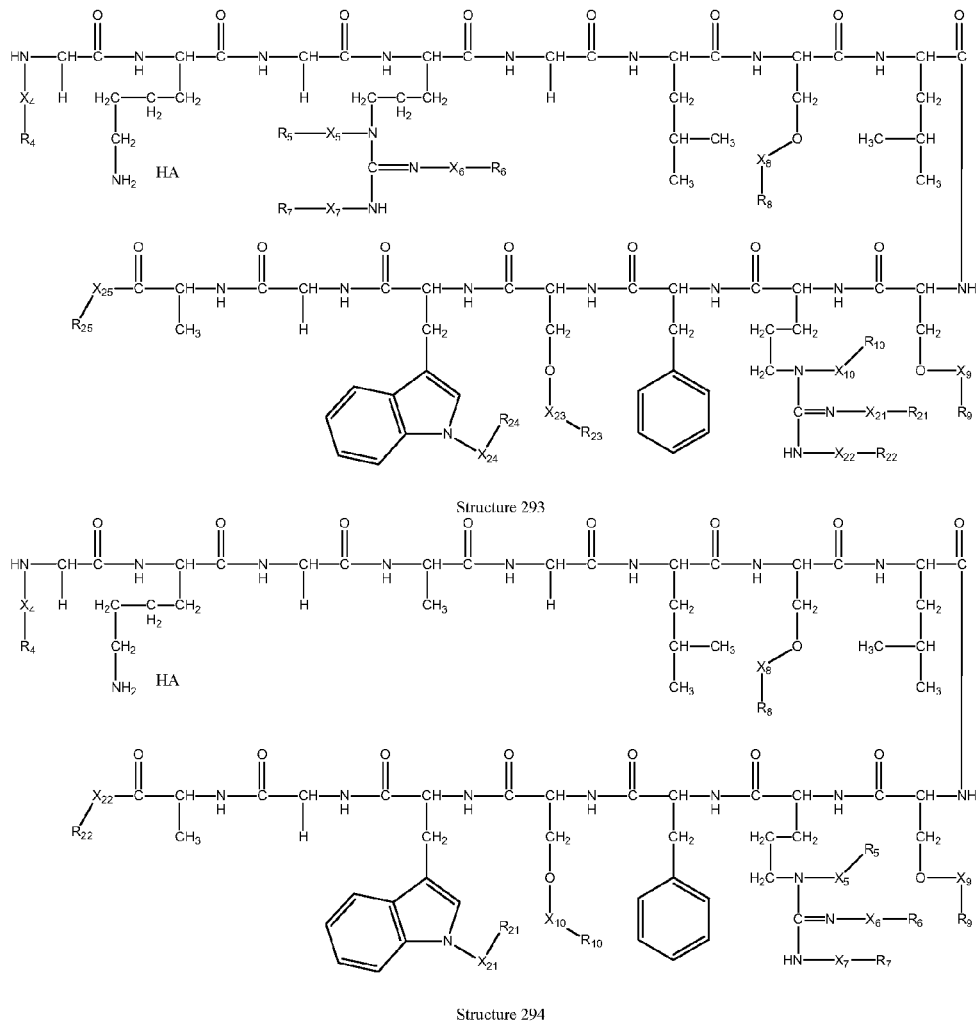
Figures 1, 161:
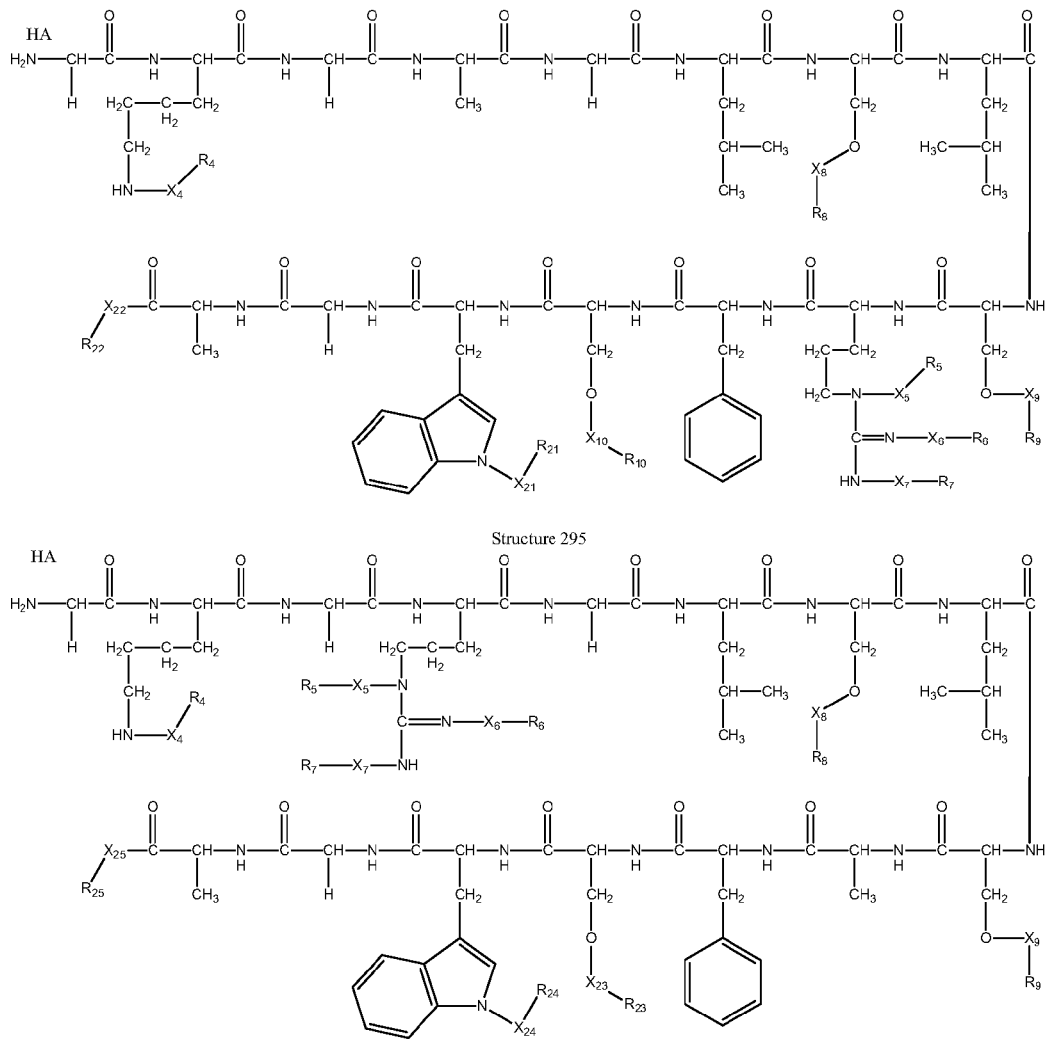
Figures 1, 162:
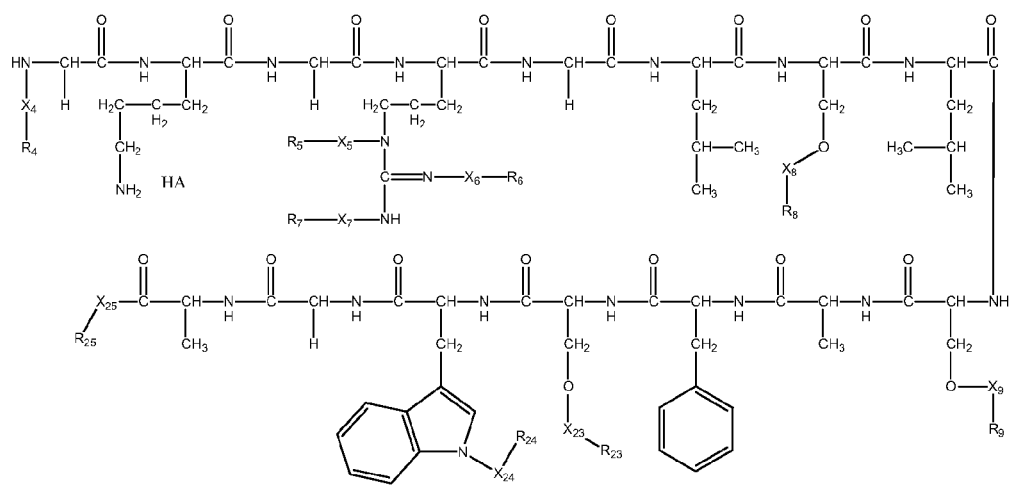
Figure 1:
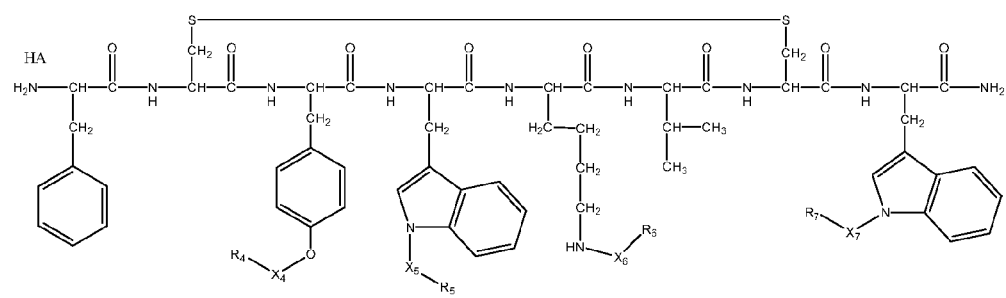
Figure 164:
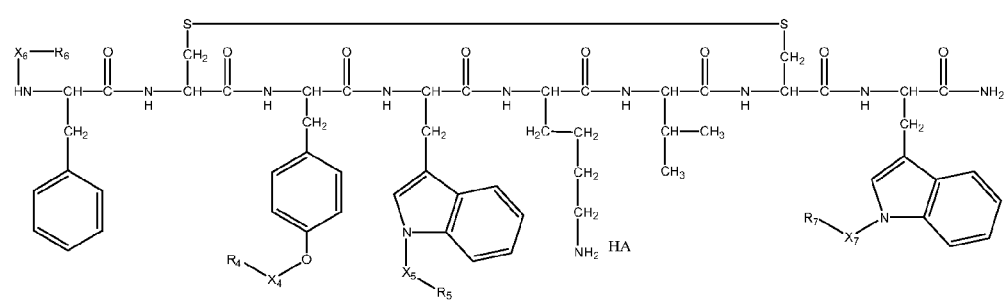
Figures 1, 165:
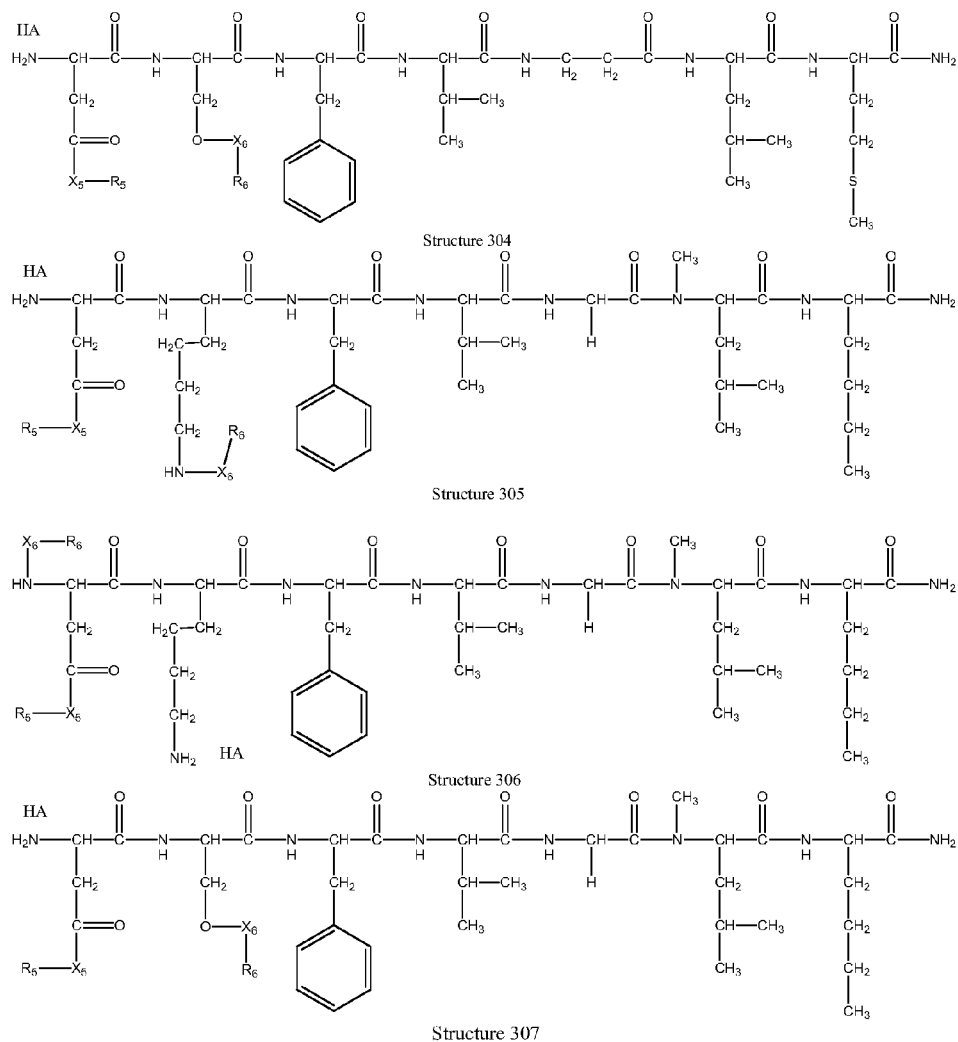
Figures 1, 166:
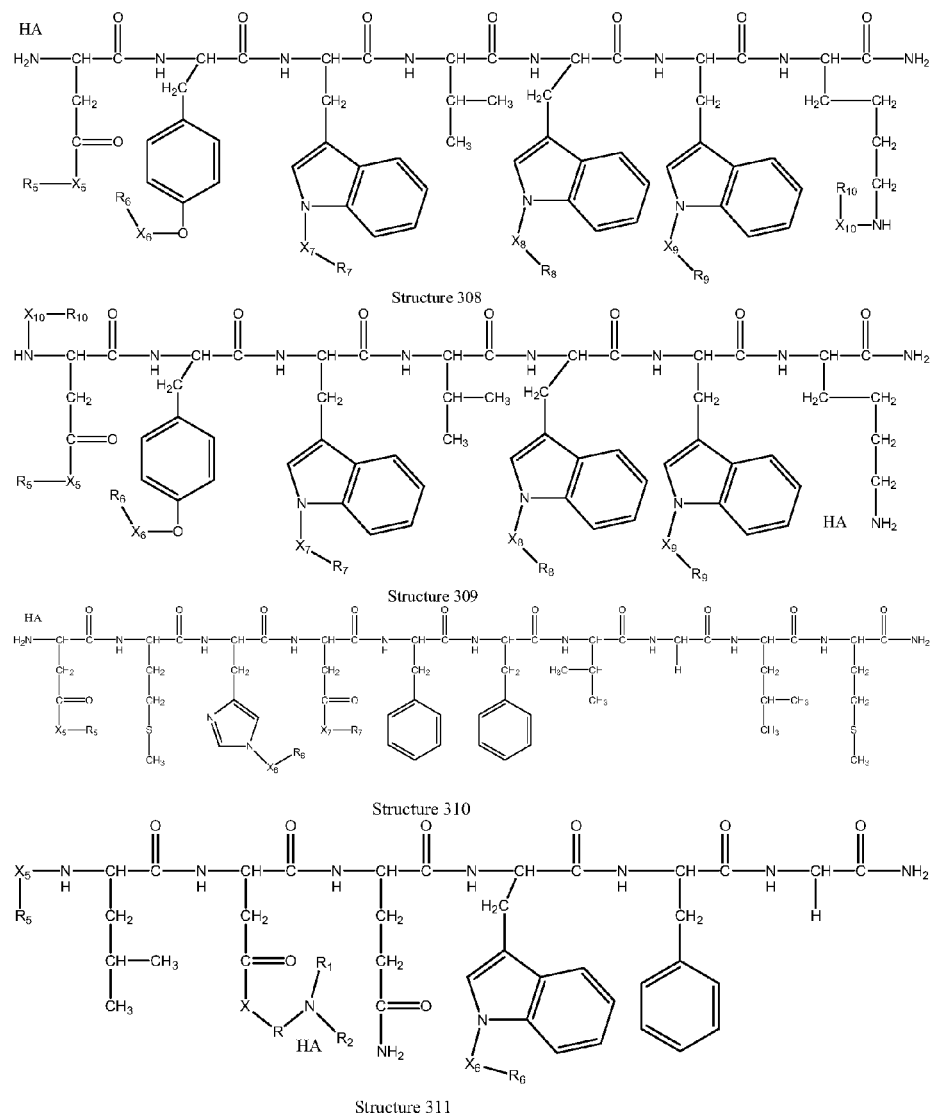
Figures 1, 167:
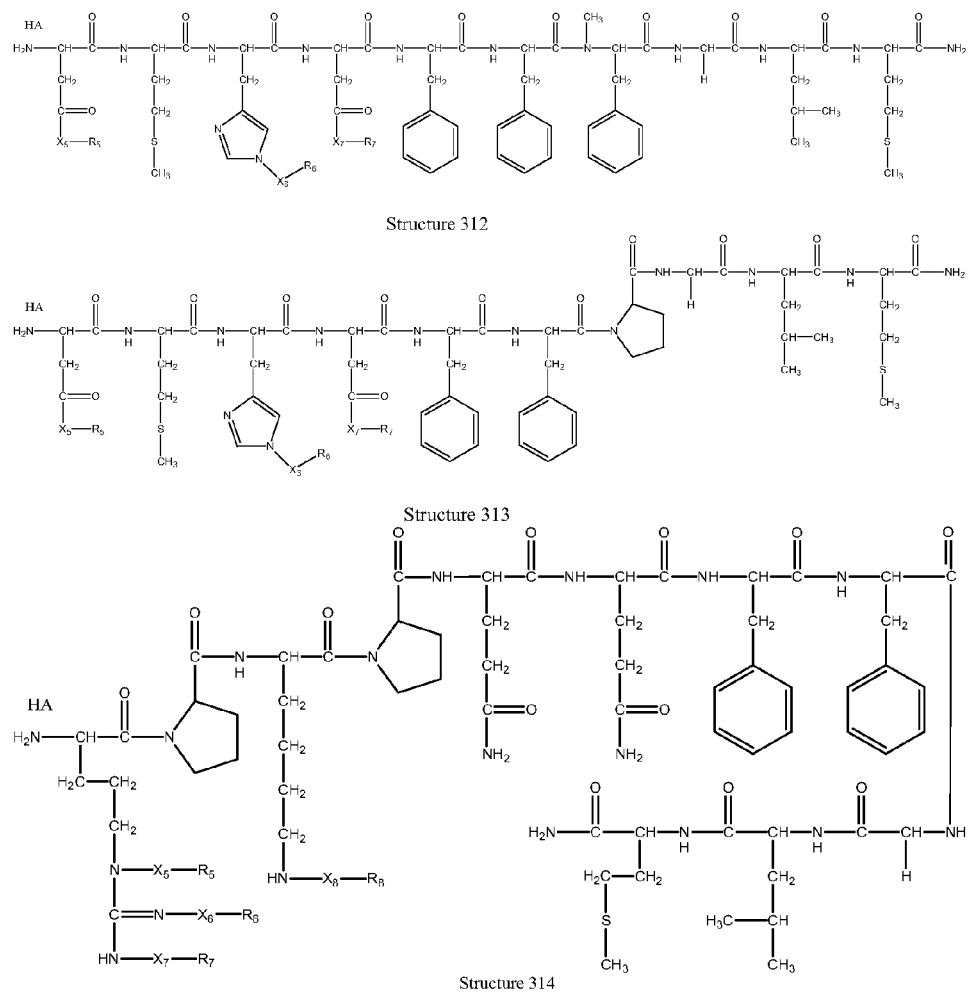
Figures 1, 168:
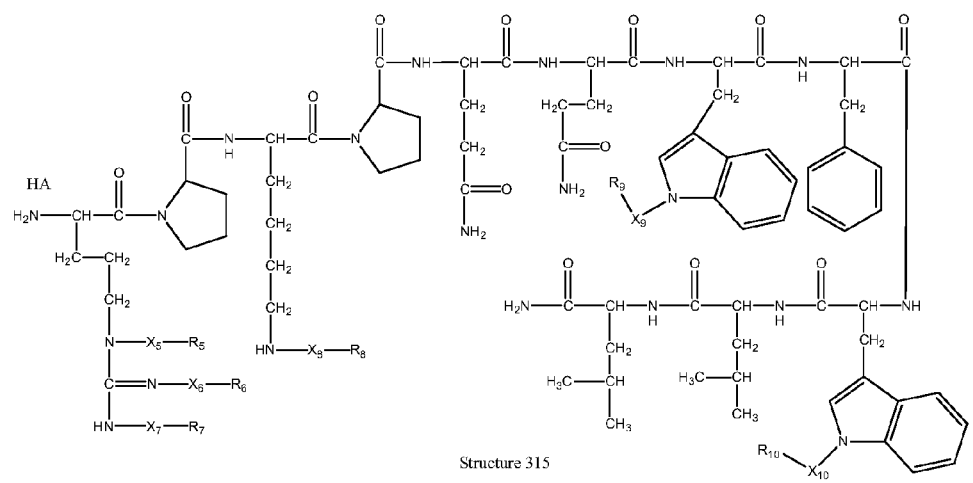
Figures 1, 169:
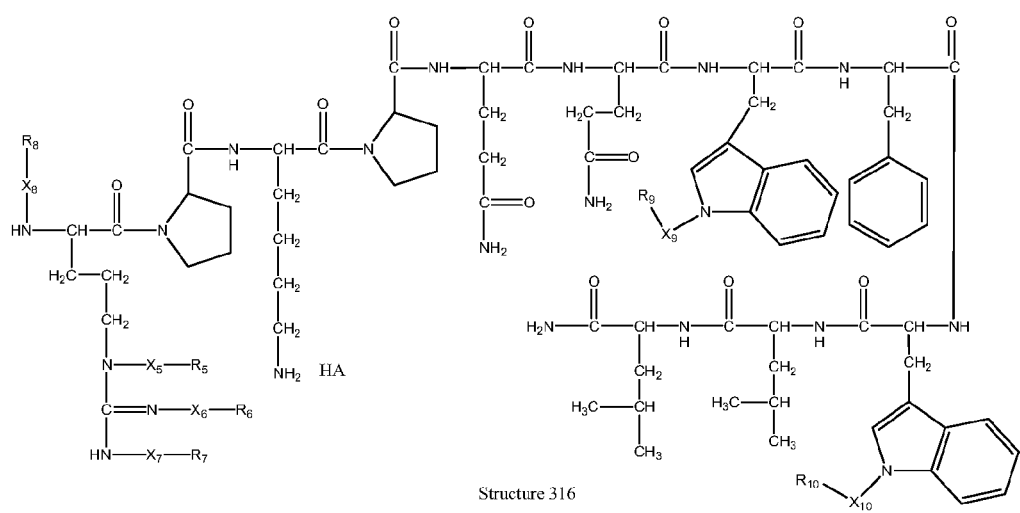
Figures 1, 170:
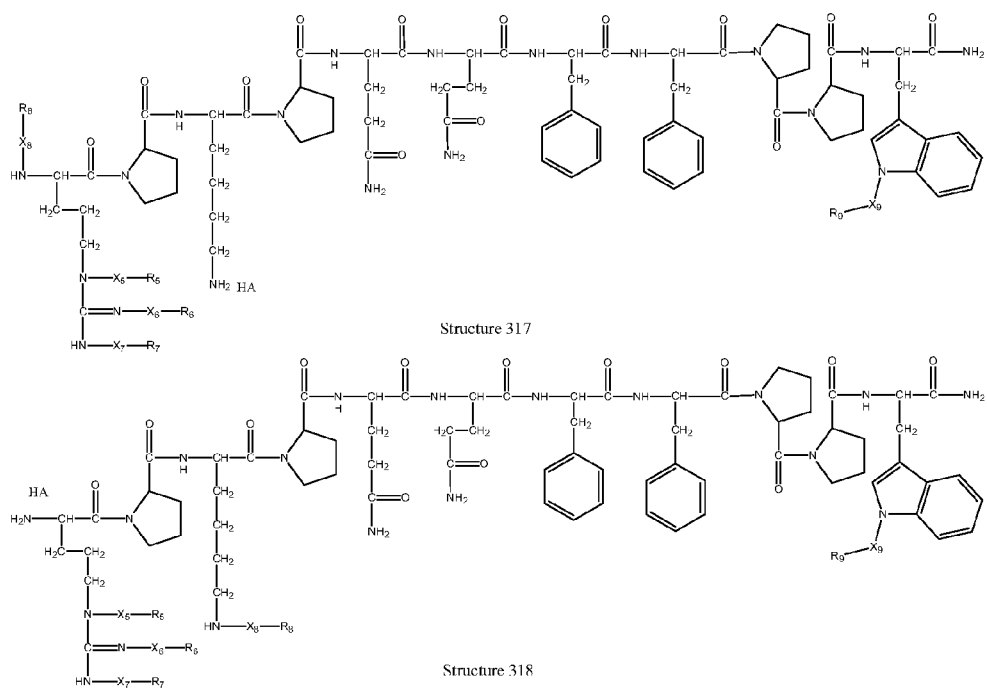
Figures 1, 172:
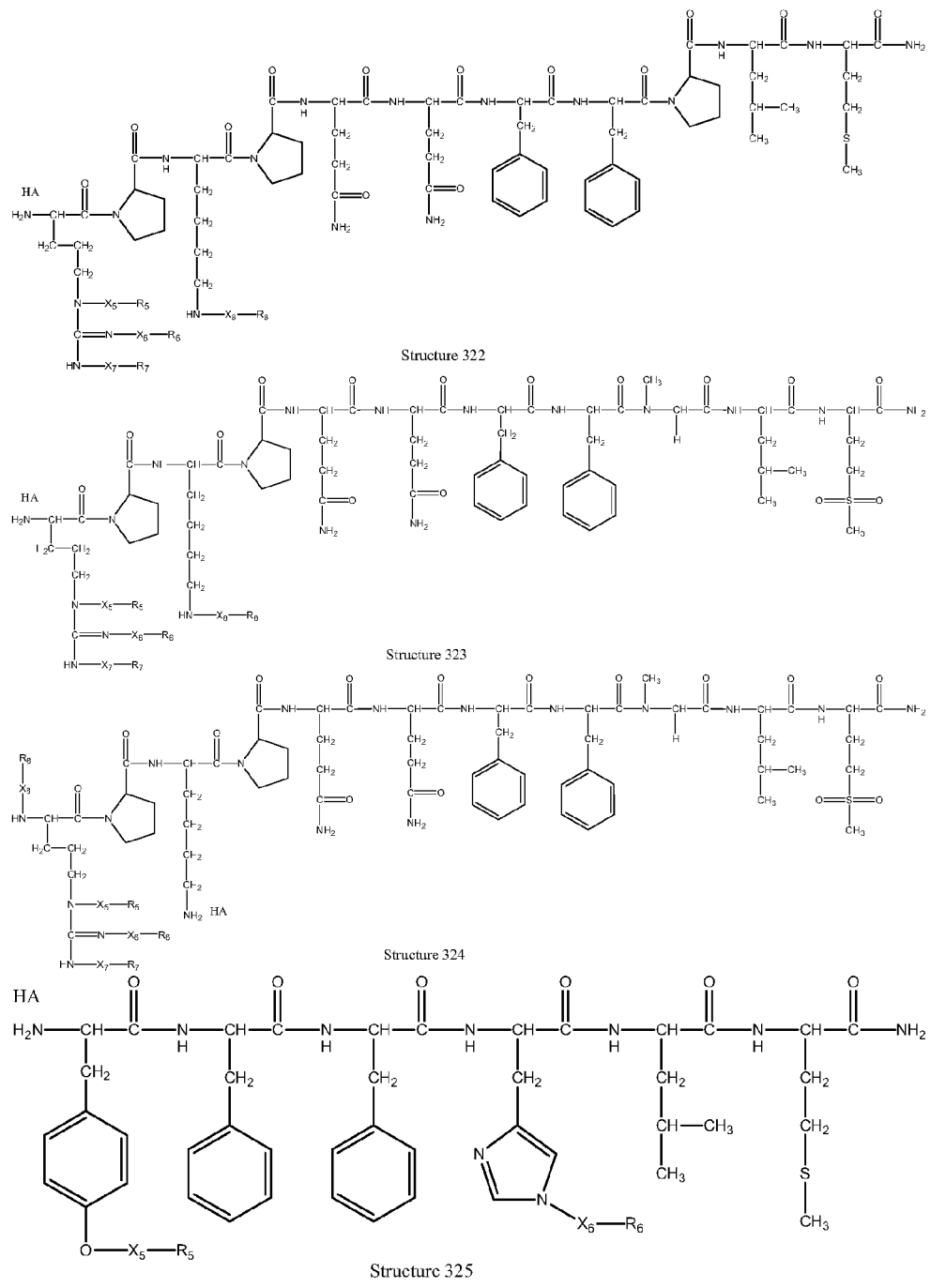
Figures 1, 173:
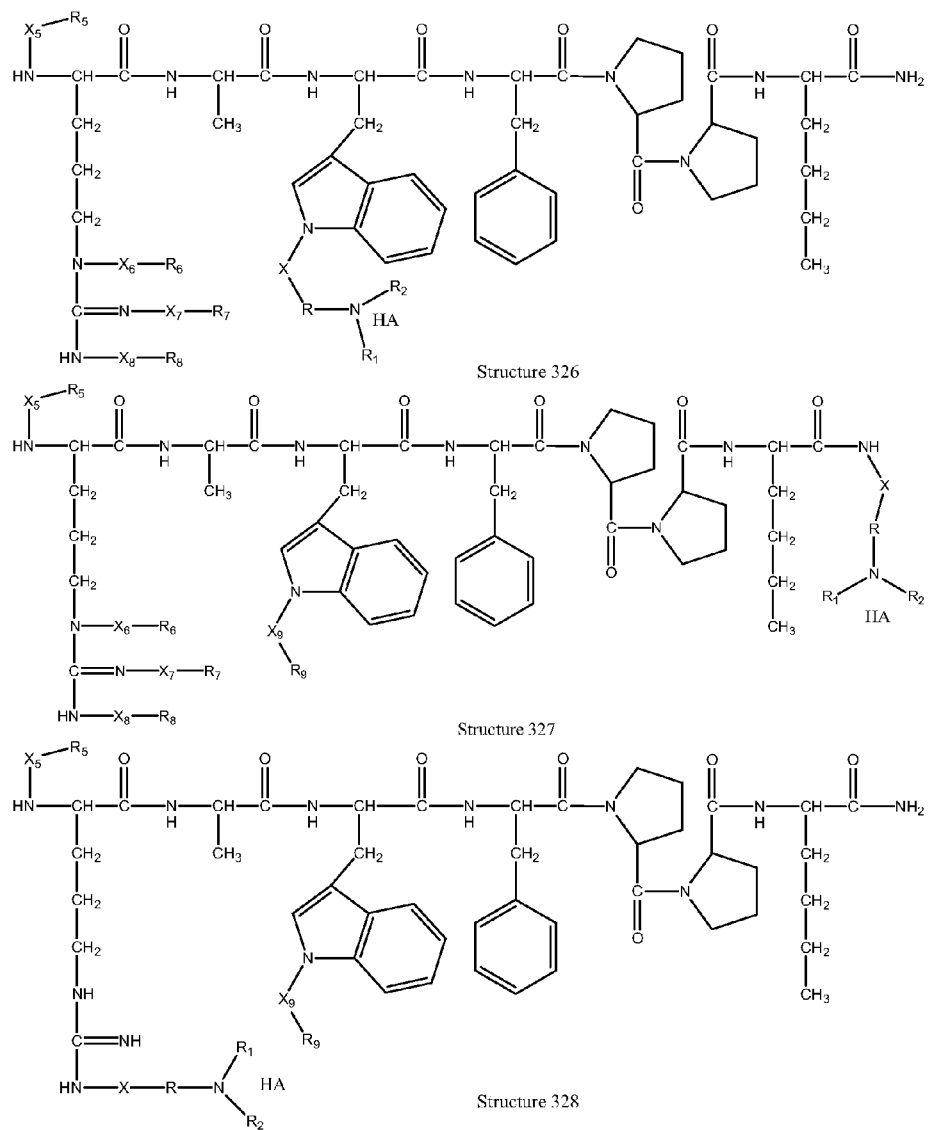
Figures 1, 175:
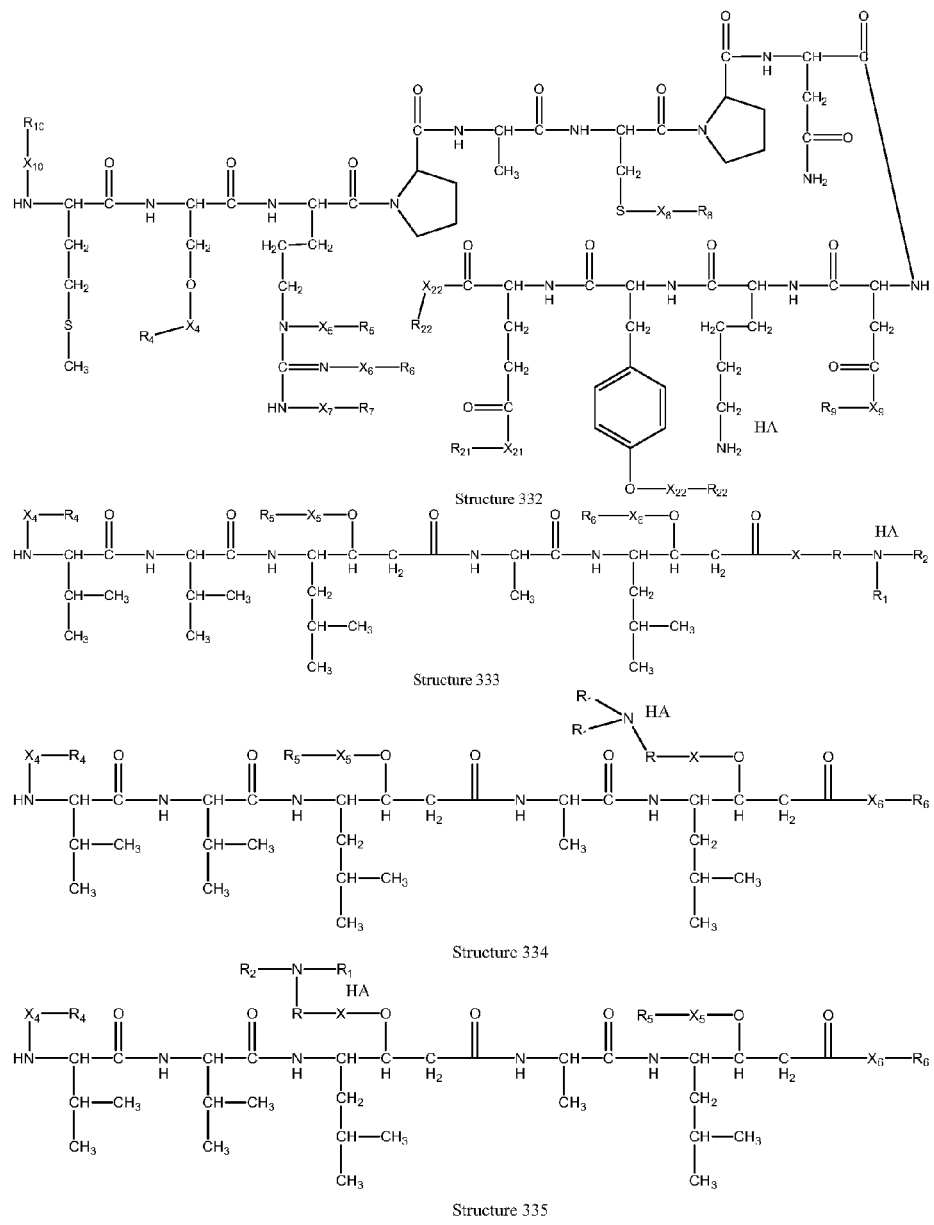
Figures 1, 176:
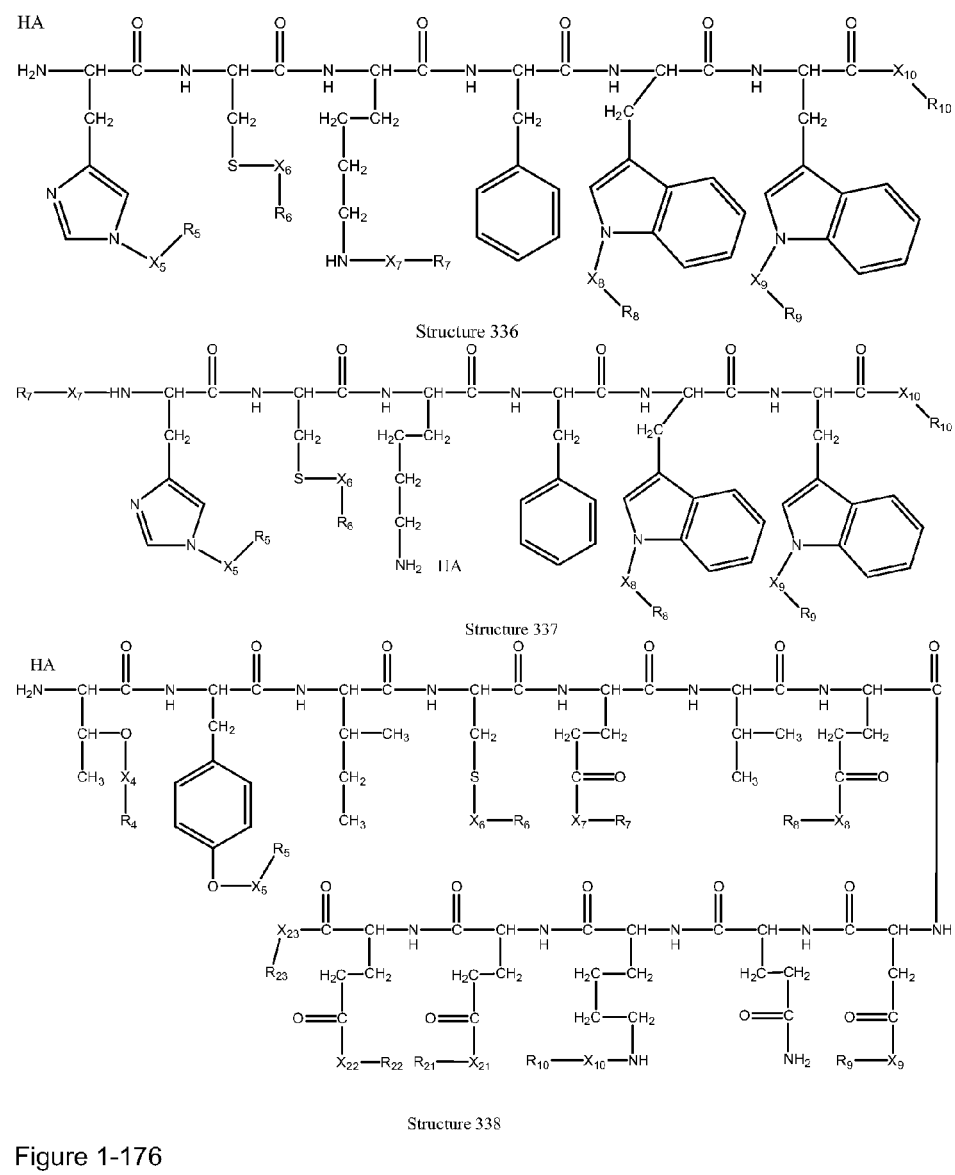
Figures 1, 177:
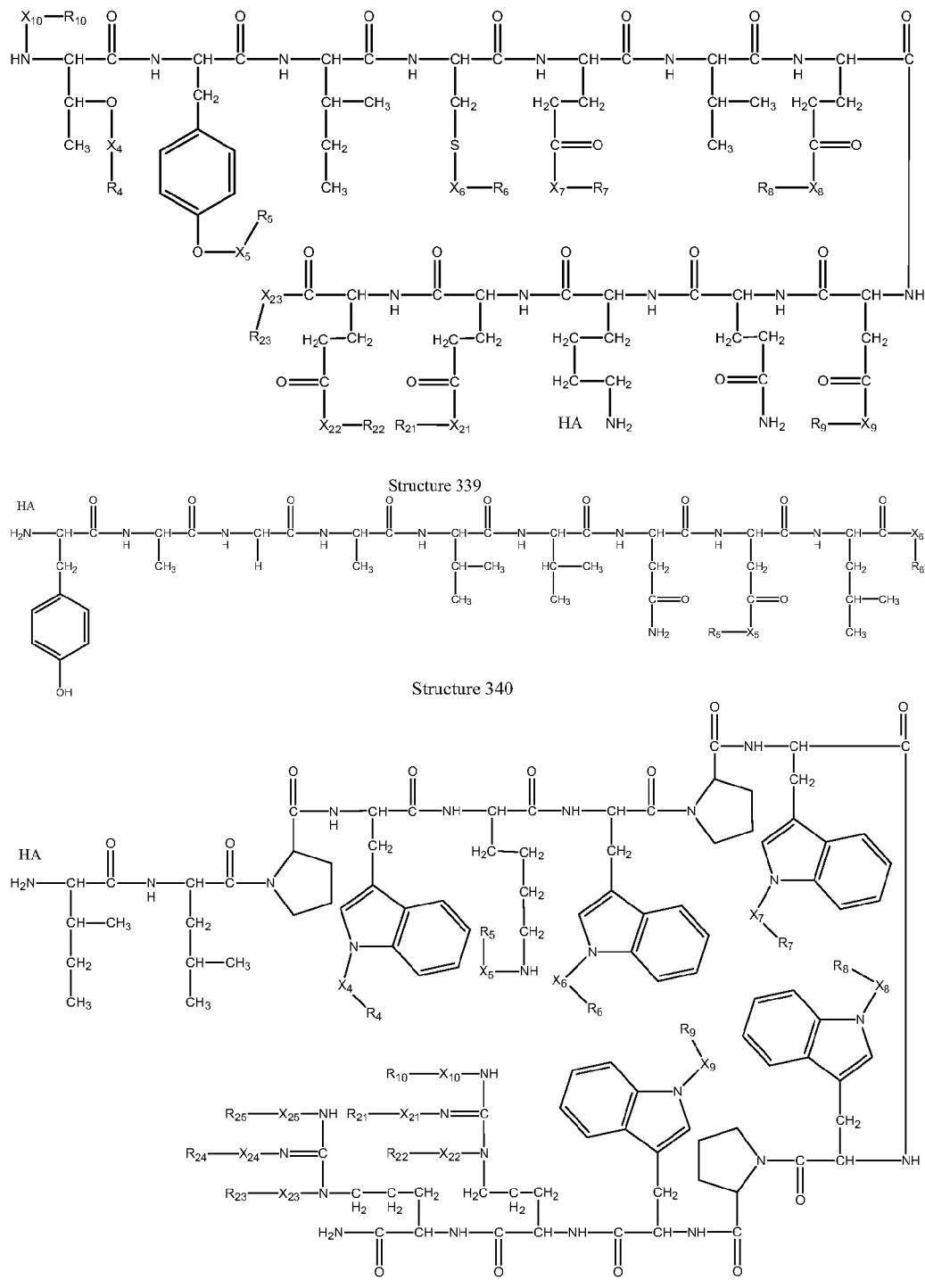
Figure 1:
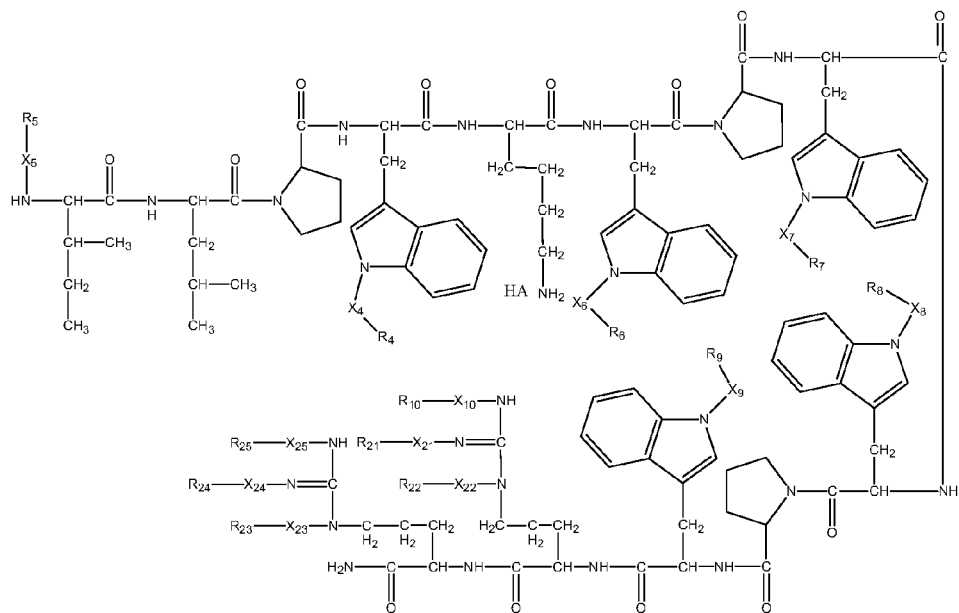
Figure 178:
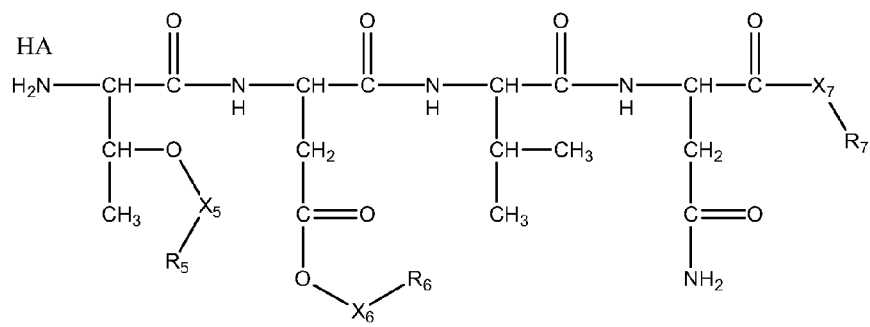
Figures 1, 179:
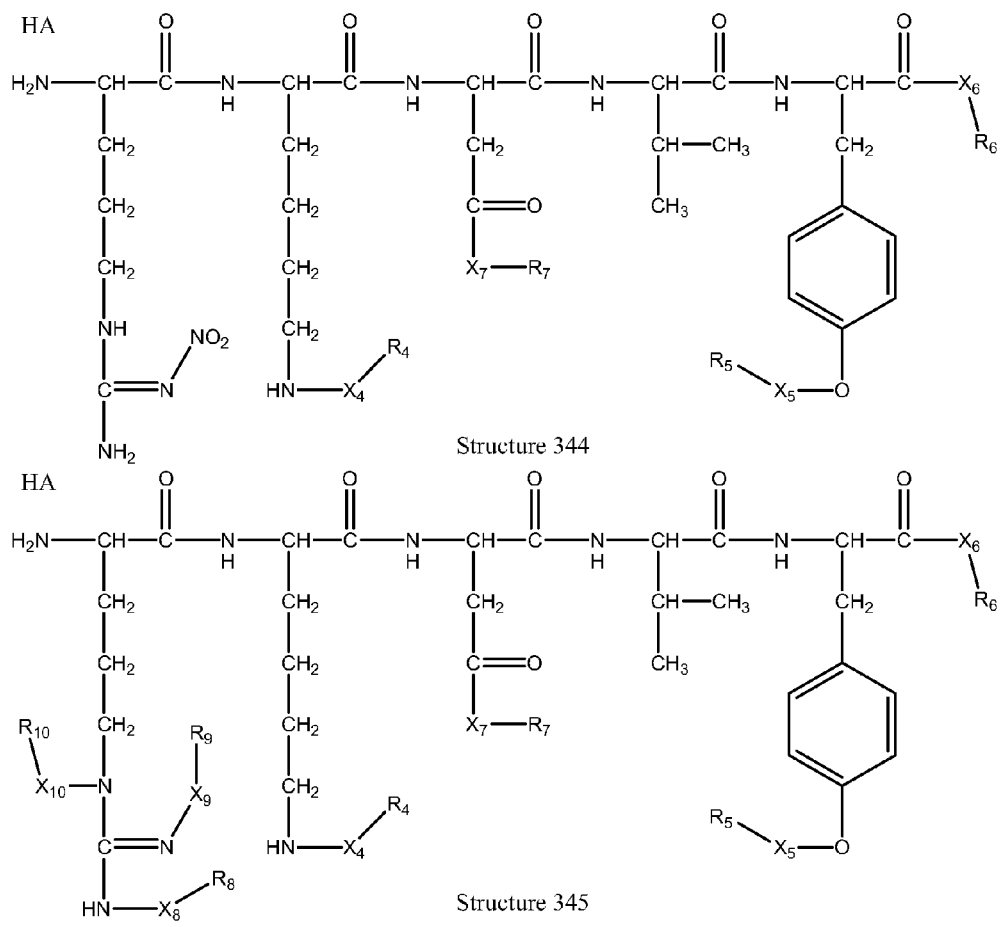
Figure 2:
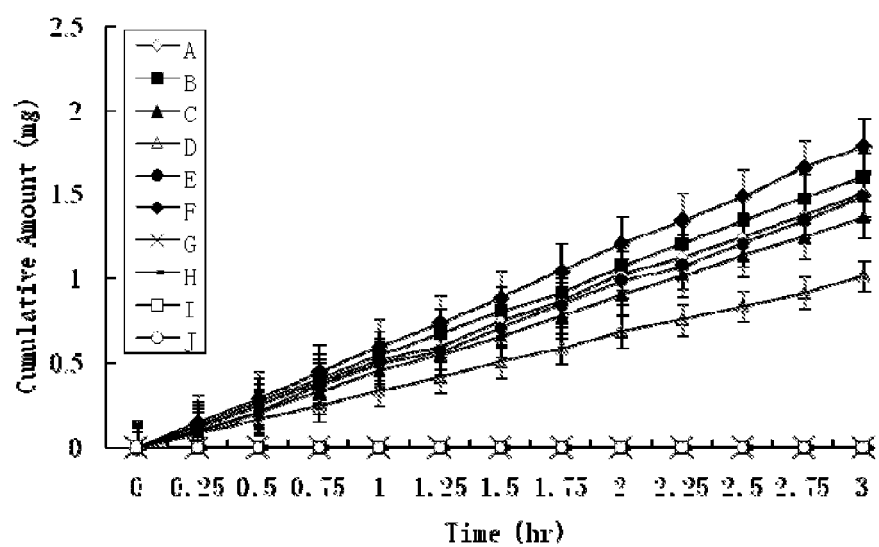

A compound tested (2 mL, 20% in 0.2 M phosphate buffer, pH 7.4) was added to the sample chamber of a Franz cell. The receiving chamber contains 10 ml of pH 7.4 phosphate buffer (0.2 M) which was stirred at 600 rpm. The amount of the tested compound penetrating the skin was determined by high-performance liquid chromatography (HPLC) method. The results were shown in FIG. 2. The apparent flux values of the tested compounds were calculated from the slopes in the FIG. 2 and summarized in Table 1 respectively.

Because the lowest detectable apparent flux values in this method was 1 μg/cm$^2$/h, parent drugs that showed an apparent flux value equal to or less than 1 μg/cm$^2$/h were considered as not detectable for penetrating across the skin tissue. The HPPs/HPCs of these parent drugs (e.g. enterostatins, Val-Pro-Gly-Pro-Arg (VPGPR)(SEQ ID NO: 11), Melanocortin II (cyclo(1,6)-Ac-Nle-Asp-His-Phe-Arg-Trp-Lys-OH)(SEQ ID NO: 173)), opioid peptides (e.g. Met-enkephalin (H-Tyr-Gly-Gly-Phe-Met-OH (SEQ ID NO: 174))were 1 μg /cm$^2$/h, therefore they were not detectable for penetrating across the skin tissue. However, their HPPs/HPCs had detectable apparent flux value. Therefore the peptide HPPs/HPCs showed a higher penetration rate (340-600 times higher) across the skin tissue comparing to their parent compounds.

TABLE 1

In vitro Penetration Rate of HPPs/HPCs and their Parent Compounds (I)

| HPP/HPC | mg/cm$^2$/h | Parent compound | mg/cm$^2$/h |
|---|---|---|---|
| Ac-Tyr(Ac)-Gly-Gly-Phe-Met-OCH$_2$CH$_2$N(CH$_2$CH$_3$)$_2$•HCl (SEQ ID NO: 178) | 0.52 | Ac-Tyr-Gly-Gly-Phe-Met-OH (SEQ ID NO: 184) | 0.001 |
| HCl•(CH$_3$)$_2$NCH$_2$CH$_2$CH$_2$CO-Tyr(Ac)-Gly-Gly-Phe-Met-OCH$_2$CH$_2$CH$_2$CH$_3$ (SEQ ID NO: 179) | 0.55 | Ac-Tyr-Gly-Gly-Phe-Met-OH (SEQ ID NO: 184) | 0.001 |
| cyclo(1,6)-Ac-Nle-Asp-His-Phe-Arg(diAc)-Trp-Lys-OCH$_2$CH$_2$N(CH$_2$CH$_3$)$_2$•HCl (SEQ ID NO: 180) | 0.46 | cyclo(1,6)-Ac-Nle-Asp-His-Phe-Arg-Trp-Lys-OH (SEQ ID NO: 173) | 0.001 |
| cyclo(1,6)-H-Nle-Asp-His-D-Phe(4-I)-Arg(Ac)-Trp-Lys-NH$_2$•HCl (SEQ ID NO: 181) | 0.34 | cyclo(1,6)-Ac-Nle-Asp-His-D-Phe(4-I)-Arg-Trp-Lys-NH$_2$ (SEQ ID NO: 185) | 0.001 |
| cyclo(1,6)-H-Nle-Asp-His-D-Ala(2-naphthyl)-Arg(NO$_2$)-Trp-Lys-NH$_2$•HCl (SEQ ID NO: 182) | 0.50 | | |
| Ac-Val-Pro-Gly-Pro-Arg(diAc)-OCH$_2$CH$_2$N(CH$_2$CH$_3$)$_2$•HCl (SEQ ID NO: 183) | 0.60 | H-Val-Pro-Gly-Pro-Arg-OH (SEQ ID NO: 186) | 0.001 |

Example 3

Conversion of HPPs/HPCs to Their Parent Drugs

Peptide HPPs/HPCs converted to the parent peptides or peptide-related compounds quickly in good yield in human plasma.

A peptide HPP/HPC (20 mg) was incubated with whole blood (1 mL) for 30 min at 37° C. and analyzed by HPLC. The results showed that most of the peptide HPPs/HPCs converted back to the parent peptides or peptide-related compounds (Table 2).

TABLE 2

Hydrolysis product analysis of peptide HPPs/HPCs in plasma

| Hydrolysis products | Amount |
|---|---|
| A) Hydrolysis of Ac-Tyr(Ac)-Gly-Gly-Phe-Met-OCH$_2$CH$_2$N(CH$_2$CH$_3$)$_2$•HCl (SEQ ID NO: 178) | |
| Peptide HPP/HPC | 3% |
| Ac-Tyr-Gly-Gly-Phe-Met-OCH$_2$CH$_2$N(CH$_2$CH$_3$)$_2$•HCl (SEQ ID NO: 192), | 2% |

TABLE 2-continued

Hydrolysis product analysis of peptide HPPs/HPCs in plasma

| Hydrolysis products | Amount |
|---|---|
| Ac-Tyr-Gly-Gly-Phe-Met-OH (SEQ ID NO: 184) | 8% |
| Parent drug | 60% |
| other side products (amino acids, dipeptides, tripeptides, tetrapeptides) | 27% |
| B) Hydrolysis of HCl•(CH$_3$)$_2$NCH$_2$CH$_2$CH$_2$CO-Tyr(Ac)-Gly-Gly-Phe-Met-OCH$_2$CH$_2$CH$_2$CH$_3$ (SEQ ID NO: 179), | |
| Peptide HPP/HPC | 5% |
| (CH$_3$)$_2$NCH$_2$CH$_2$CH$_2$CO-Tyr-Gly-Gly-Phe-Met-OCH$_2$CH$_2$CH$_2$CH$_3$ (SEQ ID NO: 192) | 6% |
| (CH$_3$)$_2$NCH$_2$CH$_2$CH$_2$CO-Tyr-Gly-Gly-Phe-Met-OH (SEQ ID NO: 193) | 10% |
| Parent drug | 55% |
| other side products (amino acids, dipeptides, tripeptides, tetrapeptides) | 24% |
| C) Hydrolysis of cyclo(1,6)-Ac-Nle-Asp-His-Phe-Arg(diAc)-Trp-Lys-OCH$_2$CH$_2$N(CH$_2$CH$_3$)$_2$•HCl (SEQ ID NO: 180) | |
| Peptide HPP/HPC | 4% |
| cyclo(1,6)-Ac-Nle-Asp-His-Phe-Arg(Ac)-Trp-Lys-OCH$_2$CH$_2$N(CH$_2$CH$_3$)$_2$•HCl (SEQ ID NO: 194), | 8% |
| cyclo(1,6)-Nle-Asp-His-Phe-Arg-Trp-Lys-OH (SEQ ID NO: 195) | 10% |
| Parent drug | 45% |
| other side products (amino acids, dipeptides, tripeptides, tetrapeptides) | 33% |

Example 4

Treatment of Obesity using Peptide HPPs/HPCs

Enterostatins [Val-Pro-Asp-Pro-Arg (VP DPR)(SEQ ID NO: 10), Val-Pro-Gly-Pro-Arg (VPGPR)(SEQ ID NO: 11), and Ala-Pro-Gly-Pro-Arg (APGPR)(SEQ ID NO: 12)] are pentapeptides derived from the NH$_2$-terminus of procolipase after tryptic cleavage and belong to the family of gut-brain peptides. They regulate fat intake and may be used for the treatment of obesity (Erlanson-Albertsson C, York D, Obes. Rev. 1997 Jul.; 5(4): 360-72 and Sorhede M, Mei J, Erlanson-Albertsson C., J. Physiol. 87:273-275, 1993). H-Val-Pro-Asp-Pro-Arg OH(SEQ ID NO: 196) produced a dose-dependent reduction in food intake when injected intraperitoneally into Osborne-Mendel rats that had been starved overnight. This inhibition of feeding was observed when the rats were fed a high-fat diet but not in rats fed a high-carbohydrate, low-fat diet (Okada S. et al. Physiol Behav., 1991 Jun.; 49(6): 1185-9).

Anti-Obesity Activity of H-Val-Pro-Gly-Pro-Arg (NO$_2$)—OCH(CH$_3$)$_2$.HCl(SEQ ID NO: 197) in Sprague Dawley Rats and DB/DB Mice.

H-Val-Pro-Gly-Pro-Arg(NO$_2$)—OCH(CH$_3$)$_2$.HCl(SEQ ID NO: 197) (administrated transdermally, as low as 0.3 mg/kg in rat) reduced food intakes and body weights in Sprague Dawley rats (SD rats) and DB/DB mice. Results were shown in Tables 3, 4 and 5.

In a first experiment, 40 female Sprague Dawley rats (15 weeks old, 318-346 g) were divided into 4 groups. In group A, 0.2 ml of water was administered to the back of rat (n=10) twice per day for 30 days. In Groups B, C, and D, 10 mg/kg, 1 mg/kg, or 0.3 mg/kg of H-Val-Pro-Gly-Pro-Arg(NO$_2$)—OCH(CH$_3$)$_2$.HCl(SEQ ID NO: 197) in 0.2 ml of water was administered transdermally to the back of rat (n=10) twice per day for 30 days respectively. The results showed that H-Val- Pro-Gly-Pro-Arg(NO₂)—OCH(CH₃)₂.HCl(SEQ ID NO: 197) reduced body weights of rats effectively (Table 3).

TABLE 3

Anti-obese activity of H-Val-Pro-Gly-Pro-Arg(NO₂)-OCH(CH₃)₂•HCl (SEQ ID NO: 197) in Sprague Dawley rats.

| Group (dosage) | Weight (g) (Day 1) | Food intake (per day & per rat) | Weight (g) (Day 30) |
|---|---|---|---|
| A (0 mg/kg) | 331.5 ± 6.3 | 24.0 ± 2.5 | 361.2 ± 6.1 |
| B (10 mg/kg) | 331.7 ± 6.2 | 19.9 ± 2.9 | 308.4 ± 4.5 |
| C (1 mg/kg) | 333.1 ± 5.1 | 21.1 ± 2.7 | 313.7 ± 5.1 |
| D (0.3 mg/kg) | 335.4 ± 5.2 | 22.1 ± 2.5 | 322.1 ± 4.3 |

In a second experiment, 40 young female Sprague Dawley (SD) rats (180-225 g) were divided into 4 groups. In group A, 0.2 ml of water was administered to the back of rat (n=10) twice per day for 30 days. In Groups B, C, and D, 10 mg/kg, 1 mg/kg, or 0.3 mg/kg of H-Val-Pro-Gly-Pro-Arg(NO₂)—OCH(CH₃)₂.HCl(SEQ ID NO: 197) in 0.2 ml of water were administered transdermally to the backs of rats (n=10) twice per day for 30 days respectively. The results showed that H-Val-Pro-Gly-Pro-Arg(NO₂)—OCH(CH₃)₂.HCl(SEQ ID NO: 197) controlled overweight of young rats effectively (Table 4).

TABLE 4

Anti-obese activity of H-Val-Pro-Gly-Pro-Arg(NO₂)-OCH(CH₃)₂•HCl (SEQ ID NO: 197) in Sprague Dawley rats.

| Group (dosage) | Weight (g) (Day 1) | Food intake (per day & per rat) | Weight (g) (Day 30) |
|---|---|---|---|
| A (0 mg/kg) | 192.1 ± 5.6 | 24.8 ± 2.2 | 354.1 ± 6.2 |
| B (10 mg/kg) | 192.7 ± 6.2 | 19.8 ± 3.3 | 307.4 ± 5.7 |
| C (1 mg/kg) | 191.6 ± 4.7 | 20.1 ± 2.8 | 323.1 ± 4.5 |
| D (0.3 mg/kg) | 195.1 ± 5.5 | 21.8 ± 2.7 | 327.2 ± 3.8 |

In a third experiment, 40 obese female DB/DB mice (SLAC/DB/DB mice, 16 weeks old, 55-60 g) were divided into 4 groups. In group A, 0.1 ml of water was administered to the back of mouse (n=10) twice per day for 30 days. In Groups B, C, and D, 15 mg/kg, 1.5 mg/kg, and 0.5 mg/kg of H-Val-Pro-Gly-Pro-Arg(NO₂)-OCH(CH₃)₂.HCl(SEQ ID NO: 197) in 0.1 ml of water was administered transdermally to the back of mouse (n=10) twice per day for 30 days respectively. The results showed that H-Val-Pro-Gly-Pro-Arg(NO₂)-OCH(CH₃)₂. HCl(SEQ ID NO: 197) reduced body weights and blood glucose levels of obese mice effectively (Table 5).

TABLE 5

Anti-obese activity of H-Val-Pro-Gly-Pro-Arg(NO₂)-OCH(CH₃)₂•HCl (SEQ ID NO: 197) in obese mice (SLAC/DB/DB).

| Group (dosage) | Weight (g) (Day 1) | Blood Glucose Levels (day 1) (mg/dL, no fasting) | Weight (g) (Day 30) | Blood Glucose Levels (day 30) (mg/dL, no fasting) |
|---|---|---|---|---|
| A(0 mg/kg) | 56.7 ± 2.3 | 190.4 ± 27.2 | 66.5 ± 4.2 | 259.4 ± 35.1 |
| B(15 mg/kg) | 57.7 ± 1.6 | 206.4 ± 21.8 | 52.1 ± 2.2 | 137.4 ± 25.2 |
| C(1.5 mg/kg) | 57.2 ± 2.1 | 201.4 ± 23.1 | 52.3 ± 1.9 | 142.4 ± 18.7 |
| B(0.5 mg/kg) | 56.2 ± 2.7 | 199.7 ± 26.8 | 54.2 ± 2.9 | 153.4 ± 26.4 |

Anti-obesity of H-Val-Pro-Gly-Pro-Arg(diAc)-OCH₂CH₂CH₂CH₃.HCl(SEQ ID NO: 198) in Sprague Dawley Rats H-Val-Pro-Gly-Pro-Arg(diAc)-OCH₂CH₂CH₂CH₃.HCl (SEQ ID NO: 198) (administrated transdermally, as low as 0.3 mg/kg in rat) reduced food intakes and body weights in SD rats and DB/DB mice. Results were shown in Tables 6, 7, and 8.

In a first experiment, 40 female Sprague Dawley (SD) rats (15 weeks old, 315-340 g) were divided into 4 groups. In group A, 0.2 ml of water was administered to the back of rat (n=10) twice per day for 30 days. In Groups B, C, and D, 10 mg/kg, 1 mg/kg, or 0.3 mg/kg of H-Val-Pro-Gly-Pro-Arg(diAc)-OCH₂CH₂CH₂CH₃.HCl(SEQ ID NO: 198) in 0.2 ml of water was administered transdermally to the back of rat (n=10) twice per day for 30 days respectively. The results showed that H-Val-Pro-Gly-Pro-Arg(diAc) OCH₂CH₂CH₂CH₃.HCl(SEQ ID NO: 198) reduced body weights of rats effectively (Table 6).

TABLE 6

Anti-obese activity of H-Val-Pro-Gly-Pro-Arg(diAc)-OCH₂CH₂CH₂CH₃•HCl (SEQ ID NO: 198) in Sprague Dawley rats.

| Group (dosage) | Weight (g) (Day 1) | Food intake (per day & per rat) | Weight (g) (Day 30) |
|---|---|---|---|
| A (0 mg/kg) | 327.5 ± 8.7 | 24.1 ± 2.2 | 361.5 ± 5.9 |
| B (10 mg/kg) | 334.1 ± 7.5 | 20.9 ± 2.2 | 329.2 ± 4.8 |
| C (1 mg/kg) | 331.6 ± 6.6 | 21.9 ± 1.9 | 336.7 ± 5.6 |
| D (0.3 mg/kg) | 333.1 ± 6.1 | 23.0 ± 1.7 | 347.1 ± 5.7 |

In a second experiment, 40 young female Sprague Dawley (SD) rats (180-230 g) were divided into 4 groups. In group A, 0.2 ml of water was administered to the back of rat (n=10) twice per day for 30 days. In Groups B, C, and D, 10 mg/kg, 1 mg/kg, or 0.3 mg/kg of H-Val-Pro-Gly-Pro-Arg(diAc)-OCH₂CH₂CH₂CH₃.HCl(SEQ ID NO: 198) in 0.2 ml of water were administered transdermally to the backs of rats (n=10) twice per day for 30 days. The results showed that H-Val-Pro-Gly-Pro-Arg(diAc)-OCH₂CH₂CH₂CH₃.HCl (SEQ ID NO: 198)controlled overweight of young rats effectively (Table 7).

TABLE 7

Anti-obese activity of H H-Val-Pro-Gly-Pro-Arg(diAc)-OCH₂CH₂CH₂CH₃•HCl (SEQ ID NO: 198) in Sprague Dawley rats.

| Group (dosage) | Weight (g) (Day 1) | Food intake (per day & per rat) | Weight (g) (Day 30) |
|---|---|---|---|
| A (0 mg/kg) | 188.5 ± 5.8 | 24.5 ± 2.9 | 358.9 ± 8.1 |
| B (10 mg/kg) | 191.7 ± 4.6 | 20.8 ± 2.8 | 317.4 ± 6.4 |
| C (1 mg/kg) | 190.6 ± 5.7 | 22.1 ± 2.8 | 334.1 ± 4.9 |
| D (0.3 mg/kg) | 191.1 ± 4.8 | 23.7 ± 2.9 | 346.2 ± 4.8 |

In a third experiment, 40 obese female DB/DB mice (SLAC/DB/DB) mice (16 weeks old, 55-60 g) were divided into 4 groups. In group A, 0.1 ml of water was administered to the back of mouse (n=10) twice per day for 30 days. In Groups B, C, and D, 15 mg/kg, 1.5 mg/kg, and 0.5 mg/kg of H-Val-Pro-Gly-Pro-Arg(diAc)-OCH₂CH₂CH₂CH₃.HCl(SEQ ID NO: 198) in 0.1 ml of water was administered transdermally to the back of mouse (n=10) twice per day for 30 days respectively. The results showed that H-Val-Pro-Gly-Pro-Arg (diAc)-OCH₂CH₂CH₂CH₃.HCl (SEQ ID NO: 198) reduced body weights and blood glucose levels of obese mice effectively (Table 8).

TABLE 8

Anti-obese activity of H-Val-Pro-Gly-Pro-Arg(diAc)-
OCH$_2$CH$_2$CH$_2$CH$_3$•HCl (SEQ ID NO: 198) in obese mice (SLAC/DB/DB).

| Group (dosage) | Weight (g) (Day 1) | Blood Glucose Levels (day 1) (mg/dL, no fasting) | Weight (g) (Day 30) | Blood Glucose Levels (day 30) (mg/dL, no fasting) |
|---|---|---|---|---|
| A(0 mg/kg) | 57.3 ± 2.7 | 197.3 ± 30.8 | 69.3 ± 4.7 | 256.7 ± 45.9 |
| B(15 mg/kg) | 56.7 ± 2.7 | 201.5 ± 24.6 | 54.7 ± 3.8 | 152.4 ± 17.9 |
| C(1.5 mg/kg) | 57.6 ± 3.8 | 195.4 ± 36.7 | 58.3 ± 2.9 | 166.4 ± 20.8 |
| B(0.5 mg/kg) | 57.9 ± 2.7 | 196.9 ± 29.8 | 59.3 ± 3.2 | 179.4 ± 21.1 |

Anti-Obesity of H-Ala-Pro-Gly-Pro-Arg(NO$_2$)—OCH$_2$CH$_2$CH$_2$CH$_2$.HCl (SEQ ID NO: 199) in Sprague Dawley Rats.

H-Ala-Pro-Gly-Pro-Arg(NO$_2$)—OCH$_2$CH$_2$CH$_2$CH$_3$.HCl (SEQ ID NO: 199) (administrated transdermally, as low as 0.3 mg/kg in rat) reduced food intakes and body weights in SD rats and DB/DB mice. Results are shown in Tables 9, 10, and 11.

In a first experiment, 40 female Sprague Dawley (SD) rats (15 weeks old, 320-345 g) were divided into 4 groups. In group A, 0.2 ml of water was administered to the back of rat (n=10) twice per day for 30 days. In Groups B, C, and D, 10 mg/kg, 1 mg/kg, or 0.3 mg/kg of H-Ala-Pro-Gly-Pro-Arg(NO$_2$)—OCH$_2$CH$_2$CH$_2$CH$_3$.HCl(SEQ ID NO: 199) in 0.2 ml of water was administered transdermally to the back of rat (n=10) twice per day for 30 days respectively. The results showed that H-Ala-Pro-Gly-Pro-Arg(NO$_2$)—OCH$_2$CH$_2$CH$_2$CH$_3$.HCl(SEQ ID NO: 199) reduced body weights of rats effectively (Table 9).

TABLE 9

Anti-obese activity of H-Ala-Pro-Gly-Pro-Arg(NO$_2$)-
OCH$_2$CH$_2$CH$_2$CH$_3$•HCl (SEQ ID NO: 199) in Sprague Dawley rats.

| Group (dosage) | Weight (g) (Day 1) | Food intake (per day & per rat) | Weight (g) (Day 30) |
|---|---|---|---|
| A (0 mg/kg) | 331.0 ± 8.5 | 24.3 ± 2.7 | 361.4 ± 5.2 |
| B (10 mg/kg) | 332.2 ± 7.4 | 20.8 ± 2.4 | 315.4 ± 3.8 |
| C (1 mg/kg) | 333.6 ± 7.8 | 21.8 ± 2.3 | 323.7 ± 4.4 |
| D (0.3 mg/kg) | 335.1 ± 6.2 | 22.7 ± 1.8 | 335.1 ± 4.8 |

In a second experiment, 40 young female Sprague Dawley (SD) rats (182-223 g) were divided into 4 groups. In group A, 0.2 ml of water was administered to the back of rat (n=10) twice per day for 30 days. In Groups B, C, and D, 10 mg/kg, 1 mg/kg, or 0.3 mg/kg of H-Ala-Pro-Gly-Pro-Arg(NO$_2$)—OCH$_2$CH$_2$CH$_2$CH$_3$.HCl(SEQ ID NO: 199) in 0.2 ml of water was administered transdermally to the backs of rats (n=10) twice per day for 30 days respectively. The results showed that H-Ala-Pro-Gly-Pro-Arg(NO$_2$)—OCH$_2$CH$_2$CH$_2$CH$_3$.HCl(SEQ IC NO: 199) controlled overweight of rats effectively (Table 10).

TABLE 10

Anti-obese activity of H-Ala-Pro-Gly-Pro-Arg(NO$_2$)-
OCH$_2$CH$_2$CH$_2$CH$_3$•HCl (SEQ ID NO: 199) in Sprague Dawley rats.

| Group (dosage) | Weight (g) (Day 1) | Food intake (per day & per rat) | Weight (g) (Day 30) |
|---|---|---|---|
| A (0 mg/kg) | 191.5 ± 5.1 | 24.9 ± 2.6 | 355.5 ± 8.2 |
| B (10 mg/kg) | 193.7 ± 4.2 | 19.5 ± 2.3 | 305.4 ± 4.7 |
| C (1 mg/kg) | 192.6 ± 4.1 | 20.3 ± 2.7 | 321.7 ± 4.0 |
| D (0.3 mg/kg) | 194.1 ± 4.5 | 21.3 ± 2.2 | 326.2 ± 4.8 |

In a third experiment, 40 obese female DB/DB mice (SLAC/DB/DB) mice (16 weeks old, 53-61 g) were divided into 4 groups. In group A, 0.1 ml of water was administered to the back of mouse (n=10) twice per day for 30 days. In Groups B, C, and D, 15 mg/kg, 1.5 mg/kg, and 0.5 mg/kg of H-Ala-Pro-Gly-Pro-Arg(NO$_2$)—OCH$_2$CH$_2$CH$_2$CH$_3$.HCl(SEQ ID NO: 199) in 0.1 ml of water was administered transdermally to the back of mouse (n=10) twice per day for 30 days respectively. The results showed that H-Ala-Pro-Gly-Pro-Arg(NO$_2$)—OCH$_2$CH$_2$CH$_2$CH$_3$.HCl (SEQ ID NO: 199) reduced body weights and blood glucose levels of obese mice effectively (Table 11).

TABLE 11

Anti-obese activity of H-Ala-Pro-Gly-Pro-Arg(NO$_2$)-
OCH$_2$CH$_2$CH$_2$CH$_3$•HCl (SEQ ID NO: 199) in obese mice (SLAC/DB/DB).

| Group (dosage) | Weight (g) (Day 1) | Blood Glucose Levels (day 1) (mg/dL, no fasting) | Weight (g) (Day 30) | Blood Glucose Levels (day 30) (mg/dL, no fasting) |
|---|---|---|---|---|
| A(0 mg/kg) | 56.5 ± 2.7 | 199.4 ± 30.7 | 67.8 ± 4.5 | 257.4 ± 38.2 |
| B(15 mg/kg) | 57.2 ± 2.2 | 202.4 ± 21.4 | 51.9 ± 2.7 | 139.5 ± 15.9 |
| C(1.5 mg/kg) | 57.1 ± 2.8 | 199.4 ± 23.7 | 53.3 ± 3.2 | 148.4 ± 16.4 |
| B(0.5 mg/kg) | 58.4 ± 2.9 | 197.6 ± 28.2 | 54.7 ± 2.7 | 159.4 ± 24.4 |

Anti-obesit of H-Val-Pro-Asp(OEt)-Pro-Arg(NO$_2$—)OCH$_2$CH$_2$CH$_2$CH$_3$.HCl(SEQ ID NO: 200) in Sprague Dawley Rats.

H-Val-Pro-Asp(OEt)-Pro-Arg(NO$_2$)—OCH$_2$CH$_2$CH$_2$CH$_3$.HCl(SEQ ID NO: 200) (administrated transdermally, as low as 0.3 mg/kg in rat) reduced food intake and body weights in SD rats and DB/DB mice. Results were shown in Tables 12, 13, and 14.

In a first experiment, 40 female Sprague Dawley (SD) rats (15 weeks old, 320-350 g) were divided into 4 groups. In group A, 0.2 ml of water was administered to the back of rat (n=10) twice per day for 30 days. In Groups B, C, and D, 10 mg/kg, 1 mg/kg, or 0.3 mg/kg of H-Val-Pro-Asp(OEt)-Pro-Arg(NO$_2$)—OCH$_2$CH$_2$CH$_2$CH$_3$.HCl(SEQ ID NO: 200) in 0.2 ml of water was administered transdermally to the back of rat (n=10) twice per day for 30 days respectively. The results showed that H-Val-Pro-Asp(OEt)-Pro-Arg(NO$_2$)—OCH$_2$CH$_2$CH$_2$CH$_3$.HCl(SEQ ID NO: 200) reduced body weights of rats effectively (Table 12).

TABLE 12

Anti-obese activity of H-Val-Pro-Asp(OEt)-Pro-Arg(NO$_2$)-
OCH$_2$CH$_2$CH$_2$CH$_3$•HCl (SEQ ID NO: 200) in Sprague Dawley rats.

| Group (dosage) | Weight (g) (Day 1) | Food intake (per day & per rat) | Weight (g) (Day 30) |
|---|---|---|---|
| A (0 mg/kg) | 330.7 ± 7.4 | 24.3 ± 2.3 | 363.5 ± 5.9 |
| B (10 mg/kg) | 330.5 ± 8.2 | 20.1 ± 3.2 | 318.1 ± 3.9 |

TABLE 12-continued

Anti-obese activity of H-Val-Pro-Asp(OEt)-Pro-Arg(NO$_2$)-OCH$_2$CH$_2$CH$_2$CH$_3$•HCl (SEQ ID NO: 200) in Sprague Dawley rats.

| Group (dosage) | Weight (g) (Day 1) | Food intake (per day & per rat) | Weight (g) (Day 30) |
|---|---|---|---|
| C (1 mg/kg) | 329.8 ± 7.8 | 21.9 ± 2.7 | 326.8 ± 2.8 |
| D (0.3 mg/kg) | 333.5 ± 7.1 | 22.7 ± 2.5 | 333.1 ± 3.9 |

In a second experiment, 40 young female Sprague Dawley (SD) rats (185-220 g) were divided into 4 groups. In group A, 0.2 ml of water was administered to the back of rat (n=10) twice per day for 30 days. In Groups B, C, and D, 10 mg/kg, 1 mg/kg, or 0.3 mg/kg of H-Val-Pro-Asp(OEt)-Pro-Arg (NO$_2$)-OCH$_2$CH$_2$CH$_2$CH$_3$.HCl(SEQ ID NO: 200) in 0.2 ml of water were administered transdermally to the backs of rats (n=10) twice per day for 30 days. The results showed that H-Val-Pro-Asp(OEt)-Pro-Arg(NO$_2$)-OCH$_2$CH$_2$CH$_2$CH$_3$.HCl(SEQ ID NO: 200) controlled overweight of rats effectively (Table 13).

TABLE 13

Anti-obese activity of H-Val-Pro-Asp(OEt)-Pro-Arg(NO$_2$)-OCH$_2$CH$_2$CH$_2$CH$_3$•HCl (SEQ ID NO: 200) in Spraque Dawley rats.

| Group (dosage) | Weight (g) (Day 1) | Food intake (per day & per rat) | Weight (g) (Day 30) |
|---|---|---|---|
| A (0 mg/kg) | 192.3 ± 5.8 | 24.1 ± 2.8 | 357.1 ± 6.2 |
| B (10 mg/kg) | 191.2 ± 5.2 | 20.4 ± 2.7 | 315.4 ± 6.7 |
| C (1 mg/kg) | 193.2 ± 4.7 | 21.3 ± 2.1 | 325.4 ± 4.9 |
| D (0.3 mg/kg) | 192.1 ± 4.6 | 22.7 ± 2.9 | 336.6 ± 5.8 |

In a third experiment, 40 obese female DB/DB mice (SLAC/DB/DB) mice (16 weeks old, 53-61 g) were divided into 4 groups. In group A, 0.1 ml of water was administered to the back of mouse (n=10) twice per day for 30 days. In Groups B, C, and D, 15 mg/kg, 1.5 mg/kg, and 0.5 mg/kg of H-Val-Pro-Asp(OEt)-Pro-Arg(NO$_2$)-OCH$_2$CH$_2$CH$_2$CH$_3$.HCl (SEQ ID NO: 200) in 0.1 ml of water was administered transdermally to the back of mouse (n=10) twice per day for 30 days respectively. The results showed that H-Val-Pro-Asp (OEt)-Pro-Arg(NO$_2$)-OCH$_2$CH$_2$CH$_2$CH$_3$.HCl(SEQ ID NO: 200) reduced body weights and blood glucose levels of obese mice effectively (Table 14).

TABLE 14

Anti-obese activity of H-Val-Pro-Asp(OEt)-Pro-Arg(NO$_2$)-OCH$_2$CH$_2$CH$_2$CH$_3$•HCl (SEQ ID NO: 200) in obese mice (SLAC/DB/DB).

| Group (dosage) | Weight (g) (Day 1) | Blood Glucose Levels (day 1) (mg/dL, no fasting) | Weight (g) (Day 30) | Blood Glucose Levels (day 30) (mg/dL, no fasting) |
|---|---|---|---|---|
| A(0 mg/kg) | 58.1 ± 2.9 | 199.4 ± 35.2 | 67.9 ± 5.1 | 259.4 ± 28.1 |
| B(15 mg/kg) | 57.9 ± 3.8 | 203.4 ± 27.4 | 52.4 ± 3.4 | 145.4 ± 25.7 |
| C(1.5 mg/kg) | 58.8 ± 3.1 | 203.4 ± 25.8 | 54.3 ± 2.9 | 152.4 ± 26.8 |
| B(0.5 mg/kg) | 58.7 ± 3.3 | 199.6 ± 31.5 | 56.7 ± 2.8 | 171.8 ± 28.4 |

Example 5

Treatment of Erectile Dysfunction (ED) and Female Sex Dysfunction with Peptide HPPs/HPCs Melanocortin II is a cyclic lactam peptides Cyclo(1,6)-Ac-Nle-Asp-His-Phe-Arg-Trp-Lys-OH (SEQ ID NO: 173). It is the Palatin's (AMEX:PTN) novel drug candidate for the treatment of male and female sexual dysfunction. First in a new class of therapies called melanocortin agonists, melanocortin II has shown promise in effectively treating erectile dysfunction (ED) and female sex dysfunction without the cardiovascular effects found in ED drugs currently available. Melanocortin II works through a mechanism involving the central nervous system rather than directly on the vascular system. As a result, it may offer significant safety and efficacy benefits over currently available products.

A HPP/HPC of Melanocortin II diffused through human skin in very high rate (~0.3-0.5 mg/h/cm$^2$), and provided almost side-effects-free methods of treating erectile dysfunction or enhancing female sexual arousal.

2 mg/kg cyclo(1,6)-Ac-Nle-Asp-His-Phe-Arg(diAc)-Trp-Lys-OCH$_2$CH$_2$N(CH$_2$CH$_3$)$_2$.HCl (SEQ ID NO: 180) (peptide A) in 0.2 ml of pH 7.0 phosphate buffer (0.1 M) was applied to the back of male rats (Group A-1, 30 rats) once per day for 5 days. The same dosage of cyclo(1,6)-Ac-Nle-Asp-His-Phe-Arg(NO$_2$)-Trp-Lys-OCH$_2$CH$_2$N(CH$_2$CH$_3$)$_2$.HCl (SEQ ID NO: 201) (peptide B) was applied to the back of another group of male rats (Group B-1, 30 rats). Rats of a control group were not treated with any drug. The results showed a 5 fold increase in solicitation and a 3 fold increase in copulation for Group A-1 comparing to the negative control group. 6 fold increase in solicitation and 3 fold increase in copulation for Group B-1 in rats were observed comparing to the control group (Table 15).

2 mg/kg peptide A and peptide B in 0.2 ml of pH 7.0 phosphate buffer (0.1M) were applied to the back of both male rats (30 rats) and female rats (30 rates) once per day for 5 days. Rats of a control group were not treated with any drug. The results showed a 6 fold increase in solicitation and 5 fold increase in copulation for both Group A-2 and Group B-2 comparing to the control group (Table 15).

TABLE 15

Increased solicitation and copulation for rats treated with HPPs/HPCs of Melanocortin II

| | Control | Peptide A | Peptide A | Peptide B | Peptide B |
|---|---|---|---|---|---|
| Male rats | | X | X | X | X |
| Female rats | | | X | | X |
| Increased Solicitation | 1 | 5 | 6 | 6 | 6 |
| Increased Copulation | 1 | 3 | 5 | 3 | 5 |

X: treated with HPP/HPC (2 mg/kg in 0.2 ml of pH 7.0 phosphate buffer (0.1M)) on the back once per day for 5 days.

Example 6

Writhing Inhibition by HPPs/HPCs of Enkephalin and Related Compounds

Opioid peptides (e.g. Met-enkephalin (H-Tyr-Gly-Gly-Phe-Met-OH (SEQ ID NO: 174)) Leu-enkephalin (H-Tyr-Gly-Gly-Phe-Leu-OH (SEQ ID NO: 175)) H-Tyr-D-Ala-Gly-N-Me-Phe-Met(O)-OL (SEQ ID NO: 176), and H-Tyr-D-Ala-Gly-Phe-Leu-OH (SEQ ID NO: 177)) exert morphine-like analgesic action. The number of writhings that occurred when mice were administered an acetic acid solution intraperitoneally were counted, and the rate of inhibition based on the control group was calculated. HCl.H-Tyr(Ac)-D-Ala-Gly-Phe-Leu-OCH$_2$(CH$_2$)$_4$—CH$_3$ (SEQ ID NO: 202) (10 mg/kg, B), Ac-Tyr(Ac)-D-Ala-Gly-Phe-Leu-OCH$_2$CH$_2$N(CH$_2$CH$_3$).HCl (SEQ ID NO: 203) (10 mg/kg, C), and HCl.H-Tyr(Ac)-D-Ala-Gly-Phe-Met(O)—OL (SEQ ID NO: 204)(10 mg/kg, D) were administered transdermally to the neck of mice. 30 minutes later, acetic acid solution was administered. The group A was the control group. The results were shown in Table 16.

TABLE 16

The rate of writhing inhibition by the HPPs/HPCs of enkephalin and related compounds.

| Group | Dose (mg/kg) | No. of Writhings | % |
|---|---|---|---|
| A | 0 | 35.0 | — |
| B | 10 | 8.6 | 75 |
| C | 10 | 5.2 | 85 |
| D | 10 | 3.2 | 91 |

Opioid peptides are natural peptides that are produced by animals and are not stable in biological systems. They are not addictive and they are not only for treatment of any pain from a toothache, headache, arthritis, any other inflammatory, fever, cancer, dysmenorrhea, and acute migraine headache, but also for the treatment of drug abuse.

The Corresponding Parent Peptides of HPPs/HPCs Appeared in Examples are Listed Below in Table D.

TABLE D

Parent peptide of HPPs/HPCs appeared in examples

| HPP/HPC | Parent drug | SEQ ID NO. | Peptide group | Function |
|---|---|---|---|---|
| Ac-Val-Pro-Asp(OEt)-Pro-Arg(diAc)-OCH$_2$CH$_2$N(CH$_2$CH$_3$)$_2$•HCl (SEQ ID NO: 189) | Val-Pro-Asp-Pro-Arg | 10 | Enterostatins | Anti-obese |
| Ac-Tyr(Ac)-Gly-Gly-Phe-Met-OCH$_2$CH$_2$N(CH$_2$CH$_3$)$_2$•HCl (SEQ ID NO: 178). | Tyr-Gly-Gly-Phe-Met. | 1 | Opioid peptide Met-enkephalin | Analgesic activity |
| Ac-Val-Pro-Gly-Pro-Arg(diAc)-OCH$_2$CH$_2$N(CH$_2$CH$_3$)$_2$•HCl (SEQ ID NO: 183) | Val-Pro-Gly-Pro-Arg | 11 | Enterostatins | Anti-obese |
| Cyclo(1,6)-Ac-Nle-Asp-His-Phe-Arg(diAc)-Trp-Lys-OCH$_2$CH$_2$N(CH$_2$CH$_3$)$_2$•HCl (SEQ ID NO: 180). | Nle-cyclo[Asp-His-D-Phe-Arg-Trp-Lys] | 9 | Melanocortin II | melanocortin agonists male and female sexual dysfunction |

---

What is claimed is:

1. A compound comprising a structure selected from the group consisting of

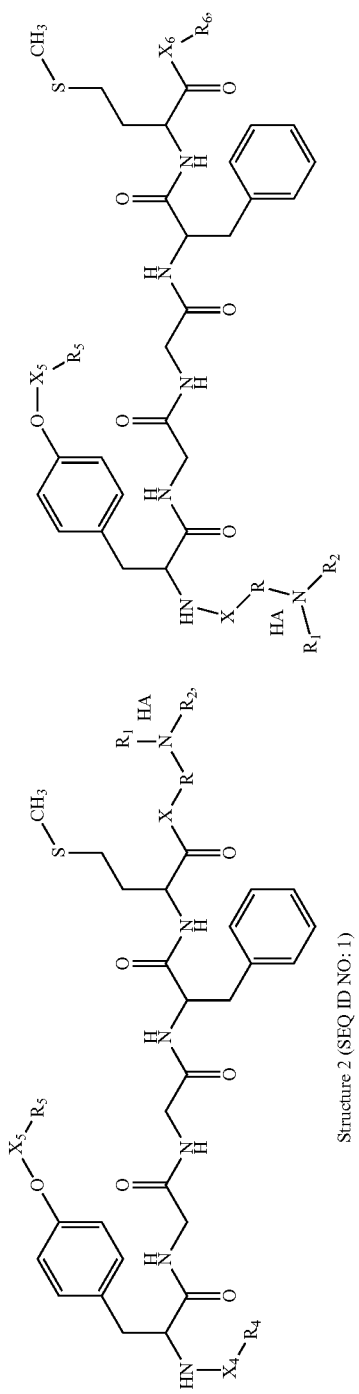
Structure 2 (SEQ ID NO: 1)
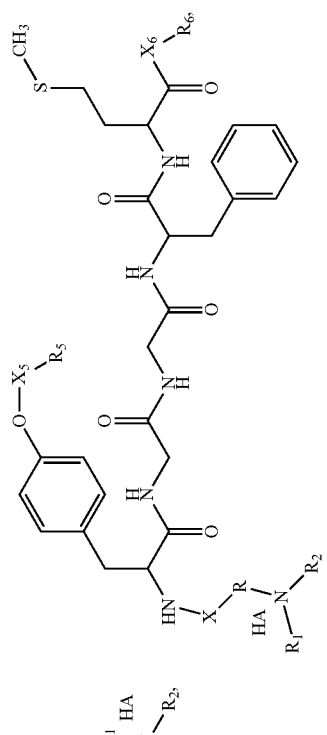
Structure 3 (SEQ ID NO: 1)
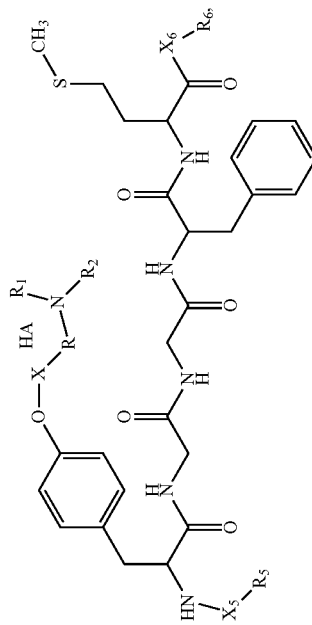
Structure 4 (SEQ ID NO: 1)
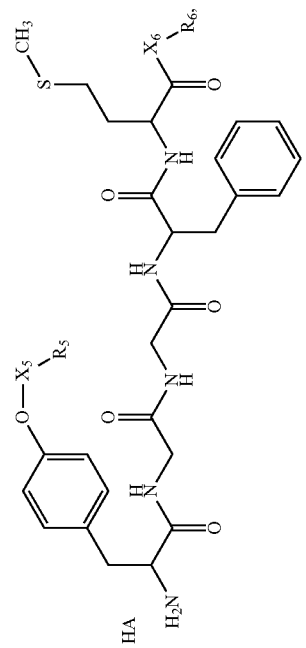
Structure 5 (SEQ ID NO: 1)
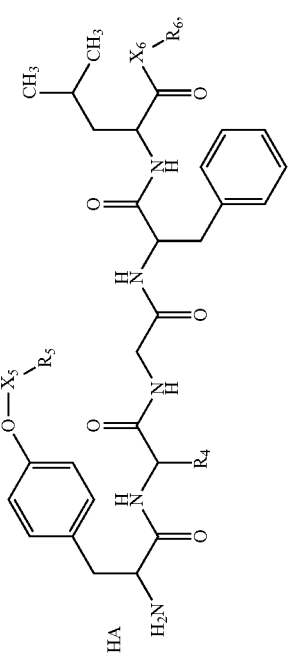
Structure 6 (SEQ ID NO: 2)
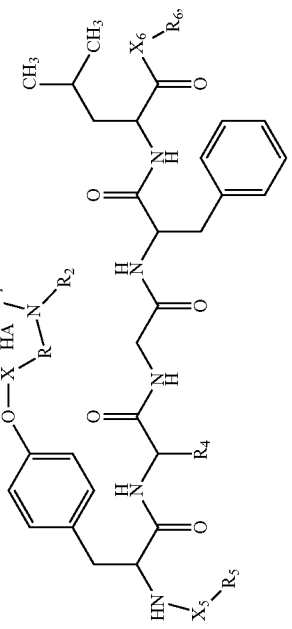
Structure 7 (SEQ ID NO: 2)

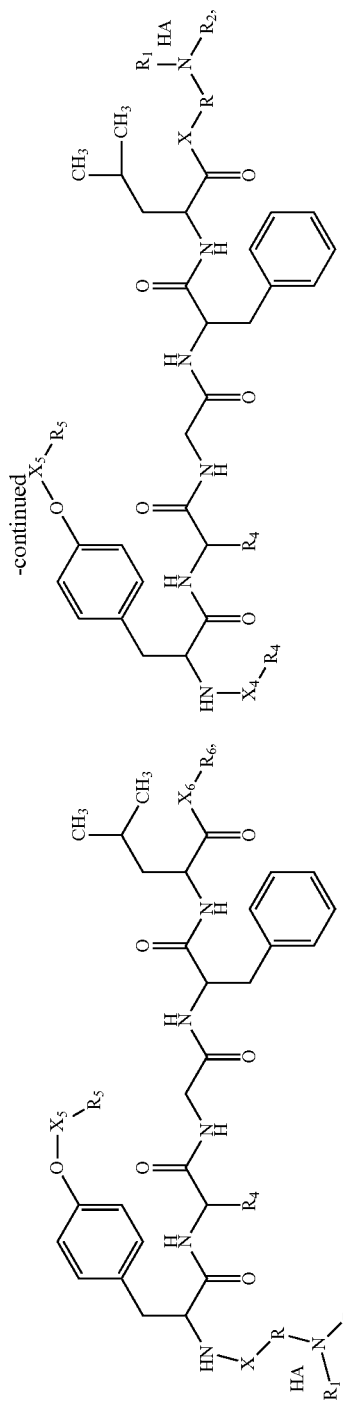
Structure 8 (SEQ ID NO: 2)
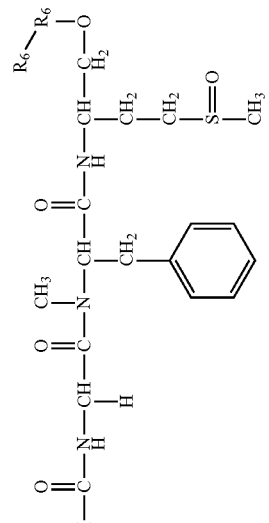
Structure 9 (SEQ ID NO: 2)
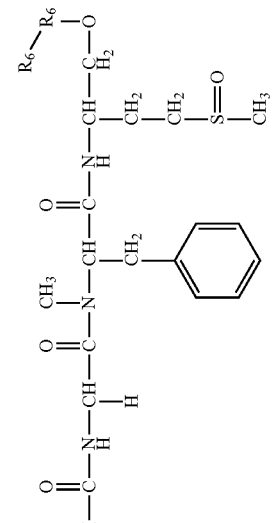
Structure 10 (SEQ ID NO: 3)
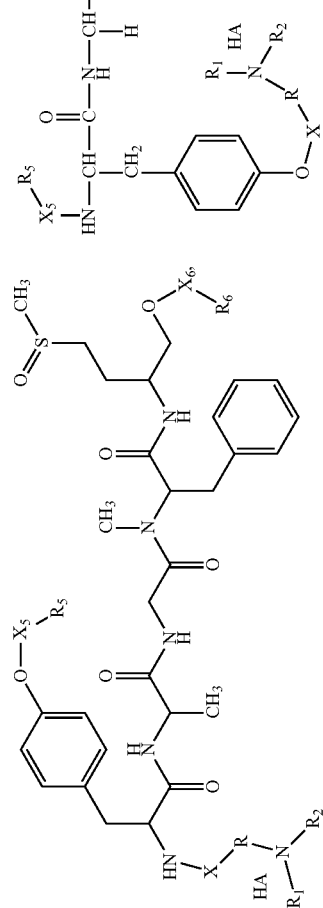
Structure 11 (SEQ ID NO: 4)
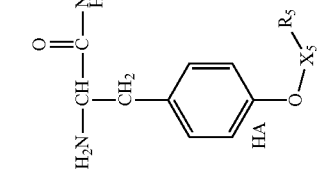
Structure 12 (SEQ ID NO: 3)
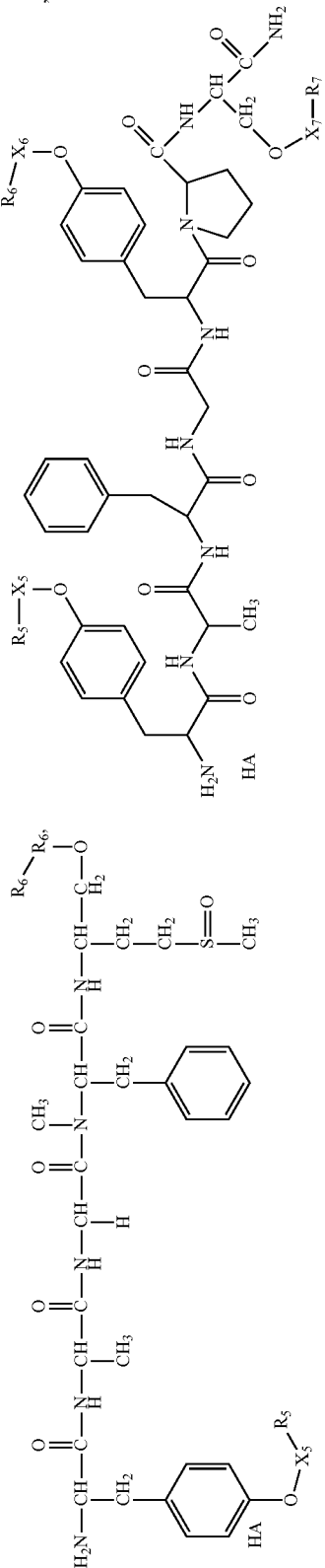
Structure 13 (SEQ ID NO: 5)

-continued
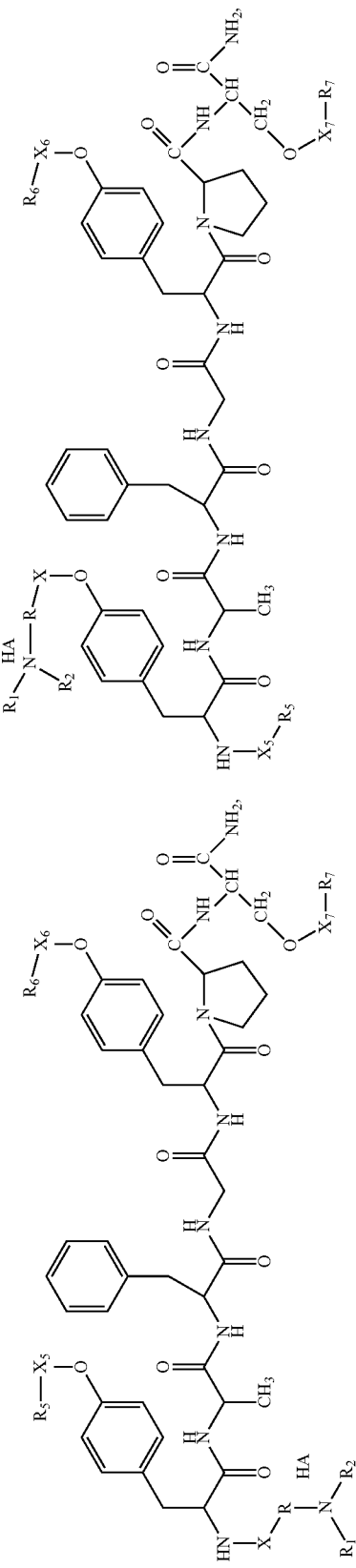
Structure 14
Structure 14 (SEQ ID NO: 5)
Structure 15 (SEQ ID NO: 5)
Structure 16 (SEQ ID NO: 5)
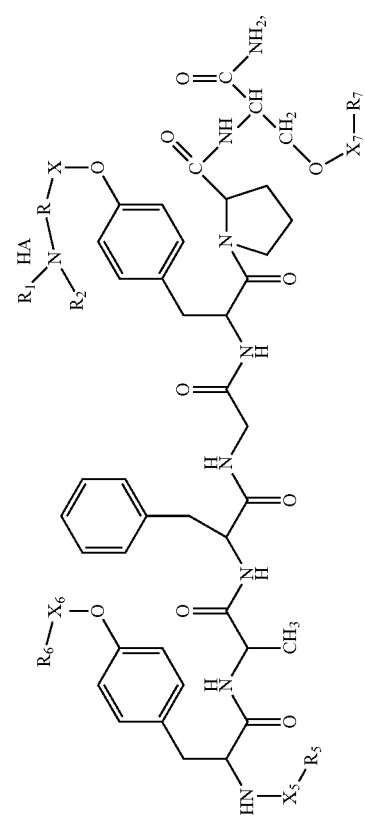
Structure 17 (SEQ ID NO: 6)

-continued
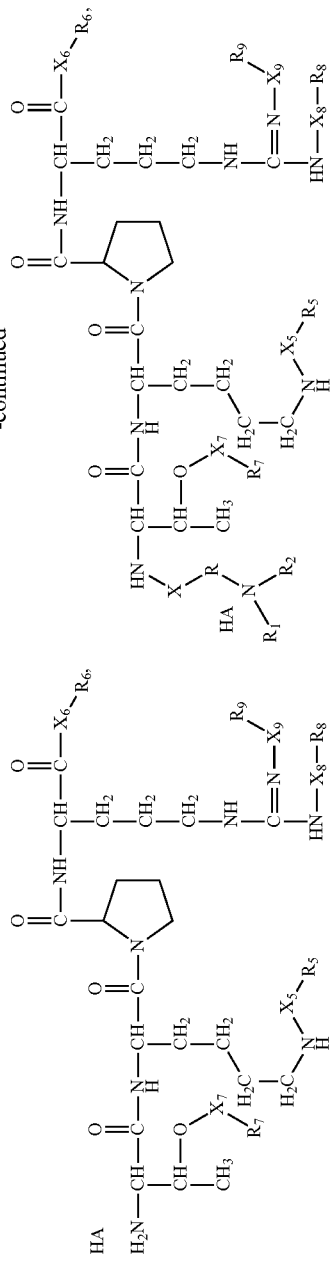
Structure 18 (SEQ ID NO: 6)
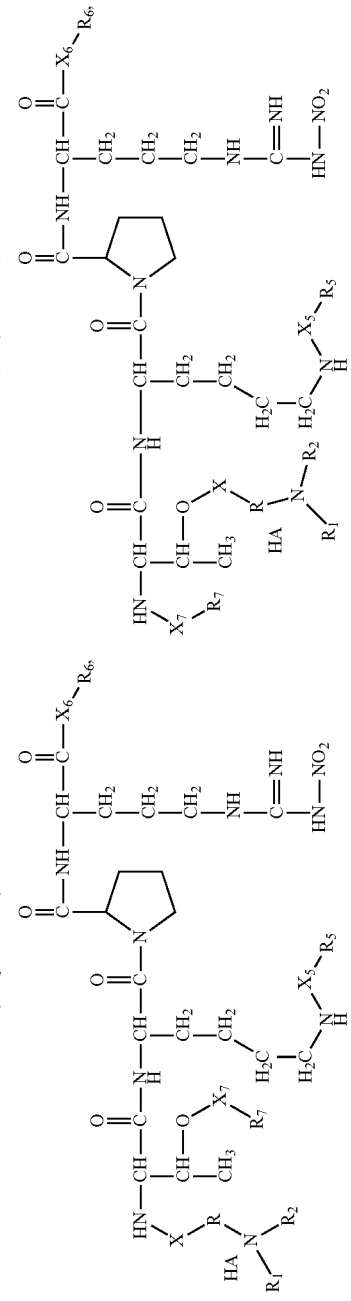
Structure 19 (SEQ ID NO: 6)
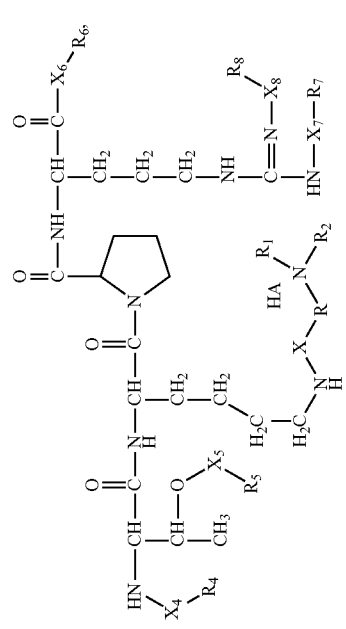
Structure 20 (SEQ ID NO: 6)
Structure 21 (SEQ ID NO: 6)
Structure 22 (SEQ ID NO: 6)
Structure 23 (SEQ ID NO: 6)

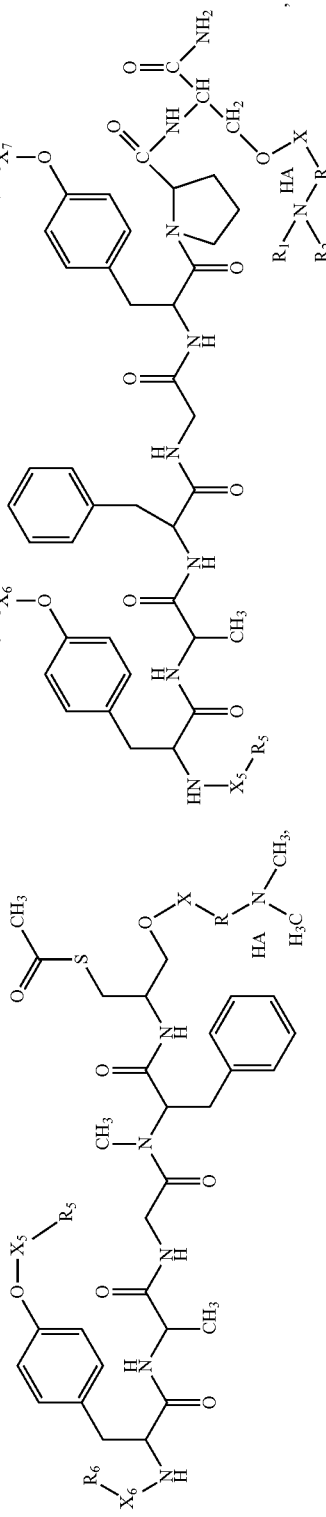
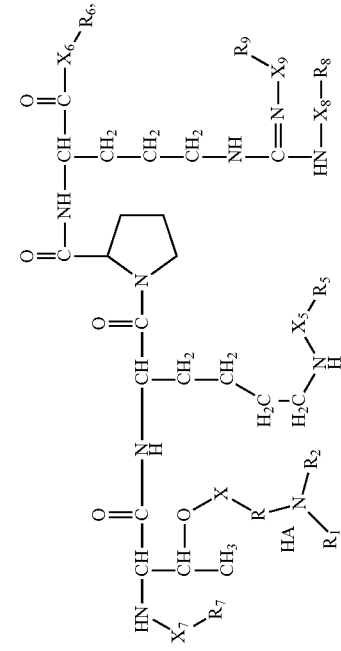
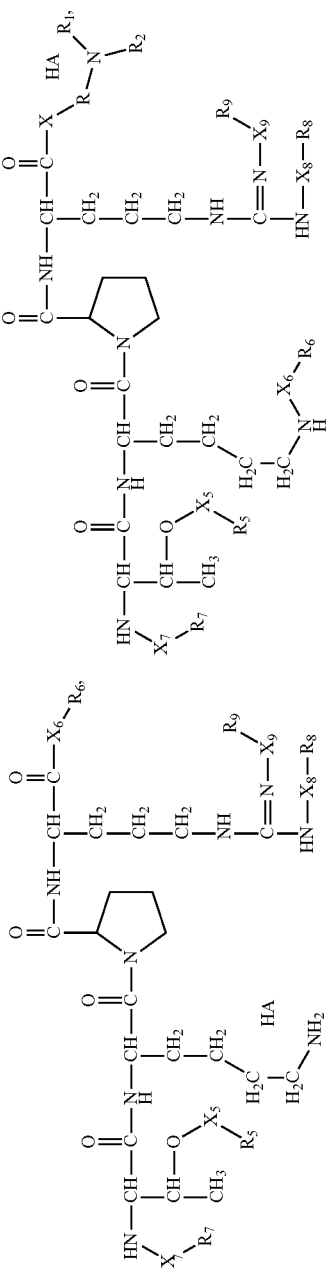
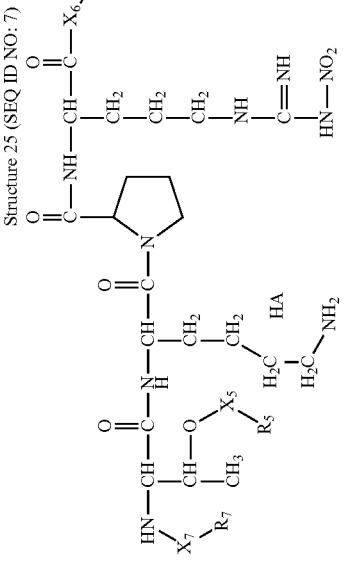
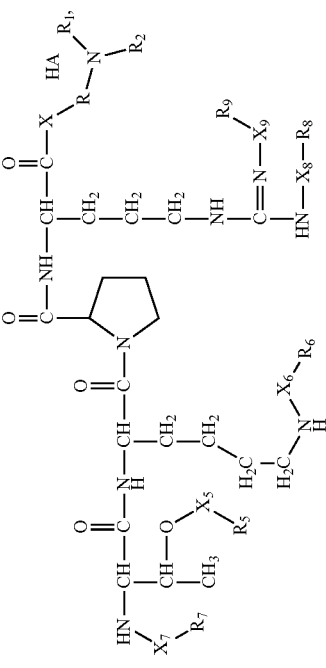

-continued
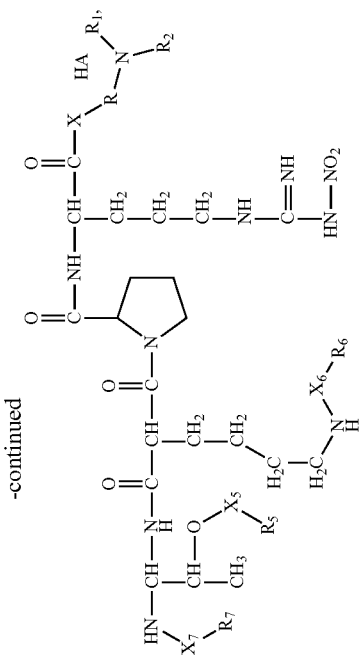
Structure 30 (SEQ ID NO: 6)
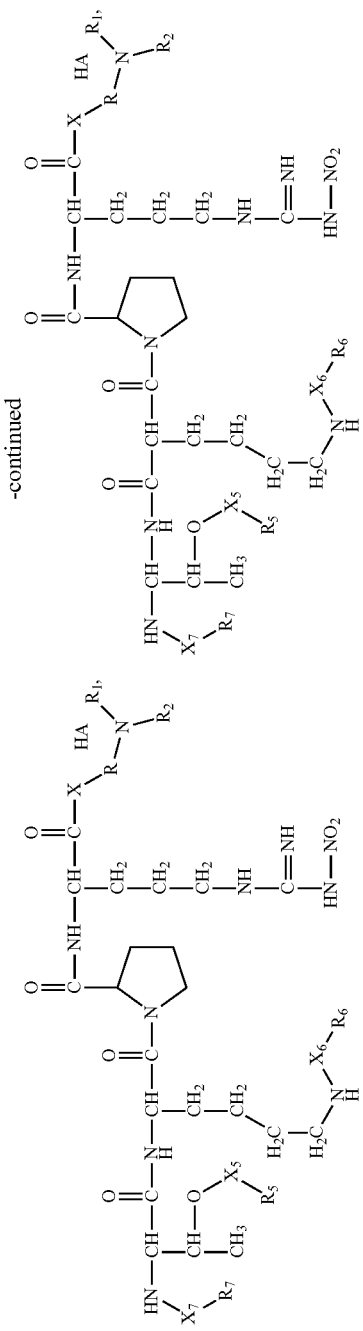
Structure 31 (SEQ ID NO: 8)
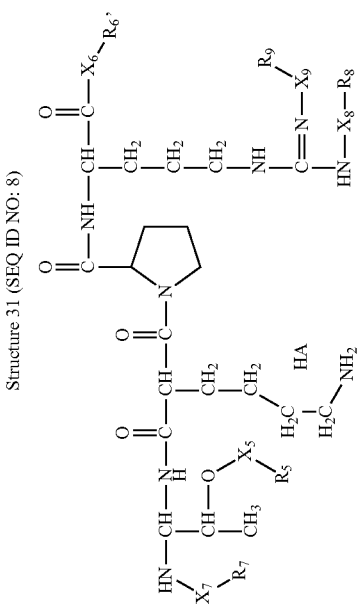
Structure 32 (SEQ ID NO: 8)
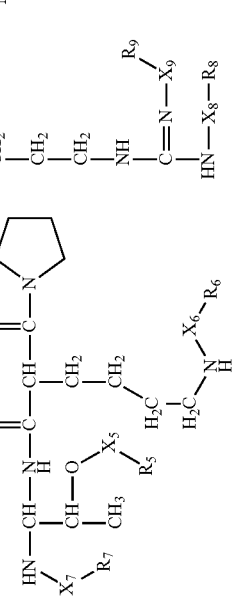
Structure 33 (SEQ ID NO: 8)
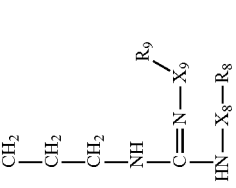
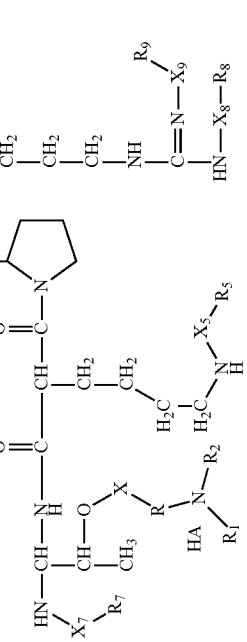
Structure 34 (SEQ ID NO: 8)
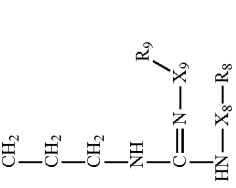
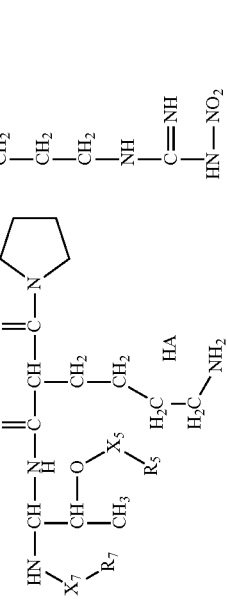
Structure 35 (SEQ ID NO: 8)

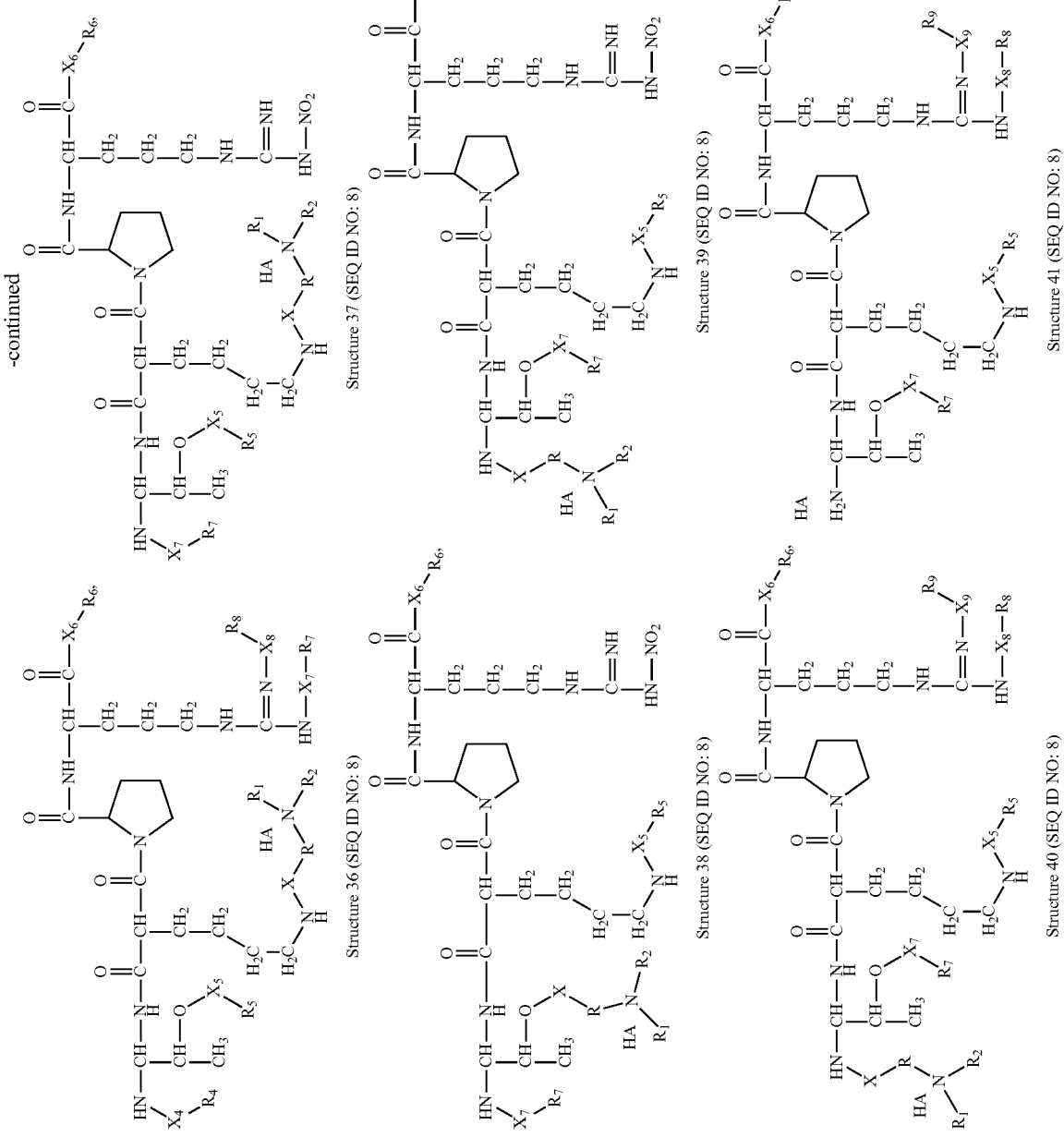

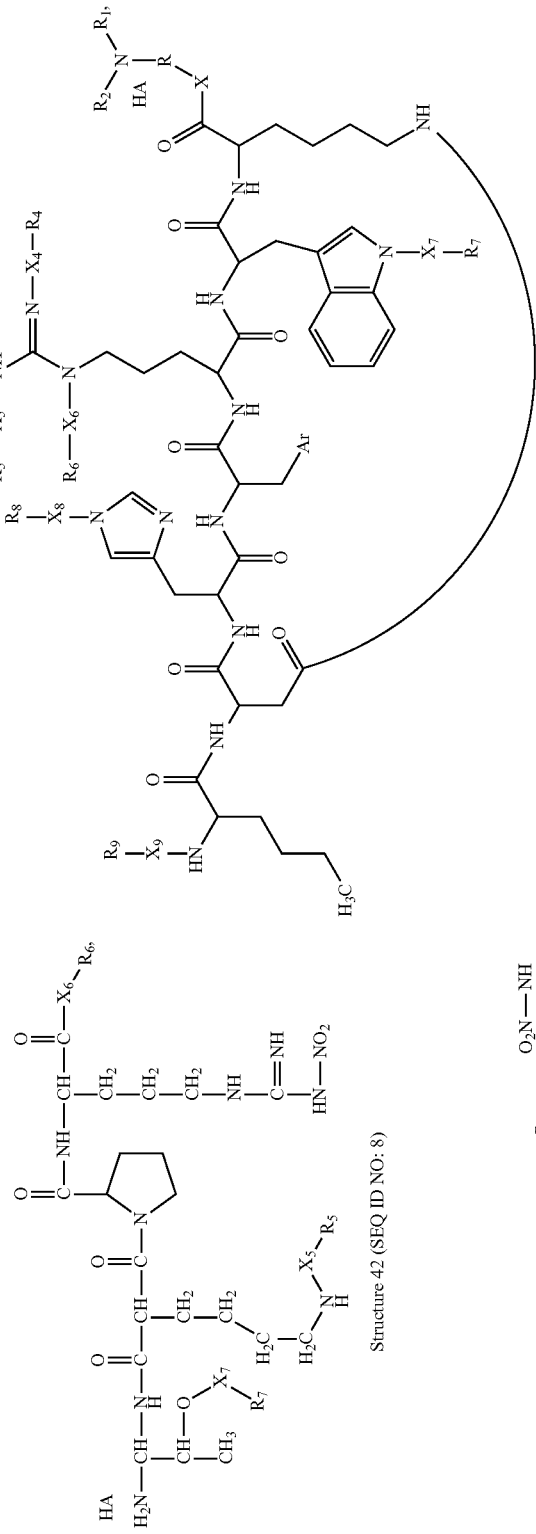
Structure 42 (SEQ ID NO: 8)
Structure 43 (SEQ ID NO: 9)
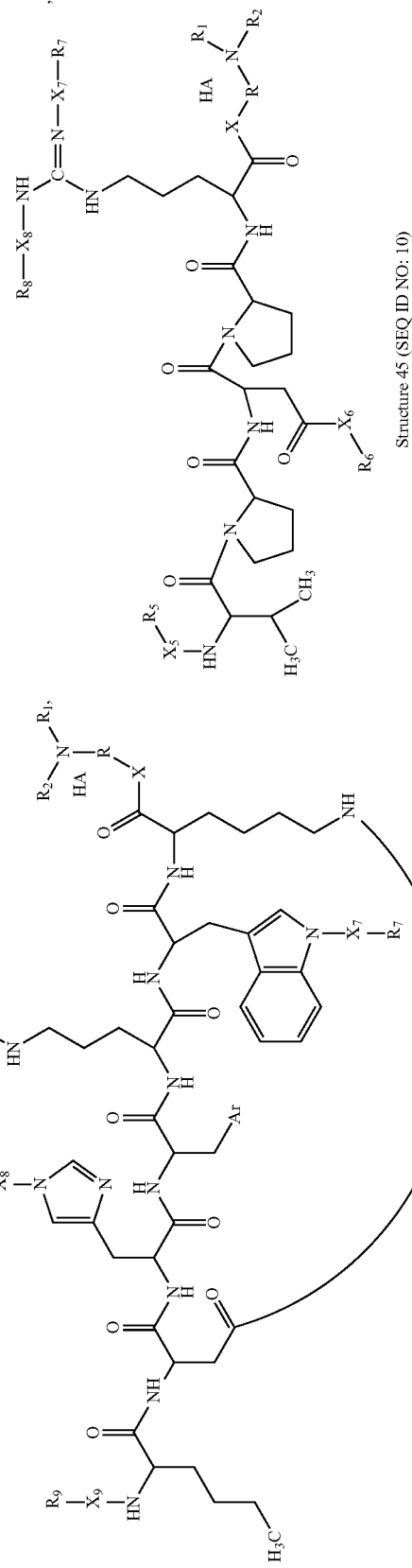
Structure 44 (SEQ ID NO: 9)
Structure 45 (SEQ ID NO: 10)

-continued
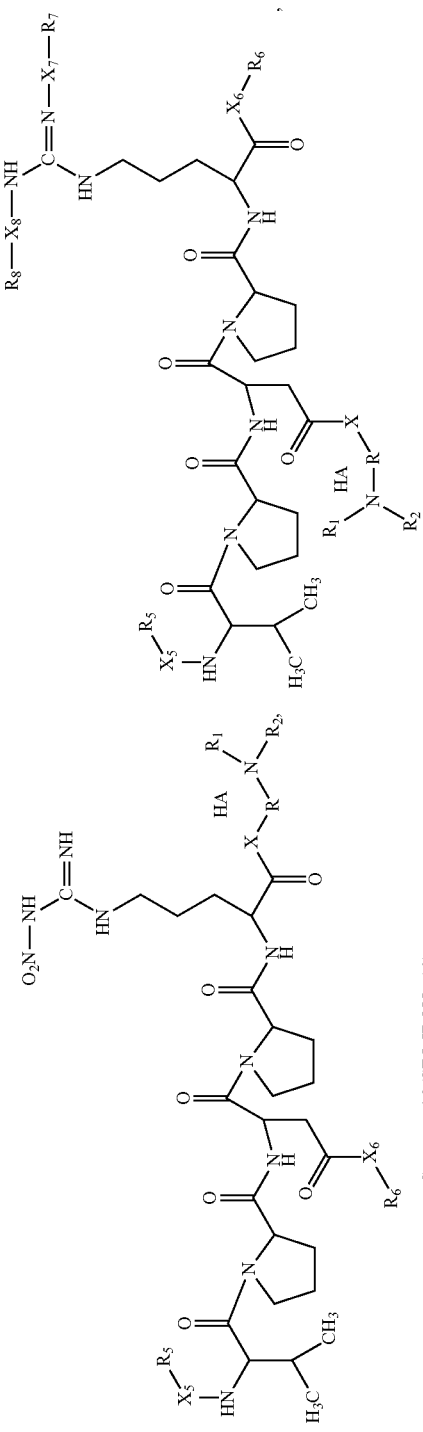
Structure 46 (SEQ ID NO: 10)
Structure 47 (SEQ ID NO: 10)
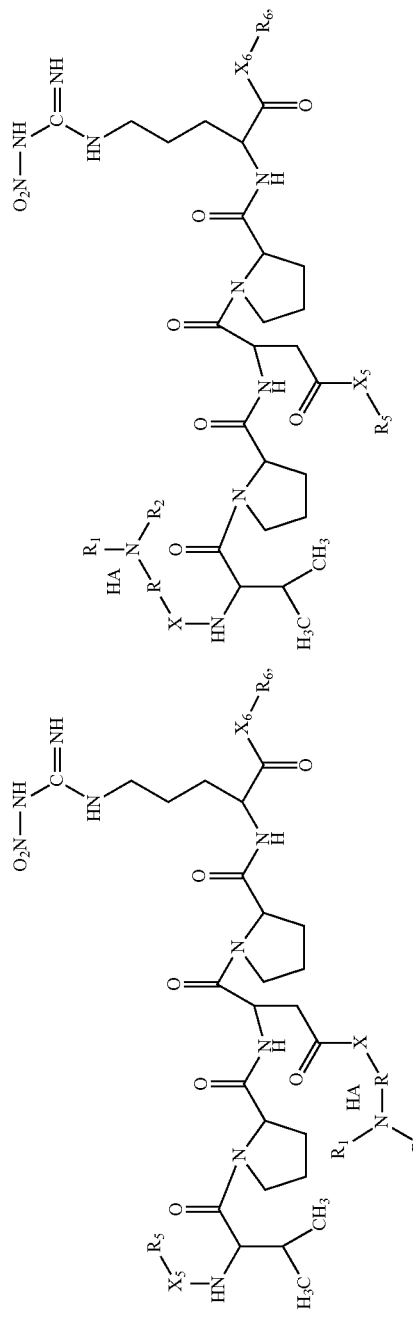
Structure 48 (SEQ ID NO: 10)
Structure 49 (SEQ ID NO: 10)

-continued
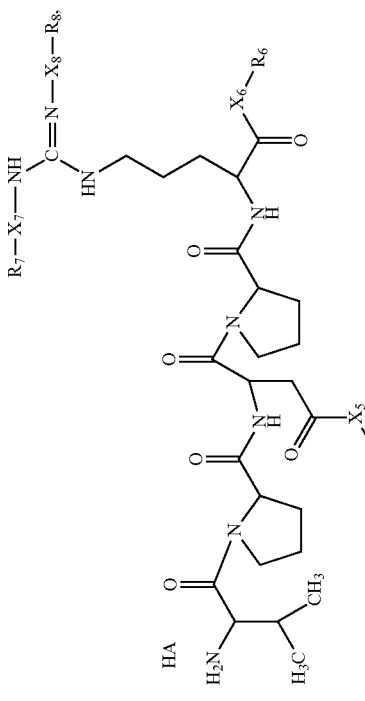
Structure 50 (SEQ ID NO: 10)
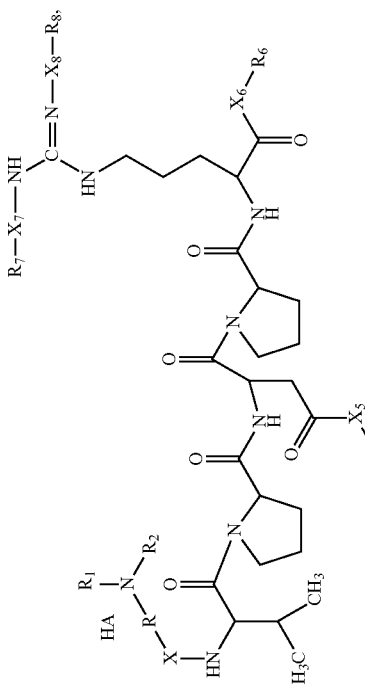
Structure 51 (SEQ ID NO: 10)
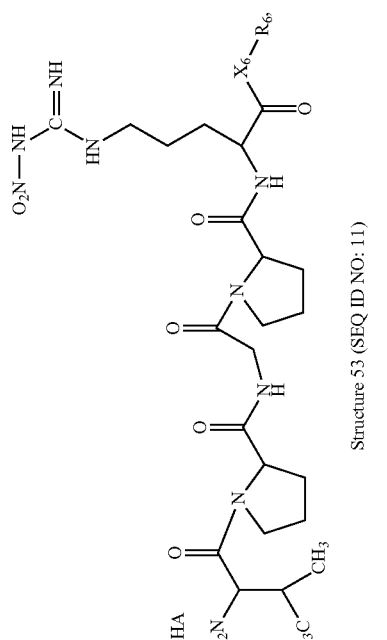
Structure 52 (SEQ ID NO: 10)
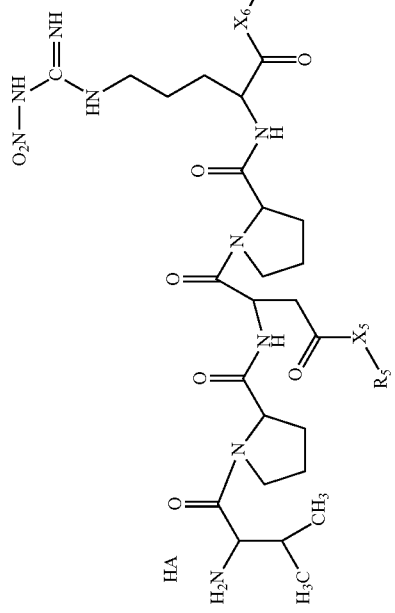
Structure 53 (SEQ ID NO: 11)

-continued
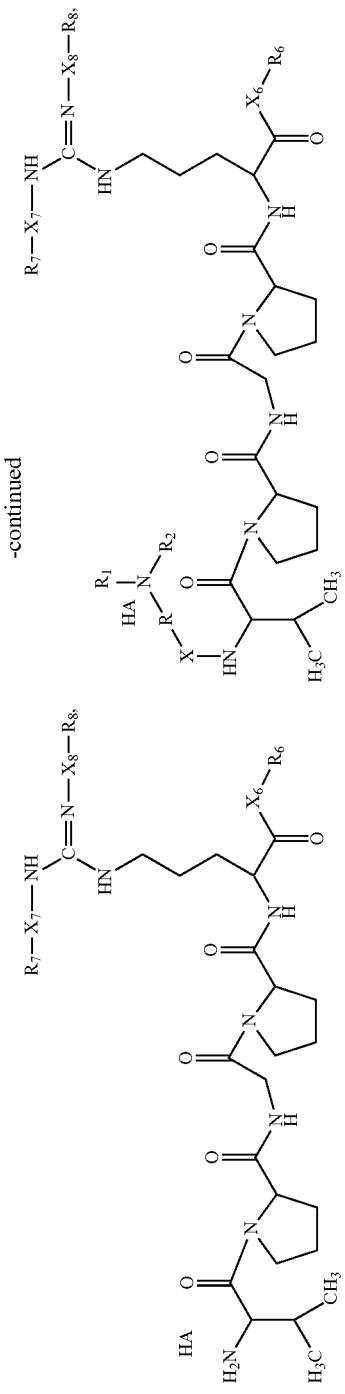
Structure 54 (SEQ ID NO: 11)
Structure 55 (SEQ ID NO: 11)
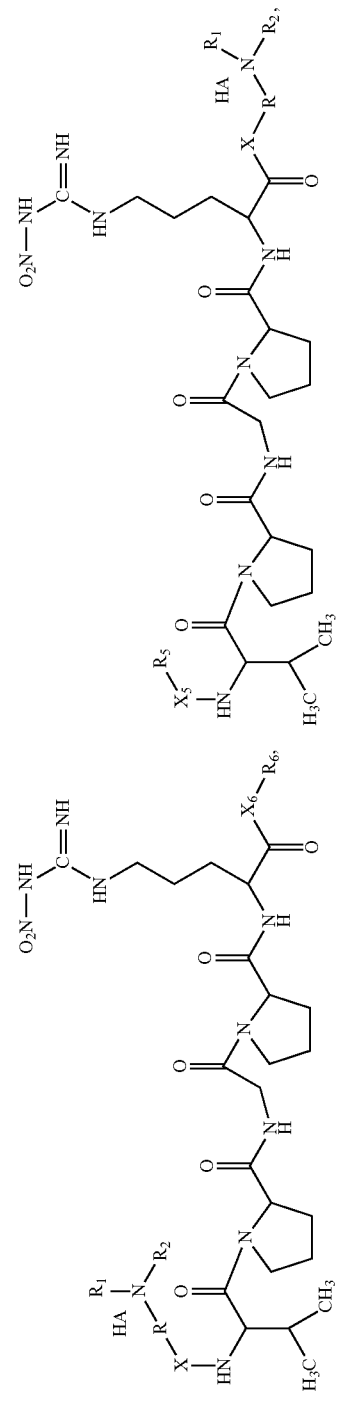
Structure 56 (SEQ ID NO: 11)
Structure 57 (SEQ ID NO: 11)
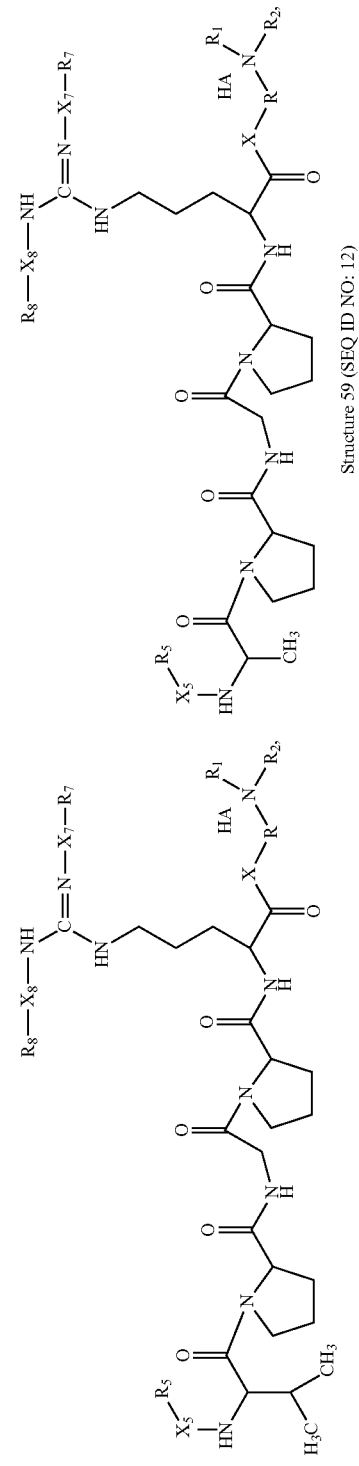
Structure 58 (SEQ ID NO: 11)
Structure 59 (SEQ ID NO: 12)

-continued
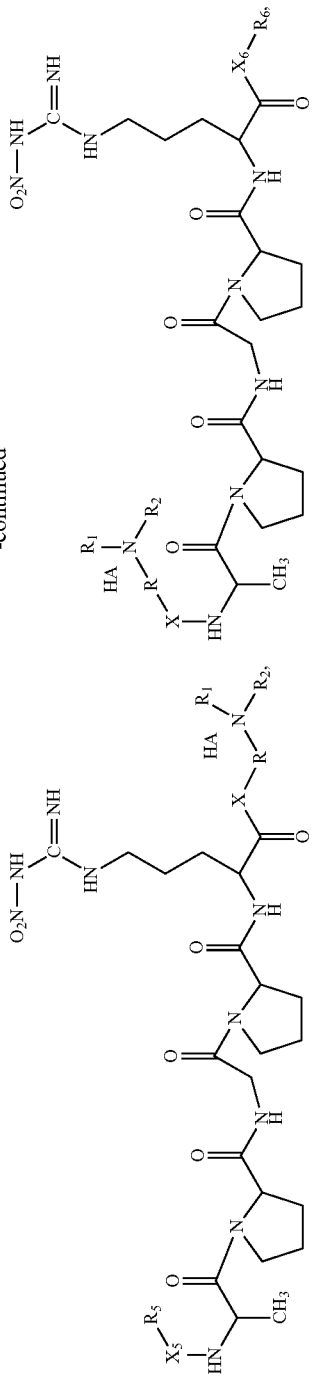
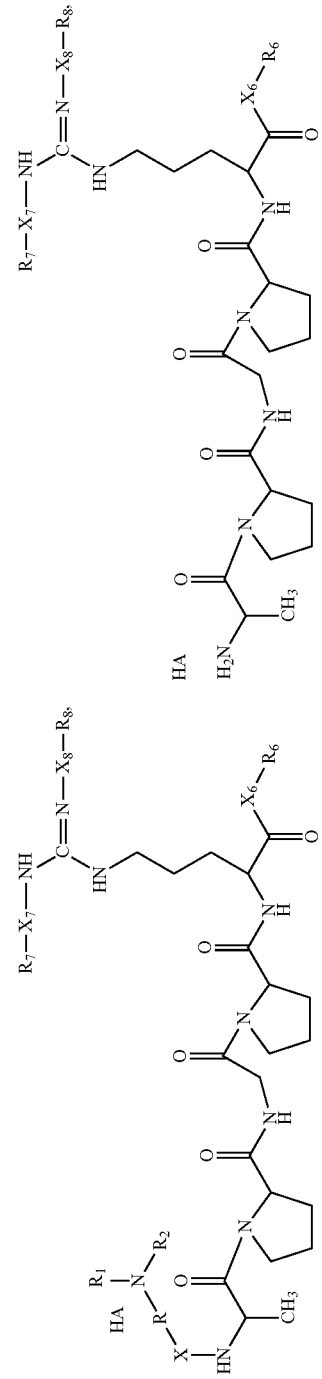
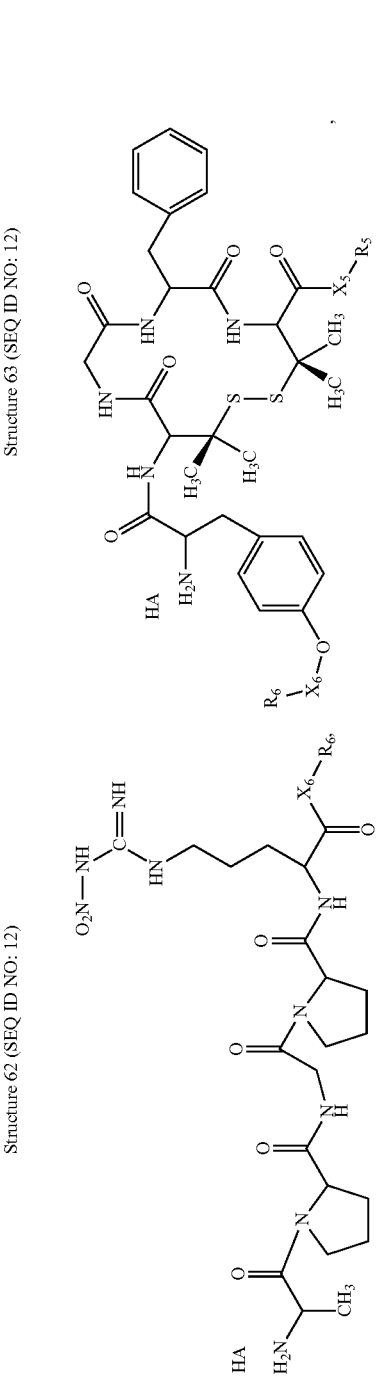

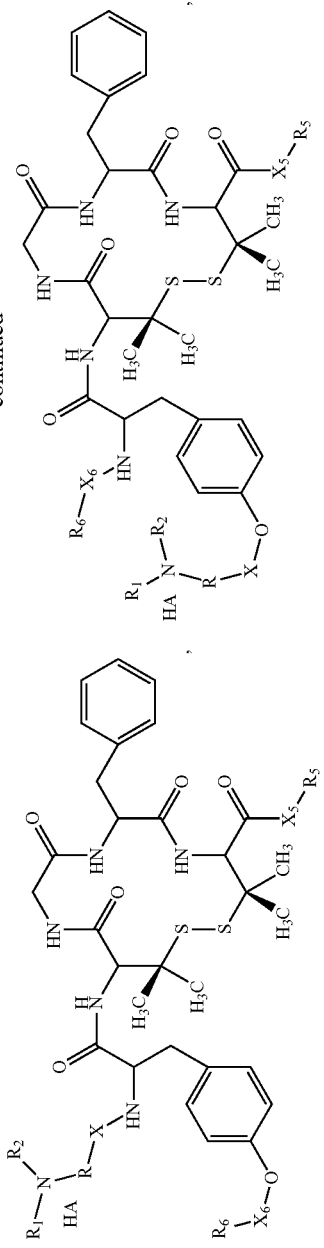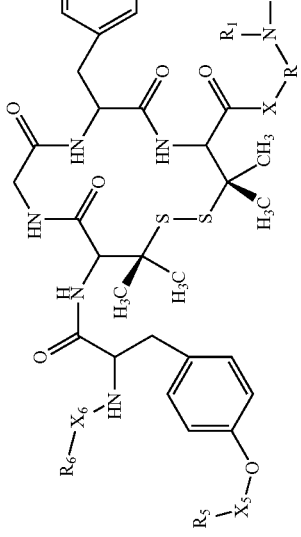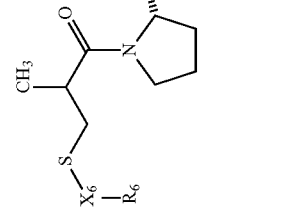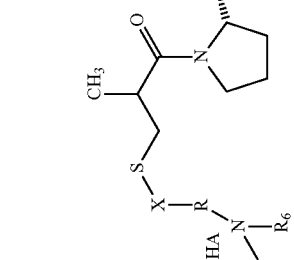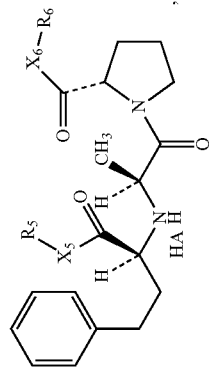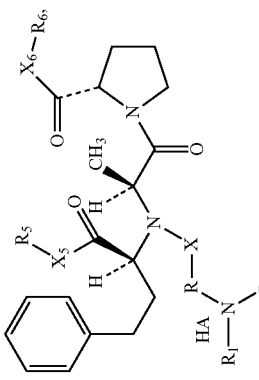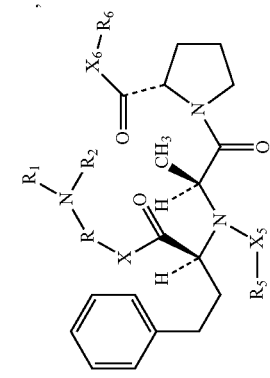

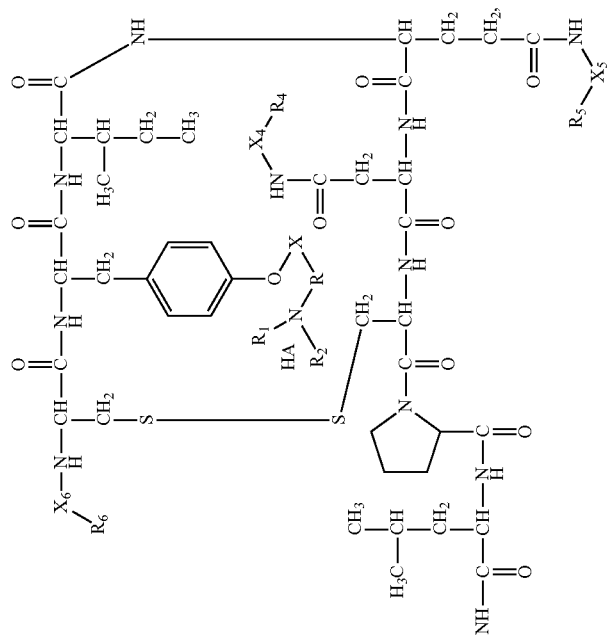
Structure 76 (SEQ ID NO: 16)
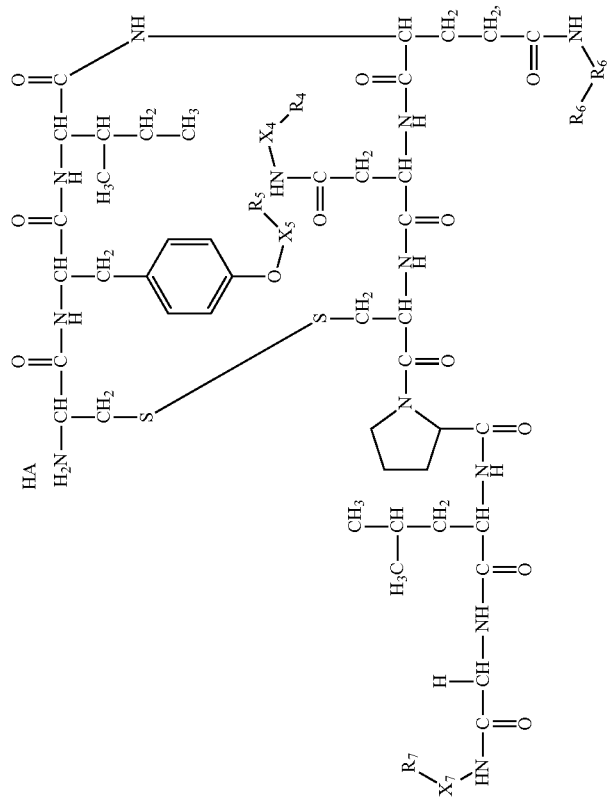
Structure 75 (SEQ ID NO: 16)

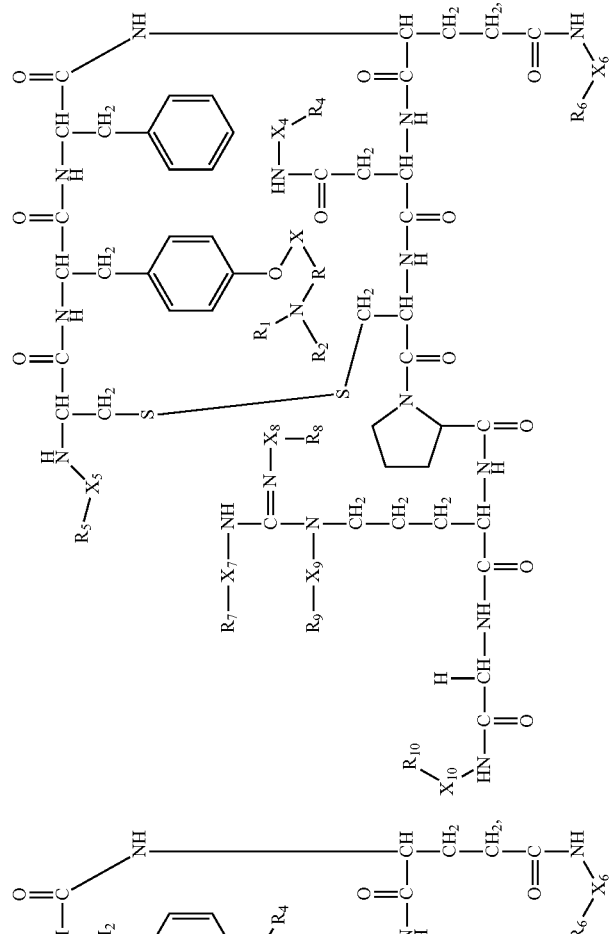
Structure 78 (SEQ ID NO: 17)
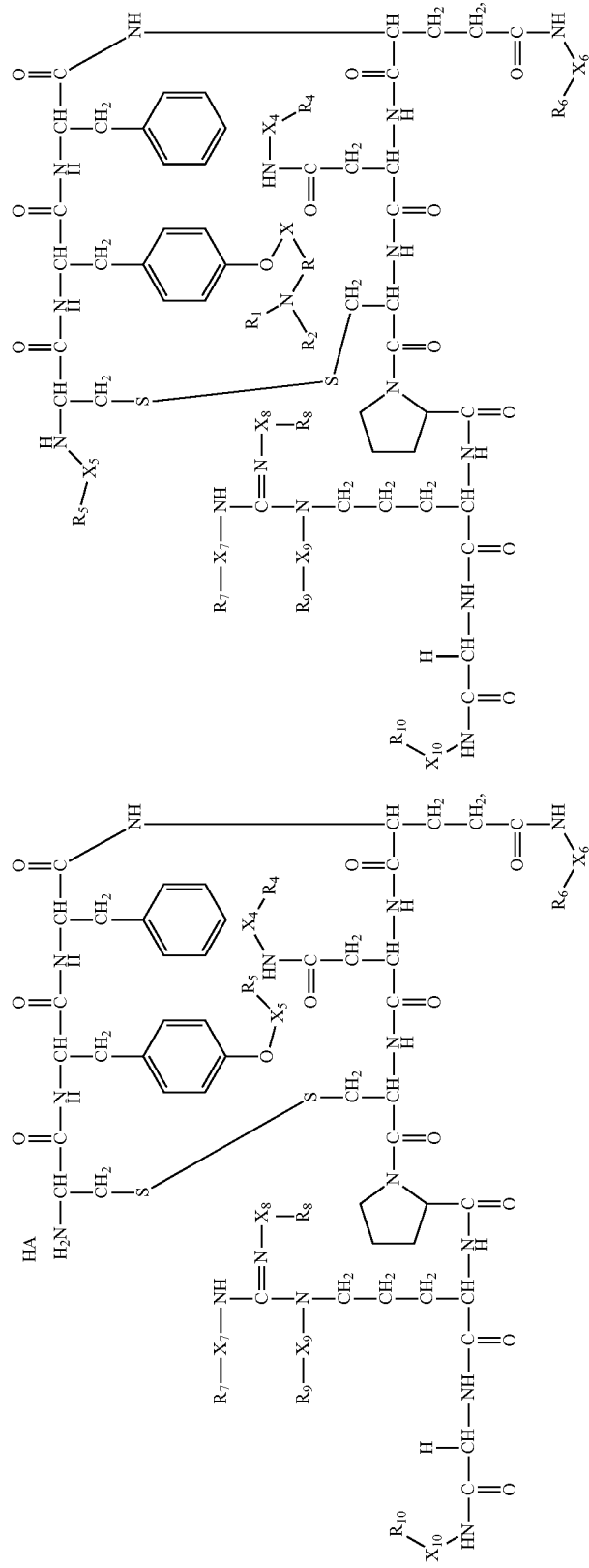
Structure 77 (SEQ ID NO: 17)

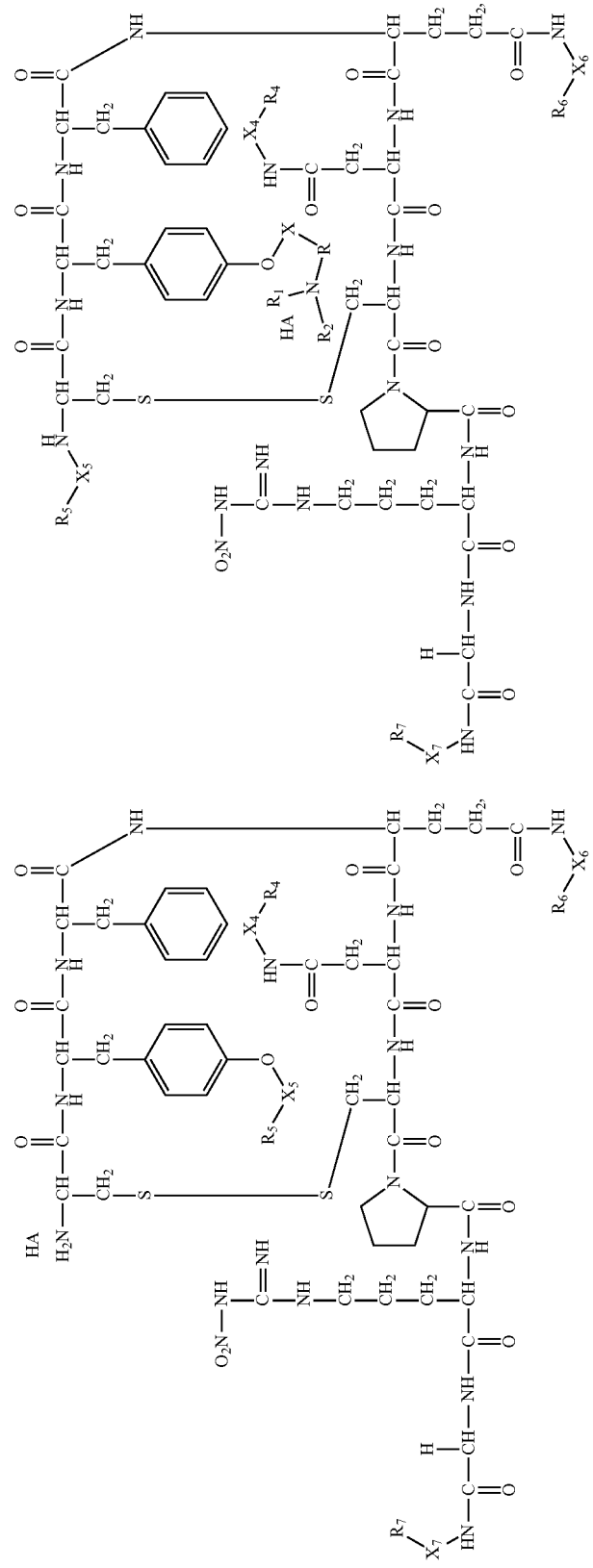
Structure 80 (SEQ ID NO: 17)
Structure 79 (SEQ ID NO: 17)

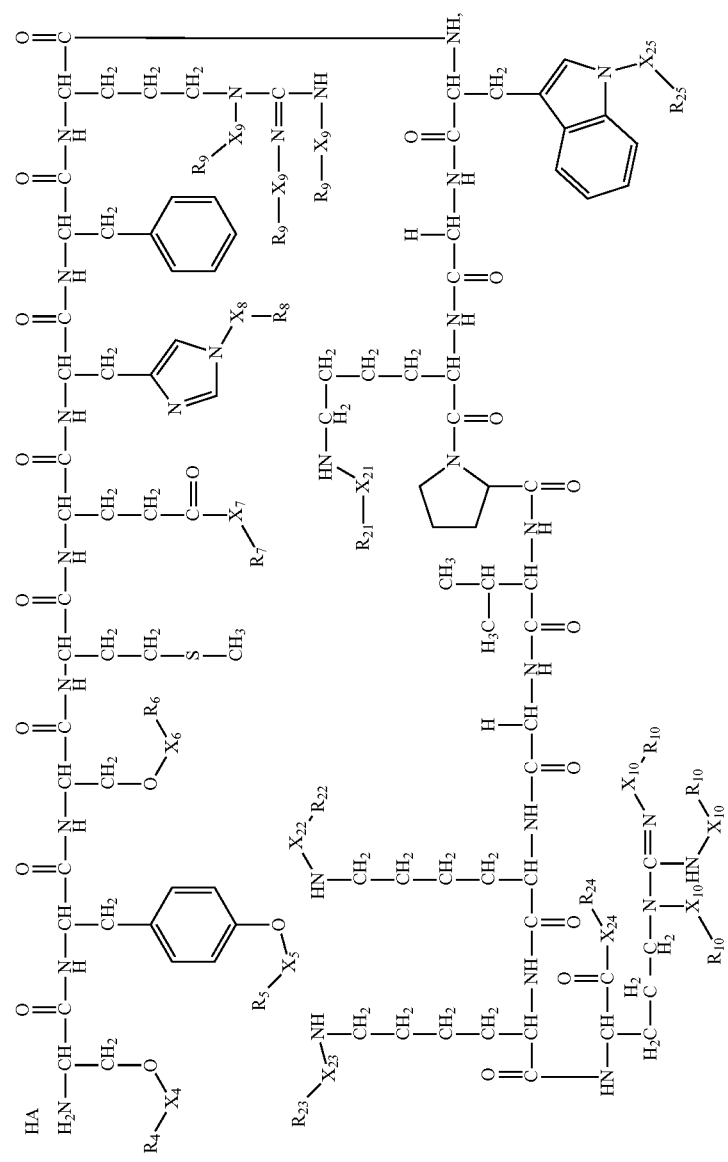
Structure 81 (SEQ ID NO: 18)

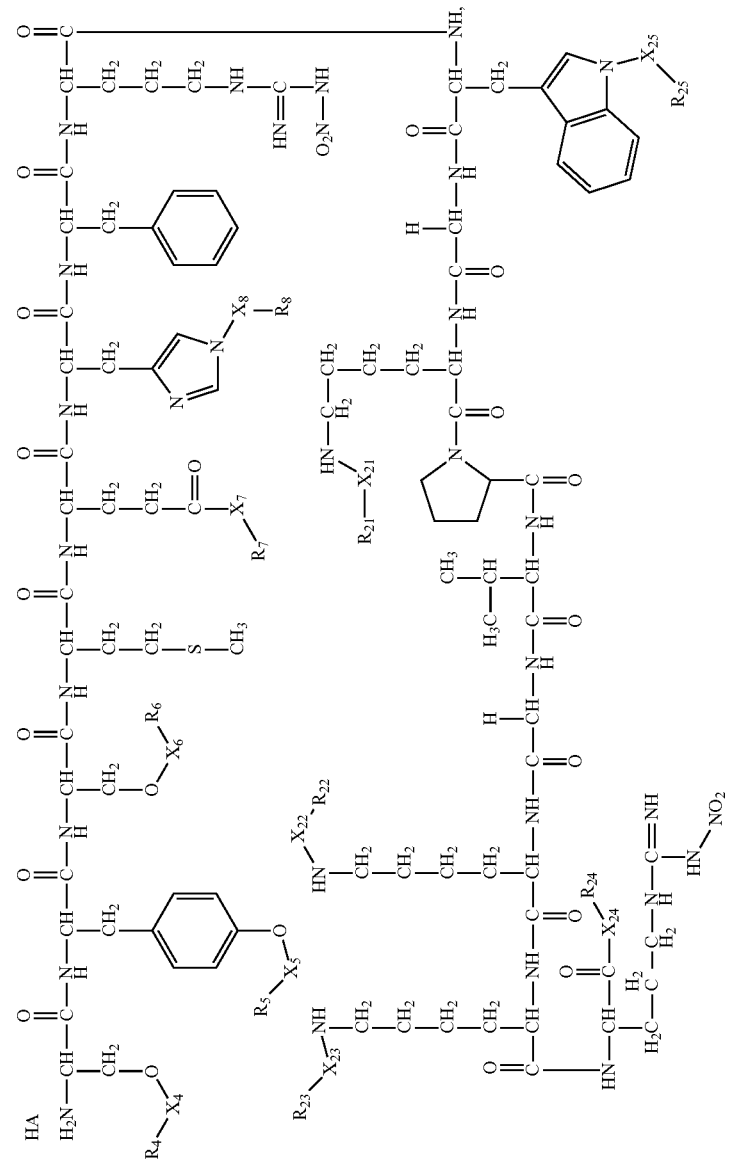
Structure 82 (SEQ ID NO: 18)

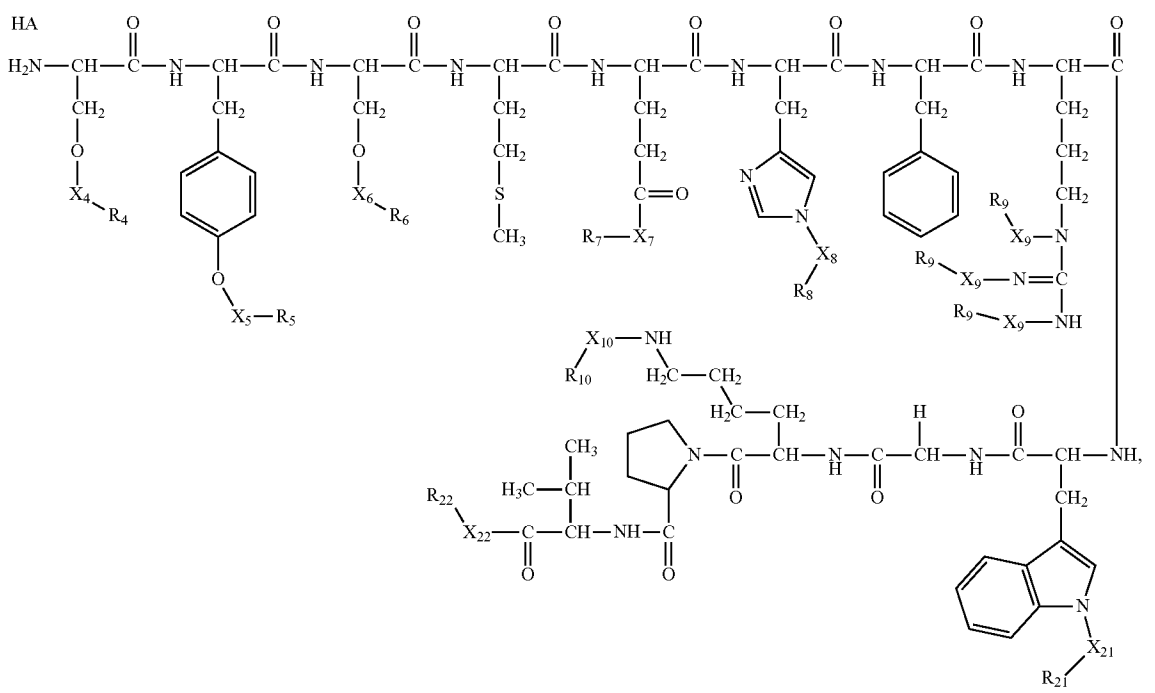
Structure 83 (SEQ ID NO: 19)

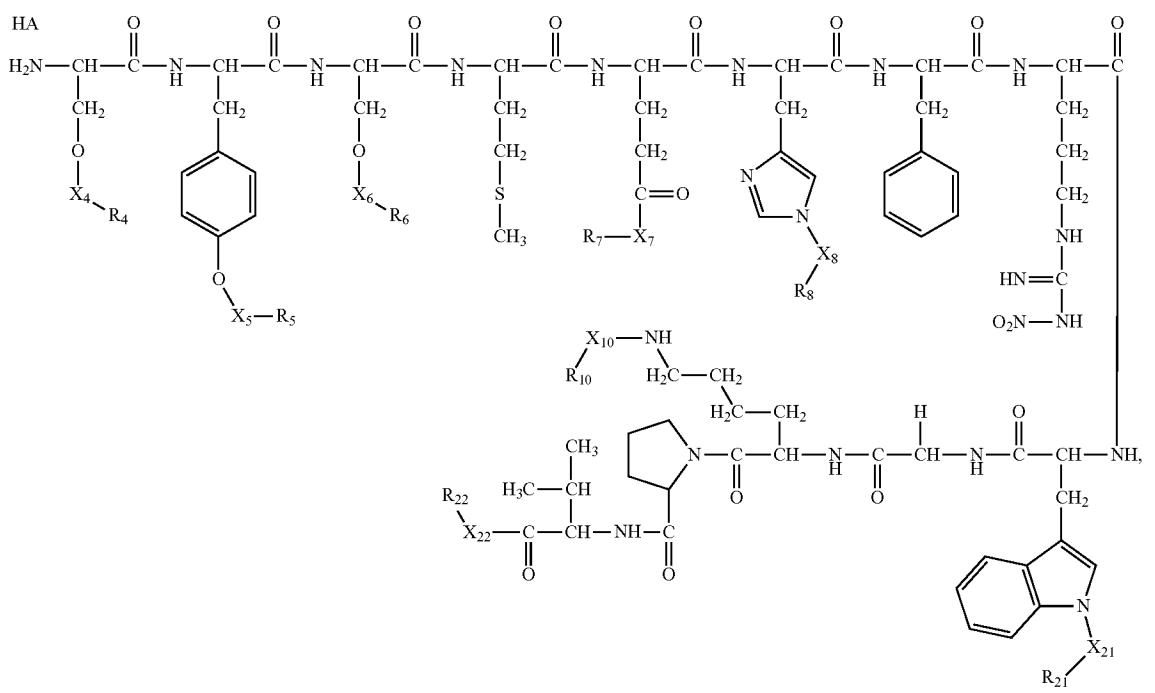
Structure 84 (SEQ ID NO: 19)

-continued
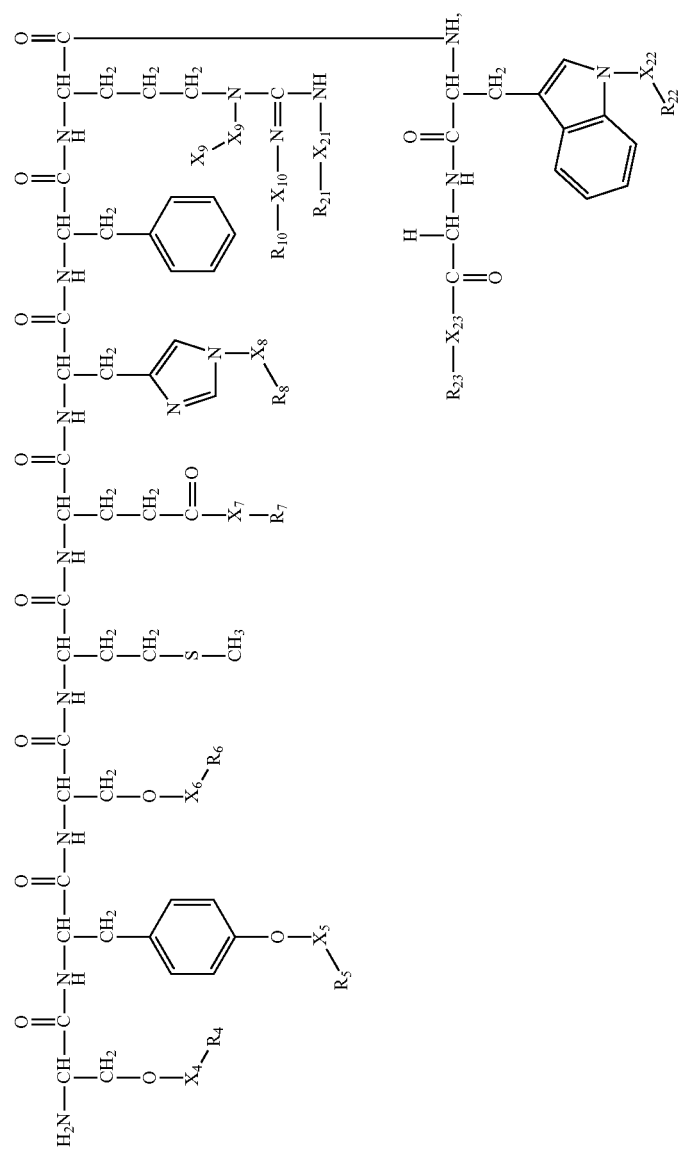
Structure 85 (SEQ ID NO: 20)

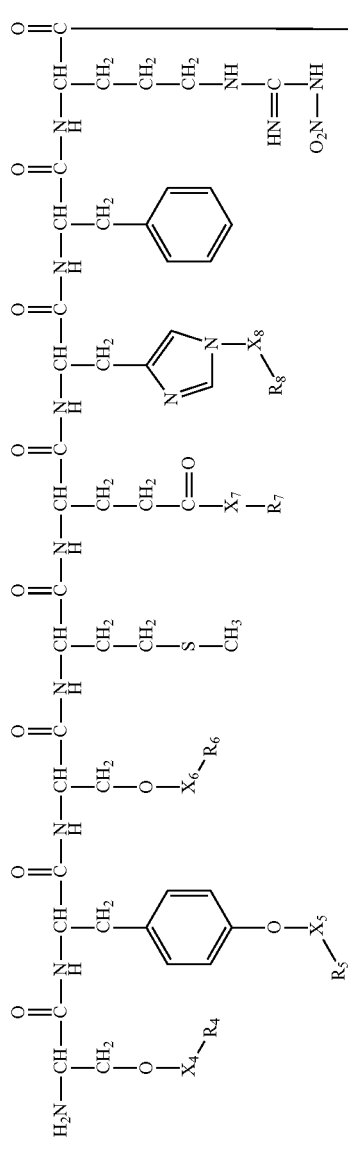
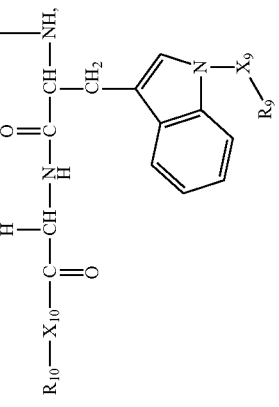
Structure 86 (SEQ ID NO: 20)

Structure 87 (SEQ ID NO: 21)

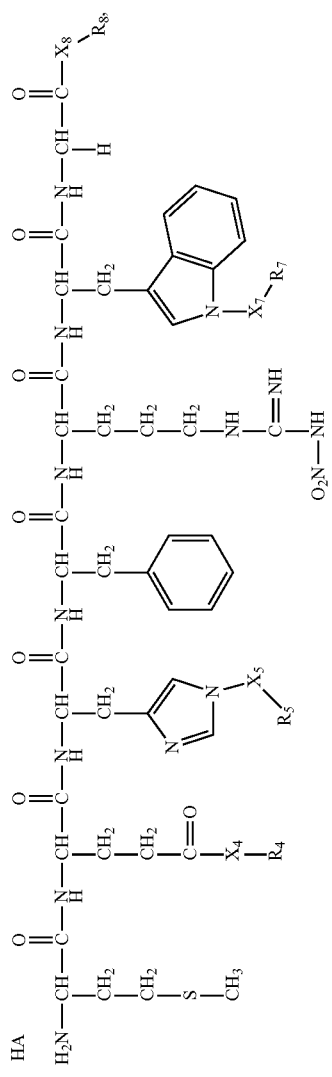
Structure 88 (SEQ ID NO: 21)
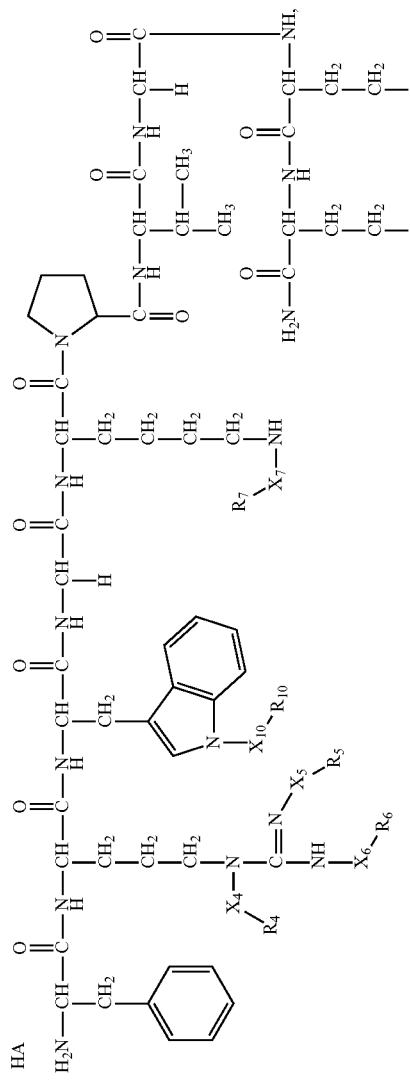
Structure 89 (SEQ ID NO: 22)

-continued
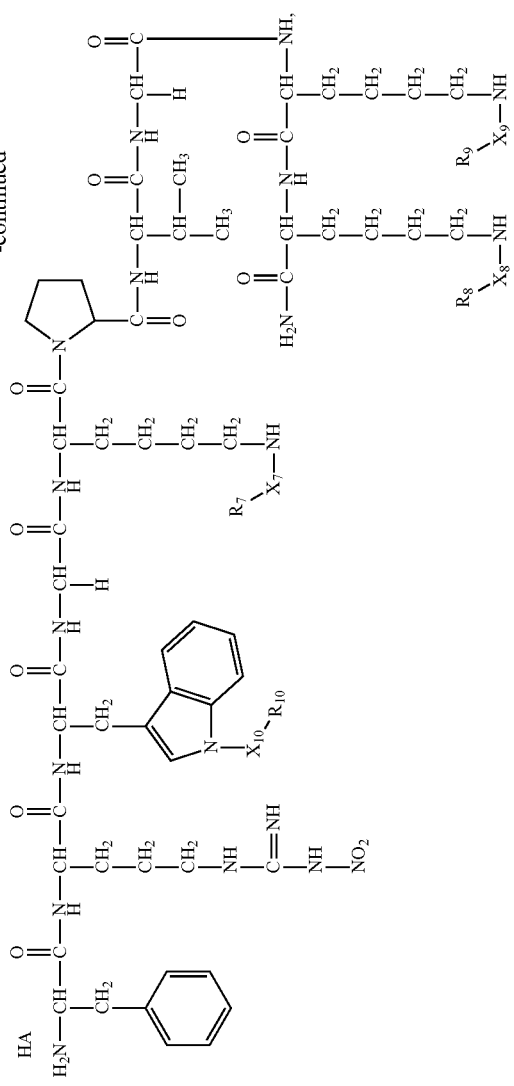
Structure 90 (SEQ ID NO: 22)
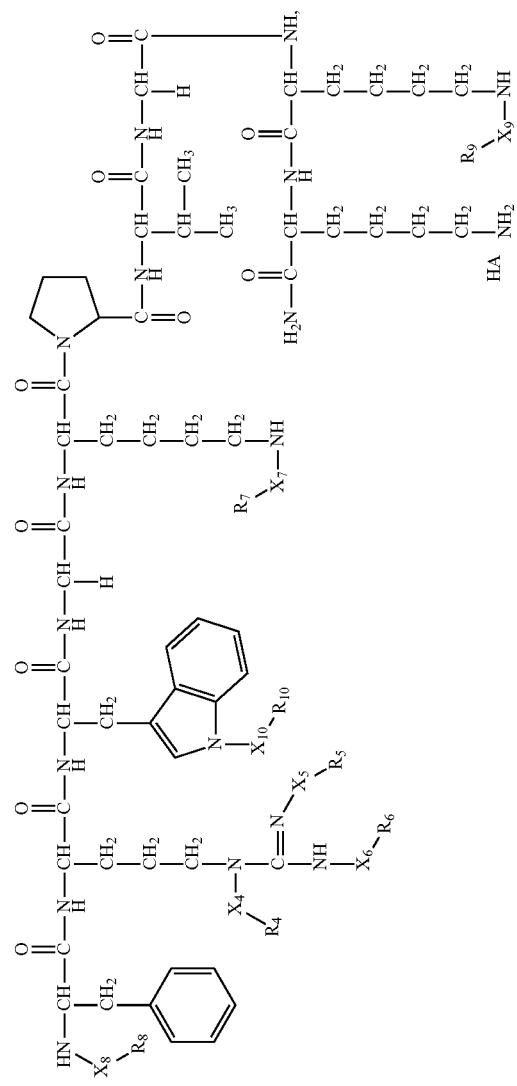
Structure 91 (SEQ ID NO: 22)

-continued
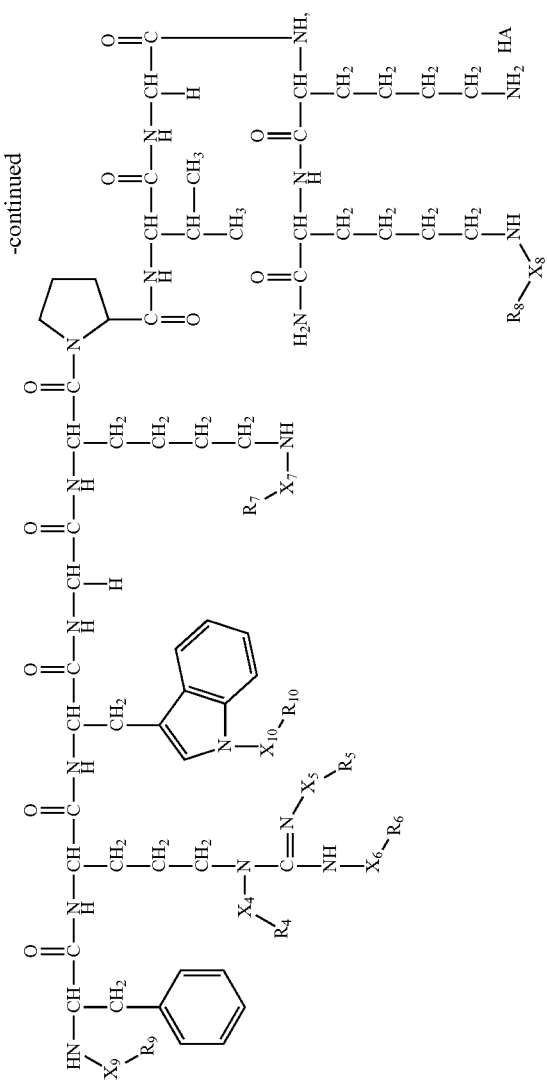
Structure 92 (SEQ ID NO: 22)
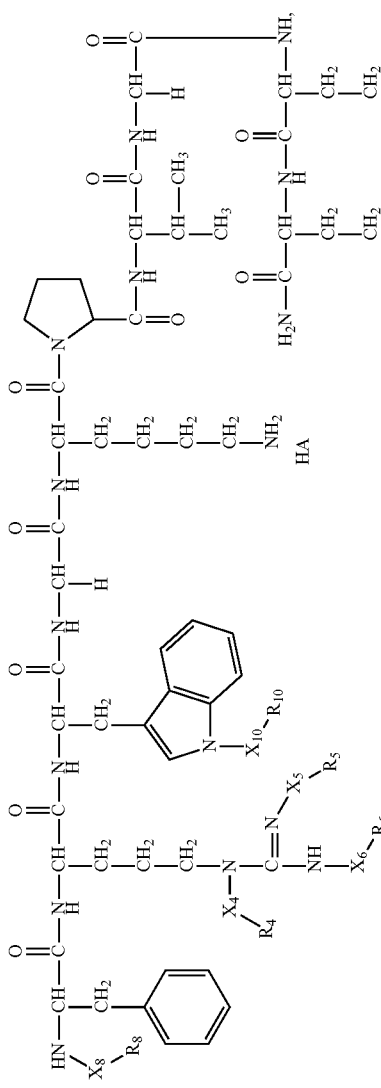
Structure 93 (SEQ ID NO: 22)

-continued
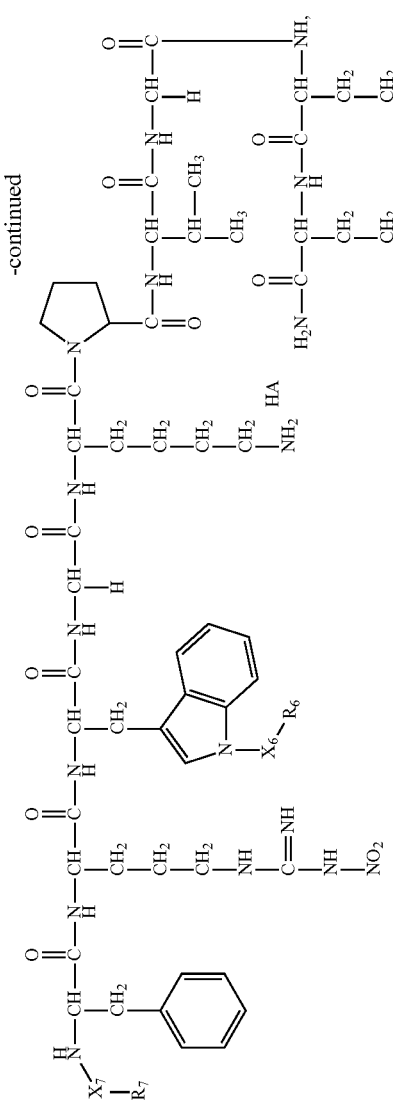
Structure 94 (SEQ ID NO: 22)
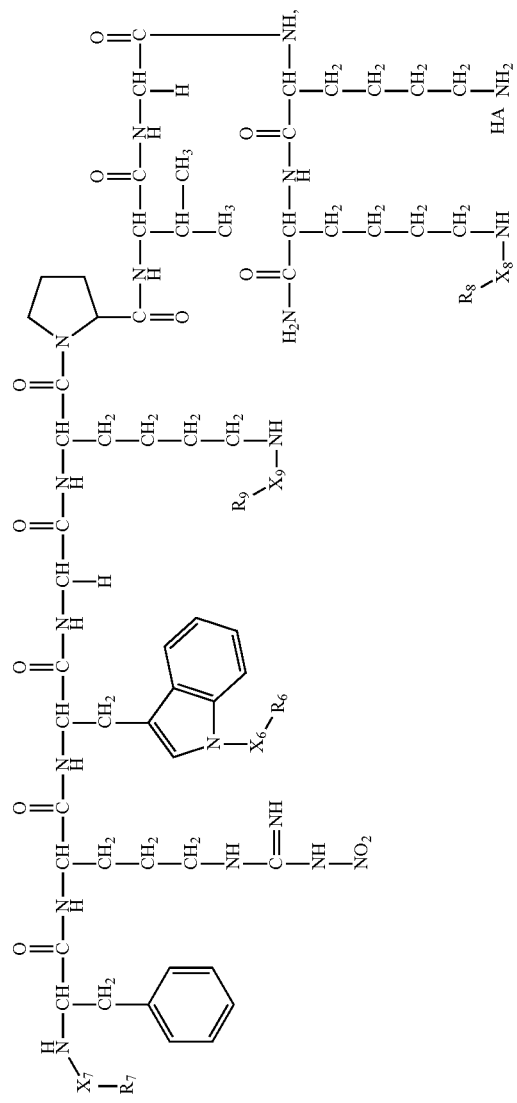
Structure 95 (SEQ ID NO: 22)

-continued
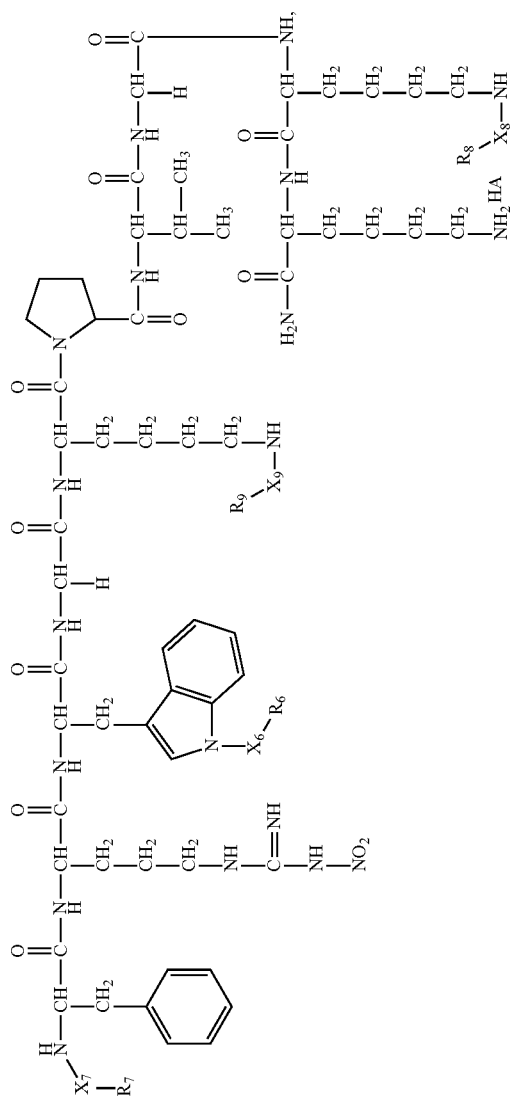
Structure 96 (SEQ ID NO: 22)

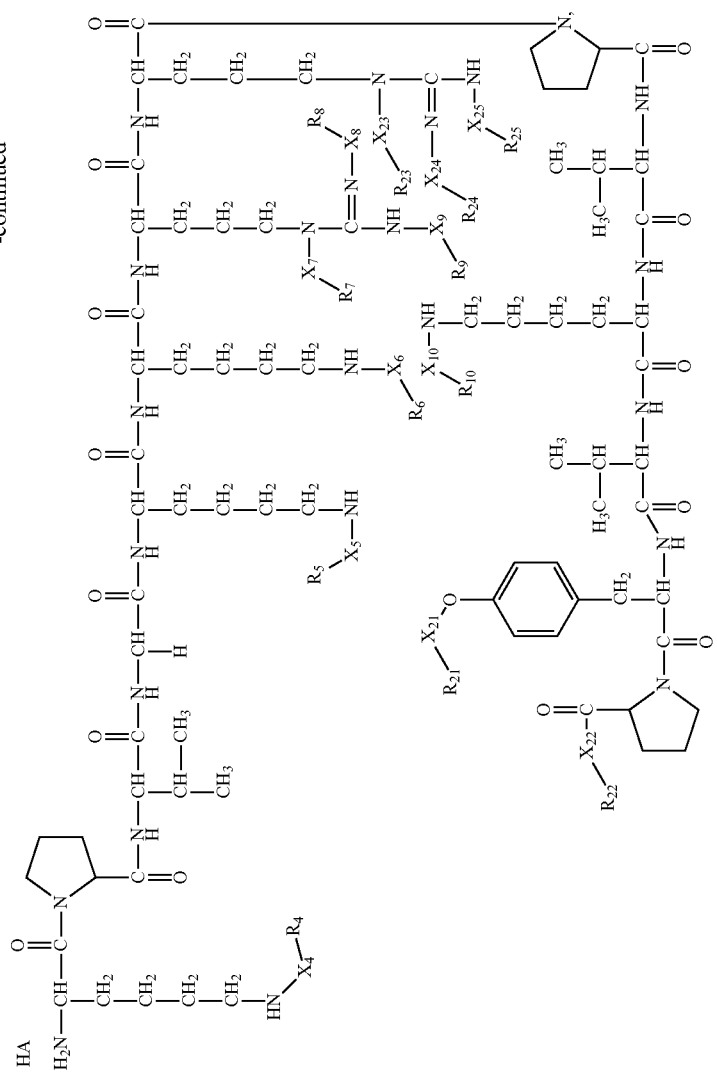
Structure 97 (SEQ ID NO: 23)

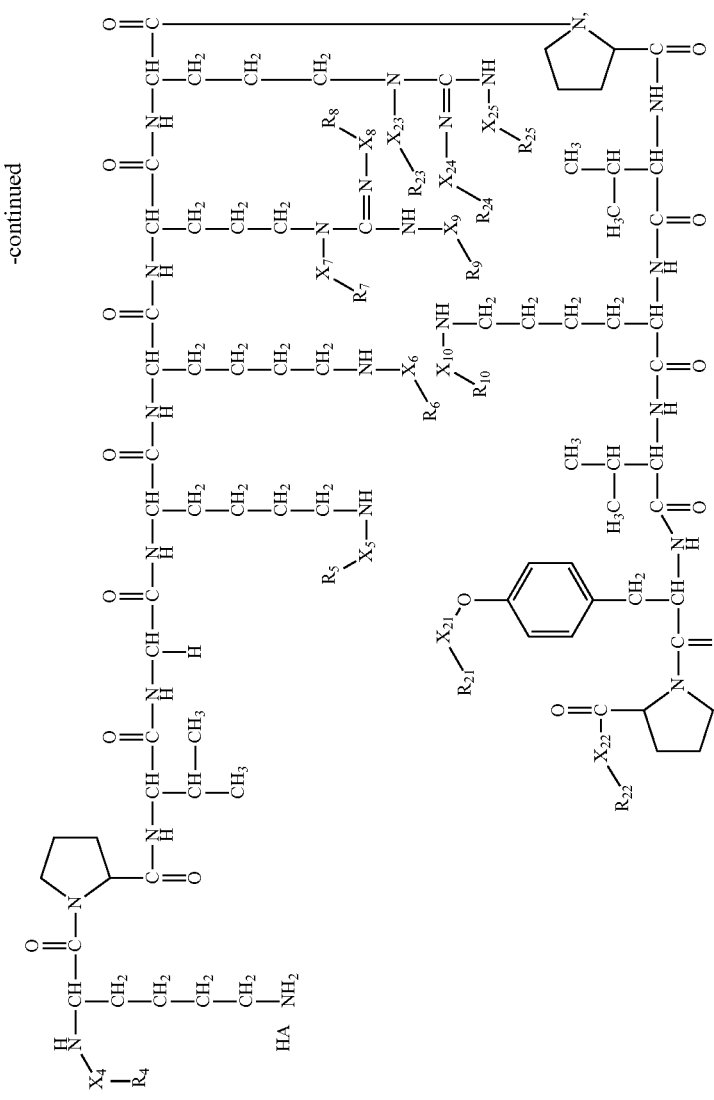
Structure 98 (SEQ ID NO: 23)

-continued
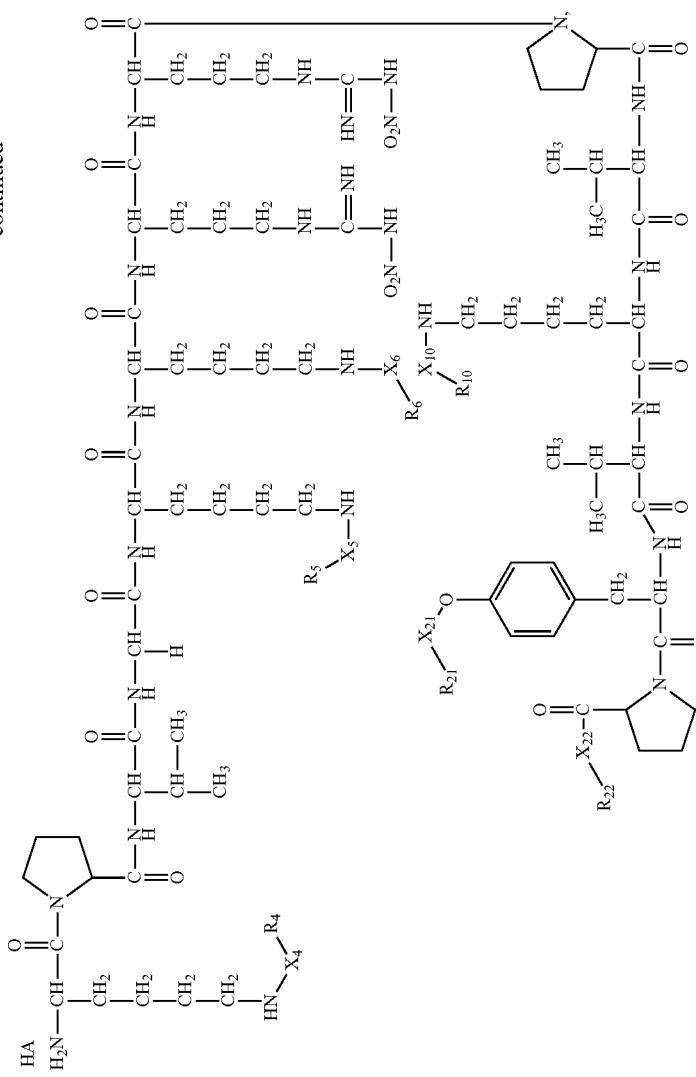
Structure 99 (SEQ ID NO: 23)

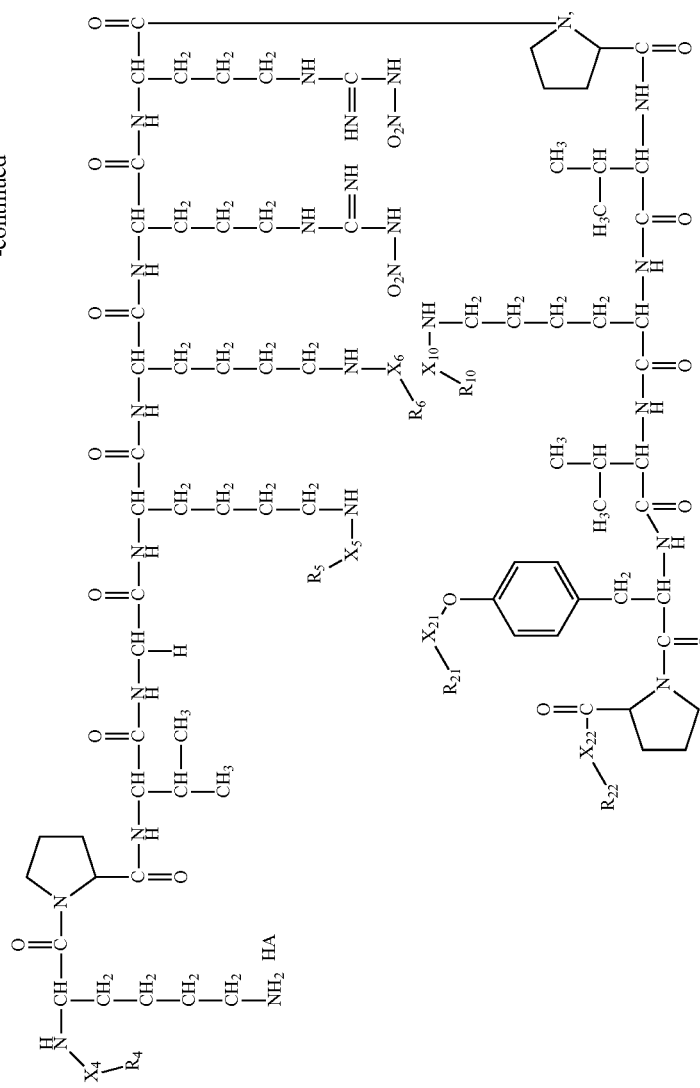
Structure 100 (SEQ ID NO: 23)

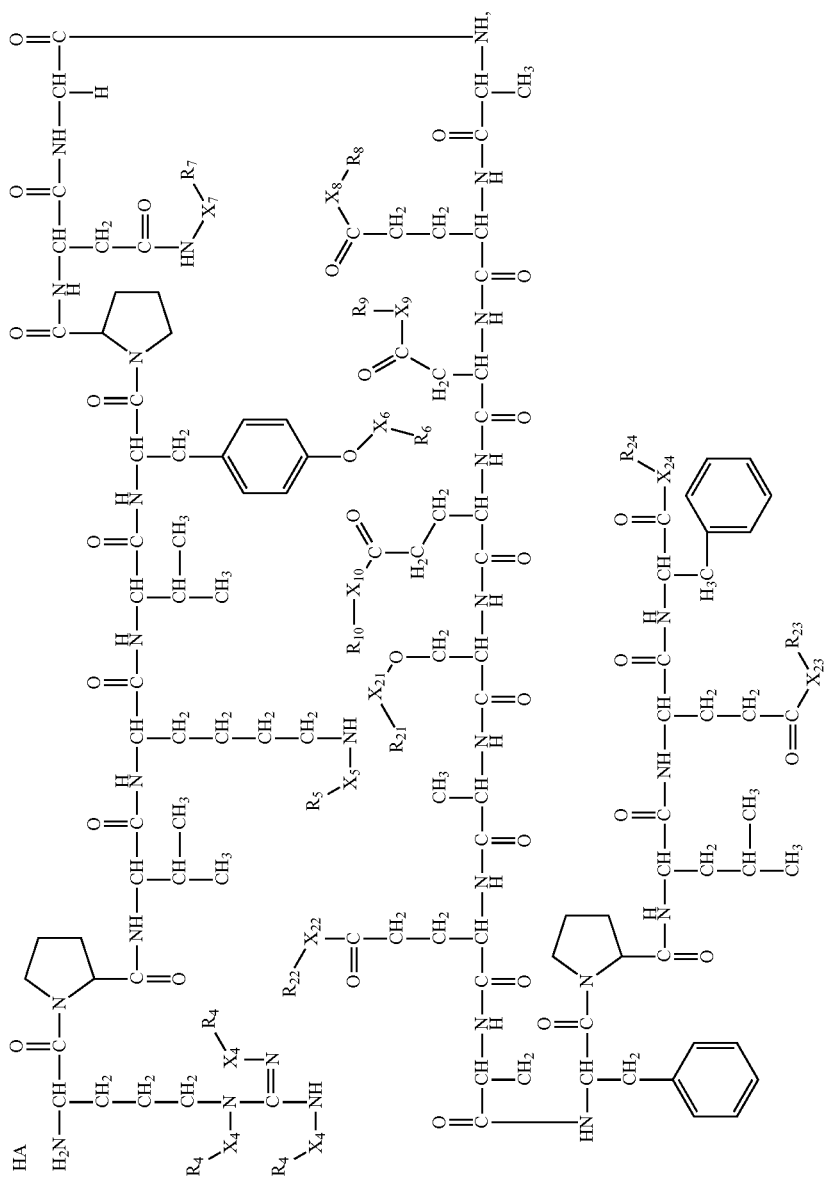
Structure 101 (SEQ ID NO: 24)

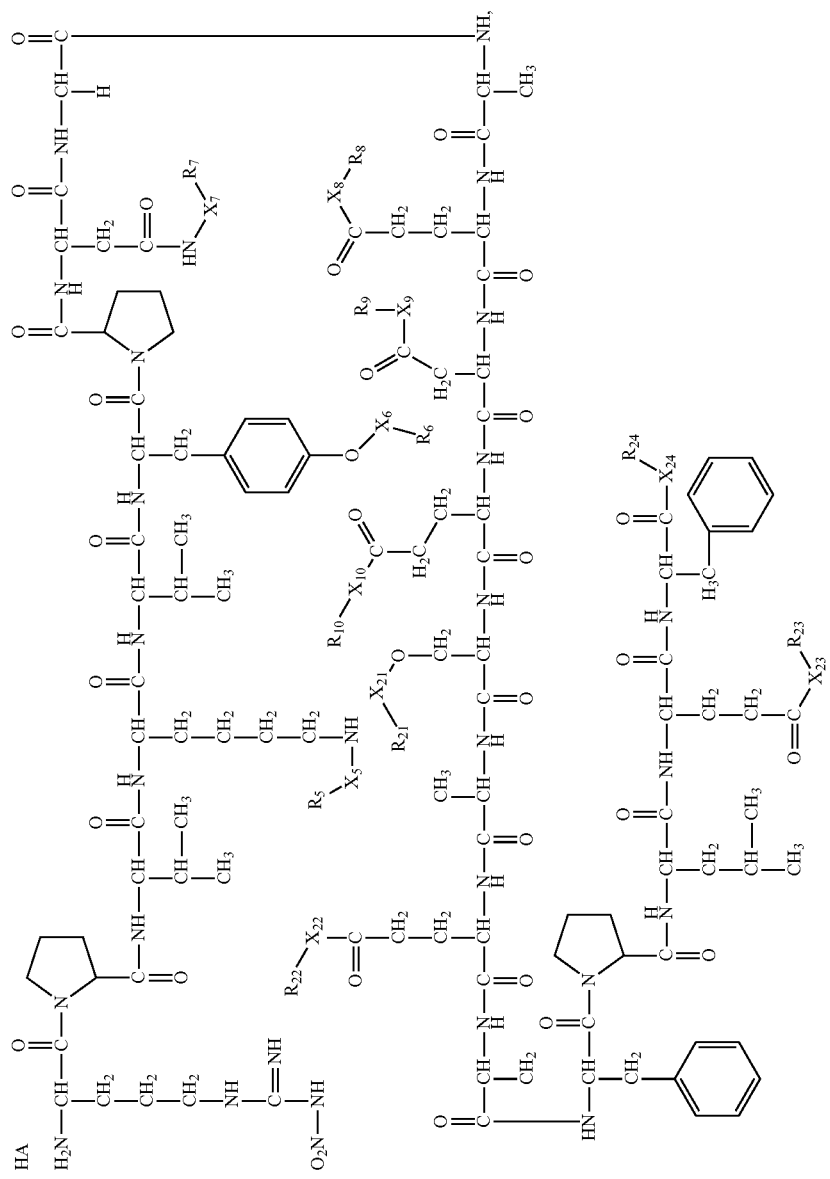
Structure 102 (SEQ ID NO: 24)

-continued
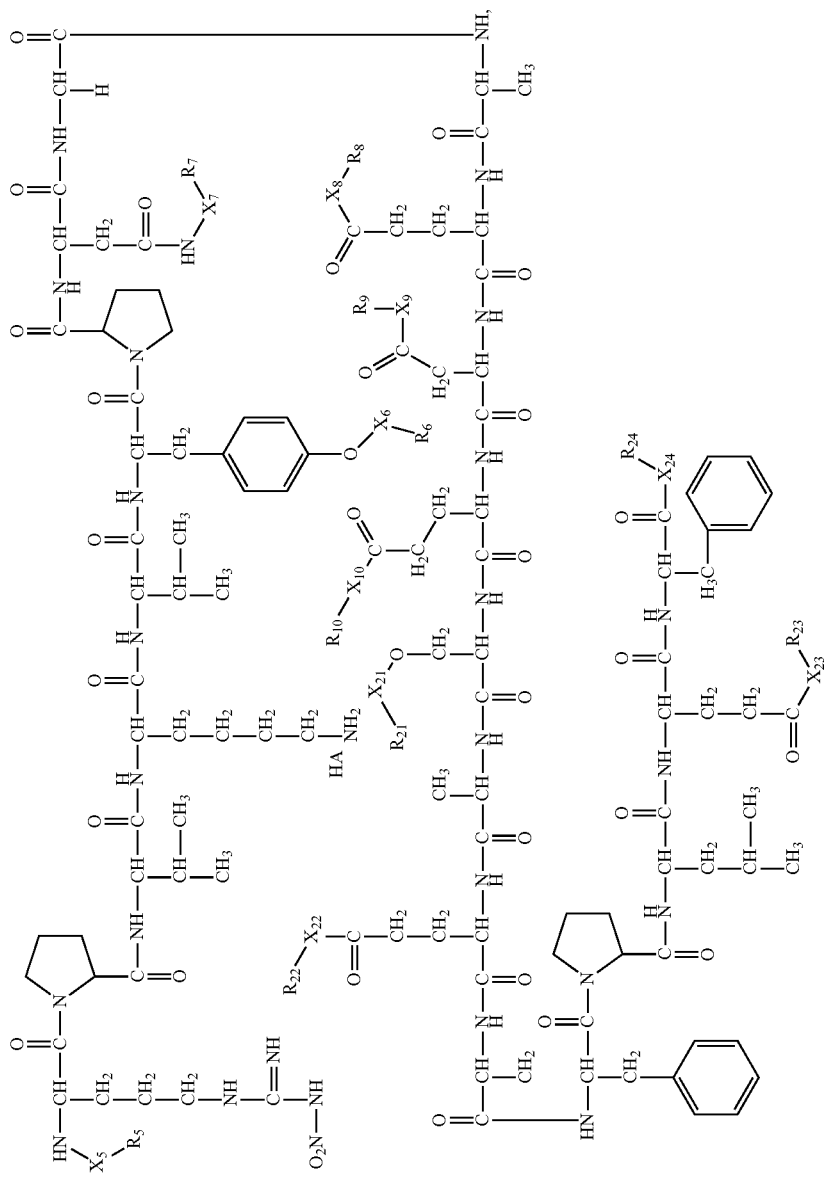
Structure 103 (SEQ ID NO: 24)

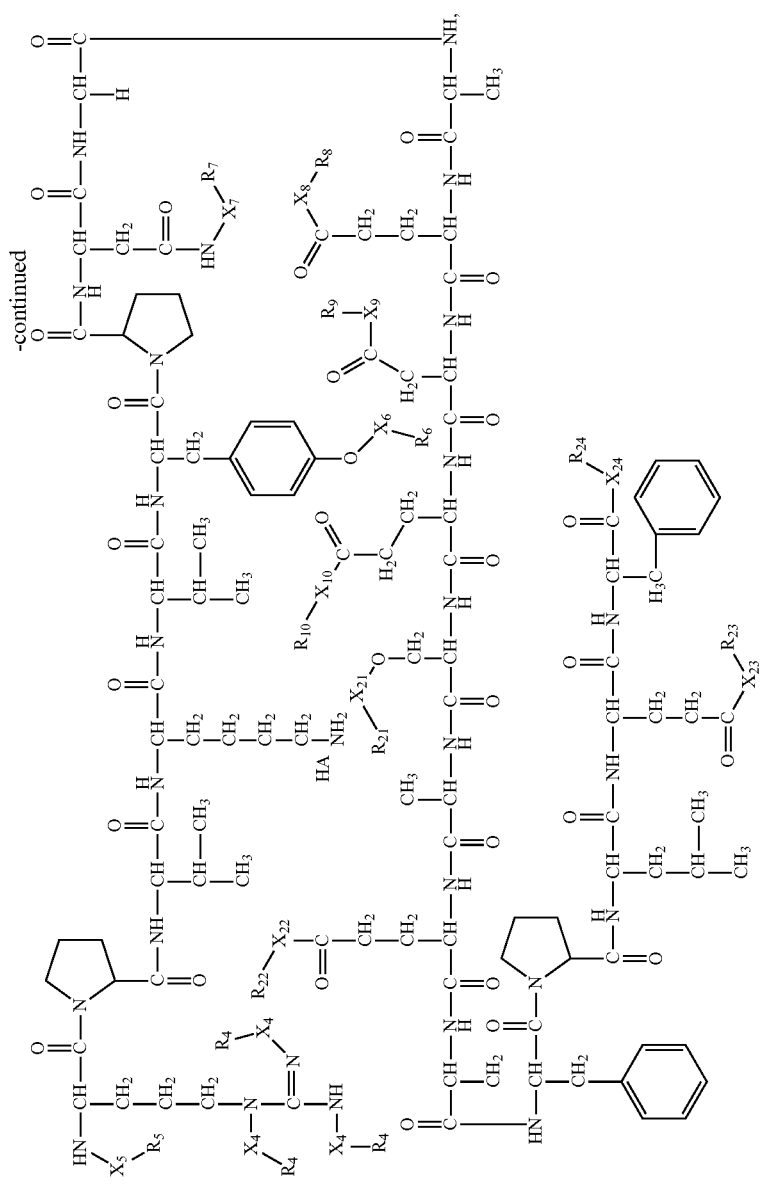
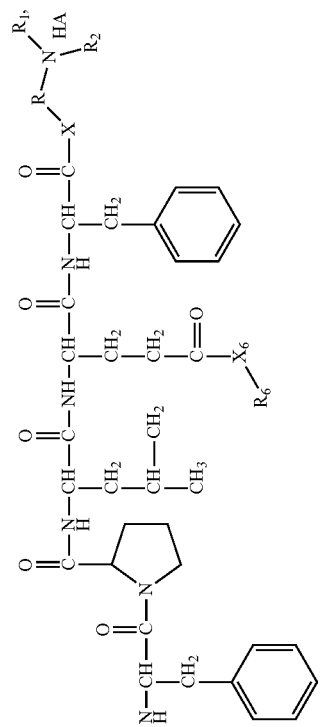
Structure 104 (SEQ ID NO: 24)
Structure 105 (SEQ ID NO: 25)
Structure 106 (SEQ ID NO: 25)

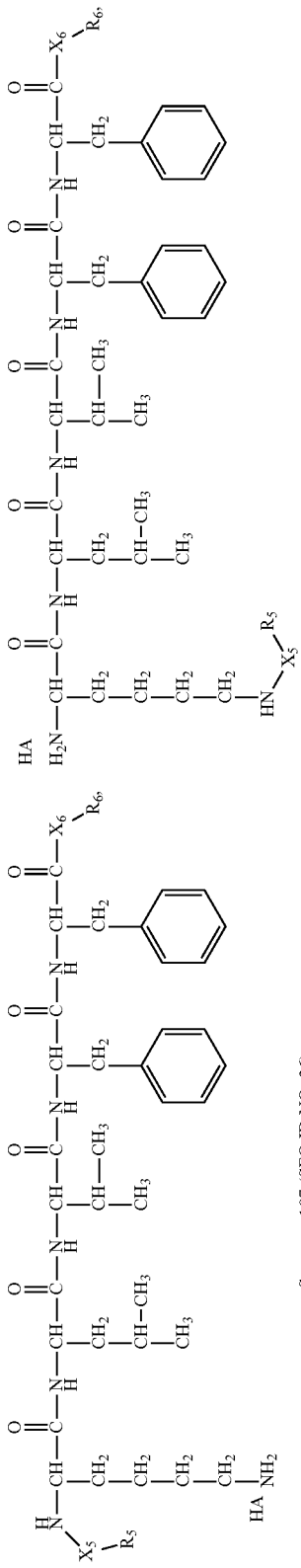
Structure 107 (SEQ ID NO: 26)
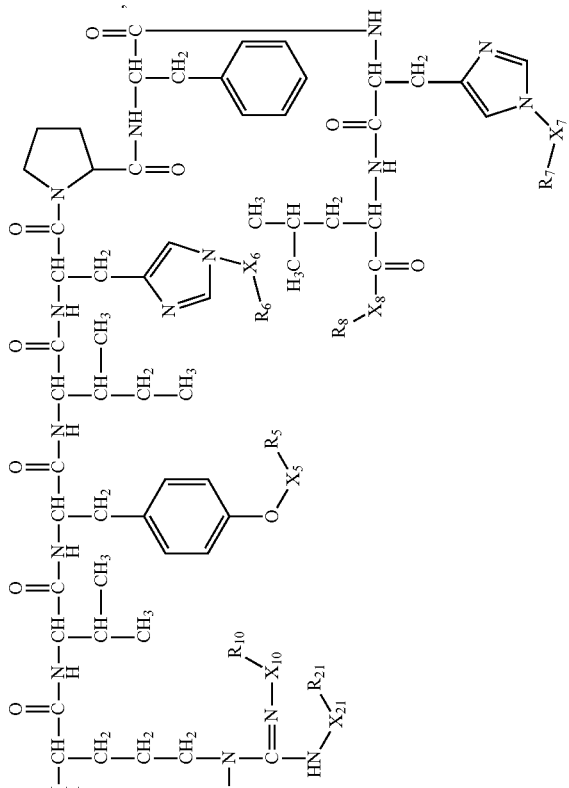
Structure 108 (SEQ ID NO: 26)
Structure 110 (SEQ ID NO: 27)
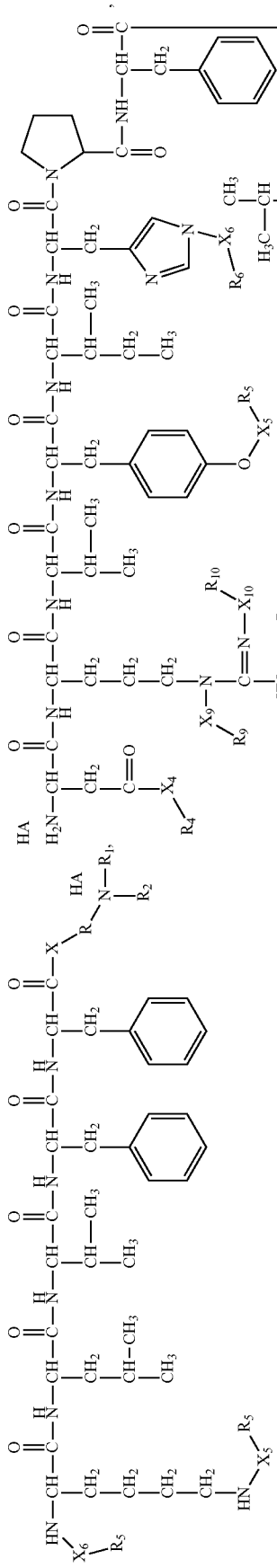
Structure 109 (SEQ ID NO: 26)

-continued
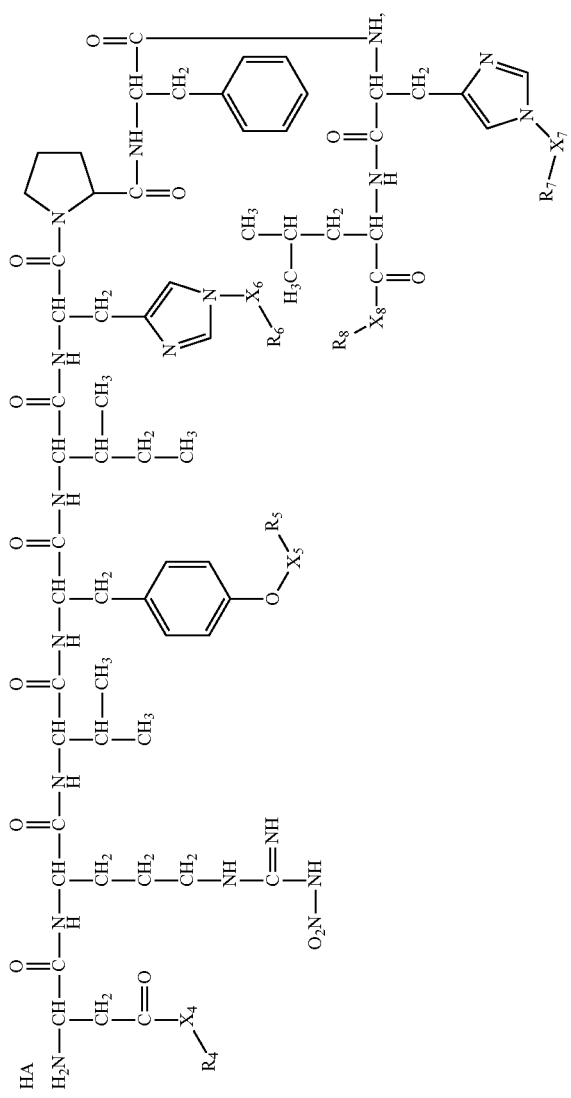
Structure 111 (SEQ ID NO: 27)
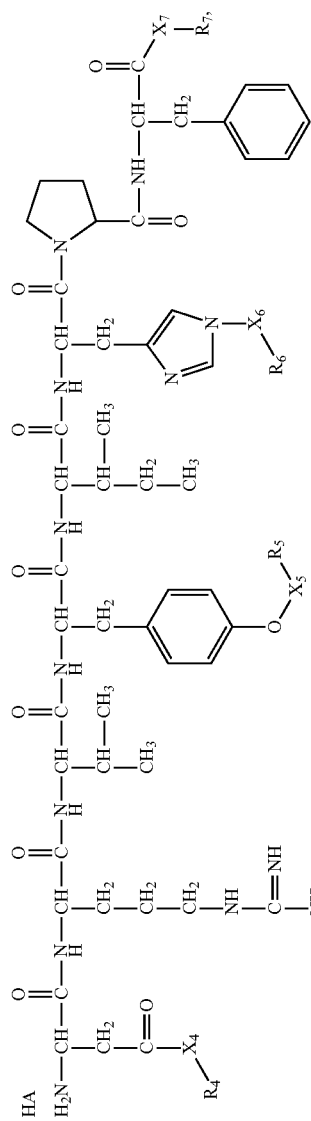
Structure 112 (SEQ ID NO: 28)

-continued
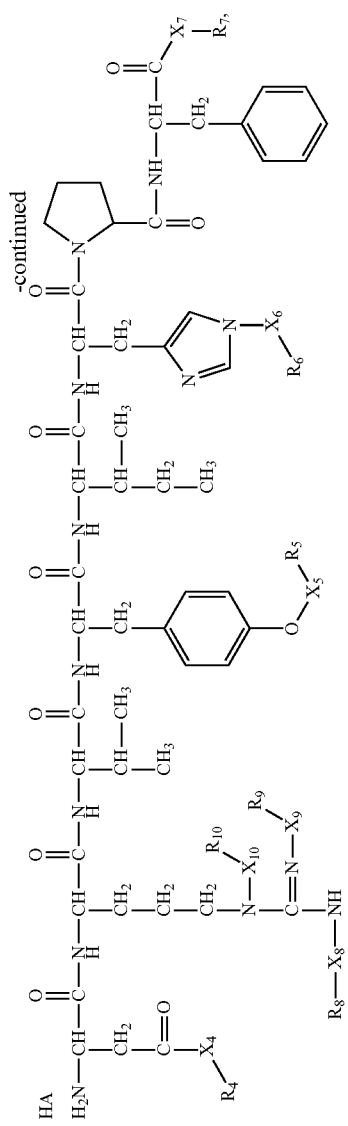
Structure 113 (SEQ ID NO: 28)
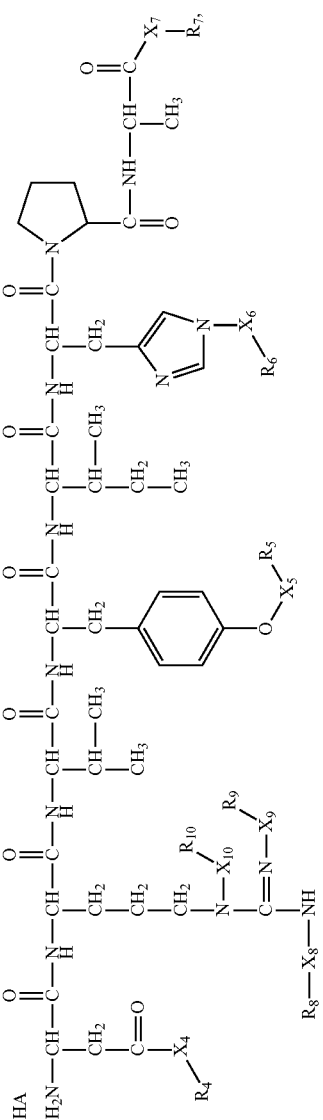
Structure 114 (SEQ ID NO: 29)
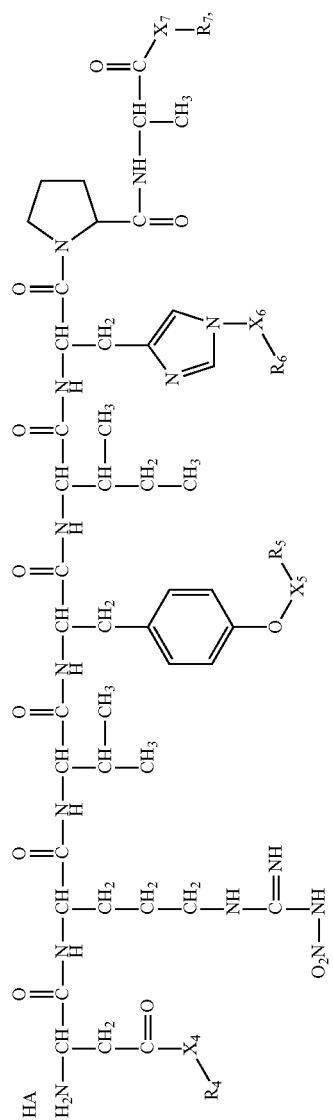
Structure 115 (SEQ ID NO: 29)

-continued
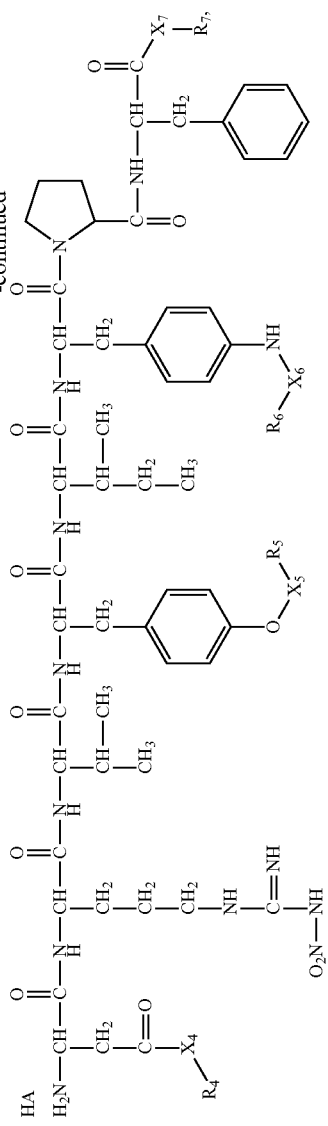
Structure 116 (SEQ ID NO: 30)
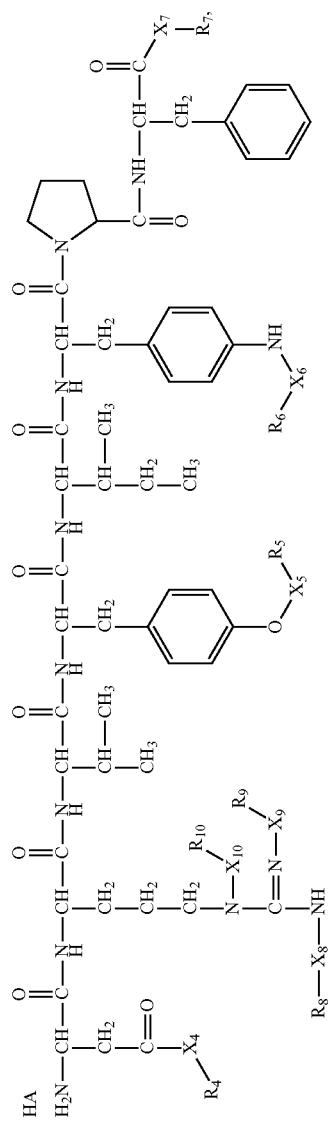
Structure 117 (SEQ ID NO: 30)
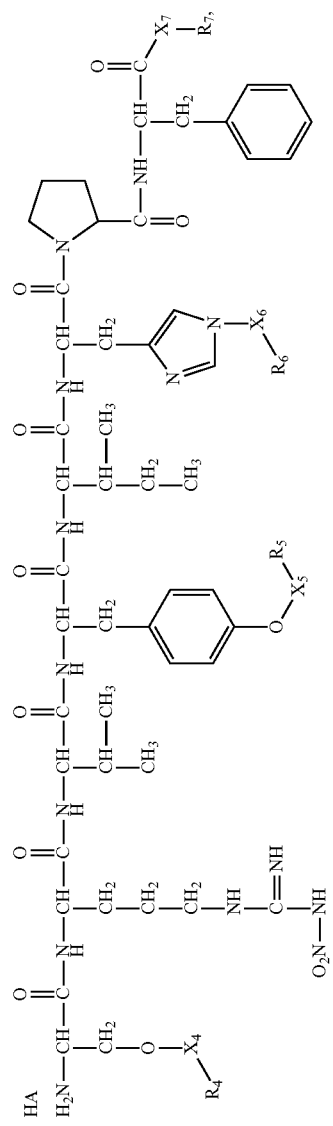
Structure 118 (SEQ ID NO: 31)

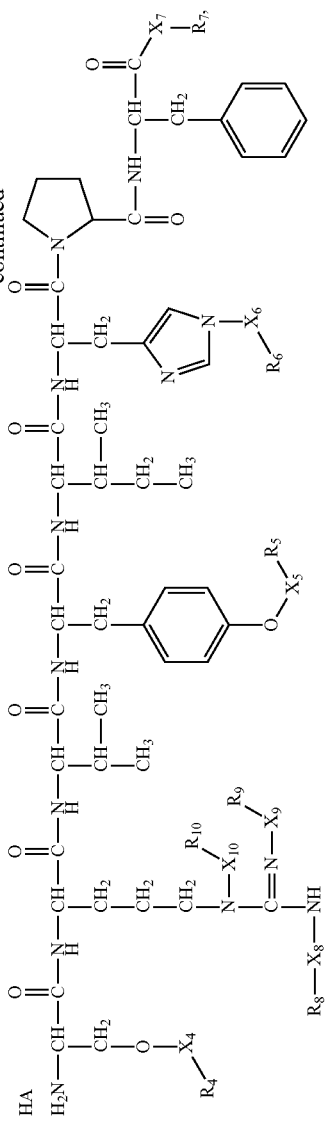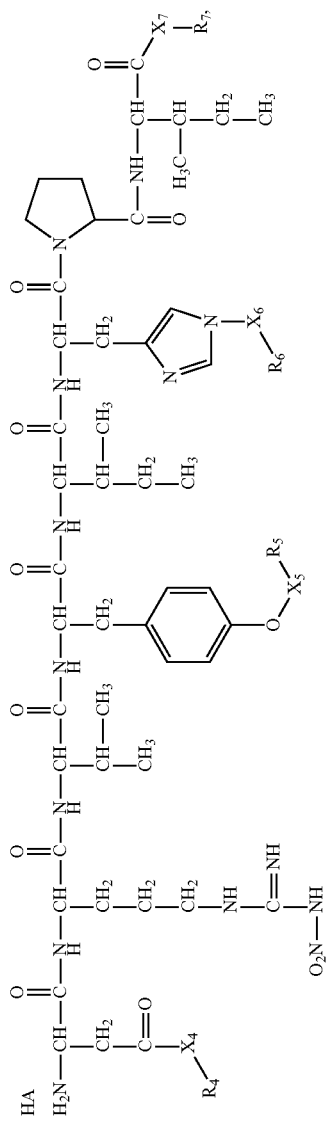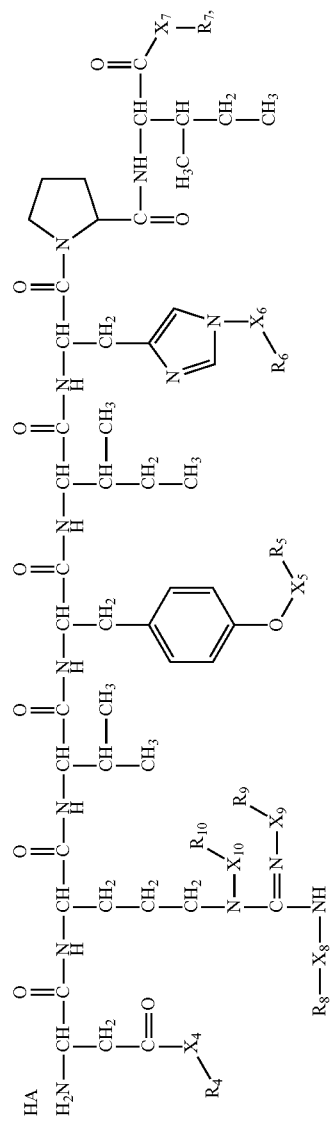

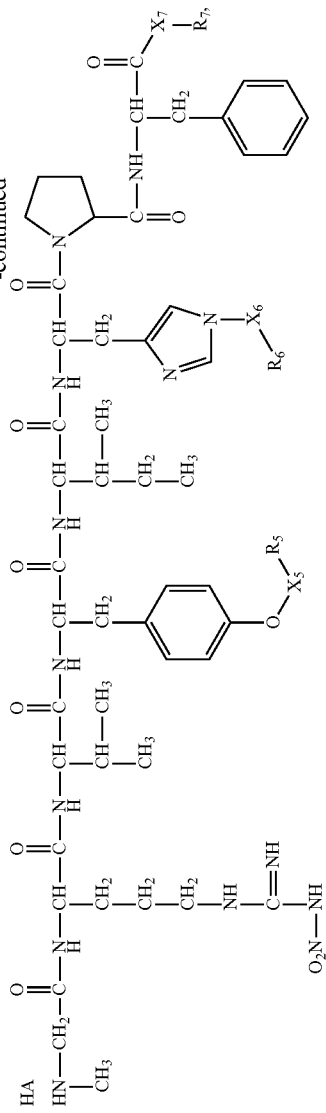
Structure 122 (SEQ ID NO: 33)
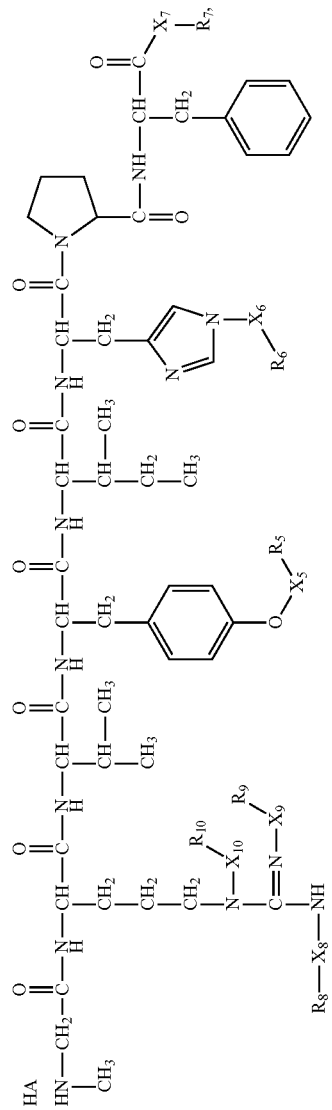
Structure 123 (SEQ ID NO: 33)
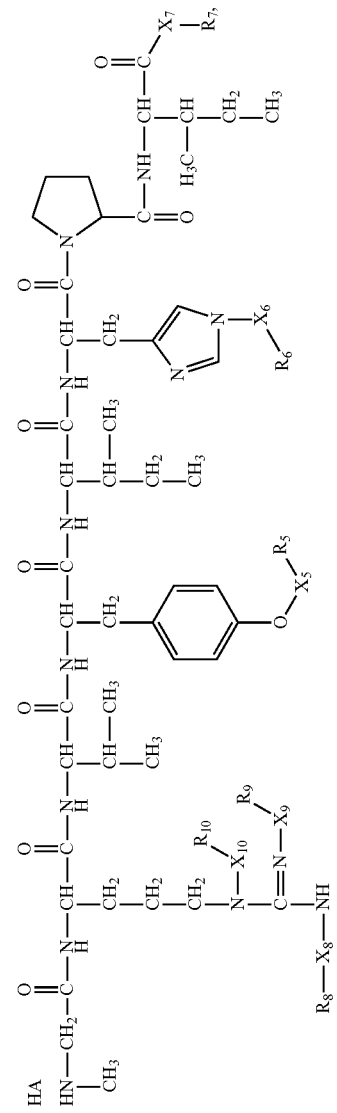
Structure 124 (SEQ ID NO: 34)

-continued
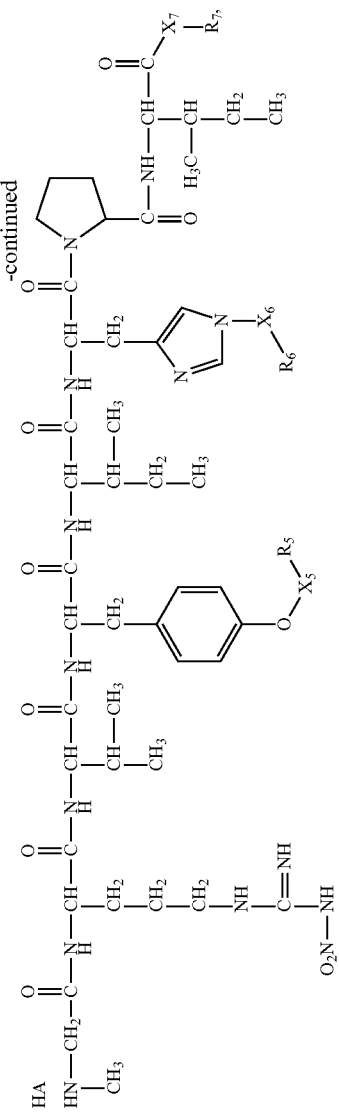
Structure 125 (SEQ ID NO: 34)
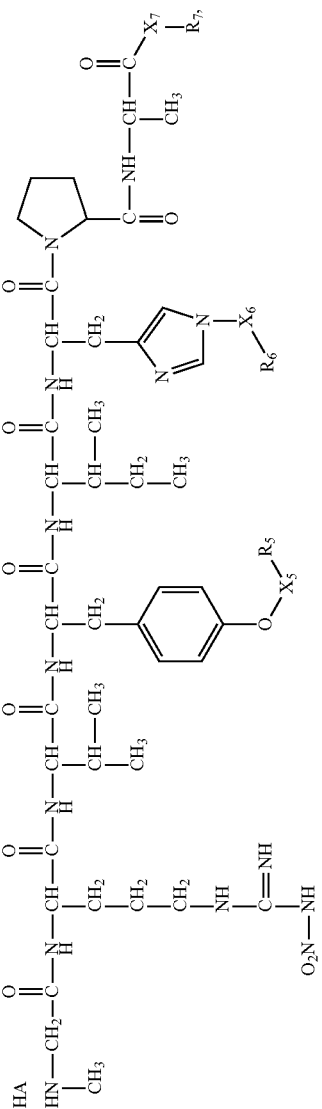
Structure 126 (SEQ ID NO: 35)
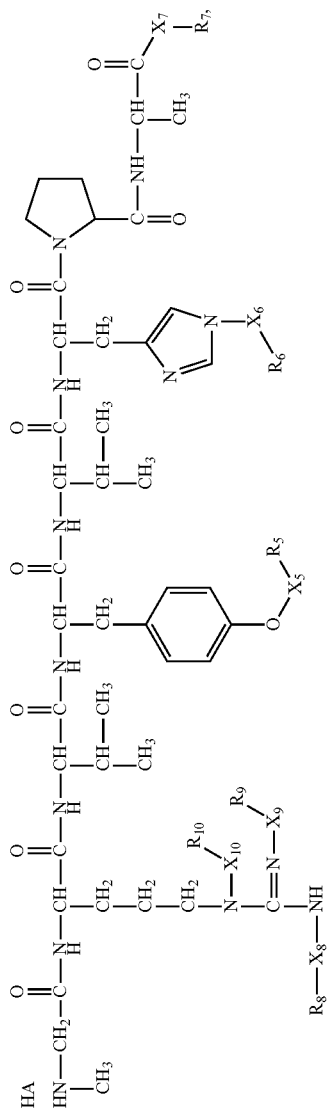
Structure 127 (SEQ ID NO: 35)

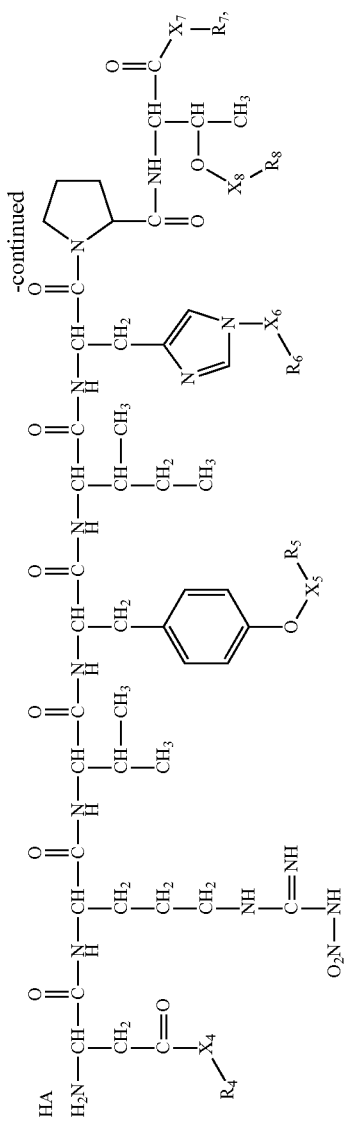
Structure 128 (SEQ ID NO: 36)
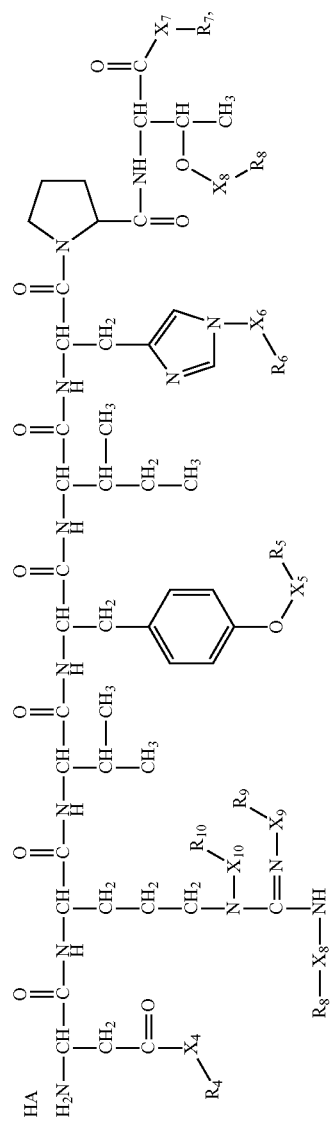
Structure 129 (SEQ ID NO: 36)
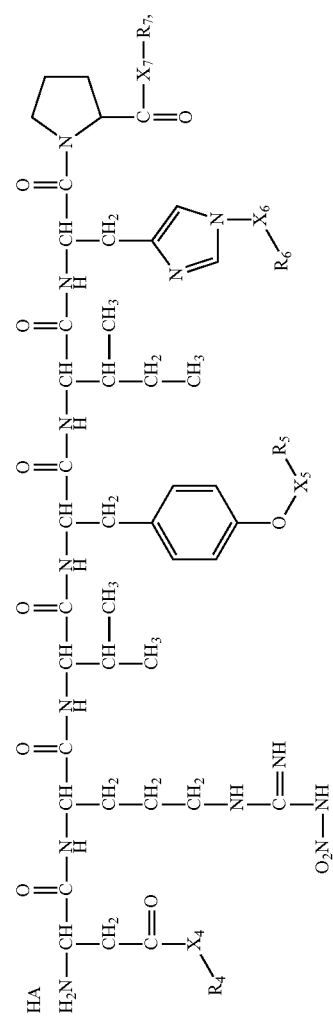
Structure 130 (SEQ ID NO: 37)

-continued
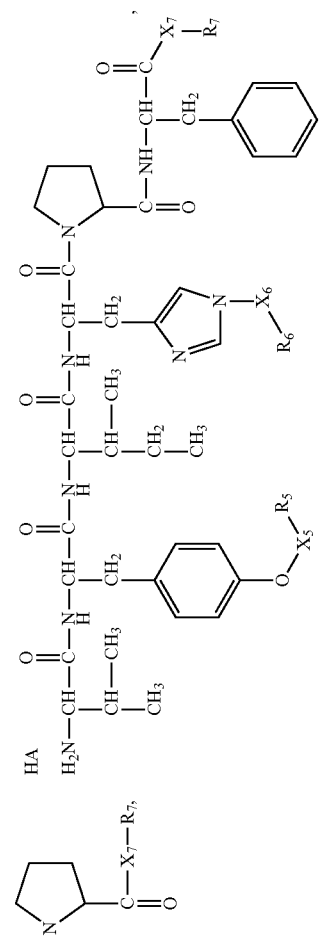
Structure 131 (SEQ ID NO: 37)
Structure 133 (SEQ ID NO: 39)
Structure 134 (SEQ ID NO: 39)
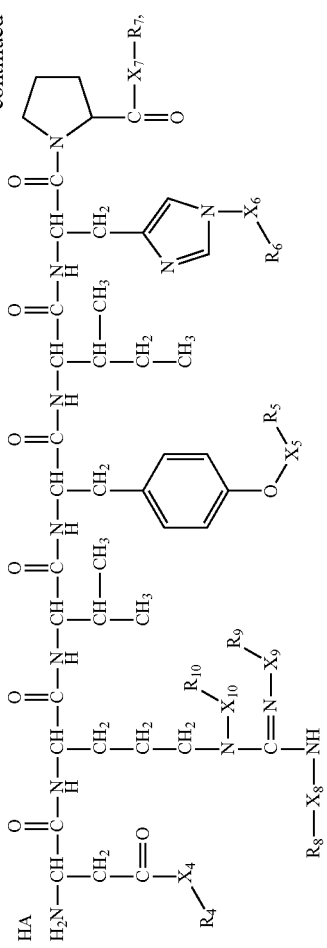
Structure 132 (SEQ ID NO: 38)
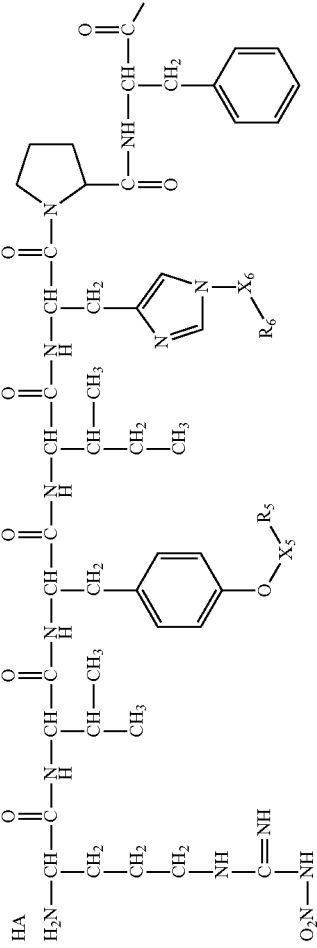
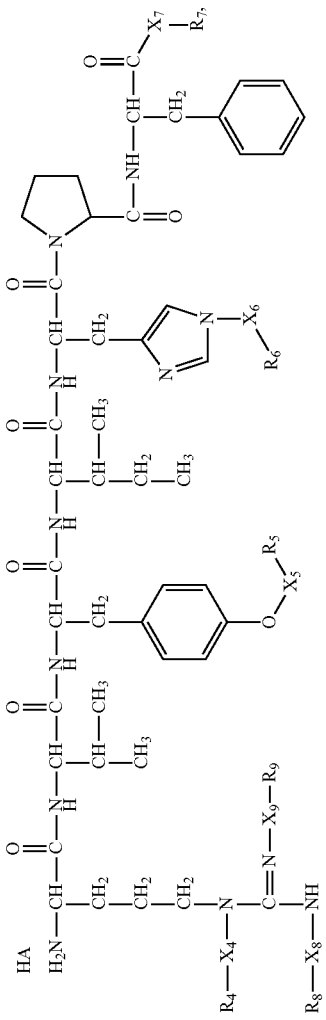

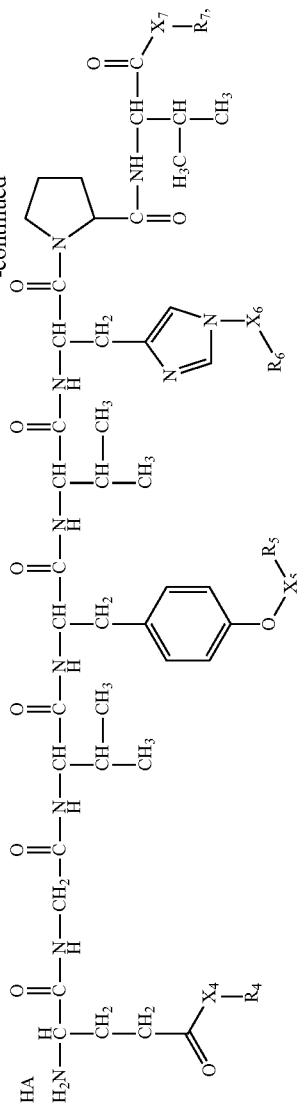
-continued
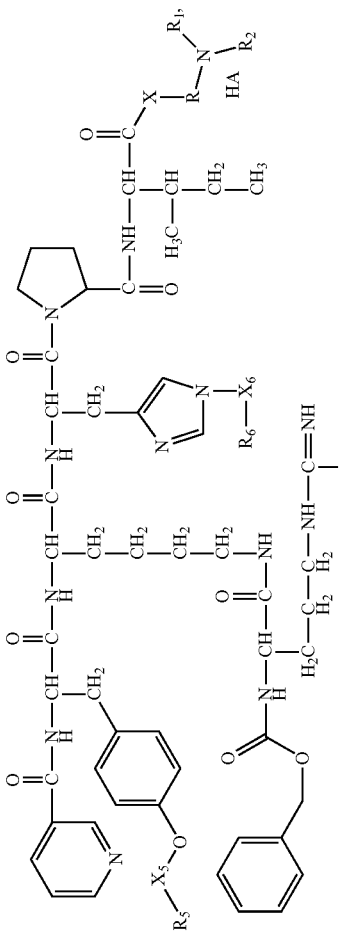
Structure 135 (SEQ ID NO: 40)
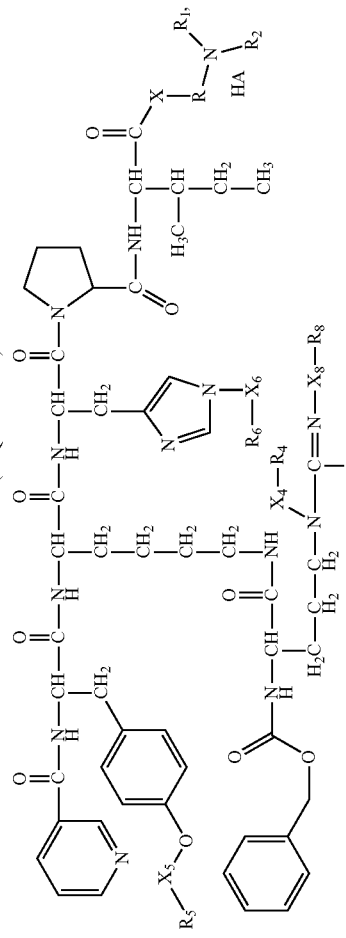
Structure 136 (SEQ ID NO: 41)
Structure 137 (SEQ ID NO: 41)

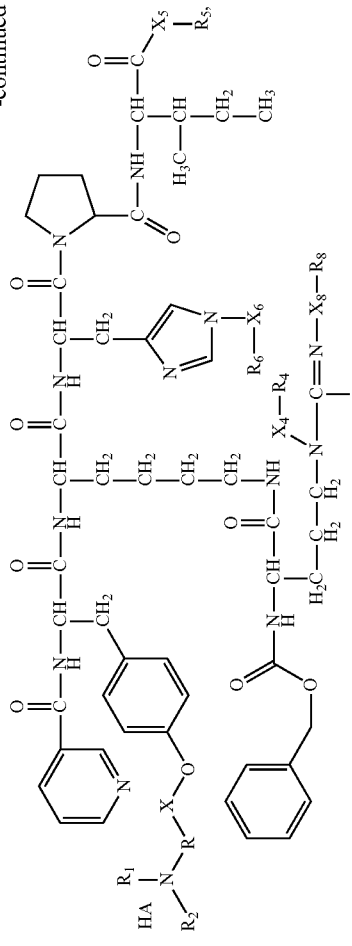
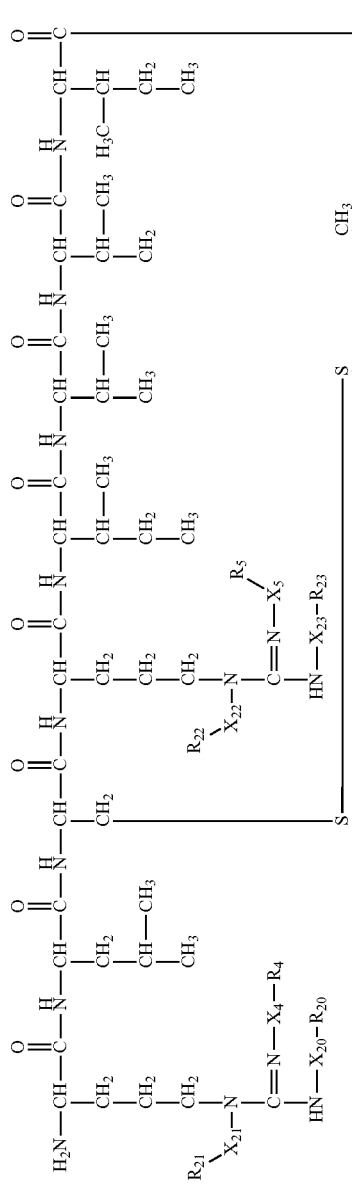
Structure 138 (SEQ ID NO: 41)
Structure 139 (SEQ ID NO: 42)

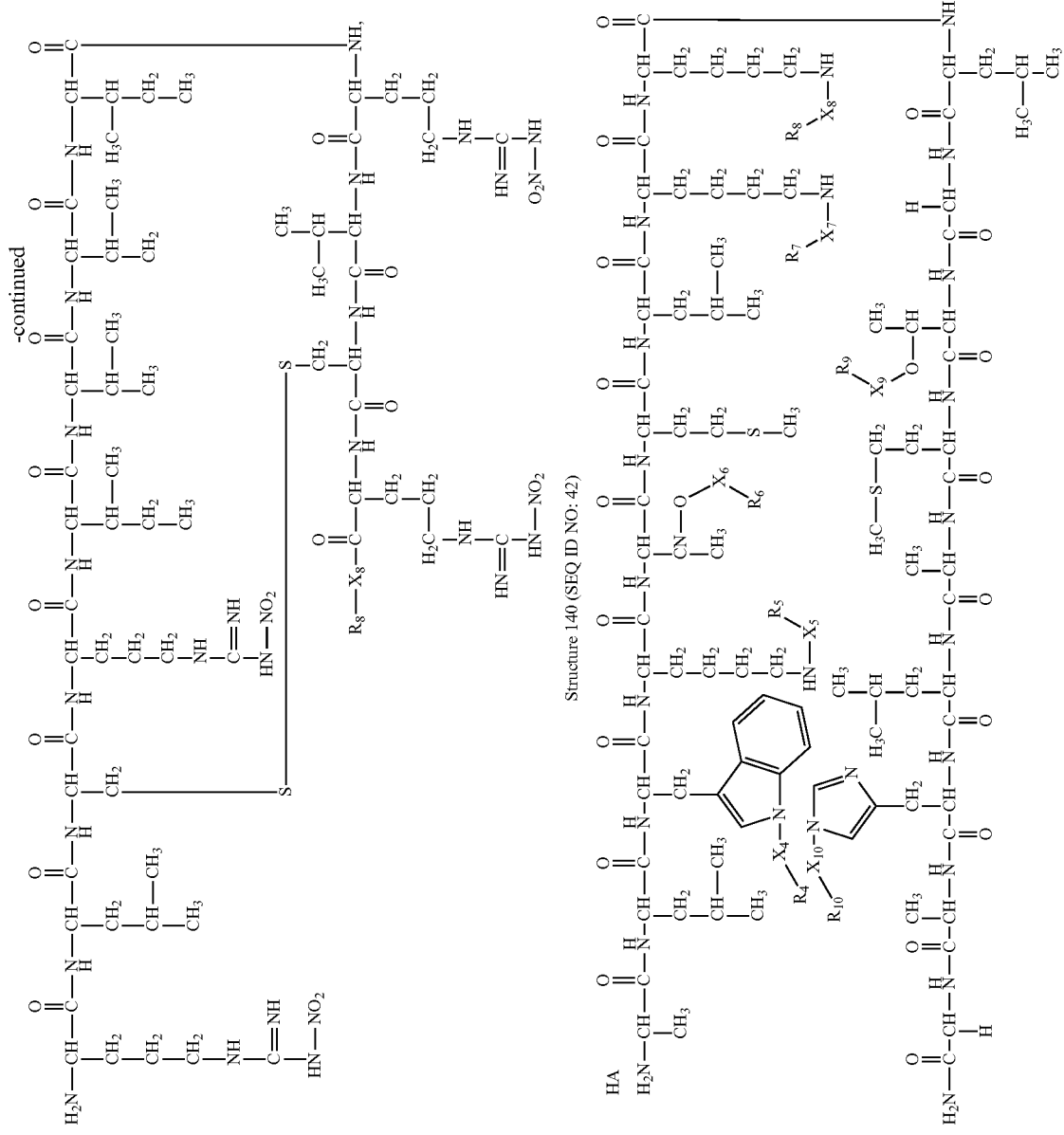
Structure 140 (SEQ ID NO: 42)
Structure 141 (SEQ ID NO: 43)

-continued
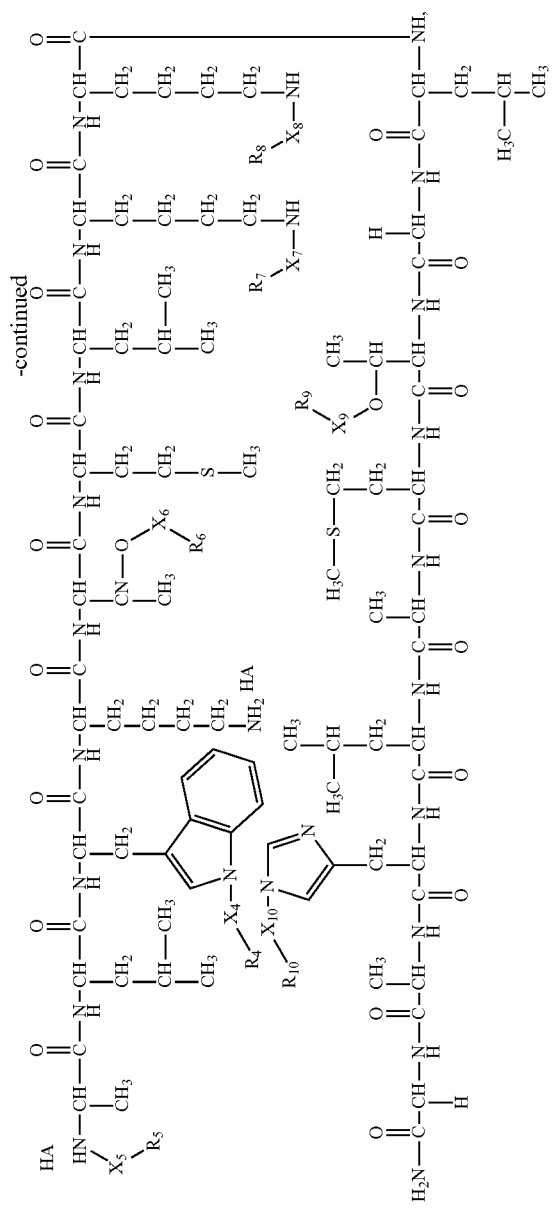
Structure 142 (SEQ ID NO: 43)
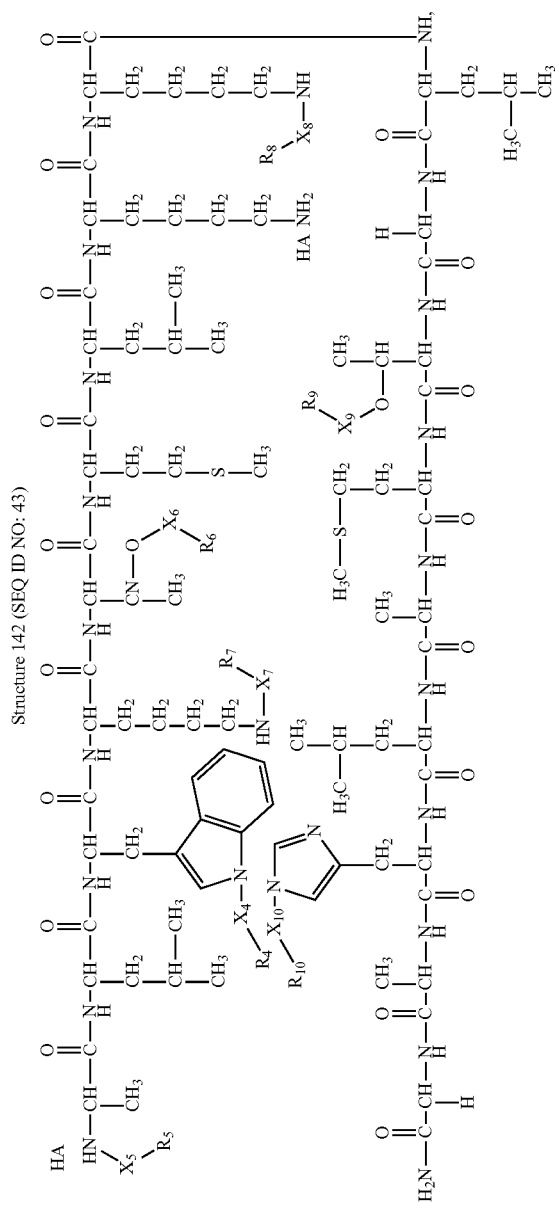
Structure 143 (SEQ ID NO: 43)

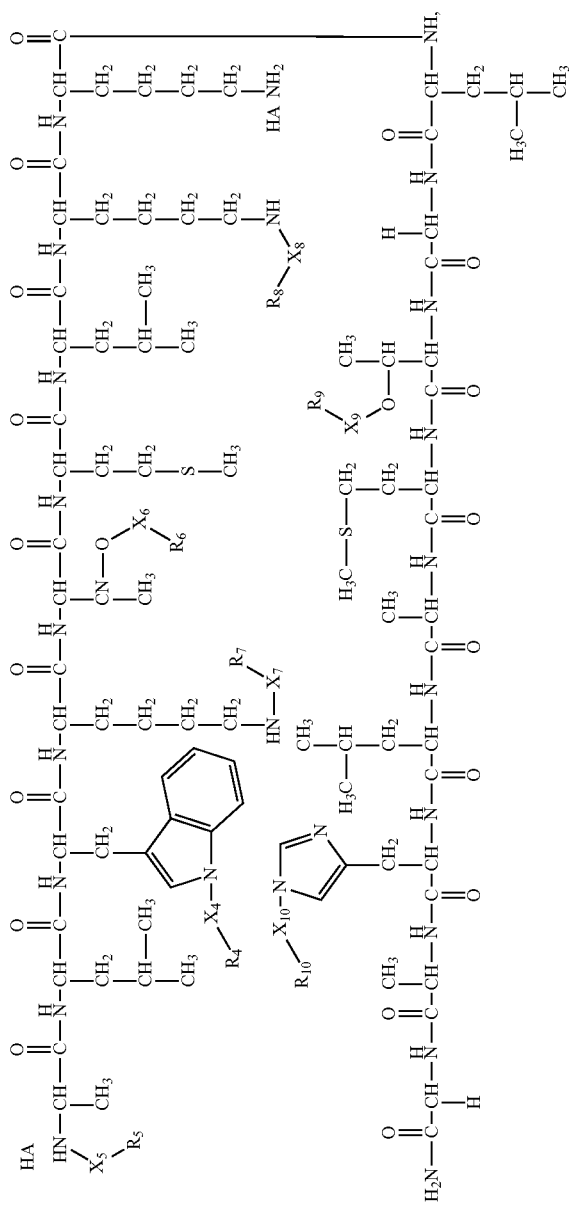
Structure 144 (SEQ ID NO: 43)

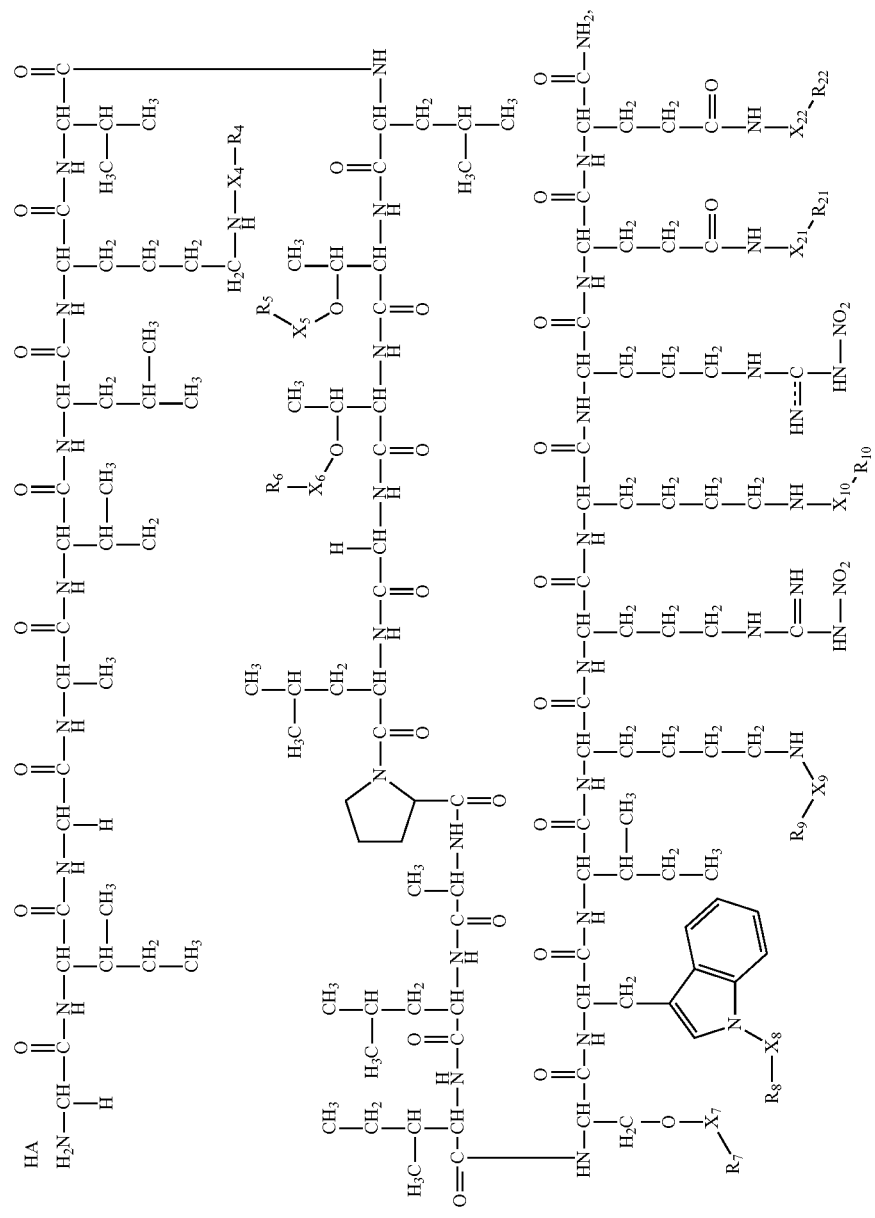
Structure 145 (SEQ ID NO: 44)

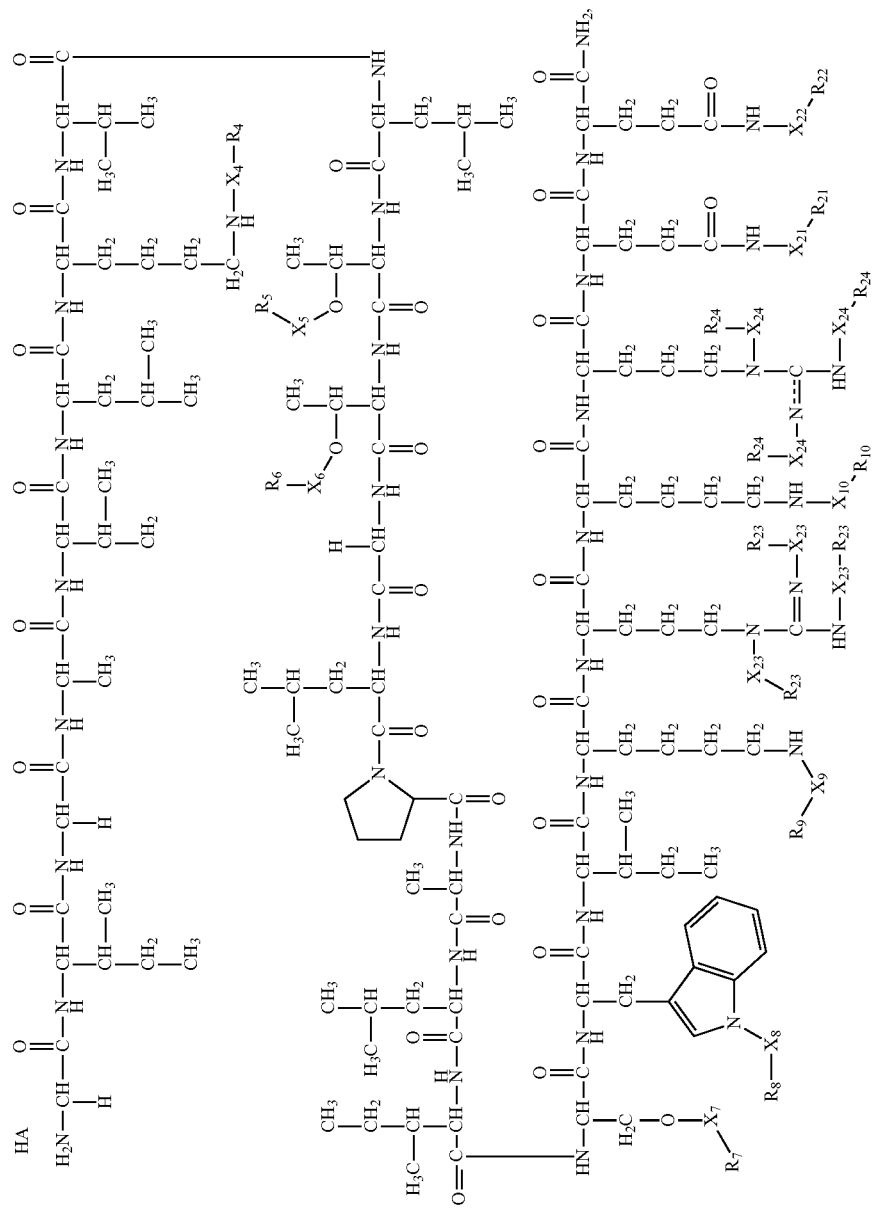
Structure 146 (SEQ ID NO: 44)

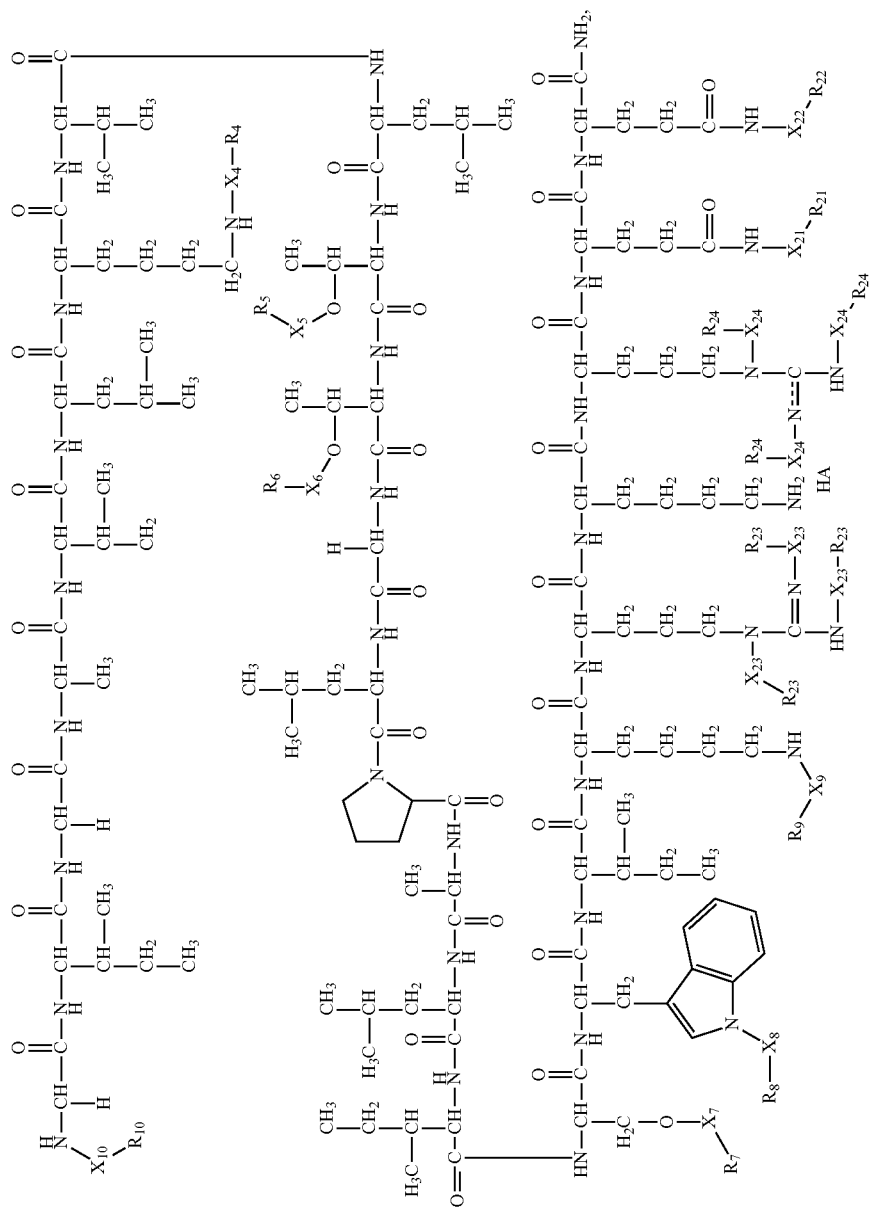
Structure 147 (SEQ ID NO: 44)

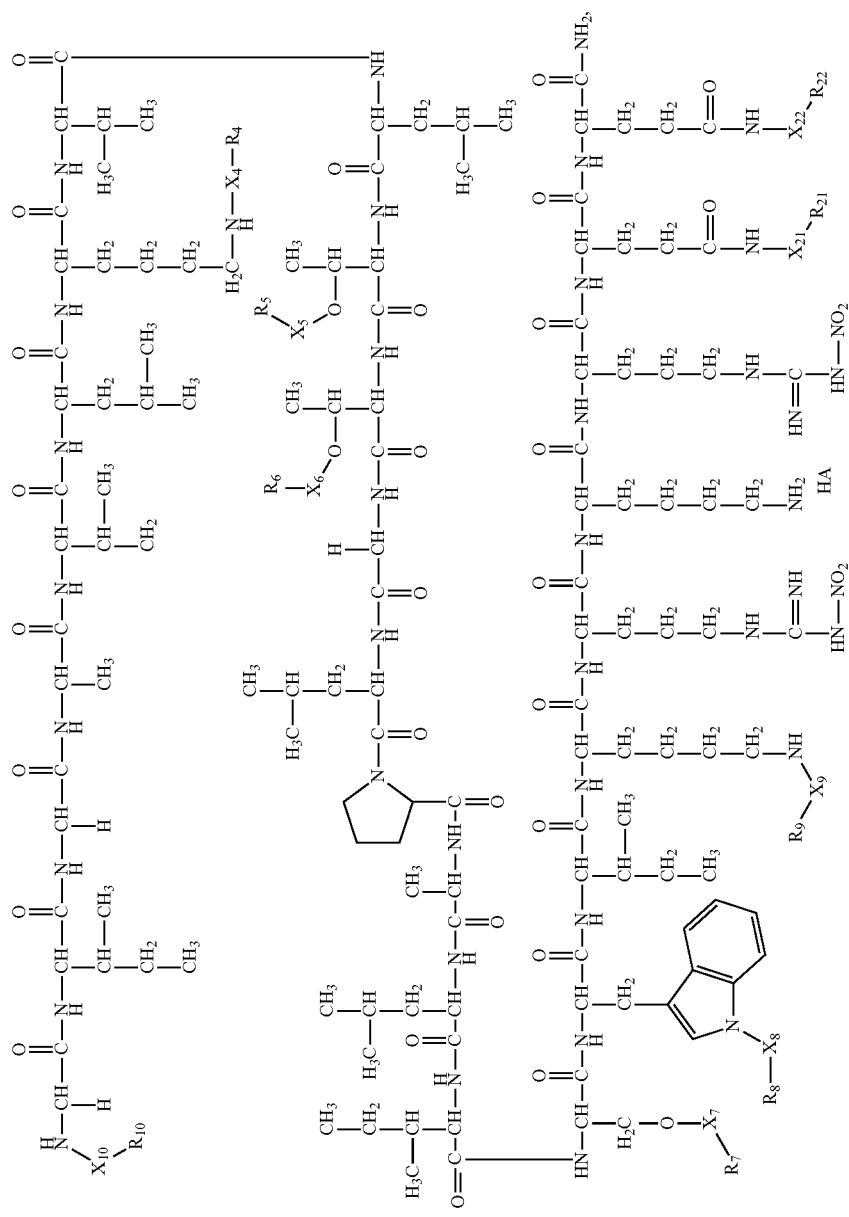
Structure 148 (SEQ ID NO: 44)

-continued
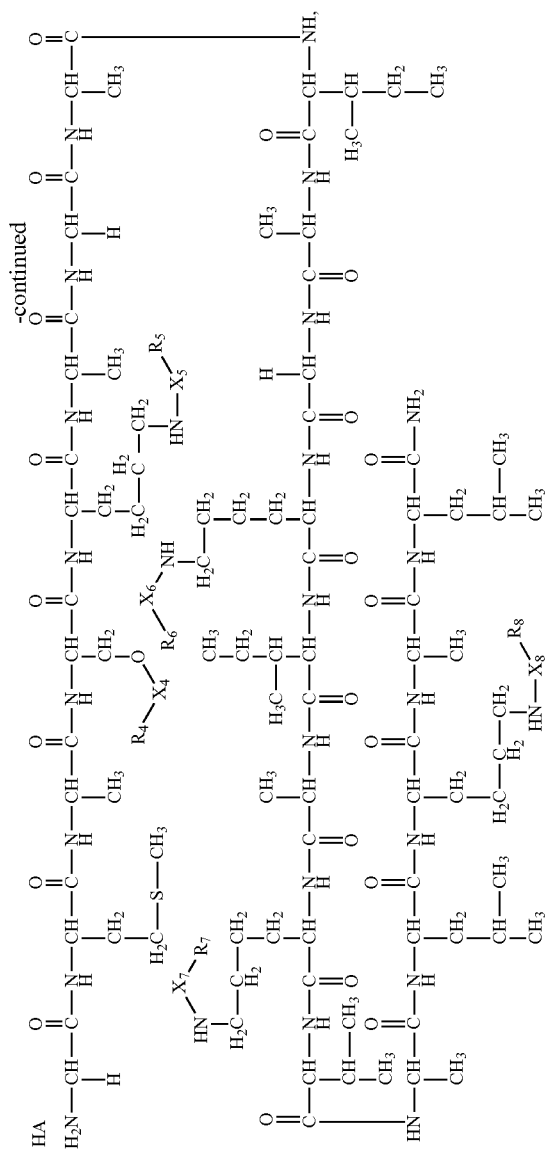
Structure 149 (SEQ ID NO: 45)
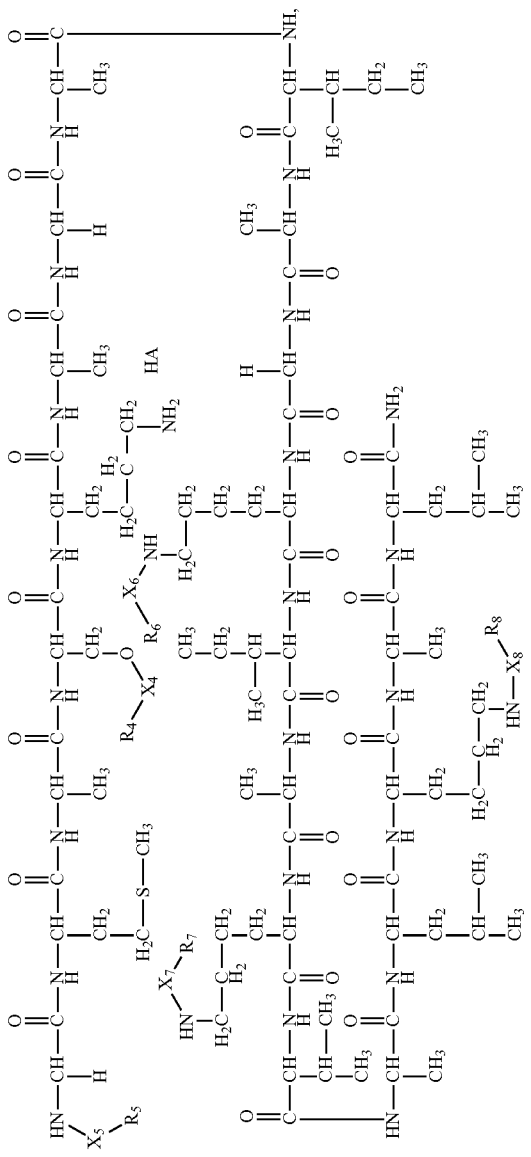
Structure 150 (SEQ ID NO: 45)

-continued
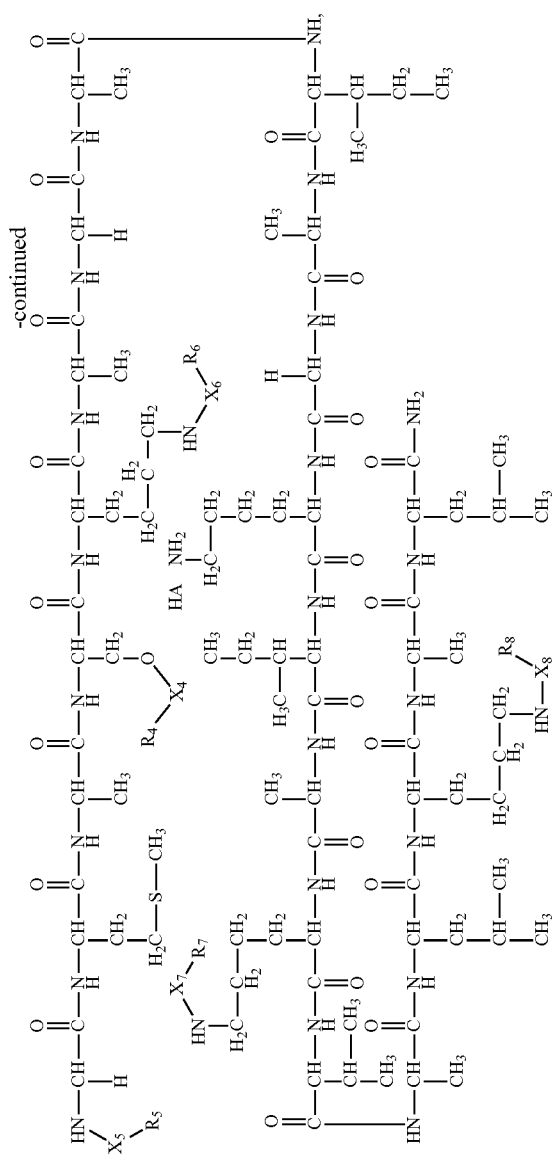
Structure 151 (SEQ ID NO: 45)
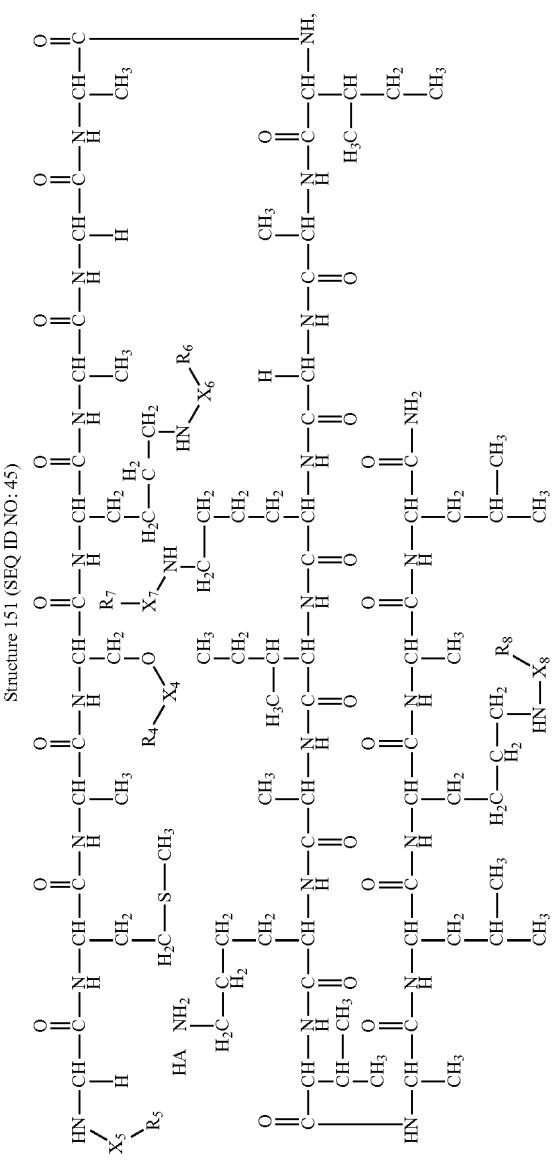
Structure 152 (SEQ ID NO: 45)

-continued
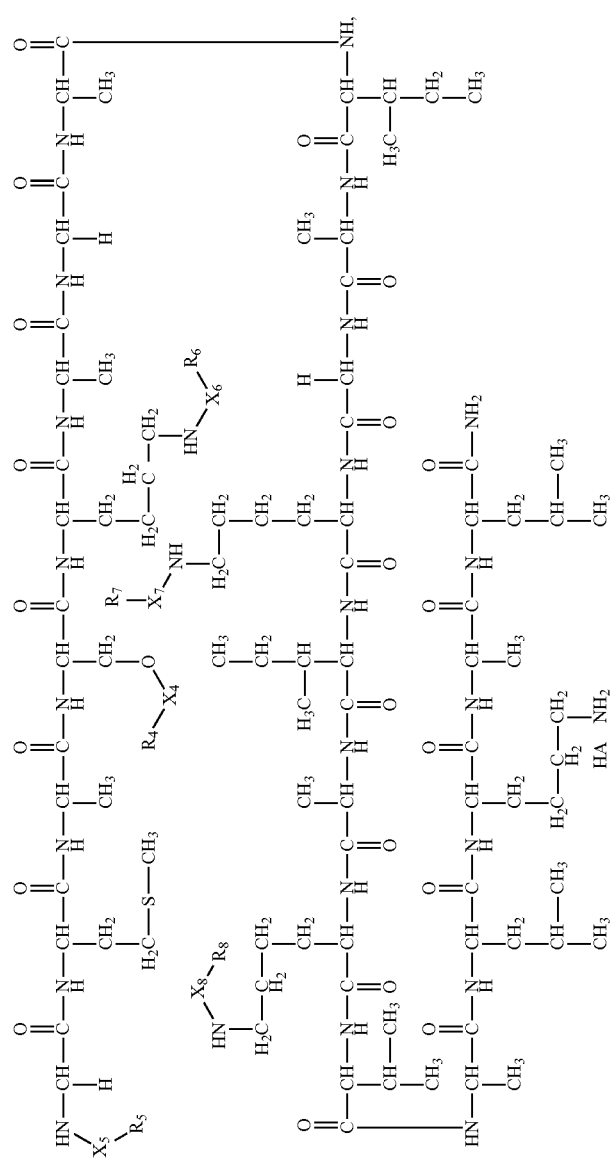
Structure 153 (SEQ ID NO: 45)
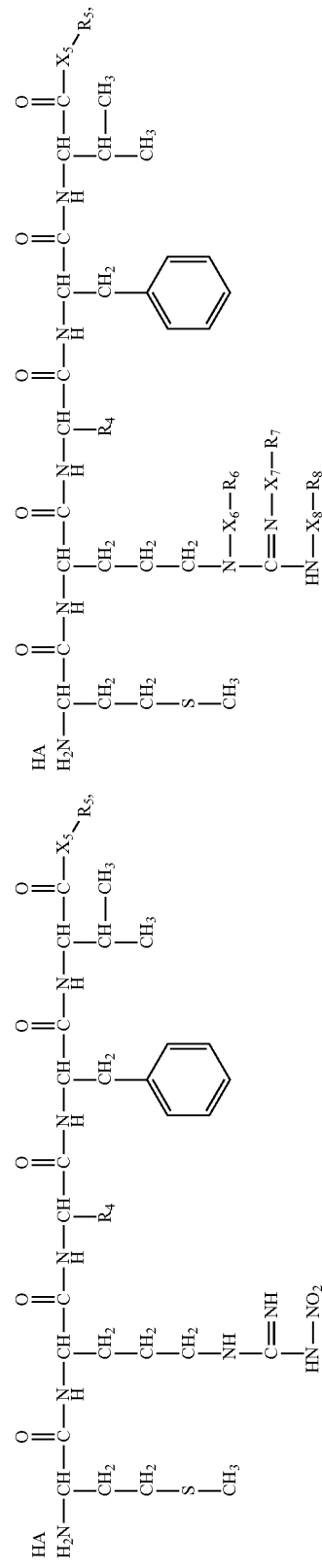
Structure 154 (SEQ ID NO: 46)
Structure 155 (SEQ ID NO: 46)

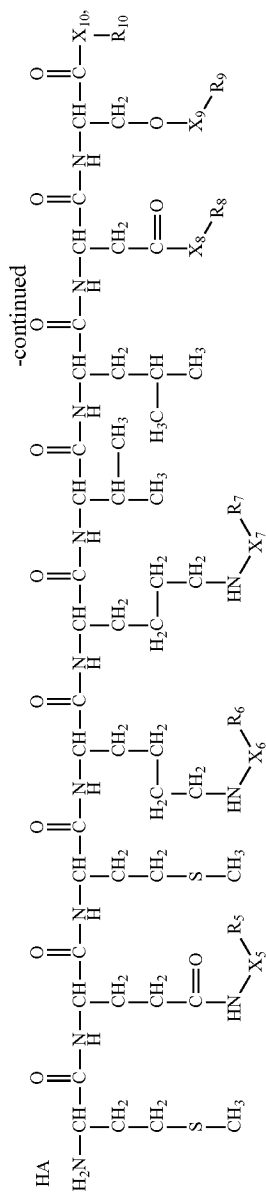
Structure 156 (SEQ ID NO: 47)
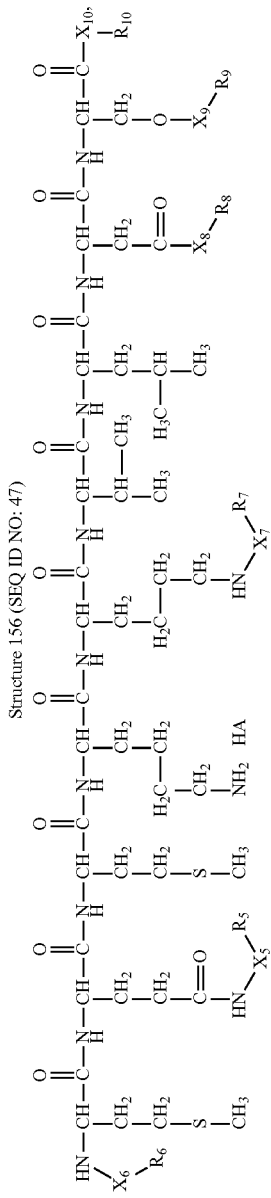
Structure 157 (SEQ ID NO: 47)
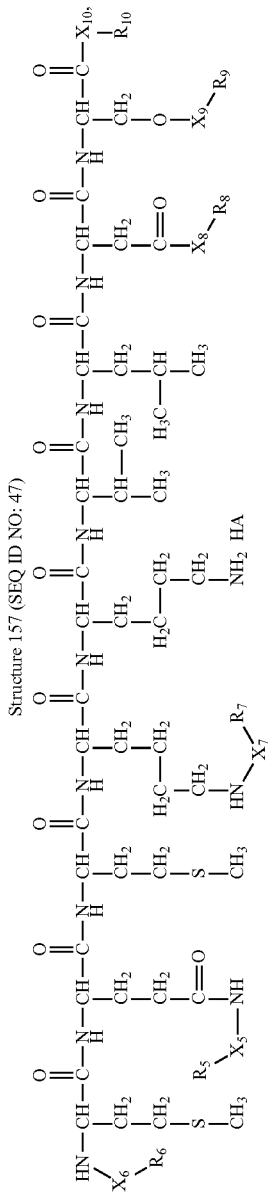
Structure 158 (SEQ ID NO: 47)
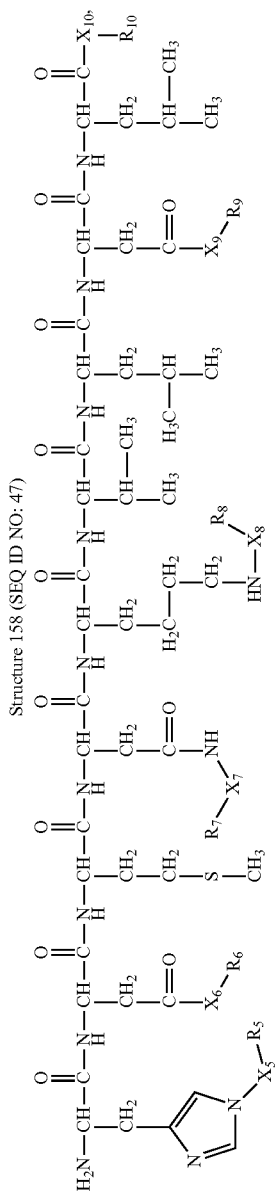
Structure 159 (SEQ ID NO: 48)

-continued
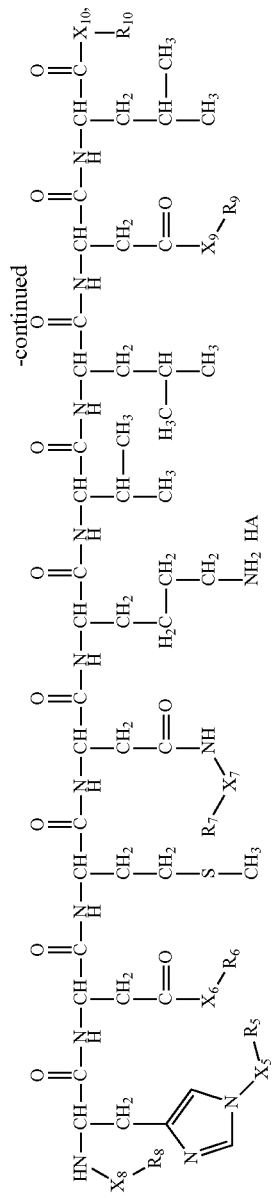
Structure 160 (SEQ ID NO: 48)
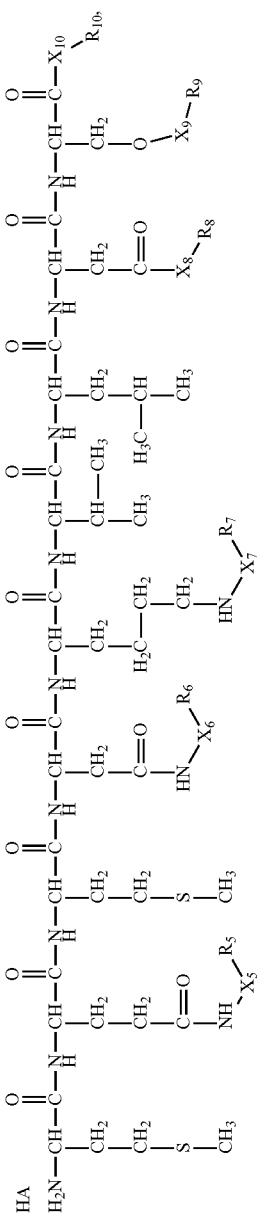
Structure 161 (SEQ ID NO: 49)
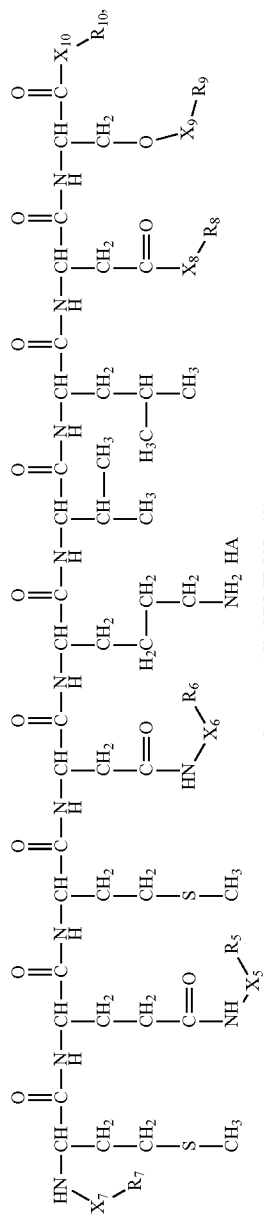
Structure 162 (SEQ ID NO: 49)

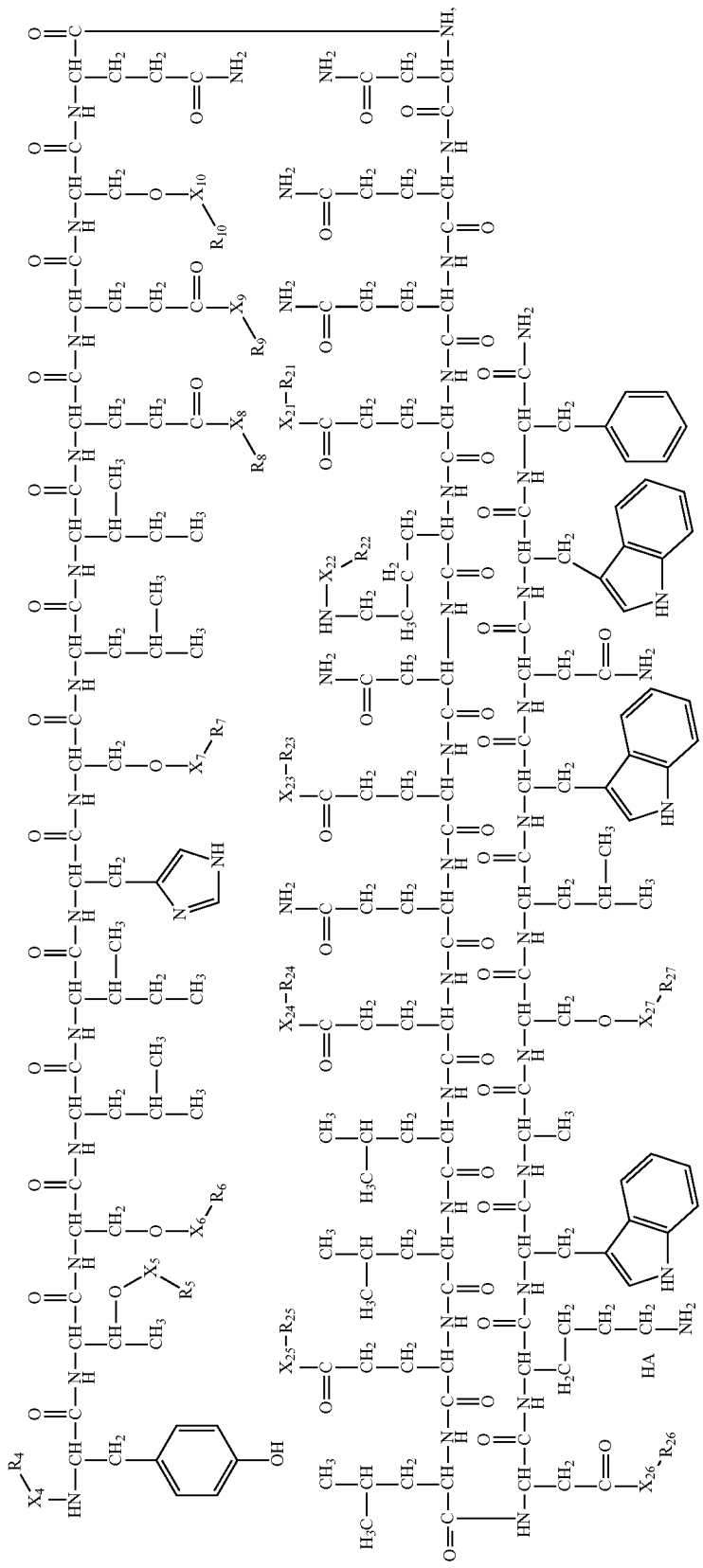
Structure 163 (SEQ ID NO: 50)

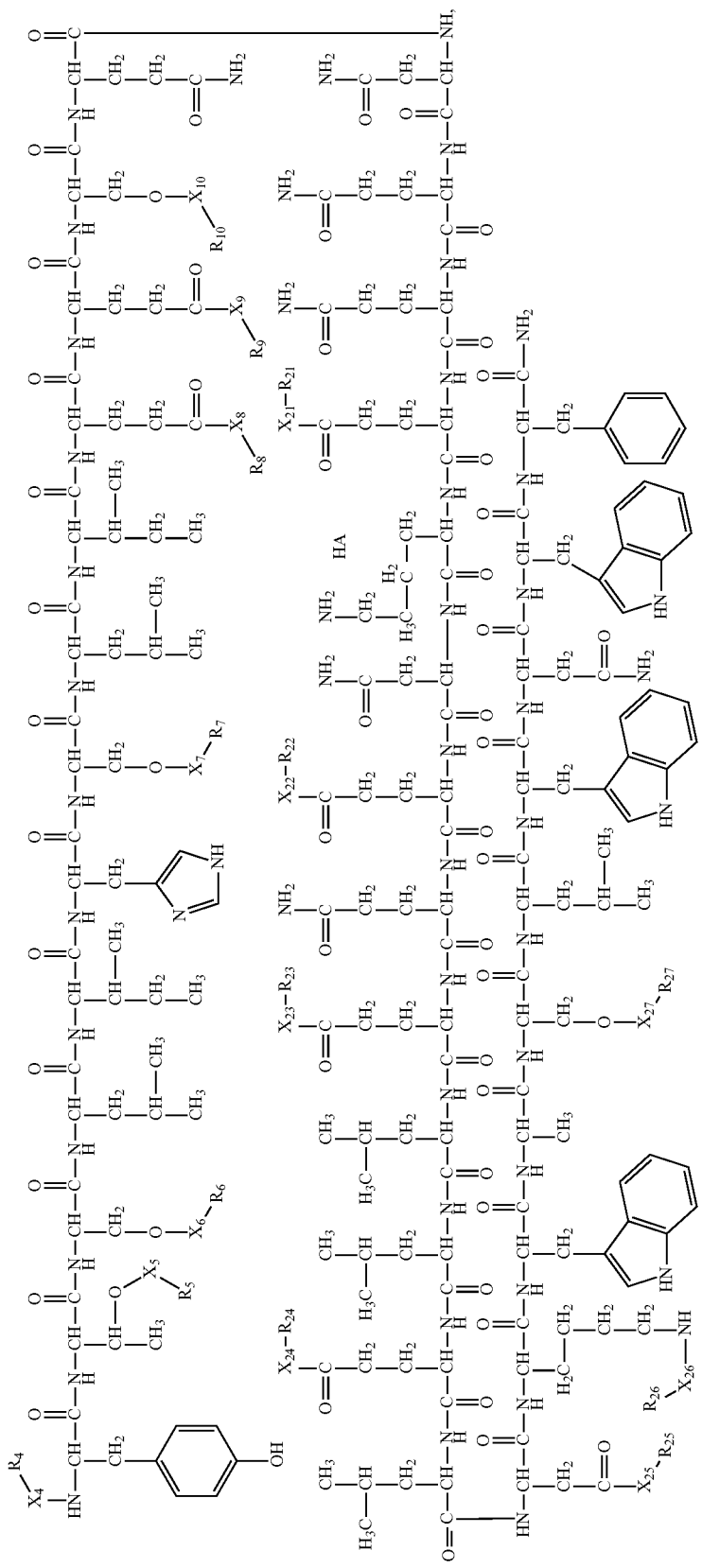
Structure 164 (SEQ ID NO: 50)

-continued
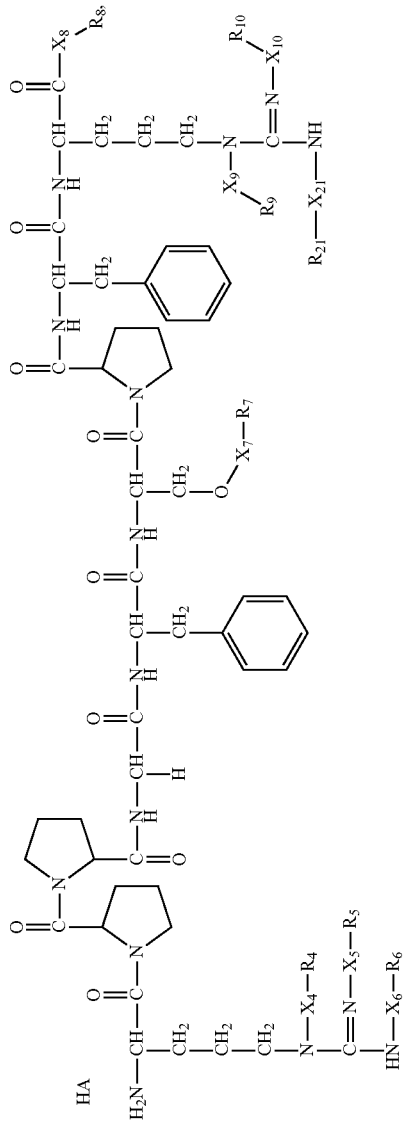
Structure 165 (SEQ ID NO: 51)
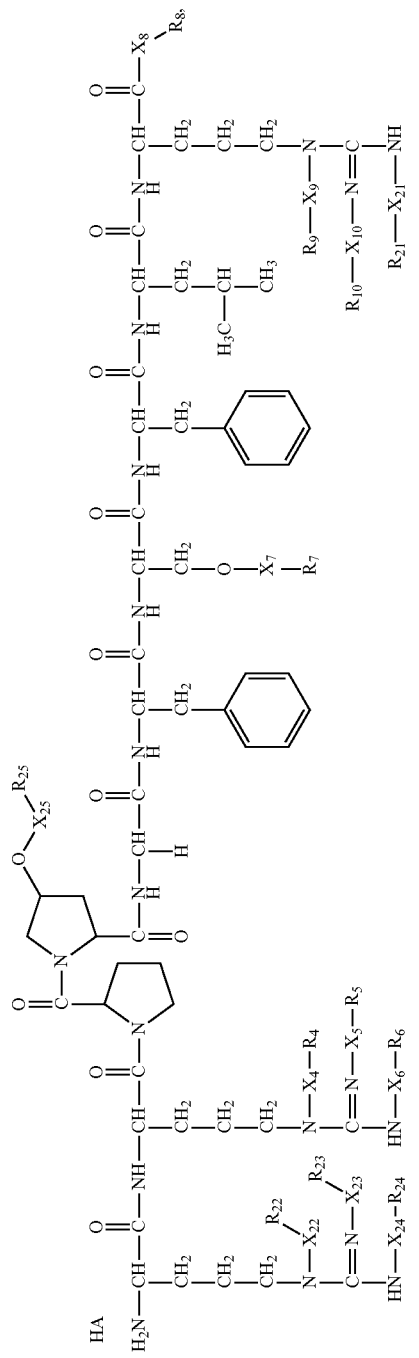
Structure 166 (SEQ ID NO: 52)

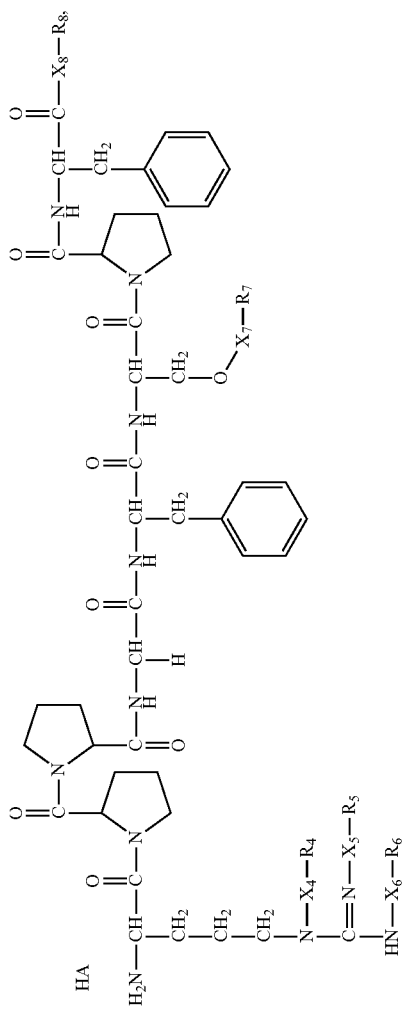
Structure 167 (SEQ ID NO: 53)
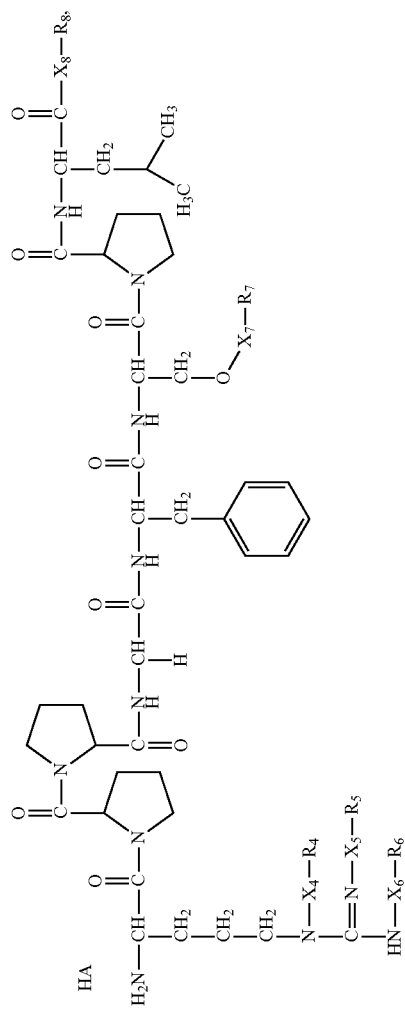
Structure 168 (SEQ ID NO: 54)

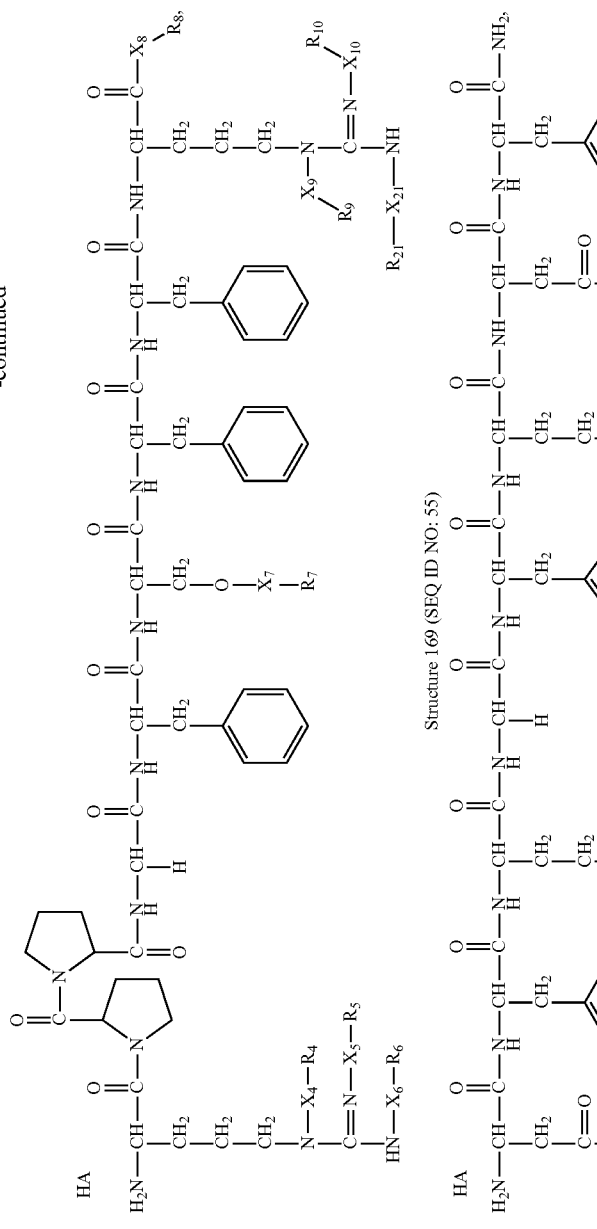
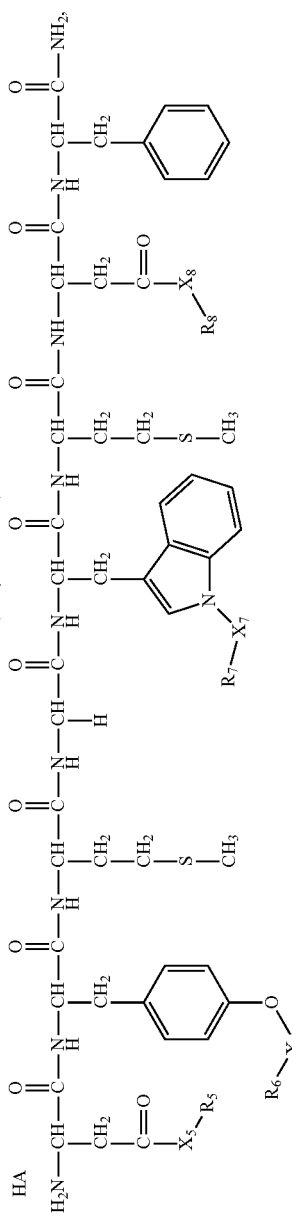
Structure 169 (SEQ ID NO: 55)
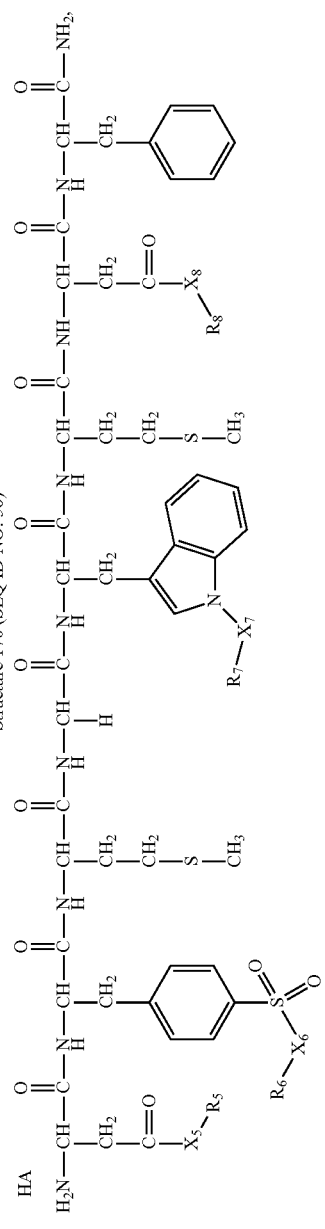
Structure 170 (SEQ ID NO: 56)
Structure 171 (SEQ ID NO: 56)

-continued
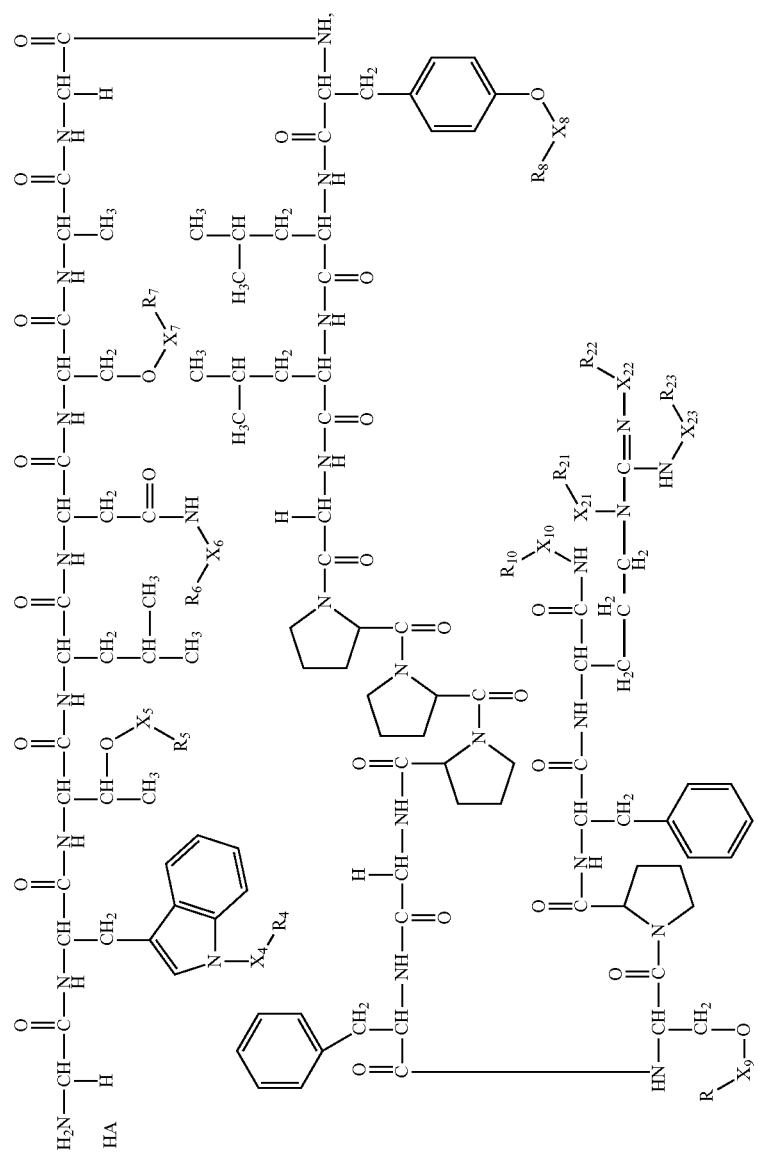
Structure 172 (SEQ ID NO: 57)

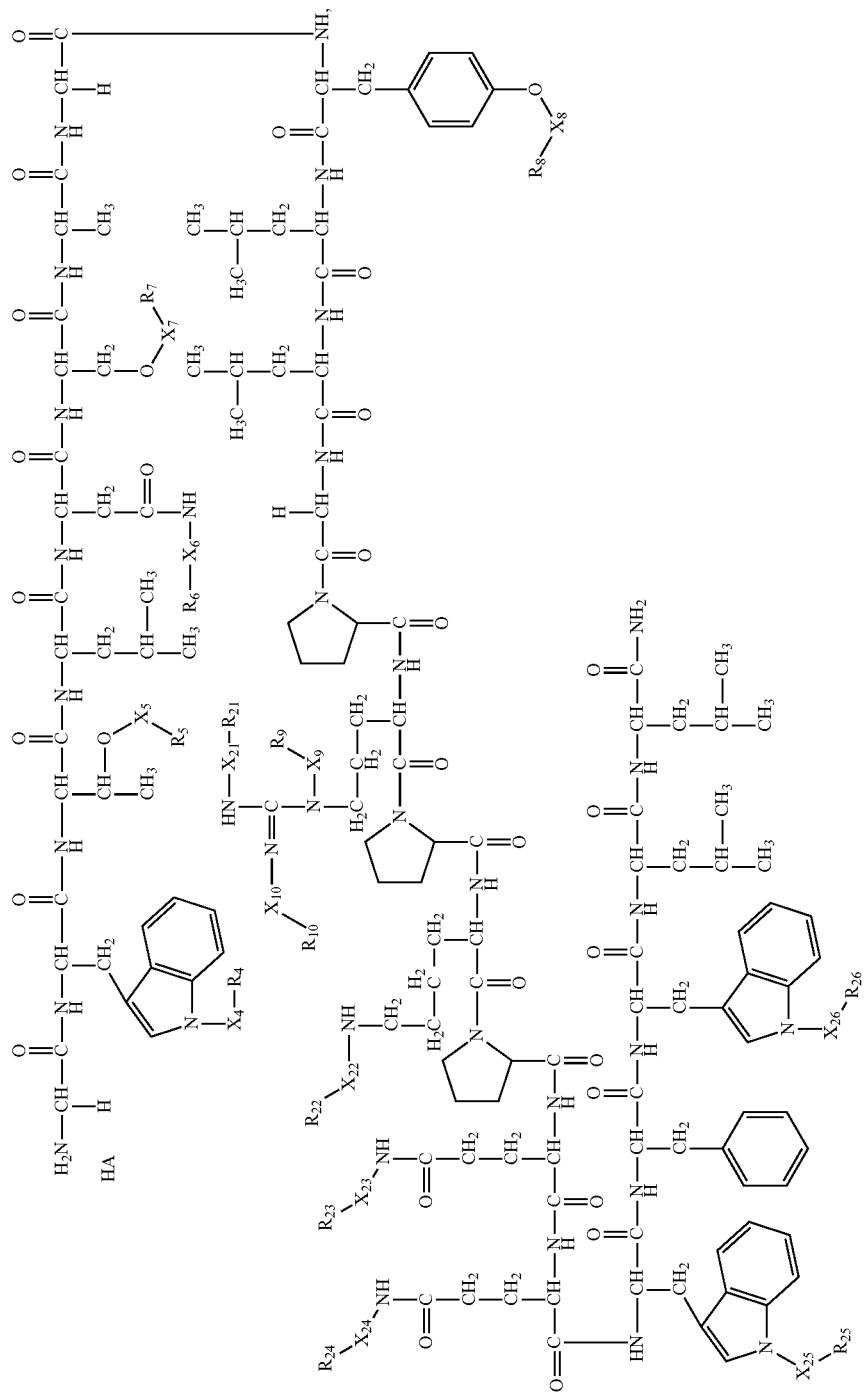
Structure 173 (SEQ ID NO: 58)

-continued
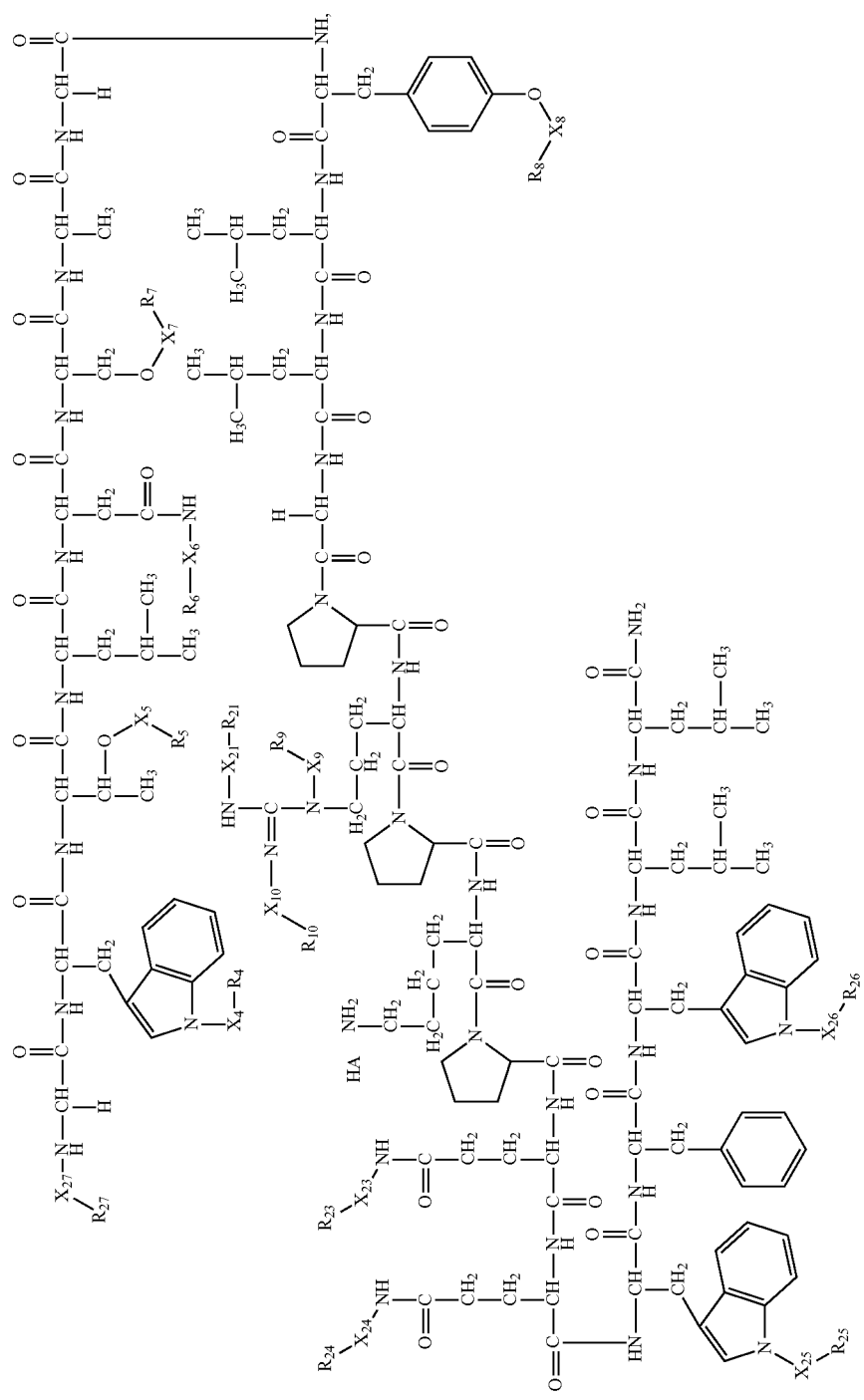
Structure 174 (SEQ ID NO: 58)

-continued
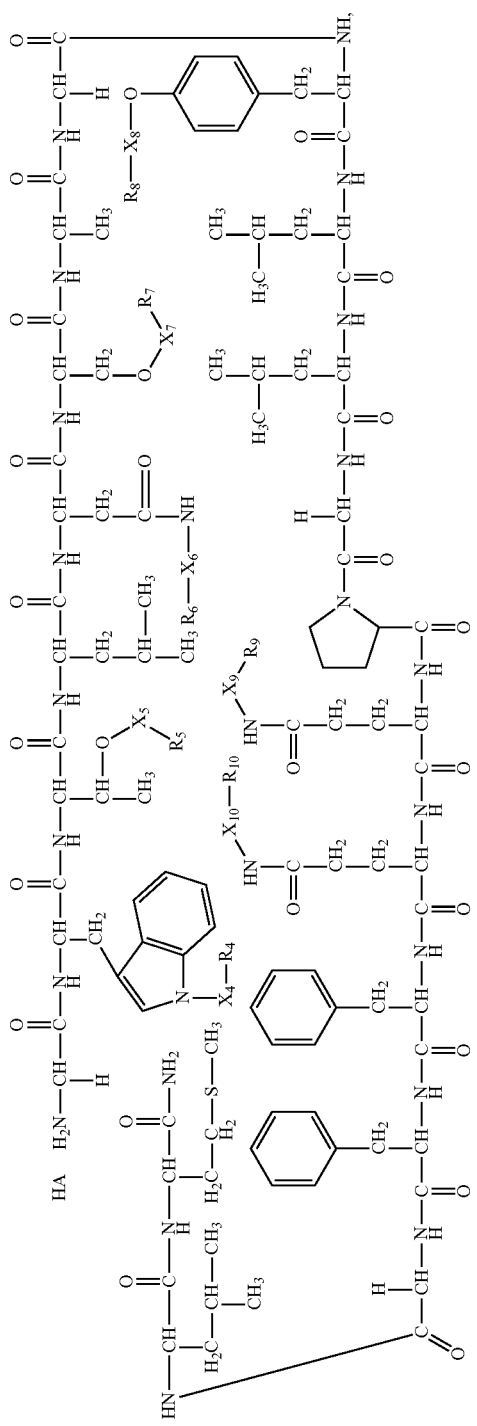
Structure 175 (SEQ ID NO: 59)

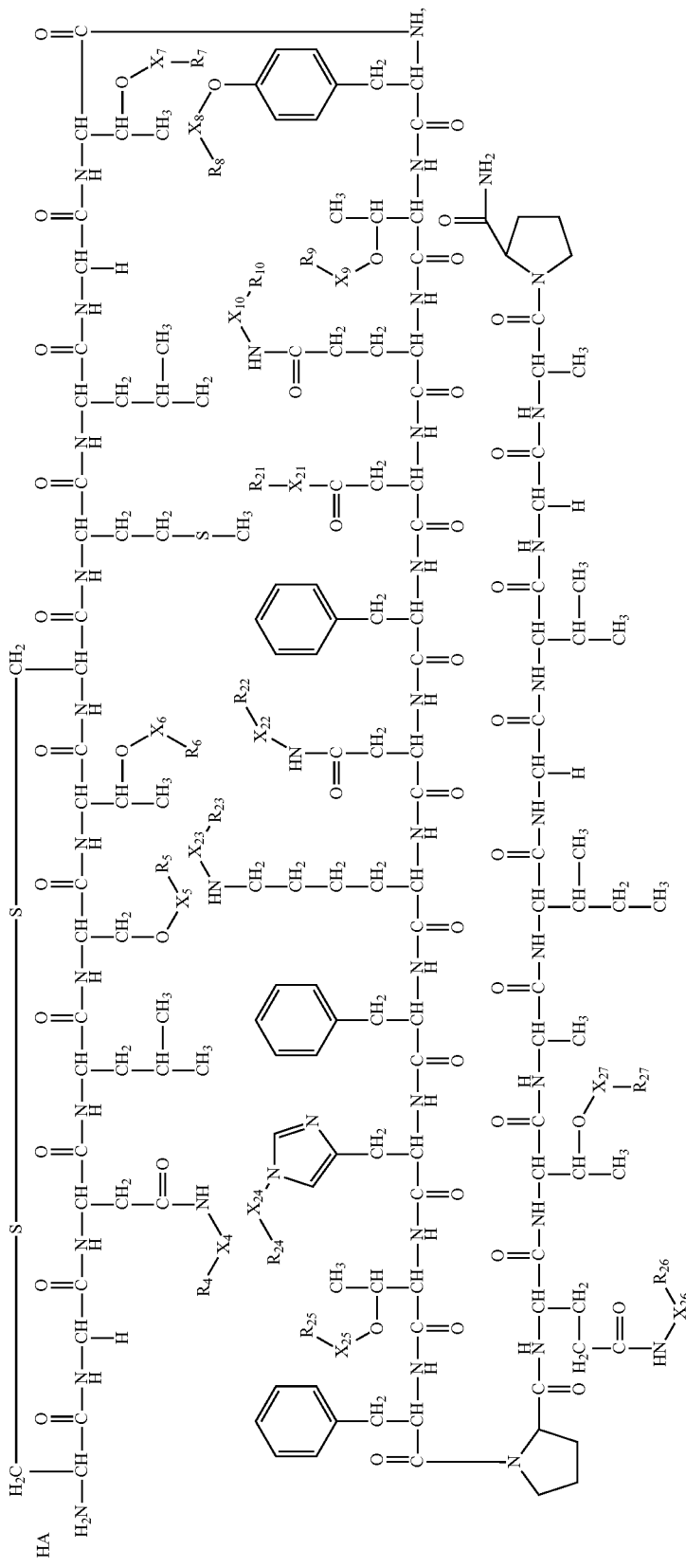
Structure 176 (SEQ ID NO: 60)

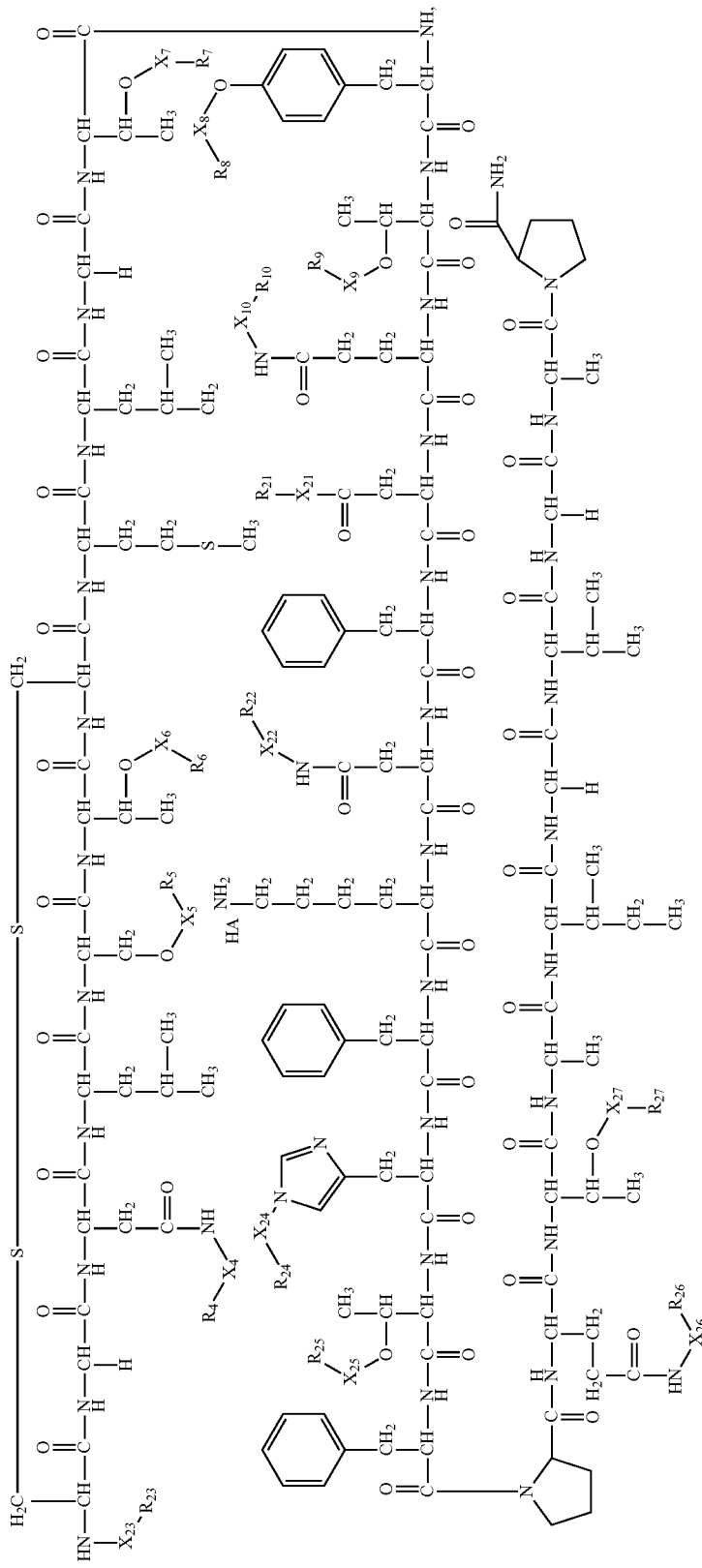
Structure 177 (SEQ ID NO: 60)

-continued
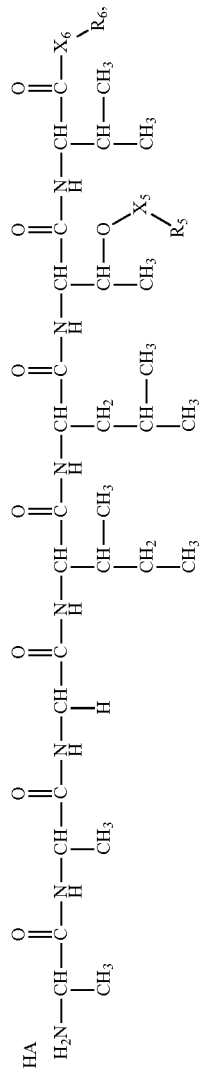
Structure 178 (SEQ ID NO: 61)
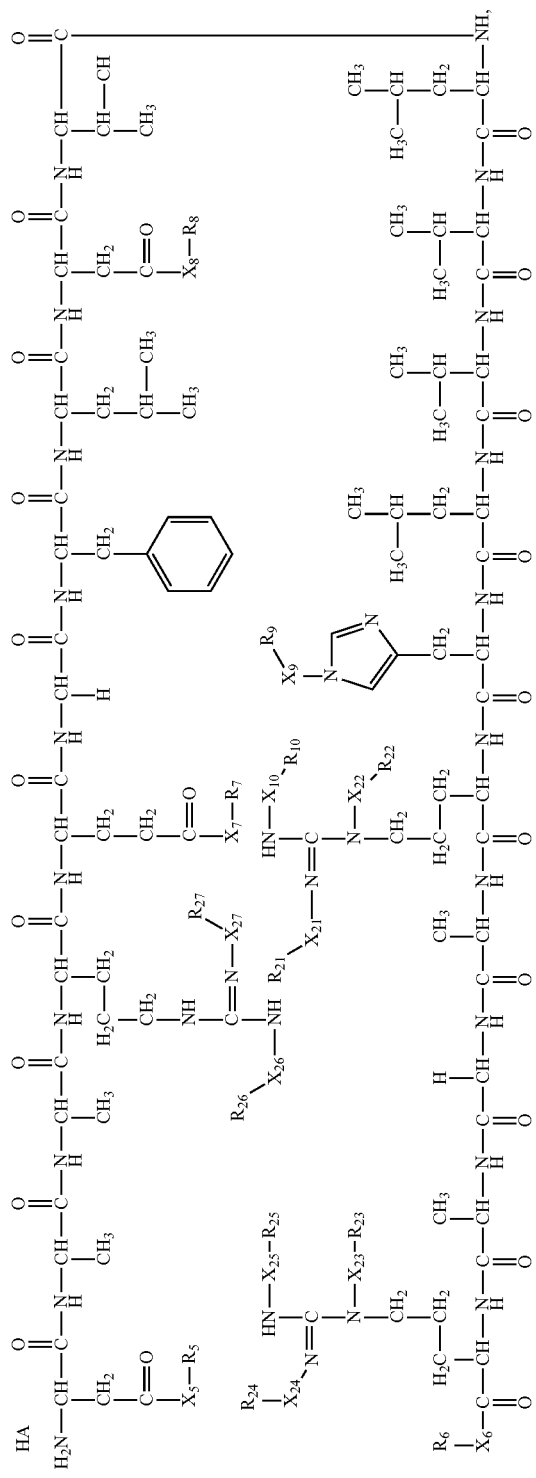
Structure 179 (SEQ ID NO: 62)

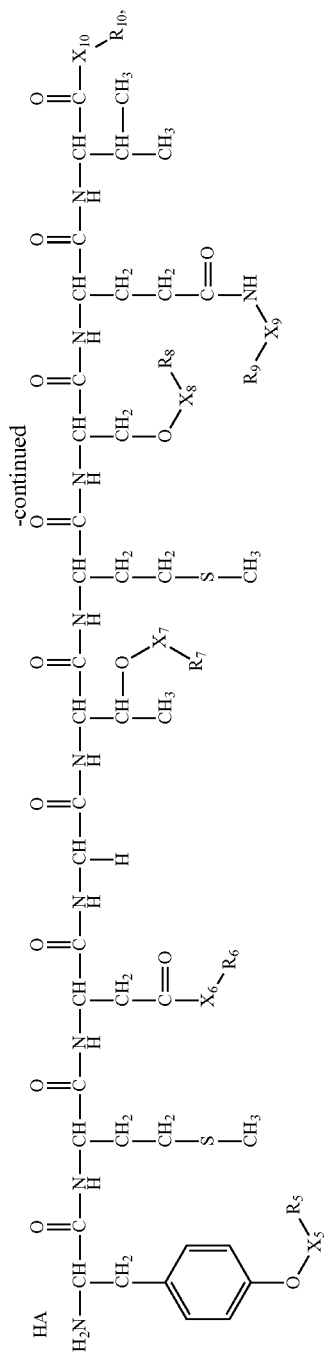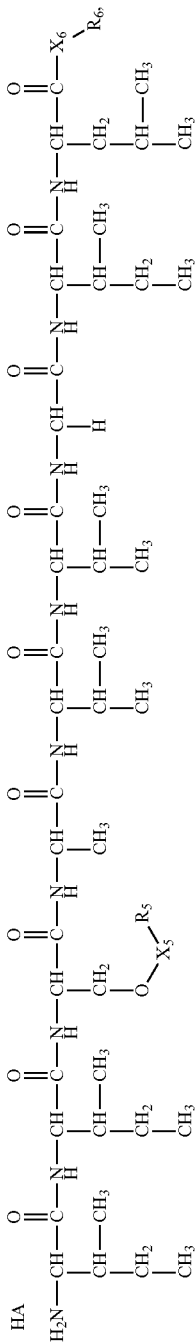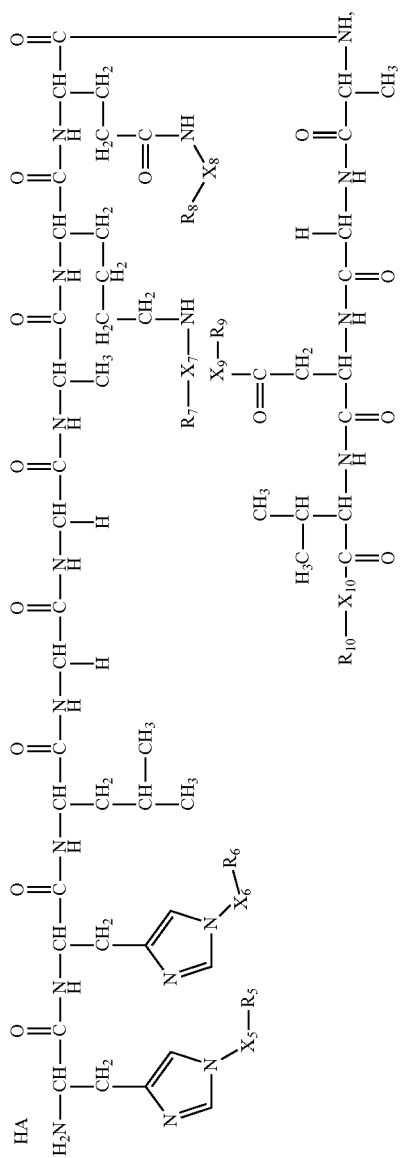

-continued
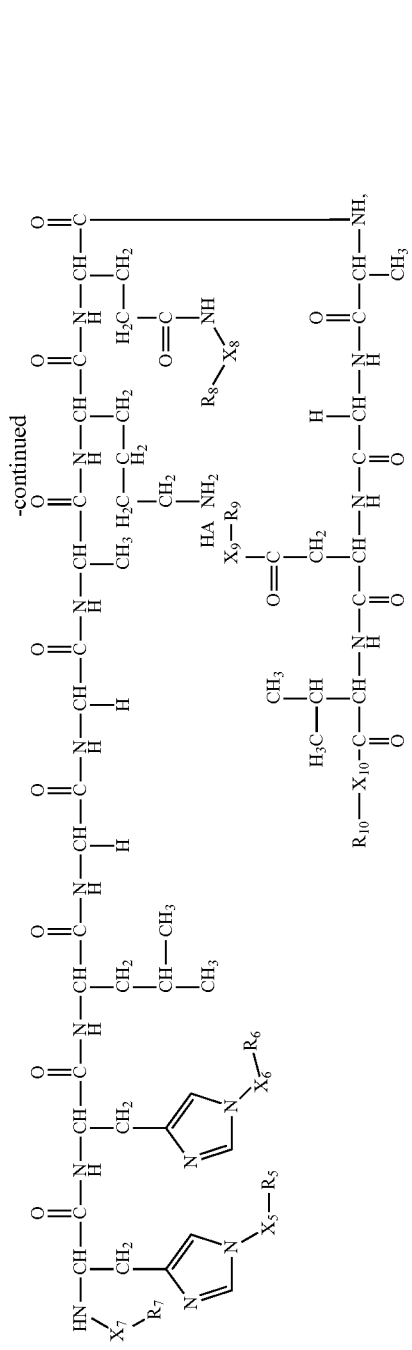
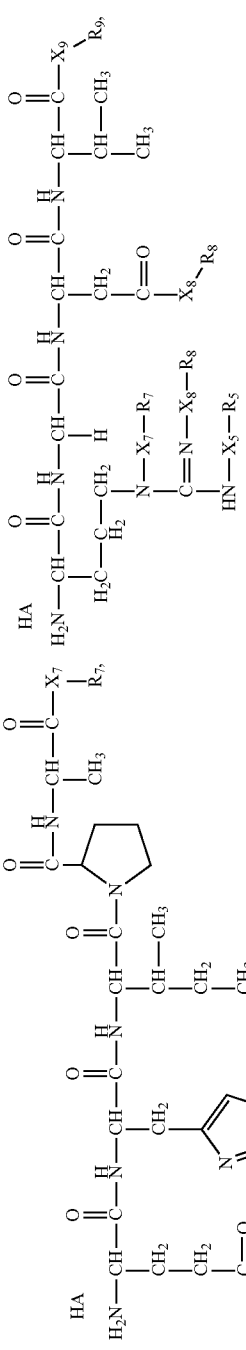
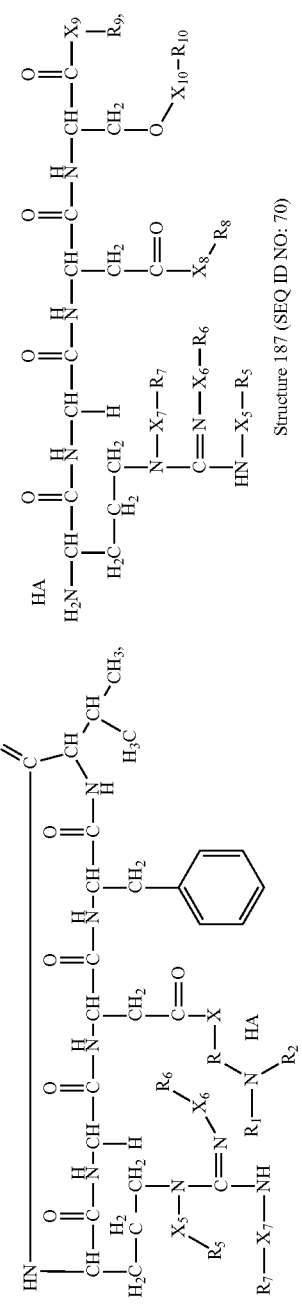
Structure 183 (SEQ ID NO: 66)
Structure 184 (SEQ ID NO: 67)
Structure 185 (SEQ ID NO: 68)
Structure 186 (SEQ ID NO: 69)
Structure 187 (SEQ ID NO: 70)

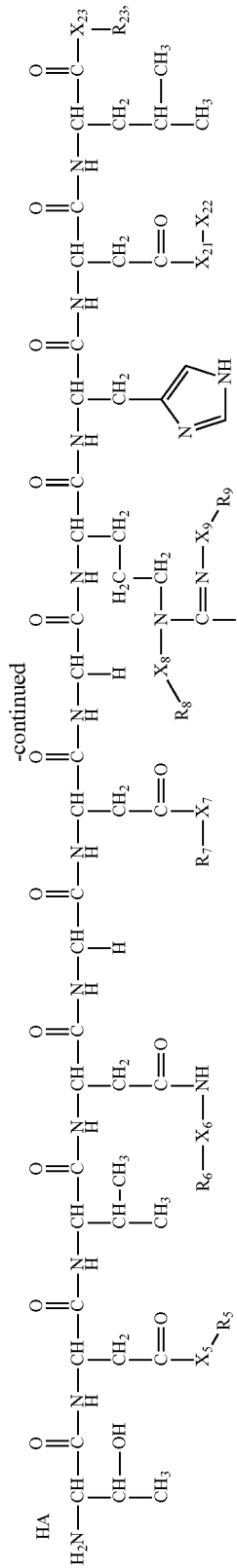
Structure 188 (SEQ ID NO: 71)
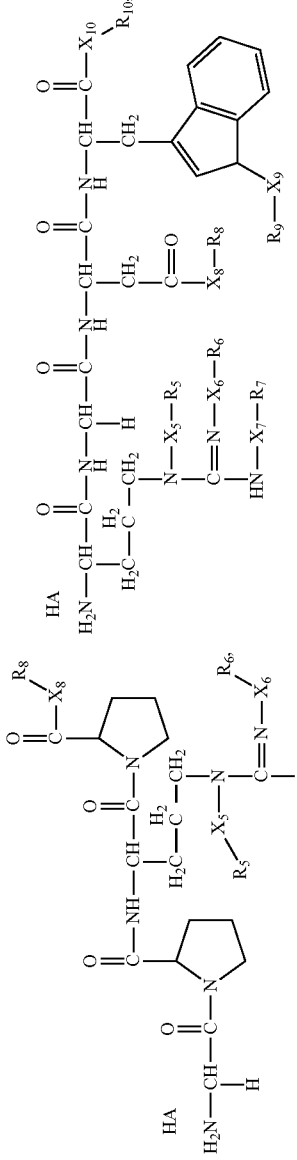
Structure 189 (SEQ ID NO: 72)
Structure 190 (SEQ ID NO: 73)
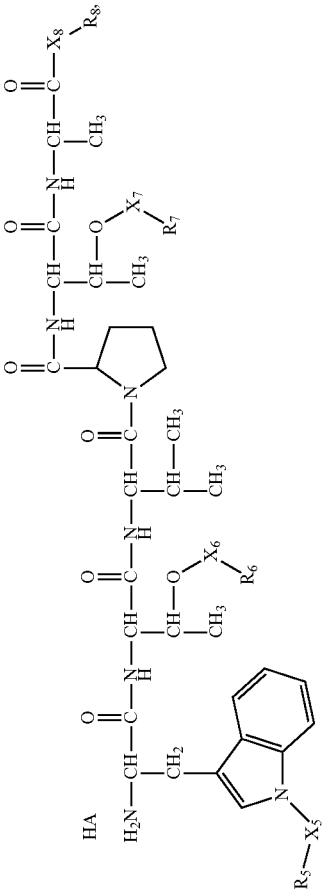
Structure 191 (SEQ ID NO: 74)

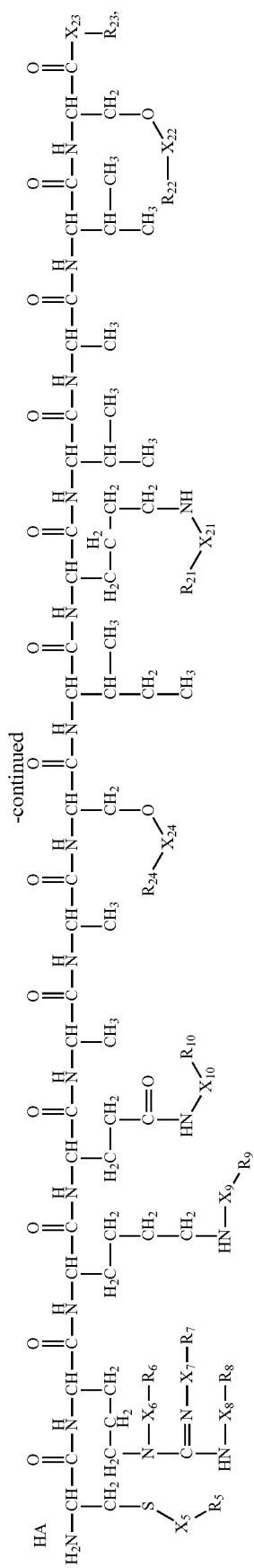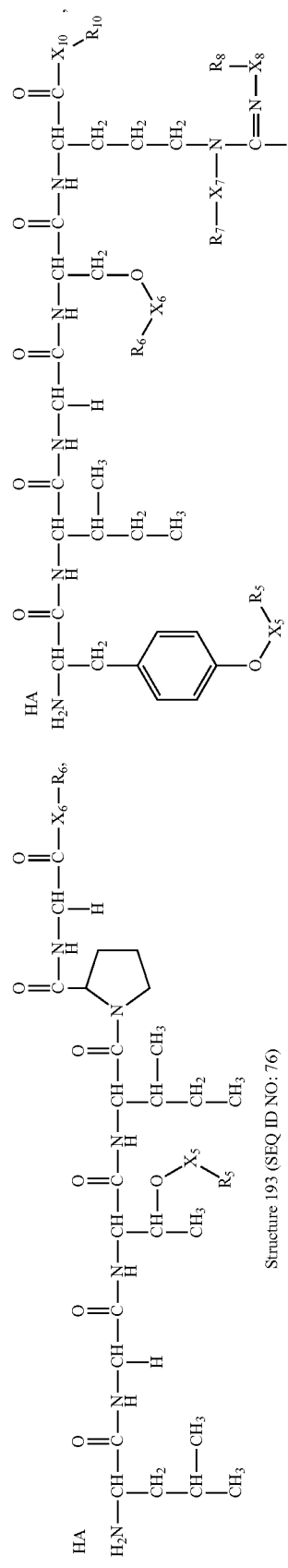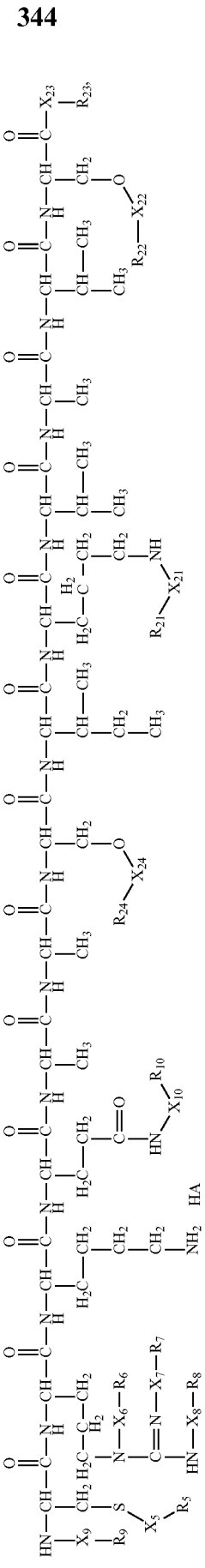

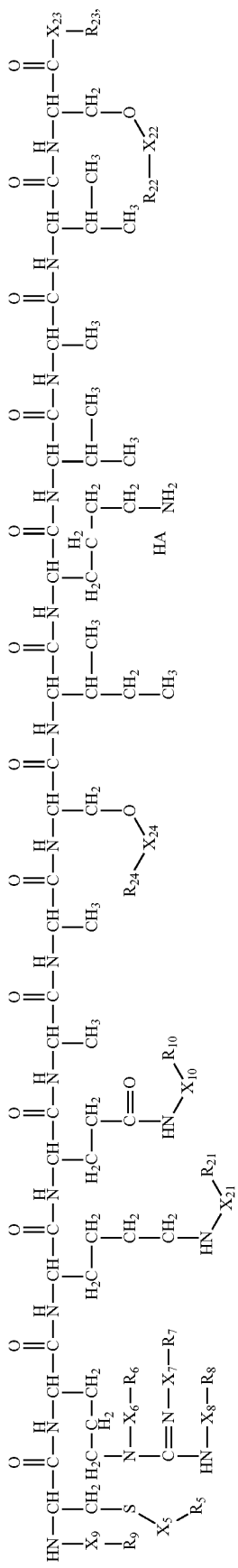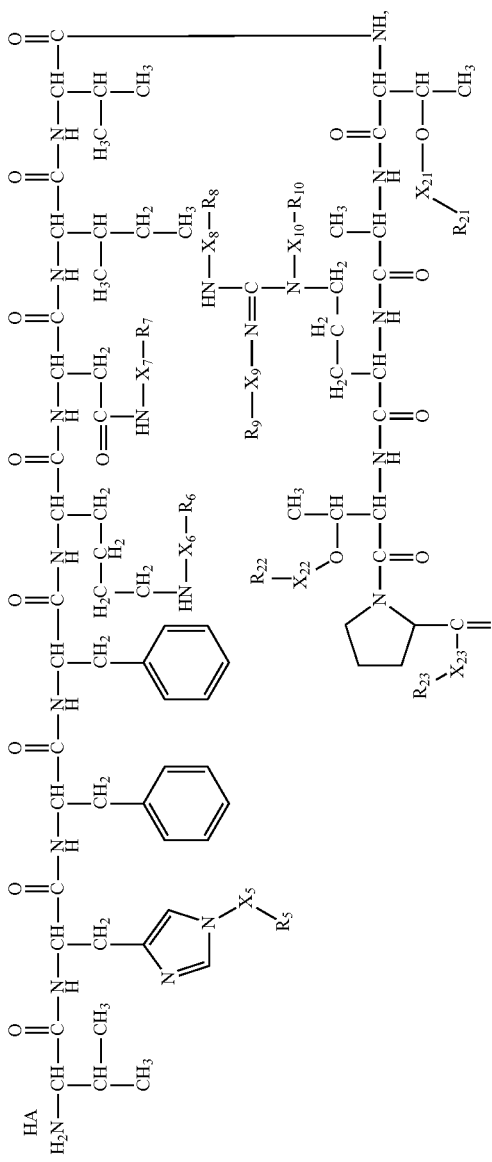
Structure 197 (SEQ ID NO: 79)
Structure 198 (SEQ ID NO: 80)

-continued
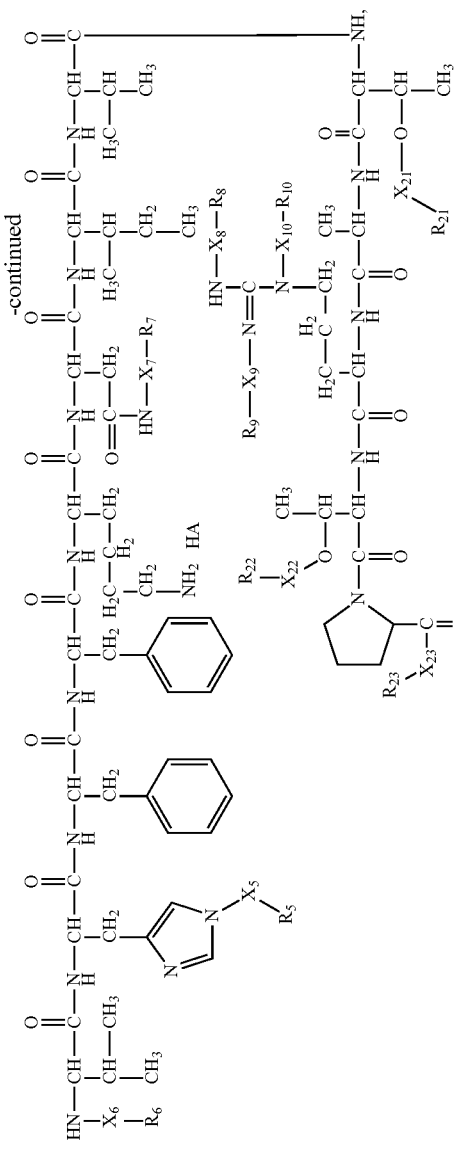
Structure 199 (SEQ ID NO: 80)
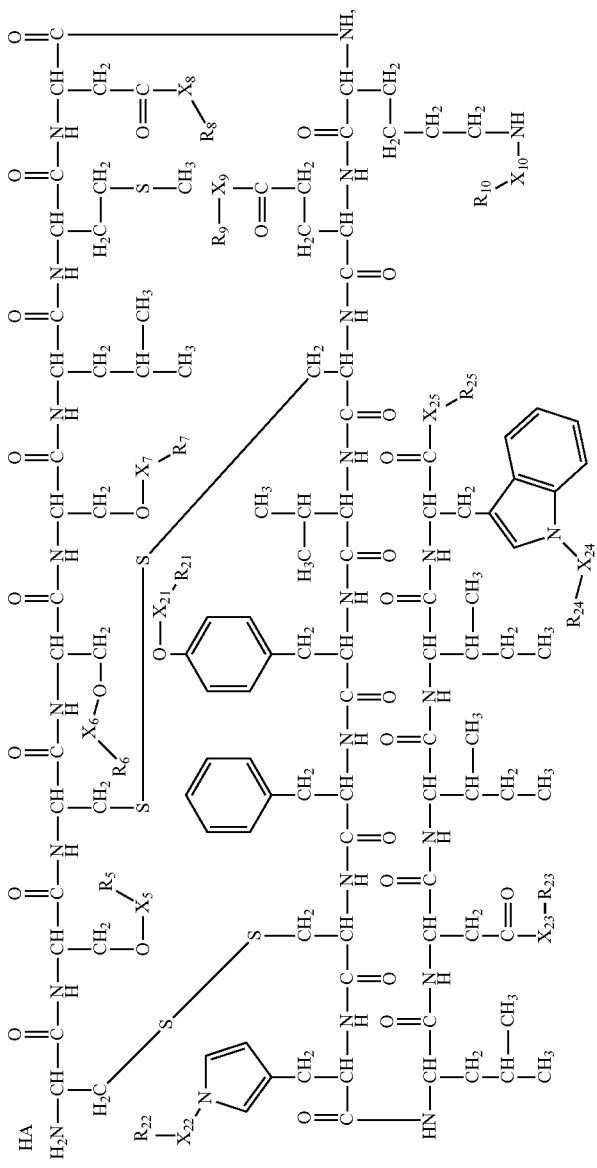
Structure 200 (SEQ ID NO: 81)

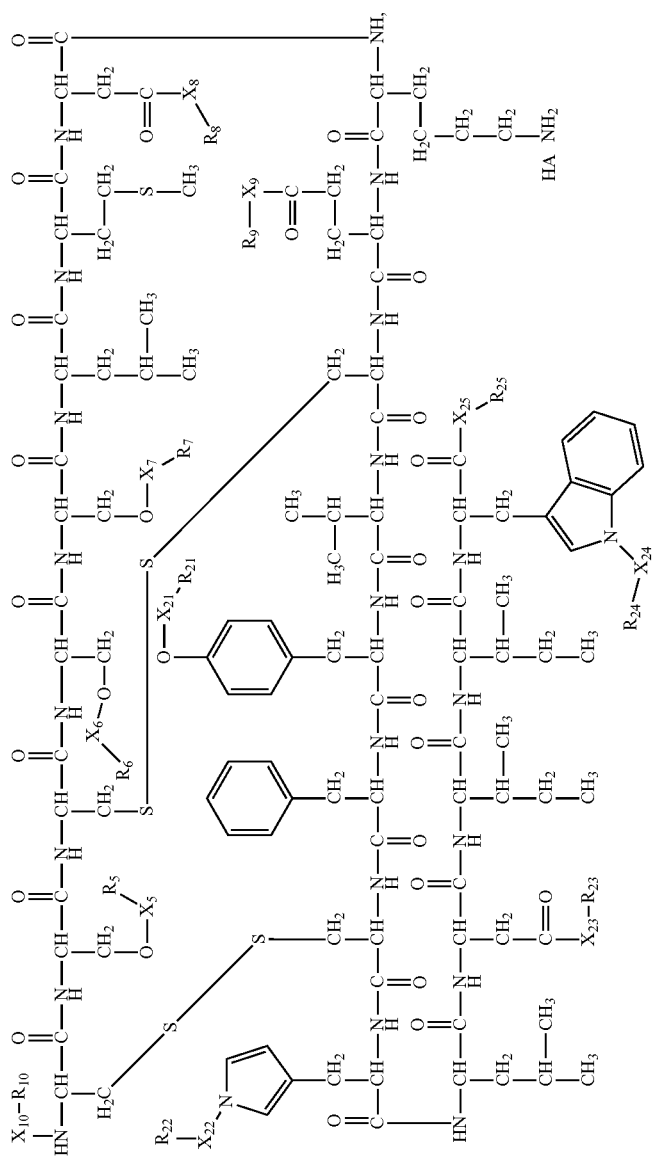
Structure 201 (SEQ ID NO: 81)

-continued
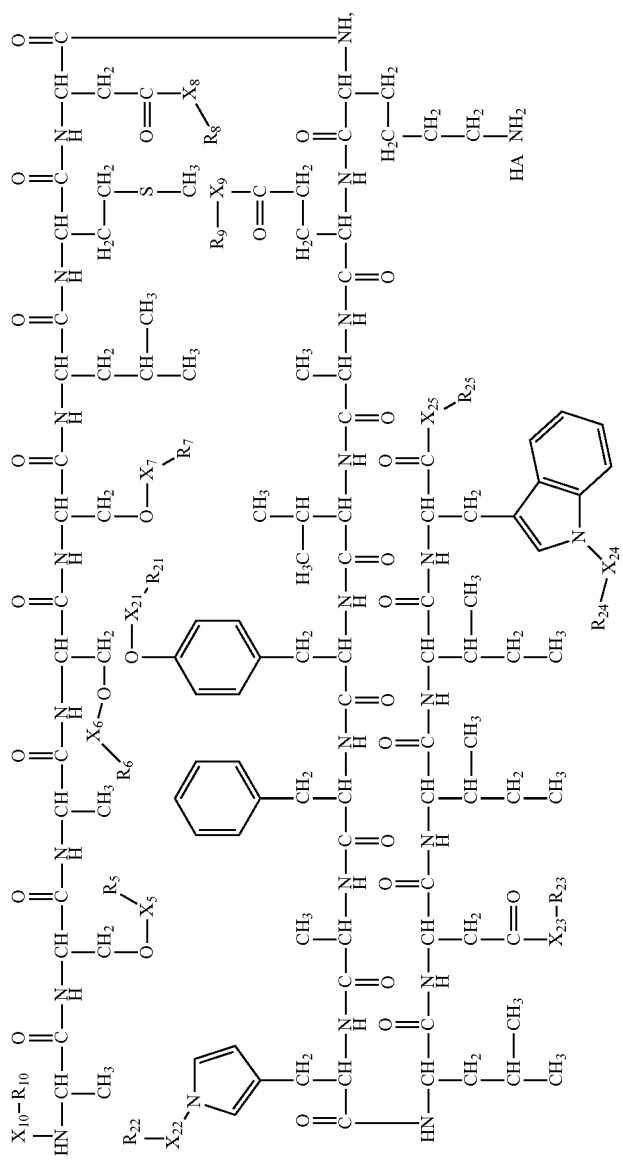
Structure 202 (SEQ ID NO: 82)

-continued
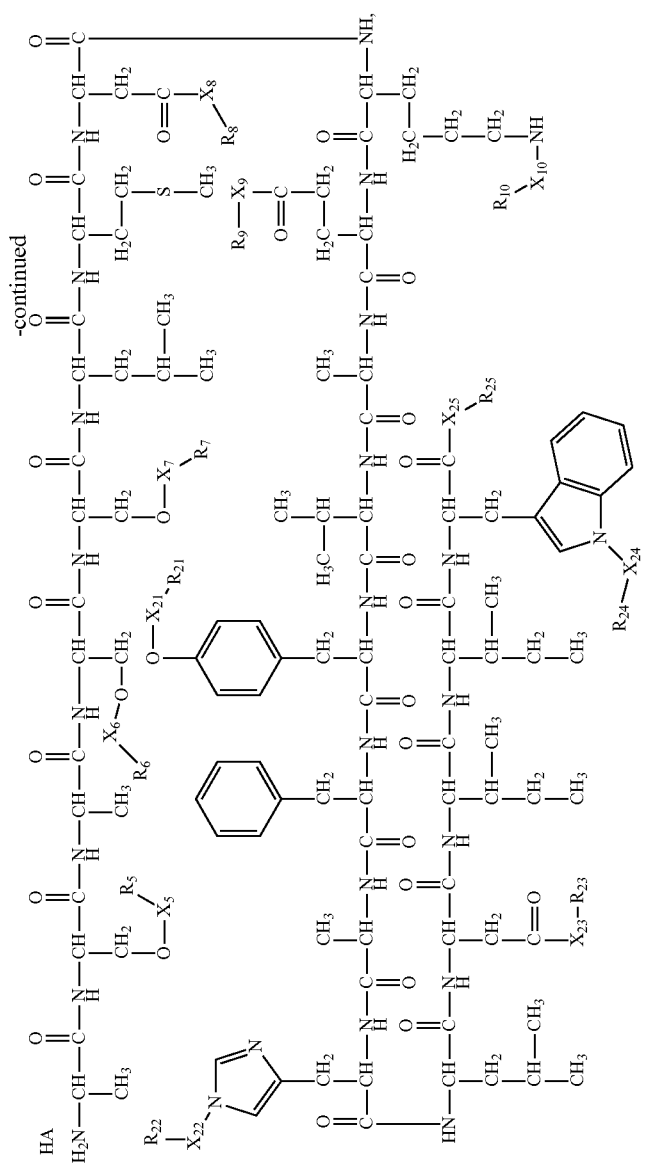
Structure 203 (SEQ ID NO: 82)
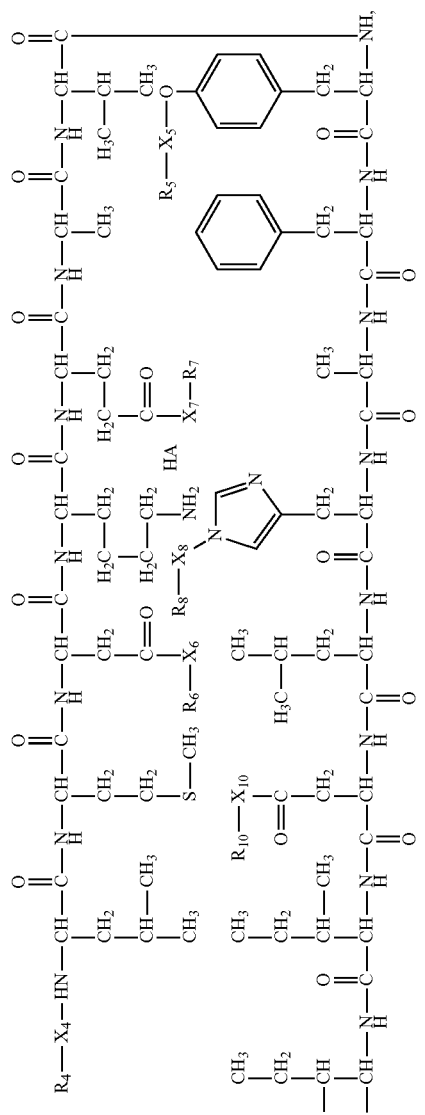
Structure 204 (SEQ ID NO: 83)

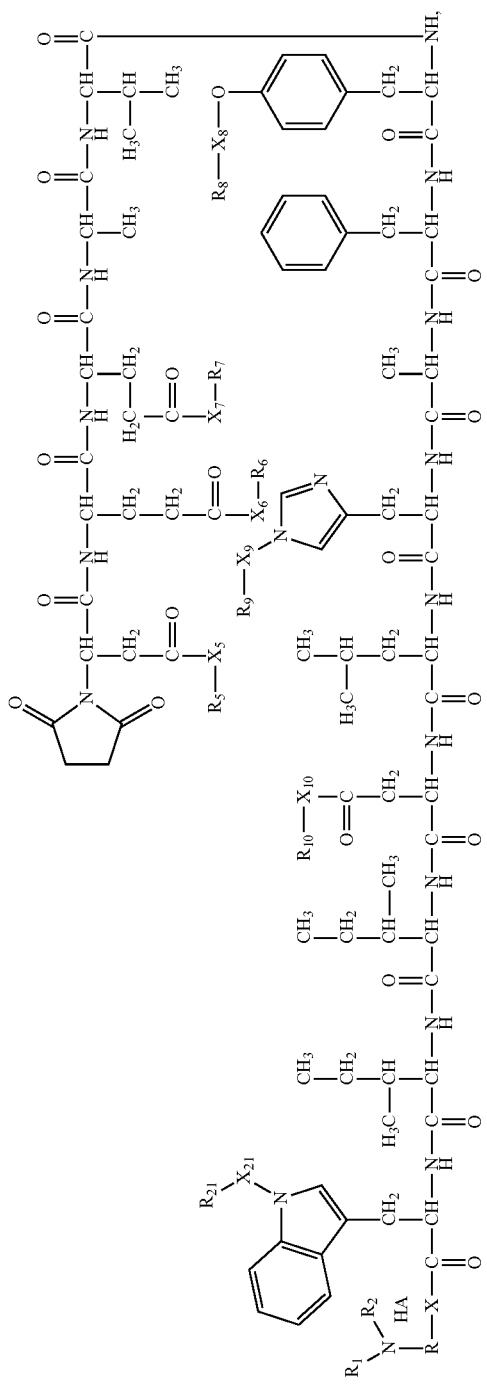
Structure 205 (SEQ ID NO: 84)
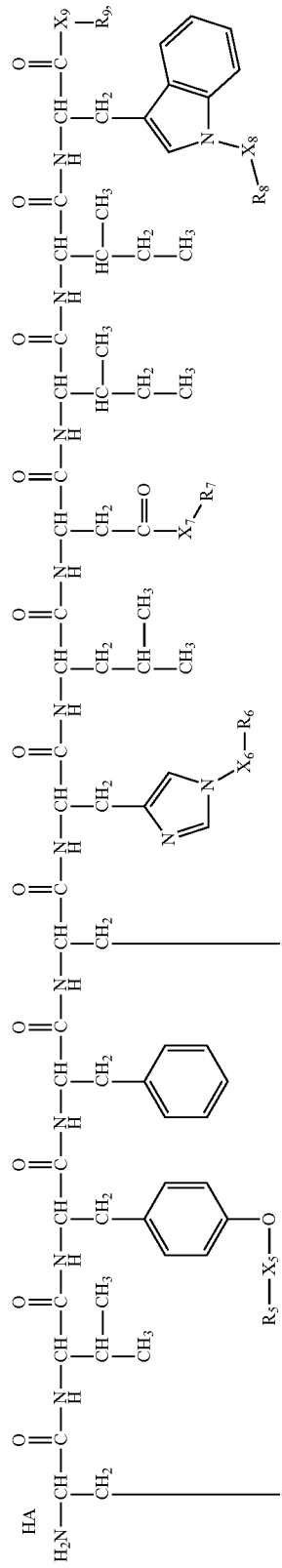
Structure 206 (SEQ ID NO: 85)

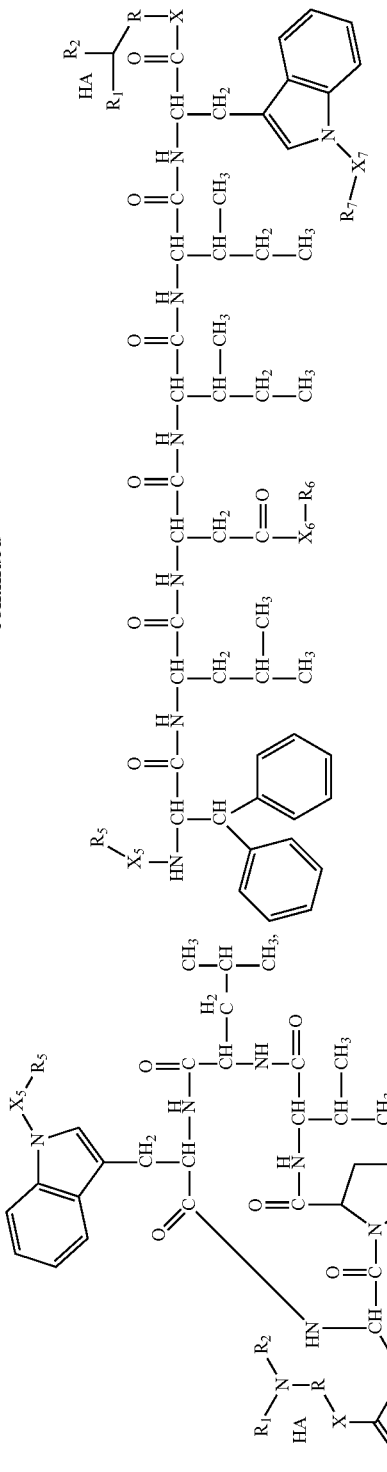
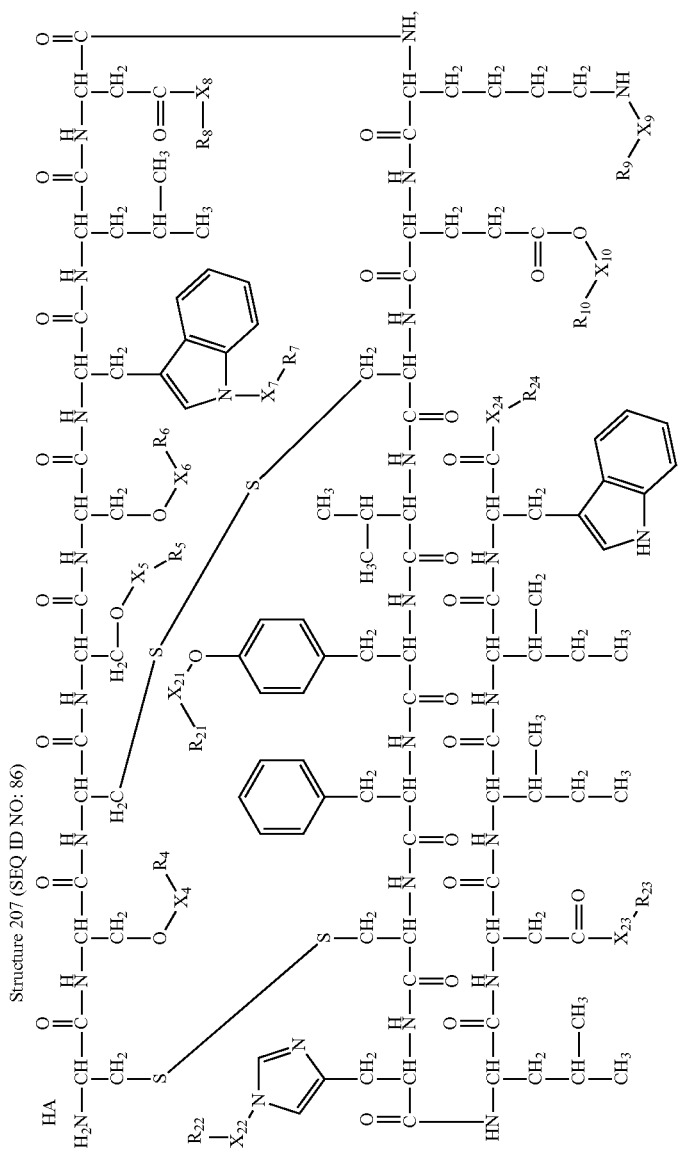
Structure 207 (SEQ ID NO: 86)
Structure 208 (SEQ ID NO: 87)
Structure 209 (SEQ ID NO: 88)

-continued
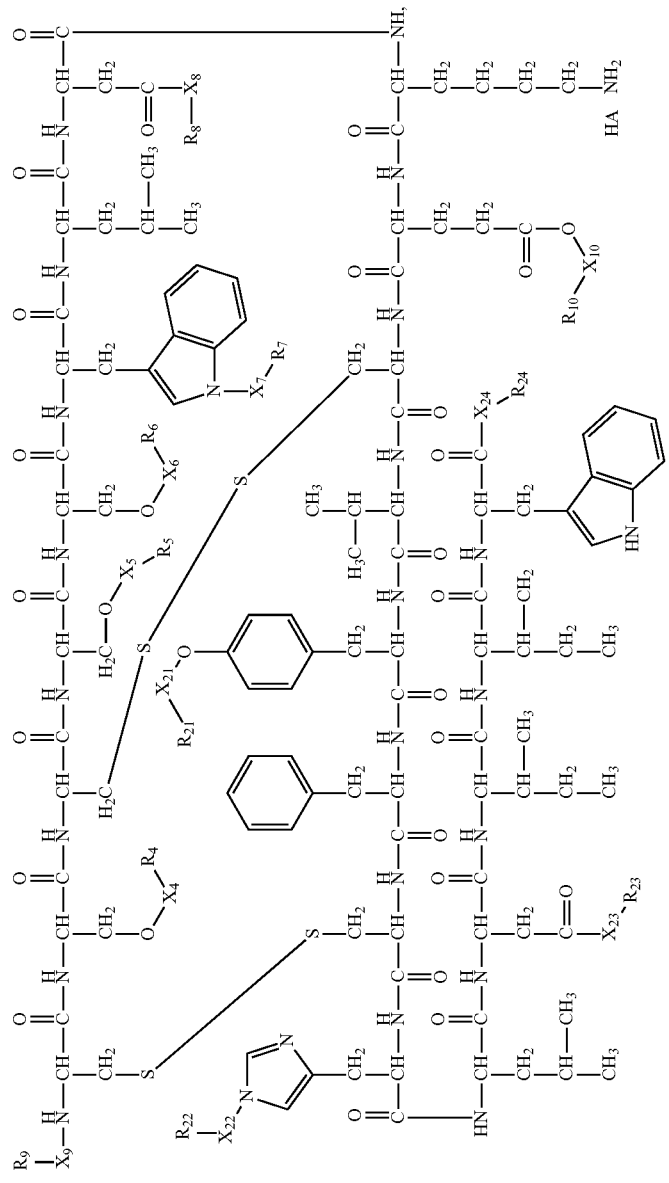
Structure 210 (SEQ ID NO: 88)

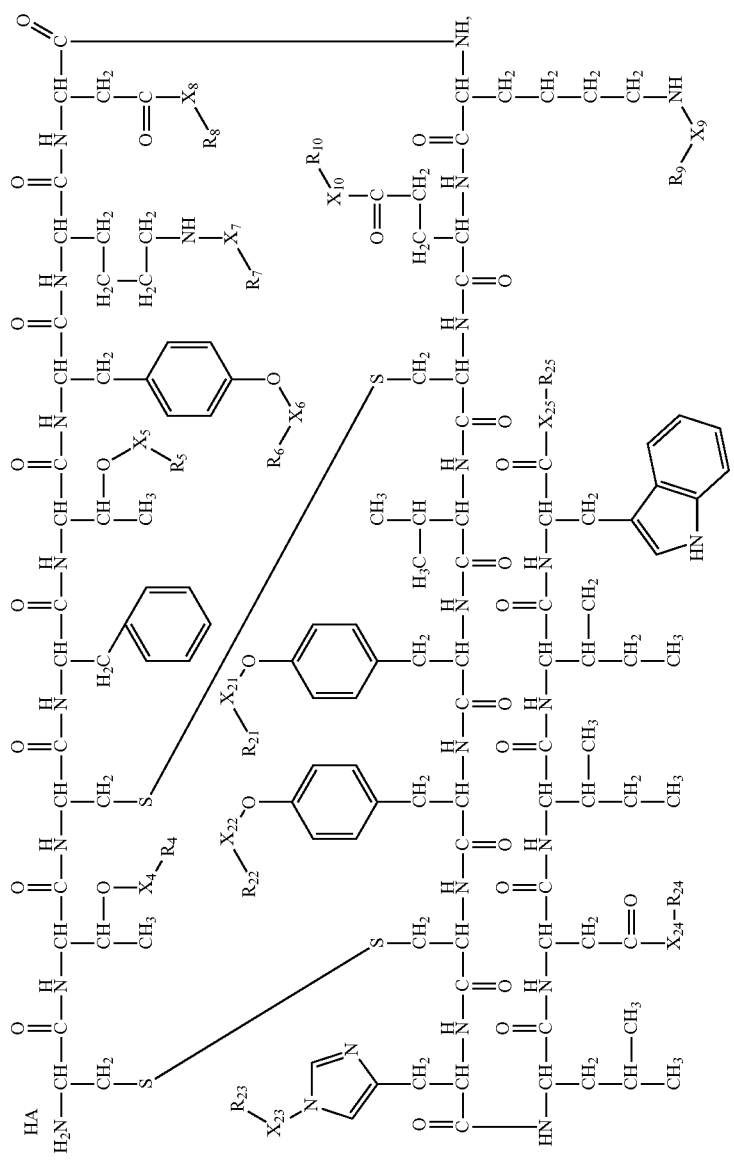
Structure 211 (SEQ ID NO: 89)

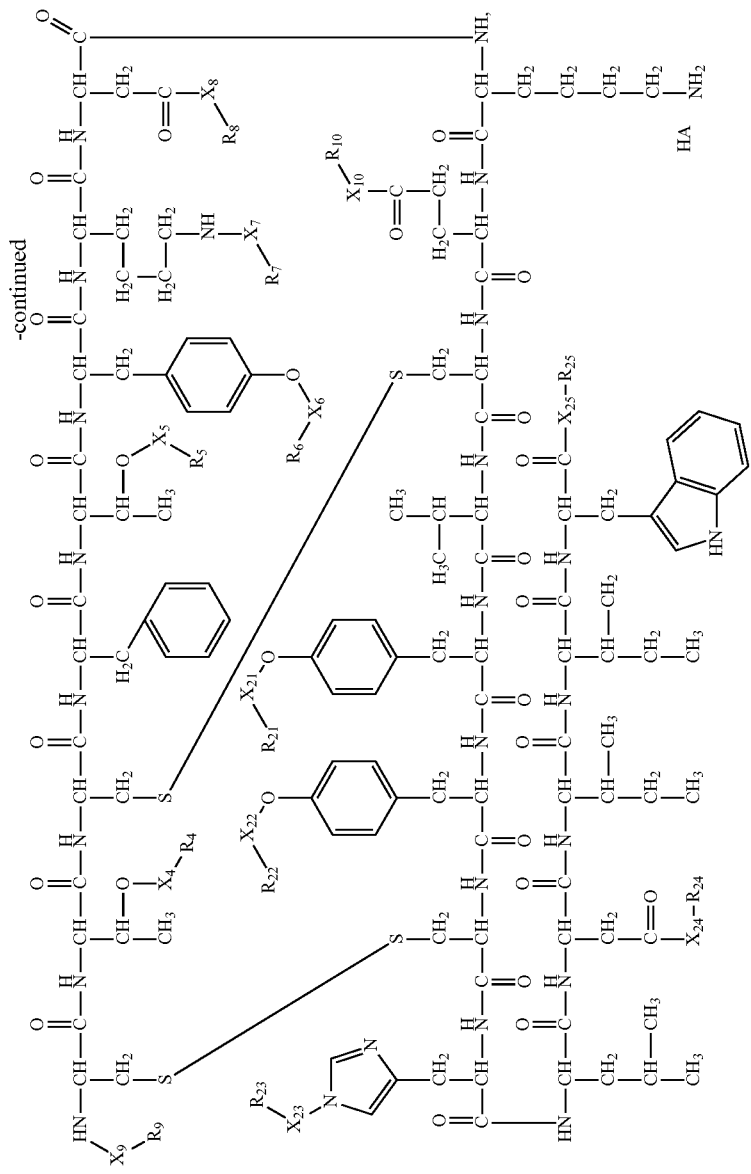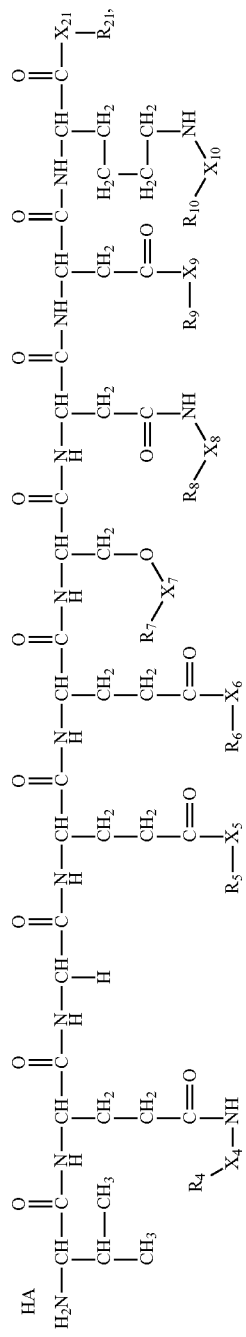

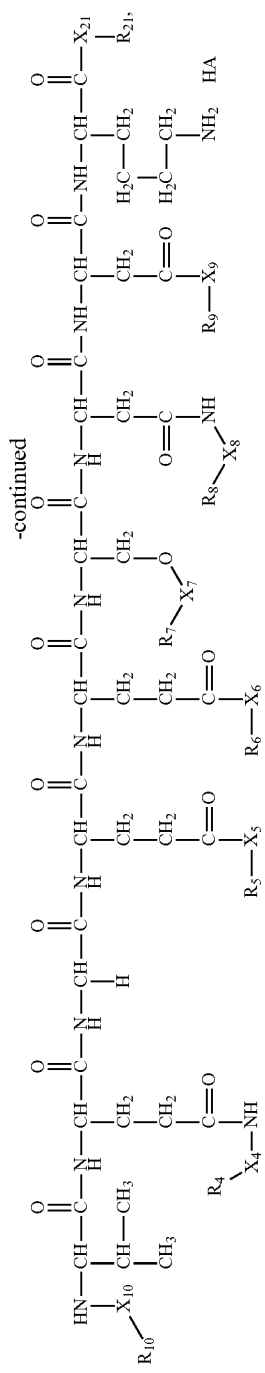
Structure 214 (SEQ ID NO: 90)
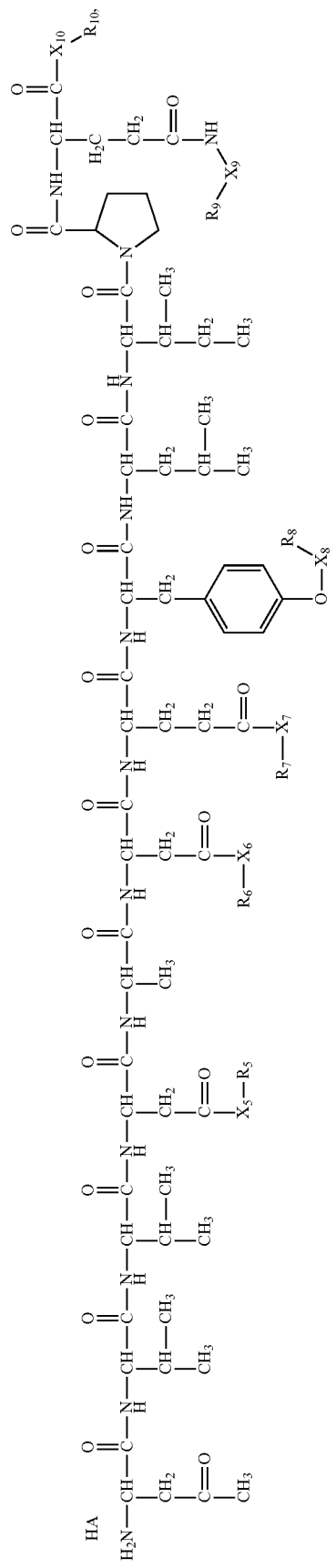
Structure 215 (SEQ ID NO: 91)
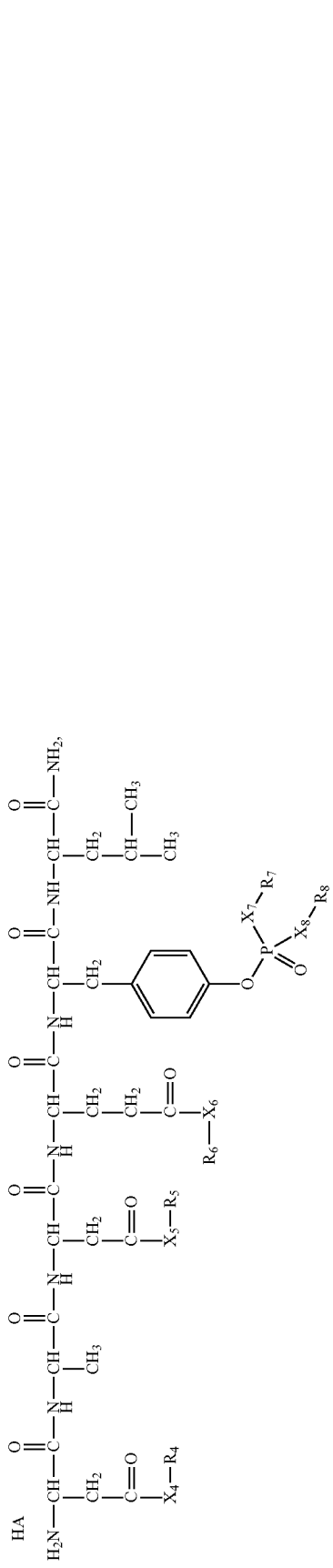
Structure 216 (SEQ ID NO: 92)

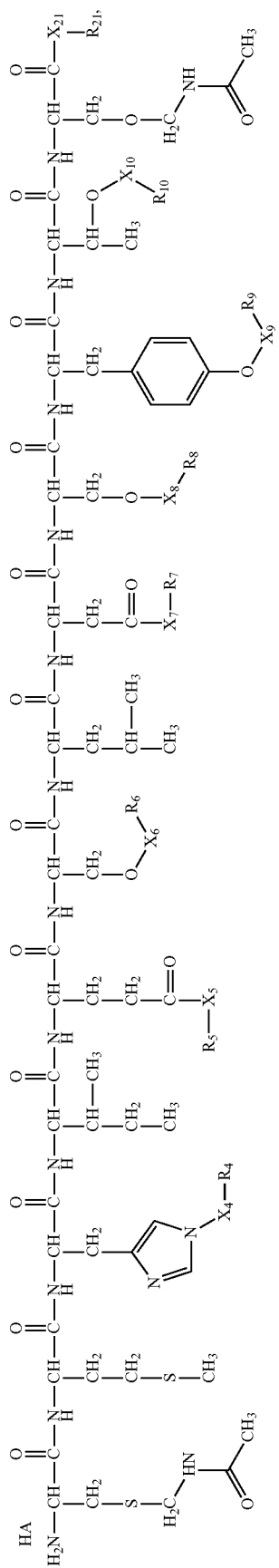
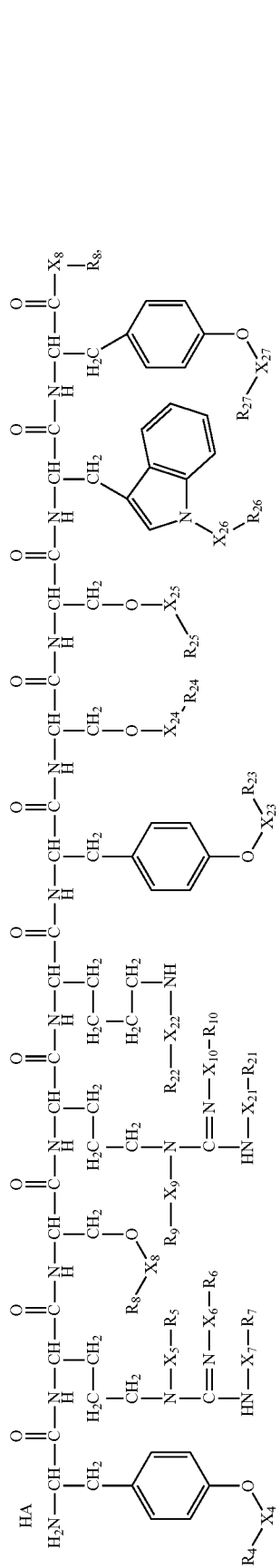
Structure 217 (SEQ ID NO: 93)
Structure 218 (SEQ ID NO: 94)

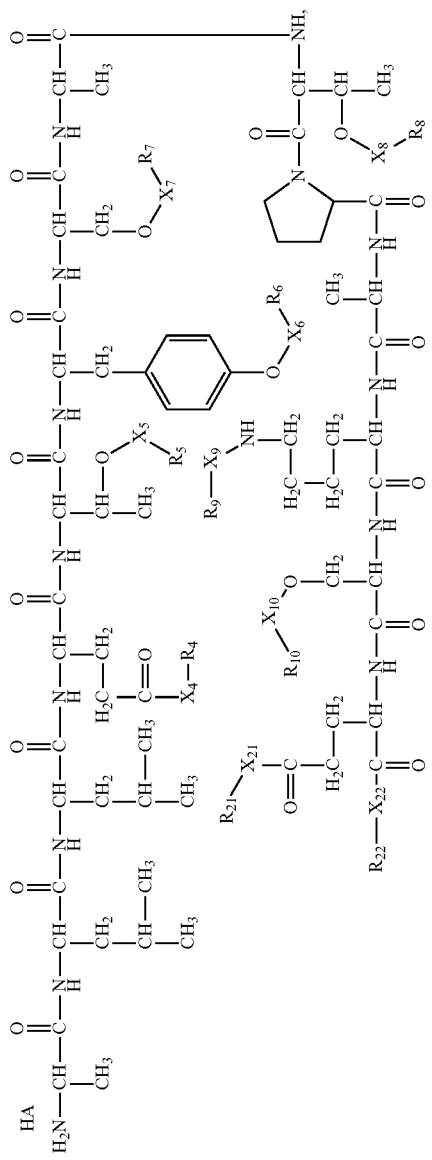
Structure 219 (SEQ ID NO: 95)
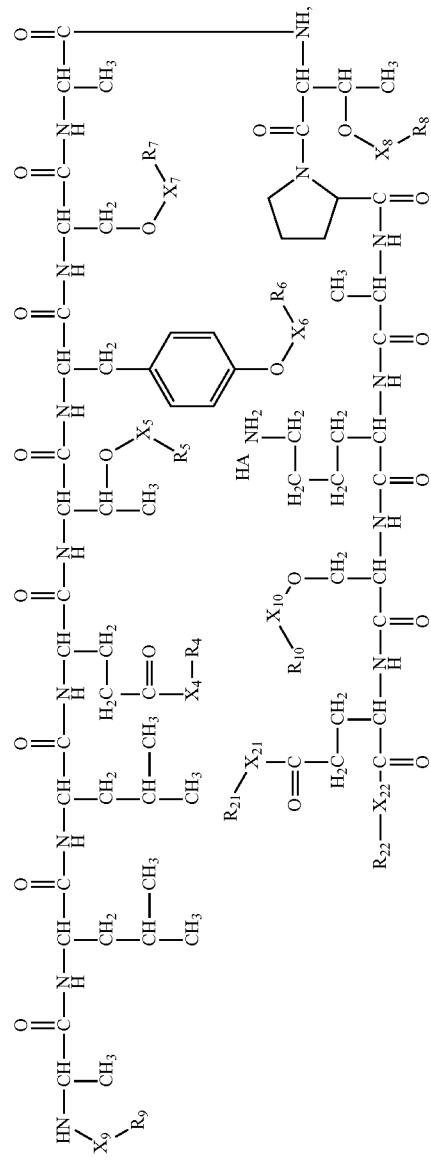
Structure 220 (SEQ ID NO: 95)

-continued
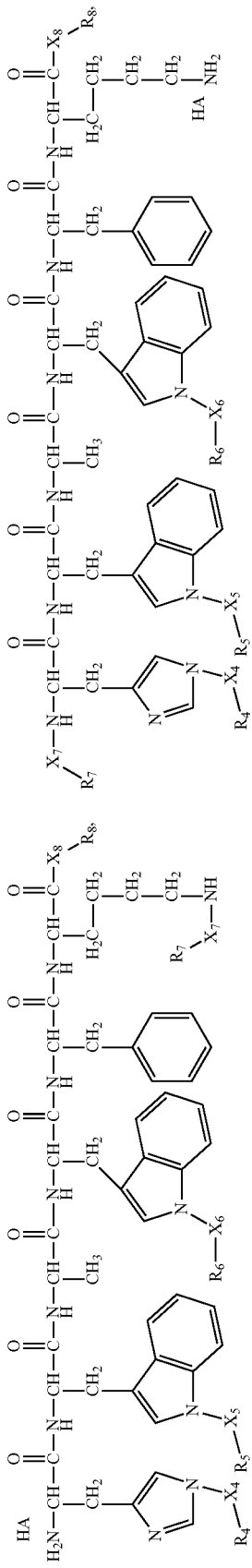
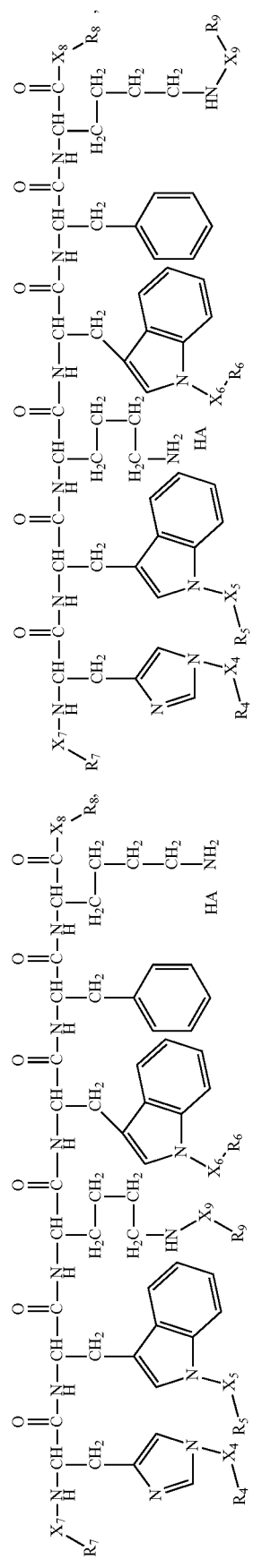
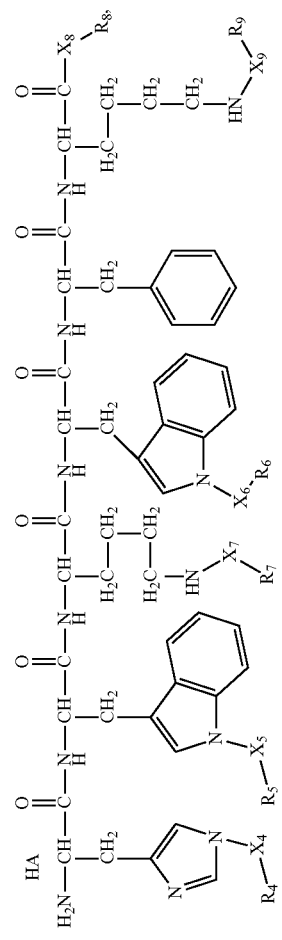

-continued
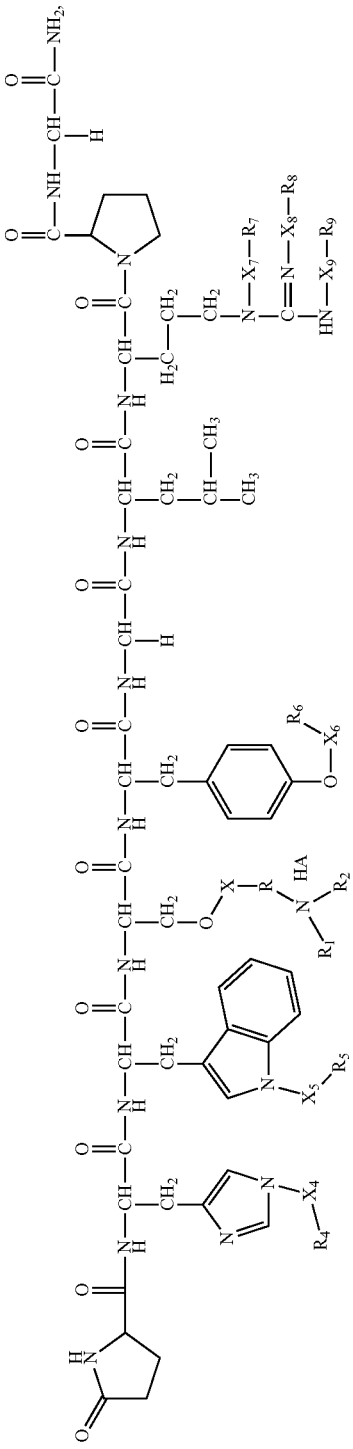
Structure 226 (SEQ ID NO: 98)
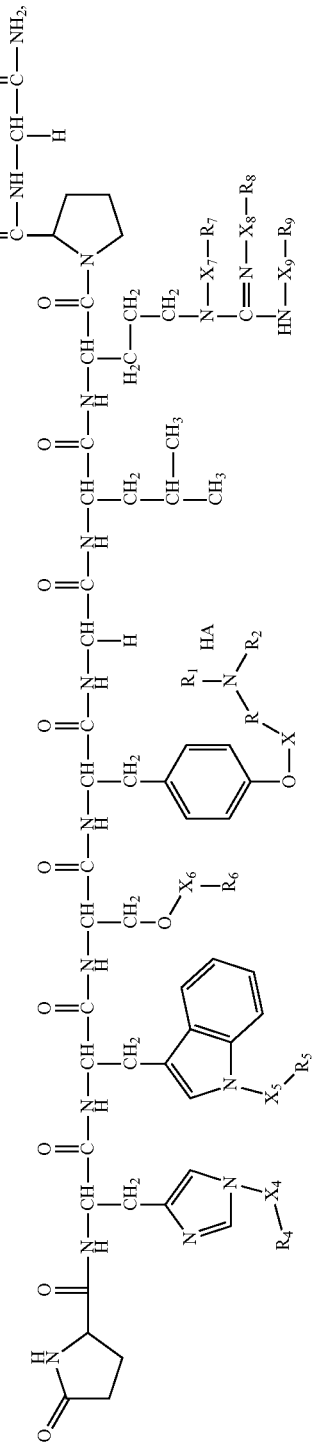
Structure 227 (SEQ ID NO: 98)
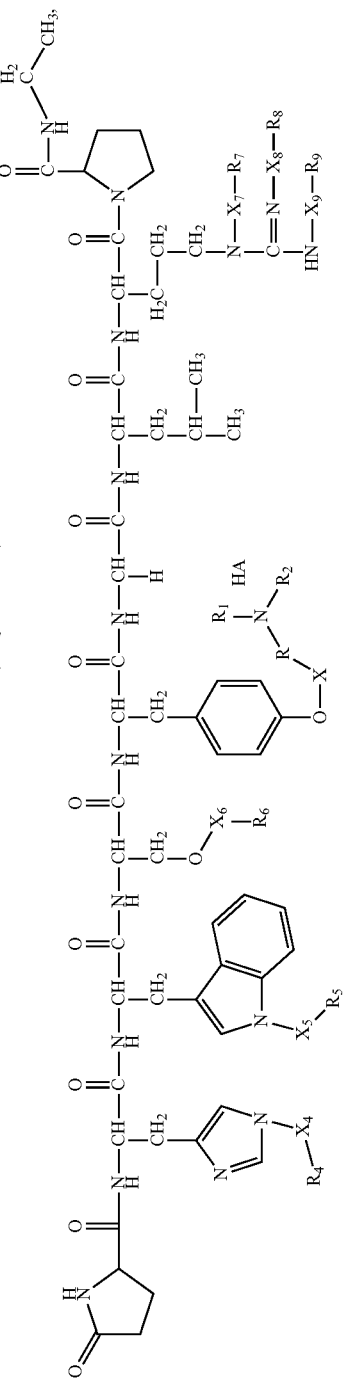
Structure 228 (SEQ ID NO: 99)

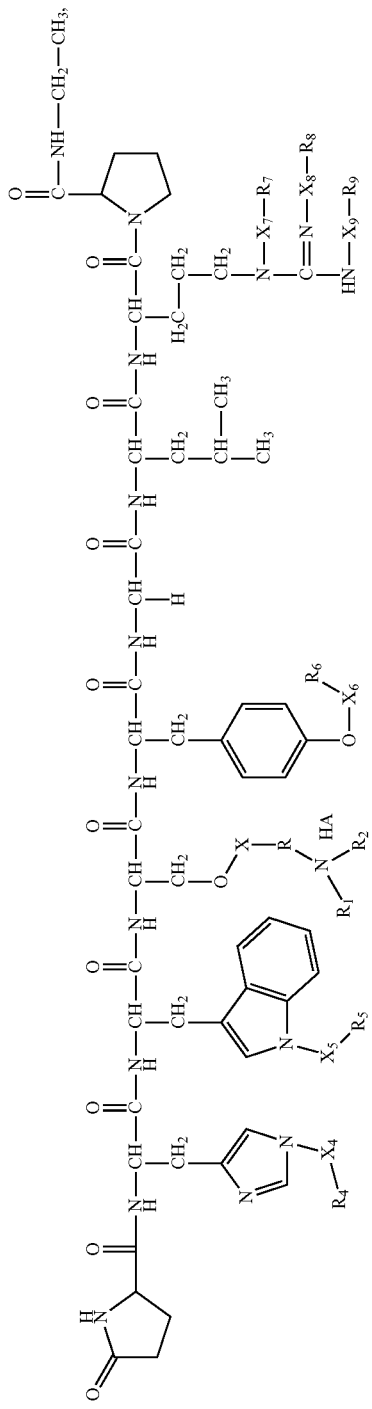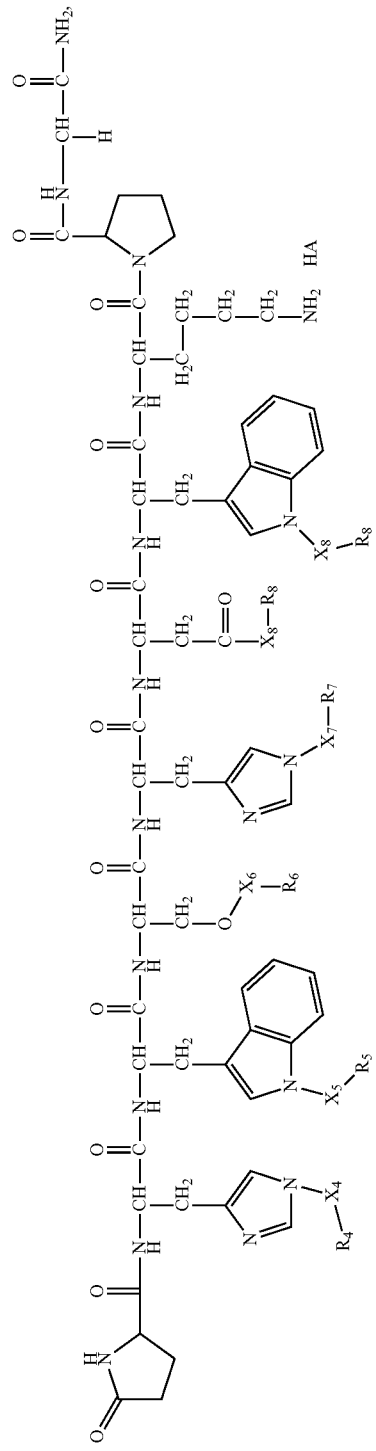

-continued
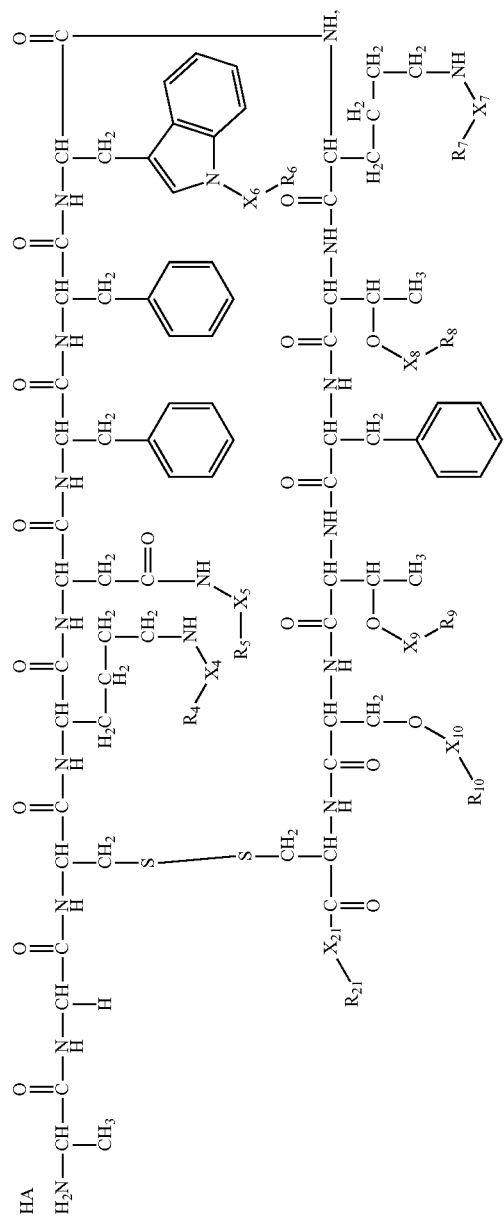
Structure 231 (SEQ ID NO: 101)
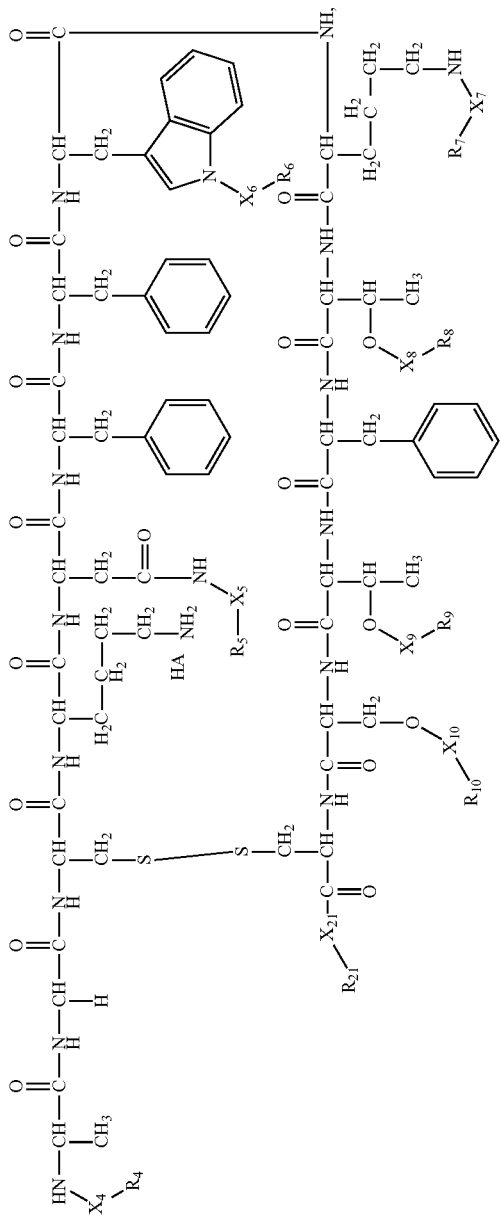
Structure 232 (SEQ ID NO: 101)

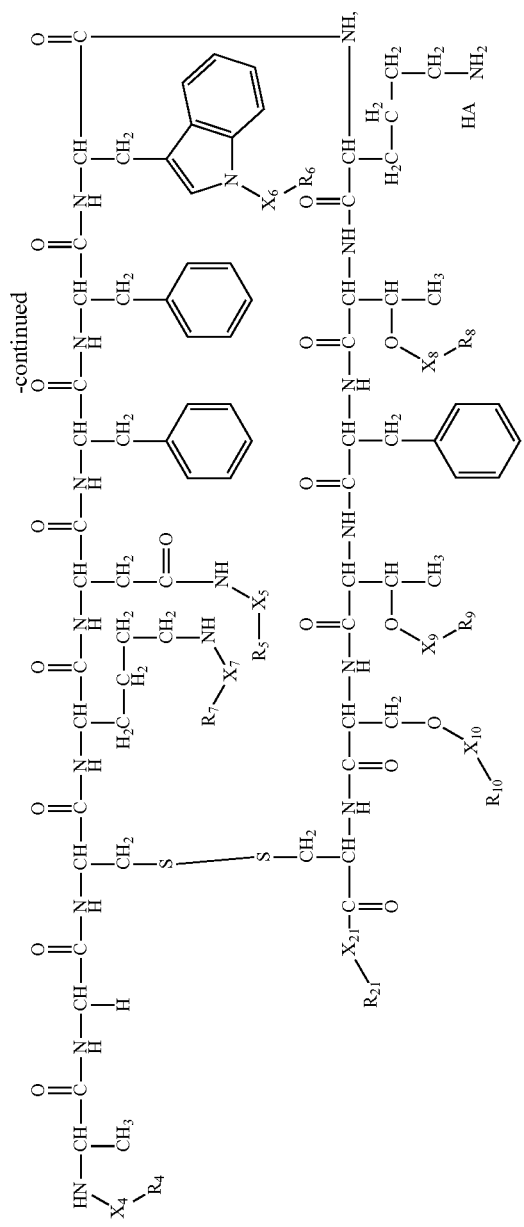
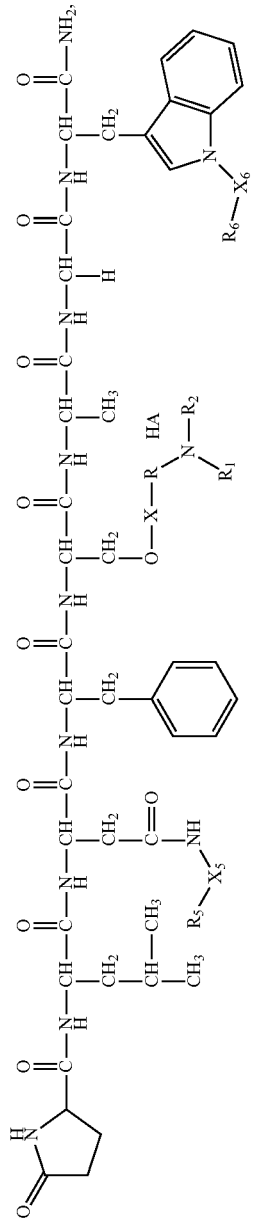
Structure 233 (SEQ ID NO: 101)
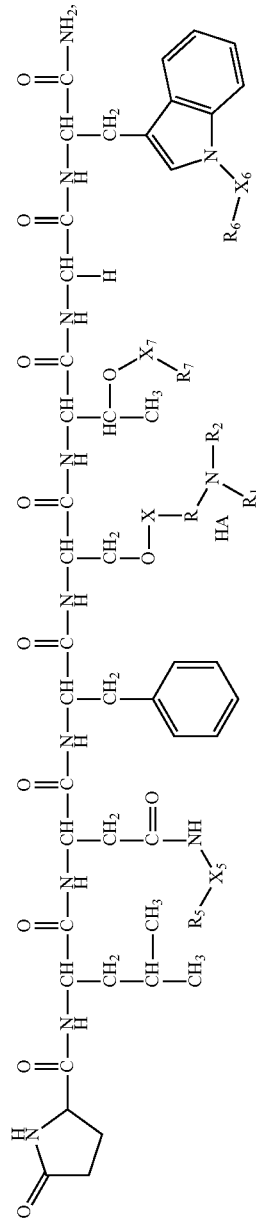
Structure 234 (SEQ ID NO: 102)
Structure 235 (SEQ ID NO: 103)

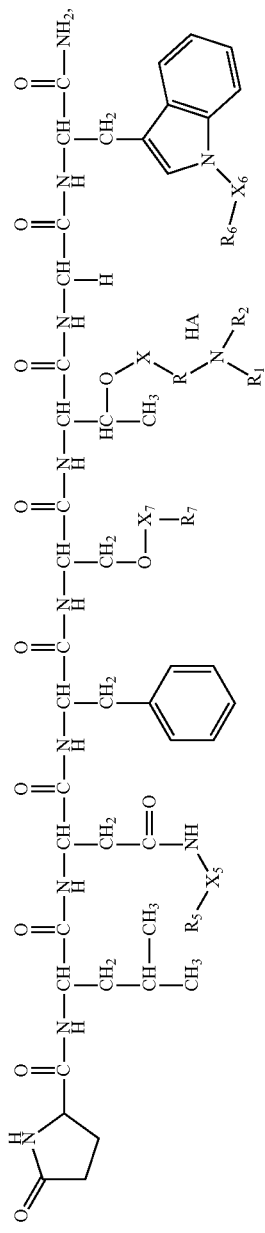
Structure 236 (SEQ ID NO: 103)
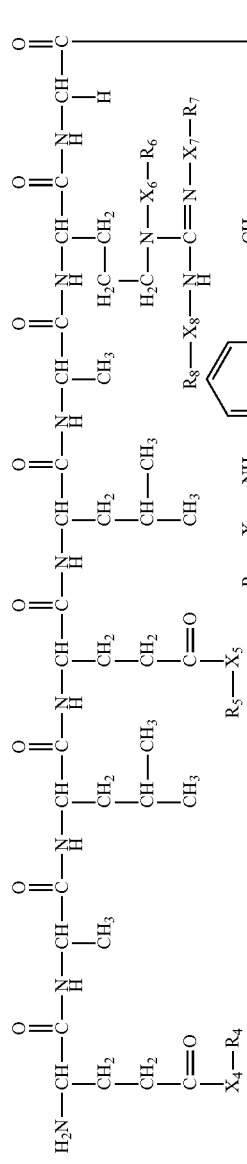
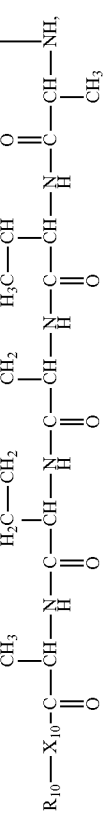
Structure 237 (SEQ ID NO: 104)

-continued
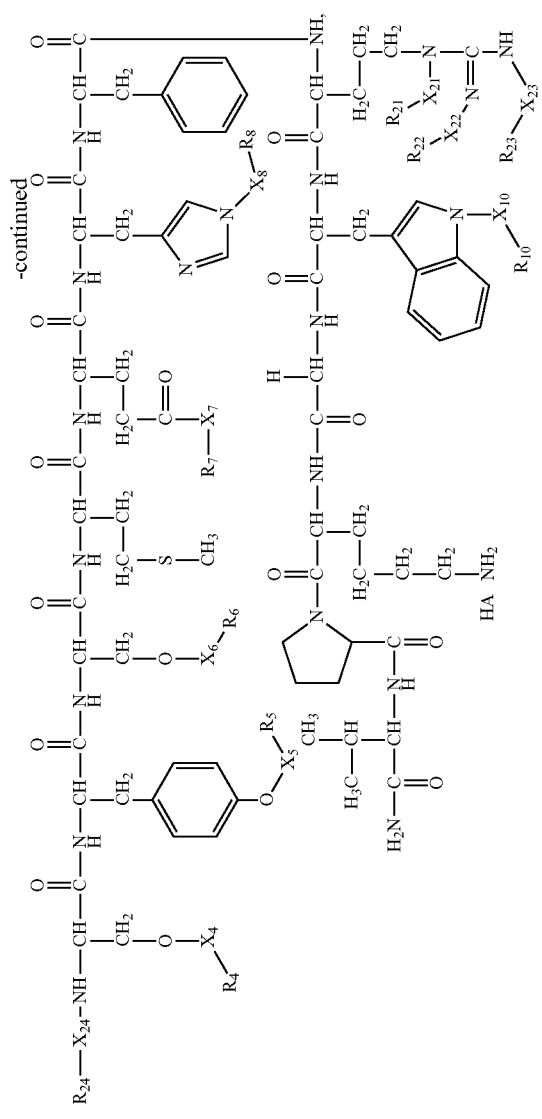
Structure 238 (SEQ ID NO: 105)
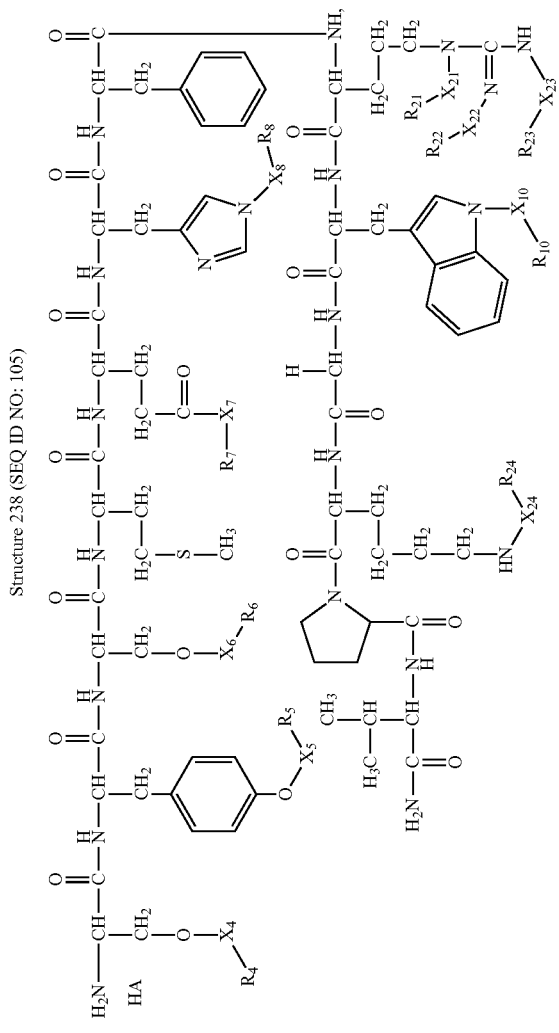
Structure 239 (SEQ ID NO: 105)

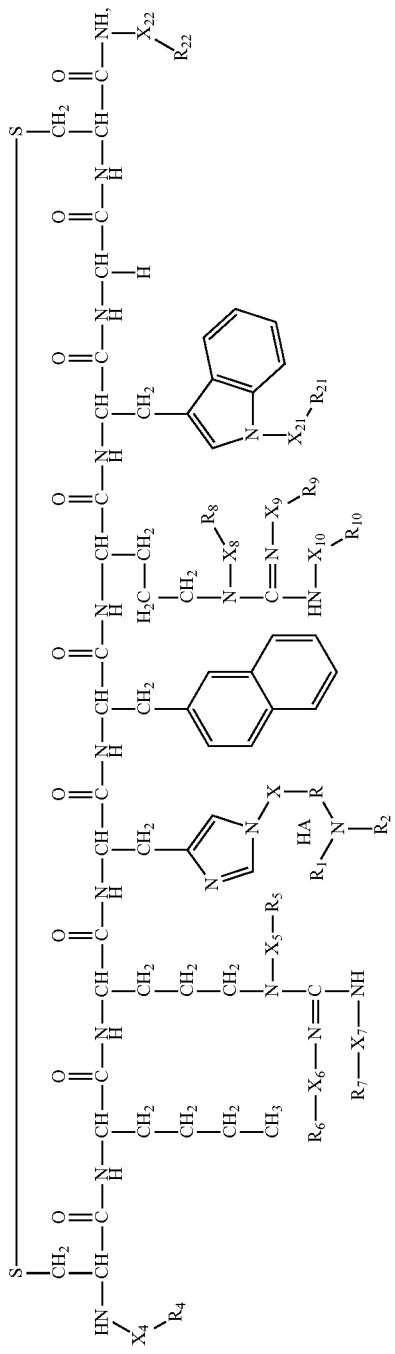
Structure 240 (SEQ ID NO: 106)
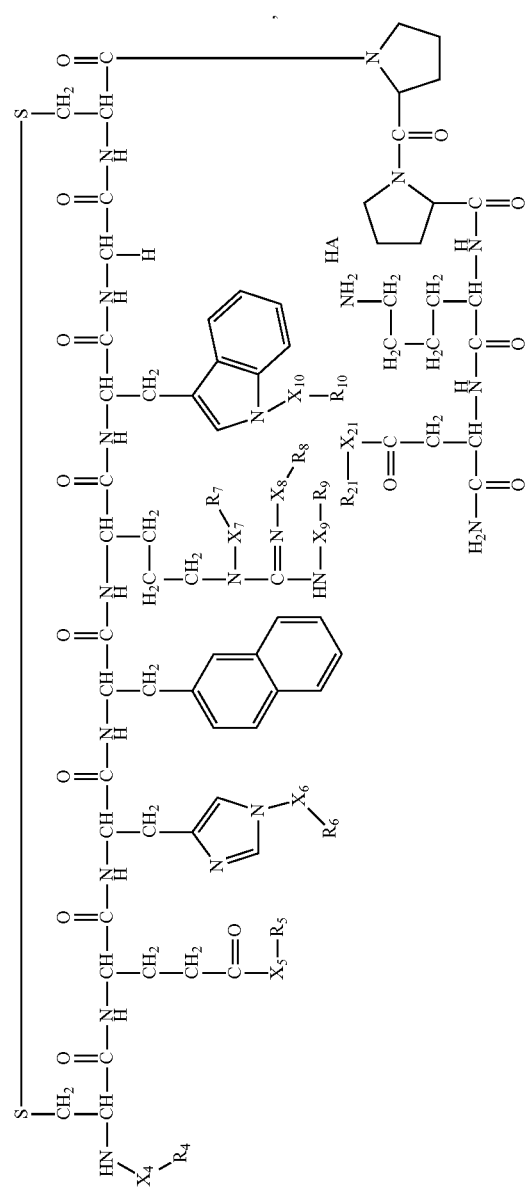
Structure 241 (SEQ ID NO: 107)

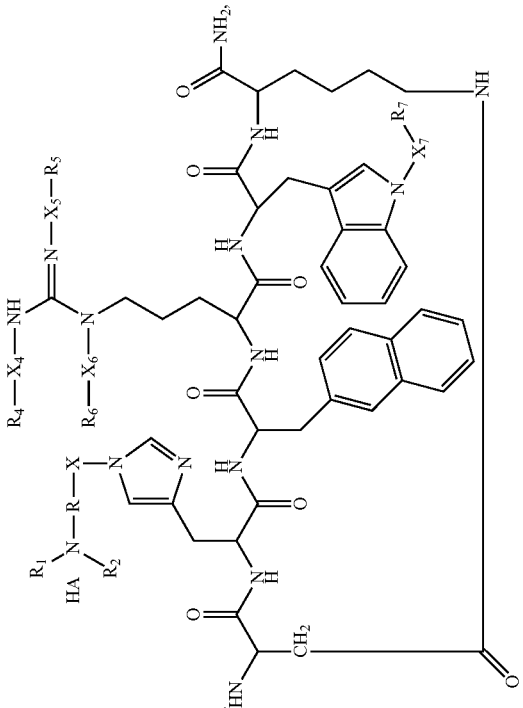
Structure 243 (SEQ ID NO: 109)
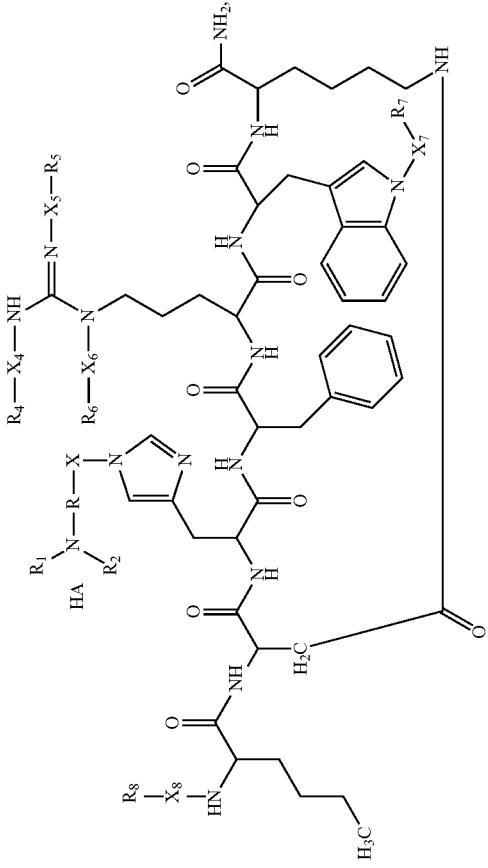
Structure 242 (SEQ ID NO: 108)
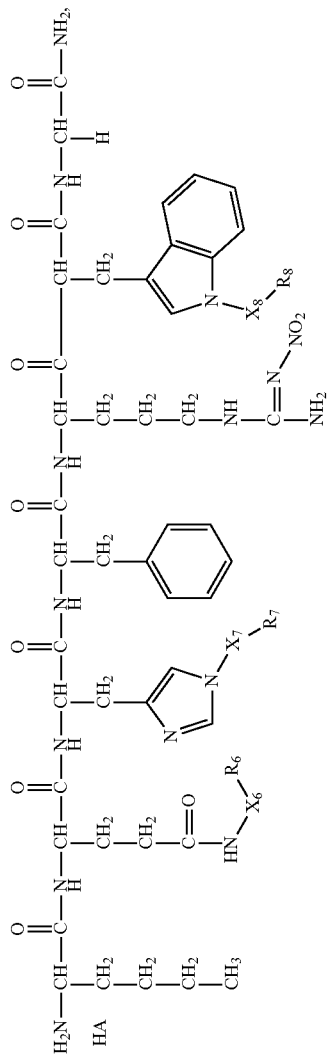
Structure 244 (SEQ ID NO: 110)

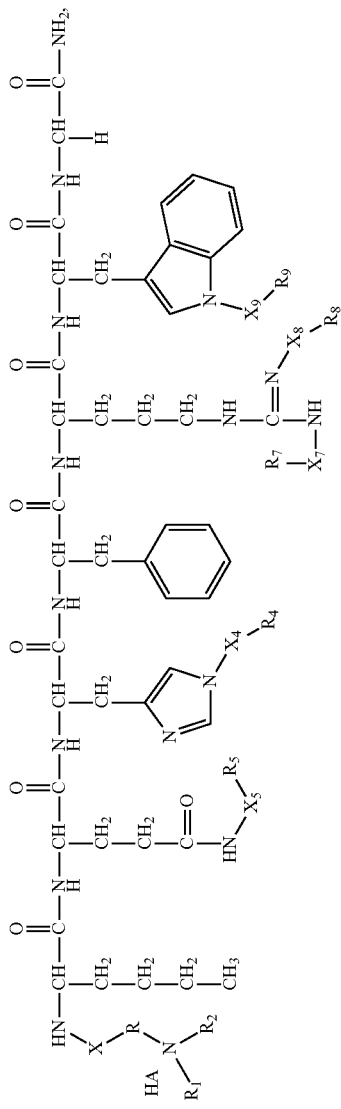
Structure 245 (SEQ ID NO: 205)
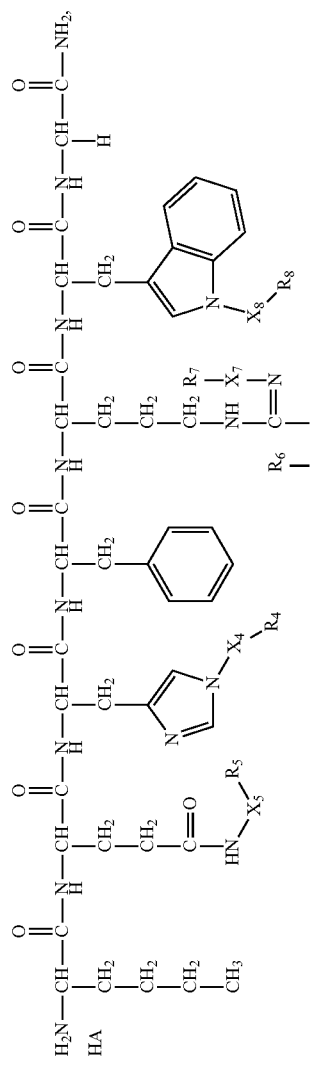
Structure 246 (SEQ ID NO: 205)

-continued
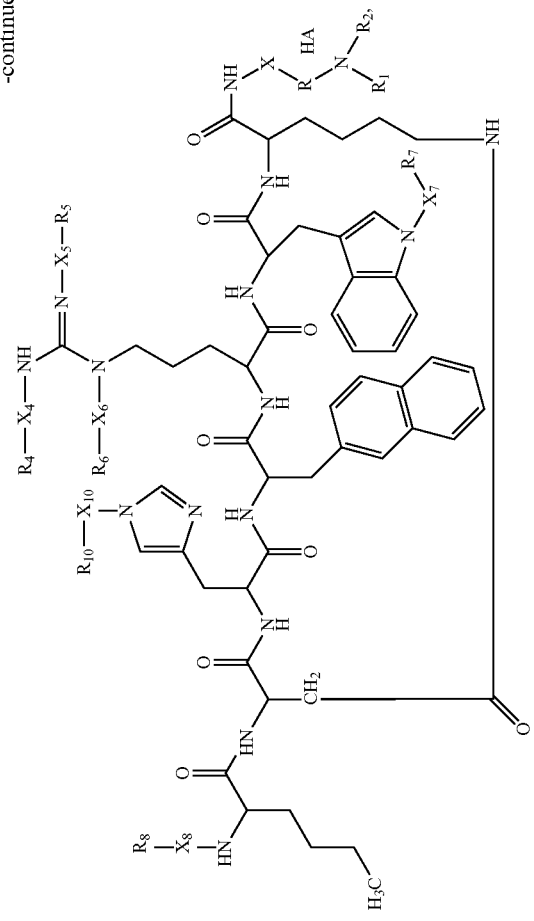
Structure 247 (SEQ ID NO: 111)
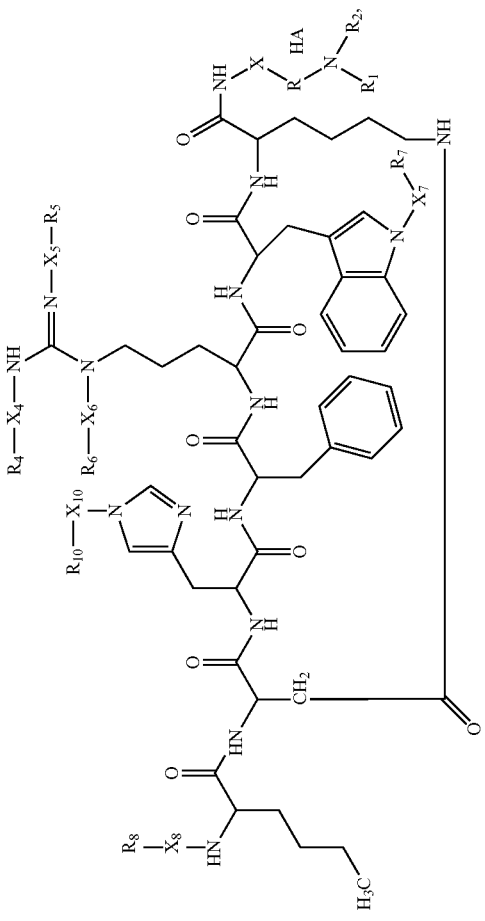
Structure 248 (SEQ ID NO: 112)

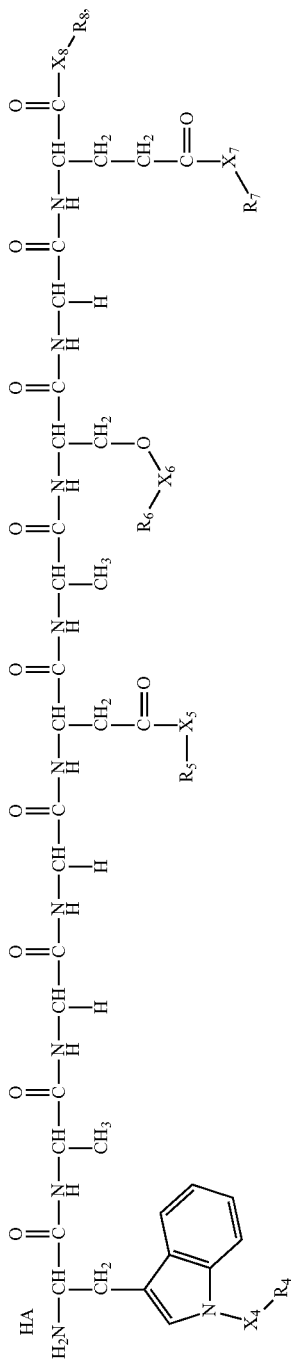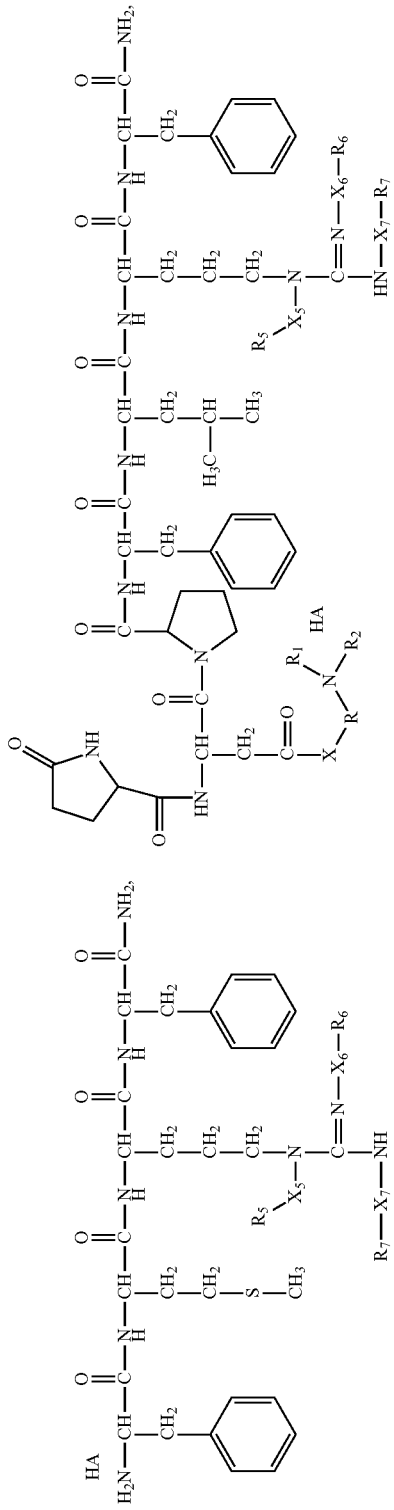

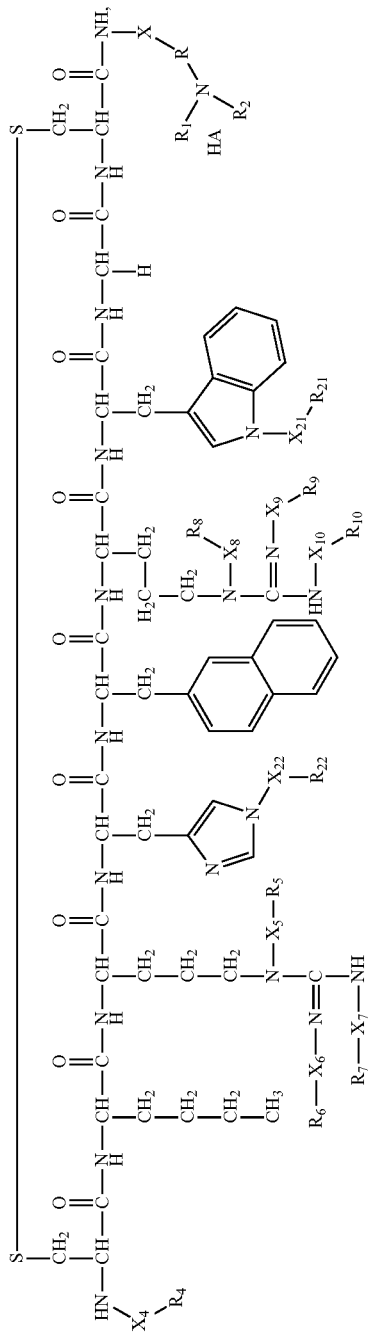
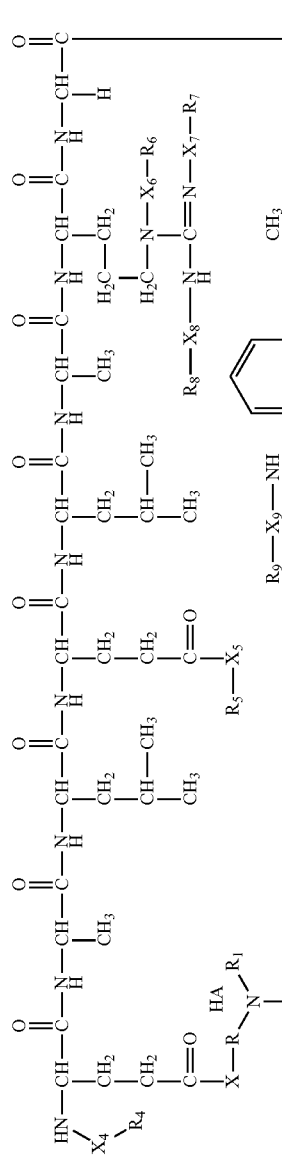
Structure 252 (SEQ ID NO: 116)
Structure 253 (SEQ ID NO: 117)

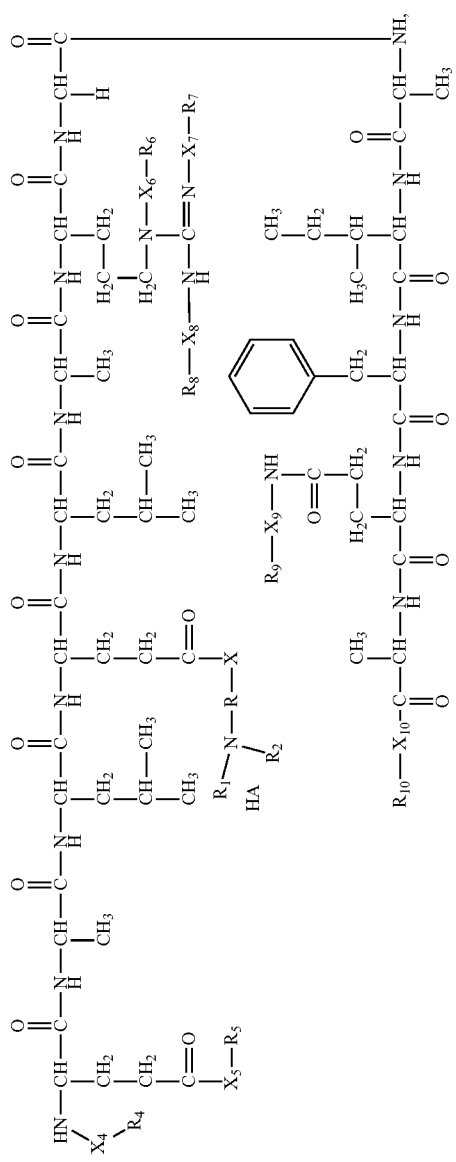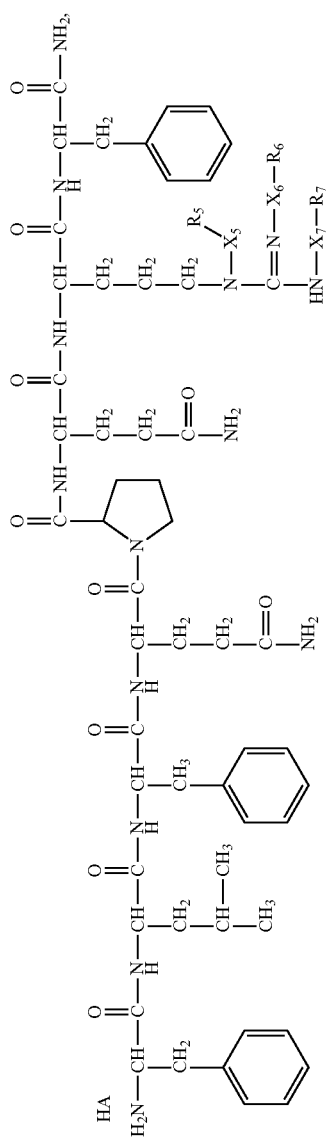

-continued
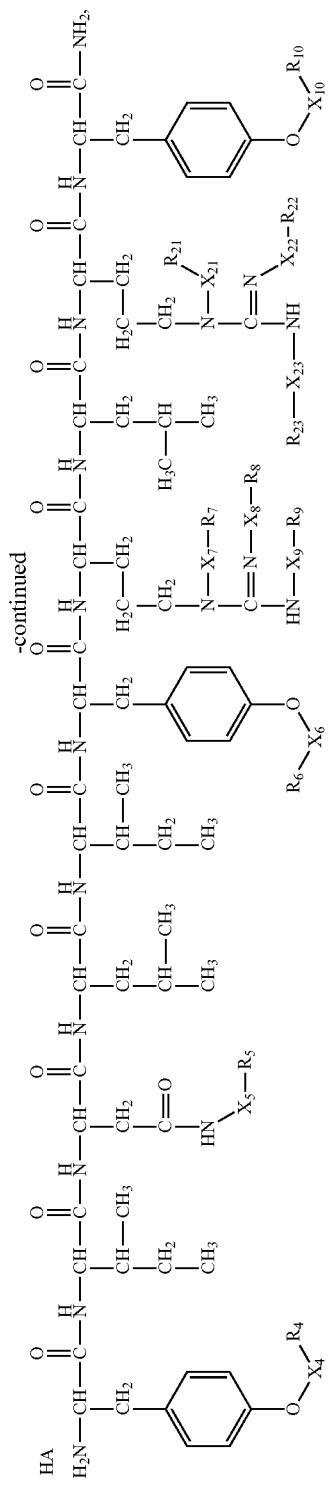
Structure 256 (SEQ ID NO: 119)
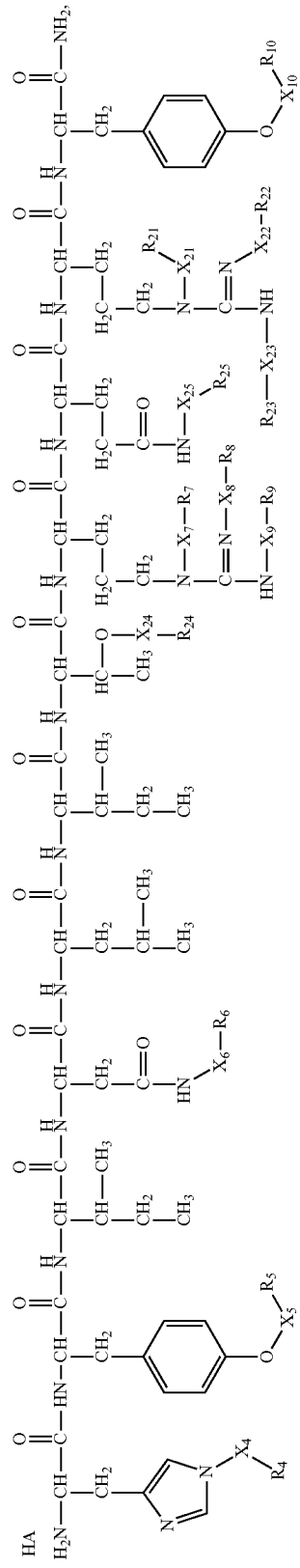
Structure 257 (SEQ ID NO: 120)
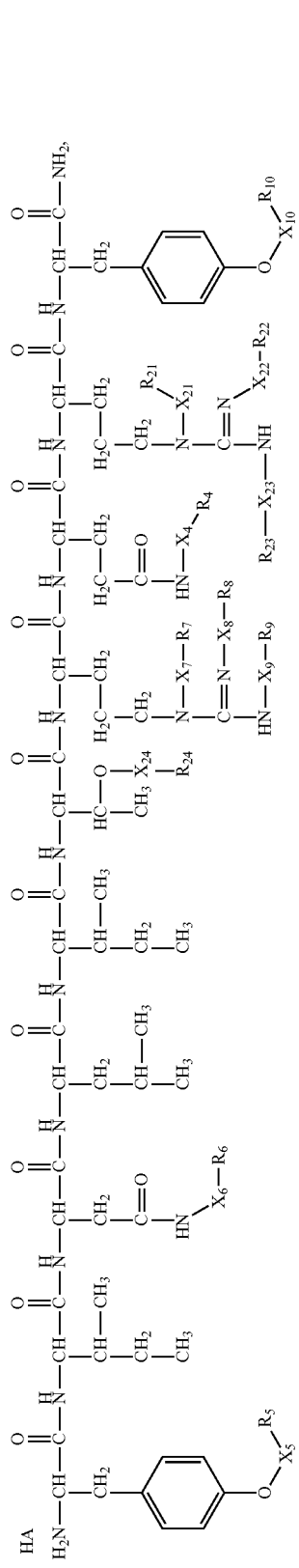
Structure 258 (SEQ ID NO: 121)

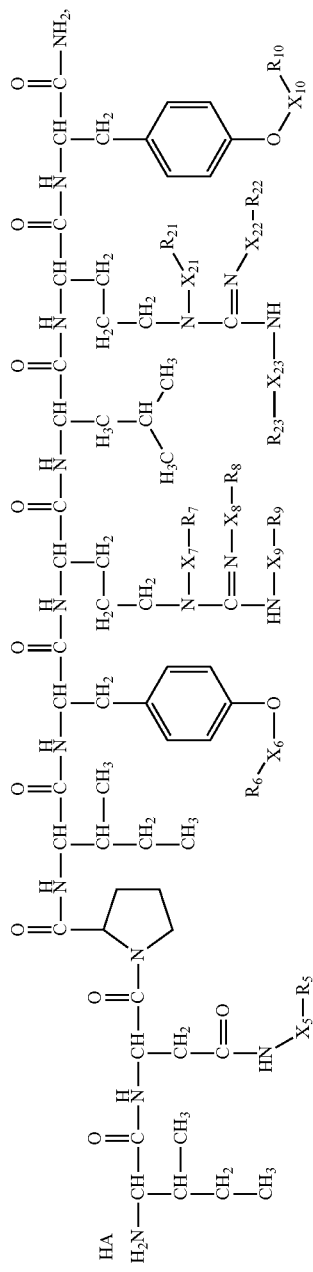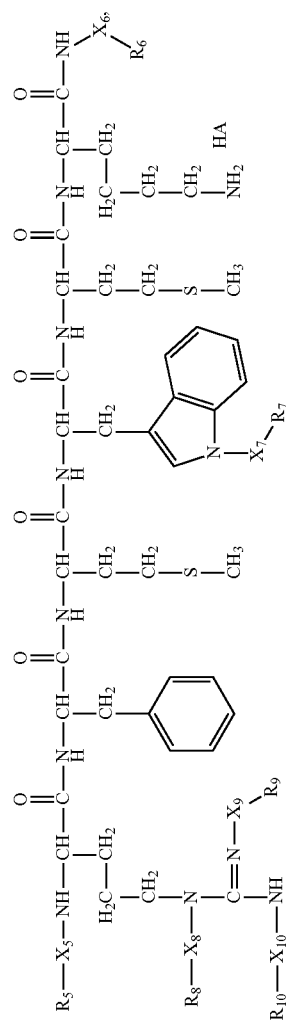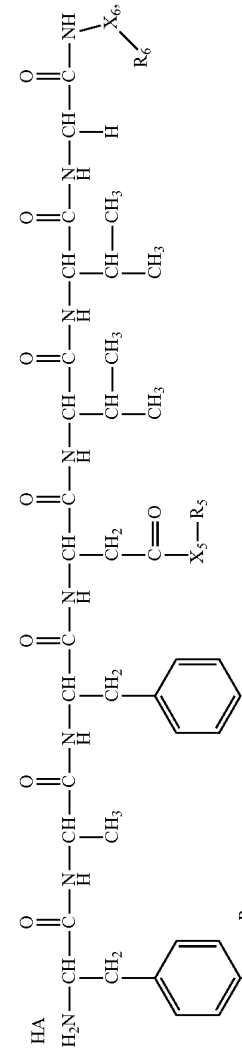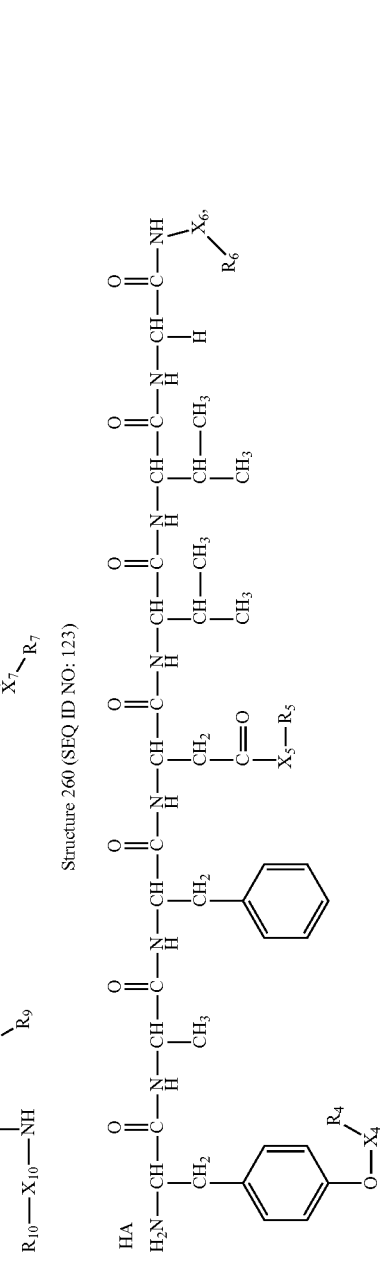
Structure 259 (SEQ ID NO: 122)
Structure 260 (SEQ ID NO: 123)
Structure 261 (SEQ ID NO: 124)

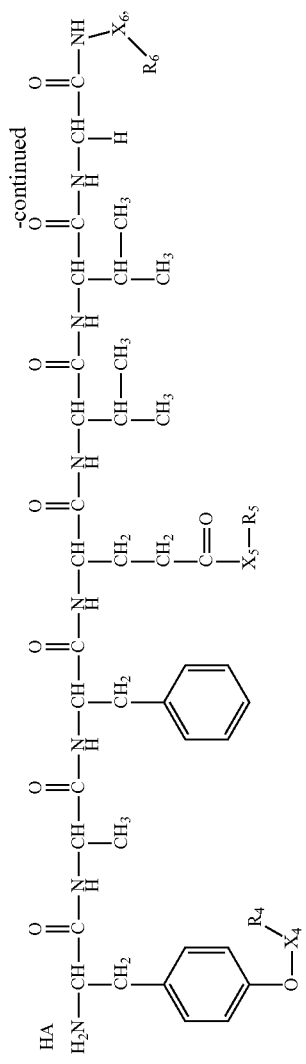
Structure 262 (SEQ ID NO: 125)
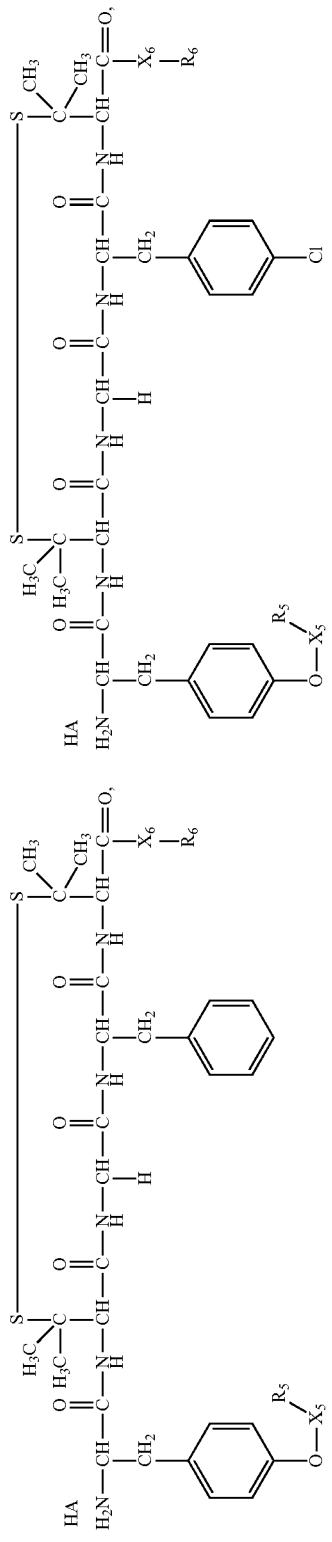
Structure 263 (SEQ ID NO: 126)
Structure 264 (SEQ ID NO: 127)
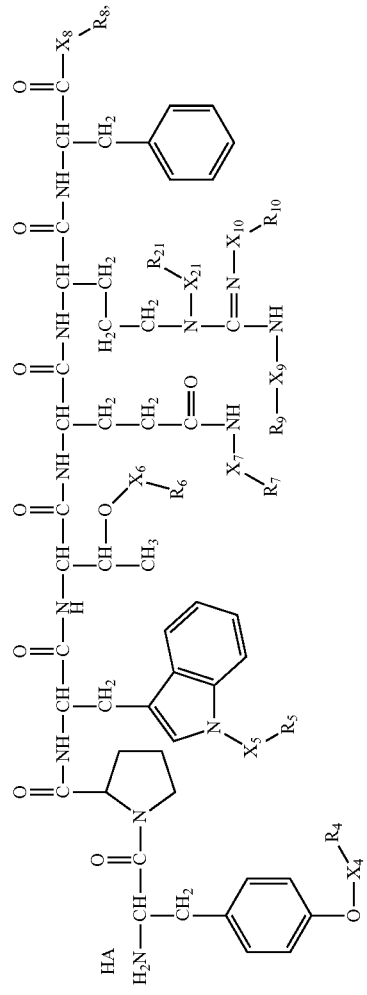
Structure 265 (SEQ ID NO: 128)

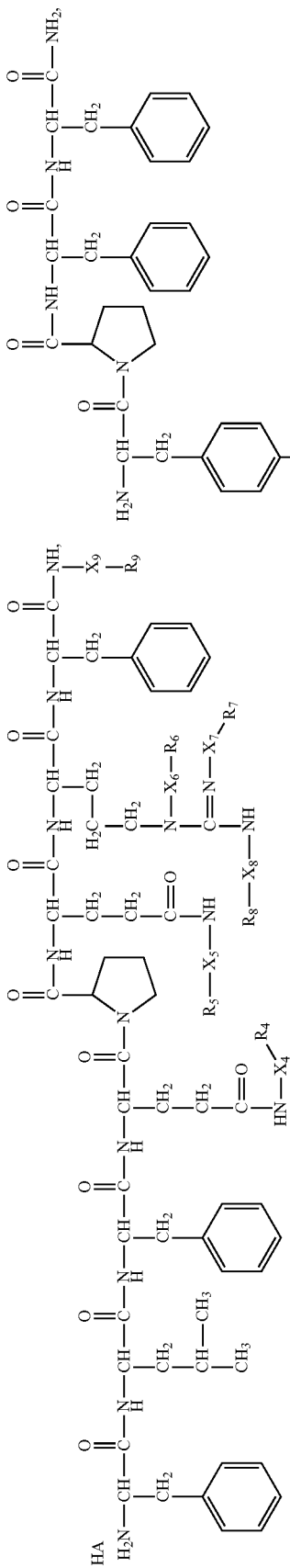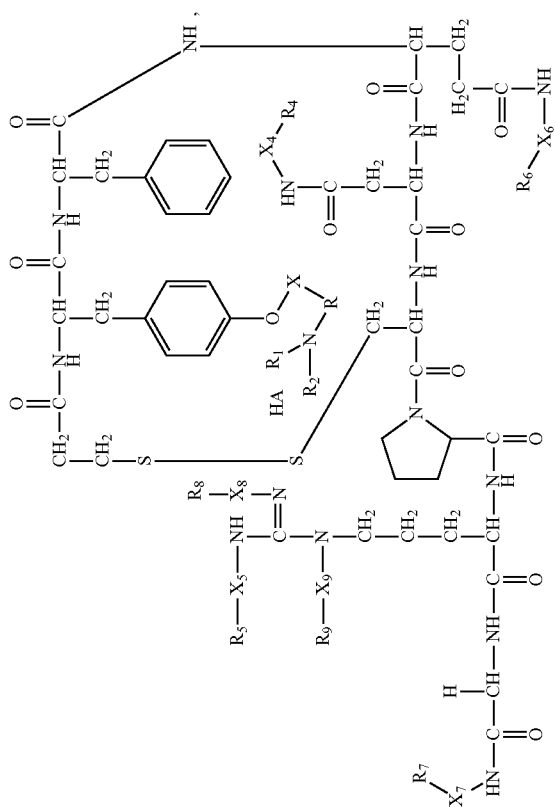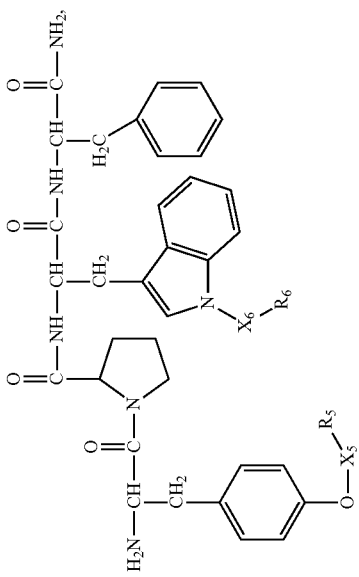

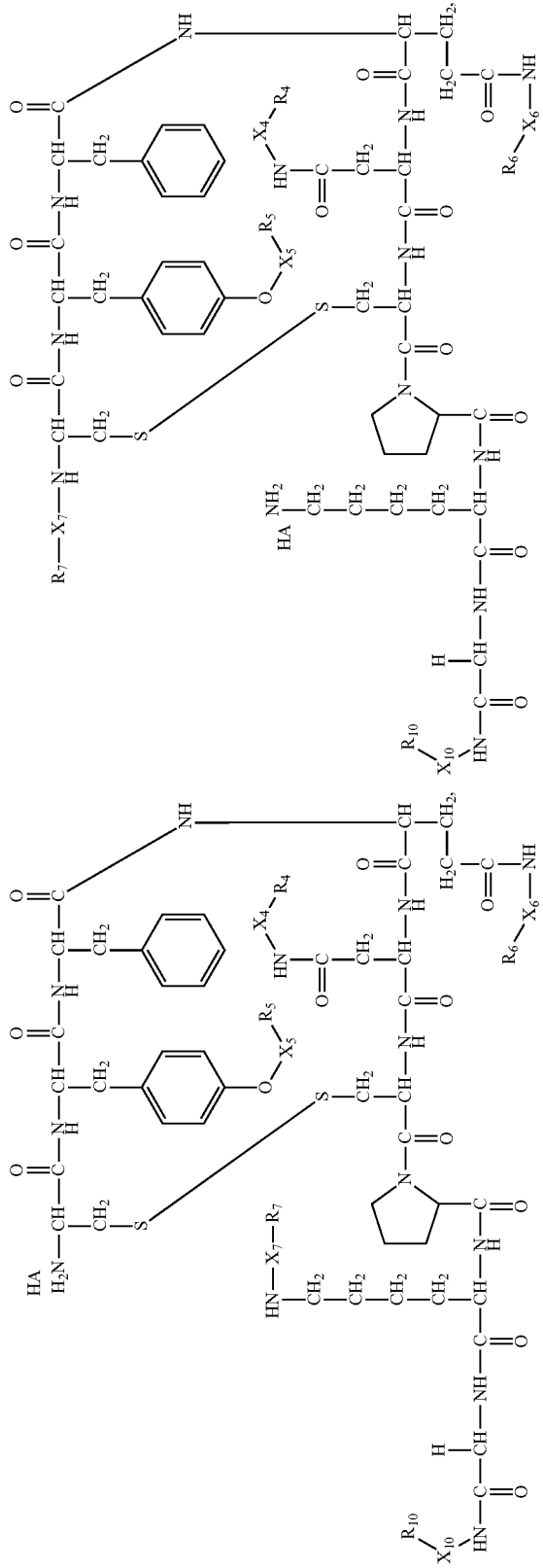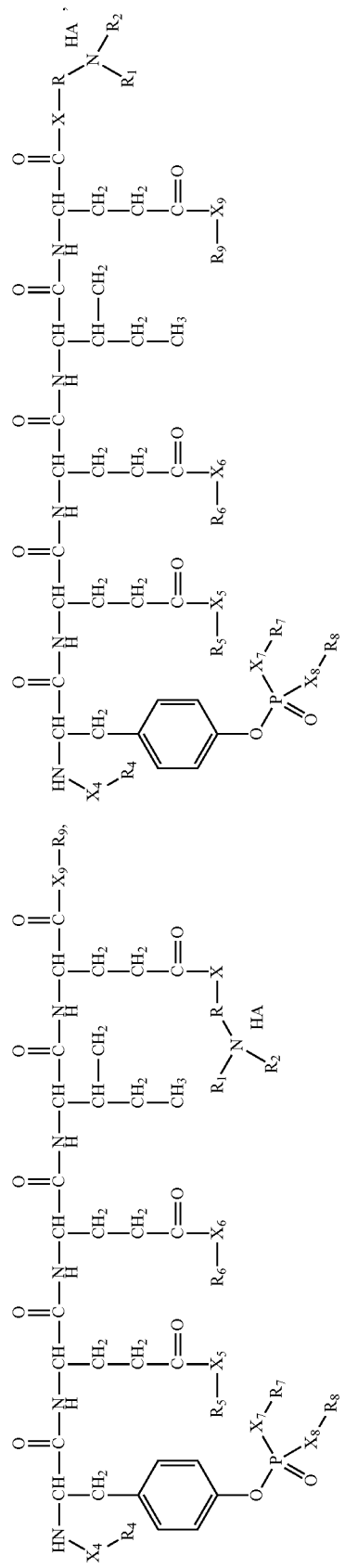

-continued
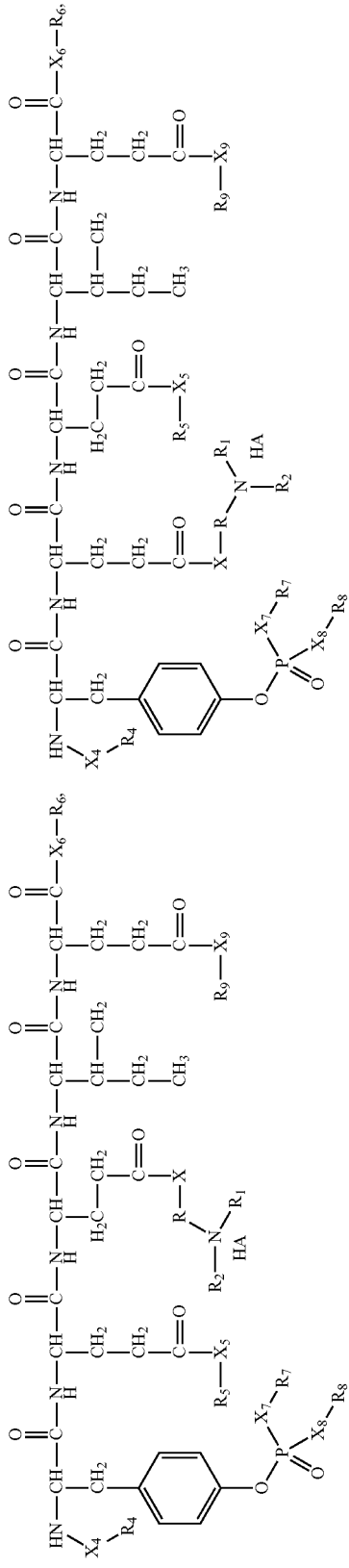
Structure 274 (SEQ ID NO: 134)
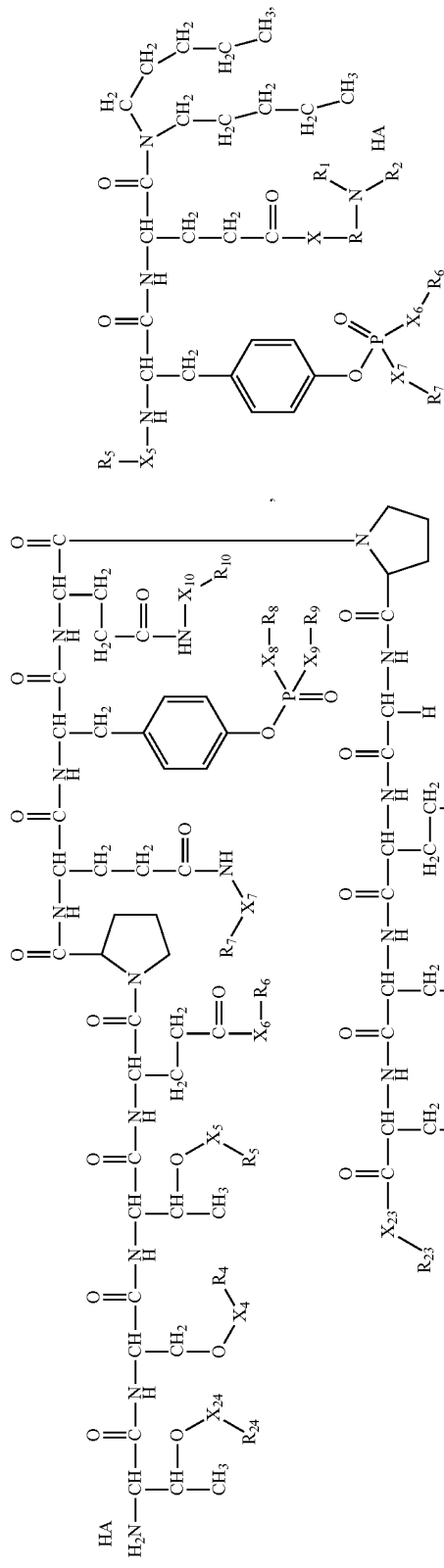
Structure 275 (SEQ ID NO: 134)
Structure 276 (SEQ ID NO: 135)
Structure 277 (SEQ ID NO: 136)

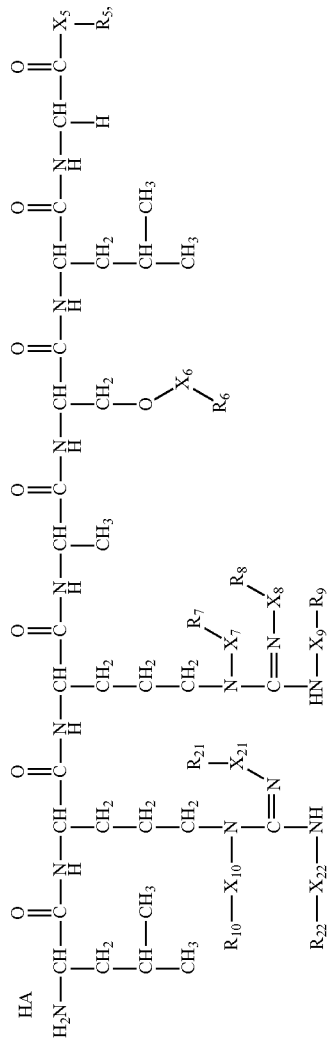
Structure 278 (SEQ ID NO: 137)
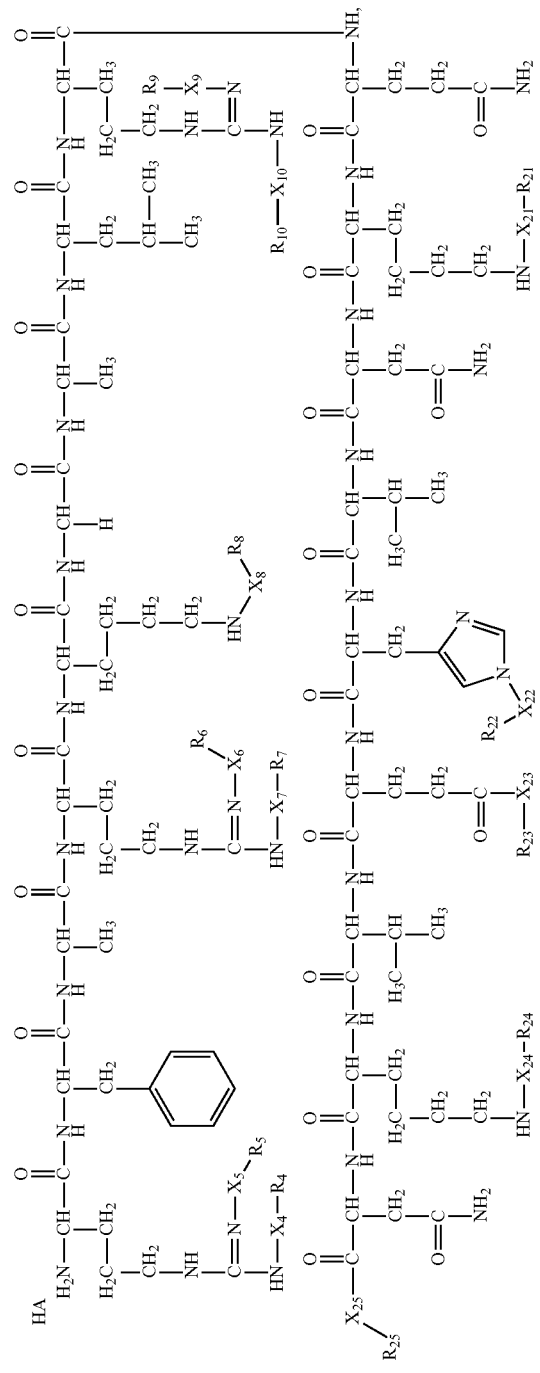
Structure 279 (SEQ ID NO: 138)

-continued
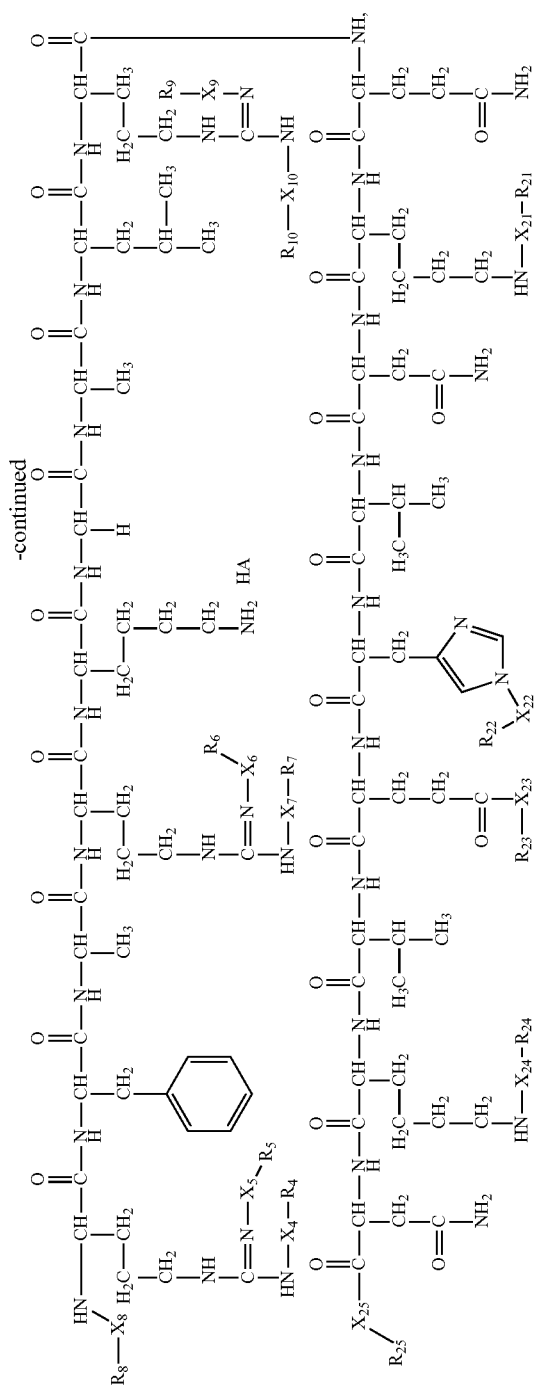
Structure 280 (SEQ ID NO: 138)
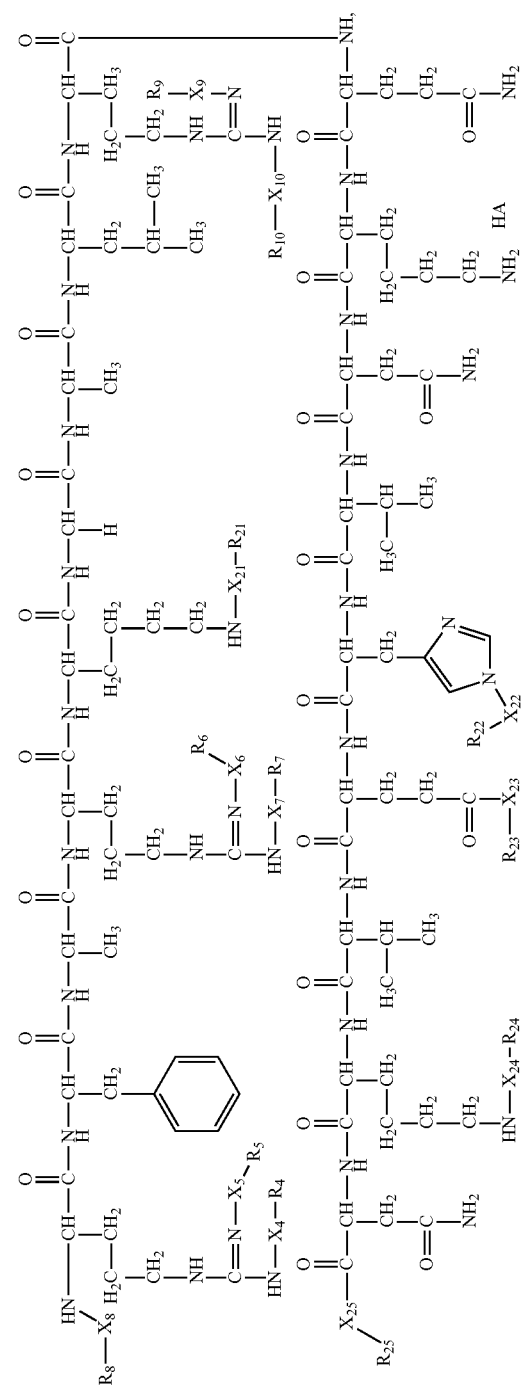
Structure 281 (SEQ ID NO: 138)

-continued
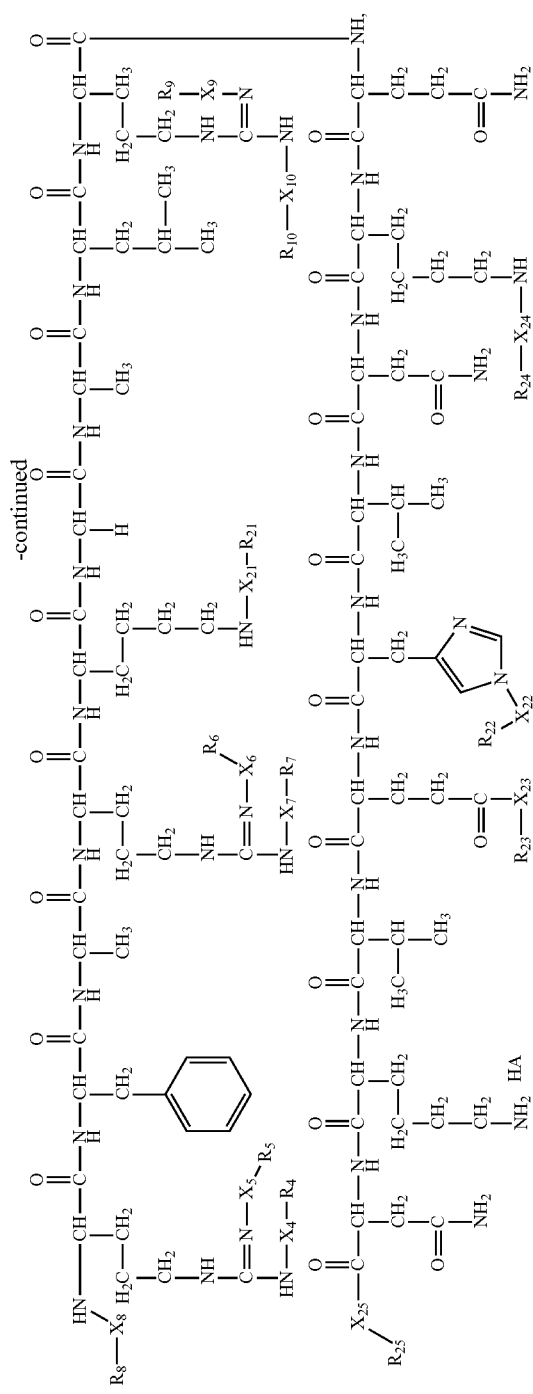
Structure 282 (SEQ ID NO: 138)
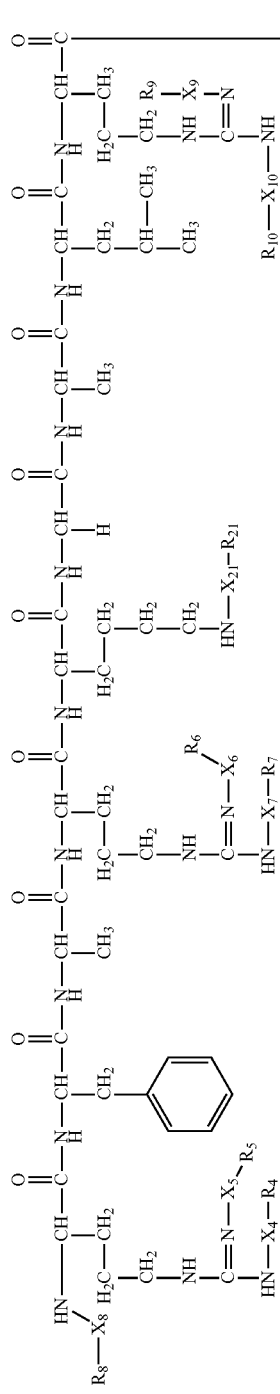
Structure 283 (SEQ ID NO: 139)

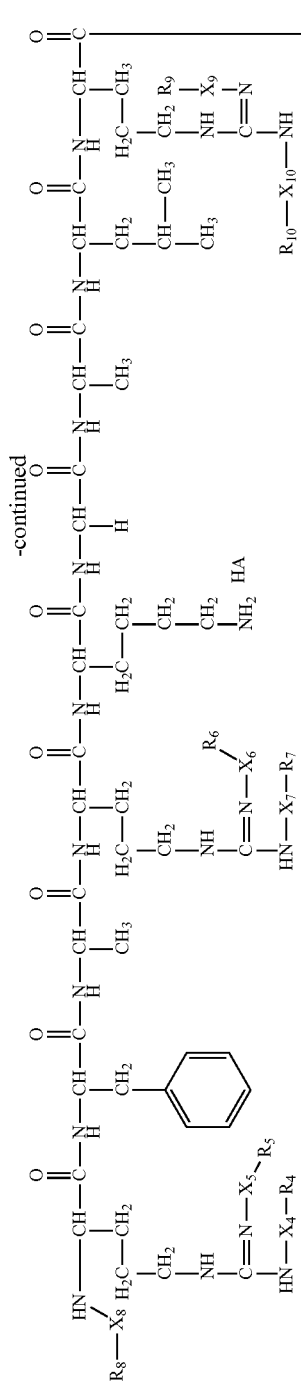
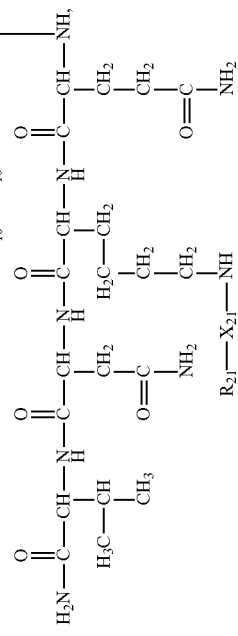
Structure 284 (SEQ ID NO: 139)
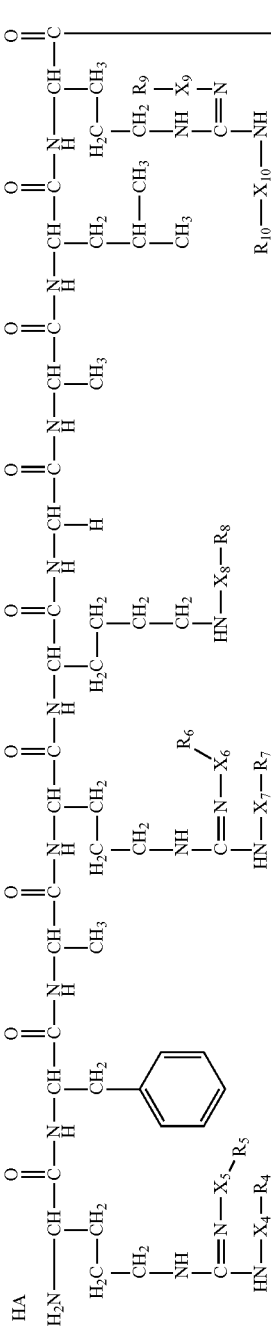
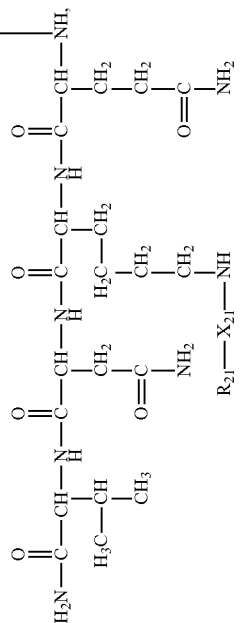
Structure 285 (SEQ ID NO: 139)

-continued
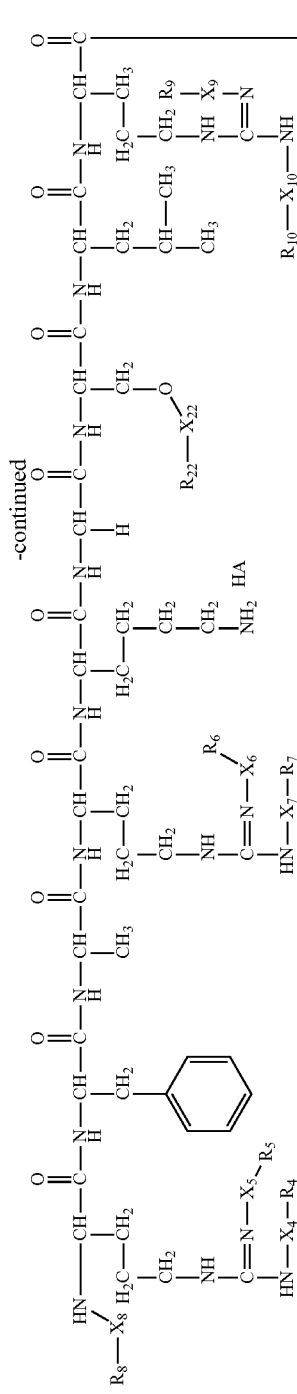
Structure 286 (SEQ ID NO: 140)
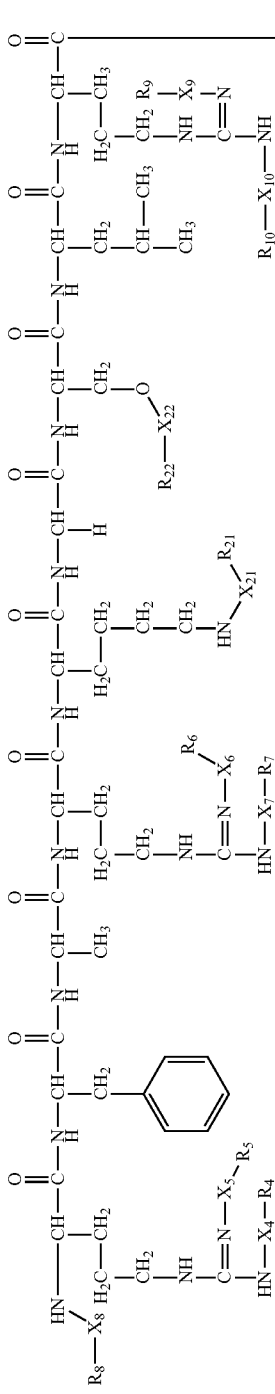
Structure 287 (SEQ ID NO: 140)

-continued
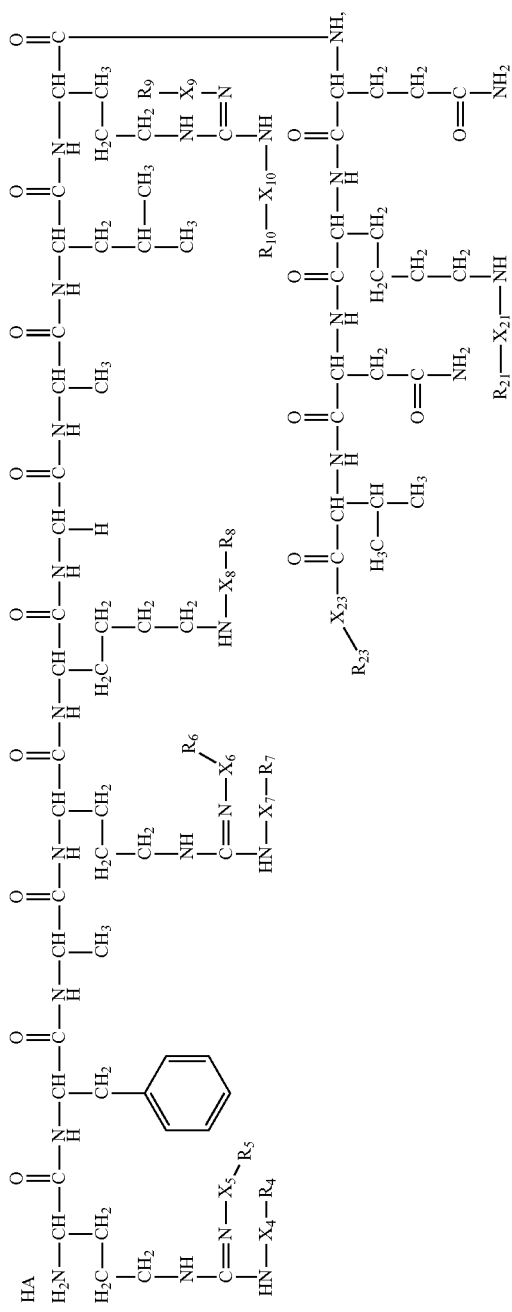
Structure 288 (SEQ ID NO: 141)
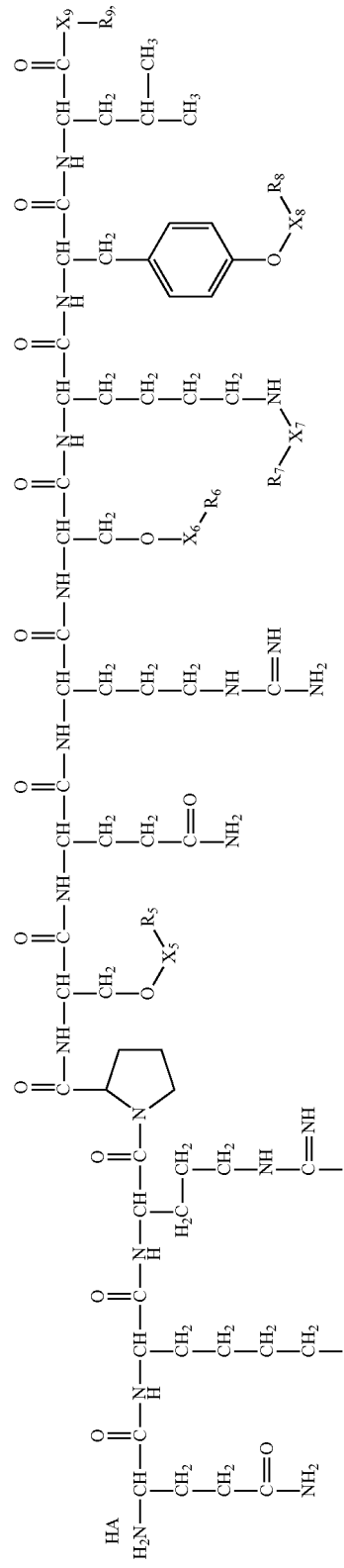
Structure 289 (SEQ ID NO: 142)

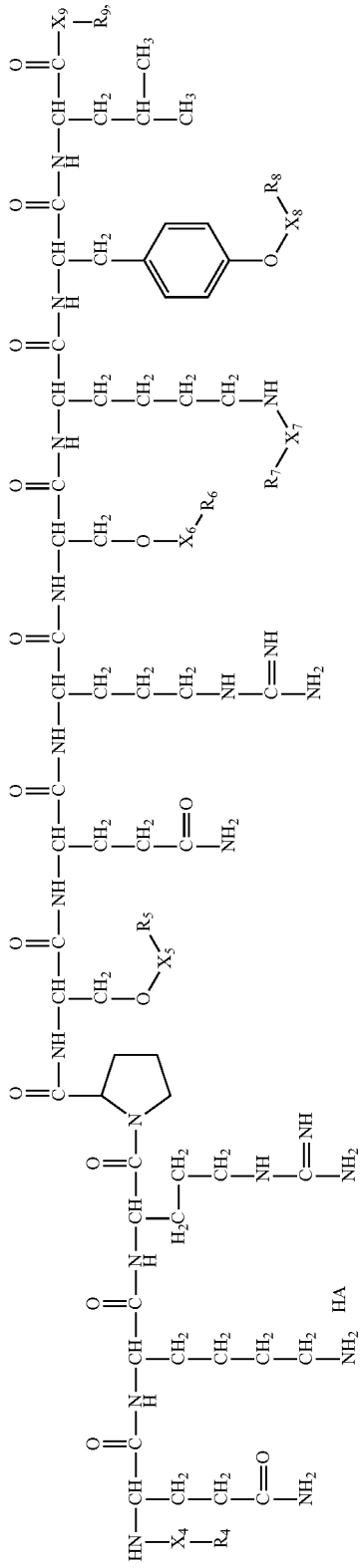
Structure 290 (SEQ ID NO: 142)
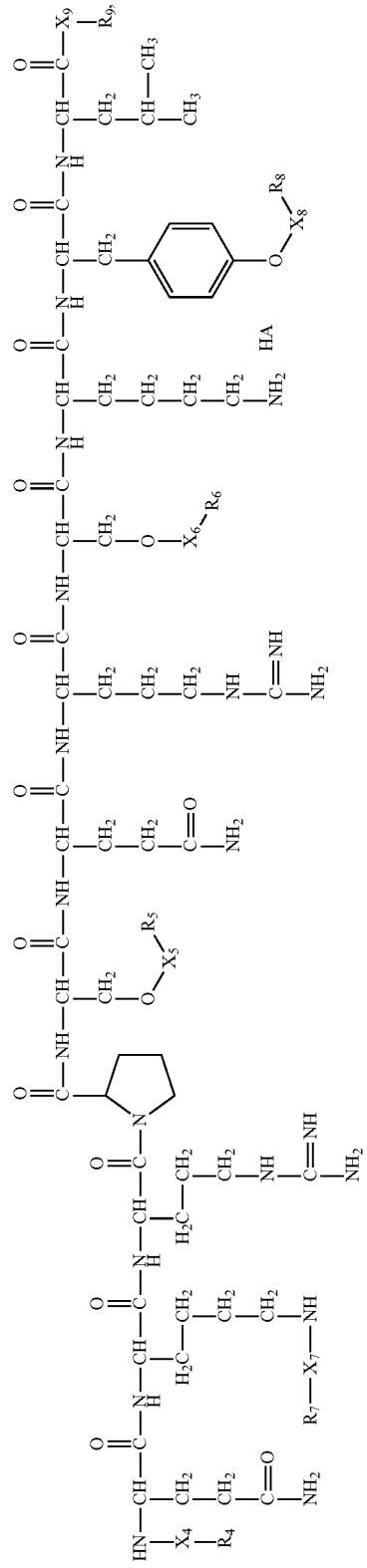
Structure 291 (SEQ ID NO: 142)

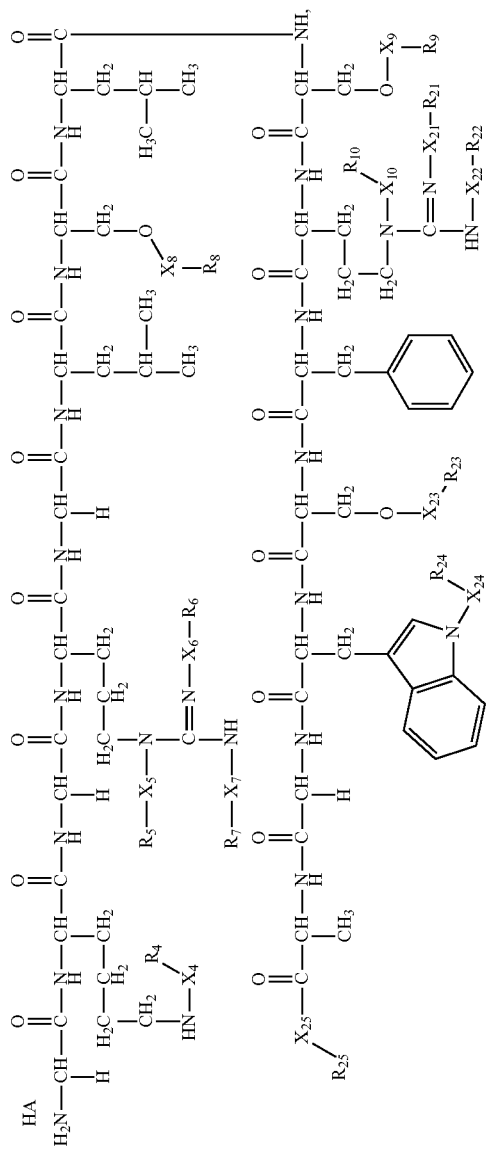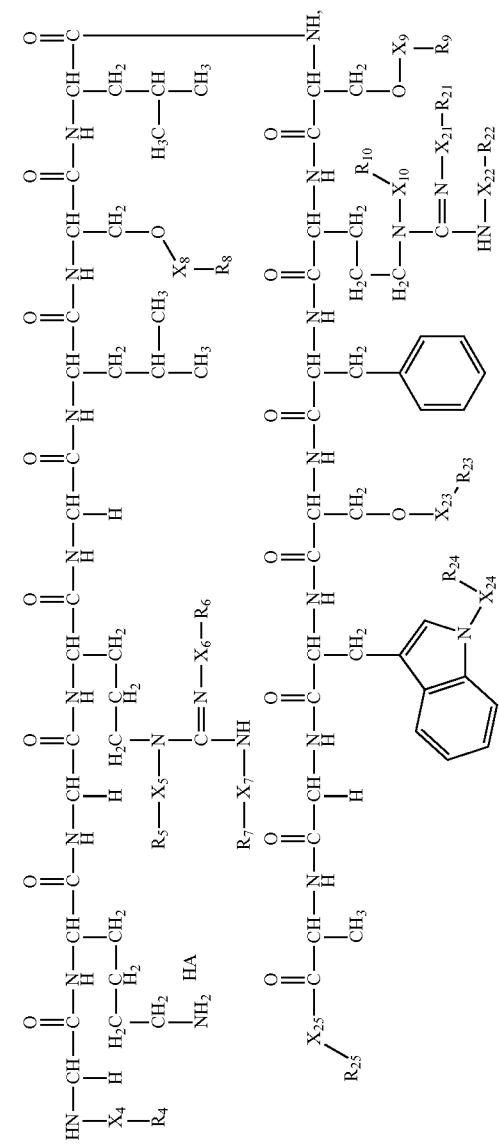

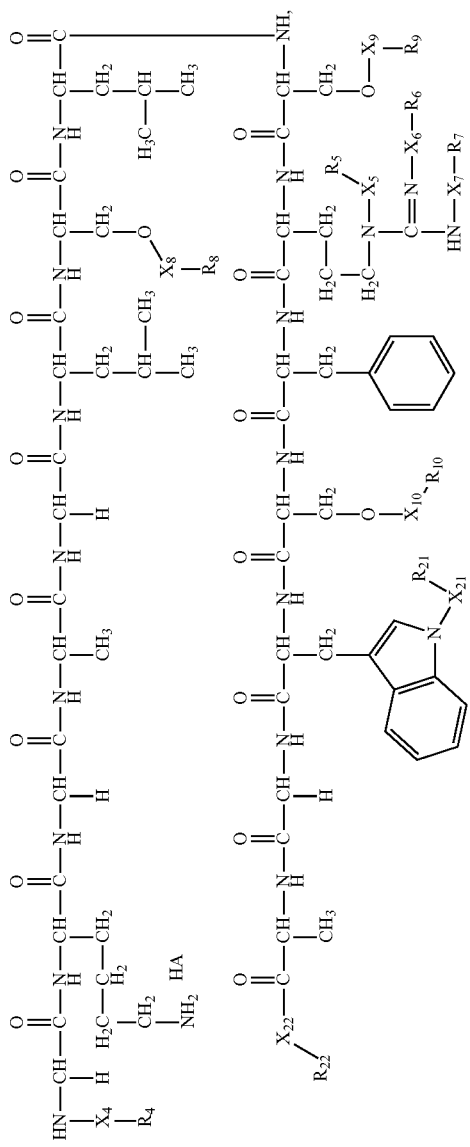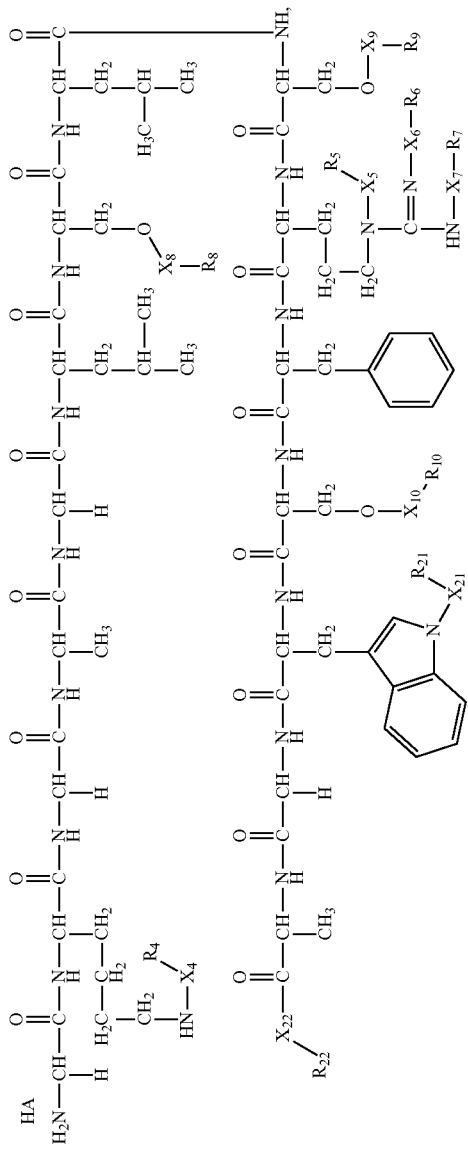

-continued
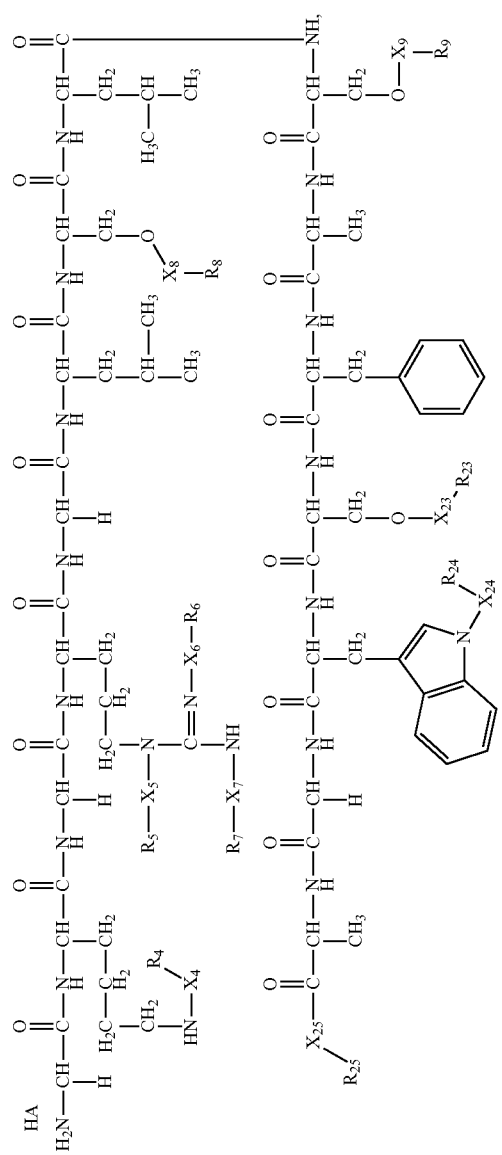
Structure 296 (SEQ ID NO: 206)
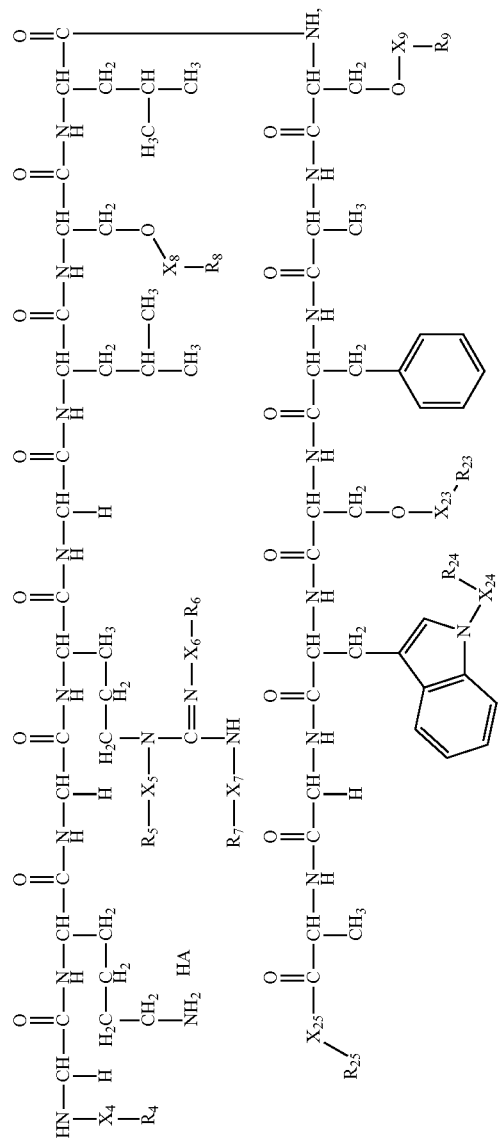
Structure 297 (SEQ ID NO: 206)

-continued
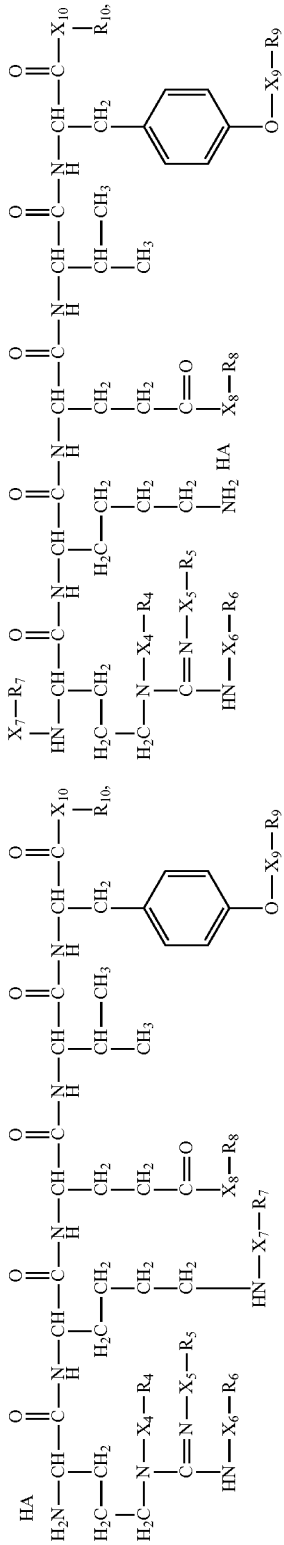
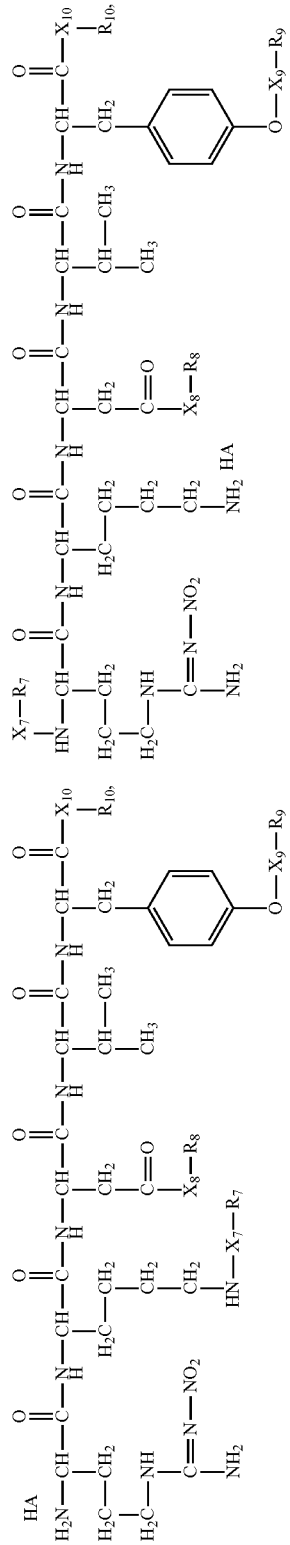
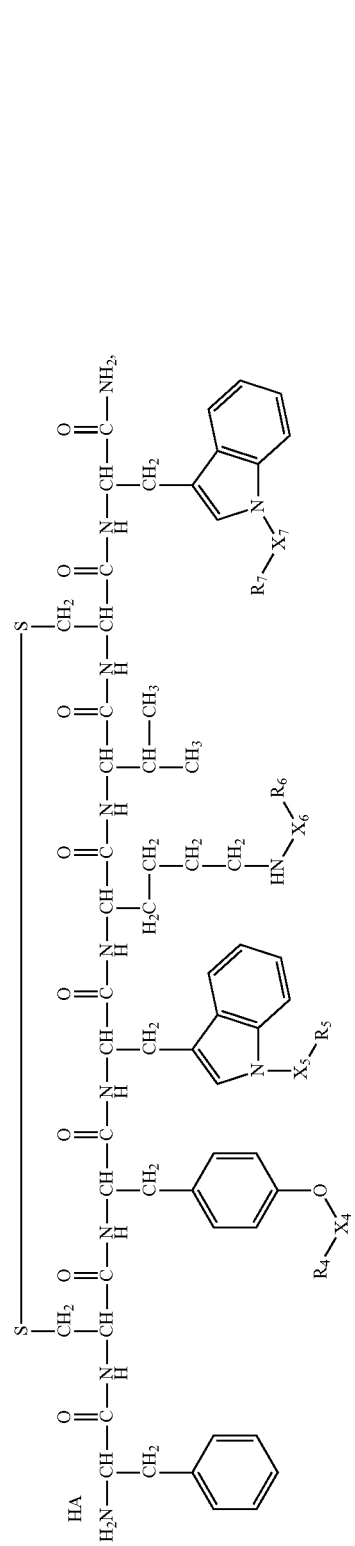

-continued
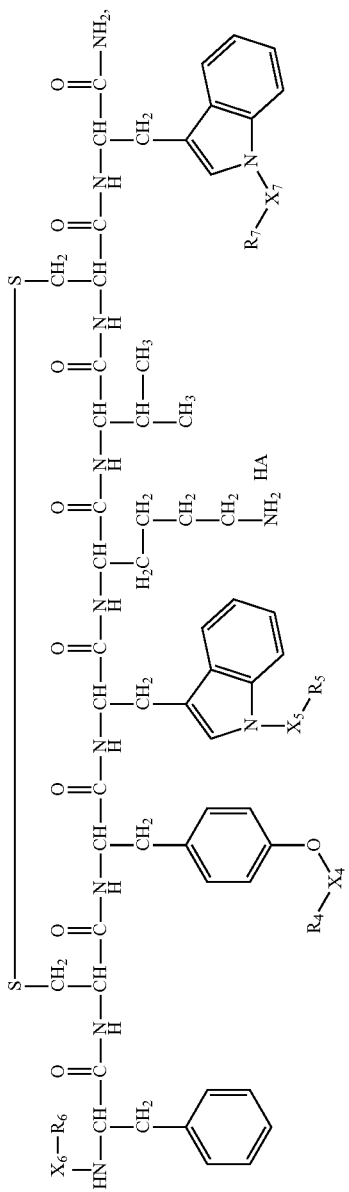
Structure 303 (SEQ ID NO: 146)
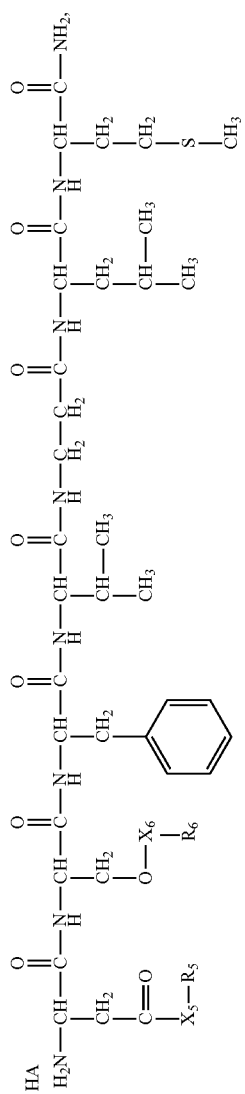
Structure 304 (SEQ ID NO: 147)
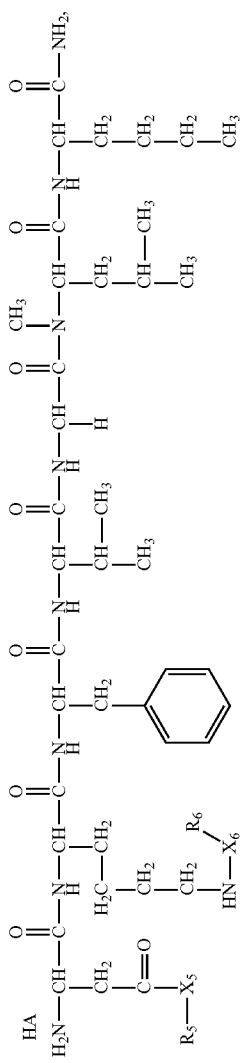
Structure 305 (SEQ ID NO: 148)

-continued
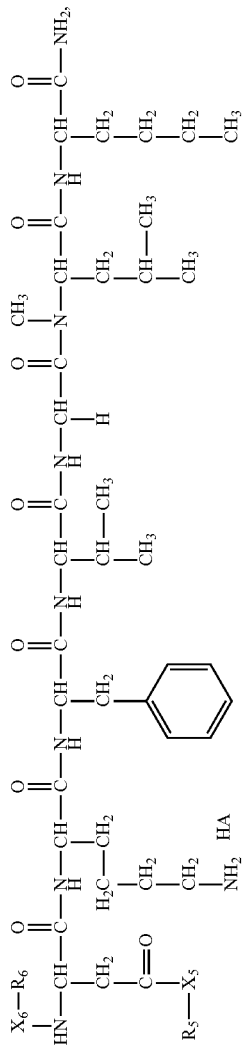
Structure 306 (SEQ ID NO: 148)
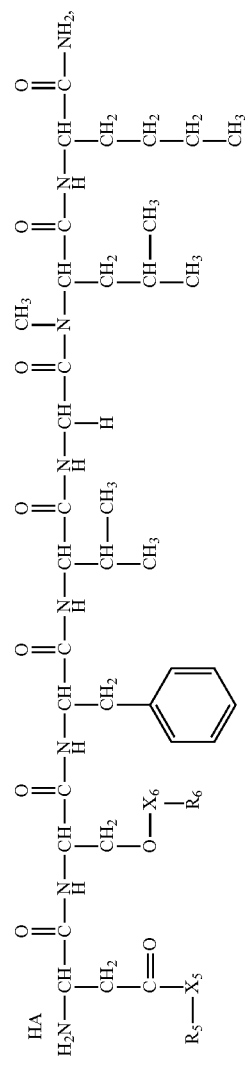
Structure 307 (SEQ ID NO: 149)
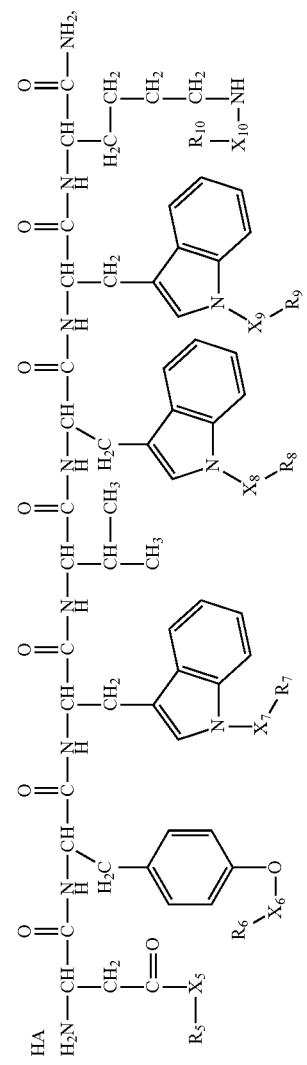
Structure 308 (SEQ ID NO: 150)

-continued
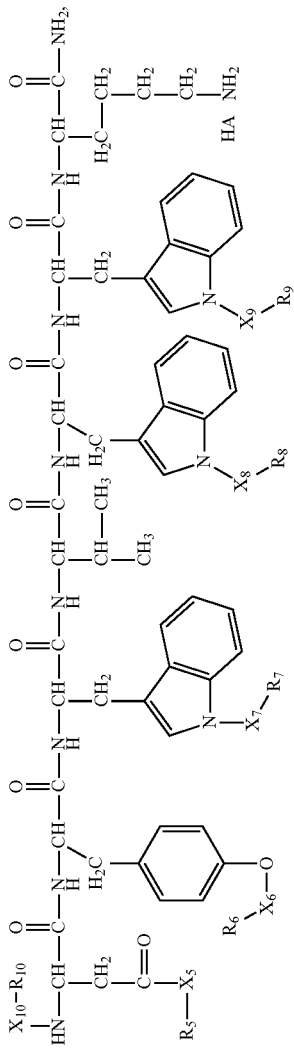
Structure 309 (SEQ ID NO: 150)
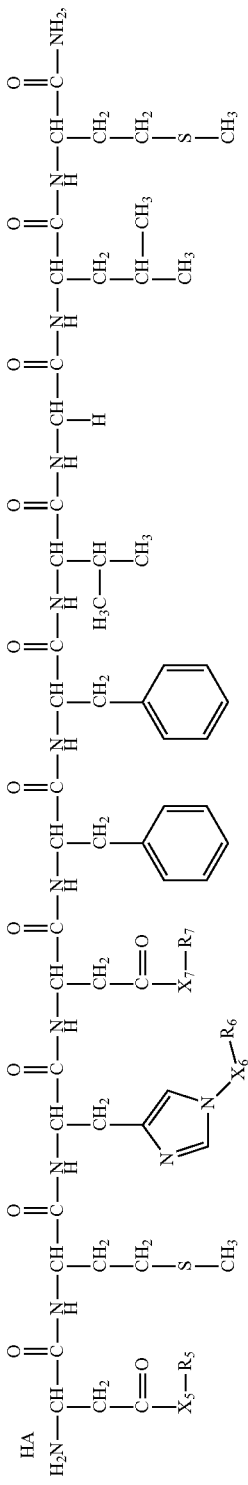
Structure 310 (SEQ ID NO: 151)
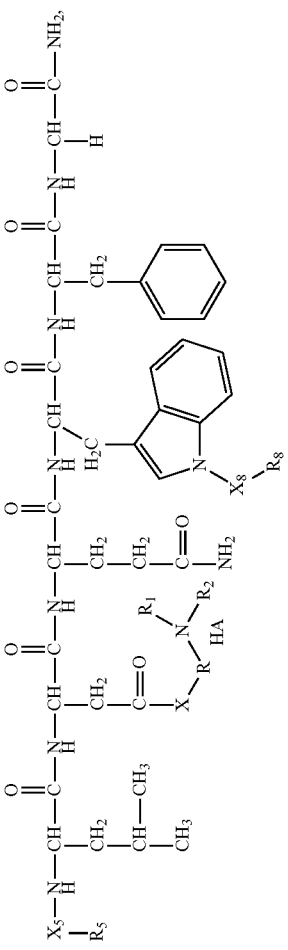
Structure 311 (SEQ ID NO: 152)

-continued
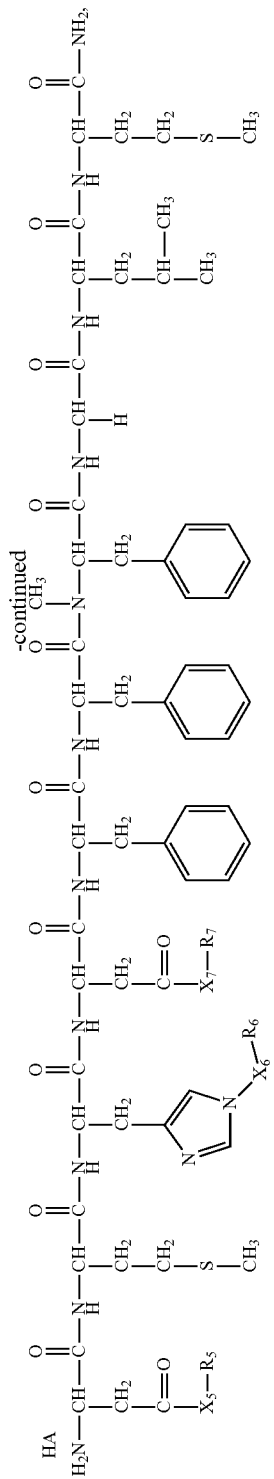
Structure 312 (SEQ ID NO: 153)
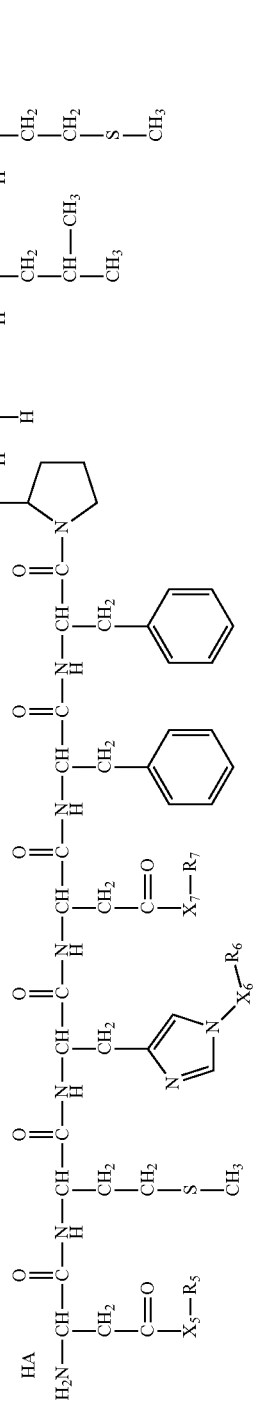
Structure 313 (SEQ ID NO: 154)
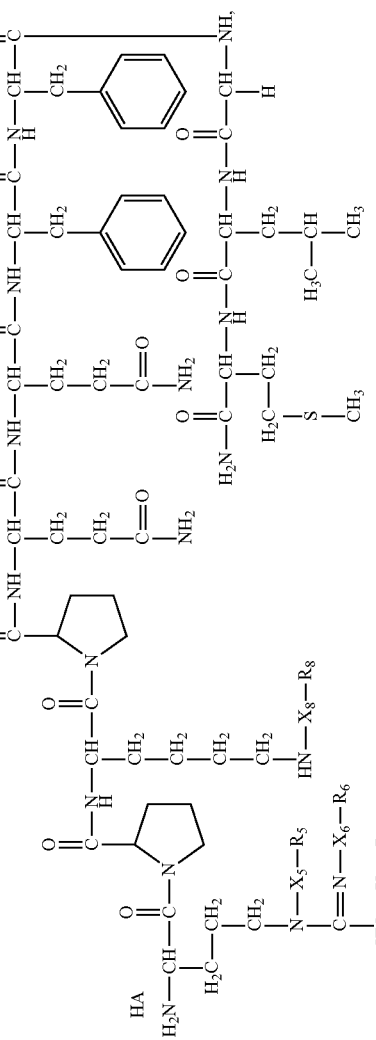
Structure 314 (SEQ ID NO: 155)

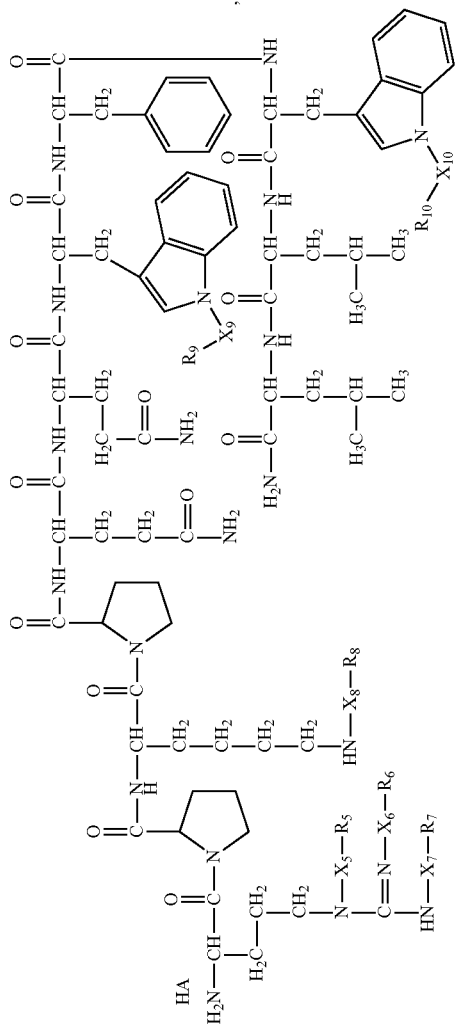
Structure 315 (SEQ ID NO: 156)
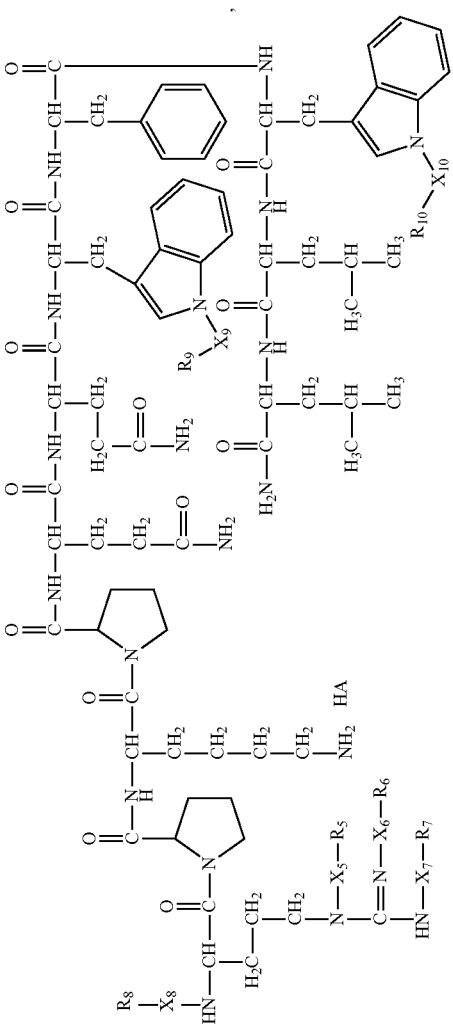
Structure 316 (SEQ ID NO: 156)

-continued
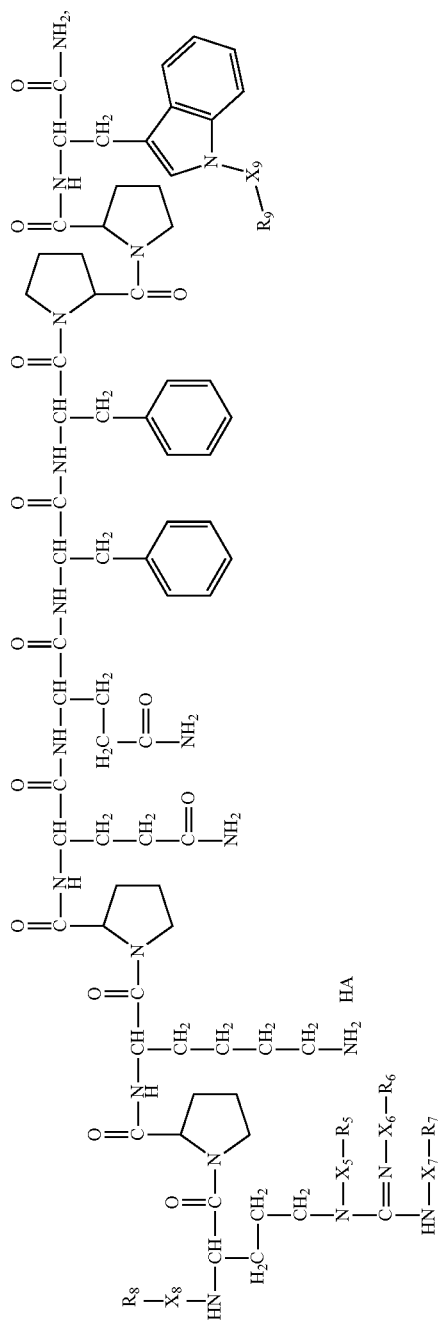
Structure 317 (SEQ ID NO: 157)
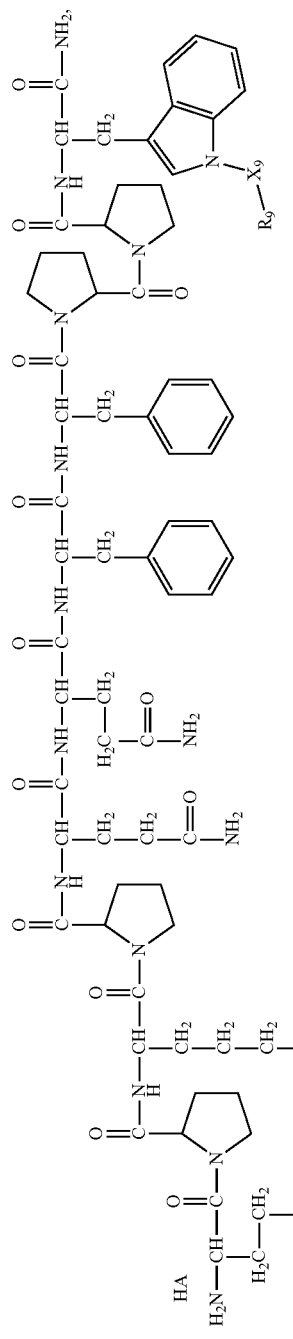
Structure 318 (SEQ ID NO: 157)

-continued
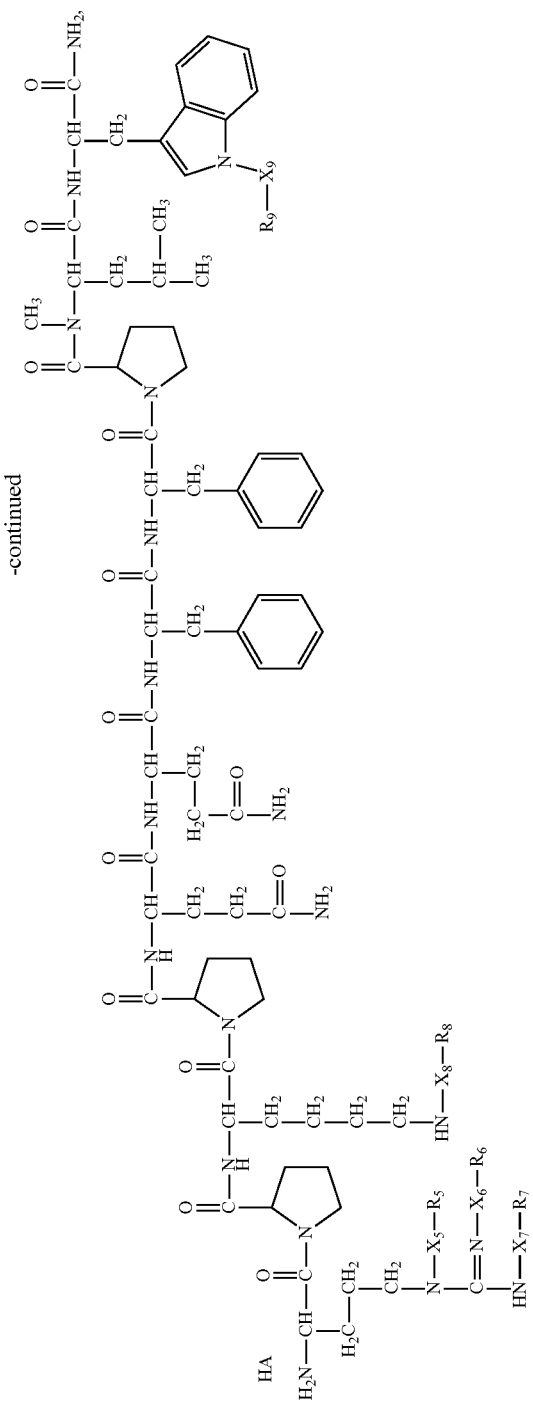
Structure 319 (SEQ ID NO: 158)
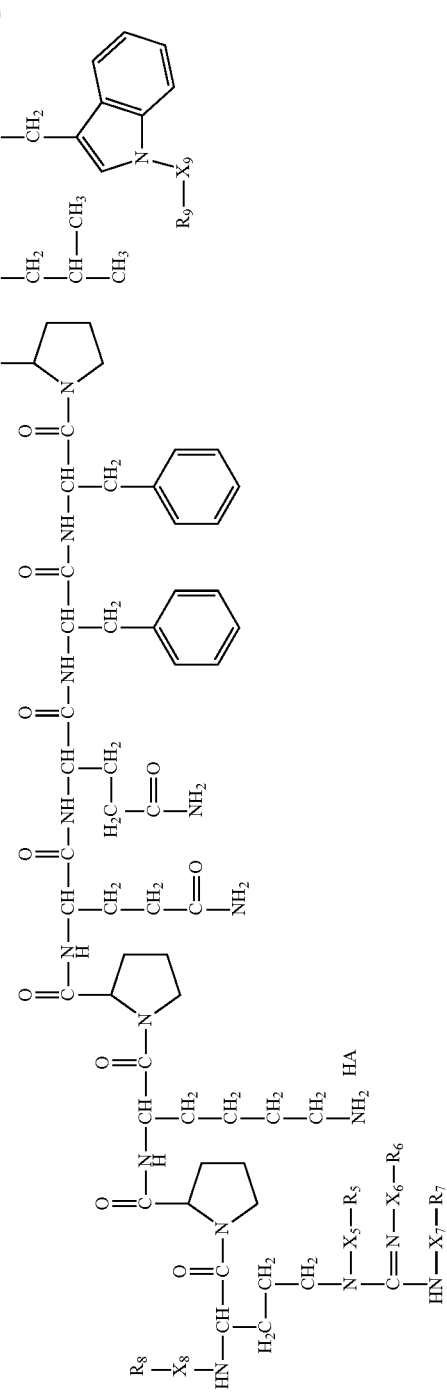
Structure 320 (SEQ ID NO: 158)

-continued
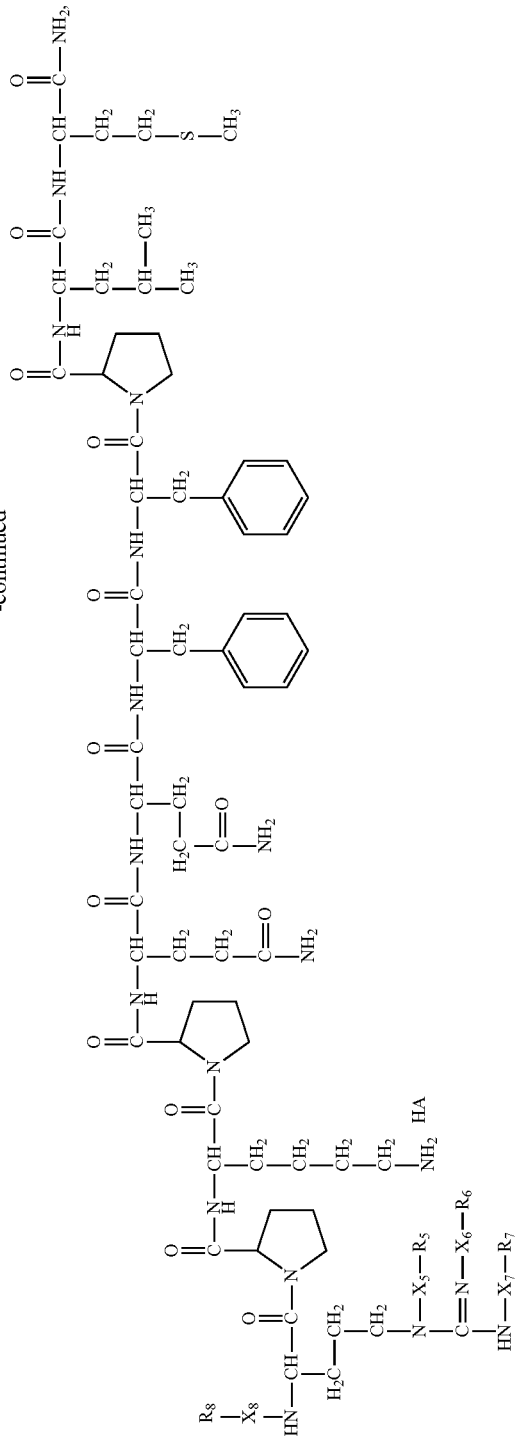
Structure 321 (SEQ ID NO: 159)
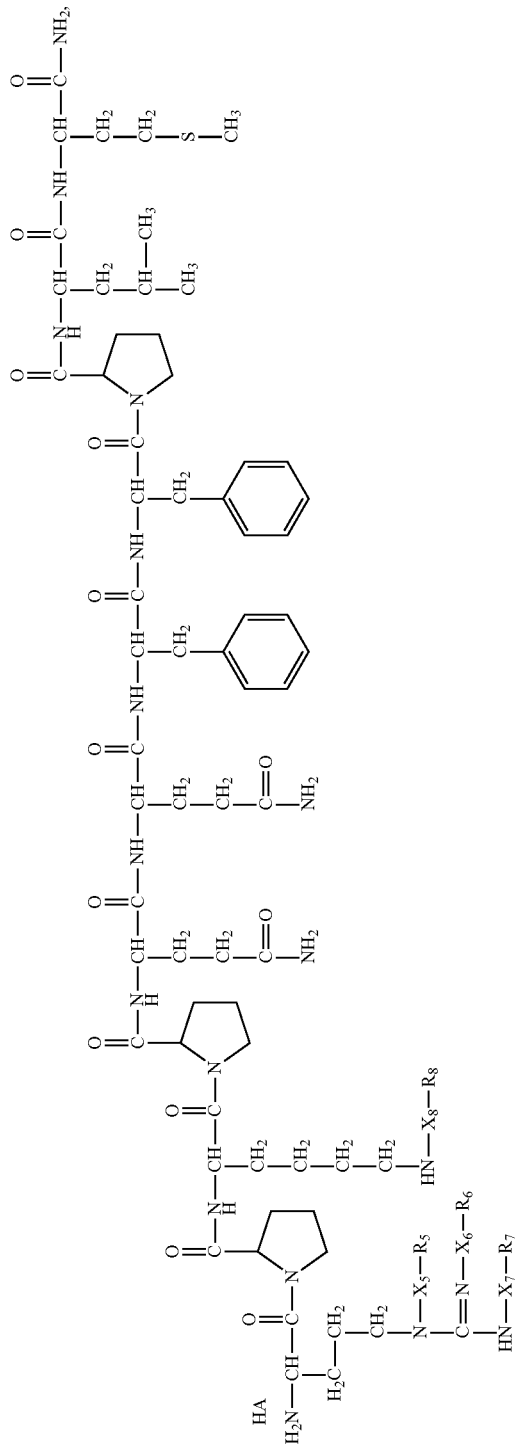
Structure 322 (SEQ ID NO: 159)

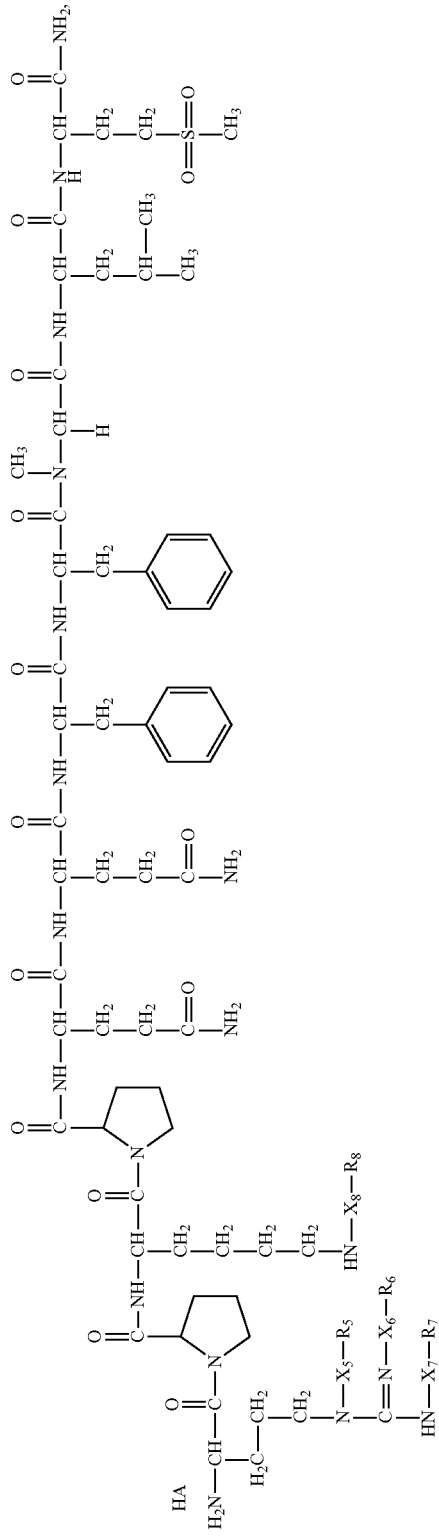
Structure 323 (SEQ ID NO: 160)
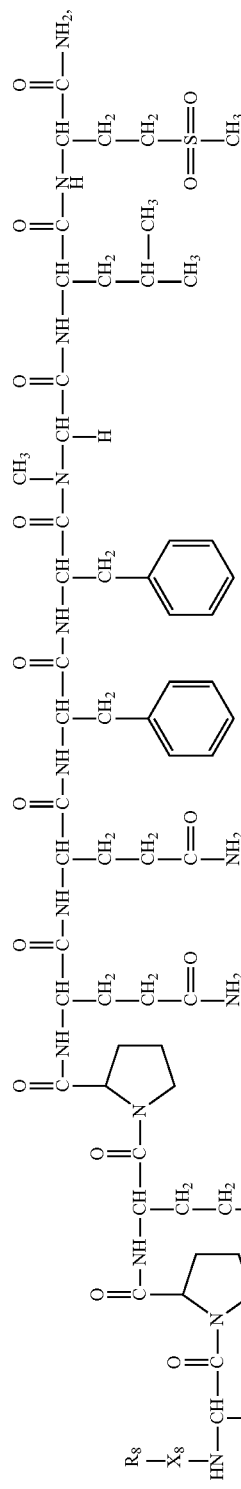
Structure 324 (SEQ ID NO: 160)

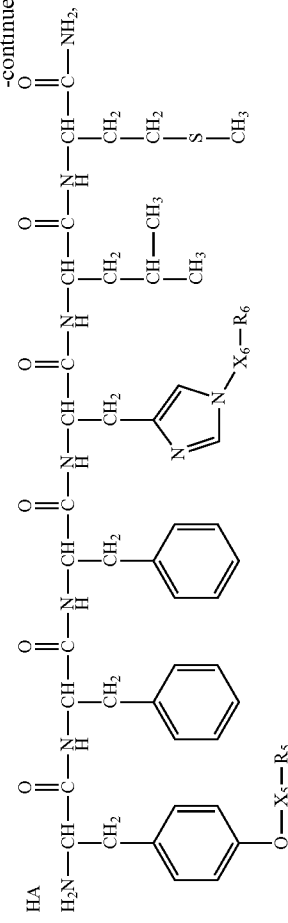
Structure 325 (SEQ ID NO: 161)
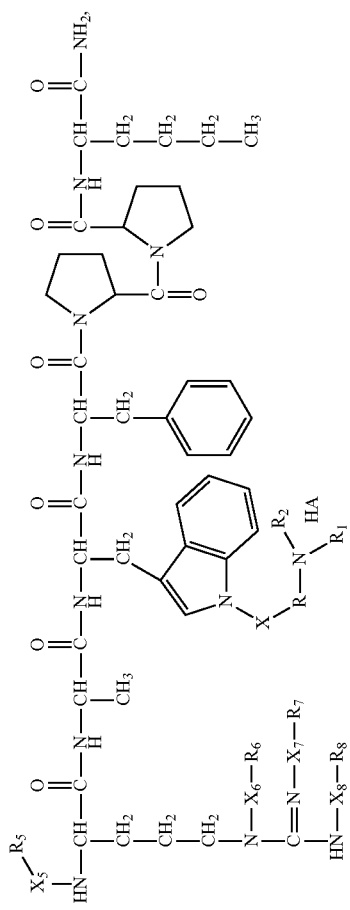
Structure 326 (SEQ ID NO: 162)
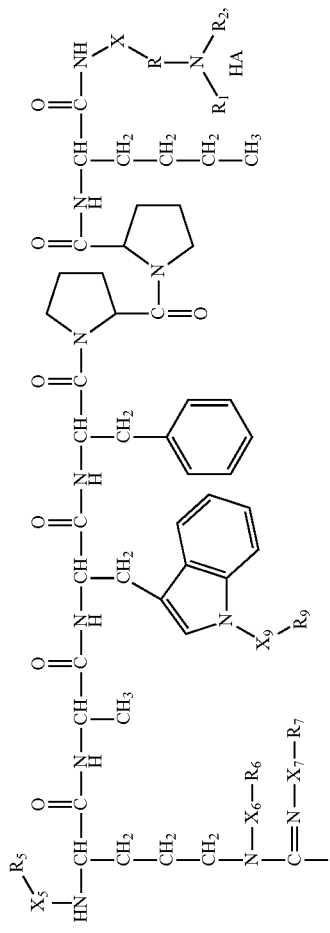
Structure 327 (SEQ ID NO: 162)

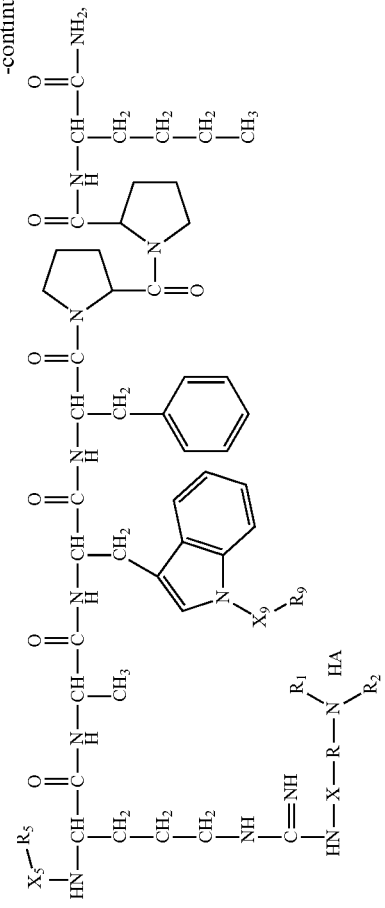
Structure 328 (SEQ ID NO: 162)
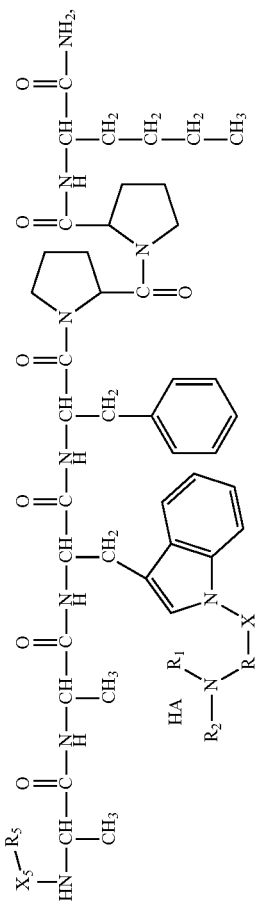
Structure 329 (SEQ ID NO: 163)
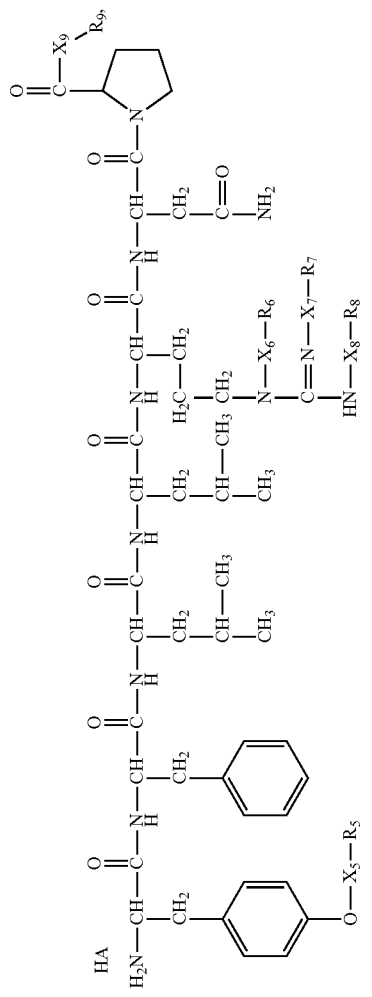
Structure 330 (SEQ ID NO: 164)

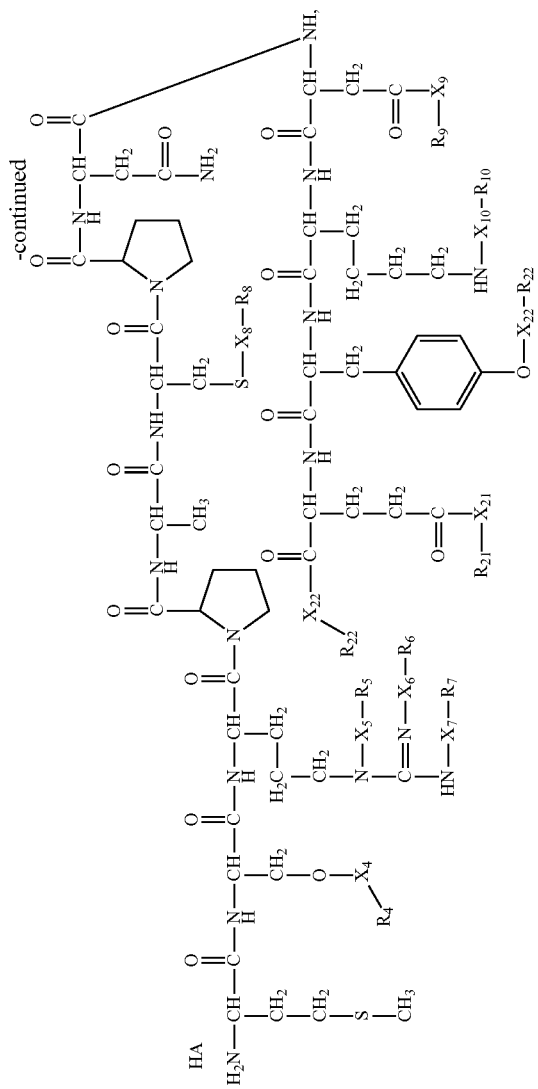
Structure 331 (SEQ ID NO: 165)
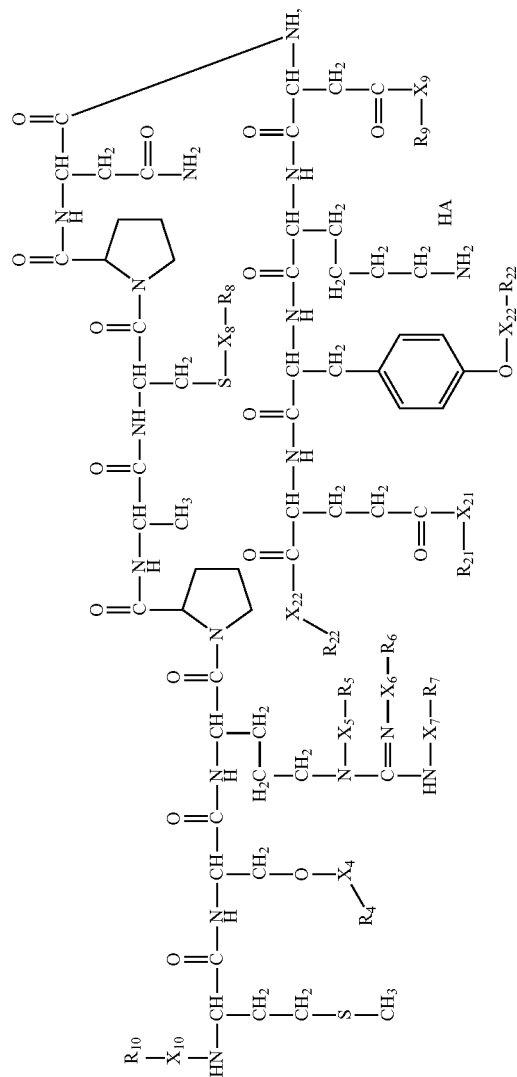
Structure 332 (SEQ ID NO: 165)

-continued
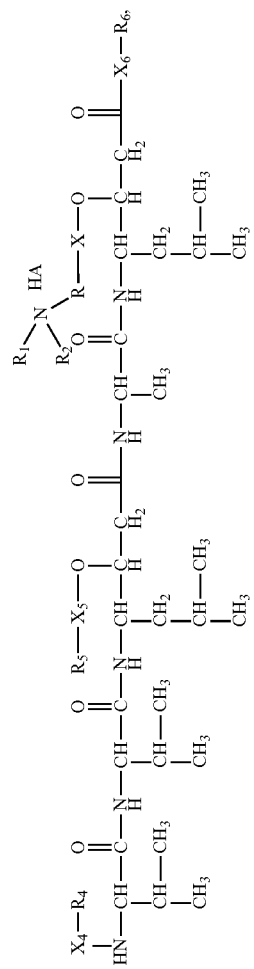
Structure 333 (SEQ ID NO: 166)
Structure 334 (SEQ ID NO: 166)
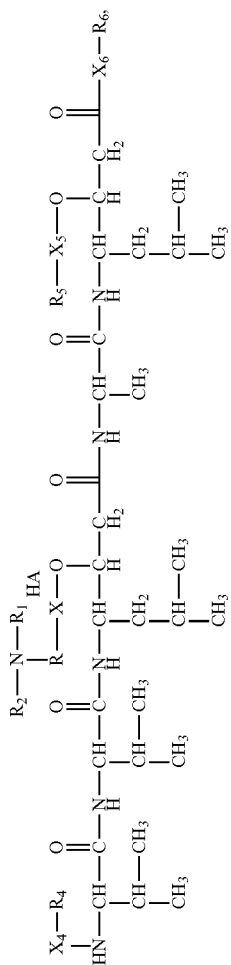
Structure 335 (SEQ ID NO: 166)
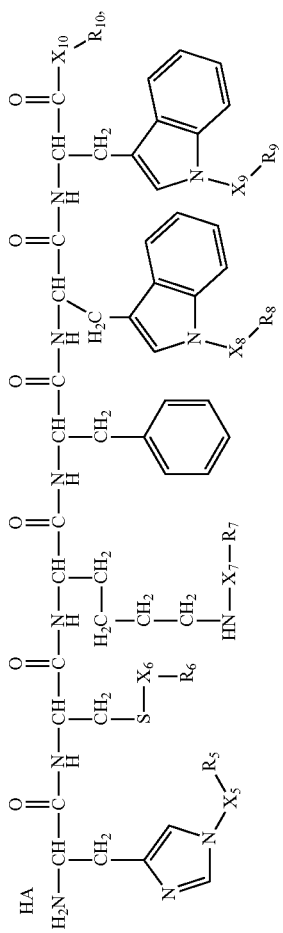
Structure 336 (SEQ ID NO: 167)

-continued
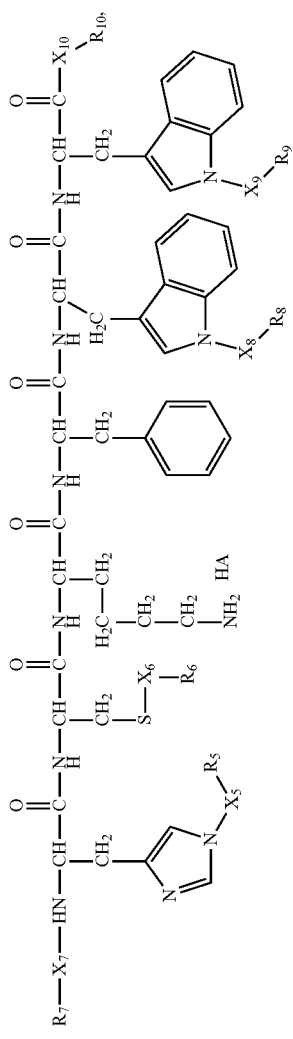
Structure 337 (SEQ ID NO: 167)
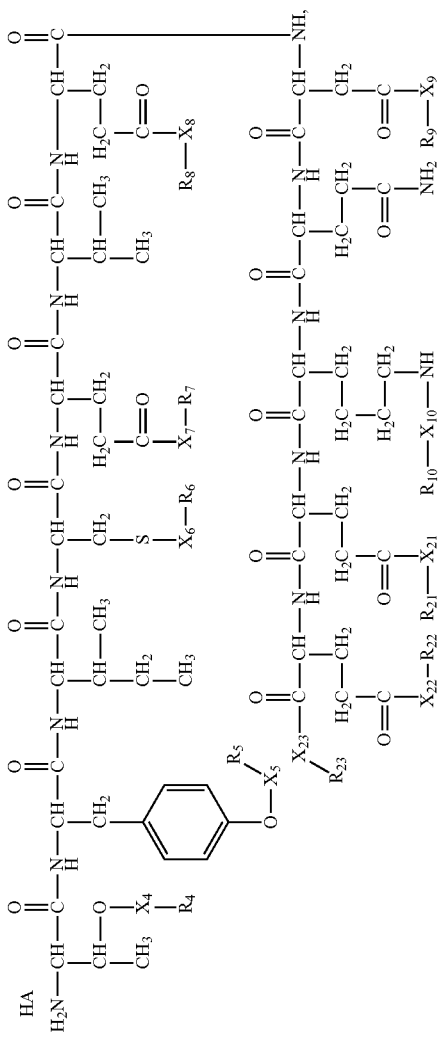
Structure 338 (SEQ ID NO: 168)

-continued
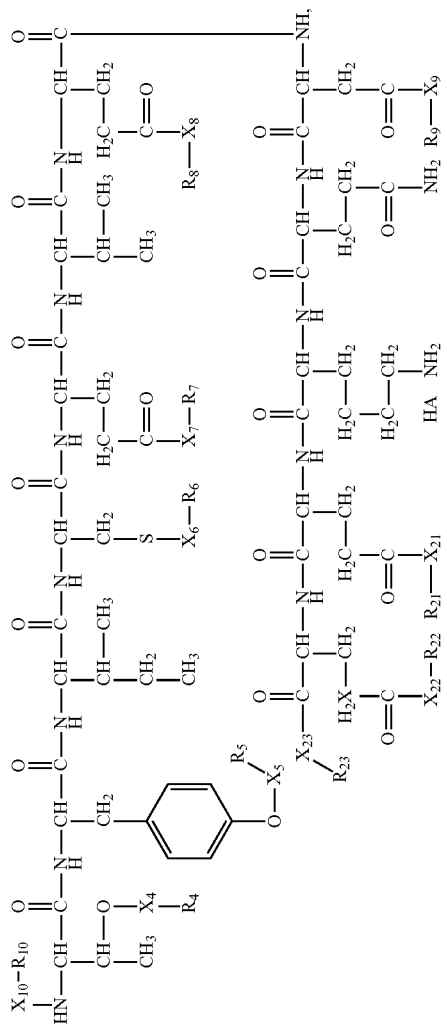
Structure 339 (SEQ ID NO: 168)
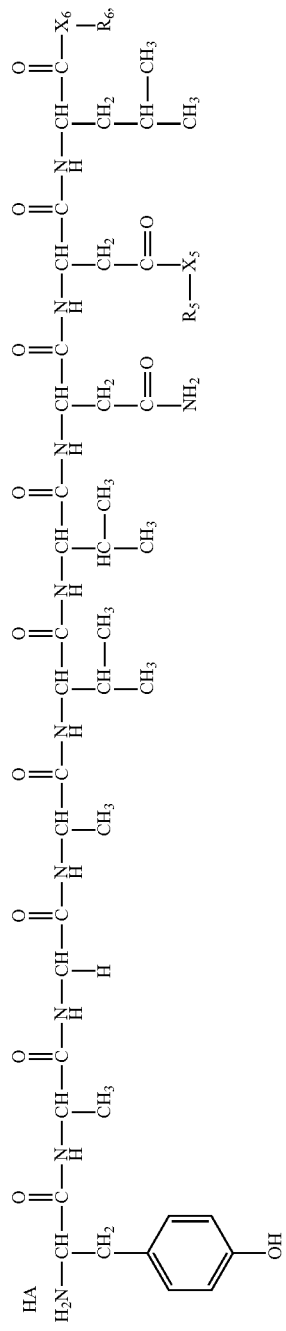
Structure 340 (SEQ ID NO: 169)

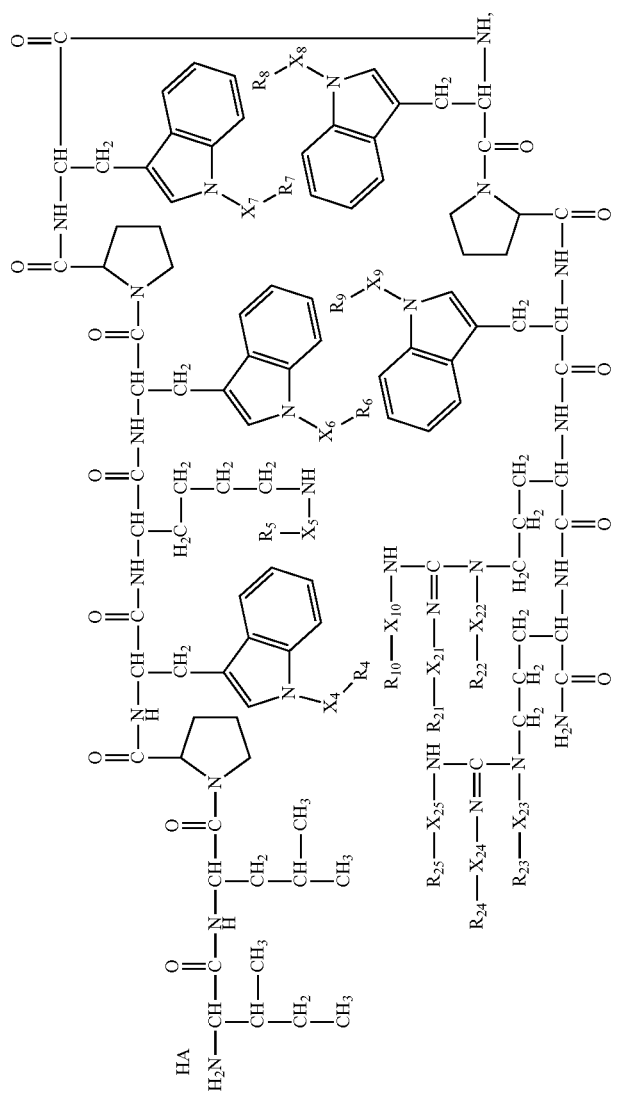
Structure 341 (SEQ ID NO: 170)

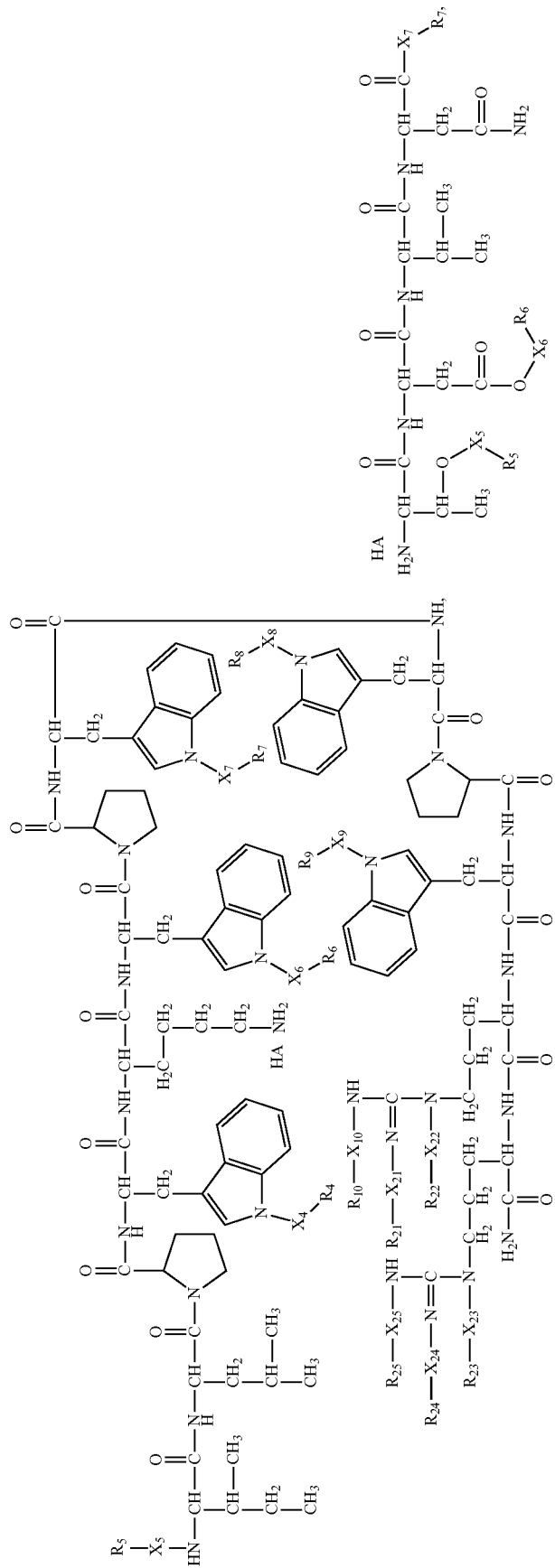
Structure 342 (SEQ ID NO: 170)
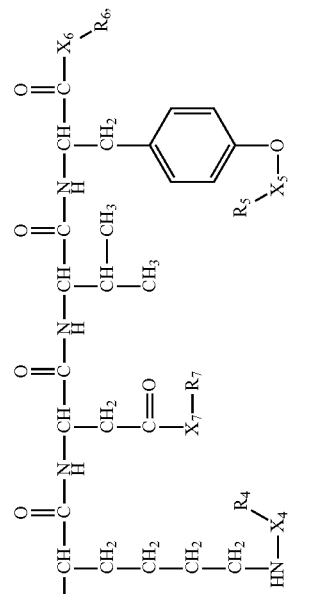
Structure 343 (SEQ ID NO: 171)
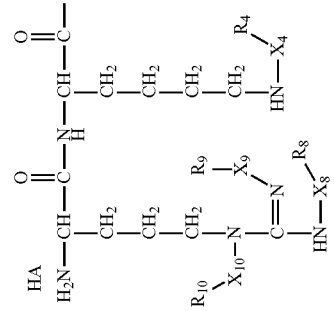
Structure 345 (SEQ ID NO: 172)
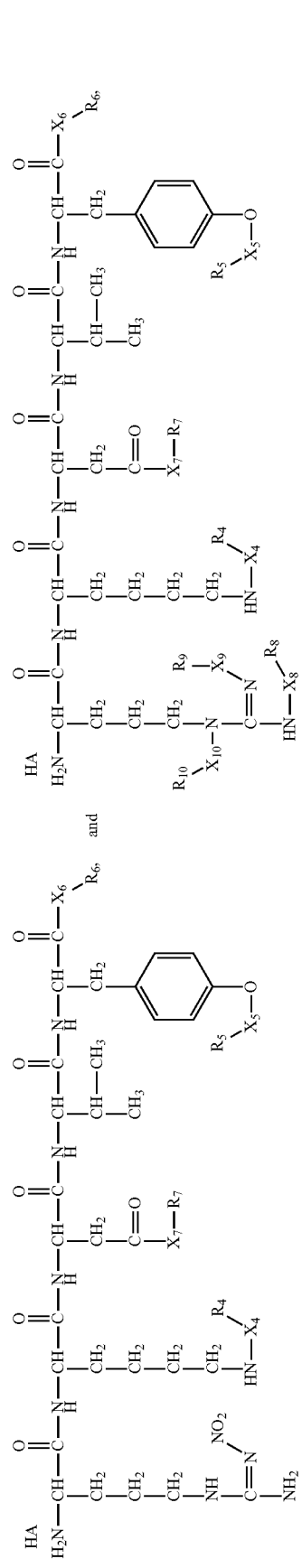
Structure 344 (SEQ ID NO: 172)
and Structure 1a

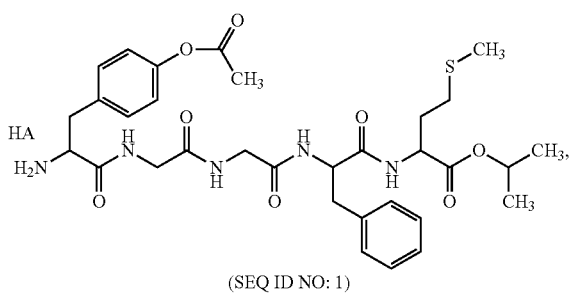

(SEQ ID NO: 1)

Structure 1c

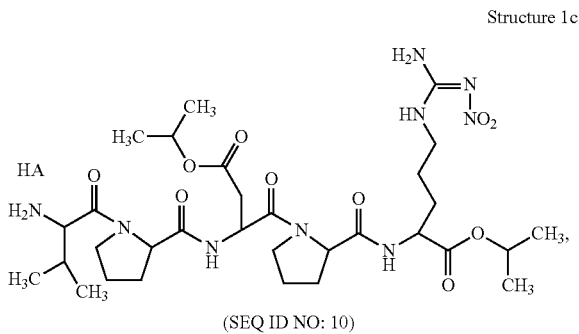

(SEQ ID NO: 10)

Structure 1d

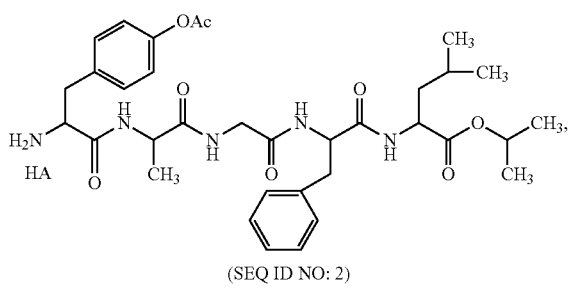

(SEQ ID NO: 2)

and

Structure 1f

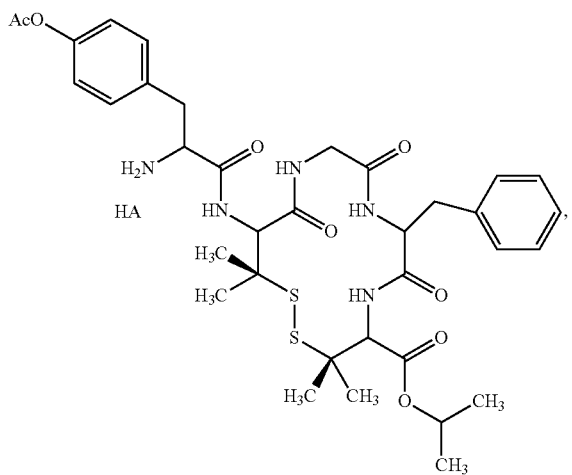

including stereoisomers and pharmaceutically acceptable salts thereof, wherein:

R is selected from the group consisting of H, substituted alkyl, unsubstituted alkyl, substituted cycloalkyl, unsubstituted cycloalkyl, substituted heterocycloalkyl, unsubstituted heterocycloalkyl, substituted alkoxyl, unsubstituted alkoxyl, substituted alkylthio, unsubstituted alkylthio, substituted alkylamino, unsubstituted alkylamino, substituted aryl, unsubstituted aryl, substituted heteroaryl, and unsubstituted heteroaryl residues;

$X$, $X_4$, $X_5$, $X_6$, $X_7$, $X_8$, $X_9$, $X_{10}$, $X_{21}$, $X_{22}$, $X_{23}$, $X_{24}$, $X_{25}$, $X_{26}$, and $X_{27}$ are independently selected from the group consisting of C=O, C=S, CSO, COO, $CH_2OCO$, $COOCH_2OCO$, $COCH_2OCO$, $CH_2$—O—CH$(CH_2OR_4)_2$, $CH_2$—O—CH($CH_2OCOR_4$)$_2$, $SO_2$, PO(OR), NO, O, S, $NR_5$, and a bond;

$R_1$, $R_2$, $R_4$, $R_5$, $R_6$, $R_7$, $R_8$, $R_9$, $R_{10}$, $R_{21}$, $R_{22}$, $R_{23}$, $R_{24}$, $R_{25}$, $R_{26}$, and $R_{27}$ are independently selected from the group consisting of H, O, $NO_2$, substituted alkyl, unsubstituted alkyl, substituted cycloalkyl, unsubstituted cycloalkyl, substituted heterocycloalkyl, unsubstituted heterocycloalkyl, substituted alkoxyl, unsubstituted alkoxyl, substituted alkylthio, unsubstituted alkylthio, substituted alkylamino, unsubstituted alkylamino, substituted alkenyl, unsubstituted alkenyl, substituted alkynyl, unsubstituted alkynyl, substituted aryl, unsubstituted aryl, substituted heteroaryl, and unsubstituted heteroaryl residues;

Ar is selected from the group consisting of phenyl, 2'-naphthyl, 4-iodophenyl, substituted aryl, unsubstituted aryl, and substituted heteroaryl, and unsubstituted heteroaryl residues; and HA is selected from the group consisting of, hydrochloride, hydrobromide, hydroiodide, nitric acid sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid; and the compound has only one or two amino groups and does not have a functional group selected from the group consisting of carboxylic, hydroxyl, and thio groups.

2. A pharmaceutical composition comprising a compound according to claim 1 and a pharmaceutically acceptable carrier.

3. The pharmaceutical composition according to claim 2, wherein the pharmaceutically acceptable carrier is polar.

4. The pharmaceutical composition according to claim 2, wherein the pharmaceutically acceptable carrier is selected from the group of alcohol, acetone, ester, water, and aqueous solution.

5. A method for treating a condition in a biological subject, comprising administrating to the biological subject the compound according to claim 1 or the pharmaceutical composition according to claim 2.

6. The method according to claim 5, wherein the condition is selected from the group consisting of pain, injuries, inflammation related conditions, microorganism related conditions, neuropeptide related conditions, hormone related conditions, tumor, abnormal blood pressure, obesity, brain injuries, allergy, male and female sexual dysfunction, metastasis, and other conditions relating to: tuftsin, antepartum, postpartum, anti-AD activities, antidiuretic activities, calcium homeostasis, melanocyte, hormone release, platelet aggregation, activities of CNS, and phagocytosis.

7. The method according to claim 6, wherein the hormone-related conditions are selected from the group consisting of menopause, bone diseases, growth hormone deficiency, hyperthyroidism, hypothyroidism, metabolism disorder conditions, abnormal blood pressure, skin condition, autoimmune disease, eye disease, preeclamptic toxemia in high-risk women, male and female sexual dysfunction, allergy, asthma, insomnia, depression and related conditions, cardiovascular diseases, and tumor.

8. The method according to claim 7, wherein the bone diseases are selected from the group consisting of osteoporosis, Paget's disease and bone metastases.

9. The method according to claim 7, wherein the metabolism disorder conditions are selected from the group consisting of obesity, abnormal blood glucose level, abnormal blood lipid level, diabetes mellitus (type I or/and type II) and diabetes-induced complications, including diabetic retinopathy, necrobiotic ulcers, and diabetic proteinuria.

10. The method according to claim 7, wherein the abnormal blood pressure is selected from the group consisting of hypertension and hypotension.

11. The method according to claim 7, wherein the skin condition is selected from the group consisting of psoriasis and psoriatic disorders, acne, cystic acne, pus-filled or reddish bumps, comedones, papules, pustules, nodules, epidermoid cysts, keratosis pilaris, abnormal vascular skin lesions, birthmarks, moles (nevi), skin tags, scleroderma, vitiligo and related diseases, or aging spots (liver spots).

12. The method according to claim 7, wherein the autoimmune disease is selected from the group consisting of discoid lupus erythematosus, systemic lupus erythematosus (SLE), autoimmune hepatitis, cleroderma, Sjogren's syndrome, rheumatoid arthritis, polymyositis, scleroderma, Hashimoto's thyroiditis, juvenile diabetes mellitus, Addison disease, vitiligo, pernicious anemia, glomerulonephritis, pulmonary fibrosis, multiple sclerosis (MS) and Crohn's disease.

13. The method according to claim 7, wherein the eye disease is selected from the group consisting of glaucoma, ocular hypertension, loss of vision after ophthalmic surgery, vision of a warm-blooded animal impaired by cystoid macular edema and cataract.

14. The method according to claim 7, wherein the cardiovascular diseases are selected from the group consisting of heart attack, unstable angina, peripheral occlusive arterial disease and stroke.

15. The method according to claim 7, wherein the tumor is selected from the group consisting of benign tumor, breast cancer, colon-rectum cancer, oral cancer, lung or other respiratory system cancers, skin cancers, uterus cancer, pancreatic cancer, prostate cancer, genital cancer, urinary organs cancers, leukemia or other blood and lymph tissues cancer.

16. The method according to claim 6, wherein the microorganisms related condition is selected from the group consisting of pain, injuries and inflammation related conditions.

17. The method according to claim 16, wherein the inflammation related condition is selected from the group consisting of prostate gland inflammation (prostatitis), prostatocystitis, prostate enlarge fibrosis, hemorrhoids, Kawasaki syndrome, gastroenteritis, type-1 membranoproliferative glomerulonephritis, Bartter's syndrome, chronic uveitis, ankylosing spondylitis, hemophilic arthropathy, inflamed hemorrhoids, post irradiation (factitial) proctitis, chronic ulcerative colitis, inflammatory bowel disease, cryptitis, periodontitis, arthritis, and an inflammatory condition in an organ selected from the group consisting of liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani.

18. The method according to claim 6, wherein the neuropeptide related conditions are selected from the group consisting of Alzheimer's diseases and Parkinson's disease.

19. The method according to claim 5, wherein the composition is administered to the biological subject through a route selected from oral, enteral, buccal, nasal, topical, rectal, vaginal, aerosol, transmucosal, epidermal, transdermal, dermal, ophthalmic, pulmonary, subcutaneous, and parenteral administration.

20. The method according to claim 5 wherein the peptides is selected from the group consisting of angiotentensin, angiotensin II antagonists, angiotentensin II AT2 receptor, antimicrobial peptides, anti-oxytocin, hormones, antidiuretic hormones, adrenocorticotropic hormones, antimicrobial peptide, anti-inflammatory peptide, bradykinin, bradykinin antagonist, endothelin peptides, endothelin peptide antagonist, gastrin, calcitonin, melanoma-associated antigen peptide, laminin peptide, fibrinogen peptide, EAE inducing peptides, growth factors, growth hormone releasing peotides, somatostatin, hormone releasing hormones, luteinizing hormone releasing hormone, neuropeptide, melanocyte stimulating hormones, sleep inducing peptide, amyloid peptide, tuftsin, retro inverso-tuftsin, enterostatins, Melanocortin II, and opioid peptides and mimics.

21. The method according to claim 20 wherein the enterostatin is selected from the group consisting of Val-Pro-Asp-Pro-Arg (VPDPR) (SEQ ID NO: 10), Val-Pro-Gly-Pro-Arg (VPGPR) (SEQ ID NO: 11), and Ala-Pro-Gly-Pro-Arg (APGPR) (SEQ ID NO: 12).

22. The method according to claim 20 wherein the opioid peptides is selected from the group consisting of Met-enkephalin (H-Tyr-Gly-Gly-Phe-Met-OH (SEQ ID NO: 174)), Leu-enkephalin (H-Tyr-Gly-Gly-Phe-Leu-OH (SEQ ID NO: 175)), H-Tyr-D-Ala-Gly-N-Me-Phe-Met(O)—OL (SEQ ID NO: 176), and H-Tyr-D-Ala-Gly-Phe-Leu-OH (SEQ ID NO: 177)).

23. A transdermal therapeutic application system comprising a compound or composition according to claim 1 as an active substance for treating conditions treatable by a parent compound thereof, wherein the system is a spray or rub-on solution further comprising a solvent selected from the group consisting of water, ethanol, isopropanol, acetone, DMSO, DMF, and combinations thereof.

24. A transdermal therapeutic application system comprising a compound or composition according to claim 1 as an active substance for treating conditions treatable by a parent compound thereof, wherein the system further comprises a subject comprising an active substance-containing matrix layer and an impermeable backing layer.

25. The transdermal therapeutic application system according to claim 24, wherein the subject is a patch or a bandage.

26. The transdermal therapeutic application system according to claim 24, wherein the subject is an active substance reservoir comprising a permeable bottom facing the skin, wherein by controlling the rate of release, the system enables the active ingredient or a metabolite of the active ingredient to reach constantly optimal therapeutic blood levels to increase effectiveness and reduce the side effects of the active ingredient or a metabolite of the active ingredient.

* * * * *

SEQUENCE LISTING

```
<160> NUMBER OF SEQ ID NOS: 207

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Gly Gly Phe Met
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Xaa is an amino acid wherein the alpha carbon
      is optionally substitued with O, NO2, substituted and
      unsubstituted alkyl, substituted and unsubstituted cycloalkyl, and
      substituted and unsubstituted heterocycloalkyl, substituted and
      unsubstituted
<220> FEATURE:
<221> NAME/KEY: MOD_RES
```

```
<222> LOCATION: (2)..(2)
<223> OTHER INFORMATION: Continued from above; alkoxyl, substituted and
      unsubstituted alkylthio, substituted and unsubstituted alkylamino,
      substituted and unsubstituted alkenyl, substituted and
      unsubstituted alkynyl, substituted and unsubstituted aryl, and
      substituted and
<220> FEATURE:
<221> NAME/KEY: MOD_RES
<222> LOCATION: (2)..(2)
<223> OTHER INFORMATION: Continued from above; unsubstituted heteroaryl
      residues

<400> SEQUENCE: 2

Tyr Xaa Gly Phe Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: MePhe
<220> FEATURE:
<221> NAME/KEY: MOD_RES
<222> LOCATION: (5)..(5)
<223> OTHER INFORMATION: Met(O2)-L

<400> SEQUENCE: 3

Tyr Ala Gly Phe Met
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: MePhe
<220> FEATURE:
<221> NAME/KEY: MOD_RES
<222> LOCATION: (5)..(5)
<223> OTHER INFORMATION: Met(O2)-L

<400> SEQUENCE: 4

Tyr Gly Gly Phe Met
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala

<400> SEQUENCE: 5

Tyr Ala Phe Gly Tyr Pro Ser
1               5
```

```
<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Lys Pro Arg
1

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Ala Phe Gly Tyr Pro Ser
1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Retroinverso-Thr

<400> SEQUENCE: 8

Thr Lys Pro Arg
1

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MISC_FEATURE
<222> LOCATION: (2)..(7)
<223> OTHER INFORMATION: Cyclized
<220> FEATURE:
<221> NAME/KEY: MOD_RES
<222> LOCATION: (4)..(4)
<223> OTHER INFORMATION: D-Phe

<400> SEQUENCE: 9

Leu Asp His Phe Arg Trp Lys
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 10

Val Pro Asp Pro Arg
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Pro Gly Pro Arg
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Pro Gly Pro Arg
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Pen
<220> FEATURE:
<221> NAME/KEY: MOD_RES
<222> LOCATION: (5)..(5)
<223> OTHER INFORMATION: D-Pen

<400> SEQUENCE: 13

Tyr Xaa Gly Phe Xaa
1               5

<210> SEQ ID NO 14
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-methyl-3-sulfanyl-propanoic acid

<400> SEQUENCE: 14

Xaa Pro
1

<210> SEQ ID NO 15
<211> LENGTH: 2
<212> TYPE: PRT
```

<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: 2-(1'-propanoic carboxyl-2'-amino)-4-phenyl-butanoic acid

<400> SEQUENCE: 15

Xaa Pro
1

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Cys Tyr Ile Gln Asn Cys Pro Leu Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Cys Tyr Phe Gln Asn Cys Pro Arg Gly
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Ser Tyr Ser Met Glu His Phe Arg Trp Gly Lys Pro Val Gly Lys Lys
1               5                   10                  15
Arg

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Ser Tyr Ser Met Glu His Phe Arg Trp Gly Lys Pro Val
1               5                   10

<210> SEQ ID NO 20
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 20

Ser Tyr Ser Met Glu His Phe Arg Trp Gly
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met Glu His Phe Arg Trp Gly
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Arg Trp Gly Lys Pro Val Gly Lys Lys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Pro Val Gly Lys Lys Arg Arg Pro Val Lys Val Tyr Pro
1               5                   10

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Pro Val Lys Val Tyr Pro Asp Gly Ala Glu Asp Glu Ser Ala Glu
1               5                   10                  15

Ala Phe Pro Leu Glu Phe
            20

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Phe Pro Leu Glu Phe

```
<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Leu Val Phe Phe
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Arg Val Tyr Ile His Pro Phe His Leu
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Arg Val Tyr Ile His Pro Phe
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Arg Val Tyr Ile His Pro Ala
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 4-amino Phe

<400> SEQUENCE: 30

Asp Arg Val Tyr Ile Phe Pro Phe
1               5

<210> SEQ ID NO 31
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Arg Val Tyr Ile His Pro Phe
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Arg Val Tyr Ile His Pro Ile
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: MeGly

<400> SEQUENCE: 33

Gly Arg Val Tyr Ile His Pro Phe
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: MeGly

<400> SEQUENCE: 34

Gly Arg Val Tyr Ile His Pro Ile
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: MeGly

<400> SEQUENCE: 35

Gly Arg Val Tyr Val His Pro Ala
1               5
```

```
<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Arg Val Tyr Ile His Pro Thr
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Arg Val Tyr Ile His Pro
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Tyr Ile His Pro Phe
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Val Tyr Ile His Pro Phe
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Gly Val Tyr Val His Pro Val
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: 3-carboxyl-pyridine
<220> FEATURE:
<221> NAME/KEY: MOD_RES
<222> LOCATION: (3)..(3)
<223> OTHER INFORMATION: Lys or Arg

<400> SEQUENCE: 41

Xaa Tyr Xaa His Pro Ile
1               5

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Leu Cys Arg Ile Val Val Ile Arg Val Cys Arg
1               5                   10

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Leu Trp Lys Thr Met Leu Lys Lys Leu Gly Thr Met Ala Leu His
1               5                   10                  15

Ala Gly

<210> SEQ ID NO 44
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Met Ala Ser Lys Ala Gly Ala Ile Ala Gly Lys Ile Ala Lys Val
1               5                   10                  15

Ala Leu Lys Ala Leu
            20

<210> SEQ ID NO 46
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Arg Gly Phe Val
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Met Gln Met Lys Lys Val Leu Asp Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Asp Met Asn Lys Val Leu Asp Leu
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Gln Met Asn Lys Val Leu Asp Ser
1               5

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Tyr Thr Ser Leu Ile His Ala Leu Ile Gln Gln Ser Gln Asn Gln Gln
1               5                   10                  15

Gln Lys Asn Glu Gln Glu Leu Leu Glu Leu Asp Lys Trp Ala Ser Leu
                20                  25                  30

Trp Asn Trp Phe
            35

<210> SEQ ID NO 51
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 51

Arg Pro Pro Gly Phe Ser Pro Phe Arg
1               5

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (4)..(4)
<223> OTHER INFORMATION: 2-carboxyl-2,3,4,5-tetrahydro-3-hydroxy-pyrrole

<400> SEQUENCE: 52

Arg Arg Pro Xaa Gly Phe Ser Phe Leu Arg
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Pro Pro Gly Phe Ser Pro Phe
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Pro Pro Gly Phe Ser Pro Leu
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Phe

<400> SEQUENCE: 55

Arg Pro Pro Gly Phe Ser Phe Phe Arg
1               5

<210> SEQ ID NO 56
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Tyr Met Gly Trp Met Asp Phe
1               5

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Trp Thr Leu Asn Ser Ala Gly Tyr Leu Leu Gly Pro Pro Pro Gly
1               5                   10                  15

Phe Ser Pro Phe Arg
            20

<210> SEQ ID NO 58
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Trp Thr Leu Asn Ser Ala Gly Tyr Leu Leu Gly Pro Arg Pro Lys
1               5                   10                  15

Pro Gln Gln Trp Phe Trp Leu Leu
            20

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Trp Thr Leu Asn Ser Ala Gly Tyr Leu Leu Gly Pro Gln Gln Phe
1               5                   10                  15

Phe Gly Leu Met
            20

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30
```

```
<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Ala Gly Ile Leu Thr Val
1               5

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Ala Ala Arg Gln Gly Phe Leu Asn Thr Leu Val Val Leu His Arg
1               5                   10                  15

Ala Gly Ala Arg
            20

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Met Asp Gly Thr Met Ser Gln Val
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Ile Ser Ala Val Val Gly Ile Leu
1               5

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

His His Leu Gly Gly Ala Lys Gln Ala Gly Asp Val
1               5                   10

<210> SEQ ID NO 66
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 66

His His Leu Gly Gly Ala Lys Gln Ala Gly Asp Val
1               5                   10

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu His Ile Pro Ala
1               5

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Gly Asp Val
1

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclized
<220> FEATURE:
<221> NAME/KEY: MOD_RES
<222> LOCATION: (4)..(4)
<223> OTHER INFORMATION: D-Phe

<400> SEQUENCE: 69

Arg Gly Asp Phe Val
1               5

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Gly Asp Ser
1

<210> SEQ ID NO 71
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 71

Thr Asp Val Asn Gly Asp Gly Arg His Asp Leu
1               5                   10

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Pro Arg Pro
1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg

<400> SEQUENCE: 73

Arg Gly Asp Trp
1

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Trp Thr Val Pro Thr Ala
1               5

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Arg Lys Gln Ala Ala Ser Ile Lys Val Ala Val Ser
1               5                   10

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

```
Leu Gly Thr Ile Pro Gly
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Ile Gly Ser Arg
1               5

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Ala Gly Thr
1

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Arg Lys Gln Ala Ala Ser Ile Lys Val Ala Val Ser
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Val His Phe Phe Lys Asn Ile Val Thr Ala Arg Thr Pro
1               5                   10

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Cys Ser Cys Ser Ser Leu Met Asn Lys Glu Cys Val Tyr Phe Cys His
1               5                   10                  15

Leu Asp Ile Ile Trp
            20

<210> SEQ ID NO 82
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Ser Ala Ser Ser Leu Met Asp Lys Glu Ala Val Tyr Phe Ala His
1               5                   10                  15

Leu Asp Ile Ile Trp
            20

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Leu Met Asp Lys Glu Ala Val Tyr Phe Ala His Leu Asp Ile Ile Trp
1               5                   10                  15

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Glu Glu Ala Val Tyr Phe Ala His Leu Asp Ile Ile Trp
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Val Tyr Phe Cys His Leu Asp Ile Ile Trp
1               5                   10

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: Cyclized
<220> FEATURE:
<221> NAME/KEY: MOD_RES
<222> LOCATION: (1)..(1)
<223> OTHER INFORMATION: D-Trp
<220> FEATURE:
<221> NAME/KEY: MOD_RES
<222> LOCATION: (2)..(2)
<223> OTHER INFORMATION: D-Asp
<220> FEATURE:
<221> NAME/KEY: MOD_RES
<222> LOCATION: (4)..(4)
```

```
<223> OTHER INFORMATION: D-Val

<400> SEQUENCE: 86

Trp Asp Pro Val Leu
1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Dip

<400> SEQUENCE: 87

Xaa Leu Asp Ile Ile Trp
1               5

<210> SEQ ID NO 88
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Cys Ser Cys Ser Ser Trp Leu Asp Lys Glu Cys Val Tyr Phe Cys His
1               5                   10                  15

Leu Asp Ile Ile Trp
            20

<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Cys Thr Cys Phe Thr Tyr Lys Asp Cys Val Tyr Tyr Cys His Leu Asp
1               5                   10                  15

Ile Ile Trp

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Gln Gly Glu Glu Ser Asn Asp Lys
1               5

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 91

Asp Val Val Asp Ala Asp Glu Tyr Leu Ile Pro Gln
1               5                   10

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Ala Asp Glu Tyr Leu
1               5

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys(Acm)
<220> FEATURE:
<221> NAME/KEY: MOD_RES
<222> LOCATION: (12)..(12)
<223> OTHER INFORMATION: Cys(Acm)

<400> SEQUENCE: 93

Cys Met His Ile Glu Ser Leu Asp Ser Tyr Thr Cys
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Tyr Arg Ser Arg Lys Tyr Ser Ser Trp Tyr
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Leu Leu Glu Thr Tyr Cys Ala Thr Pro Ala Lys Ser Glu
1               5                   10

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (5)..(5)
<223> OTHER INFORMATION: D-Phe

<400> SEQUENCE: 96

His Trp Ala Trp Phe Lys
1               5

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: D-Lys
<220> FEATURE:
<221> NAME/KEY: MOD_RES
<222> LOCATION: (5)..(5)
<223> OTHER INFORMATION: D-Phe

<400> SEQUENCE: 97

His Trp Lys Trp Phe Lys
1               5

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlf

<400> SEQUENCE: 98

Xaa His Trp Ser Tyr Gly Leu Arg Pro Gly
1               5                   10

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlf

<400> SEQUENCE: 99

Xaa His Trp Ser Tyr Gly Leu Arg Pro
1               5

<210> SEQ ID NO 100
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlf

<400> SEQUENCE: 100

Xaa His Trp Ser His Asp Trp Lys Pro Gly
1               5                   10

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Gly Cys Lys Asn Phe Phe Trp Lys Thr Phe Thr Ser Cys
1               5                   10

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlf

<400> SEQUENCE: 102

Xaa Leu Asn Phe Ser Ala Gly Trp
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlf

<400> SEQUENCE: 103

Xaa Leu Asn Phe Ser Thr Gly Trp
1               5

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Glu Ala Leu Glu Leu Ala Arg Gly Ala Ile Phe Gln Ala
1               5                   10
```

```
<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Tyr Ser Met Glu His Phe Arg Trp Gly Lys Pro Val
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (5)..(5)
<223> OTHER INFORMATION: D-Nal(2)

<400> SEQUENCE: 106

Cys Leu Arg His Xaa Arg Trp Gly Cys
1               5

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: D-D-Nal(2)

<400> SEQUENCE: 107

Cys Glu His Xaa Arg Trp Gly Cys Pro Pro Lys Asp
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle

<400> SEQUENCE: 108

Leu Asp His Phe Arg Trp Lys
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Nal(2)

<400> SEQUENCE: 109

Leu Asp His Xaa Arg Trp Lys
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
<222> LOCATION: (6)..(6)
<223> OTHER INFORMATION: D-Trp

<400> SEQUENCE: 110

Leu Gln His Phe Arg Trp Gly
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Nal(2)

<400> SEQUENCE: 111

Leu Asp His Xaa Arg Trp Lys
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
```

```
<400> SEQUENCE: 112

Leu Asp His Phe Arg Trp Lys
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Trp Ala Gly Gly Asp Ala Ser Gly Glu
1               5

<210> SEQ ID NO 114
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Phe Met Arg Phe
1

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: pGlf

<400> SEQUENCE: 115

Xaa Asp Pro Phe Leu Arg Phe
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (5)..(5)
<223> OTHER INFORMATION: D-Nal(2)

<400> SEQUENCE: 116

Cys Leu Arg His Xaa Arg Trp Gly Cys
1               5

<210> SEQ ID NO 117
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 117

Glu Ala Leu Glu Leu Ala Arg Gly Ala Ile Phe Gln Ala
1               5                   10

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Phe Leu Phe Gln Pro Gln Arg Phe
1               5

<210> SEQ ID NO 119
<211> LENGTH: 10
<212> TYPE: PRT
<213> ORGANISM: Homo sapiens

<400> SEQUENCE: 119

Tyr Ile Asn Leu Ile Tyr Arg Leu Arg Tyr
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

His Tyr Ile Asn Leu Ile Thr Arg Gln Arg Tyr
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Tyr Ile Asn Leu Ile Thr Arg Gln Arg Tyr
1               5                   10

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ile Asn Pro Ile Tyr Arg Leu Arg Tyr
1               5

<210> SEQ ID NO 123
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Phe Met Trp Met Lys
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala

<400> SEQUENCE: 124

Tyr Ala Phe Asp Val Val Gly
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Ala

<400> SEQUENCE: 125

Tyr Ala Phe Glu Val Val Gly
1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Pen
<220> FEATURE:
<221> NAME/KEY: MOD_RES
<222> LOCATION: (5)..(5)
<223> OTHER INFORMATION: D-Pen

<400> SEQUENCE: 126

Tyr Xaa Gly Phe Xaa
1               5

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: D-Pen
<220> FEATURE:
<221> NAME/KEY: MOD_RES
<222> LOCATION: (4)..(4)
<223> OTHER INFORMATION: p-chloro-Phe
<220> FEATURE:
<221> NAME/KEY: MOD_RES
<222> LOCATION: (5)..(5)
<223> OTHER INFORMATION: D-Pen

<400> SEQUENCE: 127

Tyr Xaa Gly Phe Xaa
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Tyr Pro Trp Thr Gln Arg Phe
1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Phe Leu Phe Gln Pro Gln Arg Phe
1               5

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Tyr Pro Phe Phe
1

<210> SEQ ID NO 131
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Tyr Pro Trp Phe
1

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
          peptide
<220> FEATURE:
<221> NAME/KEY: MOD_RES
<222> LOCATION: (1)..(1)
<223> OTHER INFORMATION: 3-sulfanyl-propanoic acid
<220> FEATURE:
<221> NAME/KEY: MOD_RES
<222> LOCATION: (8)..(8)
<223> OTHER INFORMATION: D-Arg

<400> SEQUENCE: 132

Xaa Tyr Phe Gln Asn Cys Pro Arg Gly
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Cys Tyr Phe Gln Asn Cys Pro Lys Gly
1               5

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Tyr Glu Glu Ile Glu
1               5

<210> SEQ ID NO 135
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Thr Ser Thr Glu Pro Gln Tyr Gln Pro Gly Glu Asn Leu
1               5                   10

<210> SEQ ID NO 136
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Tyr Glu
1

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 137

Leu Arg Arg Ala Ser Leu Gly
1               5

<210> SEQ ID NO 138
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Phe Ala Arg Lys Gly Ala Leu Arg Gln Lys Asn Val His Glu Val
1               5                   10                  15

Lys Asn

<210> SEQ ID NO 139
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Arg Phe Ala Arg Lys Gly Ala Leu Arg Gln Lys Asn Val
1               5                   10

<210> SEQ ID NO 140
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Arg Phe Ala Arg Lys Gly Ser Leu Arg Gln Lys Asn Val
1               5                   10

<210> SEQ ID NO 141
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Arg Phe Ala Arg Lys Gly Ala Leu Arg Gln Lys Asn Val
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gln Lys Arg Pro Ser Gln Arg Ser Lys Tyr Leu
1               5                   10
```

-continued

```
<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Lys Gly Arg Gly Leu Ser Leu Ser Arg Phe Ser Trp Gly Ala
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Lys Gly Ala Gly Leu Ser Leu Ser Arg Phe Ser Trp Gly Ala
1               5                   10                  15

<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Arg Lys Glu Val Tyr
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: D-Trp

<400> SEQUENCE: 146

Phe Cys Tyr Trp Lys Val Cys Trp
1               5

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: beta-amino-Ala

<400> SEQUENCE: 147

Asp Ser Phe Val Ala Leu Met
```

```
1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N-Me-Leu
<220> FEATURE:
<221> NAME/KEY: MOD_RES
<222> LOCATION: (7)..(7)
<223> OTHER INFORMATION: Nle

<400> SEQUENCE: 148

Asp Lys Phe Val Gly Leu Leu
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Nle

<400> SEQUENCE: 149

Asp Ser Phe Val Gly Leu Leu
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (5)..(6)
<223> OTHER INFORMATION: D-Trp

<400> SEQUENCE: 150

Asp Tyr Trp Val Trp Trp Lys
1               5

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asp Met His Asp Phe Phe Val Gly Leu Met
1               5                   10
```

```
<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Leu Asp Gln Trp Phe Gly
1               5

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: N-Me-Phe

<400> SEQUENCE: 153

Asp Met His Asp Phe Phe Phe Gly Leu Met
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asp Met His Asp Phe Phe Pro Gly Leu Met
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Arg Pro Lys Pro Gln Gln Phe Phe Gly Leu Met
1               5                   10

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Pro
<220> FEATURE:
<221> NAME/KEY: MOD_RES
<222> LOCATION: (7)..(7)
<223> OTHER INFORMATION: D-Trp
```

```
<220> FEATURE:
<221> NAME/KEY: MOD_RES
<222> LOCATION: (9)..(9)
<223> OTHER INFORMATION: D-Trp

<400> SEQUENCE: 156

Arg Pro Lys Pro Gln Gln Trp Phe Trp Leu Leu
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Pro

<400> SEQUENCE: 157

Arg Pro Lys Pro Gln Gln Phe Phe Pro Pro Trp
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: D-Pro
<220> FEATURE:
<221> NAME/KEY: MOD_RES
<222> LOCATION: (10)..(10)
<223> OTHER INFORMATION: Me-Leu

<400> SEQUENCE: 158

Arg Pro Lys Pro Gln Gln Phe Phe Pro Leu Trp
1               5                   10

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Pro Lys Pro Gln Gln Phe Phe Pro Leu Met
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: 2-amino-4-(methylsulfonyl)butanoic acid

<400> SEQUENCE: 160
```

```
Arg Pro Lys Pro Gln Gln Phe Phe Ser Leu Xaa
1               5                   10

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Phe
<220> FEATURE:
<221> NAME/KEY: MOD_RES
<222> LOCATION: (4)..(4)
<223> OTHER INFORMATION: D-His

<400> SEQUENCE: 161

Tyr Phe Phe His Leu Met
1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (5)..(5)
<223> OTHER INFORMATION: D-Pro
<220> FEATURE:
<221> NAME/KEY: MOD_RES
<222> LOCATION: (7)..(7)
<223> OTHER INFORMATION: Nle

<400> SEQUENCE: 162

Arg Ala Trp Phe Pro Pro Leu
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (5)..(5)
<223> OTHER INFORMATION: D-Pro
<220> FEATURE:
<221> NAME/KEY: MOD_RES
<222> LOCATION: (7)..(7)
<223> OTHER INFORMATION: Nle

<400> SEQUENCE: 163

Ala Ala Trp Phe Pro Pro Leu
1               5

<210> SEQ ID NO 164
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Tyr Phe Leu Leu Arg Asn Pro
1               5

<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Met Ser Arg Pro Ala Cys Pro Asn Asp Lys Tyr Glu
1               5                   10

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-amino-3-hydroxy-6-methyl-heptonic acid
<220> FEATURE:
<221> NAME/KEY: MOD_RES
<222> LOCATION: (5)..(5)
<223> OTHER INFORMATION: 4-amino-3-hydroxy-6-methyl-heptonic acid

<400> SEQUENCE: 166

Val Val Xaa Ala Xaa
1               5

<210> SEQ ID NO 167
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

His Cys Lys Phe Trp Trp
1               5

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Thr Tyr Ile Cys Glu Val Glu Asp Gln Lys Glu Glu
1               5                   10

<210> SEQ ID NO 169
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Tyr Ala Gly Ala Val Val Asn Asp Leu
1               5

<210> SEQ ID NO 170
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ile Leu Pro Trp Lys Trp Pro Trp Trp Pro Trp Arg Arg
1               5                   10

<210> SEQ ID NO 171
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Thr Asp Val Asn
1

<210> SEQ ID NO 172
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Arg Lys Asp Val Tyr
1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: Cyclized
<220> FEATURE:
<221> NAME/KEY: MOD_RES
<222> LOCATION: (1)..(1)
<223> OTHER INFORMATION: Ac-Nle
<220> FEATURE:
<221> NAME/KEY: MOD_RES
<222> LOCATION: (7)..(7)
<223> OTHER INFORMATION: Lys-OH

<400> SEQUENCE: 173

Leu Asp His Phe Arg Trp Lys
1               5
```

```
<210> SEQ ID NO 174
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Tyr
<220> FEATURE:
<221> NAME/KEY: MOD_RES
<222> LOCATION: (5)..(5)
<223> OTHER INFORMATION: Met-OH

<400> SEQUENCE: 174

Tyr Gly Gly Phe Met
1               5

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Tyr
<220> FEATURE:
<221> NAME/KEY: MOD_RES
<222> LOCATION: (5)..(5)
<223> OTHER INFORMATION: Leu-OH

<400> SEQUENCE: 175

Tyr Gly Gly Phe Leu
1               5

<210> SEQ ID NO 176
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Tyr
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: N-Me-Phe
<220> FEATURE:
<221> NAME/KEY: MOD_RES
<222> LOCATION: (5)..(5)
<223> OTHER INFORMATION: Met(O)-OL

<400> SEQUENCE: 176

Tyr Ala Gly Phe Met
1               5

<210> SEQ ID NO 177
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Tyr
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (5)..(5)
<223> OTHER INFORMATION: Leu-OH

<400> SEQUENCE: 177

Tyr Ala Gly Phe Leu
1               5

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Tyr(Ac)
<220> FEATURE:
<221> NAME/KEY: MOD_RES
<222> LOCATION: (5)..(5)
<223> OTHER INFORMATION: Met-OCH2CH2N(CH2CH3)2

<400> SEQUENCE: 178

Tyr Gly Gly Phe Met
1               5

<210> SEQ ID NO 179
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (CH3)2NCH2CH2CH2CO-Tyr(Ac)
<220> FEATURE:
<221> NAME/KEY: MOD_RES
<222> LOCATION: (5)..(5)
<223> OTHER INFORMATION: Met-OCH2CH2CH2CH3

<400> SEQUENCE: 179

Tyr Gly Gly Phe Met
1               5

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: Cyclized
<220> FEATURE:
<221> NAME/KEY: MOD_RES
```

```
<222> LOCATION: (1)..(1)
<223> OTHER INFORMATION: Ac-Nle
<220> FEATURE:
<221> NAME/KEY: MOD_RES
<222> LOCATION: (5)..(5)
<223> OTHER INFORMATION: Arg(diAc)
<220> FEATURE:
<221> NAME/KEY: MOD_RES
<222> LOCATION: (7)..(7)
<223> OTHER INFORMATION: Lys-OCH2CH2N(CH2CH3)2

<400> SEQUENCE: 180

Leu Asp His Phe Arg Trp Lys
1               5

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: Cyclized
<220> FEATURE:
<221> NAME/KEY: MOD_RES
<222> LOCATION: (1)..(1)
<223> OTHER INFORMATION: H-Nle
<220> FEATURE:
<221> NAME/KEY: MOD_RES
<222> LOCATION: (4)..(4)
<223> OTHER INFORMATION: D-Phe(4-I)
<220> FEATURE:
<221> NAME/KEY: MOD_RES
<222> LOCATION: (5)..(5)
<223> OTHER INFORMATION: Arg(Ac)
<220> FEATURE:
<221> NAME/KEY: MOD_RES
<222> LOCATION: (7)..(7)
<223> OTHER INFORMATION: Lys-NH2

<400> SEQUENCE: 181

Leu Asp His Phe Arg Trp Lys
1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: Cyclized
<220> FEATURE:
<221> NAME/KEY: MOD_RES
<222> LOCATION: (1)..(1)
<223> OTHER INFORMATION: H-Nle
<220> FEATURE:
<221> NAME/KEY: MOD_RES
<222> LOCATION: (4)..(4)
<223> OTHER INFORMATION: D-Ala(2-naphthyl)
<220> FEATURE:
<221> NAME/KEY: MOD_RES
<222> LOCATION: (5)..(5)
<223> OTHER INFORMATION: Arg(NO2)
<220> FEATURE:
<221> NAME/KEY: MOD_RES
<222> LOCATION: (7)..(7)
<223> OTHER INFORMATION: Lys-NH2
```

```
<400> SEQUENCE: 182

Leu Asp His Ala Arg Trp Lys
1               5

<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Val
<220> FEATURE:
<221> NAME/KEY: MOD_RES
<222> LOCATION: (5)..(5)
<223> OTHER INFORMATION: Arg(diAc)-OCH2CH2N(CH2CH3)2

<400> SEQUENCE: 183

Val Pro Gly Pro Arg
1               5

<210> SEQ ID NO 184
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Tyr
<220> FEATURE:
<221> NAME/KEY: MOD_RES
<222> LOCATION: (5)..(5)
<223> OTHER INFORMATION: Met-OH

<400> SEQUENCE: 184

Tyr Gly Gly Phe Met
1               5

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: Cyclized
<220> FEATURE:
<221> NAME/KEY: MOD_RES
<222> LOCATION: (1)..(1)
<223> OTHER INFORMATION: Ac-Nle
<220> FEATURE:
<221> NAME/KEY: MOD_RES
<222> LOCATION: (4)..(4)
<223> OTHER INFORMATION: D-Phe(4-I)
<220> FEATURE:
<221> NAME/KEY: MOD_RES
<222> LOCATION: (7)..(7)
<223> OTHER INFORMATION: Lys-NH2

<400> SEQUENCE: 185

Leu Asp His Phe Arg Trp Lys
1               5
```

```
<210> SEQ ID NO 186
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Val
<220> FEATURE:
<221> NAME/KEY: MOD_RES
<222> LOCATION: (5)..(5)
<223> OTHER INFORMATION: Arg-OH

<400> SEQUENCE: 186

Val Pro Gly Pro Arg
1               5

<210> SEQ ID NO 187
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ile Glu Ile Gly Leu Glu Gly Lys Gly Phe Glu Pro Thr Leu Glu Ala
1               5                   10                  15

Leu Phe Gly Lys
            20

<210> SEQ ID NO 188
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Lys Thr Thr Lys Gln Ser Phe Asp Leu Ser Val Lys Ala Gln Tyr Lys
1               5                   10                  15

Lys Asn Lys His
            20

<210> SEQ ID NO 189
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Val
<220> FEATURE:
<221> NAME/KEY: MOD_RES
<222> LOCATION: (3)..(3)
<223> OTHER INFORMATION: Asp(OEt)
<220> FEATURE:
<221> NAME/KEY: MOD_RES
<222> LOCATION: (5)..(5)
<223> OTHER INFORMATION: Arg(diAc)-OCH2CH2N(CH2CH3)2

<400> SEQUENCE: 189
```

```
Val Pro Asp Pro Arg
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: Cyclized
<220> FEATURE:
<221> NAME/KEY: MOD_RES
<222> LOCATION: (1)..(1)
<223> OTHER INFORMATION: Ac-Nle
<220> FEATURE:
<221> NAME/KEY: MOD_RES
<222> LOCATION: (5)..(5)
<223> OTHER INFORMATION: Arg(diAc)
<220> FEATURE:
<221> NAME/KEY: MOD_RES
<222> LOCATION: (7)..(7)
<223> OTHER INFORMATION: Lys-OH

<400> SEQUENCE: 190

Leu Asp His Phe Arg Trp Lys
1               5

<210> SEQ ID NO 191
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Tyr
<220> FEATURE:
<221> NAME/KEY: MOD_RES
<222> LOCATION: (5)..(5)
<223> OTHER INFORMATION: Met-OCH2CH2N(CH2CH3)2

<400> SEQUENCE: 191

Tyr Gly Gly Phe Met
1               5

<210> SEQ ID NO 192
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (CH3)2NCH2CH2CH2CO-Tyr
<220> FEATURE:
<221> NAME/KEY: MOD_RES
<222> LOCATION: (5)..(5)
<223> OTHER INFORMATION: Met-OCH2CH2CH2CH3

<400> SEQUENCE: 192

Tyr Gly Gly Phe Met
1               5

<210> SEQ ID NO 193
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (CH3)2NCH2CH2CH2CO-Tyr
<220> FEATURE:
<221> NAME/KEY: MOD_RES
<222> LOCATION: (5)..(5)
<223> OTHER INFORMATION: Met-OH

<400> SEQUENCE: 193

Tyr Gly Gly Phe Met
1               5

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: Cyclized
<220> FEATURE:
<221> NAME/KEY: MOD_RES
<222> LOCATION: (1)..(1)
<223> OTHER INFORMATION: Ac-Nle
<220> FEATURE:
<221> NAME/KEY: MOD_RES
<222> LOCATION: (5)..(5)
<223> OTHER INFORMATION: Arg(Ac)
<220> FEATURE:
<221> NAME/KEY: MOD_RES
<222> LOCATION: (7)..(7)
<223> OTHER INFORMATION: Lys-OCH2CH2N(CH2CH3)2

<400> SEQUENCE: 194

Leu Asp His Phe Arg Trp Lys
1               5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: Cyclized
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (7)..(7)
<223> OTHER INFORMATION: Lys-OH

<400> SEQUENCE: 195

Leu Asp His Phe Arg Trp Lys
1               5

<210> SEQ ID NO 196
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Val
<220> FEATURE:
<221> NAME/KEY: MOD_RES
<222> LOCATION: (5)..(5)
<223> OTHER INFORMATION: Arg-OH

<400> SEQUENCE: 196

Val Pro Asp Pro Arg
1               5

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Val
<220> FEATURE:
<221> NAME/KEY: MOD_RES
<222> LOCATION: (5)..(5)
<223> OTHER INFORMATION: Arg(NO2)-OCH(CH3)2

<400> SEQUENCE: 197

Val Pro Gly Pro Arg
1               5

<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Val
<220> FEATURE:
<221> NAME/KEY: MOD_RES
<222> LOCATION: (5)..(5)
<223> OTHER INFORMATION: Arg(diAc)-OCH2CH2CH2CH3

<400> SEQUENCE: 198

Val Pro Gly Pro Arg
1               5

<210> SEQ ID NO 199
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Ala
<220> FEATURE:
<221> NAME/KEY: MOD_RES
<222> LOCATION: (5)..(5)
<223> OTHER INFORMATION: Arg(NO2)-OCH2CH2CH2CH3
```

```
<400> SEQUENCE: 199

Ala Pro Gly Pro Arg
1               5

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Val
<220> FEATURE:
<221> NAME/KEY: MOD_RES
<222> LOCATION: (3)..(3)
<223> OTHER INFORMATION: Asp(OEt)
<220> FEATURE:
<221> NAME/KEY: MOD_RES
<222> LOCATION: (5)..(5)
<223> OTHER INFORMATION: Arg(NO2)-OCH2CH2CH2CH3

<400> SEQUENCE: 200

Val Pro Asp Pro Arg
1               5

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: Cyclized
<220> FEATURE:
<221> NAME/KEY: MOD_RES
<222> LOCATION: (1)..(1)
<223> OTHER INFORMATION: Ac-Nle
<220> FEATURE:
<221> NAME/KEY: MOD_RES
<222> LOCATION: (5)..(5)
<223> OTHER INFORMATION: Arg(NO2)
<220> FEATURE:
<221> NAME/KEY: MOD_RES
<222> LOCATION: (7)..(7)
<223> OTHER INFORMATION: Lys-OCH2CH2N(CH2CH3)2

<400> SEQUENCE: 201

Leu Asp His Phe Arg Trp Lys
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Tyr(Ac)
<220> FEATURE:
<221> NAME/KEY: MOD_RES
<222> LOCATION: (2)..(2)
<223> OTHER INFORMATION: D-Ala
<220> FEATURE:
```

```
<221> NAME/KEY: MOD_RES
<222> LOCATION: (5)..(5)
<223> OTHER INFORMATION: Leu-OCH2(CH2)4CH3

<400> SEQUENCE: 202

Tyr Ala Gly Phe Leu
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Tyr(Ac)
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (5)..(5)
<223> OTHER INFORMATION: Leu-OCH2CH2N(CH2CH3)

<400> SEQUENCE: 203

Tyr Ala Gly Phe Leu
1               5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Tyr(Ac)
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (5)..(5)
<223> OTHER INFORMATION: Met(O)-OL

<400> SEQUENCE: 204

Tyr Ala Gly Phe Met
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-Phe
<220> FEATURE:
<221> NAME/KEY: MOD_RES
```

```
<222> LOCATION: (6)..(6)
<223> OTHER INFORMATION: D-Trp

<400> SEQUENCE: 205

Leu Lys His Phe Arg Trp Gly
1               5

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Lys Gly Arg Gly Leu Ser Leu Ser Ala Phe Ser Trp Gly Ala
1               5                   10                  15

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N beta-D-Leu
<220> FEATURE:
<221> NAME/KEY: MOD_RES
<222> LOCATION: (2)..(3)
<223> OTHER INFORMATION: D-Arg
<220> FEATURE:
<221> NAME/KEY: MOD_RES
<222> LOCATION: (4)..(4)
<223> OTHER INFORMATION: D-Leu
<220> FEATURE:
<221> NAME/KEY: MOD_RES
<222> LOCATION: (5)..(5)
<223> OTHER INFORMATION: D-Phe-naltrexamine

<400> SEQUENCE: 207

Leu Arg Arg Leu Phe
1               5
```